US012629428B2

(12) United States Patent
Gersbach et al.

(10) Patent No.: US 12,629,428 B2
(45) Date of Patent: May 19, 2026

(54) AAV VECTOR-MEDIATED DELETION OF LARGE MUTATIONAL HOTSPOT FOR TREATMENT OF DUCHENNE MUSCULAR DYSTROPHY

(71) Applicant: Duke University, Durham, NC (US)

(72) Inventors: Charles A. Gersbach, Chapel Hill, NC (US); Karen Bulaklak, Durham, NC (US); Jacqueline N. Robinson-Hamm, Durham, NC (US)

(73) Assignee: Duke University, Durham, NC (US)

( * ) Notice: Subject to any disclaimer, the term of this patent is extended or adjusted under 35 U.S.C. 154(b) by 823 days.

(21) Appl. No.: 17/603,330

(22) PCT Filed: Apr. 14, 2020

(86) PCT No.: PCT/US2020/028148
§ 371 (c)(1),
(2) Date: Oct. 12, 2021

(87) PCT Pub. No.: WO2020/214609
PCT Pub. Date: Oct. 22, 2020

(65) Prior Publication Data
US 2022/0184229 A1     Jun. 16, 2022

Related U.S. Application Data

(60) Provisional application No. 62/833,760, filed on Apr. 14, 2019.

(51) Int. Cl.
| | |
|---|---|
| *A61K 48/00* | (2006.01) |
| *C12N 9/22* | (2006.01) |
| *C12N 15/11* | (2006.01) |
| *C12N 15/86* | (2006.01) |

(52) U.S. Cl.
CPC .............. *A61K 48/005* (2013.01); *C12N 9/22* (2013.01); *C12N 15/111* (2013.01); *C12N 15/86* (2013.01); *C12N 2310/20* (2017.05); *C12N 2320/32* (2013.01); *C12N 2750/14143* (2013.01); *C12N 2800/40* (2013.01)

(58) Field of Classification Search
CPC ........ C12N 9/22; C12N 15/111; C12N 15/86; C12N 2310/20; C12N 2320/32; C12N 2750/14143; C12N 2800/40; C12N 15/907; C12N 2510/00; C12N 15/113; C12N 15/102; C07K 14/4708
See application file for complete search history.

(56) References Cited

U.S. PATENT DOCUMENTS

| | | | |
|---|---|---|---|
| 3,687,808 A | 8/1972 | Merigan, Jr. | |
| 4,469,863 A | 9/1984 | Ts'o et al. | |
| 4,476,301 A | 10/1984 | Imbach et al. | |
| 4,501,729 A | 2/1985 | Boucher et al. | |
| 4,554,101 A | 11/1985 | Hopp | |
| 4,587,044 A | 5/1986 | Miller et al. | |
| 4,605,735 A | 8/1986 | Miyoshi et al. | |
| 4,667,025 A | 5/1987 | Miyoshi et al. | |
| 4,737,323 A | 4/1988 | Martin et al. | |
| 4,762,779 A | 8/1988 | Snitman | |
| 4,789,737 A | 12/1988 | Miyoshi et al. | |
| 4,824,941 A | 4/1989 | Gordon et al. | |
| 4,828,979 A | 5/1989 | Klevan et al. | |
| 4,835,263 A | 5/1989 | Nguyen et al. | |
| 4,845,205 A | 7/1989 | Huynh et al. | |
| 4,876,335 A | 10/1989 | Yamane et al. | |
| 4,904,582 A | 2/1990 | Tullis | |
| 4,948,882 A | 8/1990 | Ruth | |
| 4,958,013 A | 9/1990 | Letsinger | |
| 5,013,830 A | 5/1991 | Ohsuka et al. | |
| 5,023,243 A | 6/1991 | Tullis | |
| 5,034,506 A | 7/1991 | Summerton et al. | |
| 5,082,830 A | 1/1992 | Brakel et al. | |
| 5,109,124 A | 4/1992 | Ramachandran et al. | |
| 5,112,963 A | 5/1992 | Pieles et al. | |
| 5,118,802 A | 6/1992 | Smith et al. | |
| 5,130,302 A | 7/1992 | Spielvogel et al. | |
| 5,134,066 A | 7/1992 | Rogers et al. | |
| 5,138,045 A | 8/1992 | Cook et al. | |
| 5,139,941 A | 8/1992 | Muzyczka et al. | |
| 5,149,797 A | 9/1992 | Pederson et al. | |
| 5,166,315 A | 11/1992 | Summerton et al. | |
| 5,175,273 A | 12/1992 | Bischofberger et al. | |
| 5,177,196 A | 1/1993 | Meyer et al. | |
| 5,185,444 A | 2/1993 | Summerton et al. | |
| 5,188,897 A | 2/1993 | Suhadolnik et al. | |
| 5,214,134 A | 5/1993 | Weis et al. | |
| 5,214,136 A | 5/1993 | Lin et al. | |
| 5,216,141 A | 6/1993 | Benner | |

(Continued)

FOREIGN PATENT DOCUMENTS

| | | |
|---|---|---|
| AU | 2022318664 A1 | 2/2024 |
| CA | 2749305 A1 | 7/2010 |

(Continued)

OTHER PUBLICATIONS

US 11,898,176 B2, 02/2024, Gersbach et al. (withdrawn)
Shimo et al. A novel human muscle cell model of Duchenne muscular dystrophy created by CRISPR/Cas9 and evaluation of antisense-mediated exon skipping., Journal of Human Genetics (2018), 63: 365-375). (Year: 2018).*
Dikusuma et al. (Versatile single-step-assembly CRISPR/Cas9 vectors for dual gRNA expression. PLOS One (2017), 12(12): p. 1-11). (Year: 2017).*
U.S. Appl. No. 17/636,750, filed Feb. 18, 2022.
U.S. Appl. No. 17/636,754, filed Feb. 18, 2022.
U.S. Appl. No. 17/766,003, filed Apr. 1, 2022.
U.S. Appl. No. 63/314,183, filed Feb. 25, 2022.
U.S. Appl. No. 63/314,256, filed Feb. 25, 2022.
U.S. Appl. No. 63/317,847, filed Mar. 8, 2022.

(Continued)

*Primary Examiner* — Iqbal H Chowdhury
(74) *Attorney, Agent, or Firm* — Michael Best & Friedrich LLP

(57) ABSTRACT

Disclosed herein are therapeutic targets for the correction of the human dystrophin gene by gene editing and methods of use.

17 Claims, 16 Drawing Sheets

Specification includes a Sequence Listing.

(56)        References Cited

U.S. PATENT DOCUMENTS

| | | | |
|---|---|---|---|
| 5,218,105 | A | 6/1993 | Cook et al. |
| 5,219,740 | A | 6/1993 | Miller et al. |
| 5,220,007 | A | 6/1993 | Pederson et al. |
| 5,235,033 | A | 8/1993 | Summerton et al. |
| 5,245,022 | A | 9/1993 | Weis et al. |
| 5,254,469 | A | 10/1993 | Warren, III |
| 5,256,775 | A | 10/1993 | Froehler |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,321,131 | A | 6/1994 | Agrawal et al. |
| 5,366,878 | A | 11/1994 | Pederson et al. |
| 5,367,066 | A | 11/1994 | Urdea et al. |
| 5,371,241 | A | 12/1994 | Brush |
| 5,391,723 | A | 2/1995 | Priest |
| 5,399,676 | A | 3/1995 | Froehler |
| 5,403,711 | A | 4/1995 | Walder et al. |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,478,745 | A | 12/1995 | Samulski et al. |
| 5,484,908 | A | 1/1996 | Froehler et al. |
| 5,486,603 | A | 1/1996 | Buhr |
| 5,489,677 | A | 2/1996 | Sanghvi et al. |
| 5,491,133 | A | 2/1996 | Walder et al. |
| 5,502,177 | A | 3/1996 | Matteucci et al. |
| 5,510,473 | A | 4/1996 | Camerini-otero et al. |
| 5,510,475 | A | 4/1996 | Agrawal et al. |
| 5,512,439 | A | 4/1996 | Horner et al. |
| 5,512,667 | A | 4/1996 | Reed et al. |
| 5,514,785 | A | 5/1996 | Van Ness et al. |
| 5,519,126 | A | 5/1996 | Hecht |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,552 | A | 10/1996 | Magda et al. |
| 5,567,810 | A | 10/1996 | Weis et al. |
| 5,571,799 | A | 11/1996 | Tkachuk et al. |
| 5,574,142 | A | 11/1996 | Meyer et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,593,972 | A | 1/1997 | Weiner et al. |
| 5,595,726 | A | 1/1997 | Magda et al. |
| 5,596,086 | A | 1/1997 | Matteucci et al. |
| 5,596,091 | A | 1/1997 | Switzer |
| 5,597,696 | A | 1/1997 | Linn et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,633,360 | A | 5/1997 | Bischofberger et al. |
| 5,652,355 | A | 7/1997 | Metelev et al. |
| 5,652,356 | A | 7/1997 | Agrawal |
| 5,658,784 | A | 8/1997 | Eckner et al. |
| 5,663,312 | A | 9/1997 | Chaturvedula et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,922 | A | 12/1997 | Cook et al. |
| 5,714,331 | A | 2/1998 | Buchardt et al. |
| 5,719,262 | A | 2/1998 | Buchardt et al. |
| 5,741,683 | A | 4/1998 | Zhou et al. |
| 5,750,692 | A | 5/1998 | Cook et al. |
| 5,773,700 | A | 6/1998 | Van Grinsven et al. |
| 5,962,428 | A | 10/1999 | Carrano et al. |
| 6,057,152 | A | 5/2000 | Samulski et al. |
| 6,140,081 | A | 10/2000 | Barbas |
| 6,204,059 | B1 | 3/2001 | Samulski et al. |
| 6,207,453 | B1 | 3/2001 | Maass et al. |
| 6,268,213 | B1 | 7/2001 | Samulski et al. |
| 6,268,490 | B1 | 7/2001 | Imanishi et al. |
| 6,287,860 | B1 | 9/2001 | Monia et al. |
| 6,453,242 | B1 | 9/2002 | Eisenberg et al. |
| 6,462,254 | B1 | 10/2002 | Vernachio et al. |
| 6,491,907 | B1 | 12/2002 | Rabinowitz et al. |
| 6,534,261 | B1 | 3/2003 | Cox, III et al. |
| 6,596,535 | B1 | 7/2003 | Carter |
| 6,660,514 | B1 | 12/2003 | Zolotukhin et al. |
| 6,734,291 | B2 | 5/2004 | Kochkine et al. |
| 6,770,748 | B2 | 8/2004 | Imanishi et al. |
| 6,794,499 | B2 | 9/2004 | Wengel et al. |
| 6,951,753 | B2 | 10/2005 | Shenk et al. |
| 7,034,133 | B2 | 4/2006 | Wengel et al. |
| 7,053,207 | B2 | 5/2006 | Wengel |
| 7,060,809 | B2 | 6/2006 | Wengel et al. |
| 7,074,596 | B2 | 7/2006 | Darzynkiewicz et al. |
| 7,084,125 | B2 | 8/2006 | Wengel |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,449,561 | B1 | 11/2008 | Sommer et al. |
| 7,456,683 | B2 | 11/2008 | Takano et al. |
| 7,572,582 | B2 | 8/2009 | Wengel et al. |
| 7,588,772 | B2 | 9/2009 | Kay et al. |
| 7,728,118 | B2 | 6/2010 | Wood et al. |
| 7,745,651 | B2 | 6/2010 | Heyes et al. |
| 7,790,449 | B2 | 9/2010 | Gao et al. |
| 7,799,565 | B2 | 9/2010 | Maclachlan et al. |
| 7,906,111 | B2 | 3/2011 | Wilson et al. |
| 8,278,036 | B2 | 10/2012 | Kariko et al. |
| 8,450,107 | B2 | 5/2013 | Zhang et al. |
| 8,586,526 | B2 | 11/2013 | Gregory et al. |
| 8,697,359 | B1 | 4/2014 | Zhang et al. |
| 8,889,356 | B2 | 11/2014 | Zhang |
| 8,993,233 | B2 | 3/2015 | Zhang et al. |
| 9,139,554 | B2 | 9/2015 | Hope et al. |
| 9,458,205 | B2 | 10/2016 | Gregory et al. |
| 9,738,879 | B2 | 8/2017 | Gersbach et al. |

(56) References Cited

U.S. PATENT DOCUMENTS

| | | | |
|---|---|---|---|
| 9,828,582 | B2 | 11/2017 | Perez-Pinera et al. |
| 9,834,791 | B2 | 12/2017 | Zhang et al. |
| 9,890,364 | B2 | 2/2018 | Joung et al. |
| 10,011,850 | B2 | 7/2018 | Joung et al. |
| 10,190,106 | B2 | 1/2019 | Wolfe et al. |
| 10,266,850 | B2 | 4/2019 | Doudna et al. |
| 10,676,726 | B2 | 6/2020 | Gersbach et al. |
| 10,676,735 | B2 | 6/2020 | Gersbach et al. |
| 10,704,060 | B2 | 7/2020 | Gersbach et al. |
| 10,711,256 | B2 | 7/2020 | Gersbach et al. |
| 10,745,714 | B2 | 8/2020 | Gersbach et al. |
| 10,836,997 | B2 | 11/2020 | Ko |
| 11,155,796 | B2 | 10/2021 | Gersbach et al. |
| 11,421,251 | B2 | 8/2022 | Gersbach et al. |
| 11,427,817 | B2 | 8/2022 | Josephs et al. |
| 11,970,710 | B2 | 4/2024 | Gersbach et al. |
| 11,976,307 | B2 | 5/2024 | Gersbach et al. |
| 12,214,054 | B2 | 2/2025 | Gersbach et al. |
| 12,214,056 | B2 | 2/2025 | Gersbach et al. |
| 12,215,345 | B2 | 2/2025 | Perez-Pinera et al. |
| 12,215,366 | B2 | 2/2025 | Gersbach et al. |
| 12,428,631 | B2 | 9/2025 | Gersbach et al. |
| 2002/0160940 | A1 | 10/2002 | Case et al. |
| 2003/0124102 | A1 | 7/2003 | Rudnicki et al. |
| 2004/0142025 | A1 | 7/2004 | Maclachlan et al. |
| 2004/0175727 | A1 | 9/2004 | Draghia-Akli et al. |
| 2004/0192593 | A1 | 9/2004 | Draghia-Akli et al. |
| 2004/0204345 | A1 | 10/2004 | Case et al. |
| 2005/0079512 | A1 | 4/2005 | Emerson et al. |
| 2006/0068395 | A1 | 3/2006 | Wood et al. |
| 2006/0171924 | A1* | 8/2006 | Luo .................... A61K 48/0058 |
| | | | 435/456 |
| 2006/0211647 | A1 | 9/2006 | Khan |
| 2006/0270595 | A1 | 11/2006 | Jullien et al. |
| 2007/0042031 | A1 | 2/2007 | Maclachlan et al. |
| 2007/0042462 | A1 | 2/2007 | Hildinger |
| 2007/0059795 | A1 | 3/2007 | Moore et al. |
| 2007/0185042 | A1 | 8/2007 | Tsai et al. |
| 2007/0192880 | A1 | 8/2007 | Muyan et al. |
| 2008/0070299 | A1 | 3/2008 | Wood et al. |
| 2008/0090291 | A1 | 4/2008 | Wood et al. |
| 2008/0200409 | A1 | 8/2008 | Wilson et al. |
| 2009/0018031 | A1 | 1/2009 | Trinklein et al. |
| 2010/0035968 | A1 | 2/2010 | Rasmussen et al. |
| 2010/0076057 | A1 | 3/2010 | Sontheimer et al. |
| 2010/0261175 | A1 | 10/2010 | Rasmussen et al. |
| 2010/0267018 | A1 | 10/2010 | Wengel et al. |
| 2011/0145940 | A1 | 6/2011 | Voytas et al. |
| 2011/0197290 | A1 | 8/2011 | Fahrenkrug et al. |
| 2011/0236353 | A1 | 9/2011 | Wilson et al. |
| 2011/0263682 | A1 | 10/2011 | De Kimpe et al. |
| 2011/0286957 | A1 | 11/2011 | Prieve et al. |
| 2011/0301073 | A1 | 12/2011 | Gregory et al. |
| 2011/0301218 | A1 | 12/2011 | Bozzoni et al. |
| 2012/0195917 | A1 | 8/2012 | Sahin et al. |
| 2012/0207744 | A1 | 8/2012 | Mendlein et al. |
| 2013/0137173 | A1 | 5/2013 | Zang et al. |
| 2013/0274129 | A1 | 10/2013 | Katzen et al. |
| 2013/0323001 | A1 | 12/2013 | Ueki et al. |
| 2014/0068797 | A1 | 3/2014 | Doudna et al. |
| 2014/0140969 | A1 | 5/2014 | Beausejour et al. |
| 2014/0170753 | A1 | 6/2014 | Zhang |
| 2014/0179006 | A1 | 6/2014 | Zhang |
| 2014/0186958 | A1 | 7/2014 | Zhang et al. |
| 2014/0234975 | A1 | 8/2014 | Silva et al. |
| 2014/0295557 | A1 | 10/2014 | Joung et al. |
| 2014/0309177 | A1 | 10/2014 | Perez-Pinera et al. |
| 2014/0315862 | A1 | 10/2014 | Kaye |
| 2014/0356956 | A1 | 12/2014 | Church et al. |
| 2014/0357530 | A1 | 12/2014 | Zhang et al. |
| 2014/0377868 | A1 | 12/2014 | Joung et al. |
| 2015/0024499 | A1 | 1/2015 | Brouns et al. |
| 2015/0031089 | A1 | 1/2015 | Lindstrom |
| 2015/0044772 | A1 | 2/2015 | Zhao |
| 2015/0045413 | A1 | 2/2015 | De Visser et al. |
| 2015/0056705 | A1 | 2/2015 | Conway et al. |
| 2015/0079064 | A1 | 3/2015 | Gersbach et al. |
| 2015/0159178 | A1 | 6/2015 | Green et al. |
| 2015/0166980 | A1 | 6/2015 | Liu et al. |
| 2015/0225717 | A1 | 8/2015 | Lee et al. |
| 2015/0252358 | A1 | 9/2015 | Maeder et al. |
| 2016/0002634 | A1 | 1/2016 | Sazani et al. |
| 2016/0040189 | A1 | 2/2016 | Kennedy et al. |
| 2016/0058889 | A1 | 3/2016 | Olson et al. |
| 2016/0177278 | A1 | 6/2016 | Wolfe et al. |
| 2016/0199419 | A1 | 7/2016 | Miura |
| 2016/0201089 | A1 | 7/2016 | Gersbach et al. |
| 2016/0281166 | A1 | 9/2016 | Bhattacharjee et al. |
| 2016/0354487 | A1 | 12/2016 | Zhang et al. |
| 2017/0002316 | A1 | 1/2017 | Gascón Jiménez et al. |
| 2017/0037396 | A1 | 2/2017 | Lee et al. |
| 2017/0198308 | A1 | 7/2017 | Qi et al. |
| 2017/0204407 | A1 | 7/2017 | Gilbert et al. |
| 2017/0260547 | A1 | 9/2017 | Dombrowski et al. |
| 2017/0283831 | A1 | 10/2017 | Zhang et al. |
| 2017/0298331 | A1 | 10/2017 | Gersbach et al. |
| 2017/0327806 | A1 | 11/2017 | Joung et al. |
| 2017/0362635 | A1 | 12/2017 | Chamberlain et al. |
| 2018/0023064 | A1 | 1/2018 | Gersbach et al. |
| 2018/0073012 | A1 | 3/2018 | Liu et al. |
| 2018/0094238 | A1 | 4/2018 | Perez-Pinera et al. |
| 2018/0127780 | A1 | 5/2018 | Liu et al. |
| 2018/0135023 | A1 | 5/2018 | Wang et al. |
| 2018/0135109 | A1 | 5/2018 | Jayaram et al. |
| 2018/0201951 | A1 | 7/2018 | Guilak et al. |
| 2018/0237771 | A1 | 8/2018 | Kim et al. |
| 2018/0251735 | A1 | 9/2018 | Ko |
| 2018/0271069 | A1 | 9/2018 | Min et al. |
| 2018/0280539 | A1 | 10/2018 | Debs et al. |
| 2018/0291370 | A1 | 10/2018 | Gersbach et al. |
| 2018/0298380 | A1 | 10/2018 | Gao et al. |
| 2018/0305689 | A1 | 10/2018 | Sætrom et al. |
| 2018/0305704 | A1 | 10/2018 | Zhang |
| 2018/0305719 | A1 | 10/2018 | Perez-Pinera et al. |
| 2018/0319850 | A1 | 11/2018 | Payne et al. |
| 2018/0320197 | A1 | 11/2018 | Gersbach et al. |
| 2018/0327740 | A1 | 11/2018 | Gifford et al. |
| 2018/0334685 | A1 | 11/2018 | Yeo et al. |
| 2018/0334688 | A1 | 11/2018 | Gersbach et al. |
| 2018/0353615 | A1 | 12/2018 | Gersbach et al. |
| 2018/0355332 | A1 | 12/2018 | Steinberg et al. |
| 2019/0032049 | A1 | 1/2019 | Naldini et al. |
| 2019/0038776 | A1 | 2/2019 | Pyle et al. |
| 2019/0048337 | A1 | 2/2019 | Hsu et al. |
| 2019/0062790 | A1 | 2/2019 | Doudna et al. |
| 2019/0078119 | A1 | 3/2019 | Wilson et al. |
| 2019/0106710 | A1 | 4/2019 | Zhang et al. |
| 2019/0127713 | A1 | 5/2019 | Gersbach et al. |
| 2019/0134221 | A1 | 5/2019 | Bumcrot et al. |
| 2019/0136229 | A1 | 5/2019 | Josephs et al. |
| 2019/0142972 | A1 | 5/2019 | Burns et al. |
| 2019/0144845 | A9 | 5/2019 | Yin et al. |
| 2019/0151476 | A1 | 5/2019 | Gersbach et al. |
| 2019/0167815 | A1 | 6/2019 | Holmes et al. |
| 2019/0183932 | A1 | 6/2019 | Mackall et al. |
| 2019/0192691 | A1 | 6/2019 | Barrett et al. |
| 2019/0194633 | A1 | 6/2019 | Gersbach et al. |
| 2019/0201402 | A1 | 7/2019 | Jiang et al. |
| 2019/0225955 | A1 | 7/2019 | Liu et al. |
| 2019/0225991 | A1 | 7/2019 | Izpisua et al. |
| 2019/0248854 | A1 | 8/2019 | Tremblay et al. |
| 2019/0264232 | A1 | 8/2019 | Hou et al. |
| 2019/0351074 | A1 | 11/2019 | Ahituv et al. |
| 2019/0359959 | A1 | 11/2019 | Jaenisch et al. |
| 2019/0374655 | A1 | 12/2019 | Kabadi et al. |
| 2020/0002731 | A1 | 1/2020 | Frendewey et al. |
| 2020/0056206 | A1 | 2/2020 | Tremblay et al. |
| 2020/0063105 | A1 | 2/2020 | Ng et al. |
| 2020/0080108 | A1 | 3/2020 | Jaskula-Ranga et al. |
| 2020/0080112 | A1 | 3/2020 | Zhang et al. |
| 2020/0109406 | A1 | 4/2020 | Miller et al. |
| 2020/0123533 | A1 | 4/2020 | Wang et al. |
| 2020/0216549 | A1 | 7/2020 | Fukumura et al. |
| 2020/0216810 | A1 | 7/2020 | Metelitsa et al. |

(56) References Cited

U.S. PATENT DOCUMENTS

| | | |
|---|---|---|
| 2020/0260698 A1 | 8/2020 | Kyrychenko et al. |
| 2020/0275641 A1 | 9/2020 | Min et al. |
| 2020/0318139 A1 | 10/2020 | Gersbach et al. |
| 2020/0332307 A1 | 10/2020 | Hummel et al. |
| 2020/0347105 A1 | 11/2020 | Gersbach et al. |
| 2020/0361877 A1 | 11/2020 | Mahajan et al. |
| 2020/0370042 A1 | 11/2020 | Olson et al. |
| 2020/0385695 A1 | 12/2020 | Gersbach et al. |
| 2021/0002665 A1 | 1/2021 | Gersbach et al. |
| 2021/0024895 A1 | 1/2021 | Kariko et al. |
| 2021/0032654 A1 | 2/2021 | Gersbach et al. |
| 2021/0040460 A1 | 2/2021 | Gersbach et al. |
| 2021/0054448 A1 | 2/2021 | Ng et al. |
| 2021/0254049 A1 | 8/2021 | Wang et al. |
| 2021/0277379 A1 | 9/2021 | Gaudelli et al. |
| 2021/0322577 A1 | 10/2021 | Lande et al. |
| 2021/0363521 A1 | 11/2021 | Police et al. |
| 2021/0363525 A1 | 11/2021 | Sætrom et al. |
| 2022/0098561 A1 | 3/2022 | Gersbach et al. |
| 2022/0177879 A1 | 6/2022 | Gersbach et al. |
| 2022/0186199 A1 | 6/2022 | Cotta-Ramusino et al. |
| 2022/0195406 A1 | 6/2022 | Gersbach et al. |
| 2022/0244244 A1 | 8/2022 | Schmedt et al. |
| 2022/0249626 A1 | 8/2022 | Kmiec et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2023/0201375 A1 | 6/2023 | Gersbach et al. |
| 2023/0257723 A1 | 8/2023 | Gersbach et al. |
| 2023/0304000 A1 | 9/2023 | Josephs et al. |
| 2023/0348870 A1 | 11/2023 | Gersbach et al. |
| 2023/0349888 A1 | 11/2023 | Gersbach et al. |
| 2023/0383270 A1 | 11/2023 | Gersbach et al. |
| 2023/0383297 A1 | 11/2023 | Gersbach et al. |
| 2023/0392132 A1 | 12/2023 | Gersbach et al. |
| 2024/0026352 A1 | 1/2024 | Gersbach et al. |
| 2024/0052328 A1 | 2/2024 | Kwon et al. |
| 2024/0058425 A1 | 2/2024 | Gersbach et al. |
| 2024/0067968 A1 | 2/2024 | Cosgrove et al. |
| 2024/0141341 A1 | 5/2024 | Gersbach et al. |
| 2024/0279628 A1 | 8/2024 | Gersbach et al. |
| 2024/0336892 A1 | 10/2024 | Perez-Pinera et al. |
| 2025/0114482 A1 | 4/2025 | Gersbach et al. |
| 2025/0171754 A1 | 5/2025 | Gersbach et al. |
| 2025/0197823 A1 | 6/2025 | Gersbach et al. |
| 2025/0257341 A1 | 8/2025 | Gersbach et al. |
| 2025/0262326 A1 | 8/2025 | Gersbach et al. |

FOREIGN PATENT DOCUMENTS

| | | | |
|---|---|---|---|
| CA | 2981508 A1 | 10/2016 | |
| CA | 3086885 A1 | 7/2019 | |
| CA | 3101477 A1 | 12/2019 | |
| EP | 2620161 A1 | 7/2013 | |
| EP | 3009511 A2 | 4/2016 | |
| EP | 3199632 A1 | 8/2017 | |
| EP | 3712272 A1 | 9/2020 | |
| EP | 3209783 B1 | 11/2021 | |
| EP | 3995584 A1 | 5/2022 | |
| JP | 2003-512827 A | 4/2003 | |
| JP | 2013-509159 A | 3/2013 | |
| JP | 2015-534817 A | 12/2015 | |
| JP | 2016-521452 A | 7/2016 | |
| JP | 2016-521452 A2 | 7/2016 | |
| JP | 2016-521975 A | 7/2016 | |
| JP | 2016-523082 A | 8/2016 | |
| JP | 2018-011546 A | 1/2018 | |
| JP | 2019-103393 A | 6/2019 | |
| JP | 2020-517247 A | 6/2020 | |
| KR | 20190134673 A | 12/2019 | |
| WO | WO1991/18114 A1 | 11/1991 | |
| WO | WO1992/000387 A1 | 1/1992 | |
| WO | WO1993/007883 A1 | 4/1993 | |
| WO | WO1993/024640 A2 | 12/1993 | |
| WO | WO1994/016737 A1 | 8/1994 | |
| WO | WO1998/053058 A1 | 11/1998 | |
| WO | WO1998/053059 A1 | 11/1998 | |
| WO | WO1998/053060 A1 | 11/1998 | |
| WO | WO 2000/028004 A1 | 5/2000 | |
| WO | 2001/083793 A2 | 11/2001 | |
| WO | WO2001/083783 A2 | 11/2001 | |
| WO | WO 2001/092551 A2 | 12/2001 | |
| WO | WO2002/016536 A1 | 2/2002 | |
| WO | WO2003/016496 A2 | 2/2003 | |
| WO | WO2003/042397 A2 | 5/2003 | |
| WO | WO2003/072788 A1 | 9/2003 | |
| WO | WO 2004/018632 A2 | 3/2004 | |
| WO | WO2005/033321 A2 | 4/2005 | |
| WO | WO2006/110689 A2 | 10/2006 | |
| WO | WO2007/019301 A2 | 2/2007 | |
| WO | WO2008/006028 A2 | 1/2008 | |
| WO | WO2008/070859 A2 | 6/2008 | |
| WO | WO2010/053572 A2 | 5/2010 | |
| WO | WO2010/075424 A2 | 7/2010 | |
| WO | WO2010/144740 A1 | 12/2010 | |
| WO | WO2011/036640 A2 | 3/2011 | |
| WO | WO2011/126808 A2 | 10/2011 | |
| WO | 2011/146121 A1 | 11/2011 | |
| WO | WO2011/141820 A1 | 11/2011 | |
| WO | WO2011/154427 A1 | 12/2011 | |
| WO | WO2012/136476 A1 | 10/2012 | |
| WO | WO2012/170930 A1 | 12/2012 | |
| WO | WO2013/049493 A1 | 4/2013 | |
| WO | WO2013/098244 A1 | 7/2013 | |
| WO | WO2013/143555 A1 | 10/2013 | |
| WO | WO2013/163628 A2 | 10/2013 | |
| WO | WO2013/176772 A1 | 11/2013 | |
| WO | WO2013/182683 A1 | 12/2013 | |
| WO | WO2014/018423 A2 | 1/2014 | |
| WO | 2014/043519 A1 | 3/2014 | |
| WO | WO2014/059255 A1 | 4/2014 | |
| WO | WO2014/065596 A1 | 5/2014 | |
| WO | WO2014/081855 A1 | 5/2014 | |
| WO | 2014/093622 A2 | 6/2014 | |
| WO | 2014/093712 A1 | 6/2014 | |
| WO | 2014/099744 A1 | 6/2014 | |
| WO | WO2014/089290 A1 | 6/2014 | |
| WO | WO2014/093479 A1 | 6/2014 | |
| WO | WO2014/093595 A1 | 6/2014 | |
| WO | WO2014/093655 A2 | 6/2014 | |
| WO | WO2014/093661 A2 | 6/2014 | |
| WO | WO2014/093709 A1 | 6/2014 | |
| WO | WO2014/144288 A1 | 9/2014 | |
| WO | WO2014/144592 A2 | 9/2014 | |
| WO | WO2014/152432 A2 | 9/2014 | |
| WO | WO2014/172470 A2 | 10/2014 | |
| WO | WO2014/186585 A2 | 11/2014 | |
| WO | 2014/197568 A2 | 12/2014 | |
| WO | WO2014/191128 A1 | 12/2014 | |
| WO | WO2014/197748 A2 | 12/2014 | |
| WO | WO2014/204726 A1 | 12/2014 | |
| WO | WO2014/204728 A1 | 12/2014 | |
| WO | WO2015/006747 A2 | 1/2015 | |
| WO | 2015/021457 A2 | 2/2015 | |
| WO | WO2015/017519 A1 | 2/2015 | |
| WO | 2015/035139 A2 | 3/2015 | |
| WO | WO2015/035136 A2 | 3/2015 | |
| WO | WO2015/048690 A1 | 4/2015 | |
| WO | WO2015/070083 A1 | 5/2015 | |
| WO | 2015/089462 A1 | 6/2015 | |
| WO | WO2015/089419 A2 | 6/2015 | |
| WO | WO2015/089427 A1 | 6/2015 | |
| WO | WO2015/089465 A1 | 6/2015 | |
| WO | WO2015/089486 A2 | 6/2015 | |
| WO | WO2015/126927 A2 | 8/2015 | |
| WO | WO2015/155686 A2 | 10/2015 | |
| WO | WO2015/161276 A2 | 10/2015 | |
| WO | 2015/195621 A1 | 12/2015 | |
| WO | 2016/011080 A2 | 1/2016 | |
| WO | WO2016/011070 A2 | 1/2016 | |
| WO | WO2016/049258 A2 | 3/2016 | |

(56)                References Cited

FOREIGN PATENT DOCUMENTS

| | | | |
|---|---|---|---|
| WO | WO 2016/054326 A1 | 4/2016 |
| WO | WO2016/063264 A1 | 4/2016 |
| WO | WO2016/070070 A1 | 5/2016 |
| WO | WO2016/081924 A1 | 5/2016 |
| WO | WO2016/094880 A1 | 6/2016 |
| WO | WO2016/114972 A1 | 7/2016 |
| WO | WO2016/123578 A1 | 8/2016 |
| WO | WO2016/130600 A2 | 8/2016 |
| WO | WO2016/161380 A1 | 10/2016 |
| WO | WO 2016/182893 A1 | 11/2016 |
| WO | 2016/205613 A1 | 12/2016 |
| WO | WO2016/187717 A1 | 12/2016 |
| WO | WO2017/015637 A1 | 1/2017 |
| WO | 2017/016915 A1 | 2/2017 |
| WO | WO2017/035416 A2 | 3/2017 |
| WO | WO2017/049266 A2 | 3/2017 |
| WO | WO2017/049407 A1 | 3/2017 |
| WO | WO2017/066497 A2 | 4/2017 |
| WO | WO2017/070632 A2 | 4/2017 |
| WO | WO2017/072590 A1 | 5/2017 |
| WO | WO2017/075478 A2 | 5/2017 |
| WO | WO2017/095967 A2 | 6/2017 |
| WO | WO2017/139505 A2 | 8/2017 |
| WO | WO2017/165859 A1 | 9/2017 |
| WO | 2017/180976 A1 | 10/2017 |
| WO | WO2017/180915 A2 | 10/2017 |
| WO | WO2017/193029 A3 | 11/2017 |
| WO | 2018/005805 A1 | 1/2018 |
| WO | 2018/017483 A1 | 1/2018 |
| WO | WO2018/002812 A1 | 1/2018 |
| WO | WO 2018/013932 A1 | 1/2018 |
| WO | WO2018/017751 A1 | 1/2018 |
| WO | WO2018/017754 A1 | 1/2018 |
| WO | WO2018/031762 A1 | 2/2018 |
| WO | WO2018/035388 A1 | 2/2018 |
| WO | WO2018/035495 A1 | 2/2018 |
| WO | 2018/039145 A1 | 3/2018 |
| WO | WO2018/081504 A1 | 5/2018 |
| WO | WO2018/098480 A1 | 5/2018 |
| WO | 2018/107003 A1 | 6/2018 |
| WO | WO2018/129296 A1 | 7/2018 |
| WO | WO 2018/129486 A2 | 7/2018 |
| WO | WO2018/162702 A1 | 9/2018 |
| WO | 2018/179578 A1 | 10/2018 |
| WO | WO2018/191388 A1 | 10/2018 |
| WO | WO 2018/195073 A2 | 10/2018 |
| WO | 2019/009682 A2 | 1/2019 |
| WO | WO2019/002590 A1 | 1/2019 |
| WO | WO 2019/014230 A1 | 1/2019 |
| WO | WO2019/023291 A2 | 1/2019 |
| WO | WO 2019/036599 A1 | 2/2019 |
| WO | WO 2019/038776 A1 | 2/2019 |
| WO | 2019/046755 A1 | 3/2019 |
| WO | WO2019/067786 A1 | 4/2019 |
| WO | WO2019/077001 A1 | 4/2019 |
| WO | WO2019/079514 A1 | 4/2019 |
| WO | WO2019/084050 A1 | 5/2019 |
| WO | WO2019/092505 A1 | 5/2019 |
| WO | 2019/113472 A1 | 6/2019 |
| WO | WO 2019/120283 A1 | 6/2019 |
| WO | WO2019/123014 A1 | 6/2019 |
| WO | WO2019/136216 A1 | 7/2019 |
| WO | WO2019/144061 A1 | 7/2019 |
| WO | WO 2019/152609 A1 | 8/2019 |
| WO | 2019/204750 A1 | 10/2019 |
| WO | WO2019/213626 A1 | 11/2019 |
| WO | WO2019/232069 A1 | 12/2019 |
| WO | 2020/018918 A1 | 1/2020 |
| WO | 2020/079033 A1 | 4/2020 |
| WO | WO 2020/086881 A1 | 4/2020 |
| WO | 2020/101042 A1 | 5/2020 |
| WO | WO 2020/106916 A1 | 5/2020 |
| WO | WO2020/124257 A1 | 6/2020 |
| WO | WO 2020/132226 A1 | 6/2020 |
| WO | 2020/168133 A1 | 8/2020 |
| WO | WO2020/163396 A1 | 8/2020 |
| WO | WO2020/210776 A1 | 10/2020 |
| WO | WO2020/214613 A1 | 10/2020 |
| WO | WO2020/257665 A1 | 12/2020 |
| WO | WO2021/026516 A1 | 2/2021 |
| WO | WO2021/034984 A2 | 2/2021 |
| WO | WO2021/034987 A1 | 2/2021 |
| WO | WO2021/055956 A1 | 3/2021 |
| WO | 2021/076744 A1 | 4/2021 |
| WO | WO2021/067878 A1 | 4/2021 |
| WO | WO2021/113536 A1 | 6/2021 |
| WO | PCT/US2021/054292 | 10/2021 |
| WO | PCT/US2021/054636 | 10/2021 |
| WO | PCT/US2021/056122 | 10/2021 |
| WO | PCT/US2021/059270 | 11/2021 |
| WO | WO2021/222268 A1 | 11/2021 |
| WO | WO2021/222314 A1 | 11/2021 |
| WO | WO2021/222327 A1 | 11/2021 |
| WO | WO2021/222328 A1 | 11/2021 |
| WO | WO2021/226555 A2 | 11/2021 |
| WO | 2022/038264 A1 | 2/2022 |
| WO | PCT/US2022/018400 | 3/2022 |
| WO | WO 2022/055946 A1 | 3/2022 |
| WO | 2022/104159 A1 | 5/2022 |
| WO | WO 2022/103935 A1 | 5/2022 |
| WO | 2022/133062 A1 | 6/2022 |
| WO | WO2022/187288 A2 | 9/2022 |
| WO | WO 2023/283631 A2 | 1/2023 |
| WO | WO 2023/010133 A2 | 2/2023 |
| WO | WO 2023/137471 A1 | 7/2023 |
| WO | WO 2023/137472 A2 | 7/2023 |
| WO | 2023/164670 A2 | 8/2023 |
| WO | 2023/164671 A2 | 8/2023 |
| WO | PCT/US2023/072524 | 8/2023 |
| WO | PCT/US2023/076920 | 10/2023 |
| WO | PCT/US2023/078124 | 10/2023 |
| WO | WO2023/200998 A2 | 10/2023 |
| WO | WO 2024/015881 A2 | 1/2024 |
| WO | WO2024/040253 A1 | 2/2024 |
| WO | WO 2024/064642 A2 | 3/2024 |
| WO | PCT/US2024/025594 | 4/2024 |
| WO | WO2024/081937 A1 | 4/2024 |
| WO | 2024/092258 A2 | 5/2024 |
| WO | WO 2024/040254 A3 | 5/2024 |
| WO | WO 2024/220947 A2 | 10/2024 |
| WO | 2024/229292 A2 | 11/2024 |
| WO | WO 2025/038982 A2 | 2/2025 |
| WO | WO 2025/049903 A2 | 3/2025 |
| WO | WO 2025/117868 A2 | 6/2025 |

OTHER PUBLICATIONS

U.S. Appl. No. 63/325,037, filed Mar. 29, 2022.
U.S. Appl. No. 63/325,039, filed Mar. 29, 2022.
U.S. Appl. No. 63/330,679, filed Apr. 13, 2022.
U.S. Appl. No. 63/372,373, filed Mar. 8, 2022.
U.S. Appl. No. 63/330,691, filed Apr. 13, 2022.
U.S. Appl. No. 17/471,935, filed Sep. 10, 2021, 2022/0098561, Mar. 31, 2022.
U.S. Appl. No. 17/603,243, filed Oct. 12, 2021.
U.S. Appl. No. 17/603,329, filed Oct. 12, 2021.
U.S. Appl. No. 17/603,330, filed Oct. 12, 2021.
Colombian Patent Office Action for Application No. NC2021/0013692 dated Mar. 14, 2024 (24 pages, English translation included).
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/ll2rg-/-mice" Nat Biotechnol., 2007, 25(8): 903-910.
Bhakta et al., "The generation of zinc finger proteins by modular assembly," Methods Mol. Biol., 2010, 649: 3-30.

(56) References Cited

OTHER PUBLICATIONS

Bloomfield, "Quasi-Elastic Light Scattering Applications in Biochemistry and Biology," Ann. Rev. Biophys. Bioeng., 1981, 10: 421-450.

Boris-Lawrie et al., "Recent advances in retrovirus vector technology," Cur. Opin. Genet. Develop., 1993, 3: 102-109.

Bouhairie et al., "Familial hypercholesterolemia," Cardiol. Clin., 2015, 33(2): 169-179.

Braliou et al., "The v-ErbA oncoprotein quenches the activity of an erythroid-specific enhancer," Oncogene, 2001, 20(7): 775-87.

Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.

Broude et al., "p21 (CDKN1A) is a negative regulator of p53 stability," Cell Cycle, 2007, 6(12): 1468-1471.

Buckingham, M. et al. "The role of Pax genes in the development of tissues and organs: Pax3 and Pax7 regulate muscle progenitor cell functions." Annu. Rev. Cell Dev. Biol. 23 (2007): 645-673.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.

Cano-Rodriguez et al., "Epigenetic Editing: On the Verge of Reprogramming Gene Expression at Will," Curr Genet Med Rep, 2016, 4: 170-179.

Carlens et al., "Ex vivo T lymphocyte expansion for retroviral transduction: influence of serum-free media on variations in cell expansion rates and lymphocyte subset distribution," Exp Hematol, 2000, 28(10): 1137-46.

Cavalieri et al., "Human T lymphocytes transduced by lentiviral vectors in the absence of TCR activation maintain an intact immune competence," Blood, 2003, 102(2): 497-505.

Aubert et al. "553. AAV-Mediated Delivery of HSV-Specific Homing Endonucleases To Neurons of the Trigeminal Ganglia for HSV-1 Inhibition." Molecular Therapy 22 (2014).

Chen et al., "Fusion protein linkers: property, design and functionality," Adv. Drug Deliv. Rev., 2013, 65(10): 1357-1369.

Chicaybam et al., "An efficient low cost method for gene transfer to T lymphocytes," PLoS One, 2013, 8(3): e60298, 11 pages.

Chylinski et al., "The tracrRNA and Cas9 families of type II CRISPR-Cas immunity systems," RNA Biol., 2013, 10(5): 726-737.

Cooper et al., "T-cell clones can be rendered specific for CD19: toward the selective augmentation of the graft-versus-B-lineage leukemia effect," Blood, 2003, 101(4): 1637-1644.

Cortes-Mancera et al., "Gene-Targeted DNA Methylation: Towards Long-Lasting Reprogramming of Gene Expression?" Adv Exp Med Biol., 2022, 1389: 515-533.

Das et al., "Tet-On Systems For Doxycycline-inducible Gene Expression," Current Gene Therapy, 2016, 16: 156-167.

Defesche et al., "Familial hypercholesterolaemia," Nat. Rev. Dis. Primers, 2017, 3: 17093, 20 pages.

Deng et al., "Highly sensitive electrochemical methyltransferase activity assay," Anal Chem., 2014, 86: 2117-2123.

Fuks, "DNA methylation and histone modifications: teaming up to silence genes," Current Opinion in Genetics & Development, 2005, 15(5): 490-495.

Gersbach et al., "Synthetic zinc finger proteins: the advent of targeted gene regulation and genome modification technologies," Acc. Chem. Res., 2014, 47(8): 2309-18.

Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.

Gowher et al., "Molecular enzymology of the catalytic domains of the Dnmt3a and Dnmt3b DNA methyltransferases," J. Biol. Chem., 2002, 277(23): 20409-20414.

Hochstrasser et al., "CasA mediates Cas3-catalyzed target degradation during CRISPR RNA-guided interference," PNAS, 2014, 111(18): 6618-23.

Huang et al., "Ch 9: DNA transposons for modification of human primary T lymphocytes," Methods Mol Biol, 2009, 506: 115-126.

Jia et al., "Structure of Dnmt3a bound to Dnmt3L suggests a model for de novo DNA methylation," Nature, 2007, 449(7159): 248-251.

Johnston, "Biolistic transformation: microbes to mice," Nature, 1990, 346: 776-777.

Kao et al., "Ectopic DNMT3L triggers assembly of a repressive complex for retroviral silencing in somatic cells," J Virol., 2014, 88(18): 10680-95.

Kim et al., "Zinc-fingers and homeoboxes 1 (ZHX1) binds DNA methyltransferase (DNMT) 3B to enhance DNMT3B-mediated transcriptional repression," Biochemical and Biophysical Research Communications, 2007, 355(2): 318-323.

Koste et al., "T-cell receptor transfer into human T cells with ecotropic retroviral vectors," Gene Ther, 2014, 21(5): 533-538.

Lagace, "PCSK9 and LDLR degradation: regulatory mechanisms in circulation and in cells," Curr. Opin. Lipidol., 2014, 25(5): 387-393.

Lei et al., "Targeted DNA methylation in vivo using an engineered dCas9-MQ1 fusion protein," Nat. Commun, 2017, 8: 16026, 10 pages.

Li et al., "Development of fluorescent methods for DNA methyltransferase assay," Methods Appl. Fluoresc., 2017, 5: 012002, 8 pages.

Li et al., "The histone methyltransferase SETDB1 and the DNA methyltransferase DNMT3A interact directly and localize to promoters silenced in cancer cells," J. Biol. Chem., 2006, 281(28): 19489-19500.

Liu et al., "Design of polydactyl zinc-finger proteins for unique addressing within complex genomes," PNAS, 1997, 94(11): 5525-5530.

Ma et al., "Pol III Promoters to Express Small RNAs: Delineation of Transcription Initiation," Molecular Therapy—Nucleic Acids, 2014, 3: e161, 11 pages.

Makarova et al., "Annotation and Classification of CRISPR-Cas Systems," Methods Mol. Biol, 2015, 1311: 47-75.

Manuri et al., "piggyBac transposon/transposase system to generate CD19-specific T cells for the treatment of B-lineage malignancies," Hum Gene Ther, 2010, 21(4): 427-437.

Mavrothalassitis et al., "Proteins of the ETS family with transcriptional repressor activity," Oncogene, 2000, 19: 6524-6532.

Miller et al., "Improved retroviral vectors for gene transfer and expression," BioTechniques, 1989, 7(9): 980-990.

Miller, "Retrovirus packaging cells," Human Gene Therapy, 1990, 1: 5-14.

Milone et al., "Clinical use of lentiviral vectors," Leukemia, 2018, 32(7): 1529-1541.

Mok et al., "Stabilized plasmid-lipid particles: factors influencing plasmid entrapment and transfection properties," Biochimica et Biophysica Acta, 1999, 1419(2): 137-150.

Moon et al., "Recent advances in the CRISPR genome editing tool set," Exp. Mol. Med., 2019, 51(11): 130, 11 pages.

Moussa et al., "Here to stay: Writing lasting epigenetic memories," Cell, 2021, 184(9): 2281-2283.

Murphy et al., "The Transcriptional Repressive Activity of KRAB Zinc Finger Proteins Does Not Correlate with Their Ability to Recruit TRIM28," PLoS One, 2016, 11(9): e0163555, 19 pages.

O'Geen et al., "Determinants of heritable gene silencing for KRAB-dCas9 + DNMT3 and Ezh2-dCas9 + DNMT3 hit-and-run epigenome editing," Nucleic Acids Res, 2022, 50(6): 3239-3253.

Orth et al., "Structural basis of gene regulation by the tetracycline inducible Tet repressor-operator system," natural structural biology, 2000, 7(3): 215-219.

Park et al., "Treating cancer with genetically engineered T cells," Trends Biotechnol, 2011, 29(11): 550-557.

Peterson et al., "PCSK9 function and physiology," J. Lipid Res., 2008, 49(6): 1152-1156.

Pickar-Oliver et al., "The next generation of CRISPR-Cas technologies and applications," Nature Reviews Molecular Cell Biology, 2019, 20(8): 490-507.

Poh et al., "DNA Methyltransferase Activity Assays: Advances and Challenges," Theranostics, 2016, 6(3): 369-391.

(56) References Cited

OTHER PUBLICATIONS

Poirier et al., "The proprotein convertase PCSK9 induces the degradation of low density lipoprotein receptor (LDLR) and its closest family members VLDLR and ApoER2" J. Biol. Chem., 2008, 283: 2363-2372.

Policarpi et al., "Epigenetic editing: Dissecting chromatin function in context," Bioessays, 2021, 43(5): e2000316, 16 pages.

Saha et al., "The NIH Somatic Cell Genome Editing program," Nature, 2021, 592: 195-204.

Scarpa et al., "Characterization of recombinant helper retroviruses from moloney-based vectors in ecotropic and amphotropic packaging cell lines," Virology, 1991, 180: 849-852.

Schellenberger et al., "A recombinant polypeptide extends the in vivo half-life of peptides and proteins in a tunable manner," Nature Biotechnology, 2009, 27(12): 1186-1190.

Sharma et al., "Efficient Sleeping Beauty DNA Transposition From DNA Minicircles," Molec Ther Nucl Acids, 2013, 2(2): e74, 10 pages.

Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.

Thakore et al., "385. Inhibiting the Myostatin Signaling Pathway using CRISPR/Cas9-Based Repressors." Molecular Therapy 2016, 24: S153.

Tycko et al., "High-Throughput Discovery and Characterization of Human Transcriptional Effectors," Cell, 2020, 183(7): 2020-2035.

Van Tedeloo et al., "High-level transgene expression in primary human T lymphocytes and adult bone marrow CD34+ cells via electroporation-mediated gene delivery," Gene Therapy, 2000, 7(16): 1431-1437.

Verhoeyen et al., "Ch 8: Lentiviral vector gene transfer into human T cells," Methods Mol Biol, 2009, 506: 97-114.

Wang et al., "Phenotypic and functional attributes of lentivirus modified CD19-specific human CD8+ central memory T cells manufactured at clinical scale," J. Immunother, 2012, 35(9): 689-701.

Wright et al., "Rational design of a split-Cas9 enzyme complex," PNAS, 2015, 112(10): 2984-2989.

Wright et al., "Standardized reagents and protocols for engineering zinc finger nucleases by modular assembly," Nat. Protoc., 2006, 1(3): 1637-1652.

Zetsche et al., "A split-Cas9 architecture for inducible genome editing and transcription modulation," Nat. Biotechnol, 2015, 33(2): 139-142.

Chilean Patent Office Action for Application No. 202102680 dated Dec. 18, 2023 (14 pages, English statement of relevance included).

Echevarria et al., "Exon-skipping advances for Duchenne muscular dystrophy," Human Molecular Genetics, 2018, 27(R2): R163-R172.

Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.

Ryu et al., "Adenine base editing in mouse embryos and an adult mouse model of Duchenne muscular dystrophy," Nature Biotechnology, 2018, 36(6): 536-539.

Rees et al., "Base editing: precision chemistry on the genome and transcriptome of living cells," Nature Reviews Genetics, 2018, 19(12): 770-788.

Nelson et al., "Long-term evaluation of genome editing for Duchenne muscular dystrophy," Duke Presentation, 2019, 123 pages. Retrieved from the Internet: <https://static.seekingalpha.com/uploads/sa_presentations/453/41453/original.pdf>.

Young, "Development of a Therapeutic CRISPR/Cas9 Plataform for Duchenne Muscular Dystrophy," UCLA Electronic Theses and Dissertations, Jan. 1, 2018, 136 pages.

Kwon et al., "In Vivo Gene Editing of Muscle Stem Cells with Adeno-Associated Viral Vectors in a Mouse Model of Duchenne Muscular Dystrophy," Molecular Therapy, 2020, 19: 320-329.

Chinese Patent Office Action for Application No. 202080028248.2 dated Dec. 29, 2023 (29 pages, English translation included).

United States Patent Office Action for U.S. Appl. No. 16/098,464 dated Feb. 12, 2024 (16 pages).

United States Patent Office Action for U.S. Appl. No. 15/779,633 dated Mar. 7, 2024 (5 pages).

United States Patent Office Corrected Notice of Allowance for U.S. Appl. No. 16/318,715 dated Mar. 27, 2024 (2 pages).

Prykhozhij et al., "CRISPR MultiTargeter: A Web Tool to Find Common and Unique CRISPR Single Guide RNA Targets in a Set of Similar Sequences," PLoS One, 2015, 10(3): e011932.

United States Patent Office Action for U.S. Appl. No. 15/779,633 dated Jun. 3, 2022 (15 pages).

Chilean Patent Office Examination Report for Application No. 202102680 dated Jun. 12, 2023 (19 pages, English language summary of objections included).

Chao et al., "Several log increase in therapeutic transgene delivery by distinct adeno-associated viral serotype vectors," (2000) Molecular Therapy 2:619.

Chen et al., "In vivo CD8+ T cell CRISPR screening reveals control by Fli1 in infection and cancer," Cell, 2021, 184(5): 1262-1280.

Corces et al., "An improved ATAC-seq protocol reduces background and enables interrogation of frozen tissues," Nature Methods. 2017, 14: 959-962.

Galletti et al., "Two subsets of stem-like CD8+ memory T cell progenitors with distinct fate commitments in humans," Nature Immunology, 2020, 21: 1552-1562.

Gao et al., "Clades of Adeno-Associated Viruses Are Widely Disseminated in Human Tissues," (2004) J. Virology 78:6381-6388.

GenBank Accession No. AF028704.1, (1998).

GenBank Accession No. AF028705.1, (1998).

GenBank Accession No. AF043303.1, (2010).

GenBank Accession No. AF063497.1, (1999).

GenBank Accession No. AF288061.1, (2001).

GenBank Accession No. AF513851.1, (2002).

GenBank Accession No. AFS13852.1, (2015).

GenBank Accession No. AH009962.2, (2016).

GenBank Accession No. AY028223.1, (2001).

GenBank Accession No. AY028226.1, (2001).

GenBank Accession No. AY530579.1, (2004).

GenBank Accession No. J01901.1, (1993).

GenBank Accession No. J02275.1, (1995).

GenBank Accession No. NC_000883.2, (2018).

GenBank Accession No. NC_001358.1, (2015).

GenBank Accession No. NC_001401, (2018).

GenBank Accession No. NC_001510.1, (2018).

GenBank Accession No. NC_001540.1, (2018).

GenBank Accession No. NC_001701.1, (2018).

GenBank Accession No. NC_001729, (2018).

GenBank Accession No. NC_001829.1, (2018).

GenBank Accession No. NC_001862.1, (2004).

GenBank Accession No. NC_001863.1, (2004).

GenBank Accession No. NC_002077, (2018).

GenBank Accession No. NC_006152.1, (2018).

GenBank Accession No. NC_006261.1, (2018).

GenBank Accession No. U89790.1, (1997).

GenBank Accession No. X01457.1, (2005).

Hao et al., "Integrated analysis of multimodal single-cell data," Cell, 2021, 184: 3573-3587.e29.

Hart et al., "Kruppel-like factors in lymphocyte biology," J Immunol, 2012, 188(2): 521-526.

Joung et al., "Transcription Factor Atlas of Directed Differentiation," Cell, 2023, 186(1): 209-229.e26.

Jung et al. "BLIMP1 and NR4A3 transcription factors reciprocally regulate antitumor CAR T cell stemness and exhaustion," Cancer Immunotherapy, 2022, 14: eabn7336.

Kaminskiy et al., "Neglected, yet significant role of FOXP1 in T-cell quiescence, differentiation and exhaustion," Front. Immunol, 2022, 13: 971045.

Krishna et al., "Stem-like CD8 T cells mediate response of adoptive cell immunotherapy against human cancer," Science, 2020, 370: 1328-1334.

Kuleshov et al., "Enrichr: a comprehensive gene set enrichment analysis web server 2016 update," Nucleic Acids Research, 2016, 44: 90-97.

(56) References Cited

OTHER PUBLICATIONS

Liao et al., "featureCounts: an efficient general purpose program for assigning sequence reads to genomic features," Bioinformatics, 2013, 30(7): 923-30.

Martin et al., "CCR7 Deficiency in NOD Mice Leads to Thyroiditis and Primary Hyperthyroidism," The Journal of Immunology, 2009, 183(5): 3073-3080.

Mimitou et al., "Expanding the CITE-seq tool-kit: Detection of proteins, transcriptomes, clonotypes and CRISPR perturbations with multiplexing, in a single assay," Nat. Methods, 2019, 16: 409-412.

Mori et al., "Two novel adeno-associated viruses from cynomolgus monkey: pseudotyping characterization of capsid protein," (2004) Virology 330: 375-383.

Muzyczka, "Use of adeno-associated virus as a general transduction vector for mammalian cells," (1992) Curr. Topics Microbial. Immunol. 158: 97-129.

Philip et al., "Chromatin states define tumour-specific T cell dysfunction and reprogramming," Nature, 2017, 545: 452-456.

Pritykin et al., "A unified atlas of CD8 T cell dysfunctional states in cancer and infection," Mol. Cell 2021, 81: 2477-2493.

Ramirez et al., "deepTools: a flexible platform for exploring deep-sequencing data," Nucleic Acids Research, 2014, 42:W187-91.

Schubert et al., "Autosomal dominant immune dysregulation syndrome in humans with CTLA4 mutations," Nature Medicine, 2014, 20(2): 1410-1416.

Sen et al., "The epigenetic landscape of T cell exhaustion," Science, 2016, 354(6316): 1165-1169.

Vojta et al., "Repurposing the CRISPR-Cas9 system for targeted DNA methylation," Nucleic Acids Research, 2016, 44(12): 5615-5628.

Wherry et al., "Molecular Signature of CD8+ T Cell Exhaustion during Chronic Viral Infection," Immunity, 2007, 27(4): 670-684.

Woolf et al., "Runx3 and Runx1 are required for CD8 T cell development during thymopoiesis," PNAS, 2003, 100(13): 7731-7736.

Yang et al., "The transcriptional regulators Id2 and Id3 control the formation of distinct memory CD8+ T cell subsets," Nat Immunol, 2011, 12: 1221-1229.

Yu et al., "ChIPseeker: an R/Bioconductor package for ChIP peak annotation, comparison and visualization," Bioinformatics, 2015, 31(14): 2382-2383.

Yuan et al., "Genetic Modulation of RNA Splicing with a CRISPR-Guided Cytidine Deaminase," Molecular Cell, 2018, 72(2): 380-394.

Zhang et al., "Model-based analysis of ChIP-Seq (MACS)," Genome Biology, 2008, 9(9): R137.

Zheng et al., "Landscape of Infiltrating T Cells in Liver Cancer Revealed by Single-Cell Sequencing," Cell, 2017, 169: 1342-1356.

Egypt Patent Office Action for Application No. PCT 1599/2021 dated Feb. 12, 2024 (8 pages, English translation included).

Japanese Patent Office Action for Application No. 2021-560849 dated Apr. 2, 2024 (4 pages, English translation included).

Kuwait Patent Office Examination Report for Application No. KW/P/2021/000417 dated May 8, 2024 (5 pages).

United States Patent Office Notice of Allowance for U.S. Appl. No. 15/779,633 dated May 22, 2024 (8 pages).

Adamson et al., "A Multiplexed Single-Cell CRISPR Screening Platform Enables Systematic Dissection of the Unfolded Protein Response," Cell, 2016, 167: 1867-1882.e21.

Aloia, "Epigenetic Regulation of Cell-Fate Changes That Determine Adult Liver Regeneration After Injury," Front. Cell Dev. Biol., 2021, 9: 643055.

Amabile et al., "Inheritable Silencing of Endogenous Genes by Hit-and-Run Targeted Epigenetic Editing," Cell, 2016, 167(1): 219-232.e14.

Amabile et al., "Permanent Epigenetic Silencing of Human Genes With Artificial Transcriptional Repressors,", Molecular Therapy, 2015, 23(Suppl. 1): S275.

Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.

Asrani et al., "Burden of liver diseases in the world," J Hepatol, 2019, 70(1): 151-171.

Baratta et al., "Cellular organization of normal mouse liver: a histological, quantitative immunocytochemical, and fine structural analysis," Histochem Cell Biol, 2009, 131(6): 713-726.

Barrangou et al., "CRISPR provides acquired resistance against viruses in prokaryotes," Science, 2007, 315(5819): 1709-1712.

Bartel et al., "Isolation of new ribozymes from a large pool of random sequences," Science, 1993, 261(5127): 1411-1418.

Beaudry et al., "Directed evolution of an RNA enzyme," Science, 1992, 257(5070): 635-641.

Bieth et al., "Highly restricted deletion of the SNORD116 region is implicated in Prader-Willi Syndrome," Eur J Hum Genet, 2015, 23: 252-255.

Bittel et al., "Prader-Willi syndrome: clinical genetics, cytogenetics and molecular biology," Expert Rev Mol Med, 2005, 7(14): 1-20.

Blakemore et al., "Editing of Human Genes May Begin by Year's End in the U.S." Smithsonian.com, <https://www.smithsonianmag.com/smart-news/editing-human-genes-may-begin-years-end-us-180959532/?no-ist> 2016.

Blancafort et al., "Writing and rewriting the epigenetic code of cancer cells: from engineered proteins to small molecules," Mol. Pharmacol., 2013, 83(3): 563-576.

Braasch et al., "Novel Antisense and Peptide Nucleic Acid Strategies for Controlling Gene Expression," Biochemistry, 2002, 41: 4503-4510.

Breaker et al., "Inventing and improving ribozyme function rational design versus iterative selection methods," TIBTECH, 1994, 12: 268-274.

Breaker, "Are engineered proteins getting competition from RNA?," Curr. Op. Biotech., 1996, 7(4): 442-448.

Briner et al., "Guide RNA Functional Modules Direct Cas9 Activity and Orthogonality," Molecular Cell, 2014, 56(2): 333-339.

Briner et al., "Lactobacillus buchneri genotyping on the basis of clustered regularly interspaced short palindromic repeat (CRISPR) locus diversity," Appl. Environ. Microbiol., 2014, 80: 994-1001.

Brummelkamp et al., "A system for stable expression of short interfering RNAs in mammalian cells," Science, 2002, 296(5567): 550-553.

Buiting, "Prader-Willi syndrome and Angelman syndrome," Am J Med Genet C Semin Med Genet, 2010, 154C(3): 365-376.

Burnett et al., "Deficiency in prohormone convertase PC1 impairs prohormone processing in Prader-Willi syndrome," J Clin Invest, 2017, 127: 293-305.

Cano-Rodriguez et al., "Writing of H3K4Me3 overcomes epigenetic silencing in a sustained but context-dependent manner," Nat Commun, 2016, 7: 12284.

Carroll, "A CRISPR approach to gene targeting," Molecular Therapy, 2012, 20: 1658-1660.

Cassidy et al., "Prader-Willi syndrome," Eur J Hum Genet, 2009, 17(1): 3-13.

Cassidy et al., "Prader-Willi syndrome," Genet Med, 2012, 14: 10-26.

Cencic et al., "Protospacer adjacent motif (PAM)-distal sequences engage CRISPR Cas9 DNA target cleavage," PLoS one, 2014, 9, e109213, 13 pages.

Chang et al., "Integrating Combinatorial Lipid Nanoparticle and Chemically Modified Protein for Intracellular Delivery and Genome Editing," Acc. Chem. Res., 2019, 52: 665-675.

Chen et al., "Acetylation of RelA at discrete sites regulates distinct nuclear functions of NF-kB," The EMBO Journal, 2002, 21(23): 6539-6548.

Chen et al., "Genome-wide CRISPR screen in a mouse model of tumor growth and metastasis," Cell, 2015, 160: 1246-1260.

Chen et al., "Targeted activation of diverse CRISPR-Cas systems for mammalian genome editing via proximal CRISPR targeting," Nature Communications, 2017, 8: 14958.

(56)     References Cited

OTHER PUBLICATIONS

Chen et al., "Vitamin D receptor suppresses proliferation and metastasis in renal cell carcinoma cell lines via regulating the expression of the epithelial Ca2+ channel TRPV5," PLoS One, 2018, 13: e0195844.

Christoffersen et al., "Ribozymes as human therapeutic agents," J. Med. Chem., 1995, 38(12): 2023-2037.

Concise Encyclopedia of Polymer Science And Engineering, 1990, pp. 858-859.

Corces et al., "The chromatin accessibility landscape of primary human cancers," Science, 2018, 362(6413): eaav1898.

Crooke et al., "Pharmacokinetic properties of several novel oligonucleotide analogs in mice," J. Pharmacol. Exp. Ther., 1996, 277(2): 923-937.

Cruvinel et al., "Reactivation of maternal SNORD116 cluster via SETDB1 knockdown in Prader-Willi syndrome iPSCs," Hum Mol Genet, 2014, 23: 4674-4685.

Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.

Datlinger et al., "Pooled CRISPR screening with single-cell transcriptome readout," Nat. Methods, 2017, 14: 297-301.

De Mesmaeker et al., "Antisense Oligonucleotides," Ace. Chem. Res., 1995, 28: 366-374.

De Smith et al., "A deletion of the HBII-85 class of small nucleolar RNAs (snoRNAs) is associated with hyperphagia, obesity and hypogonadism," Hum Mol Genet, 2009, 18: 3257-3265.

Dempster et al., "Extracting Biological Insights from the Project Achilles Genome-Scale CRISPR Screens in Cancer Cell Lines," Cold Spring Harbor Laboratory, 2019, 35 pages.

Diao et al., "A new class of temporarily phenotypic enhancers identified by CRISPR/Cas9-mediated genetic screening," Genome Res, 2016, 26: 397-405.

Dirks et al., "Triggered amplification by hybridization chain reaction," Proceedings of the National Academy of Sciences of the United States of America, 2004, 101(43): 15275-15278.

Dixit et al., "Perturb-Seq: Dissecting Molecular Circuits with Scalable Single-Cell RNA Profiling of Pooled Genetic Screens," Cell, 2016, 167: 1853-1866.e17.

Duan et al., "Genome-wide identification of CRISPR/Cas9 off-targets in human genome," Cell research, 2014, 24(8): 1009-12.

Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.

Dykeman, "An implementation of the Gillespie algorithm for RNA kinetics with logarithmic time update," Nucleic Acids Research, 2015, 45(12): 5708-5715.

Englisch et al., Chemically Modified Oligonucleotides as Probes and Inhibitors, Angewandle Chemie, International Edition, 1991, 30(6): 613-629.

Eraslan et al., "Deep learning: new computational modelling techniques for genomics," Nat. Rev. Genet., 2019, 20: 389-403.

Farasat et al., "A Biophysical Model of CRISPR/Cas9 Activity for Rational Design of Genome Editing and Gene Regulation," PLOS Computational Biology, 2016, 12(1):e1004724.

Farasat, "Sequence-to-Function Models for Efficient Optimization of Metabolic Pathways and Genetic Circuits," Ph. D. Thesis, 2015, 254 pages.

Flamm et al., "RNA folding at elementary step resolution," Rna, 2000, 6: 325-338.

Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.

Frank et al., "HDAC inhibitors cause site-specific chromatin remodeling at PU.1-bound enhancers in K562 cells," Epigenetics Chromatin, 2016, 9: 15.

Fu et al., "Landscape of target: guide homology effects on Cas9-mediated cleavage," Nucleic Acids Research, 2014, 42(22): 13778-13787.

Fulco et al., "Activity-by-contact model of enhancer-promoter regulation from thousands of CRISPR perturbations," Nature Genetics, 2019, 51: 1664-1669.

Fulco et al., "Systematic mapping of functional enhancer-promoter connections with CRISPR interference," Science, 2016, 354: 769-773.

Fulmer-Smentek et al., "Association of acetylated histones with paternally expressed genes in the Prader-Willi deletion region," Hum Mol Genet, 2001, 10: 645-652.

Gait, "Oligoribonucleotides," Antisense Research and Applications, 1993, Chapter 16, pp. 290-299.

Gasiunas et al., "Cas9-crRNA ribonucleoprotein complex mediates specific DNA cleavage for adaptive immunity in bacteria," Proc. Natl. Acad. Sci., 2012, 109: E2579-E2586.

Gasperini et al., "A Genome-wide Framework for Mapping Gene Regulation via Cellular Genetic Screens," Cell, 2018, 176(1-2); 377-390.e19.

Gaudelli et al., "Directed evolution of adenine base editors with increased activity and therapeutic application," Nat Biotechnol, Jul. 2020, 38(7): 892-900.

Gaudelli et al., "Programmable base editing of A•T to G•C in genomic DNA without DNA cleavage," Nature, Nov. 2017, 551(7681): 464-471.

Gebeyehu et al., "Novel biotinylated nucleotide—analogs for labeling and colorimetric detection of DNA," Nucl. Acids Res., 1987, 15(11): 4513-4534.

Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.

Gemberling et al., "Transgenic mice for in vivo epigenome editing with CRISPR-based systems," Nat Methods, 2021, 18(8): 965-974.

Genbank Accenssion AP006627.1 (2016).

Genbank Accenssion BA000004.3 (2016).

Genbank Accenssion BAB04055.1 (2016).

GenBank Accession No. AAC75803.1 (2018).

GenBank Accession No. AIN33136.1 (2014).

GenBank Accession No. BAB04055.1 (2017).

GenBank Accession No. EOT14076.1 (2013).

GenBank Accession No. AK019325 (2010).

GenBank Accession No. BB730912 (2001).

GenBank Accession No. BC010291 (2006).

GenBank Accession No. BC026642.1 (2007).

GenBank Accession No. BI143915 (2011).

GenBank Accession No. NM_020562.1 (2004).

GenBank P38036.2 (2013).

Ghisletti et al., "Identification and characterization of enhancers controlling the inflammatory gene expression program in macrophages," Immunity, 2010, 32: 317-328.

Gibson et al., "Enzymatic assembly of DNA molecules up to several hundred kilobases," Nature Methods, 2009, 6(5): 343-345.

Gillespie, "A general method for numerically simulating the stochastic time evolution of coupled chemical reactions," Journal of computational physics, 1976, 22: 403-434.

Gomaa et al., "Programmable Removal of Bacterial Strains by Use of Genome-Targeting CRISPR-Cas Systems," 2014, mBio 5(1): e00928-13.

Gonda "Aerosols for delivery of therapeutic and diagnostic agents to the respiratory tract," Critical Reviews in Therapeutic Drug Carrier Systems, 1990 6:273-313.

Gong et al., "Molecular insights into DNA interference by CRISPR-associated nuclease-helicase Cas3," Proc Natl Acad Sci U S A, 2014, 111(46):16359-64.

Gray et al., "G quadruplexes are genomewide targets of transcriptional helicases XPB and XPD," Nat. Chem. Biol, 2014, 10: 313-318.

Grissa et al., "CRISPRFinder: a web tool to identify clustered regularly interspaced short palindromic repeats," Nucleic Acids Res., 2007, 35(Web Server issue):W52-57.

Guo et al., "Directed evolution of an enhanced and highly efficient Fokl cleavage domain for zinc finger nucleases," J Mol Biol, 2010, 400: 96-107.

(56)     References Cited

OTHER PUBLICATIONS

Hacein-Bey-Abina et al., "LMO2-associated clonal T cell proliferation in two patients after gene therapy for SCID-X1," Science, 2003, 302: 415-419.

Hart et al., "High-Resolution CRISPR Screens Reveal Fitness Genes and Genotype-Specific Cancer Liabilities," Cell, 2015, 163: 1515-1526.

Hayward et al., "Whole-genome landscapes of major melanoma subtypes," Nature, 2017, 545: 175-180.

He et al., "Molecular Genetic Mechanisms of Hereditary Spherocytosis: Current Perspectives," Acta Haematol., 2018, 139: 60-66.

Heasman, "Morpholino oligos: making sense of antisense?," Dev. Biol., 2002, 243(2): 209-214.

Henikoff et al., "Amino acid substitution matrices from protein blocks," Proc. Natl. Acad. Sci. USA, 1992, 89: 10915-9.

Henning et al., "Epigenetic control of CD8 + T cell differentiation," Nat Rev Immunol, 2018, 18(5): 340-356.

Hori et al., "Simple and reproducible hepatectomy in the mouse using the clip technique," World J Gastroenterol, 2012, 18(22): 2767-2774.

Howarth et al., "A monovalent streptavidin with a single femtomolar biotin binding site," Nature methods, 2006, 3(4): 267-273.

Hsu et al., "Development and applications of CRISPR-Cas9 for genome engineering," Cell, 2014, 157(6): 1262-1278.

Huang et al., "Generation and comparison of CRISPR-Cas9 and Cre-mediated genetically engineered mouse models of sarcoma," Nature Communications, 2017, 8(15999): 1-11.

Huntriss et al., "Imprinted expression of SNRPN in human preimplantation embryos," Am J Hum Genet, 1998, 63: 1009-1014.

Jansen et al., "Identification of genes that are associated with DNA repeats in prokaryotes," Mol Microbiol, 2002, 43(6): 1565-1575.

Jeltsch et al., "Application of DNA methyltransferases in targeted DNA methylation," Appl. Microbiol. Biotechnol., 2007, 75(6): 1233-1240.

Jepsen et al., "Locked nucleic acid: a potent nucleic acid analog in therapeutics and biotechnology," Oligonucleotides, 2004, 14(2): 130-146.

Jiang et al., "A Cas9-guide RNA complex preorganized for target DNA recognition," Science, 2015, 348, 1477-1481.

Jiang et al., "RNA-guided editing of bacterial genomes using CRISPR-Cas systems," Nat. Biotechnol., 2013, 31:233-239.

Jimenez et al., "Activation of the beta-globin locus control region precedes commitment to the erythroid lineage," Proceedings of the National Academy of Sciences, 1992, 89: 10618-10622.

Jobling et al., "Chitayat-Hall and Schaaf-Yang syndromes:a common aetiology: expanding the phenotype of MAGEL2-related disorders," J Med Genet, 2018, 55: 316-321.

Josephs et al., "Structure and specificity of the RNA-guided endonuclease Cas9 during DNA interrogation, target binding and cleavage," Nucleic Acids Research, 2015, 43(18): 8924-8941.

Joyce, "Amplification, mutation and selection of catalytic RNA," Gene, 1989, 82(1): 83-87.

Joyce, "Directed molecular evolution," Scientific American, 1992, 267(6): 90-97.

Jurkowska and Jeltsch, "Silencing of Gene Expression by Targeted DNA Methylation: Concepts and Approaches," Methods Mol. Biol. 649, 2010, Chapter 9: 149-161.

Kabadi et al., "Engineering Synthetic TALE and CRISPR/Cas9 Transcription Factors for Regulating Gene Expression," Methods, 2014, 69(2): 188-197.

Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259: 327-330.

Karlin et al., "Applications and statistics for multiple high-scoring segments in molecular sequences," Proc. Natl. Acad. Sci. USA, 1993, 90: 5873-77.

Kauppinen et al., "Locked nucleic acid (LNA): High affinity targeting of RNA for diagnostics and therapeutics," Drug Discov Today Technol, 2005, 2(3): 287-290.

Kempfer et al., "Methods for mapping 3D chromosome architecture," Nat. Rev. Genet., 2020, 21: 207-226.

Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.

Khodakov et al., "Protected DNA strand displacement for enhanced single nucleotide discrimination in double-stranded DNA," Scientific reports, 2015, 5: 8721.

Khurana et al., "Role of non-coding sequence variants in cancer," Nat. Rev. Genet., 2016, 17: 93-108.

Kim et al., "Epigenetic therapy of Prader-Willi Syndrome," Transl Res, 2019, 208: 105-118.

Kim et al., "Histone acetylation contributes to chromatin looping between the locus control region and g]obin gene by influencing hypersensitive site formation," Biochim Biophys Acta, 2013, 1829: 963-969.

Kim et al., "Targeting the histone methyltransferase G9a activates imprinted genes and improves survival of a mouse model of Prader-Willi syndrome," Nat Med, 2017, 23: 213-222.

Kim et al., "Engineering and Application of Zinc Finger Proteins and TALEs for Biomedical Research," Mol Cells, 2017, 40(8): 533-541.

Klann et al., "Genome-wide annotation of gene regulatory elements linked to cell fitness," bioRxiv doi: 10.1101/2021.03.08.434470. Preprint posted Mar. 9, 2021, 42 pages.

Kleinstiver et al., "Engineered CRISPR-Cas9 nucleases with altered PAM specificities," Nature, 2015, 523(7561): 481-485.

Koblan et al., "Improving cytidine and adenine base editors by expression optimization and ancestral reconstruction," Oct. 2018, 36(9): 843-846.

Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.

Kocher et al., "Phylogenetic Analysis of the SNORD116 Locus," Genes, 2017, 8(12): 358.

Komor et al., "Programmable editing of a target base in genomic DNA without double-stranded DNA cleavage," Nature, 2016, 533(7603): 420-424.

Kornberg et al., "DNA Replication," 1980, pp. 75-77.

Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.

Kuhnel et al., "Tumor-specific adenoviral gene therapy: Transcriptional repression of gene expression by utilizing p53-signal transduction pathways," Cancer Gene Ther., 2004, 11: 28-40.

Kumar et al., "Artificial evolution and natural ribozymes," FASEB Journal, 1995, 9: 1183-1195.

Kurreck, "Antisense technologies. Improvement through novel chemical modifications," European Journal of Biochemistry, 2003, 270(8): 1628-1644.

Kwa et al., "Chromatin modifying agents—the cutting edge of anticancer therapy," Drug Discovery Today, 2011, 16(13/14):543-547.

Lacerra et al., "Restoration of hemoglobin A synthesis in erythroid cells from peripheral blood of thalassemic patients," Proc. Natl. Acad. Sci., 2000, 97(17): 9591-9596.

Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.

Langouet et al., "Zinc finger protein 274 regulates imprinted expression of transcripts in Prader-Willi syndrome neurons," Hum Mol Genet, 2018, 27: 505-515.

Laumont et al., "Noncoding regions are the main source of targetable tumor-specific antigens," Sci. Transl. Med., 2018, 10(470): eaau5516, 11 pages.

Lawrence et al., "Discovery and saturation analysis of cancer genes across 21 tumour types," Nature, 2014, 505: 495-501.

(56)        References Cited

OTHER PUBLICATIONS

Lee et al., "Expression of small interfering RNAs targeted against HIV-1 rev transcripts in human cells," Nature Biotechnol, 2002, 20(5): 500-505.

Lenoir et al., "Pickles: the database of pooled in-vitro CRISPR knockout library essentiality screens," Nucleic Acids Res, 2018, 46: D776-D780.

Lesnik et al., "Relative thermodynamic stability of DNA, RNA, and DNA: RNA hybrid duplexes: relationship with base composition and structure," Biochemistry, 1995, 34(34): 10807-10815.

Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.

Levin et al., "Position-dependent effects of locked nucleic acid (LNA) on DNA sequencing and PCR primers," Nuc. Acids. Res., 2006, 34: e142.

Levskaya et al., "Synthetic biology: engineering *Escherichia coli* to see light," Nature, 2005, 438:441-442.

Li et al., "Chimeric DNA methyltransferases target DNA methylation to specific DNA sequences and repress expression of target genes," Nucleic Acids Res., 2007, 35(1): 100-112.

Li et al., "Ex vivo cell-based CRISPR/Cas9 genome editing for therapeutic applications," Biomaterials, 2020, 234: 119711.

Li et al., "The autism-related gene SNRPN regulates cortical and spine development via controlling nuclear receptor Nr4a1," Sci Rep, 2016, 6: 29878.

Liao et al., "In Vivo Target Gene Activation via CRISPR/Cas9-Mediated Trans-epigenetic Modulation," Cell, 2017, 171: 1495-1507.

Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.

Liu et al., "Editing DNA Methylation in the Mammalian Genome," Cell, Sep. 2016, 167(1): 233-247.

Liu et al., "Monte Carlo simulation for single RNA unfolding by force," Biophysical journal, 2005, 88(1): 76-84.

Luo et al., "Repurposing endogenous type I CRISPR-Cas systems for programmable gene repression," Nucleic Acids Research, 2014, 43(1): 674-681.

Ma et al., "Targeted gene suppression by inducing de novo DNA methylation in the gene promoter," Epigenetics Chromatin, 2014, 7: 20.

Machinek et al., "Programmable energy landscapes for kinetic control of DNA strand displacement," Nature communications, 2014, 5: 5324, 9 pages.

MacPherson et al., "Flexible guide-RNA design for CRISPR applications using Protospacer Workbench," Nature biotechnology, 2015, 33(8): 805-806.

Mader et al., "CRISPR RNA-guided activation of endogenous human genes," Nature Methods, 2013, 10(10): 977-979.

Maeder et al., "Robust, synergistic regulation of human gene expression using TALE activators," Nat Methods, 2013, 10(3): 243-245.

Majzner et al., "Clinical lessons learned from the first leg of the CAR T cell journey," Nature Medicine, 2019, 25(9): 1341-1355.

Makarova et al., "An updated evolutionary classification of CRISPR-Cas systems," Nature Reviews Microbiology, 2015, 13:722-736.

Makarova et al., "Evolution and classification of the CRISPR-Cas systems," Nature Reviews Microbiology, 2011, pp. 467-477.

Manoharan et al., "Chemical Modifications to Improve Uptake and Bioavailability of Antisense Oligonucleotides," Ann. N. Y. Acad. Sci., 1992, 660: 306-309.

Manoharan et al., "Cholic acid-oligonucleotide conjugates for antisense applications," Bioorg. Med. Chem. Let., 1994, 4(8): 1053-1060.

Manoharan et al., "Introduction of a lipophilic thioether tether in the minor groove of nucleic acids for antisense applications," Bioorg. Med. Chem. Let., 1993, 3(12): 2765-2770.

Manoharan et al., "Lipidic Nucleic Acids," Tetrahedron Lett, 1995, 36: 3651-3654.

Manoharan et al., "Oligonucleotide Conjugates: Alteration of the Pharmacokinetic Properties of Antisense Agents," Nucleosides & Nucleotides, 1995, 14: 969-973.

Martin et al, "A New Access to 2'-O-Alkylated Ribonucleosides and Properties of 2'-O-Alkylated Oligoribonucleotides," Helv. Chim. Acta, 1995, 78: 486-504.

Mastellos et al., "Inducing and characterizing liver regeneration in mice: Reliable models, essential "readouts" and critical perspectives," Curr Protoc Mouse Biol., 2013, 3(3): 141-170.

Mathews et al., "Expanded sequence dependence of thermodynamic parameters improves prediction of RNA secondary structure," Journal of Molecular Biology, 1999, 288(5): 911-940.

Maurano et al., "Systematic localization of common disease-associated variation in regulatory DNA," Science, 2012, 337: 1190-1195.

Maxwell et al., "A detailed cell-free transcription-translation-based assay to decipher CRISPR protospacer-adjacent motifs," Methods, 2018, 143: 48-57.

McCarthy et al., "Schaaf-Yang syndrome overview: Report of 78 individuals," Am J Med Genet A, 2018, 176(12): 2564-2574.

McTigue et al., "Sequence-dependent thermodynamic parameters for locked nucleic acid (LNA)-DNA duplex formation," Biochemistry, 2004, 43(18): 5388-5405.

Mevissen et al., "Molecular basis of Lys11-polyubiquitin specificity in the deubiquitinase Cezanne," Nature, 2016, 538(7625): 402-405.

Min et al., "CRISPR Correction of Duchene Muscular Dystrophy," Annual Review of Medicine, Epub Oct. 2018, 70: 239-255.

Mishra et al., "Improved leishmanicidal effect of phosphorotioate antisense oligonucleotides by LDL-mediated delivery," Biochim. Biophys. Acta, 1995, 1264(2): 229-237.

Miyagishi et al., "U6 promoter-driven siRNAs with four uridine 3' overhangs efficiently suppress targeted gene expression in mammalian cells," Nature Biotechnol, 2002, 20(5): 497-500.

Mojica et al., "Intervening sequences of regularly spaced prokaryotic repeats derive from foreign genetic elements," J Molec Evolution, 2005, 60(2): 174-182.

Mojica et al., "Short motif sequences determine the targets of the prokaryotic CRISPR defence system," Microbiology, 2009, 155: 733-740.

Moore et al., "Transcription Activator-like Effectors: A Toolkit for Synthetic Biology," ACS Synth Biol, 2014, 3(10): 708-716.

Murray et al., "Codon usage in plant genes," Nucl. Acids Res., 1989, 17:477-498.

Naguibneva et al., "An LNA-based loss-of-function assay for micro-RNAs," Biomed Pharmacother, 2006, 60: 633-638.

Nam et al., "Cas5d protein processes pre-crRNA and assembles into a Cascade-like interference complex in Subtype I-C/Dvulg CRISPR-Cas system," Structure, 2012, 20:1574-1584.

Nasevicius et al., "Effective targeted gene 'knockdown' in zebrafish," Nat. Genet., 2000, 26(2): 216-220.

Nguyen et al., "Transcriptional Enhancers in the Regulation of T Cell Differentiation," Front. Immunol., 2015, 6: 462.

Nielsen et al., "Sequence-selective recognition of DNA by strand displacement with a thymine-substituted polyamide," Science, 1991, 254: 1497-1500.

Nikfarjam et al., "A Model of Partial Hepatectomy in Mice," Journal of Investigative Surgery, 2004, 17(5): 291-294.

Nowotny et al., "Crystal structures of RNase H bound to an RNA/DNA hybrid: substrate specificity and metal-dependent catalysis," Cell, 2005, 121(7): 1005-1016.

Nuñez et al., "Genome-wide programmable transcriptional memory by CRISPR-based epigenome editing," Cell, 2021, 184(9): P2503-2519.

O'Brien et al., "GT-Scan: identifying unique genomic targets," Bioinformatics, 2014, 30: 2673-2675.

Oberhauser et al., "Effective incorporation of 2'-O-methyl-oligoribonucleotides into liposomes and enhanced cell association through modification with thiocholesterol," Nucl. Acids Res., 1992, 20(3): 533-538.

(56) References Cited

OTHER PUBLICATIONS

Obika et al., "Stability and structural features of the duplexes containing nucleoside analogues with a fixed N-type conformation, 2'-O,4'-C-methyleneribonucleosides," Tetrahedron Lett. 1998, 39(30): 5401-5404.

O'Connell et al., "Programmable RNA recognition and cleavage by CRISPR/Cas9," Nature, 2014, 516: 263-266.

O'Geen et al., "dCas9-based epigenome editing suggests acquisition of histone methylation is not sufficient for target gene repression," Nucleic Acids Res, 2017, 45: 9901-9916.

Orgel, "Selection in vitro," Proc. R. Soc. B, 1979, 205: 435-442.

Orlando et al., "Promoter capture Hi-C-based identification of recurrent noncoding mutations in colorectal cancer," Nat. Genet., 2018, 50: 1375-1380.

Orom et al., "LNA-modified oligonucleotides mediate specific inhibition of microRNA function," Gene, 2006, 372: 137-141.

Ousterout, "Genetic Correction of Duchenne Muscular Dystrophy using Engineered Nucleases," Dept. of Biomedical Engineering Duke University (Dissertation), 2014, pp. 1-204.

Paddison et al., "Short hairpin RNAs (shRNAs) induce sequence-specific silencing in mammalian cells," Genes & Dev, 2002, 16(8): 948-958.

Paez-Espino et al., "CRISPR immunity drives rapid phage genome evolution in *Streptococcus thermophilus*," mBio, 2015, 6(2): e00262-15.

Paul et al., "Effective expression of small interfering RNA in human cells," Nature Biotechnol, 2002, 20(5): 505-508.

Penczek et al., "Three-dimensional reconstruction of single particles embedded in ice," Ultramicroscopy, 1992, 40, 33-53.

Perez-Pinera et al., "Synergistic and tunable human gene activation by combinations of synthetic transcription factors," Nat Methods, 2013, 10: 239-242.

Pinello et al., "Analyzing CRISPR genome-editing experiments with CRISPResso," Nat Biotechnol, 2016, 34(7):695-697.

Ponting et al., "Evolution and functions of long noncoding RNAs," Cell, 2009, 136(4): 629-641.

Povero et al., "Lipid-induced toxicity stimulates hepatocytes to release angiogenic microparticles that require Vanin-1 for uptake by endothelial cells," Sci Signal, 2013, 6(296): ra88.

Powell et al., "A Prader-Willi locus lncRNA cloud modulates diurnal genes and energy expenditure," Hum Molec Genet, 2013, 22: 4318-4328.

Puccini et al., "Colorectal cancer: epigenetic alterations and their clinical implications", Biochim Biophys Acta, 2017, vol. 1868, No. 2, pp. 439-448.

Raeburn et al., "Techniques for drug delivery to the airways, and the assessment of lung function in animal models," J. Pharmacol. Toxicol. Meth., 1992, 27:143-159.

Rajagopal et al., "High-throughput mapping of regulatory DNA," Nat. Biotechnol, 2016, 34: 167-174.

Ran et al., "Genome engineering using the CRISPR-Cas9 system," Nature Protocols, 2013, 8(11): 2281-2308.

Ratcliff et al., "A novel single-molecule study to determine protein-protein association constants," Journal of the American Chemical Society, 2001, 123(24): 5632-5635.

Rauscher et al., "GenomeCRISPR—a database for high-throughput CRISPR/Cas9 screens," Nucleic Acids Res, 2017, 45: D679-D686.

Rheinbay et al., "Analyses of non-coding somatic drivers in 2,658 cancer whole genomes," Nature, 2020, 578: 102-111.

Rhodes et al., "G-quadruplexes and their regulatory roles in biology," Nucleic Acids Res, 2015, 43: 8627-8637.

Richter et al., "Phage-assisted evolution of an adenine base editor with improved Cas domain compatibility and activity," Nat Biotechnol, Jul. 2020, 38(7): 883-891.

Rmilah et al., "Understanding the marvels behind liver regeneration," Wiley Interdiscip Rev Dev Biol., 2019, 8(3): e340.

Rodriguez et al., "Clustering by fast search and find of density peaks," Science, 2014, 344(6191): 1492-1496.

Russa et al. "The New State of the Art: Cas9 for Gene Activation and Repression," Molecular and Cellular Biology, 2015, 35(22):3800-3809.

Rutkauskas et al., "Directional R-loop formation by the CRISPR-Cas surveillance complex cascade provides efficient off-target site rejection," Cell reports, 2015, 10, 1534-1543.

Sahoo et al., "Prader-Willi phenotype caused by paternal deficiency for the HBII-85 C/D box small nucleolar RNA cluster," Nat Genet, 2008, 40: 719-721.

Saitoh et al., "Parent-of-Origin Histone Acetylation and Reactivation of a Key Imprinted Gene Locus in Prader-Willi Syndrome," Am J Hum Genet, 2000, 66: 1958-1962.

Sanghvi et al., "Heterocyclic Base Modifications in Nucleic Acids and their Applications in Antisense Oligonucleotides," 1993, Antisense Research and Applications, Chapter 15, pp. 274-285.

Sanjana et al., "High-resolution interrogation of functional elements in the noncoding genome," Science, 2016, 353: 1545-1549.

SantaLucia et al., "Improved nearest-neighbor parameters for predicting DNA duplex stability," Biochemistry, 1996, 35(11): 3555-3562.

Schaaf et al., "Truncating mutations of MAGEL2 cause Prader-Willi phenotypes and autism," Nat Genet, 2013, 45(11): 1405-1408.

Schifrut et al., "Genome-wide CRISPR Screens in Primary Human T Cells Reveal Key Regulators of Immune Function," Cell, 2018, 175(7): 1958-1971.e15.

Schmidt et al., "GenomeRNAi: a database for cell-based and in vivo RNAi phenotypes, 2013 update," Nucleic Acids Res, 2013, 41: D1021-6.

Schmittgen et al., "Analyzing real-time PCR data by the comparative CT method," Nature Protocols, 2008, 3(6): 1101-1108.

Schreck et al., "DNA hairpins destabilize duplexes primarily by promoting melting rather than by inhibiting hybridization," Nucleic Acids Research, 2015, 43(13): 6181-6190.

Schreck et al., "DNA hairpins primarily promote duplex melting rather than inhibiting hybridization," 2014, arXiv preprint arXiv:1408.4401.

Segal and Meckler, "Genome Engineering at the Dawn of the Golden Age," Annu. Rev. Genomics Hum. Genet., 2013, 14: 135-158.

Semenova et al., "The Cas6e ribonuclease is not required for interference and adaptation by the *E. coli* type I-E CRISPR-Cas system," Nucleic Acids Res, 2015, 43(12):6049-61.

Sengupta et al., "Super-Enhancer-Driven Transcriptional Dependencies in Cancer," Trends Cancer Res, 2017, 3: 269-281.

Sentmanat et al., "A Survey of Validation Strategies for CRISPR-Cas9 Editing," Scientific Reports, 2018, 8: 888.

Serra et al., "Predicting thermodynamic properties of RNA," Methods in Enzymology, 1995, 259: 242-261.

Shalem et al., "Genome-scale CRISPR-Cas9 knockout screening in human cells," Science, 2014, 343: 84-87.

Shea et al., "Synthesis, hybridization properties and antiviral activity of lipid-oligodeoxynucleotide conjugates," Nucl. Acids Res, 1990, 18: 3777-3783.

Shlyakhtenko et al., "Silatrane-based surface chemistry for immobilization of DNA, protein-DNA complexes and other biological materials," Ultramicroscopy, 2003, 97: 279-287.

Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.

Simpson, "Contacts between *Escherichia coli* RNA polymerase and thymines in the lac UV5 promoter," Proc. Natl. Acad. Sci. USA, 1979, 76: 3233-3237.

Singh et al. "Protein Engineering Approaches in the Post-Genomic Era," Current Protein and Peptide Science, 2017, 18: 1-11.

Soejima et al., "Imprinting centers, chromatin structure, and disease," J Cell Biochem, 2005, 95(2): 226-233.

Stanton et al., "Chemical modification study of antisense gapmers," Nucleic Acid Ther., 2012, 22(5): 344-359.

Stemmer et al., "CCTop: An Intuitive, Flexible and Reliable CRISPR/Cas9 Target Prediction Tool," PLoS One, 2015, 10(4): e0124633.

Stephens, "False discovery rates: a new deal," Biostatistics, 2017, 18: 275-294.

(56) References Cited

OTHER PUBLICATIONS

Stepper et al., "Efficient targeted DNA methylation with chimeric dCas9-Dnmt3a-Dnmt3L methyltransferase," Nucleic Acids Res., 2017, 45(4): 1703-1713.

Stolzenburg et al., "Targeted silencing of the oncogenic transcription factor SOX2 in breast cancer," Nucleic Acids Res., 2012, 40(14): 6725-6740.

Su et al., "Identification of biologically relevant enhancers in human erythroid cells," J Biol Chem, 2013, 288: 8433-8444.

Sugimoto et al., "Thermodynamic parameters to predict stability of RNA/DNA hybrid duplexes," Biochemistry, 1995, 34: 11211-11216.

Sugimoto et al., "Thermodynamics-structure relationship of single mismatches in RNA/DNA duplexes," Biochemistry, 2000, 39: 11270-11281.

Sui et al., "A DNA vector-based RNAi technology to suppress gene expression in mammalian cells," PNAS, 2002, 99(8): 5515-5520.

Sun et al., "Phage mutations in response to CRISPR diversification in a bacterial population," Environmental microbiology, 2013, 15(2): 463-470.

Sur et al., "The role of enhancers in cancer," Nat. Rev. Cancer., 2016, 16: 483-493.

Sutcliffe et al., "Deletions of a differentially methylated CpG island at the SNRPN gene define a putative imprinting control region," Nature Genetics, 1994, 8: 52-58.

Svinarchuk et al., "Inhibition of HIV proliferation in MT-4 cells by antisense oligonucleotide conjugated to lipophilic groups," Biochimie, 1993, 75: 49-54.

Szczelkun et al., "Direct observation of R-loop formation by single RNA-guided Cas9 and Cascade effector complexes," Proceedings of the National Academy of Sciences, 2014, 6 pages.

Szostak, "in Vitro Genes," TIBS, 1993, 17: 89-93.

Szymczak et al., "Correction of multi-gene deficiency in vivo using a single 'self-cleaving' 2A peptide-based retroviral vector," Nature Biotechnology, 2004, 22(5): 589-594.

Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.

Tam et al., "Benefits and limitations of genome-wide association studies," Nat. Rev. Genet., 2019, 20: 467-484.

Tan et al., "Rationally engineered *Staphylococcus aureus* Cas9 nucleases with high genome-wide specificity," Proc. Nat. Acad. Sci. USA, 2019, 116(46): 20969-20976.

Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.

Tsai et al., "GUIDE-seq enables genome-wide profiling of off-target cleavage by CRISPR-Cas nucleases," Nature biotechnology, 2015, 33(2): 187-197.

Tyle, "Iontophoretic Devices for Drug Delivery," Pharm. Res., 1986, 3: 318-326.

U.S. Appl. No. 17/471,935, filed Sep. 10, 2021, by Gersbach et al.

U.S. Appl. No. 17/636,750, filed Feb. 18, 2022, by Gersbach et al.

U.S. Appl. No. 17/636,754, filed Feb. 18, 2022, by Gersbach et al.

Urrutia, "KRAB-containing zinc-finger repressor proteins," Genome Biol., 2003, 4(10): 231.

Usman et al., "Catalytic RNA (Ribozymes) as Drugs," Ann. Rep. Med. Chem., 1995, Chapter 30, pp. 285-294.

Van der Oost et al., "Unravelling the structural and mechanistic basis of CRISPR-Cas systems," Nature Reviews Microbiology, 2014, 12: 479-492.

Wada et al., "Codon usage tabulated from the GenBank genetic sequence data," Nucl. Acids Res., 1990, 18: 2367-2411.

Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.

Wang et al., "Gene Essentiality Profiling Reveals Gene Networks and Synthetic Lethal Interactions with Oncogenic Ras," Cell, 2017, 168: 890-903.e15.

Wang et al., "Genetic screens in human cells using the CRISPR-Cas9 system," Science, 2014, 343: 80-84.

Wang et al., "Identification and characterization of essential genes in the human genome," Science, 2015, 350: 1096-1101.

Wang et al., "Potential of Epigenetic Therapy for Pader-Willi Syndrome," Trends in Pharmacological Sciences, 2019, 40(9): 605-608.

Wang et al., "Unbiased detection of off-target cleavage by CRISPR-Cas9 and TALENs using integrase-defective lentiviral vectors," Nature biotechnology, 2015, 33(2): 175-8.

Watkins et al., "Thermodynamic contributions of single internal rA.dA, rC.dC, rG.dG and rU.dT mismatches in RNA/DNA duplexes," Nucleic acids research, 2011, 39(5): 1894-1902.

Wei et al., "Targeting Regnase-1 programs long-lived effector T cells for cancer therapy," Nature, 2019, 576(7787): 471-476.

Wherry, "T cell exhaustion," Nat. Immunology, 2011, 12: 492-499.

Wiggins et al., "High flexibility of DNA on short length scales probed by atomic force microscopy," Nature nanotechnology, 2006, 1(2): 137-141.

Wilbie et al., "Delivery Aspects of CRISPR/Cas for in Vivo Genome Editing," Acc Chem Res, 2019, 52(6): 1555-1564.

Wiles et al., "CRISPR-Cas9_mediated genome editing and guide RNA design," Mammalian Genome, 2015, 26(9): 501-510.

Wu et al., "Genome-wide binding of the CRISPR endonuclease Cas9 in mammalian cells," Nature biotechnology, 2014, 32(7): 670-6.

Wu et al., "Induction of anion exchanger-1 translation and its opposite roles in the carcinogenesis of gastric cancer cells and differentiation of K562 cells," Oncogene, 2010, 29: 1987-1996.

Wu et al., "Unusual Processing Generates SPA LncRNAs that Sequester Multiple RNA Binding Proteins," Mol Cell, 2016, 64: 534-548.

Xie et al., "Multiplexed Engineering and Analysis of Combinatorial Enhancer Activity in Single Cells," Mol. Cell, 2017, 66: 285-299.e5.

Yang et al., "Determination of protein-DNA binding constants and specificities from statistical analyses of single molecules: MutS-DNA interactions," Nucleic acids research, 2005, 33(13): 4322-4334.

Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.

Yin et al., "Long noncoding RNAs with snoRNA ends," Mol Cell, 2012, 48(2): 219-230.

Yin et al., "Programming biomolecular self-assembly pathways," Nature, 2008, 451(7176): 318-323.

You et al., "Design of LNA probes that improve mismatch discrimination," Nuc. Acids. Res., 2006, 34(8): e60.

Younossi et al., "Epidemiology of chronic liver diseases in the USA in the past three decades," Gut, 2020, 69(3): 564-568.

Yu et al., "RNA interference by expression of short-interfering RNAs and hairpin RNAs in mammalian cells," PNAS, 2002, 99(9): 6047-6052.

Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.

Zhang et al., "Gene activation in human cells using CRISPR/Cpf1-p300 and CRISPR/Cpf1-SunTag systems," Protein Cell, 2018, 9: 380-383.

Zhang et al., "Myoediting: Toward Prevention of Muscular Dystrophy by Therapeutic Genome Editing," Physiological Reviews, 2018, 98(3): 1205-1240.

Zhang et al., "Propagated Perturbations from a Peripheral Mutation Show Interactions Supporting WW Domain Thermostability," Structure, 2018, 26: 1474-1485.

(56)         References Cited

OTHER PUBLICATIONS

Zhao et al., "High-efficiency transfection of primary human and mouse T lymphocytes using RNA electroporation," Mol. Ther., 2006, 13: 151-159.

Zhao et al., "Intracellular delivery of artificial transcription factors fused to the protein transduction domain of HIV-1 Tat," Protein Expr Purif, 2013, 90(1): 27-33.

Zheng et al., "Foxp3 in control of the regulatory T cell lineage," Nat. Immunol. 2007, 8: 457-462.

Zhu et al., "The role of histone deacetylase 7 (HDAC7) in cancer cell proliferation: regulation on c-Myc," J. Mol. Med, 2011, 89: 279-289.

NCBI Reference Sequence XM011532698.1 (2015).

NCBI Reference Sequence NM_004020.2 (2010).

NCBI Reference Sequence NG_028016.2 (2013).

European Patent Office Extended Search Report for Application No. 20790851.8 dated Oct. 27, 2022 (11 pages).

Iran Patent Office Action for Application No. 140050140003005681 dated Aug. 17, 2022 (17 pages, English translation included).

Gulf Cooperation Council Patent Office Examination Report for Application No. 2020/39547 dated Mar. 31, 2022 (4 pages).

United States Patent Office Notice of Allowance for U.S. Appl. No. 16/318,745 dated Oct. 27, 2022 (9 pages).

United States Patent Office Action for U.S. Appl. No. 16/098,464 dated Nov. 3, 2022 (13 pages).

United States Patent Office Action for U.S. Appl. No. 15/779,633 dated Dec. 21, 2022 (10 pages).

'T Hoen et al., "Generation and characterization of transgenic mice with the full-length human DMD gene," J. Biol. Chem., 2008, 283: 5899-5907.

Aartsma-Rus et al., "Antisense-mediated exon skipping: a versatile tool with therapeutic and research applications," RNA 13, 2007, 1609-1624.

Aartsma-Rus et al., "Exploring the frontiers of therapeutic exon skipping for Duchenne muscular dystrophy by double targeting within one or multiple exons," Mol Ther, 2006, 14:401-407.

Aartsma-Rus et al., "Theoretic applicability of antisense-mediated exon skipping for Duchenne muscular dystrophy mutations," Hum Mutat, 2009, 30:293-299.

Acosta et al., "Use of two gRNAs for CRISPR/Cas9 improves bi-allelic homologous recombination efficiency in mouse embryonic stem cells," Genesis, 2018, 56(5): 1-8.

Adamson et al., "A Multiplexed Single-Cell CRISPR Screening Platform Enables Systematic Dissection of the Unfolded Protein Response," Cell, 2016, 167: 1867-1882 e1821.

Adler et al., "Nonviral direct conversion of primary mouse embryonic fibroblasts to neuronal cells," Molecular therapy, 2012 Nucleic acids 1, e32.

Aguilar et al., "Transcriptional and Chromatin Dynamics of Muscle Regeneration after Severe Trauma," Stem Cell Rep, 2016, 7: 983-997.

Ahlenius et al., "FoxO3 regulates neuronal reprogramming of cells from postnatal and aging mice," Proc Natl Acad Sci U S A, 2016, 113: 8514-8519.

Aiuti, A. et al., "Lentiviral hematopoietic stem cell gene therapy in patients with Wiskott-Aldrich syndrome," Science, 2013, 341(6148): p. 1233151.

Albuquerque et al., "Mammalian nicotinic acetylcholine receptors: from structure to function," Physiol Rev, 2009, 89: 73-120.

Amoasii et al., "Gene editing restores dystrophin expression in a canine model of Duchenne muscular dystrophy," Science, 2018, 362: 86-91.

Amoasii et al., "Single-cut genome editing restores dystrophin expression in a new mouse model of muscular dystrophy," Sci Transl Med, Nov. 2017, 9(418): eaan8081.

Anders et al., "Differential expression analysis for sequence count data," Genome biology 11, 2010, R106.

Anders et al., "Structural basis of PAM-dependent target DNA recognition by the Cas9 endonuclease," Nature, 2014, 513: 569-573.

Andersen et al., "Dual role of delta-like 1 homolog (DLK1) in skeletal muscle development and adult muscle regeneration," Development, 2013, 140: 3743-3753.

Anguela et al., "Robust ZFN-mediated genome editing in adult hemophilic mice," Blood, 2013, 122:3283-3287.

Aoki et al., "Bodywide skipping of exons 45-55 in dystrophic mdx52 mice by systemic antisense delivery," Proc Natl Acad Sci USA, 2012, 109:13763-13768.

Arnett et al., "Adeno-associated viral vectors do not efficiently target muscle satellite cells," Molecular Therapy Methods & Clinical Development, 2014, 1: 14038.

Arnold et al., "Genome-wide quantitative enhancer activity maps identified by STARR-seq," Science, 2013, 339(6123): 1074-1077.

Asokan et al., "Reengineering a receptor footprint of adeno-associated virus enables selective and systemic gene transfer to muscle," Nat Biotechnol, 2010, 28: 79-82.

Asokan et al., "The AAV Vector Toolkit: Poised at the Clinical Crossroads," Mol Ther, 2012, 20: 699-708.

Ayyanathan et al., "Regulated recruitment of HP1 to a euchromatic gene induces mitotically heritable, epigenetic gene silencing: a mammalian cell culture model of gene variegation," Genes Dev, 2003, 17: 1855-1869.

Bae et al., "Cas-OFFinder: a fast and versatile algorithm that searches for potential off-target sites of Cas9 RNA-guided endonucleases," Bioinformatics, 2014, 30: 1473-1475.

Balboa et al., "Conditionally Stabilized dCas9 Activator for Controlling Gene Expression in Human Cell Reprogramming and Differentiation," Stem Cell Rep, 2015, 5: 448-459.

Barberi et al., "Derivation of engraftable skeletal myoblasts from human embryonic stem cells," Nat Med, 2007, 13: 642-648.

Barr et al., "Predominant Expression of Alternative PAX3 and PAX7 Forms in Myogenic and Neural Tumor Cell Lines," Cancer Res, 1999, 59: 5443-5448.

Bartsevich et al., "Engineered zinc finger proteins for controlling stem cell fate," Stem Cells 21, 2003, 632-637.

Bauer et al., "An erythroid enhancer of BCL11A subject to genetic variation determines fetal hemoglobin level," Science 342, 2013, 253-257.

Beerli et al., "Chemically regulated zinc finger transcription factors," J Biol Chem, 2000, 275(42): p. 32617-27.

Beerli et al., "Engineering polydactyl zinc-finger transcription factors," Nat Biotechnol 20, 2002, 135-141.

Beerli et al., "Positive and negative regulation of endogenous genes by designed transcription factors," Proc Natl Acad Sci U S A 97, 2000, 1495-1500.

Beerli et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.

Beltran et al., "Re-activation of a dormant tumor suppressor gene maspin by designed transcription factors," Oncogene 26, 2007, 2791-2798.

Bender et al., "Independent formation of DnaseI hypersensitive sites in the murine beta-globin locus control region," Blood, 2000, 95: 3600-3604.

Benedetti et al., "Repair or Replace? Exploiting Novel Gene and Cell Therapy Strategies for Muscular Dystrophies," FEBS Journal (2013).

Bengtsson et al., "Muscle-specific CRISPR/Cas9 dystrophin gene editing ameliorates pathophysiology in a mouse model for Duchenne muscular dystrophy," Nat Commun, 2017, 8: 1-10.

Berghella et al., "Reversible immortalization of human myogenic cells by site-specific excision of a retrovirally transferred oncogene," Human gene therapy 10, 1999, 1607-1617.

Bernstein et al., "An integrated encyclopedia of DNA elements in the human genome," Nature, 2012, 489: 57-74.

Bernstein et al., "The NIH Roadmap Epigenomics Mapping Consortium," Nat Biotechnol, 2010, 28: 1045-1048.

Beverley, "Primer: making sense of T-cell memory," Nat. Clin Pract. Rheumatol., 2008, 4: 43-49.

Bhakta et al., "Highly active zinc-finger nucleases by extended modular assembly," Genome Res, 2013, 530-538.

(56) References Cited

OTHER PUBLICATIONS

Bidou et al., "Sense from nonsense: therapies for premature stop codon diseases," Trends in Molecular Medicine 18, 2012, 679-688.

Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.

Bladen et al., "The Treat-NMD DMD Global Database: analysis of more than 7,000 Duchenne muscular dystrophy mutations," Human Mutation, 2015, 36(4):395-402.

Blancafort et al., "Scanning the human genome with combinatorial transcription factor libraries," Nat Biotechnol 21, 2003, 269-274.

Boch et al., "Breaking the code of DNA binding specificity of TAL-type III effectors," Science 326, 2009, 1509.

Boldrin et al., "Donor satellite cell engraftment is significantly augmented when the host niche is preserved and endogenous satellite cells are incapacitated," Stem Cells, 2012, 30: 1971-1984.

Boshart et al., "A very strong enhancer is located upstream of an immediate early gene of human cytomegalovirus," Cell, 1985, 41(2): 521-530.

Bowles et al., "Phase 1 Gene Therapy for Duchenne Muscular Dystrophy Using a Translation Optimized AAV Vector," Molecular Therapy 20, 2012, 443-455.

Boyle et al., "High-resolution mapping and characterization of open chromatin across the genome," Cell, 2008, 132: 311-322.

Briguet et al., "Histological parameters for the quantitative assessment of muscular dystrophy in the mdx-mouse," Neuromuscul. Disord., 2004, 14: 675-682.

Brunet et al., "Chromosomal translocations induced at specific loci in human stem cells," Proc Natl Acad Sci USA, 2009, 106:10620-10625.

Brunger et al., "CRISPR/Cas9 Editing of Murine Induced Pluripotent Stem Cells for Engineering Inflammation-Resistant Tissues," Arthritis Rheumatol, 2017, 69: 1111-1121.

Brunger et al., "Genome Engineering of Stem Cells for Autonomously Regulated, Closed-Loop Delivery of Biologic Drugs," Stem Cell Reports, 2017, 8: 1202-1213.

Buenrostro et al., "Transposition of native chromatin for fast and sensitive epigenomic profiling of open chromatin, DNA-binding proteins and nucleosome position," Nat Methods, 2013, 10: 1213-1218.

Buler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, vol. 287, No. 3, pp. 1847-1860, Jan. 13, 2012.

Bultmann et al., "Targeted transcriptional activation of silent oct4 pluripotency gene by combining designer TALEs and inhibition of epigenetic modifiers," Nucleic Acids Res 40, 2012, 5368-5377.

Busskamp et al., "Rapid neurogenesis through transcriptional activation in human stem cells," Mol Syst Biol, 2014, 10: 760.

Carrillo et al., "The Multiple Sequence Alignment Problem in Biology," SIAM J. Applied Math, 1988, 48: 1073.

Carter et al., "Long-range chromatin regulatory interactions in vivo," Nat Genet, 2002, 32: 623-626.

Cerletti et al., "Highly efficient, functional engraftment of skeletal muscle stem cells in dystrophic muscles," Cell 134, 2008, 37-47.

Cermak et al., "Efficient design and assembly of custom TALEN and other TAL effector-based constructs for DNA targeting," Nucleic Acids Res 30, 2011, e82.

Chakraborty et al., "A CRISPR/Cas9-based system for reprogramming cell lineage specification," Stem Cell Reports, 2014, 3: 940-947.

Chal et al., "Differentiation of pluripotent stem cells to muscle fiber to model Duchenne muscular dystrophy," Nat Biotechnol, 2015, 33: 962-969.

Chamberlain et al., "Progress toward Gene Therapy for Duchenne Muscular Dystrophy," Mol. Ther., 2017, 25: 1125-1131.

Chanda et al., "Generation of induced neuronal cells by the single reprogramming factor ASCL1," Stem Cell Reports, 2014, 3: 282-296.

Chapdelaine et al., "Meganucleases can restore the reading frame of a mutual dystrophin," Gene therapy 17, 2010, 846-858.

Chavez et al., "Comparison of Cas9 activators in multiple species," Nat Methods, 2016, 13: 563-67.

Chavez et al., "Highly efficient Cas9-mediated transcriptional programming," Nat Methods, 2015, 12: 326-328.

Cheloufi et al., "The histone chaperone CAF-1 safeguards somatic cell identity," Nature, 2015, 528: 218-224.

Chen et al., "Dynamic imaging of genomic loci in living human cells by an optimized CRISPR/Cas systemm," Cell, 2013, 155: 1479-1491.

Chen et al., "Enrichr: interactive and collaborative HTML5 gene list enrichment analysis tool," BMC Bioinformatics, 2013, 14: 128.

Chen et al., "Expanding the CRISPR imaging toolset with *Staphylococcus aureus* Cas9 for simultaneous imaging of multiple genomic loci," Nucleic Acids Research, 2016, 44(8): e75, 13 pages.

Chen et al., "Life and death of transcriptional co-activator p300," Epigenetics, 2011, 6: 957-961.

Chen et al., "microRNA-1 and microRNA-206 regulate skeletal muscle satellite cell proliferation and differentiation by repressing Pax7," J Cell Biol, 2010, 190: 867-879.

Chen et al., "Two upstream enhancers collaborate to regulate the spatial patterning and timing of MyoD transcription during mouse development," Dev Dyn, 2001, 221: 274-288.

Cheng et al., "Multiplexed activation of endogenous genes by CRISPR-on, an RNA-guided transcriptional activator system," Cell Res, 2013, 23(10): p. 1163-1171.

Chew et al., "A multifunctional AAV-CRISPR-Cas9 and its host response," Nat Methods, 2016, 13: 868-74.

Childers et al., "Gene therapy prolongs survival and restores function in murine and canine models of myotubular myopathy," Sci Transl Med, 2014, 6: 220ra210.

Cho et al., "Analysis of off-target effects of CRISPR/Cas-derived RNA-guided endonucleases and nickases," Genome Res, 2014, 24:132-141.

Cho et al., "Targeted genome engineering in human cells with the Cas9 RNA-guided endonuclease," Nat Biotechnol 31, 2013, 230-232.

Choy et al., "Eukaryotic activators function during multiple steps of preinitiation complex assembly," Nature, 1993, 366: 531-536.

Christian et al., "Targeting DNA double-strand breaks with TAL effector nucleases," Genetics 186, 2010, 757-761.

Chronis et al., "Cooperative Binding of Transcription Factors Orchestrates Reprogramming," Cell, 2017, 168: 442-459 e420.

Chu et al., "SV40 Dna transfection of cells in suspension: analysis of efficiency of transcription and translation of T-antigen," Gene, 1981, 13:197.

Cirak et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.

Cong et al., "Comprehensive interrogation of natural TALE DNA-binding modules and transcriptional repressor domains," Nat Commun, 2012, 3: 968.

Cong et al., "Multiplex Genome Engineering Using CRISPR/Cas Systems," Science 339, 2013, 819-823.

Consortium, "An integrated encyclopedia of DNA elements in the human genome," Nature, 2012, 489: 57-74.

Cooper et al., "Improved induction of immune tolerance to factor IX by hepatic AAV-8 gene transfer," Hum Gene Ther, 2009, 20: 767-776.

Cordier et al., "Muscle-specific promoters may be necessary for adeno-associated virus-mediated gene transfer in the treatment of muscular dystrophies," Hum. Gene Ther., 2001, 12: 205-215.

Cornu et al., "DNA-binding specificity is a major determinant of the activity and toxicity of zinc-finger nucleases," Mol Ther, 2008, 16:352-358.

Cornu et al., "Quantification of zinc finger nuclease-associated toxicity," Meth Mol Biol, 2010, 649:237-245.

(56)      References Cited

OTHER PUBLICATIONS

Cradick et al., "CRISPR/Cas9 systems targeting beta-globin and CCR5 genes have substantial off-target activity," Nucleic Acids Res, 2013, 41(20): p. 9584-92.

Crawford et al., "Genome-wide mapping of DNase hypersensitive sites using massively parallel signature sequencing (MPSS)," Genome Res, 2006, 16: 123-131.

Crocker et al., "TALE-mediated modulation of transcriptional enhancers in vivo," Nature Methods, 2013, 10: 762-767.

D'Alessio et al., "A Systematic Approach to Identify Candidate Transcription Factors that Control Cell Identity," Stem Cell Reports, 2015, 5: 763-775.

Daley et al., "CRISPhieRmix: a hierarchical mixture model for CRISPR pooled screens," Genome Biol, 2018, 19: 159.

Darabi et al., "Functional skeletal muscle regeneration from differentiating embryonic stem cells," Nat Med, 2008, 14: 134-143.

Darabi et al., "Human ES-and iPS-derived myogenic progenitors restore dystrophin and improve contractility upon transplantation in dystrophic mice," Cell Stem Cell 10, 2012, 610-619.

Darmanis et al., "A survey of human brain transcriptome diversity at the single cell level," Proc Natl Acad Sci U S A, 2015, 112: 7285-7290.

De Groote et al., "Epigenetic Editing: targeted rewriting of epigenetic marks to modulate expression of selected target genes," Nucleic Acids Res, 2012, 40(21): 10596-10613.

Dean et al., "Inducible transcription of five globin genes in K562 human leukemia cells," Proceedings of the National Academy of Sciences of the United States of America, 1983, 80: 5515-5519.

Deconinck et al., "Utrophin-Dystrophin-Deficient Mice as a Model for Duchenne Muscular Dystrophy," Cell, 1997, 90(4): 717-727.

Deltcheva et al., "CRISPR RNA maturation by trans-encoded small RNA and host factor RNase III," Nature, 2011, 471(7340): 602-607.

Delvecchio et al., "Structure of the p300 catalytic core and implications for chromatin targeting and HAT regulation," Nat Struct Mol Biol 20, 2013, 1040-1046.

Deng et al., "Reactivation of developmentally silenced globin genes by forced chromatin looping," Cell, 2014, 158: 849-860.

Dezawa et al., "Bone marrow stromal cells generate muscle cells and repair muscle degeneration," Science Signaling 309, 2005, 314.

Dijkema et al., "Cloning and expression of the chromosomal immune interferon gene of the rat," EMBO J, 1985, 4(3): 761-767.

Ding et al., "A TALEN Genome-Editing System for Generating Human Stem Cell-Based Disease Models," 2013, Cell Stem Cell 12, 238-251.

Ding et al., "Enhanced efficiency of human pluripotent stem cell genome editing through replacing TALENs with CRISPRs," Cell Stem Cell, 2013, 12:393-394.

Ding et al., "Permanent Alteration of PCSK9 Within Vivo CRISPR-Cas9 Genome Editing," Circulation Research, 2014, 115(5): 488-492.

Doench et al., "Optimized sgRNA design to maximize activity and minimize off-target effects of CRISPR-Cas9," Nat Biotechnol, 2016, 34: 184-191.

Doench et al., "Rational design of highly active sgRNAs for CRISPR-Cas9-mediated gene inactivation," Nat Biotechnol, 2014, 32: 1262-1267.

Dostie et al., "Chromosome Conformation Capture Carbon Copy (SC): a massively parallel solution for mapping interactions between genomic elements," Genome Research, 2006, 16: 1299-1309.

Doudna et al., "Genome editing. The new frontier of genome engineering with CRISPR-Cas9," Science, 2014, 346: 1258096.

Doyle et al., "TAL Effector-Nucleotide Targeter (TALE-NT) 2.0: tools for TAL effector design and target prediction," Nucleic Acids Res 40, 2012, W117-122.

Doyon et al., "Enhancing zinc-finger-nuclease activity with improved obligate heterodimeric architectures," Nat Methods 8, 2010, 74-79.

Du et al., "Genetic interaction mapping in mammalian cells using CRISPR interference," Nat Methods, 2017, 14: 577-580.

Duan et al., "Expanding AAV packaging capacity with transsplicing or overlapping vectors: a quantitative comparison," Molecular Therapy, 2001, 4: 383-391.

Duan, "Systemic AAV Micro-dystrophin Gene Therapy for Duchenne Muscular Dystrophy," Molecular Therapy, 2018, 26(10): 2337-2356.

Dumont et al., "Dystrophin expression in muscle stem cells regulates their polarity and asymmetric division," Nat Med, 2015, 21: 1455-1463.

Dumont et al., "Intrinsic and extrinsic mechanisms regulating satellite cell function," Development, 2015, 142: 1572-1581.

Dunbar et al., "Gene therapy comes of age," Science, 2018, 359: eaan4672.

EBI Accession No. GSP: BCJ39961 (2016).

Edelstein et al., "Gene therapy clinical trials worldwide 1989-2004—an overview," J. Gene Med. vol. 6, pp. 597-602, 2004.

Egger et al., "Epigenetics in human disease and prospects for epigenetic therapy," Nature, 2004, 429: 457-463.

Eguchi et al., "Reprogramming cell fate with a genome-scale library of artificial transcription factors," Proc Natl Acad Sci U S A, 2016, 113: E8257-E8266.

Ernsberger, "Role of neurotrophin signalling in the differentiation of neurons from dorsal root ganglia and sympathetic ganglia," Cell Tissue Res, 2009, 336: 349-384.

Erwin et al., "Synthetic transcription elongation factors license transcription across repressive chromatin," Science, 2017, 358: 1617-1622.

Esvelt et al., "Orthogonal Cas9 proteins for RNA-guided gene regulation and editing," Nature Methods 2013, 10(11): p. 1116-21.

Fagerlund et al., "The Cpf1 CRISPR-Cas protein expands genome-editing tools," Genome Biology, 2015, 16:251.

Fairclough et al., "Therapy for Duchenne muscular dystrophy: renewed optimism from genetic approaches," Nat. Rev. Genet., 2013, 14: 373-378.

Farinelli et al., "Lentiviral vectors for the treatment of primary immunodeficiencies," J Inherit Metab Dis, 2014.

Farzadfard et al., "Tunable and Multifunctional Eukaryotic Transcription Factors Based on CRISPR/Cas," ACS Synth Biol, 2013, 604-613.

FDA approval brings first gene therapy to the United States, <https://www.fda.gov/newsevents/newsroom/pressannouncements/ucm574058.htm> (Aug. 30, 2017).

FDA approves first drug for spinal muscular atrophy, <https://www.fda.gov/newsevents/newsroom/pressannouncements/ucm534611.htm> (Dec. 23, 2016).

FDA approves first-of-its kind targeted RNA-based therapy to treat a rare disease, <https://www.fda.gov/newsevents/newsroom/pressannouncements/ucm616518.htm> (Aug. 10, 2018).

FDA approves novel gene therapy to treat patients with a rare form of inherited vision loss, <https://www.fda.gov/newsevents/newsroom/pressannouncements/ucm589467.htm> (Dec. 18, 2017).

FDA grants accelerated approval to first drug for Duchenne muscular dystrophy, <https://www.fda.gov/newsevents/newsroom/pressannouncements/ucm521263.htm> (Sep. 19, 2016).

Ferretti et al., "Complete genome sequence of an MI strain of *Streptococcus pyogenes,* " Proc Natl Acad Sci US A, 2001, 98(8): 4658-63.

Fine et al., "Trans-spliced Cas9 allows cleavage of HBB and CCR5 genes in human cells using compact expression cassettes," Sci Rep. 2015, 5: 10777.

Flandin et al., "Lhx6 and Lhx8 coordinately induce neuronal expression of Shh that controls the generation of interneuron progenitors," Neuron, 2011, 70: 939-950.

Flanigan et al., "Mutational spectrum of DMD mutations in dystrophinopathy patients: application of modern diagnostic techniques to a large cohort," Human mutation 30, 2009, 1657-1666.

Fonfara et al., "Phylogeny of Cas9 determines functional exchangeability of dual-RNA and Cas9 among orthologous type II CRISPR-Cas systems," Nucleic Acids Res, 2013.

Fontenot et al., "Regulatory Tcell lineage specification by the forkhead transcription factor foxp3," Immunity, 2005, 22: 329-341.

Forget, "Molecular basis of hereditary persistence of fetal hemoglobin," Ann N Y Acad Sci, 1998, 850, 38-44.

(56) References Cited

OTHER PUBLICATIONS

Friedland et al., "Characterization of *Staphylococcus aureus* Cas9: a smaller Cas9 for all-in-one adeno-associated virus delivery and paired nickase applications," Genome Biology, 2015, 16(16):257, 10 pages.

Friedland et al., "*Staphyloccocus aureus* Cas9: An Alternative Cas9 for Genome Editing Applications," Molecular Therapy, 2015, 23(Suppl. 1):S224.

Friedland et al., "*Staphyloccocus aureus* Cas9: An Alternative Cas9 for Genome Editing Applications," Retrieved from the Internet: <http://www.editasmedicine.com/data/documents/ASGCT% 20poster 2015 Ari.pdf> Retrieved on Feb. 28, 2018.

Fu et al., "High-frequency off-target mutagenesis induced by CRISPR-Cas nucleases in human cells," Nat Biotechnol, 2013, 31(9): p. 822-6.

Fu et al., "Improving CRISPR-Cas nuclease specificity using truncated guide RNAs," 2014, Nat Biotechnol 32, 279-284.

Gaj et al., "Structure-Guided Reprogramming of Serine Recombinase DNA Sequence Specificity," Proc Natl Acad Sci U S A, 2011, 108(2): 498-503.

Gaj et al., "Targeted gene knockout by direct delivery of zinc-finger nuclease proteins," Nature Methods, 2012.

Gaj et al., "ZFN, TALEN, and CRISPR/Cas-based methods for genome engineering," Trends Biotechnol, 2013, 31:397-405.

Gao et al., "Comparison of TALE designer transcription factors and the CRISPR/dCas9 in regulation of gene expression by targeting enhancers," Nucleic Acids Res, 2014, 42: e155.

Gao et al., "Complex transcriptional modulation with orthogonal and inducible dCas9 regulators," Nat Methods, 2016, 13: 1043-1049.

Gao et al., "Reprogramming to Pluripotency Using Designer TALE Transcription Factors Targeting Enhancers," Stem Cell Reports, 2013, 1(2): 183-197.

Garg et al., "Engineering synthetic TAL effectors with orthogonal target sites," Nucleic Acids Res 40, 2012, 7584-7595.

Garriga-Canut et al., "Synthetic zinc finger repressors reduce mutant huntingtin expression in the brain of R6/2 mice," Proceedings of the National Academy of Sciences of the United States of America, 2012, 109: E3136-E3145.

Gascon et al., "Direct Neuronal Reprogramming: Achievements, Hurdles, and New Roads to Success," Cell Stem Cell, 2017, 21: 18-34.

GenBank Accession AF214528.1 (2000).

GenBank Accession X51934.1 (1997).

Gersbach et al., "Activating human genes with zinc finger proteins, transcription activator-like effectors and CRISPR/Cas9 for gene therapy and regenerative medicine," Expert Opin Ther Targets, 2014, 18(8): 835-839.

Gersbach et al., "Targeted plasmid integration into the human genome by an engineered zinc-finger recombinase," Nucleic Acids Res, 2011, 39: 7868-7878.

Gersbach, "Genome engineering: the next genomic revolution," Nat Methods, 2014, 11: 1009-1011.

Gerstein et al., "Architecture of the human regulatory network derived from ENCODE data," Nature, 2012, 489: 91-100.

Gertz et al., "Transposase mediated construction of RNA-seq libraries," Genome Res 22, 2012, 134-141.

Gilbert et al., "Genome-Scale CRISPR-Mediated Control of Gene Repression and Activation," Cell, 2014, 159: 647-661.

Gilman et al., "Distal CCAAT box deletion in the A gamma globin gene of two black adolescents with elevated fetal A gamma globin," Nucleic Acids Res 16, 1988, 10635-10642.

Goemans et al., "Systemic administration of PRO051 in Duchenne's muscular dystrophy," The New England journal of medicine 364, 2011, 1513-1522.

Goldstein et al., "In Situ Modification of Tissue Stem and Progenitor Cell Genomes," Cell Reports, 2019, 27: 1254-1264.e7.

Gorman et al., "The Rous sarcoma virus long terminal repeat is a strong promoter when introduced into a variety of eukaryotic cells by DNA-mediated transfection," Proc. Natl. Acad. Sci. USA, 1982, 79(22): 6777-6781.

Gou et al., "A novel approach for the construction of multiple shRNA expression vectors," J Gene Med, 2007, 9(9): p. 751-63.

Graham et al., "A new technique for the assay of infectivity of human adenovirus 5 DNA," Virol., 1973, 52: 456-467.

Graslund et al., "Exploring strategies for the design of artificial transcription factors: targeting sites proximal to known regulatory regions for the induction of gamma-globin expression and the treatment of sickle cell disease," J Biol Chem 280, 2005, 3707-3714.

Gregorevic et al., "Systemic delivery of genes to striated muscles using adeno-associated viral vectors," Nat Med, 2004, 10:828-834.

Gregorevic et al., "Systemic microdystrophin gene delivery improves skeletal muscle structure and function in old dystrophic mdx mice," Mol Ther, 2008, 16: 657-664.

Grimmer et al., "Analysis of an artificial zinc finger epigenetic modulator: widespread binding but limited regulation," Nucleic Acids Research, 2014, 42: 10856-10868.

Groner et al., "KRAB-zinc finger proteins and KAP1 can mediate long-range transcriptional repression through heterochromatin spreading," PLoS Genet, 2010, 6: el000869.

Guo et al., "Harnessing accurate non-homologous end joining for efficient prease deletion in CRISPR/Cas9-mediated genome editing," Genome Biology, 2018, 19: 170, 20 pages.

Guo, J et al., "Directed evolution of an enhanced and highly efficient Fokl cleavage domain for zinc finger nucleases," J Mol Biol, 2010.

Guschin, D. Y. et al., "A rapid and general assay for monitoring endogenous gene modification," Methods Mol Biol 649, 2010, 247-256.

Hakim et al., "Evaluation of Muscle Function of the Extensor Digitorum Longus Muscle Ex vivo and Tibialis Anterior Muscle In situ in Mice," J. Vis. Exp., 2013, 1-8.

Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.

Hall et al., "Prevention of Muscle Aging by Myofiber-Associated Satellite Cell Transplantation," Sci Transl Med, 2010, 2: 57ra83.

Hamar et al., "Small interfering RNA targeting Fas protects mice against renal ischemia-reperfusion injury," PNAS, 2004, 101: 14883-14888.

Hardison et al., "Locus control regions of mammalian beta-globin gene clusters: combining phylogenetic analyses and experimental results to gain functional insights," Gene, 1997, 205: 73-94.

Hardy et al., "Comparative Study of Injury Models for Studying Muscle Regeneration in Mice," PLoS One, 2016, 11: e0147198.

Harper et al., "Modular flexibility of dystrophin: implications for gene therapy of Duchenne muscular dystrophy," Nat. Med., 2002, 8: 253-261.

Harrow et al., "GENCODE: The reference human genome annotation for The ENCODE Project," Genome Res, 2012, 22: 1760-1774.

Hathaway et al., "Dynamics and memory of heterochromatin in living cells," Cell, 2012, 149: 1447-1460.

Heagerty et al., "Time-dependent ROC curves for censored survival data and a diagnostic marker," Biometrics, 2000, 56: 337-344.

Heintzman et al., "Distinct and predictive chromatin signatures of transcriptional promoters and enhancers in the human genome," Nat Genet, 2007, 39: 311-318.

Hilton et al., "Enabling functional genomics with genome engineering," Genome Research, 2015, 25(10):1442-1455.

Hilton et al., "Epigenome editing by a CRISPR-Cas9-based acetyltransferase activates genes from promoters and enhancers," Nat Biotechnol, 2015, 33: 510-517.

Himeda et al., "Design and Testing of Regulatory Cassettes for Optimal Activity in Skeletal and Cardiac Muscles," Methods Mol Biol, 2011, 709: 3-19 (Published Online Dec. 2010).

Hockemeyer et al., "Efficient targeting of expressed and silent genes in human ESCs and iPSCs using zinc-finger nucleases," Nat Biotechnol, 2009, 27(9): p. 851-7.

Hockemeyer et al., "Genetic engineering of human pluripotent cells using TALE nucleases," Nat Biotechnol 29, 2011, 731-734.

(56)　　　　　References Cited

OTHER PUBLICATIONS

Hoffman et al., "Dystrophin: the protein product of the Duchenne muscular dystrophy locus," Cell, 1987, 51:919.

Hotta et al., "Isolation of human iPS cells using EOS lentiviral vectors to select for pluripotency," Nat Methods, 2009, 6: 370-376.

Hou et al., "Efficient genome engineering in human pluripotent stem cells using Cas9 from Neisseria meningitidis," Proc Natl Acad Sci USA, 2013, 110:15644-15649.

Hsu et al., "Dissecting Neural Function Using Targeted Genome Engineering Technologies", ACS Chem. Neurosci., 2012, pp. 603-610.

Hsu et al., "DNA targeting specificity of RNA-guided Cas9 nucleases," Nature Biotechnology 31, 2013, 827-832.

Hsu et al., "Development and applications of CRISPR-Cas9 for genome engineering," Cell, 2014, 157: 1262-1278.

Hu et al., "Direct activation of human and mouse Oct4 genes using engineered TALE and Cas9 transcription factors," Nucleic Acids Res, 2014, 42: 4375-4390.

Huang et al., "Impaired respiratory function in mdx and mdx/utrn+/− mice," Muscle & Nerve, 2011, 43(2): 263-267.

Humbert et al., "Targeted gene therapies: tools, applications, optimization", Critical Reviews in Biochemistry and Molecular Biology, CRC Press, vol. 47, No. 3, Apr. 2012, pp. 264-281.

Hwang et al., "Efficient genome editing in zebrafish using CRISPR-Cas system," Nat Biotechnol, 2013, 31(3): p. 227-9.

Ikonomi et al., "Levels of GATA-1/GATA-2 transcription factors modulate expression of embryonic and fetal hemoglobins," Gene, 2000, 261: 277-287.

Inoue et al., "Runx transcription factors in neuronal development," Neural Dev, 2008, 3: 20.

Isaac et al., "Dystrophin and utrophin "double knockout" dystrophic mice exhibit a spectrum of degenerative musculoskeletal abnormalities," Journal of Orthopaedic Research, 2013, 31(3): 343-349.

Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.

Ji et al., "Engineered zinc-finger transcription factors activate OCT4 (POU5FI), SOX2, KLF4, c-MYC (MYC) and miR302/367," Nucleic Acids Res, 2014, 42: 6158-6167.

Jiang et al., "Notch signaling deficiency underlies age-dependent depletion of satellite cells in muscular dystrophy," Disease Models & Mechanisms, 2014, 7: 997-1004.

Jinek et al., "A programmable dual-RNA-guided DNA endonuclease in adaptive bacterial immunity," Science 337, 2012, 816-821.

Jinek et al., "RNA-programmed genome editing in human cells," eLife 2, 2013, e00471.

Jinek et al., "Structures of Cas9 endonucleases reveal RNA-mediated conformational activation," Science, 2014, 343(6176): p. 1247997.

Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.

Jooss et al., "Transduction of dendritic cells by DNA viral vectors directs the immune response to transgene products in muscle fibers," J. Virol., 1998, 72: 4212-4223.

Jörg, "Engineering of the epigenome: synthetic biology to define functional causality and develop innovative therapies," Epigenomics, 2016, 8(2): 153-156.

Joung et al., "TALENs: a widely applicable technology for targeted genome editing," Nature Reviews Molecular Cell Biology 14, 2013, 49-55.

Kabadi et al., "Multiplex CRISPR/Cas9-based genome engineering from a single lentiviral vector," Nucleic Acids Res, 2014, 42: e147.

Kayali et al., "Site-directed gene repair of the dystrophin gene mediated by PNA-ssODNs," Human Molecular Genetics, vol. 19, No. 16, Aug. 15, 2010, pp. 3266-3281.

Kearns et al., "Cas9 effector-mediated regulation of transcription and differentiation in human pluripotent stem cells," Development, 2014, 141(1): p. 219-23.

Kearns et al., "Functional annotation of native enhancers with a Cas9-histone demethylase fusion," Nat Methods, 2015, 12(5): 401-403.

Keefe et al., "Muscle stem cells contribute to myofibers in sedentary adult mice," Nat Commun, 2015, 6: 7087.

Keil et al., "Brain transcriptome databases: a user's guide," J Neurosci, 2018, 38(10): 2399-2412.

Keung et al., "Using targeted chromatin regulators to engineer combinatorial and spatial transcriptional regulation, " Cell, 2014, 158: 110-120.

Khambata-Ford et al., "Identification of Promoter Regions in the Human Genome by Using a Retroviral Plasmid Library-Based Functional Reporter Gene Assay," Genome Research, 2003, 13: 1765-1774.

Khoury et al., "Efficient new cationic liposome formulation for systemic delivery of small interfering RNA silencing tumor necrosis factor a in experimental arthritis," Arthritis Rheumatol, 2006, 54: 1867-1877.

Kim et al., "A Histone acetylation contributes to chromatin looping between the locus control region and globin gene by influencing hypersensitive site formation," Biochim Biophys Acta, 2013, 1829: 963-969.

Kim et al., "Expansion and Purification Are Critical for the Therapeutic Application of Pluripotent Stem Cell-Derived Myogenic Progenitors," Stem Cell Rep, 2017, 9: 12-22.

Kim et al., "Surrogate reporters for enrichment of cells with nuclease-induced mutations," Nat Methods, 2011, 8:941-943.

Kim et al., "TALENs and ZFNs are associated with different mutation signatures," Nat Methods, 2013.

Kim et al., "Use of the human elongation factor 1α promoter as a versatile and efficient expression system," Gene, 1990, 91(2): 217-223.

Kimura et al., "Cell-lineage regulated myogenesis for dystrophin replacement: a novel therapeutic approach for treatment of muscular dystrophy," Hum Mol Genet 17, 2008, 2507-2517.

Klann et al., "CRISPR-based methods for high-throughput annotation of regulatory DNA," Curr Opin Biotechnol, 2018, 52: 32-41.

Kleinstiver et al., "Broadening the targeting range of *Staphylococcus aureus* CRISPR-Cas9 by modifying PAM recognition," Nature Biotechnology, 2015, 7 pages.

Kleinstiver et al., "Genome-wide specificities of CRISPR-Cas Cpf1 nucleases in human cells," Nature Biotechnology, 2016, 34(8):869-874.

Kodaka et al., "Skeletal Muscle Cell Induction from Pluripotent Stem Cells," Stem Cells Int, Apr. 2017, Article ID 1376151, 16 pages.

Koerber et al., "DNA shuffling of adeno-associated virus yields functionally diverse viral progeny," Mol Ther, 2008, 16: 1703-1709.

Konermann et al., "Genome-scale transcriptional activation by an engineered CRISPR-Cas9 complex," Nature, 2015, 517: 583-588.

Konermann et al., "Optical control of mammalian endogenous transcription and epigenetic states," Nature, 2013, 500(7463): p. 472-6.

Konieczny et al., "Gene and cell-mediated therapies for muscular dystrophy," Muscle Nerve, 2013, 47:649-663.

Koo et al., "Functional Rescue of Dystrophin Deficiency in Mice Caused by Frameshift Mutations Using Campylobacter jejuni Cas9," Molecular Therapy, 2018 26(6): 1529-1538.

Koopmans et al., "SynGO: An Evidence-Based, Expert-Curated Knowledge Base for the Synapse," Neuron, 2019, 103: 217-234 e214.

Koppanati et al., "Improvement of the mdx mouse dystrophic phenotype by systemic in utero AAV8 delivery of a minidystrophin gene," Gene Ther, 2010, 17: 1355-1362.

Kotin, "Prospects for the use of adeno-associated virus as a vector for human gene therapy," Hum Gene Ther, 1994, 5: 793-801.

Kreis et al., "The Multifaceted p21 (Cip1/Waf1/CDKN1A) in Cell Differentiation, Migration and Cancer Therapy," Cancers (Basel), 2019, 11(9): 1220.

(56)　　　　　References Cited

OTHER PUBLICATIONS

Kubokawa et al., "Molecular characterization of the 5'-UTR of retinal dystrophin reveals a cryptic intron that regulates translational activity," Molecular Vision, 2010, vol. 16, pp. 2590-2597.

Kuscu et al., "Genome-wide analysis reveals characteristics of off-target sites bound by the Cas9 endonuclease," Nat Biotechnol, 2014, 32(7): 677-683.

Kwon et al., "Myogenic Progenitor Cell Lineage Specification by CRISPR/Cas9-Based Transcriptional Activators," Stem cell reports, 2020, 14: 755-769.

Kyte et al., "A Simple Method for Displaying the Hydropathic Character of a Protein," J. Mol. Biol., 1982, 157:105-132.

La Russa et al., "The New State of the Art: Cas9 for Gene Activation and Repression," Molecular and Cellular Biology, 2015, 35(22): 3800-3809.

Lai et al., "Partial restoration of cardiac function with ΔPDZ nNOS in aged mdx model of Duchenne cardiomyopathy," Hum Mol Genet., 2014, 23(12): 3189-3199.

Lake et al., "Integrative single-cell analysis of transcriptional and epigenetic states in the human adult brain," Nat Biotechnol, 2018, 36: 70-80.

Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.

Lambert et al., "The Human Transcription Factors," Cell, 2018, 172: 650-665.

Lamey et al., "Pax genes in myogenesis: alternate transcripts add complexity," Histol Histopathol, 2004, 19: 1289-1300.

Landen et al., "Intraperitoneal delivery of liposomal siRNA for therapy of advanced ovarian cancer," Cancer Biol. Ther., 2006, 5(12): 1708-1713.

Langmead et al., "Fast gapped-read alignment with Bowtie 2," Nat Methods, 2012, 9: 357-359.

Langmead et al., "Ultrafast and memory-efficient alignment of short DNA sequences to the human genome," Genome biology 10, 2009, R25.

Larson et al., "CRISPR interference (CRISPRi) for sequence-editing control of gene expression," Nat Protoc, 2013, 8(11): p. 2180-96.

Latta-Mahieu et al., "Gene transfer of a chimeric trans-activator is immunogenic and results in short-lived transgene expression," Human Gene Therapy, vol. 13, No. 13, pp. 1611-1620, Sep. 2002.

Lattanzi et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.

Lee et al., "Activation of innate immunity is required for efficient nuclear reprogramming," Cell, 2012, 151: 547-558.

Lee et al., "Nanoparticle delivery of Cas9 ribonucleoprotein and donor DNA in vivo induces homology-directed DNA repair," Nat Biomed Eng, 2017, 1: 889-901.

Lee et al., "Role of satellite cells versus myofibers in muscle hypertrophy induced by inhibition of the myostatin/activin signaling pathway," Proc Natl Acad Sci US A, 2012, 109(35): E2353-E2360.

Lee et al., "Targeted chromosomal deletions in human cells using zinc finger nucleases," Genome research 20, 2010, 81-89.

Lee, "Regulation of muscle mass by myostatin," Annu Rev Cell Dev Biol, 2004, 20: 61-86.

Li et al., "In vivo genome editing restores haemostasis in a mouse model of haemophilia," Nature 475, 2011, 217-221.

Li et al., "Engineering and selection of shuffled AAV genomes: a new strategy for producing targeted biological nanoparticles," Mol Ther, 2008, 16: 1252-1260.

Li et al., "Extensive promoter-centered chromatin interactions provide a topological basis for transcription regulation," Cell, 2012, 148: 84-98.

Li et al., "Locus control regions," Blood, 2002, 100: 3077-3086.

Li et al., "Marginal level dystrophin expression improves clinical outcome in a strain of dystrophin/utrophin double knockout mice," PLoS One, 2010, 5:e15286.

Li et al., "Modularly assembled designer TAL effector nucleases for targeted gene knockout and gene replacement in eukaryotes," Nucleic Acids Research, 2011, vol. 39, No. 14, pp. 6315-6325.

Li et al., "Precise correction of the dystrophin gene in duchenne muscular dystrophy patient induced pluripotent stem cells by TALEN and CRISPR-Cas9," Stem Cell Reports, 2015, 4: 143-154.

Li et al., "Preservation of muscle force in Mdx3cv mice correlates with low-level expression of a near full-length dystrophin protein," Am. J. Pathol., 2008, 172: 1332-1341.

Li et al., "RSEM: accurate transcript quantification from RNA-Seq data with or without a reference genome," BMC Bioinformatics, 2011, 12: 323.

Li et al., "Synthetic muscle promoters: activities exceeding naturally occurring regulatory sequences," Nature Biotechnology, 1999, 17: 241-245.

Li et al., "The role of chromatin during transcription," Cell, 2007, 128: 707-719.

Li et al., "The Sequence Alignment/Map format and SAM tools," Bioinformatics, 2009, 25: 2078-2079.

Li et al., "Transcription activator-like effector hybrids for conditional control and rewiring of chromosomal transgene expression," Scientific reports 2, 2012, 897.

Lian et al., "Robust cardiomyocyte differentiation from human pluripotent stem cells via temporal modulation of canonical Wnt signaling," Proc Natl Acad Sci, 2012, 109: E1848-E1857.

Liang et al., "Engineering biological systems with synthetic RNA molecules," Mol Cell 43, 2011, 915-926.

Liao et al., "The Subread aligner: fast, accurate and scalable read mapping by seed-and-vote," Nucleic Acids Res, 2013, 41: e108.

Lim et al., "Application of CRISPR/Cas9 for the Treatment of Duchenne Muscular Dystrophy," Journal of Personalized Medicine, 2018, 8(4): 1-20.

Limberis et al., "Transduction efficiencies of novel AAV vectors in mouse airway epithelium in vivo and human ciliated airway epithelium in vitro," Molecular therapy: the journal of the American Society of Gene Therapy, 2009, 17: 294-301.

Liu et al., "Adeno-associated virus-mediated microdystrophin expression protects young mdx muscle from contraction-induced injury," Mol. Ther., 2005, 11: 245-256.

Liu et al., "CRISPR Activation Screens Systematically Identify Factors that Drive Neuronal Fate and Reprogramming," Cell Stem Cell, 2018, 23: 758-771 e758.

Liu et al., "CRISPR-Based Chromatin Remodeling of the Endogenous Oct4 or Sox2 Locus Enables Reprogramming to Pluripotency," Cell Stem Cell, 2018, 22: 252-261 e254.

Lohmueller et al., "A tunable zinc finger-based framework for Boolean logic computation in mammalian cells," Nucleic Acids Res 40, 2012, 5180-5187.

Long et al., "Postnatal genome editing partially restores dystrophin expression in a mouse model of muscular dystrophy," Science, 2016, 351(6271):400-403.

Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.

Lu et al., "The status of exon skipping as a therapeutic approach to duchenne muscular dystrophy," Molecular Therapy 19, 2011, 9-15.

Lund et al. "Promoter-targeted phage display selections with preassembled synthetic zinc finger libraries for endogenous gene regulation." Journal of Molecular Biology, vol. 340, pp. 599-613, 2004.

Luo et al., "Synthetic DNA delivery systems," Nature Biotechnology, vol. 18, pp. 33-37, 2000.

Madigan et al., "Engineering AAV receptor footprints for gene therapy," Curr Opin Virol, 2016, 18: 89-96.

Madisen et al., "A robust and high-throughput Cre reporting and characterization system for the whole mouse brain," Nat Neurosci, 2010, 13: 133-140.

Maeder et al., "CRISPR RNA-guided activation of endogenous human genes," Nat Methods, 2013, 10: 977-979.

(56)     References Cited

OTHER PUBLICATIONS

Maeder et al., "Robust, synergistic regulation of human gene expression using TALE activators," Nature Methods, vol. 10, No. 3, pp. 243-246, Feb. 10, 2013, including pp. 1/14-14/14 of Supplementary Material.

Maeder, "Targeted DNA demethylation and activation of endogenous genes using programmable TALE-TET1 fusion proteins," Nat Biotechnol, 2013, 31(12): p. 1137-42.

Magli et al., "PAX7 Targets, CD54, Integrin α9β1, and SDC2, Allow Isolation of Human ESC/iPSC-Derived Myogenic Progenitors," Cell Rep, 2017, 19: 2867-2877.

Magnenat et al., "In vivo selection of combinatorial libraries and designed affinity maturation of polydactyl zinc finger transcription factors for ICAM-1 provides new insights into gene regulation," J Mol Biol, 2004, 341: 635-649.

Maheshri et al., "Directed evolution of adeno-associated virus yields enhanced gene delivery vectors," Nat Biotechnol, 2006, 24: 198-204.

Mali et al., "Cas9 as a versatile tool for engineering biology," Nat Methods, 2013, 10(10): p. 957-63.

Mali et al., "CAS9 transcriptional activators for target specificity screening and paired nickases for cooperative genome engineering," Nat Biotechnol, 2013, 31(9): p. 833-8.

Mali et al., "RNA-Guided Human Genome Engineering via Cas9," Science 339, 2013, 823-826.

Mamchaoui et al., "Immortalized pathological human myoblasts: towards a universal tool for the study of neuromuscular disorders," Skelet Muscle 1, 2011, 1-11.

Maniatis et al., "Regulation of inducible and tissue-specific gene expression," Science, 1987, 236(4806): 1237-1245.

Mann et al., "Improved antisense oligonucleotide induced exon skipping in the mdx mouse model of muscular dystrophy," J. Gene Med., 2002, 4: 644-654.

Manning et al., "What has the mdx mouse model of duchenne muscular dystrophy contributed to our understanding of this disease?," Journal of Muscle Research and Cell Motility, 2015, 36: 155-167.

Maruyama et al., "Epigenetic Regulation of Cell Type-Specific Expression Patterns in the Human Mammary Epithelium," PLoS Genetics, 2011, 7(4): e1001369, 15 pages.

Matsushita et al., "Adeno-associated virus vectors can be efficiently produced without helper virus," Gene Therapy, 1998, 5: 938.

McCarty et al, "Self-complementary recombinant adeno-associated virus (scAAV) vectors promote efficient transduction independently of DNA synthesis," Gene Ther, 2001, 8: 1248-1254.

McDowell et al., "A Structural and functional cross-talk between a distant enhancer and the epsilon-globin gene promoter shows interdependence of the two elements in chromatin," Molecular and Cellular Biology, 1999, 19: 7600-7609.

McFadden et al., "The Hand1 and Hand2 transcription factors regulate expansion of the embryonic cardiac ventricles in a gene dosage-dependent manner," Development, 2005, 132: 189-201.

McGreevy et al., "Animal models of Duchenne muscular dystrophy: from basic mechanisms to gene therapy," Disease Models Mechanisms, 2015, 8(3): 195-213.

Memedula et al., "Sequential recruitment of HAT and SWI/SNF components to condensed chromatin by VP16," Curr Biol, 2003, 13: 241-246.

Mendell et al., "Dystrophin immunity in Duchenne's muscular dystrophy," New England Journal of Medicine 363, 2010, 1429-1437.

Mendenhall et al., "Locus-specific editing of histone modification at endogenous enhancers," Nat Biotechnol, 2013, 31(12): p. 1133-6.

Mercer et al., "Regulation of Endogenous Human Gene Expression by Ligand-Inducible TALE Transcription Factors," ACS Synth Biol, 2013.

Mertens et al., "Evaluating cell reprogramming, differentiation and conversion technologies in neuroscience," Nat Rev Neurosci, 2016, 17: 424-437.

Miller et al., "A TALE nuclease architecture for efficient genome editing," Nat Biotechnol 29, 2011, 143-148.

Miller et al., "Transcriptional landscape of the prenatal human brain," Nature, 2014, 508: 199-206.

Mittler et al., "A novel docking site on Mediator is critical for activation by VP 16 in mammalian cells," EMBO J, 2003, 22: 6494-6504.

Mizushima et al., "pEF-BOS, a powerful mammalian expression vector," Nuc. Acids. Res., 1990, 18(17): 5322.

Montalbano et al., "High-Throughput Approaches to Pinpoint Function within the Noncoding Genome," Molecular Cell, 2017, 68: 44-59.

Montarras, "Direct Isolation of Satellite Cells for Skeletal Muscle Regeneration," Science, 2005, 309: 2064-2067.

Morris et al., "Dissecting engineered cell types and enhancing cell fate conversion via CellNet," Cell, 2014, 158: 889-902.

Morrissey et al., "Activity of stabilized short interfering RNA in a mouse model of hepatitis B virus replication," Hepatol, 2005, 41: 1349-1356.

Moscou et al., "A simple cipher governs DNA recognition by TAL effectors," Science 326, 2009, 1501.

Muir et al., "Engraftment potential of dermal fibroblasts following in vivo myogenic conversion in immunocompetent dystrophic skeletal muscle," Mol. Ther. Methods Clin. Dev., 2014, 1:14025.

Murphy et al., "The in vitro transcription of the 7SK RNA gene by RNA polymerase III is dependable only on the presence of an upstream promoter," Cell, 1987, 51:81-87.

Mussolino et al., "A novel TALE nuclease scaffold enables high genome editing activity in combination with low toxicity," Nucleic Acids Res 39, 2011, 9283-9293.

Muzycka, "Use of adeno-associated virus as a general transduction vector for mammalian cells," Curr. Top. Microbiol. Inmunol., 1992, 158: 97-129.

Myslinski et al., "An unusually compact external promoter for RNA polymerase III transcription of the human H1RNA gene," Nucleic Acids Res, 2001, 29:2502-2509.

Najm et al., "Orthologous CRISPR-Cas9 enzymes for combinatorial genetic screens," Nat Biotechnol, 2018, 36: 179-189.

Naldini, "Gene therapy returns to centre stage," Nature, 2015, 526: 351-360.

Nance et al., "AAV9 Edits Muscle Stem Cells in Normal and Dystrophic Adult Mice," Molecular Therapy, 2019, 27: 1568-1585.

Negroni et al., "In Vivo Myogenic Potential of Human CD133+ Muscle-derived Stem Cells: A Quantitative Study," Molecular Therapy 17, 2009, 1771-1778.

Nelson et al., "Engineering Delivery Vehicles for Genome Editing," Annual review of chemical and biomolecular engineering, 2016, 7: 637-662.

Nelson et al., "Genome engineering: a new approach to gene therapy for neuromuscular disorders," Nat Rev Neurol, 2017, 13: 647-661.

Nelson et al., "In vivo genome editing improves muscle function in a mouse model of Duchenne muscular dystrophy," Science, 2016, 351(6271):403-407.

Nelson et al., "Local and Systemic Gene Editing in a Mouse Model of Duchenne Muscular Dystrophy," Molecular Therapy, 2016, 24(Supp 1):S191.

Nelson et al., "Long-term evaluation of AAV-CRISPR genome editing for Duchenne muscular dystrophy," Nature Medicine, 2019, 25(3): 427-432.

Nishimasu et al., "Crystal structure of cas9 in complex with guide RNA and target DNA Cell," 2014, 156(5): p. 935-49.

Nissim et al., "Multiplexed and Programmable Regulation of Gene Networks with an Integrated RNA and CRISPR/Cas Toolkit in Human Cells," Mol Cell, 2014, 54: 698-710.

Nordhoff et al., "Comparative analysis of human, bovine, and murine Oct-4 upstream promoter sequences," Mamm Genome, 2001, 12: 309-317.

Odom et al., "Microutrophin Delivery Through rAAV6 Increases Lifespan and Improves Muscle Function in Dystrophic Dystrophin/ Utrophin-deficient Mice," Molecular Therapy, 2008, 16(9): 1539-1545.

O'Geen et al., "Ezh2-dCas9 and KRAB-dCas9 enable engineering of epigenetic memory in a context-dependent manner," Epigenetics Chromatin, 2019, 12: 26.

(56) References Cited

OTHER PUBLICATIONS

Ogryzko et al., "The transcriptional coactivators p300 and CBP are histone acetyltransferases," Cell, 1996, 87: 953-959.

Ohshima et al., "Nucleotide sequence of mouse genomic loci including a gene or pseudogene for U6 (4.85) nuclear RNA," Nucleic Acids Res, 1981, 9:5145-5158.

Okkenhaug et al., "PI3K in lymphocyte development, differentiation and activation," Nat. Rev. Immunol., 2003, 3(4): 317-330.

Olguin et al., "Pax-7 up-regulation inhibits myogenesis and cell cycle progression in satellite cells: a potential mechanism for self-renewal," Dev Biol, 2004, 275: 375-388.

Ong et al., "Enhancer function: new insights into the regulation of tissue-specific gene expression," Nature reviews. Genetics, 2011, 12: 283-293.

Osakabe et al., "FLAG-NLS-SpCas9-2A-GFBSD2 [Binary vector pEgP526-2A-GFBSD2]," National Center for Biotechnology Information, Genbank Entry, Retrieved from the Internet on Sep. 18, 2017 <https://www .ncbi.nlmnih gov/protein/BAVO1234>.

Ousterout et al., "Correction of dystrophin expression in cells from duchenne muscular dystrophy patients through genomic excision of exon 51 by zinc finger nucleases," Molecular Therapy 23, 2015, 523-532.

Ousterout et al., "Multiplex CRISPR/Cas9-based genome editing for correction of dystrophin mutations that cause Duchenne muscular dystrophy," Nature Communications, 2015, 6:6244.

Ousterout et al., "Reading frame correction by targeted genome editing restores dystrophin expression in cells from Duchenne muscular dystrophy patients," Mol Ther, 2013, 21:1718-1726.

Palu et al., "In pursuit of new developments for gene therapy of human diseases," J. Biotechnol. vol. 68, pp. 1-13, 1999.

Pang et al., "Induction of human neuronal cells by defined transcription factors," Nature, 2011, 476: 220-223.

Papapetrou, "Induced pluripotent stem cells, past and future," Science, 2016, 353: 991-992.

Papayannakos et al., "Understanding lentiviral vector chromatin targeting: working to reduce insertional mutagenic potential for gene therapy," Gene Ther, 2013, 20(6): p. 581-8.

Parekh et al., "Mapping Cellular Reprogramming via Pooled Overexpression Screens with Paired Fitness and Single-Cell RNA-Sequencing Readout," Cell Systems, 2018, 7: 548-555.e548.

Park et al., "Multi-Parametric MRI at 14T for Muscular Dystrophy Mice Treated with AAV Vector-Mediated Gene Therapy," PLoS One, 2015, 10(4): e0124914.

Park et al., "Phenotypic alteration of eukaryotic cells using randomized libraries of artificial transcription factors," Nat Biotechnol 21, 2003, 1208-1214.

Pattanayak et al., "High-throughput profiling of off-target DNA cleavage reveals RNA-programmed Cas9 nuclease specificity," Nat Biotechnol, 2013, 31(9): p. 839-43.

Pawlikowski et al., "Regulation of skeletal muscle stem cells by fibroblast growth factors," Dev Dyn, 2017, 246: 359-367.

Peault et al., "Stem and progenitor cells in skeletal muscle development, maintenance, and therapy," Molecular Therapy 15, 2007, 867-877.

Perez et al., "Establishment of HIV-1 resistance in CD4+ T cells by genome editing using zinc-finger nucleases," Nature biotechnology 26, 2008, 808-816.

Perez-Pinera et al., "Advances in targeted genome editing," Current Opinion in Chemical Biology 16, 2012, 268-277.

Perez-Pinera et al., "Gene targeting to the ROSA26 locus directed by engineered zinc finger nucleases," Nucleic Acids Research, 2012, 40:3741-3752.

Perez-Pinera et al., "RNA-guided gene activation by CRISPR-Cas9-based transcription factors," Nat Methods, 2013, 10: 973-976.

Perez-Pinera et al., "Synergistic and tunable human gene activation by combinations of synthetic transcription factors," Nature Methods, vol. 10, No. 3, pp. 239-244, Feb. 3, 2013, including pp. 1/12-12-12 of Supplementary Material.

Perez-Pinera et al., "Synergistic Transcriptional Activation by Combinations of Engineered TALEs" presented at the American Society of Gene & Cell Therapy's 15th Annual Meeting in Philadelphia, Pennsylvania, May 19, 2012. Abstract 855.

Persons, "Lentiviral vector gene therapy: effective and safe?" Mol Ther, 2010, 18(5): p. 861-2.

Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.

Pichavant et al., "Current status of pharmaceutical and genetic therapeutic approaches to treat DMD," Molecular Therapy 19, 2011, 830-840.

Pigozzo et al., "Revertant Fibers in the mdx Murine Model of Duchenne Muscular Dystrophy: An Age- and Muscle-Related Reappraisal," PLoS One, 2013, 8(8): e72147.

Polstein et al., "A light-inducible CRISPR-Cas9 system for control of endogenous gene activation," Nature Chemical Biology, 2015, 11: 198-200.

Polstein et al., "Genome-wide specificity of DNA-binding, gene regulation, and chromatin remodeling by TALE- and CRISPR/Cas9-based transcriptional activators," Genome Res, 2015, 25: 1158-1169.

Polstein et al., "Light-inducible spatiotemporal control of gene activation by customizable zinc finger transcription factors," J Am Chem Soc, 2012, 134(40): p. 16480-3.

Popplewell et al., "Gene correction of a duchenne muscular dystrophy mutation by meganuclease-enhanced exon knock-in," Hum Gene Ther, 2013, 24:692-701.

Qi et al., "Repurposing CRISPR as an RNA-guided platform for sequence-specific control of gene expression," Cell 152, 2013, 1173-1183.

Rackham et al., "A predictive computational framework for direct reprogramming between human cell types," Nature Genetics, 2016, 48: 331-335.

Rada-Iglesias et al., "A unique chromatin signature uncovers early developmental enhancers in humans," Nature, 2011, 470: 279-283.

Rahdar et al., "Synthetic CRISPR RNA-Cas9-Guided Genome Editing in Human Cells," Proceedings to the National Academy of Sciences of USA, 2015, 112(51): E7110-E7117.

Ramachandran et al., "Nitric Oxide Signaling Pathway in Duchenne Muscular Dystrophy Mice: Upregulation of L-arginine Transport," Biochem. J., 2012, 449: 133-142.

Ran et al., "Double nicking by RNA-guided CRISPR Cas9 for enhanced genome editing specificity," Cell, 2013, 154(6): p. 1380-9.

Ran et al., "In vivo genome editing using Staphylococcus aureus Cas9," Nature 520, 2015, 186-191.

Rao et al., "Engineering human pluripotent stem cells into a functional skeletal muscle tissue," Nat Commun, 2018, 9: 126.

Rebar et al., "Induction of angiogenesis in a mouse model using engineered transcription factors," Nat Med 8, 2002, 1427-1432.

Reynolds et al., "NuRD-mediated deacetylation of H3K27 facilitates recruitment of Polycomb Repressive Complex 2 to direct gene repression," The EMBO Journal, 2012, 31: 593-605.

Reyon et al., "FLASH assembly of TALENs for high-throughput genome editing," Nat Biotechnol 30, 2012, 460-465.

Riley, "PD-1 signaling in primary T cells," Immunological Reviews, 2009, 229: 114-125.

Riordan et al., "Application of CRISPR/Cas9 for biomedical discoveries," Cell & Bioscience, 2015, 5(1):11 pages.

Rivenbark et al., "Epigenetic reprogramming of cancer cells via targeted DNA methylation," Epigenetics, 2012, 7: 350-360.

Roadmap Epigenomics Consortium, "Integrative analysis of 111 reference human epigenomes," Nature, 2015, 518: 317-330.

Roudaut et al., "Restriction of calpain3 expression to the skeletal muscle prevents cardiac toxicity and corrects pathology in a murine model of limb-girdle muscular dystrophy," Circulation, 2013, 128: 1094-1104.

Rousseau et al., "Endonucleases: tools to correct the dystrophin gene" The Journal of Gene Medicine, 2011, vol. 13, pp. 522-537.

Sacco et al., "Short Telomeres and Stem Cell Exhaustion Model Duchenne Muscular Dystrophy in mdx/mTR Mice," Cell, 2010, 143: 1059-1071.

(56) References Cited

OTHER PUBLICATIONS

Sagal et al., "Proneural transcription factor Atoh1 drives highly efficient differentiation of human pluripotent stem cells into dopaminergic neurons," Stem Cells Transl Med, 2014, 3: 888-898.

Saito et al., "Specific activation of microRNA-127 with downregulation of the proto-oncogene BCL6 by chromatin-modifying drugs in human cancer cells," Cancer Cell, 2006, vol. 9, pp. 435-443.

Salmon et al., "Production and titration of lentiviral vectors," Curr Protoc Hum Genet, 2007, Chapter 12, Unit 12.10, Supplement 54, 24 pages.

Salmon et al., "Production and titration of lentiviral vectors," Curr Protoc Neurosci, 2006, Chapter 4: Unit 4 21.

Salva et al., "Design of tissue-specific regulatory cassettes for high-level rAAV-mediated expression in skeletal and cardiac muscle," Mol. Ther., 2007, 15:320-329.

Sambasivan et al., "Embryonic founders of adult muscle stem cells are primed by the determination gene Mrf4," Developmental Biology, 2013, 381: 241-255.

Sambrook et al., Molecular Cloning and Laboratory manual, Second Ed., Cold Spring Harbor (1989).

Sanson et al., "Optimized libraries for CRISPR-Cas9 genetic screens with multiple modalities," Nat Commun, 2018, 9: 5416.

Schmid-Burgk et al., "A ligation-independent cloning technique for high-throughput of transcription activator-like effector genes," Nat Biotechnol 31, 2012, 76-81.

Scholze et al., "TAL effectors are remote controls for gene activation," Current Opinion in Microbiology, vol. 14, pp. 47-53, Jan. 2011.

Schultz et al., "Recombinant adeno-associated virus transduction and integration," Molecular Therapy 16, 2008, 1189-1199.

Schultz et al., "SETDBI: a novel KAP-I-associated histone H3, lysine 9-specific methyltransferase that contributes to HPI-mediated silencing of euchromatic genes by KRAB zinc-finger proteins," Genes & Development, 2002, 16: 919-932.

Sebastiano et al., "In Situ Genetic Correction of the Sickle Cell Anemia Mutation in Human Induced Pluripotent Stem Cells Using Engineered Zinc Finger Nucleases," Stem Cells 29, 2011, 1717-1726.

Seidel et al., "Chromatin-modifying agents in anti-cancer therapy," Biochimie, 2012, vol. 94, pp. 2264-2279.

Sequence alignment: Seq ID No. 102920 (2019).

Sequence alignment: Seq ID No. 102921 (2019).

Sequence alignment: Seq ID No. 103735 (2019).

Sequence alignment: Seq ID No. 103736 (2019).

Seto et al., "Gene Replacement Therapies for Duchenne Muscular Dystrophy Using Adeno-Associated Viral Vectors," Current Gene Therapy, 2012, 12:139-151.

Sharma et al., "Efficiency of nonhomologous DNA and joining varies among somatic tissues, despite similarity in mechanism," Cellular and Molecular Life Science 68, 2011, 661-676.

Sharma et al., "In vivo genome editing of the albumin locus as a platform for protein replacement therapy," Blood, 2015, 126: 1777-1784.

Shelton et al., "Derivation and Expansion of PAX7-Positive Muscle Progenitors from Human and Mouse Embryonic Stem Cells," Stem Cell Rep, 2014, 3: 516-529.

Shen et al., "Combinatorial CRISPR-Cas9 screens for de novo mapping of genetic interactions," Nat Methods, 2017, 14: 573-576.

Shen et al., "Engraftment of a galactose receptor footprint onto adeno-associated viral capsids improves transduction efficiency," J. Biol. Chem., 2013, 288:28814-28823.

Shin et al., "Microdystrophin Ameliorates Muscular Dystrophy in the Canine Model of Duchenne Muscular Dystrophy," Mol. Ther., 2013, 21: 750-757.

Silva et al., "Meganucleases and other tools for targeted genome engineering: perspective and challenges for gene therapy," Current gene therapy, 2011, 11:11-27.

Skene et al., "Genetic identification of brain cell types underlying schizophrenia," Nat Genet, 2018, 50: 825-833.

Smith et al., "Myostatin inhibitors as therapies for muscle wasting associated with cancer and other disorders," Curr Opin Support Palliat Care, 2013, 7: 352-60.

Snowden et al., "Gene-specific targeting of H3K9 methylation is sufficient for initiating repression in vivo," Curr Biol, 2002, 12: 2159-2166.

Şöllü et al., "Autonomous zinc-finger nuclease pairs for targeted chromosomal deletion," Nucleic acids research 38, 2010, 8269-8276.

Song et al., "Dnase-seq: a high-resolution technique for mapping active gene regulatory elements across the genome from mammalian cells," Cold Spring Harbor protocols 2010, pdb prot5384.

Song et al., "Non-immunogenic utrophin gene therapy for the treatment of muscular dystrophy animal models," Nature Medicine, 2019, 25(10): 1505-1511.

Song et al., "Open chromatin defined by DNasel and FAIRE identifies regulatory elements that shape cell-type identify," Genome Res 21, 2011, 1757-1767.

Soutschek et al., "Therapeutic silencing of an endogenous gene by systemic administration of modified siRNAs," Nature, 2004, 432: 173-178.

Spitz et al., "Transcription factors: from enhancer binding to developmental control," Nat. Rev. Genet., 2012, 13: 613-626.

Sripathy et al., "The KAP1 corepressor functions to coordinate the assembly of de novo HP1-demarcated microenvironments of heterochromatin required for KRAB zinc finger protein-mediated transcriptional repression," Molecular and Cellular Biology, 2006, 26: 8623-8638.

Sternberg et al., "Conformational Control of DNA Target Cleavage by CR1SPR-Cas9," Nature, 2015, 527(7576): 110-113.

Sternberg et al., "DNA interrogation by the CRISPR RNA-guided endonuclease Cas9," Nature, 2014, 507: 62-67.

Stuelsatz et al., "A Contemporary Atlas of the Mouse Diaphragm: Myogenicity, Vascularity, and the Pax3 Connection" J Histochem Cytochem, 2012, 60(9): 638-657.

Su et al., "In vitro and in vivo mRNA delivery using lipid-enveloped pH-responsive polymer nanoparticles," Mol. Pharmaceutics, 2011, 8: 774-787.

Sun et al., "Optimized TAL effector nucleases (TALENs) for use in treatment of sickle cell disease," Molecular bioSystems 8, 2012, 1255-1263.

Suzuki et al., "In vivo genome editing via CRISPR/Cas9 mediated homology-independent targeted integration," Nature, 2016, 540: 144-149.

Szyf, "Epigenetics, DNA methylation, and chromatin modifying drugs," Annual Review of Pharmacology and Toxicology, 2009, vol. 49, pp. 243-263.

Tabebordbar et al., "In vivo gene editing in dystrophic mouse muscle and muscle stem cells," Science, 2015, 351(6271):407-411.

Takahashi et al., "A decade of transcription factor-mediated reprogramming to pluripotency," Nature Reviews, 2016, 17: 183-193.

Takahashi et al., "Induction of pluripotent stem cells from adult human fibroblasts by defined factors," Cell, 2007, 1131: 861-872.

Takahashi et al., "Induction of pluripotent stem cells from mouse embryonic and adult fibroblast cultures by defined factors," Cell, 2006, 126: 663-676.

Takeshima et al., "Mutation spectrum of the dystrophin gene in 442 Duchene/Becker muscular dystrophy cases from one Japanese referral center," Journal of Human Genetics, 2010, 55: 379-388.

Tan et al., "Efficient derivation of lateral plate and paraxial mesoderm subtypes from human embryonic stem cells through GSKi-mediated differentiation," Stem Cells Dev, 2013, 22: 1893-1906.

Tanenbaum et al., "A Protein-Tagging System for Signal Amplification in Gene Expression and Fluorescence Imaging," Cell, 2014, 159(3): 635-646.

Taniguchi-Ikeda et al., "Pathogenic exon-trapping by SVA retrotransposon and rescue in Fukuyama muscular dystrophy," Nature 478, 2011, 127-131.

Tebas et al., "Gene editing of CCR5 in autologous CD4 T cells of persons infected with HIV," N Engl J Med, 2014, 370:901-910.

Tedesco et al., "Repairing skeletal muscle: regenerative potential of skeletal muscle stem cells," J Clin Invest, 2010, 120:11-19.

(56) References Cited

OTHER PUBLICATIONS

Tedesco et al., "Stem Cell-Mediated Transfer of a Human Artificial Chromosome Ameliorates Musculat Dystrophy," Science Translational Medicine 3, 96ra78-96ra78, 2011.

Tedesco et al., "Transplantation of Genetically Corrected Human iPSC-Derived Progenitors in Mice with Limb-Girdle Muscular Dystrophy," Science Translational Medicine 4, 140ra189, 2012.

Teratani-Ota et al., "Induction of specific neuron types by overexpression of single transcription factors," In Vitro Cell Dev Biol Anim, 2016, 52(9): 961-973.

Thakore et al., "Editing the epigenome: technologies for programmable transcription and epigenetic modulation," Nat Methods, 2016, 13: 127-137.

Thakore et al., "RNA-guided transcriptional silencing in vivo with S. aureus CRISPR-Cas9 repressors," Nat Commun, 2018, 9: 1674.

Theodorou et al., "A high throughput embryonic stem cell screen identifies Oct-2 as a bifunctional regulator of neuronal differentiation," Genes Dev, 2009, 23: 575-588.

Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," Virol., 1994, 204: 304-311.

Thorgeirsson et al., "A variant associated with nicotine dependence, lung cancer and peripheral arterial disease," Nature, 2008, 452: 638-642.

Thurman et al., "The accessible chromatin landscape of the human genome," Nature, 2012, 489: 75-82.

Tian et al., "CRISPR Interference-Based Platform for Multimodal Genetic Screens in Human iPSC-Derived Neurons," Neuron, 2019, 104: 239-255 e212.

Tinsley et al., "Amelioration of the dystrophic phenotype of mdx mice using a truncated utrophin transgene," Nature, 1996, 384(6607): 349-353.

Tone et al., "Smad3 and NFAT cooperate to induce Foxp3 expression through its enhancer," Nat. Immunol., 2008, 9: 194-202.

Truong et al., "Development of an intein-mediated split-Cas9 system for gene therapy," Nucleic Acids Res., 2015, 43: 6450-6458.

Tsuchiya et al., "The "Spanning Protocol": A new DNA extraction method for efficient single-cell genetic diagnosis," Journal of Assisted Reproduction Genetics, 2005, 22(11-12):407-14.

Tsunemoto et al., "Diverse reprogramming codes for neuronal identity," Nature, 2018, 557: 375-380.

Tuan et al., "Transcription of the hypersensitive site HS2 enhancer in erythroid cells," Proceedings of the National Academy of Sciences of the United States of America, 1992, 89: 11219-11223.

Tycko et al., "Screening S. aureus CRISPR-Cas9 Paired Guide RNAs for Efficient Targeted Deletion in Duchenne Muscular Dystrophy," Editas, Poster presented on May 5, 2016.

Uchida et al, "In Vivo Messenger RNA Introduction into the Central Nervous System Using Polyplex Nanomicelle," PLoS One, 2013, 8: e56220.

Uetsuki et al., "Isolation and Characterization of the Human Chromosomal Gene for Polypeptide Chain Elongation Factor-1α," J. Biol. Chem., 1989, 264(10): 5791-5798.

Urnov et al., "Highly efficient endogenous human gene correction using designed zinc-finger nucleases," Nature 435, 2005, 646-651.

Vakoc et al., "Proximity among distant regulatory elements at the beta-globin locus requires GATA-1 and FOG-1," Molecular Cell, 2005, 17: 453-462.

Van Arensbergen et al., "Genome-wide mapping autonomous promoter activity in human cells," Nature Biotechnology, 2017, 35(2): 145-153.

Van Deutekom et al., "Advances in Duchenne muscular dystrophy gene therapy," Nat. Rev. Genet., 2003, 4: 774-783.

Van Putten et al., "Low dystrophin levels in heart can delay heart failure in mdx mice," J Mol Cell Cardiol, 2014, 69C:17-23.

Van Putten et al., "Low dystrophin levels increase survival and improve muscle pathology and function in dystrophin/utrophin double-knockout mice," FASEB J, 2013, 27:2484-2495.

Vaquerizas et al., "A census of human transcription factors: function, expression and evolution," Nat Rev Genet, 2009, 10: 252-263.

Veltrop et al., "A dystrophic Duchenne mouse model for testing human antisense oligonucleotides," PLoS One, 2018, 13(2): e0193289, 18 pages.

Verkhusha et al., "GFP-like flourescent proteins and chromoproteins of the class Anthozoa," Protein Structures: Kaleidoscope of Structural Properties and Functions, 2003, 405-439.

Verma et al., "Gene Therapy: Twenty-first century medicine," Annual Review of Biochemistry, vol. 74, pp. 711-738, 2005.

Verma et al., "Gene therapy—promises, problems and prospects," Nature, vol. 389, pp. 239-242, 1997.

Vierbuchen et al., "Direct conversion of fibroblasts to functional neurons by defined factors," Nature 463, 2010, 1035-1041.

Vierbuchen et al., "Direct lineage conversions: unnatural but useful? ," Nat Biotechnol, 2011, 29: 892-907.

Vierbuchen et al., "Molecular roadblocks for cellular reprogramming," Mol Cell, 2012, 47: 827-838.

Visel et al., "ChIP-seq accurately predicts tissue-specific activity of enhancers," Nature, 2009, 457: 854-858.

Vorobyov et al., "Expression of two protein isoforms of PAX7 is controlled by competing cleavage-polyadenylation and splicing," Gene, 2004, 342: 107-112.

Voss et al., "The role of enhancers in the regulation of cell-type-specific transcriptional control," Trends Biochem. Sci., 1986, 11(7): 287-289.

Waddell et al., "DIk1 Is Necessary for Proper Skeletal Muscle Development and Regeneration," PLoS One, 2010, 5(11): e15055.

Wagner et al., "A phase 1/11 trial of MYO-029 in adult subjects with muscular dystrophy," Ann Neurol, 2008, 63: 561-571.

Waldrop et al., "Update in Duchenne and Becker muscular dystrophy," Current Opinion in Neurology, 2019, 32: 722-727.

Wang et al., "Adeno-associated virus serotype 8 efficiently delivers genes to muscle and heart," Nat. Biotechnol., 2005, 23: 321-328.

Wang et al., "Adeno-associated virus vector carrying human minidystrophin genes effectively ameliorates muscular dystrophy in mdx mouse model," Proc Natl Acad Sci US A. (2000) 97(25):13714-13719.

Wang et al., "Construction and analysis of compact muscle-specific promoters for AAV vectors," Gene Ther, 2008, 15: 1489-1499.

Wang et al., "Efficient delivery of genome-editing proteins using bioreducible lipid nanoparticles," Proc Natl Acad Sci USA, 2016, 113(11): 2868-2873.

Wang et al., "Epstein-Barr virus nuclear protein 2 interacts with p300, CBP, and PCAF histone acetyltransferases inactivation of the LMP1 promoter," Proc Natl Acad Sci USA, 2000, 97: 430-435.

Wang et al., "Genome-wide mapping of HATs and HDACs reveals distinct functions inactive and inactive genes," Cell, 2009, 138: 1019-1031.

Wang et al., "One-Step Generation of Mice Carrying Mutations in Multiple Genes by CRISPR-Cas-Mediated Genome Engineering," Cell, 2013, 153(4): p. 910-8.

Wang et al., "Systemic human minidystrophin gene transfer improves functions and life span of dystrophin and dystrophin/utrophin-deficient mice," J. Orthop. Res., 2009, 27: 421-426.

Wapinski et al., "Hierarchical mechanisms for direct reprogramming of fibroblasts to neurons," Cell, 2013, 155: 621-635.

Wein et al., "Efficient bypass of mutations in dysferlin deficient patient cells by antisense-induced exon skipping," Hum Mutat 31, 2010, 136-142.

Welch et al., "PTC124 targets genetic disorders caused by nonsense mutations," Nature 447, 2007, 87-91.

Weltner et al., "Human pluripotent reprogramming with CRISPR activators," Nat Commun Lond, 2018, 9: 1-12.

Westendorp et al., "E2F7 represses a network of oscillating cell cycle genes to control S-phase progression," Nucleic Acids Res, 2012, 40: 3511-3523.

Whisstock et al., "Prediction of protein function from protein sequence," Q Rev Biophysics, 2003, 36(3): 307-340.

Wienert et al., "Editing the genome to introduce a beneficial naturally occurring mutation associated with increased fetal globin," Nat Commun 6, 2015, 7085.

(56) References Cited

OTHER PUBLICATIONS

Willmann et al., "Mammalian animal models for Duchenne muscular dystrophy," Neuromuscular Disorders, 2009, 19(4): 241-249.

Wood, "Neuromuscular disease: CRISPR/Cas9 gene-editing platform corrects mutations associated with Duchenne muscular dystrophy," Nature Reviews Neurology, 2015, 11(4):184.

Wu et al., "A Myogenic Double-Reporter Human Pluripotent Stem Cell Line Allows Prospective Isolation of Skeletal Muscle Progenitors," Cell Rep, 2018, 25: 1966-1981.e4.

Wu et al., "Genome-wide binding of the CRISPR endonuclease Cas9 in mammalian cells," Nat Biotechnol, 2014, 32: 670-676.

Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039.e6.

Wylie et al., "Distinct transcriptomes define rostral and caudal serotonin neurons," J Neurosci, 2010, 30: 670-684.

Xie et al., "sgRNAcas9: a software package for designing CRISPR sgRNA and evaluating potential off-target cleavage sites," PLoS One, 2014, 9(6): e100448.

Xu et al., "CRISPR-mediated Genome Editing Restores Dystrophin Expression and Function in mdx Mice," Molecular Therapy: The Journal of the American Society of Gene Therapy, 2016, 24(3):564-569.

Xu et al., "Direct lineage reprogramming: strategies, mechanisms, and applications," Cell Stem Cell, 2015, 16: 119-134.

Xu et al., "Human Satellite Cell Transplantation and Regeneration from Diverse Skeletal Muscles," Stem Cell Rep, 2015, 5: 419-434.

Xu et al., "Recent advances in neuroepigenetic editing," Curr Opin Neurobiol, 2019, 59: 26-33.

Xue et al., "Synthetic mRNAs Drive Highly Efficient iPS Cell Differentiation to Dopaminergic Neurons," Stem Cells Transl Med, 2019, 8: 112-123.

Yan et al., "Drugging the Undruggable: Transcription Therapy for Cancer," Biochimica et Biophysica Acta, vol. 1835, No. 1, pp. 76-85, Jan. 2013.

Yang et al., "Generation of pure GABAergic neurons by transcription factor programming," Nat Methods, 2017, 14: 621-628.

Yang, "Optimization of scarless human stem cell genome editing," Nucleic Acids Res, 2013, 41:9049-9061.

Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.

Young et al., "Creation of a Novel Humanized Dystrophic Mouse Model of Duchenne Muscular Dystrophy and Application of a CRISPR/Cas9 Gene Editing Therapy," Journal of Neuromuscular Diseases, 2017, 4(2): 139-145.

Youngblood et al., "Chronic virus infection enforces demethylation of the locus that encodes PD-1 in antigen-specific cos+ T cells," Immunity, 2011, 35: 400-412.

Yusa et al., "Targeted gene correction of α1-antitrypsin deficiency in induced pluripotent stem cells," Nature 478, 2011, 391-394.

Zetsche et al., "Cpf1 Is a Single RNA-Guided Endonuclease of a Class 2 CRISPR-Cas System," Cell, 2015, 163(3):759-71.

Zhang et al. "Efficient construction of sequence-specific TAL effectors for modulating mammalian transcription," Nat Biotechnol 29, 2011, 149-153.

Zhang et al., "Adenovirus-Adeno-Associated Virus Hybrid for Large-Scale Recombinant Adeno-Associated Virus Production," Hum Gene Ther, 2009, 20: 922-929.

Zhang et al., "Comprehensive Structure-Function Study of Neurogenin3 Disease-Causing Alleles during Human Pancreas and Intestinal Organoid Development," Dev Cell, 2019, 50(3): 367-380.e7.

Zhang et al., "Efficient precise knockin with a double cute HDR donor after CRISPR/Cas9-mediated double-stranded DNA cleavage," Genome Biol, 2017 18(35): 18 pages.

Zhang et al., "Model-based analysis of ChIP-Seq (MACS)," Genome Biology, 2008, 9: R137.

Zhang et al., "Rapid single-step induction of functional neurons from human pluripotent stem cells," Neuron, 2013, 78: 785-798.

Zhao et al., "The LIM-homeobox gene Lhx8 is required for the development of many cholinergic neurons in the mouse forebrain," Proc Natl Acad Sci U S A, 2003, 100: 9005-9010.

Zheng et al., "Role of conserved non-coding DNA elements in the Foxp3 gene in regulatory T-cell fate," Nature, 2010, 463: 808-812.

Zhou et al., "Haploinsufficiency of utrophin gene worsens skeletal muscle inflammation and fibrosis in mdx mice," Journal of the Neurological Sciences, 2008, 264(1): 106-111.

Zhou et al., "High-throughput screening of a CRISPR/Cas9 library for functional genomics in human cells," Nature, 2014, 509(7501): 487-491.

Zhu et al., "Cellular senescence in human telomerase reverse transcriptase and cyclin—dependent kinase 4: consequences in aging muscle and therapeutic strategies for muscular dystrophies," Aging cell 6, 2007, 515-523.

Zincarelli et al., "Analysis of AAV serotypes 1-9 mediated gene expression and tropism in mice after systemic injection," Mol Ther, 2008, 16: 1073-1080.

Zou et al., "Site-specific gene correction of a point mutation in human iPS cells derived from an adult patient with sickle cell disease," Blood 118, 2011, 4599-4608.

Ousterout et al., "Genetic Correction of Duchenne Muscular Dystrophy Using Zinc Finger Nucleases," Mol. Ther., 2013, vol. 21, Supplement 1, 292, p. S111-S112.

Rousseau et al., "New TALENs To Correct the Reading Frame of Exon 54 of the Dystrophin Gene," Mol. Ther., 2013, vol. 21, Supplement 1, 293, p. S112.

Invitation to Pay Additional Fees for Application No. PCT/US2017/042921 dated Sep. 22, 2017 (3 pages).

International Search Report and Written Opinion for Application No. PCT/US2017/042921 dated Nov. 9, 2017 (21 pages).

International Search Report and Written Opinion for Application No. PCT/US2016/064285 dated Apr. 6, 2017 (21 pages).

International Search Report and Written Opinion for Application No. PCT/US2017/031351 dated Nov. 21, 2017 (22 pages).

International Search Report and Written Opinion for Application No. PCT/US2020/028154 dated Sep. 30, 2020 (17 pages).

International Search Report and Written Opinion for Application No. PCT/US2020/028148 dated Jul. 28, 2020 (13 pages).

International Search Report and Written Opinion for Application No. PCT/US2020/045544 dated Oct. 6, 2020 (16 pages).

International Search Report and Written Opinion for Application No. PCT/US2020/047083 dated Feb. 2, 2021 (17 pages).

International Search Report and Written Opinion for Application No. PCT/US2020/047080 dated Feb. 12, 2021 (14 pages).

International Search Report and Written Opinion for Application No. PCT/US2020/063150 dated Mar. 10, 2021 (11 pages).

International Search Report and Written Opinion for Application No. PCT/US2021/0029482 dated Sep. 1, 2021 (13 pages).

International Search Report and Written Opinion for Application No. PCT/US2021/029424 dated Sep. 17, 2021 (15 pages).

International Search Report and Written Opinion for Application No. PCT/US2021/029498 dated Sep. 17, 2021 (15 pages).

International Search Report and Written Opinion for Application No. PCT/US2021/056122 dated Mar. 24, 2022 (16 pages).

United States Patent Office Action for U.S. Appl. No. 16/098,464 dated Jun. 21, 2021 (12 pages).

United States Patent Office Action for U.S. Appl. No. 16/318,745 dated Jul. 13, 2021 (9 pages).

United States Patent Office Action for U.S. Appl. No. 15/779,633 dated Aug. 31, 2021 (8 pages).

United States Patent Office Action for U.S. Appl. No. 16/098,464 dated Nov. 15, 2021 (12 pages).

United States Patent Office Action for U.S. Appl. No. 16/318,745 dated Jan. 3, 2022 (9 pages).

United States Patent Office Action for U.S. Appl. No. 15/779,633 dated Dec. 15, 2021 (13 pages).

Gulf Cooperation Council Patent Office Examination Report for Application No. 2020/39547 dated Aug. 18, 2021 (5 pages).

Bulcha et al., "Viral vector platforms within the gene therapy landscape," Signal Transduction and Targeted Therapy, 2021, 6: 53.

Duchêne et al., "CRISPR-Induced Deletion with SaCas Restores Dystrophin Expression in Dystrophic Models In Vitro and In Vivo,"

(56)　　　　　　References Cited

OTHER PUBLICATIONS

Molecular Therapy: The Journal of the American Society of Gene Therapy, 2018, 26(11): 2604-2616.

Taiwanese Patent Office Action for Application No. 109112555 dated Jul. 1, 2024 (16 pages, English translation included).

Saudi Arabia Patent Office Examination Report for Application No. 521430583 dated Jun. 13, 2024 (14 pages, English translation included).

Colombian Patent Office Action for Application No. NC2021/0013692 dated Jul. 16, 2024 (48 pages, English translation included).

Chinese Patent Office Action for Application No. 202080028248.2 dated Aug. 8, 2024 (27 pages, English translation included).

United States Patent Office Notice of Allowance for U.S. Appl. No. 15/779,633 dated Sep. 5, 2024 (8 pages).

Hideki et al., Geneseq Accession No. BFK30060, 2018. Reference in U.S. Appl. No. 16/963,034, U. S. Patent Office Action dated Jun. 27, 2024.

Kotterman et al., "Engineering adeno-associated viruses for clinical gene therapy," Nature Reviews, 2014, 15(7): 445-451.

Lenzi et al., "Oversight and Review of Clinical Gene Transfer Protocols: Assessing the Role of the Recombinant DNA Advisory Committee," NCBI Bookshelf, A Service of the National Library of Medicine, National Institute of Health, Washington, DC, National Academies Press, US, 2014, pp. 1-16.

Liao, "Targeted disruption of DNMT1, DNMT3A and DNMT3B in human embryonic stem cells," Nature Genetics, 2015, 47(5): 469-478.

Long et al., "Correction of Diverse Muscular Dystrohpy Mutations in Human Engineered Heart Muscle by Single-Site Genome Editing," Sci Adv, 2018, 4(1): eaap9004.

Maggio et al., "Adenoviral vectors encoding CRISPR/Cas9 multiplexes rescue dystrophin synthesis in unselected populations of DMD muscle cells," Scientific Reports, 2016, 6: 37051.

Shim et al., "Nonviral Delivery Systems for Cancer Gene Therapy: Strategies and Challenges," Current Gene Therapy, 2017, 17(5): 1-18.

Swiech et al., "In vivo interrogation of gene function in the mammalian brain using CRISPR-Cas9," Nature Biotechnology, 2014, 33(1): 102-106 (Supplementary Information included).

Thule et al., "Engineered Insulin Secretion in Human Primary Thyroid Cells," Molecular Therapy, 2012, 20(Supplement 1): S164, Article 421.

United States Patent Office Notice of Allowance for U.S. Appl. No. 16/318,745 dated Aug. 22, 2024 (8 pages).

Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.

Min et al., "CRISPR Correction of Duchene Muscular Dystrophy Exon 44 Deletion Mutations in Mice and Human Cells," Science Advances, 2019, 5: eaav4324.

Robinson-Hamm et al., "Gene therapies that restore dystrophin expression for the treatment of Duchenne muscular dystrophy," Human Genetics, 2016, 135(9): 1029-1040.

Yu et al., "Dystrophin-deficient large animal models: translational research and exon skipping," Am J Transl Res, 2015, 7(8): 1314-1331.

United States Patent Office Action for U.S. Appl. No. 15/779,633 dated Apr. 19, 2023 (12 pages).

Saudi Arabia Patent Office Examination Report for Application No. 521430583 dated Mar. 26, 2023 (11 pages, English translation included).

Canadian Patent Office Action for Application No. 3,137,248 dated May 5, 2023 (5 pages).

Park et al., "Cas-Designer: a web-based tool for choice of CRISPR-Cas9 target sites," Bioinformatics, 2015, 31(24): 4014-4016.

Shen et al., "Massively parallel cis-regulatory analysis in the mammalian central nervous system," Genome Research, 2015, 26(2): 238-255.

Chhatwal et al., "Identification of cell-type-specific promoters within the brain using lentiviral vectors," Gene Therapy, 2007, 14(7): 575-583.

Trinklein et al., "Identification and functional analysis of human transcriptional promoters," Genome Research, 2003, 13(2): 308-312.

United States Patent Office Action for U.S. Appl. No. 16/098,464 dated Aug. 1, 2023 (16 pages).

U.S. Appl. No. 18/180,718, filed Mar. 8, 2023.

U.S. Appl. No. 18/279,996, filed Mar. 1, 2022.

U.S. Appl. No. 18/415,321, filed Jan. 17, 2024.

U.S. Appl. No. 18/405,995, filed Jan. 5, 2024.

U.S. Appl. No. 18/036,862, filed Jan. 25, 2024.

U.S. Appl. No. 18/180,718, filed Feb. 22, 2024.

United States Office Action for U.S. Appl. No. 16/318,745 dated Aug. 11, 2023 (12 pages).

Liu et al., "A CRISPR-Cas9 Strategy for Activating the Saccharopolyspora erythraea Erythromycin Biosynthetic Gene Cluster with Knock-in Bidirectional Promoters," ACS Synth. Biol. 2019, 8(5): 1134-1143.

Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.

Razzouk, "CRISPR-Cas9: A cornerstone for the evolution of precision medicine," Annal of Human Genetics, 2018, 82 (6): 331-357.

Simeonov et al., "Discovery of stimulation-responsive immune enhancers with CRISPR activation," Nature, 2017, 549 (7670): 111-115.

Canadian Patent Office Action for Application No. 3,137,248 dated Oct. 7, 2024 (6 pages, English translation included).

Japanese Patent Office Action for Application No. 2021-560849 dated Sep. 30, 2024 (5 pages, English translation included).

United Arab Emirates Patent Office Examination Report for Application No. P6001873/2021 dated Sep. 9, 2024 (11 pages).

Adikusuma et al., "Versatile single-step-assembly CRISPR/Cas9 vectors for dual gRNA expression," 2017, 12(12): e0187236.

Carcagno et al., "Neurogenin3 Restricts Serotonergic Neuron Differentiation to the Hindbrain," The Journal of Neuroscience, 2014, 34(46): 15223-15233.

Kalsner et al., "Prader-Willi, Angelman, and 15q11-q13 Duplication Syndromes," Pediatric Clinics of North America United States, 2015, 62(3): 587-606.

Ohta et al., "Imprinting-Mutation Mechanisms in Prader-Willi Syndrome," The American Journal of Human Genetics, 1999, 64(2): 397-413.

Yang et al., "A dual AAV system enables the Cas9-mediated correction of a metabolic liver disease in newborn mice," Nature Biotechnology, 2016, 34(3): 334-338.

United States Patent Office Notice of Allowance for U.S. Appl. No. 15/779,633 dated Sep. 28, 2023 (9 pages).

Eurasian Patent Office Action for Application No. 202192815 dated Sep. 19, 2023 (6 pages, English translation included).

Singapore Patent Office Search Report and Written Opinion for Application No. 11202111172Q dated Nov. 3, 2023 (12 pages).

Black et al., "Synthetic transcription factors for cell fate reprogramming," Current Opinion in Genetics & Development 2018, 52, 13-21.

Ahern, "Biochemical, Reagents Kits Offer Scientists Good Return On Investment," The Scientist Magazine, (accessed at https://www.the-scientist.com/technology/biochemical-reagents-kits-offer-scientists-good-return-on-investment-58425 on Dec. 14, 2023) (Year: 1995).

Bennett et al., "Detection of mutations in the dystrophin gene via automated DHPLC screening and direct sequencing," BMC Genet, 2001, 2: 17.

Bikard et al., "Programmable repression and activation of bacterial gene expression using an engineered CRISPR-Cas system," Nucleic Acids Research, 2013, 41(15): 7429-7437.

Echigoya et al., "Multiple Exon Skipping in the Duchenne Muscular Dystrophy Hot Spots: Prospects and Challenges," J Pers Med, 2018, 8(4): 41.

(56) References Cited

OTHER PUBLICATIONS

Jangid et al., "Biodirectional promoters exhibit characteristic chromatin modification signature associated with transcription elongation in both sense and antisense directions," BMC Genomics, 2018, 19: 313.

Mitsunobu et al., "Beyond Native Cas9: Manipulating Genomic Information and Function," Trends in Biotechnology, 2017, 35(10): 986-996.

NCBI Reference Sequence: NG_012232.1, "*Homo sapiens* dystrophin (DMD), RefSeqGene (LRG_199) on chromosome X," National Library of Medicine (accessed at: https://www.ncbi.nlm.nih.gov/nuccore/NG_012232.1/) (Year: 1993).

NCBI Reference Sequence: WP_038431314.1 "type II CRISPR RNA-guided endonuclease Cas9 [*Streptococcus pyogenes*]," National Library of Medicine (accessed at: https:// www.ncbi.nlm.nih.gov/protein/WP_038431314.1) (Year: 2005).

Pinder et al., "Nuclear domain 'knock-in' screen for the evaluation and identification of small molecule enhancers of CRISPR-based genome editing," Nucleic Acids Research, 2015, 43(19): 9379-9392.

Colombian Patent Office Action for Application No. NC2021/0013692 dated Dec. 2, 2024 (41 pages, English translation included).

Tremblay et al., "Gene Editing for Duchenne Muscular Dystrophy Using the CRISPR/Cas9 Technology: The Importance of Fine-tuning the Approach," Molecular Therapy, The Journal of the American Society of Gene Therapy, 2016, 24(11): 1888-1889.

Warnock et al., "Introduction to Viral Vectors," Viral Vectors for Gene Therapy: Methods in Molecular Biology, 2011, vol. 737, Chapter 1, 25 pages.

United States Patent Office Action for U.S. Appl. No. 17/603,329 dated Jan. 13, 2025 (31 pages).

Singapore Patent Office Search Report and Written Opinion for Application No. 11202111172Q dated Nov. 26, 2024 (7 pages).

Thailand Patent Office Action for Application No. 2101006328 dated Dec. 16, 2024 (6 pages, English translation included).

Abdennur et al., "Cooler: scalable storage for Hi-C data and other genomically labeled arrays," Bioinformatics, 2020, 36: 311-316.

Achterberg et al., "The nano-scale mechanical properties of the extracellular matrix regulate dermal fibroblast function," J. Invest. Dermatol, 2014, 134: 1862-1872.

Akter et al., "FAM98A associates with DDX1-C14orf166-FAM98B in a novel complex involved in colorectal cancer progression," Int. J. Biochem. Cell Biol., 2017, 84: 1-13.

Andreu et al.,"Mechanical force application to the nucleus regulates nucleocytoplasmic transport," Nat. Cell Biol., 2022, 24: 896-905.

Arda et al., "Quantitative assessment of normal soft-tissue elasticity using shear-wave ultrasound elastography," AJR Am. J. Roentgenol., 2011, 197: 532-536.

Aubel et al., "Mammalian synthetic biology—from tools to therapies," BioEssays, 2010, 32(4): 332-345.

Babic et al., "CYR61, a product of a growth factor-inducible immediate early gene, promotes angiogenesis and tumor growth," Proc. Natl. Acad. Sci. U.S.A., 1998, 95: 6355-6360.

Baek et al., "DNA-free two-gene knockout in Chlamydomonas reinhardtii via CRISPR-Cas9 ribonucleoproteins," Scientific Reports, 2016, 6:30620.

Balko et al., "Activation of MAPK pathways due to DUSP4 loss promotes cancer stem cell-like phenotypes in basal-like breast cancer," Cancer Res, 2013, 73: 6346-6358.

Behan et al., "Prioritization of cancer therapeutic targets using CRISPR-Cas9 screens," Nature, 2019, 568: 511-516.

Benabdallah et al., "Decreased Enhancer-Promoter Proximity Accompanying Enhancer Activation," Mol. Cell, 2019, 76: 473-484.e7.

Beningo et al., "Traction forces of fibroblasts are regulated by the Rho-dependent kinase but not by the myosin light chain kinase," Arch. Biochem. Biophys., 2006, 456: 224-231.

Berginski et al., "The Focal Adhesion Analysis Server: a web tool for analyzing focal adhesion dynamics," F1000Res., 2013, 2: 68.

Bischoff et al., "RanGAP1 induces GTPase activity of nuclear Ras-related Ran," Proc. Natl. Acad. Sci. U.S.A., 1994, 91: 2587-2591.

Bolger et al., "Trimmomatic: a flexible trimmer for Illumina sequence data," Bioinformatics, 2014, 30: 2114-2120.

Braun et al., "Rapid and reversible epigenome editing by endogenous chromatin regulators," Nat Commun, 2017, 8(1): 560.

Canver et al., "BCL11A enhancer dissection by Cas9-mediated in situ saturating mutagenesis," Nature, 2015, 527: 192-197.

Chang et al., "GEF-H1 couples nocodazole-induced microtubule disassembly to cell contractility via RhoA," Mol Biol Cell, 2008, 19: 2147-2153.

Chang et al., "The SWI/SNF complex is a mechanoregulated inhibitor of YAP and TAZ," Nature, 2018, 563: 265-269.

Chen et al., "Connective Tissue Growth Factor: From Molecular Understandings to Drug Discovery," Front Cell Dev Biol, 2020, 8: 593269.

Chen et al., "Geometric control of cell life and death," Science, 1997, 276: 1425-1428.

Chen, "Mechanotransduction—a field pulling together?" J. Cell Sci., 2008, 121: 3285-3292.

Chrzanowska-Wodnicka et al., "Rho-stimulated contractility drives the formation of stress fibers and focal adhesions," J Cell Biol, 1996, 133: 1403-1415.

Clement et al., "CRISPResso2 provides accurate and rapid genome editing sequence analysis," Nat. Biotechnol., 2019, 37: 224-226.

Corces et al., "Omni-ATAC-seq: improved ATAC-seq protocol" Protocol exchange, [Preprint] 2017.

Cosgrove et al., "Mechanosensitive genomic enhancers potentiate the cellular response to matrix stiffnes," Posted Jan. 10, 2024. bioRxiv Jan. 10, 2024:2024.01.10.574997.

Darnell et al. "RNA-seq reveals diverse effects of substrate stiffness on mesenchymal stem cells," Biomaterials, 2018, 181: 182-188.

Devos et al., "Practical Limits of Fuction Prediction," Proteins: Structure, Function, and Genetics, 2000, 41: 98-107.

Ding et al., "Improving CRISPR-Cas9 Genome Editing Efficiency by Fusion with Chromatin-Modulating Peptides," CRISPR J, 2019, 2: 51-63.

Dobin et al., "STAR: ultrafast universal RNA-seq aligner," Bioinformatics, 2013, 29: 15-21.

Dupont et al., "Mechanical regulation of chromatin and transcription," Nat. Rev. Genet., 2022, 23: 624-643.

Dupont et al., "Role of YAP/TAZ in mechanotransduction," Nature, 2011, 474: 179-183.

Durand et al., "Juicer Provides a One-Click System for Analyzing Loop-Resolution Hi-C Experiments," Cell Syst, 2016, 3: 95-98.

Effendi et al., "Connective Tissue Growth Factor in Idiopathic Pulmonary Fibrosis: Breaking the Bridge," Int. J. Mol. Sci., 2022, 23.

Ehrbar et al., "Elucidating the role of matrix stiffness in 3D cell migration and remodeling," Biophys. J., 2011, 100: 284-293.

Elosegui-Artola et al., "Force triggers YAP nuclear entry by regulating transport across nuclear pores," Cell, 2017, 171: 1397-1410. e14.

ENCODE Project Consortium, "An integrated encyclopedia of DNA elements in the human genome," Nature, 2012, 2012, 489: 57-74.

ENCODE Project Consortium, "Expanded encyclopaedias of DNA elements in the human and mouse genomes," Nature, 2020, 583: 699-710.

Engler et al., "Matrix elasticity directs stem cell lineage specification," Cell, 2006, 126: 677-689.

Ernst et al., "ChromHMM: automating chromatin-state discovery and characterization," Nat Methods, 2012, 9: 215-216.

Fan et al., "Hsp90{beta} and p130(cas): novel regulatory factors of MMP-13 expression in human osteoarthritic chondrocytes," Ann. Rheum. Dis., 2009, 68: 976-982.

Finak et al., "MAST: a flexible statistical framework for assessing transcriptional changes and characterizing heterogeneity in single-cell RNA sequencing data," Genome Biol., 2015, 16: 278.

Fiore et al., "Publisher Correction: Mechanics of a multilayer epithelium instruct tumour architecture and function," Nature, 2020, 586: E9.

(56) References Cited

OTHER PUBLICATIONS

Freeberg et al., "Mechanical Feed-Forward Loops Contribute to Idiopathic Pulmonary Fibrosis," Am. J. Pathol., 2021, 191: 18-25.

Fulco et al., "Activity-by-contact model of enhancer-promoter regulation from thousands of CRISPR perturbations," Nat. Genet., 2019, 51: 1664-1669.

Galli et al., "YAP Drives Growth by Controlling Transcriptional Pause Release from Dynamic Enhancers," Molecular Cell, 2015, 60(2): P328-337.

Gasperini et al., "A Genome-wide Framework for Mapping Gene Regulation via Cellular Genetic Screens," Cell, 2019, 176: 377-390.e19.

GenBank Accession No. U94396.1 "Human dystrophin (DMD) gene, exon 44 and partial cds," 2016.

Gilbert et al., "CRISPR-mediated modular RNA-guided regulation of transcription in eukaryotes," Cell, 2013, 154: 442-451.

Gordon et al., "lentiMPRA and MPRAflow for high-throughput functional characterization of gene regulatory elements," Nat. Protoc., 2020, 15(8): 2387-2412.

Habermann et al., "Single-cell RNA sequencing reveals profibrotic roles of distinct epithelial and mesenchymal lineages in pulmonary fibrosis," Sci Adv, 2020, 6: eaba197.

Hall et al., "Polarity of the CRISPR roadblock to transcription," Nat. Struct. Mol. Biol., 2022, 29: 1217-1227.

Han et al., "CRISPR screens in cancer spheroids identify 3D growth-specific vulnerabilities," Nature, 2020, 580: 136-141.

Hanmandlu et al., "Transcriptomic and Epigenetic Profiling of Fibroblasts in Idiopathic Pulmonary Fibrosis," Am J Respir Cell Mol Biol, 2022, 66(1): 53-63.

Heinz et al., "Simple combinations of lineage-determining transcription factors prime cis-regulatory elements required for macrophage and B cell identities," Mol. Cell, 2010, 38: 576-589.

Heinz et al., "The selection and function of cell type-specific enhancers," Nat. Rev. Mol. Cell Biol., 2015, 16: 144-154.

Heo et al., "Differentiation alters stem cell nuclear architecture, mechanics, and mechano-sensitivity," Elife, 2016, 5.

Herrera et al., "Extracellular matrix as a driver of progressive fibrosis," J. Clin. Invest., 2018, 128: 45-53.

Ho et al., "Lamin A/C and emerin regulate MKL1-SRF activity by modulating actin dynamics," Nature, 2013, 497: 507-511.

Hoffman et al., "Dynamic molecular processes mediate cellular mechanotransduction," Nature, 2011, 475: 316-323.

Horlbeck et al., "Compact and highly active next-generation libraries for CRISPR-mediated gene repression and activation," Elife, 2016, 5: e19760.

Humphrey et al., "Mechanotransduction and extracellular matrix homeostasis," Nat. Rev. Mol. Cell Biol., 2014, 15: 802-812.

Isaac et al., "Nucleosome breathing and remodeling constrain CRISPR-Cas9 function," Elife, 2016, 5: e13450.

Jang et al., "Mechanical cue-induced YAP instructs Skp2-dependent cell cycle exit and oncogenic signaling," EMBO J., 2017, 36: 2510-2528.

Jeffrey et al., "Targeting dual-specificity phosphatases: manipulating MAP kinase signalling and immune responses," Nat. Rev. Drug Discov., 2007, 6: 391-403.

Jiang et al., "Systematic investigation of cytokine signaling activity at the tissue and single-cell levels," Nat. Methods, 2021, 18: 1181-1191.

Johne et al., "Spred1 and TESK1—two new interaction partners of the kinase MARKK/TAO1 that link the microtubule and actin cytoskeleton," Mol. Biol. Cell, 2008, 19: 1391-1403.

Jones et al., "Mechanoepigenetic regulation of extracellular matrix homeostasis via Yap and Taz," Proc. Natl. Acad. Sci. U.S.A., 2023, 120: e2211947120.

Jones et al., "No place like home: anatomy and function of the stem cell niche," Nat. Rev. Mol. Cell Biol., 2008, 9: 11-21.

Jones et al., "ZNF416 is a pivotal transcriptional regulator of fibroblast mechanoactivation," J. Cell Biol., 2021, 220.

Juric et al., "MAPS: Model-based analysis of long-range chromatin interactions from PLAC-seq and HiChIP experiments," PLoS Comput. Biol., 2019, 15: e1006982.

Katsura et al., "Human Lung Stem Cell-Based Alveolospheres Provide Insights into SARS-CoV-2-Mediated Interferon Responses and Pneumocyte Dysfunction," Cell Stem Cell, 2020, 27(6): 890-904.e8.

Kechin et al., "cutPrimers: A New Tool for Accurate Cutting of Primers from Reads of Targeted Next Generation Sequencing," J. Comput. Biol., 2017, 24: 1138-1143.

Khemlina et al., "The biology of Hepatocellular carcinoma: implications for genomic and immune therapies," Mol. Cancer, 2017, 16: 149.

Kisselev, "Polypeptide Release Factors in Prokaryotes and Eukaryotes: Same Function, Different Structure," Structure, 2002, 10: 8-9.

Klann et al., "CRISPR-Cas9 epigenome editing enables high-throughput screening for functional regulatory elements in the human genome," Nat. Biotechnol., 2017, 35: 561-568.

Korkmaz et al., "Functional genetic screens for enhancer elements in the human genome using CRISPR-Cas9," Nat. Biotechnol., 2016, 34: 192-198.

Krietenstein et al., "Ultrastructural Details of Mammalian Chromosome Architecture," Mol. Cell, 2020, 78(3): 554-565.e7.

Kurppa et al., "Treatment-Induced Tumor Dormancy through YAP-Mediated Transcriptional Reprogramming of the Apoptotic Pathway," Cancer Cell, 2020, 37: 104-122.e12.

Langmead, "Aligning short sequencing reads with Bowtie," Curr. Protoc. Bioinformatics, 2010, Chapter 11, Unit 11.7.

Lau et al., "In vivo epigenome editing and transcriptional modulation using CRISPR technology," Transgenic Res. 2018, 27(6): 489-509.

Le et al., "Mechanical regulation of transcription controls Polycomb-mediated gene silencing during lineage commitment," Nature Cell Biology, 2016, 18(8): 864-875.

Lee et al., "The novel PIAS-like protein hZimp10 is a transcriptional co-activator of the p53 tumor suppressor," Nucleic Acids Res., 2007, 35: 4523-4534.

Leight et al., "Matrix rigidity regulates a switch between TGF-β1-induced apoptosis and epithelial-mesenchymal transition," Mol. Biol. Cell, 2012, 23: 781-791.

Li et al., "MicroRNA-21 preserves the fibrotic mechanical memory of mesenchymal stem cells," Nat. Mater., 2017, 16: 379-389.

Liao et al., "featureCounts: an efficient general purpose program for assigning sequence reads to genomic features," Bioinformatics, 2014, 30: 923-930.

Liu et al., "Modulating chromatin accessibility by transactivation and targeting proximal dsgRNAs enhances Cas9 editing efficiency in vivo," Genome Biol, 2019, 20(1): 145.

Love et al., "Moderated estimation of fold change and dispersion for RNA-seq data with DESeq2," Genome Biol., 2014, 15: 550.

Ma et al., "Mechanotransduction and anoikis: death and the homeless cell," Cell Cycle, 2008, 7: 2462-2465.

McBeath et al., "Cell shape, cytoskeletal tension, and RhoA regulate stem cell lineage commitment," Dev. Cell, 2004, 6: 483-495.

McDowell et al., "Glucocorticoid receptor recruits to enhancers and drives activation by motif-directed binding," Genome Res., 2018, 28: 1272-1284.

Meng et al., "RAP2 mediates mechanoresponses of the Hippo pathway," Nature, 2018, 560: 655-660.

Meyers et al., "Computational correction of copy number effect improves specificity of CRISPR-Cas9 essentiality screens in cancer cells," Nat. Genet., 2017, 49: 1779-1784.

Miano, "Serum response factor: toggling between disparate programs of gene expression," J. Mol. Cell. Cardiol., 2003, 35: 577-593.

Mifsud et al., "Mapping long-range promoter contacts in human cells with high-resolution capture Hi-C," Nat. Genet., 2015, 47: 598-606.

Miralles et al., "Actin dynamics control SRF activity by regulation of its coactivator MAL," Cell, 2003, 113: 329-342.

Miroshnikova et al., "Emerging roles of mechanical forces in chromatin regulation," J. Cell Sci., 2017, 130: 2243-2250.

(56) References Cited

OTHER PUBLICATIONS

Molineros et al., "Mechanistic Characterization of Variants Identifies an hnRNP-K-Regulated Transcriptional Enhancer Contributing to SLE Susceptibility," Front. Immunol., 2019, 10: 1066.

Moore et al., "Regulation and Relevance of Myofibroblast Responses in Idiopathic Pulmonary Fibrosis," Curr. Pathobiol. Rep., 2013, 1: 199-208.

Morrison et al., "Stem cells and niches: mechanisms that promote stem cell maintenance throughout life," Cell, 2008, 132: 598-611.

Muerdter et al., "Resolving systematic errors in widely used enhancer activity assays in human cells," Nat. Methods, 2018, 15: 141-149.

Murthy et al., "Human distal lung maps and lineage hierarchies reveal a bipotent progenitor," Nature, 2022, 604(7904): 111-119.

Namavar et al., "Classification, diagnosis and potential mechanisms in pontocerebellar hypoplasia," Orphanet J. Rare Dis., 2011, 6: 50.

Nava et al., "Heterochromatin-Driven Nuclear Softening Protects the Genome against Mechanical Stress-Induced Damage," Cell, 2020, 181: 800-817.e22.

Noonan et al., "Genomics of long-range regulatory elements," Annu. Rev. Genomics Hum. Genet., 2010, 11: 1-23.

Oliver-De La Cruz et al., "Substrate mechanics controls adipogenesis through YAP phosphorylation by dictating cell spreading," Biomaterials, 2019, 205: 64-80.

Open2C et al., "Pairtools: From sequencing data to chromosome contacts," PLoS Comput. Biol., 2024, 20: e1012164.

Paoli et al., "Anoikis molecular pathways and its role in cancer progression," Biochim. Biophys. Acta, 2013, 1833: 3481-3498.

Parker et al., "Fibrotic extracellular matrix activates a profibrotic positive feedback loop," J. Clin. Invest., 2014, 124: 1622-1635.

Paszek et al., "Tensional homeostasis and the malignant phenotype," Cancer Cell, 2005, 8: 241-254.

Paulmann et al., "The OTUD6B-LIN28B-MYC axis determines the proliferative state in multiple myeloma," EMBO J., 2022, 41: e110871.

Pelham Jr et al., "Cell locomotion and focal adhesions are regulated by substrate flexibility," Proc. Natl. Acad. Sci. U.S.A., 1997, 94: 13661-13665.

Piccolo et al., "The biology of YAP/TAZ: hippo signaling and beyond," Physiol. Rev., 2014, 94: 1287-1312.

Plikus et al., "Fibroblasts: Origins, definitions, and functions in health and disease," Cell, 2021, 184: 3852-3872.

Quinlan et al., "BEDTools: a flexible suite of utilities for comparing genomic features," Bioinformatics, 2010, 26: 841-842.

Quinlan, "BEDTools: The Swiss-Army Tool for Genome Feature Analysis," Curr. Protoc. Bioinformatics, 2014, 47: 11.12.1-34.

Ramírez et al., "deepTools: a flexible platform for exploring deep-sequencing data," Nucleic Acids Res., 2014, 42: W187-91.

Ritterhoff et al., "The RanBP2/RanGAP1*SUMO1/Ubc9 SUMO E3 ligase is a disassembly machine for Crm1-dependent nuclear export complexes," Nat. Commun., 2016, 7: 11482.

Robinson et al., "edgeR: a Bioconductor package for differential expression analysis of digital gene expression data," Bioinformatics, 2010, 26: 139-140.

Royer et al., "Mechanobiology in the Comorbidities of Ehlers Danlos Syndrome," Front Cell Dev Biol, 2022, 10: 874840.

Sanson et al., "Optimized libraries for CRISPR-Cas9 genetic screens with multiple modalities," Nat. Commun., 2018, 9: 1-15.

Sanyal et al., "The long-range interaction landscape of gene promoters," Nature, 2012, 489: 109-113.

Schmelzle et al., "Functional role and oncogene-regulated expression of the BH3-only factor Bmf in mammary epithelial anoikis and morphogenesis," Proc. Natl. Acad. Sci. U.S.A., 2007, 104: 3787-3792.

Seo et al., "RNAi-based functional selection identifies novel cell migration determinants dependent on PI3K and AKT pathways," Nat. Commun., 2014, 5: 5217.

Simeonov et al., "Discovery of stimulation-responsive immune enhancers with CRISPR activation," Nature, 2017, 549: 111-115.

Sollis et al., "THE NHGRI-EBI GWAS Catalog: knowledgebase and deposition resource," Nucleic Acids Res., 2023, 51: D977-D985.

Song et al., "β-catenin induces A549 alveolar epithelial cell mesenchymal transition during pulmonary fibrosis," Mol. Med. Rep., 2015, 11: 2703-2710.

Stowers et al., "Matrix stiffness induces a tumorigenic phenotype in mammary epithelium through changes in chromatin accessibility," Nat Biomed Eng, 2019, 3: 1009-1019.

Stuart et al., "Comprehensive Integration of Single-Cell Data," Cell, 2019, 177: 1888-1902.e21.

Sun et al., "Effects of Matrix Stiffness on the Morphology, Adhesion, Proliferation and Osteogenic Differentiation of Mesenchymal Stem Cells," Int. J. Med. Sci., 2018, 15: 257-268.

Sun et al., "Force-induced gene up-regulation does not follow the weak power law but depends on H3K9 demethylation," Sci Adv, 2020, 6: eaay9095.

Swift et al., "Nuclear lamin-A scales with tissue stiffness and enhances matrix-directed differentiation," Science, 2013, 341: 1240104.

Tajik et al., "Transcription upregulation via force-induced direct stretching of chromatin," Nat. Mater., 2016, 15: 1287-1296.

Thakore et al., "Highly specific epigenome editing by CRISPR-Cas9 repressors for silencing of distal regulatory elements," Nat. Methods, 2015, 12: 1143-1149.

Torrungruang et al., "DNA binding and gene activation properties of the Nmp4 nuclear matrix transcription factors," J. Biol. Chem., 2002, 277: 16153-16159.

Tycko et al., "Mitigation of off-target toxicity in CRISPR-Cas9 screens for essential non-coding elements," Nat. Commun., 2019, 10: 4063.

Vartiainen et al., "Nuclear actin regulates dynamic subcellular localization and activity of the SRF cofactor MAL," Science, 2007, 316: 1749-1752.

Vicente-Manzanares et al., "Non-muscle myosin II takes centre stage in cell adhesion and migration" Nat. Rev. Mol. Cell Biol., 2009, 10: 778-790.

Vierbuchen et al., "AP-1 Transcription Factors and the BAF Complex Mediate Signal-Dependent Enhancer Selection," Mol. Cell, 2017, 68: 1067-1082.e12.

Vishwanath et al., "Mechanisms of aortic carboxypeptidase-like protein secretion and identification of an intracellularly retained variant associated with Ehlers-Danlos syndrome," J. Biol. Chem., 2020, 295: 9725-9735.

Wei et al., "HiCAR is a robust and sensitive method to analyze open-chromatin-associated genome organization," Mol. Cell, 2022, 82: 1225-1238.e6.

Wells, "Tissue mechanics and fibrosis," Biochim. Biophys. Acta, 2013, 1832: 884-890.

Witkowski et al., "Conversion of a β-Ketoacyl Synthase to a Malonyl Decarboxylase by Replacement of the Active-Site Cysteine with Glutamine," Biochemistry, 1999, 38: 11643-11650.

Yan et al., "Zinc finger protein 384 enhances colorectal cancer metastasis by upregulating MMP2," Oncol. Rep., 2022, 47.

Yao et al., "The ENCODE4 Consortium, Multi-center integrated analysis of non-coding CRISPR screens," https://doi.org/10.1101/2022.12.21.520137, posted Dec. 22, 2022.

Yu et al., "ChIPseeker: an R/Bioconductor package for ChIP peak annotation, comparison and visualization," Bioinformatics, 2015, 31: 2382-2383.

Zanconato et al., "Genome-wide association between YAP/TAZ/TEAD and AP-1 at enhancers drives oncogenic growth," Nat. Cell Biol., 2015, 17: 1218-1227.

Zhang et al., "BAALC-AS1/G3BP2/c-Myc feedback loop promotes cell proliferation in esophageal squamous cell carcinoma," Cancer Commun., 2021, 41: 240-257.

Zhang et al., "Model-based analysis of ChIP-Seq (MACS)," Genome Biol., 2008, 9: R137.

Zhang et al., "The matricellular protein Cyr61 is a key mediator of platelet-derived growth factor-induced cell migration," J. Biol. Chem., 2015, 290: 8232-8242.

Zhao et al., "Cell detachment activates the Hippo pathway via cytoskeleton reorganization to induce anoikis," Genes Dev., 2012, 26: 54-68.

(56)                References Cited

OTHER PUBLICATIONS

Zhao et al., "Substrate stiffness regulated migration and angiogenesis potential of A549 cells and HUVECs," J. Cell. Physiol, 2018, 233: 3407-3417.
Zhao et al., "TEAD mediates YAP-dependent gene induction and growth control," Genes Dev., 2008, 22: 1962-1971.
Zhou et al., "Novel identified associations of RGS1 and RASGRP1 variants in IgA Nephropathy," Sci. Rep., 2016, 6: 35781.
Lee et al., "Synthetically modified guide RNA and donor DNA are a versatile platform for CRISPR-Cas9 engineering," eLife, 2017, 6: e25312.
Kwon et al., "626. Directing Skeletal Myogenic Progenitor Cell Lineage Specification with CRISPR/Cas9 Transcriptional Activators," Molecular Therapy, 2016, 24: S248.
Jiang et al., "CRISPR-Cas9 Structures and Mechanisms," Annu Rev Biophys, 2017, 46: 505-529.
Mathias et al., "Unraveling Immune-Related lncRNAs in Breast Cancer Molecular Subtypes," Front. Oncol., 2021, 11: 692170.
Cui et al., "Long non-coding RNA LINC02613 is a prognostic biomarker for breast cancer and correlates with the cell cycle and immune infiltration based on TCGA data," Translational Cancer Research, 2022, 11(4): 615-628.
Hori et al., "Control of Regulatory T Cell Development by the Transcription Factor Foxp3," Science, 2003, 299: 1057-1061.
Reiner et al., "Epigenetics meets GPCR: inhibition of histone H3 methyltransferase (G9a) and histamine H3 receptor for Prader-Willi Syndrome," Scientific Reports, 2020, 10: 13558.
Burr et al., "Mitochondrial Protein Lipoylation and the 2-Oxoglutarate Dehydrogenase Complex Controls HIF1α Stability in Aerobic Conditions," Cell Metab, 2016, 24(5): 740-752.
Leandro et al., "DHTKD1 and OGDH display in vivo substrate overlap and form a hybrid ketoacid dehydrogenase complex," bioRxiv preprint version posted May 22, 2019.
Bailey et al., "ABHD11 maintains 2-oxoglutarate metabolism by preserving functional lipoylation of the 2-oxoglutarate dehydrogenase complex," Nature Communications, 2020, 11: 4046.
Hesselson et al., "Suppression of Ptf1a Activity Induces Acinar-to-Endocrine Conversion," Current Biology, 2011, 21: 712-717.
Chung et al., "Prader-Willi syndrome: reflections on seminal studies and future therapies," Open Biology, 2020, 10: 200195.
Australian Patent Office Examination Report No. 1 for Application No. 2020257898 dated Jun. 2, 2025 (4 pages).
Chinese Patent Office Action for Application No. 202080028248.2 dated Feb. 13, 2025 (22 pages, English translation included).
European Patent Office Action for Application No. 20790851.8 dated Mar. 24, 2025 (11 pages).
European Patent Office Extended Search Report for Application No. 21883936.3 dated Mar. 20, 2025 (7 pages).
Japanese Patent Office Action for Application No. 2023-524339 dated Aug. 14, 2025 (8 pages, English translation included).
Korean Patent Office Action for Application No. 10-2021-7036783 dated Aug. 17, 2025 (8 pages, English translation included).
Mexican Patent Office Action for Application No. MX/a/2021/073583 dated Aug. 28, 2025 (11 pages, English language summary included).
Saudi Arabia Patent Office Examination Report for Application No. 521430583 dated Mar. 15, 2025 (12 pages, English translation included).
United States Patent Office Action for U.S. Appl. No. 16/098,464 dated Mar. 19, 2025 (20 pages).
United States Patent Office Action for U.S. Appl. No. 17/633,467 dated Jun. 4, 2025 (18 pages).
United States Patent Office Action for U.S. Appl. No. 17/603,329 dated Jun. 10, 2025 (25 pages).
United States Patent Office Action for U.S. Appl. No. 17/636,754 dated Jun. 11, 2025 (20 pages).

United States Patent Office Action for U.S. Appl. No. 17/782,112 dated Jul. 29, 2025 (14 pages).
United States Patent Office Action for U.S. Appl. No. 17/636,750 dated Sep. 10, 2025 (23 pages).
United States Patent Office Action for U.S. Appl. No. 17/636,754 dated Oct. 14, 2025 (10 pages).
Cataletto et al., "Prader-Willi syndrome: A primer for clinicians," Int J Pediatr Endocrinol, 2011, 2011(1): 12.
Chen et al., "Functional disruption of dystrophin gene in rhesus monkey using CRISPR/Cas9," Human Molecular Genetics, 2015, 24(13): 3764-3774.
Heigwer et al., "E-CRISP: fast CRISPR target site identification," Nature Methods, 2014, 11(2): 122-123.
Nemoto et al., "Rescue of imprinted genes by epigenome editing in human cellular models of Prader-Willi syndrome," Nat Commun, 2025, 16(1): 9442.
U.S. Appl. No. 17/921,336 dated Dec. 23, 2025 (10 pages).
U.S. Appl. No. 17/921,332 dated Dec. 11, 2025 (14 pages).
U.S. Appl. No. 17/633,467 dated Dec. 22, 2025 (18 pages).
U.S. Appl. No. 16/098,464 dated Nov. 19, 2025 (20 pages).
U.S. Appl. No. 17/603,329 dated Jan. 6, 2026 (27 pages).
Chilean Patent Office Action for Application No. 202102680 dated Nov. 4, 2025 (4 pages, English statement of relevance included).
Israeli Patent Office Action for Application No. 287163 dated Dec. 15, 2025 (4 pages).
Taiwanese Patent Office Action for Application No. 114119381 dated Oct. 28, 2025 (7 pages, English translation included).
Adikusuma et al., "Versatile single-step-assembly CRISPR/Cas9 vectors for dual gRNA expression," PLoS One, 2017, 12(12): e0187236.
Bai et al., "Feasibility of using NF1-GRD and AAV for gene replacement therapy in NF1-associated tumors," Gene Ther, 2019, 26(6): 277-286.
Bednarski et al., "Targeted Integration of a Super-Exon into the CFTR Locus Leads to Functional Correction of a Cystic Fibrosis Cell Line Model," PLoS One, 2016, 11(8): e0161072.
Dreier et al., "Development of Zinc Finger Domains for Recognition of the 5'-CNN-3' Family DNA Sequences and Their Use in the Construction of Artificial Transcription Factors," The Journal of Biological Chemistry, 2005, 280(42): 35588-35597.
GenBank Accession X96744.1 "H.sapiens PAX7 gene, exon 1(and joined CDS)" (2006).
Li et al., "Plant Genome Editing with CRISPR Systems," Methods in Molecular Biology, 2019, 1917: 285-296.
Moutal et al., "CRISPR/Cas9 editing of Nf1 gene identifies CRMP2 as a therapeutic target in neurofibromatosis type 1-related pain that is reversed by (S)-Lacosamide," Pain, 2017, 158(12): 2301-2319.
Segal et al., "Attenuation of HIV-1 Replication in Primary Human Cells with a Designed Zinc Finger Transcription Factor," The Journal of Biological Chemistry, 2004, 279(15): 14509-14519.
United States Patent Office Notice of Allowance for U.S. Appl. No. 17/636,754 dated Feb. 3, 2026 (15 pages).
United States Patent Office Action for U.S. Appl. No. 17/636,750 dated Mar. 6, 2026 (20 pages).
Canadian Patent Office Action for Application No. 3,137,248 dated Feb. 17, 2026 (5 pages).
Eurasian Patent Office Action for Application No. 202590357 dated Feb. 20, 2026 (6 pages, English translation included).
Japanese Patent Office Action No. 2023-524339 dated Jan. 26, 2026 (5 pages, English translation included).
Malaysia Patent Office Action for Application No. PI2021006150 dated Feb. 12, 2026 (4 pages).
Mexican Patent Office Action for Application No. MX/a/2021/012511 dated Feb. 24, 2026 (20 pages, English language summary included).
United States Patent Office Action for U.S. Appl. No. 17/921,316 dated Mar. 10, 2026 (13 pages).

* cited by examiner

Traditional two-vector system
(used previously)

SaCas9

2x gRNAs

OR

SaCas9 + 1x gRNA

SaCas9 + 1x gRNA

One-vector system

SaCas9 + 2x gRNAs

~3.2 kb

ITR | U6 | gRNA #1 | EFS | SaCas9 | 3xHA | Mini-PA | H1 | gRNA #2 | ITR

SEQUENCE LISTING

<160> NUMBER OF SEQ ID NOS: 42

<210> SEQ ID NO 1
<211> LENGTH: 130
<212> TYPE: DNA
<213> ORGANISM: Artificial Sequence
<220> FEATURE:
<223> OTHER INFORMATION: Synthetic

<400> SEQUENCE: 1
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                           130

<210> SEQ ID NO 2
<211> LENGTH: 22

```
<212> TYPE: DNA
<213> ORGANISM: Artificial Sequence
<220> FEATURE:
<223> OTHER INFORMATION: Synthetic

<400> SEQUENCE: 2
acatttcctc tctatacaaa tg                                                 22

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
atatagtaat gaaattattg gcac                                               24

<210> SEQ ID NO 4
<211> LENGTH: 76
<212> TYPE: DNA
<213> ORGANISM: Artificial Sequence
<220> FEATURE:
<223> OTHER INFORMATION: Synthetic

<400> SEQUENCE: 4
tctcgccaac aagttgacga gataaacacg gcattttgcc ttgttttagt agattctgtt        60
tccagagtac taaaac                                                        76

<210> SEQ ID NO 5
<211> LENGTH: 249
<212> TYPE: DNA
<213> ORGANISM: Artificial Sequence
<220> FEATURE:
<223> OTHER INFORMATION: Synthetic

<400> SEQUENCE: 5
ggtgtttcgt cctttccaca agatatataa agccaagaaa tcgaaatact ttcaagttac        60
ggtaagcata tgatagtcca tttaaaaca taatttaaa actgcaaact acccaagaaa         120
ttattacttt ctacgtcacg tattttgtac taatatcttt gtgtttacag tcaaattaat       180
tccaattatc tctctaacag ccttgtatcg tatatgcaaa tatgaaggaa tcatgggaaa       240
taggccctc                                                               249

<210> SEQ ID NO 6
<211> LENGTH: 215
<212> TYPE: DNA
<213> ORGANISM: Artificial Sequence
<220> FEATURE:
<223> OTHER INFORMATION: Synthetic

<400> SEQUENCE: 6
gaacgctgac gtcatcaacc cgctccaagg aatcgcgggc ccagtgtcac taggcgggaa        60
cacccagcgc gcgtgcgccc tggcaggaag atggctgtga gggacagggg agtggcgccc       120
tgcaatattt gcatgtcgct atgtgttctg ggaaatcacc ataaacgtga aatgtctttg       180
gatttgggaa tcttataagt tctgtatgag accac                                  215

<210> SEQ ID NO 7
<211> LENGTH: 252
<212> TYPE: DNA
<213> ORGANISM: Artificial Sequence
<220> FEATURE:
```

-continued

<223> OTHER INFORMATION: Synthetic

<400> SEQUENCE: 7

```
tcgagtggct ccggtgcccg tcagtgggca gagcgcacat cgcccacagt ccccgagaag      60
ttggggggag gggtcggcaa ttgaaccggt gcctagagaa ggtggcgcgg ggtaaactgg     120
gaaagtgatg tcgtgtactg gctccgcctt tttcccgagg gtgggggaga accgtatata     180
agtgcagtag tcgccgtgaa cgttcttttt cgcaacgggt ttgccgccag aacacaggtg     240
tcgtgaccgc gg                                                         252
```

<210> SEQ ID NO 8
<211> LENGTH: 449
<212> TYPE: DNA
<213> ORGANISM: Artificial Sequence
<220> FEATURE:
<223> OTHER INFORMATION: Synthetic

<400> SEQUENCE: 8

```
ctagactagc atgctgccca tgtaaggagg caaggcctgg ggacacccga gatgcctggt      60
tataattaac ccagacatgt ggctgccccc cccccccaa cacctgctgc ctctaaaaat     120
aaccctgcat gccatgttcc cggcgaaggg ccagctgtcc cccgccagct agactcagca     180
cttagtttag gaaccagtga gcaagtcagc ccttgggca gcccatacaa ggccatgggg     240
ctgggcaagc tgcacgcctg ggtccggggt gggcacggtg cccgggcaac gagctgaaag     300
ctcatctgct ctcaggggcc cctccctggg gacagcccct cctggctagt cacaccctgt     360
aggctcctct atataaccca ggggcacagg ggctgccctc attctaccac cacctccaca     420
gcacagacag acactcagga gccagccag                                      449
```

<210> SEQ ID NO 9
<211> LENGTH: 387
<212> TYPE: DNA
<213> ORGANISM: Artificial Sequence
<220> FEATURE:
<223> OTHER INFORMATION: Synthetic

<400> SEQUENCE: 9

```
gagctccacc gcggtggcgg ccgtccgcct tcggcaccat cctcacgaca cccaaatatg      60
gcgacgggtg aggaatggtg gggagttatt tttagagcgg tgaggaaggt gggcaggcag     120
caggtgttgg cgctctaaaa ataactcccg ggagttattt ttagagcgga ggaatggtgg     180
acacccaaat atggcgacgg ttcctcaccc gtcgccatat ttgggtgtcc gccctcggcc     240
ggggccgcat tcctgggggc cgggcggtgc tcccgcccgc ctcgataaaa ggctccgggg     300
ccggcggcgg cccacgagct acccggagga gcgggaggcg ccaagctcta gaactagtgg     360
atcccccggg ctgcaggaat tcgatat                                        387
```

<210> SEQ ID NO 10
<211> LENGTH: 810
<212> TYPE: DNA
<213> ORGANISM: Artificial Sequence
<220> FEATURE:
<223> OTHER INFORMATION: Synthetic

<400> SEQUENCE: 10

```
gtttaaacaa gcttgcatgt ctaagctaga cccttcagat taaaaataac tgaggtaagg      60
gcctgggtag gggaggtggt gtgagacgct cctgtctctc ctctatctgc ccatcggccc     120
tttggggagg aggaatgtgc ccaaggacta aaaaaaggcc atggagccag aggggcgagg     180
```

-continued

```
gcaacagacc tttcatgggc aaaccttggg gccctgctgt ctagcatgcc ccactacggg        240
tctaggctgc ccatgtaagg aggcaaggcc tggggacacc cgagatgcct ggttataatt        300
aacccagaca tgtggctgcc cccccccccc caacacctgc tgcctctaaa aataaccctg        360
tccctggtgg atcccctgca tgcgaagatc ttcgaacaag gctgtggggg actgagggca        420
ggctgtaaca ggcttggggg ccagggctta tacgtgcctg ggactcccaa agtattactg        480
ttccatgttc ccggcgaagg gccagctgtc ccccgccagc tagactcagc acttagttta        540
ggaaccagtg agcaagtcag cccttggggc agcccataca aggccatggg gctgggcaag        600
ctgcacgcct gggtccgggg tgggcacggt gcccgggcaa cgagctgaaa gctcatctgc        660
tctcaggggc ccctccctgg ggacagcccc tcctggctag tcacaccctg taggctcctc        720
tatataaccc aggggcacag gggctgccct cattctacca ccacctccac agcacagaca        780
gacactcagg agccagccag cggcgcgccc                                         810
```

<210> SEQ ID NO 11
<211> LENGTH: 3156
<212> TYPE: DNA
<213> ORGANISM: Artificial Sequence
<220> FEATURE:
<223> OTHER INFORMATION: Synthetic

<400> SEQUENCE: 11

```
aagcggaact acatcctggg cctggacatc ggcatcacca gcgtgggcta cggcatcatc         60
gactacgaga cacgggacgt gatcgatgcc ggcgtgcggc tgttcaaaga ggccaacgtg        120
gaaaacaacg agggcaggcg gagcaagaga ggcgccagaa ggctgaagcg gcggaggcgg        180
catagaatcc agagagtgaa gaagctgctg ttcgactaca acctgctgac cgaccacagc        240
gagctgagcg gcatcaaccc ctacgaggcc agagtgaagg gcctgagcca gaagctgagc        300
gaggaagagt tctctgccgc cctgctgcac ctggccaaga aagaggcgt gcacaacgtg        360 aacgaggtgg aagaggacac cggcaacgag ctgtccacca aagagcagat cagccggaac        420
agcaaggccc tggaagagaa atacgtggcc gaactgcagc tggaacggct gaagaaagac        480
ggcgaagtgc ggggcagcat caacagattc aagaccagca ctacgtgaa agaagccaaa        540 cagctgctga aggtgcagaa ggcctaccac cagctggacc agagcttcat cgacacctac        600
atcgacctgc tggaaacccg gcggacctac tatgagggac ctggcgaggg cagccccttc        660
ggctggaagg acatcaaaga atggtacgag atgctgatgg ccactgcac ctacttcccc        720 gaggaactgg ggagcgtgaa gtacgcctac aacgccgacc tgtacaacgc cctgaacgac        780
ctgaacaatc tcgtgatcac cagggacgag aacgagaagc tggaatatta cgagaagttc        840
cagatcatcg agaacgtgtt caagcagaag aagaagccca ccctgaagca gatcgccaaa        900
gaaatcctcg tgaacgaaga ggatattaag ggctacagag tgaccagcac cggcaagccc        960
gagttcacca acctgaaggt gtaccacgac atcaaggaca ttaccgcccg gaaagagatt       1020
attgagaacg ccgagctgct ggatcagatt gccaagatcc tgaccatcta ccagagcagc       1080
gaggacatcc aggaagaact gaccaatctg aactccgagc tgacccagga agagatcgag       1140
cagatctcta atctgaaggg ctataccggc acccacaacc tgagcctgaa ggccatcaac       1200
ctgatcctgg acgagctgtg gcacaccaac gacaaccaga tcgctatctt caaccggctg       1260
aagctggtgc ccaagaaggt ggacctgtcc cagcagaaag agatccccac caccctggtg       1320
gacgacttca tcctgagccc cgtcgtgaag agaagcttca tccagagcat caaagtgatc       1380
```

```
aacgccatca tcaagaagta cggcctgccc aacgacatca ttatcgagct ggcccgcgag      1440
aagaactcca aggacgccca gaaaatgatc aacgagatgc agaagcggaa ccggcagacc      1500
aacgagcgga tcgaggaaat catccggacc accggcaaag agaacgccaa gtacctgatc      1560
gagaagatca agctgcacga catgcaggaa ggcaagtgcc tgtacagcct ggaagccatc      1620
cctctggaag atctgctgaa caaccccttc aactatgagg tggaccacat catccccaga      1680
agcgtgtcct tcgacaacag cttcaacaac aaggtgctcg tgaagcagga agaaaacagc      1740
aagaagggca accggacccc attccagtac ctgagcagca gcgacagcaa gatcagctac      1800
gaaaccttca agaagcacat cctgaatctg gccaagggca agggcagaat cagcaagacc      1860
aagaaagagt atctgctgga agaacgggac atcaacaggt tctccgtgca gaaagacttc      1920
atcaaccgga acctggtgga taccagatac gccaccagag gcctgatgaa cctgctgcgg      1980
agctacttca gagtgaacaa cctggacgtg aaagtgaagt ccatcaatgg cggcttcacc      2040
agctttctgc ggcggaagtg gaagtttaag aaagagcgga acaaggggta caagcaccac      2100
gccgaggacg ccctgatcat tgccaacgcc gatttcatct tcaaagagtg gaagaaactg      2160
gacaaggcca aaaaagtgat ggaaaaccag atgttcgagg aaaagcaggc cgagagcatg      2220
cccgagatcg aaaccgagca ggagtacaaa gagatcttca tcaccccca ccagatcaag      2280 cacattaagg acttcaagga ctacaagtac agccaccggg tggacaagaa gcctaataga      2340
gagctgatta cgacaccct gtactccacc cggaaggacg acaagggcaa caccctgatc      2400
gtgaacaatc tgaacggcct gtacgacaag gacaatgaca agctgaaaaa gctgatcaac      2460
aagagccccg aaaagctgct gatgtaccac cacgacccc agacctacca gaaactgaag      2520
ctgattatgg aacagtacgg cgacgagaag aatcccctgt acaagtacta cgaggaaacc      2580
gggaactacc tgaccaagta ctccaaaaag gacaacggcc ccgtgatcaa gaagattaag      2640
tattacggca acaaactgaa cgcccatctg gacatcaccg acgactaccc caacagcaga      2700
aacaaggtcg tgaagctgtc cctgaagccc tacagattcg acgtgtacct ggacaatggc      2760
gtgtacaagt tcgtgaccgt gaagaatctg gatgtgatca aaaaagaaaa ctactacgaa      2820
gtgaatagca agtgctatga ggaagctaag aagctgaaga agatcagcaa ccaggccgag      2880
tttatcgcct ccttctacaa caacgatctg atcaagatca acggcgagct gtatagagtg      2940
atcggcgtga caacgacct gctgaaccgg atcgaagtga acatgatcga catcacctac      3000
cgcgagtacc tggaaaacat gaacgacaag aggcccccca ggatcattaa gacaatcgcc      3060
tccaagaccc agagcattaa gaagtacagc acagacattc tgggcaacct gtatgaagtg      3120
aaatctaaga agcaccctca gatcatcaaa aagggc                               3156
```

<210> SEQ ID NO 12
<211> LENGTH: 60
<212> TYPE: DNA
<213> ORGANISM: Artificial Sequence
<220> FEATURE:
<223> OTHER INFORMATION: Synthetic

<400> SEQUENCE: 12

```
tagcaataaa ggatcgttta ttttcattgg aagcgtgtgt tggttttttg atcaggcgcg        60
```

<210> SEQ ID NO 13
<211> LENGTH: 232
<212> TYPE: DNA
<213> ORGANISM: Artificial Sequence
<220> FEATURE:
<223> OTHER INFORMATION: Synthetic

<400> SEQUENCE: 13

```
ctagagctcg ctgatcagcc tcgactgtgc cttctagttg ccagccatct gttgtttgcc      60
cctcccccgt gccttccttg accctggaag gtgccactcc cactgtcctt tcctaataaa     120
atgaggaaat tgcatcgcat tgtctgagta ggtgtcattc tattctgggg ggtggggtgg     180
ggcaggacag caaggggggag gattgggaag agaatagcag gcatgctggg ga            232
```

<210> SEQ ID NO 14
<211> LENGTH: 7236
<212> TYPE: DNA
<213> ORGANISM: Artificial Sequence
<220> FEATURE:
<223> OTHER INFORMATION: Synthetic

<400> SEQUENCE: 14

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gagagggcct atttcccatg attccttcat atttgcatat     180
acgatacaag gctgttagag agataattgg aattaatttg actgtaaaca caaagatatt     240
agtacaaaat acgtgacgta gaaagtaata atttcttggg tagtttgcag ttttaaaatt     300 atgtttttaaa atggactatc atatgcttac cgtaacttga agtatttcg atttcttggc     360 tttatatatc ttgtggaaag gacgaaacac cgcatttgta tagagaggaa atgtgtttta     420
gtactctgga aacagaatct actaaaacaa ggcaaaatgc cgtgtttatc tcgtcaactt     480
gttggcgaga tttttctcga gtcgagtggc tccggtgccc gtcagtgggc agagcgcaca     540
tcgcccacag tccccgagaa gttggggggga ggggtcggca attgaaccgg tgcctagaga     600
aggtggcgcg gggtaaactg ggaaagtgat gtcgtgtact ggctccgcct ttttcccgag     660
ggtgggggag aaccgtatat aagtgcagta gtcgccgtga acgttctttt tcgcaacggg     720
tttgccgcca gaacacaggt gtcgtgaccg cggccatggc cccaaagaag aagcggaagg     780
tcggtatcca cggagtccca gcagccaagc ggaactacat cctgggcctg gacatcggca     840
tcaccagcgt gggctacggc atcatcgact acgagacacg ggacgtgatc gatgccggcg     900
tgcggctgtt caaagaggcc aacgtggaaa caacgagggg caggcggagc aagagaggcg     960
ccagaaggct gaagcggcgg aggcggcata gaatccagag agtgaagaag ctgctgttcg    1020
actacaacct gctgaccgac cacagcgagc tgagcggcat caaccccta gaggccagag    1080 tgaagggcct gagccagaag ctgagcgagg aagagttctc tgccgccctg ctgcacctgg    1140
ccaagagaag aggcgtgcac aacgtgaacg aggtggaaga ggacaccggc aacgagctgt    1200
ccaccaaaga gcagatcagc cggaacagca aggccctgga agagaaatac gtggccgaac    1260
tgcagctgga acggctgaag aaagacggcg aagtgcgggg cagcatcaac agattcaaga    1320
ccagcgacta cgtgaaagaa gccaaacagc tgctgaaggt gcagaaggcc taccaccagc    1380
tggaccagag cttcatcgac acctacatcg acctgctgga aacccggcgg acctactatg    1440
agggacctgg cgagggcagc cccttcggct ggaaggacat caagaatggg tacgagatgc    1500
tgatgggcca ctgcacctac ttccccgagg aactgcggag cgtgaagtac gcctacaacg    1560
ccgacctgta caacgccctg aacgacctga acaatctcgt gatcaccagg gacgagaacg    1620
agaagctgga atattacgag aagttccaga tcatcgagaa cgtgttcaag cagaagaaga    1680
agcccaccct gaagcagatc gccaaagaaa tcctcgtgaa cgaagaggat attaagggct    1740
```

-continued

```
acagagtgac cagcaccggc aagcccgagt tcaccaacct gaaggtgtac cacgacatca   1800
aggacattac cgcccggaaa gagattattg agaacgccga gctgctggat cagattgcca   1860
agatcctgac catctaccag agcagcgagg acatccagga agaactgacc aatctgaact   1920
ccgagctgac ccaggaagag atcgagcaga tctctaatct gaagggctat accggcaccc   1980
acaacctgag cctgaaggcc atcaacctga tcctggacga gctgtggcac accaacgaca   2040
accagatcgc tatcttcaac cggctgaagc tggtgcccaa gaaggtggac ctgtcccagc   2100
agaaagagat ccccaccacc ctggtggacg acttcatcct gagccccgtc gtgaagagaa   2160
gcttcatcca gagcatcaaa gtgatcaacg ccatcatcaa gaagtacggc ctgcccaacg   2220
acatcattat cgagctggcc cgcgagaaga actccaagga cgcccagaaa atgatcaacg   2280
agatgcagaa gcggaaccgg cagaccaacg agcggatcga ggaaatcatc cggaccaccg   2340
gcaaagagaa cgccaagtac ctgatcgaga agatcaagct gcacgacatg caggaaggca   2400
agtgcctgta cagcctggaa gccatccctc tggaagatct gctgaacaac cccttcaact   2460
atgaggtgga ccacatcatc cccagaagcg tgtccttcga caacagcttc aacaacaagg   2520
tgctcgtgaa gcaggaagaa aacagcaaga agggcaaccg gacccccattc cagtacctga   2580 gcagcagcga cagcaagatc agctacgaaa ccttcaagaa gcacatcctg aatctggcca   2640
agggcaaggg cagaatcagc aagaccaaga aagagtatct gctggaagaa cgggacatca   2700
acaggttctc cgtgcagaaa gacttcatca accggaacct ggtggatacc agatacgcca   2760
ccagaggcct gatgaacctg ctgcggagct acttcagagt gaacaacctg gacgtgaaag   2820
tgaagtccat caatggcggc ttcaccagct ttctgcggcg gaagtggaag tttaagaaag   2880
agcggaacaa ggggtacaag caccacgccg aggacgccct gatcattgcc aacgccgatt   2940
tcatcttcaa agagtggaag aaactggaca aggccaaaaa agtgatggaa aaccagatgt   3000
tcgaggaaaa gcaggccgag agcatgcccg agatcgaaac cgagcaggag tacaaagaga   3060
tcttcatcac cccccaccag atcaagcaca ttaaggactt caaggactac aagtacagcc   3120
accgggtgga caagaagcct aatagagagc tgattaacga caccctgtac tccacccgga   3180
aggacgacaa gggcaacacc ctgatcgtga caatctgaa cggcctgtac gacaaggaca   3240
atgacaagct gaaaaagctg atcaacaaga gccccgaaaa gctgctgatg taccaccacg   3300
acccccagac ctaccagaaa ctgaagctga ttatggaaca gtacggcgac gagaagaatc   3360
ccctgtacaa gtactacgag gaaaccggga actacctgac caagtactcc aaaaaggaca   3420 acggcccccgt gatcaagaag attaagtatt acggcaacaa actgaacgcc catctggaca   3480
tcaccgacga ctaccccaac agcagaaaca aggtcgtgaa gctgtccctg aagccctaca   3540
gattcgacgt gtacctggac aatggcgtgt acaagttcgt gaccgtgaag aatctggatg   3600
tgatcaaaaa agaaaactac tacgaagtga atagcaagtg ctatgaggaa gctaagaagc   3660
tgaagaagat cagcaaccag gccgagttta tcgcctcctt ctacaacaac gatctgatca   3720
agatcaacgg cgagctgtat agagtgatcg gcgtgaacaa cgacctgctg aaccggatcg   3780
aagtgaacat gatcgacatc acctaccgcg agtacctgga aaacatgaac gacaagaggc   3840
cccccaggat cattaagaca atcgcctcca gacccagag cattaagaag tacagcacag   3900
acattctggg caacctgtat gaagtgaaat ctaagaagca ccctcagatc atcaaaaagg   3960
gcaaaaggcc ggcggccacg aaaaaggccg gccaggcaaa aagaaaaag ggatcctacc   4020 catacgatgt tccagattac gcttacccat acgatgttcc agattacgct tacccatacg   4080
atgttccaga ttacgcttaa gaattctagc aataaaggat cgtttatttt cattggaagc   4140
```

```
gtgtgttggt tttttgatca ggcgcgggta ccgaacgctg acgtcatcaa cccgctccaa    4200
ggaatcgcgg gcccagtgtc actaggcggg aacacccagc gcgcgtgcgc cctggcagga    4260
agatggctgt gagggacagg ggagtggcgc cctgcaatat ttgcatgtcg ctatgtgttc    4320
tgggaaatca ccataaacgt gaaatgtctt tggatttggg aatcttataa gttctgtatg    4380
agaccacata tagtaatgaa attattggca cgttttagta ctctggaaac agaatctact    4440
aaaacaaggc aaaatgccgt gtttatctcg tcaacttgtt ggcgagattt ttggtaccag    4500
gaacccctag tgatggagtt ggccactccc tctctgcgcg ctcgctcgct cactgaggcc    4560
gggcgaccaa aggtcgcccg acgcccgggc tttgcccggg cggcctcagt gagcgagcga    4620
gcgcgcagct gcctgcaggg gcgcctgatg cggtattttc tccttacgca tctgtgcggt    4680
atttcacacc gcatacgtca aagcaaccat agtacgcgcc ctgtagcggc gcattaagcg    4740
cggcgggtgt ggtggttacg cgcagcgtga ccgctacact tgccagcgcc ctagcgcccg    4800
ctcctttcgc tttcttccct tcctttctcg ccacgttcgc cggctttccc cgtcaagctc    4860
taaatcgggg gctcccttta gggttccgat ttagtgcttt acggcacctc gaccccaaaa    4920
aacttgattt gggtgatggt tcacgtagtg ggccatcgcc ctgatagacg gtttttcgcc    4980
ctttgacgtt ggagtccacg ttctttaata gtggactctt gttccaaact ggaacaacac    5040
tcaaccctat ctcgggctat tcttttgatt tataagggat tttgccgatt tcggcctatt    5100
ggttaaaaaa tgagctgatt taacaaaaat ttaacgcgaa ttttaacaaa atattaacgt    5160
ttacaatttt atggtgcact ctcagtacaa tctgctctga tgccgcatag ttaagccagc    5220
cccgacaccc gccaacaccc gctgacgcgc cctgacgggc ttgtctgctc ccggcatccg    5280
cttacagaca agctgtgacc gtctccggga gctgcatgtg tcagaggttt tcaccgtcat    5340
caccgaaacg cgcgagacga aagggcctcg tgatacgcct attttttatag gttaatgtca    5400 tgataataat ggtttcttag acgtcaggtg gcacttttcg gggaaatgtg cgcggaaccc    5460
ctatttgttt attttttctaa atacattcaa atatgtatcc gctcatgaga caataacccct    5520 gataaatgct tcaataatat tgaaaaagga agagtatgag tattcaacat ttccgtgtcg    5580
cccttattcc cttttttgcg gcattttgcc ttcctgtttt tgctcaccca gaaacgctgg    5640
tgaaagtaaa agatgctgaa gatcagttgg gtgcacgagt gggttacatc gaactggatc    5700
tcaacagcgg taagatcctt gagagttttc gccccgaaga acgttttcca atgatgagca    5760
cttttaaagt tctgctatgt ggcgcggtat tatcccgtat tgacgccggg caagagcaac    5820
tcggtcgccg catacactat tctcagaatg acttggttga gtactcacca gtcacagaaa    5880
agcatcttac ggatggcatg acagtaagag aattatgcag tgctgccata accatgagtg    5940
ataacactgc ggccaactta cttctgacaa cgatcggagg accgaaggag ctaaccgctt    6000
ttttgcacaa catgggggat catgtaactc gccttgatcg ttgggaaccg gagctgaatg    6060
aagccatacc aaacgacgag cgtgacacca cgatgcctgt agcaatggca acaacgttgc    6120
gcaaactatt aactggcgaa ctacttactc tagcttcccg gcaacaatta atagactgga    6180
tggaggcgga taaagttgca ggaccacttc tgcgctcggc ccttccggct ggctggttta    6240
ttgctgataa atctggagcc ggtgagcgtg aagccgcgg tatcattgca gcactggggc    6300
cagatggtaa gccctcccgt atcgtagtta tctacacgac ggggagtcag gcaactatgg    6360
atgaacgaaa tagacagatc gctgagatag gtgcctcact gattaagcat tggtaactgt    6420
cagaccaagt ttactcatat atactttaga ttgatttaaa acttcatttt taatttaaaa    6480
```

-continued

```
ggatctaggt gaagatcctt tttgataatc tcatgaccaa aatcccttaa cgtgagtttt    6540
cgttccactg agcgtcagac cccgtagaaa agatcaaagg atcttcttga gatccttttt    6600
ttctgcgcgt aatctgctgc ttgcaaacaa aaaaaccacc gctaccagcg gtggtttgtt    6660
tgccggatca agagctacca actctttttc cgaaggtaac tggcttcagc agagcgcaga    6720
taccaaatac tgtccttcta gtgtagccgt agttaggcca ccacttcaag aactctgtag    6780
caccgcctac atacctcgct ctgctaatcc tgttaccagt ggctgctgcc agtggcgata    6840
agtcgtgtct taccgggttg gactcaagac gatagttacc ggataaggcg cagcggtcgg    6900
gctgaacggg gggttcgtgc acacagccca gcttggagcg aacgacctac accgaactga    6960
gatacctaca gcgtgagcta tgagaaagcg ccacgcttcc cgaagggaga aaggcggaca    7020
ggtatccggt aagcggcagg gtcggaacag gagagcgcac gagggagctt ccaggggggaa    7080 acgcctggta tctttatagt cctgtcgggt ttcgccacct ctgacttgag cgtcgatttt    7140
tgtgatgctc gtcaggggg cggagcctat ggaaaaacgc cagcaacgcg gcctttttac    7200
ggttcctggc cttttgctgg ccttttgctc acatgt    7236
```

```
<210> SEQ ID NO 15
<211> LENGTH: 7444
<212> TYPE: DNA
<213> ORGANISM: Artificial Sequence
<220> FEATURE:
<223> OTHER INFORMATION: Synthetic

<400> SEQUENCE: 15
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact    120
aggggttcct gcggcctcta gagagggcct atttcccatg attccttcat atttgcatat    180
acgatacaag gctgttagag agataattgg aattaatttg actgtaaaca caaagatatt    240
agtacaaaat acgtgacgta gaaagtaata atttcttggg tagtttgcag ttttaaaatt    300 atgtttttaaa atggactatc atatgcttac cgtaacttga aagtatttcg atttcttggc    360
tttatatatc ttgtggaaag gacgaaacac cgcatttgta tagagaggaa atgtgtttta    420
gtactctgga aacagaatct actaaaacaa ggcaaaatgc cgtgtttatc tcgtcaactt    480
gttggcgaga ttttttctcga gctagactag catgctgccc atgtaaggag gcaaggcctg    540
gggacacccg agatgcctgg ttataattaa cccagacatg tggctgcccc ccccccccca    600
acacctgctg cctctaaaaa taaccctgca tgccatgttc ccggcgaagg gccagctgtc    660 cccgccagc tagactcagc acttagttta ggaaccagtg agcaagtcag cccttggggc    720
agcccataca aggccatggg gctgggcaag ctgcacgcct gggtccgggg tgggcacggt    780
gcccgggcaa cgagctgaaa gctcatctgc tctcaggggc ccctccctgg ggacagcccc    840
tcctggctag tcacaccctg taggctcctc tatataaccc aggggcacag gggctgccct    900
cattctacca ccacctccac agcacagaca gacactcagg agccagccag caccggtgcc    960
accatggccc caaagaagaa gcggaaggtc ggtatccacg gagtcccagc agccaagcgg    1020
aactacatcc tgggcctgga catcggcatc accagcgtgg gctacggcat catcgactac    1080
gagacacggg acgtgatcga tgccggcgtg cggctgttca aagaggccaa cgtggaaaac    1140
aacgagggca ggcggagcaa gagaggcgcc agaaggctga gcggcggag gcggcataga    1200 atccagagag tgaagaagct gctgttcgac tacaacctgc tgaccgacca cagcgagctg    1260
agcggcatca accccctacga ggccagagtg aagggcctga gccagaagct gagcgaggaa    1320
```

-continued

```
gagttctctg ccgccctgct gcacctggcc aagagaagag gcgtgcacaa cgtgaacgag    1380
gtggaagagg acaccggcaa cgagctgtcc accaaagagc agatcagccg gaacagcaag    1440
gccctggaag agaaatacgt ggccgaactg cagctggaac ggctgaagaa agacggcgaa    1500
gtgcggggca gcatcaacag attcaagacc agcgactacg tgaaagaagc caaacagctg    1560
ctgaaggtgc agaaggccta ccaccagctg gaccagagct tcatcgacac ctacatcgac    1620
ctgctggaaa cccggcggac ctactatgag ggacctggcg agggcagccc cttcggctgg    1680
aaggacatca agaatggta cgagatgctg atgggccact gcacctactt ccccgaggaa    1740
ctgcggagcg tgaagtacgc ctacaacgcc gacctgtaca cgccctgaa cgacctgaac    1800 aatctcgtga tcaccaggga cgagaacgag aagctggaat attacgagaa gttccagatc    1860
atcgagaacg tgttcaagca gaagaagaag cccaccctga agcagatcgc caaagaaatc    1920
ctcgtgaacg aagaggatat taagggctac agagtgacca gcaccggcaa gcccgagttc    1980
accaacctga aggtgtacca cgacatcaag gacattaccg cccggaaaga gattattgag    2040
aacgccgagc tgctggatca gattgccaag atcctgacca tctaccagag cagcgaggac    2100
atccaggaag aactgaccaa tctgaactcc gagctgaccc aggaagagat cgagcagatc    2160
tctaatctga agggctatac cggcacccac aacctgagcc tgaaggccat caacctgatc    2220
ctggacgagc tgtggcacac caacgacaac cagatcgcta tcttcaaccg gctgaagctg    2280
gtgcccaaga aggtggacct gtcccagcag aaagagatcc ccaccaccct ggtggacgac    2340
ttcatcctga gccccgtcgt gaagagaagc ttcatccaga gcatcaaagt gatcaacgcc    2400
atcatcaaga gtacggcct gcccaacgac atcattatcg agctggcccg cgagaagaac    2460
tccaaggacg cccagaaaat gatcaacgag atgcagaagc ggaaccggca gaccaacgag    2520
cggatcgagg aaatcatccg gaccaccggc aaagagaacg ccaagtacct gatcgagaag    2580
atcaagctgc acgacatgca ggaaggcaag tgcctgtaca gcctggaagc catccctctg    2640
gaagatctgc tgaacaaccc cttcaactat gaggtggacc acatcatccc cagaagcgtg    2700
tccttcgaca cagcttcaa caacaaggtg ctcgtgaagc aggaagaaaa cagcaagaag    2760
ggcaaccgga ccccattcca gtacctgagc agcagcgaca gcaagatcag ctacgaaacc    2820
ttcaagaagc acatcctgaa tctggccaag ggcaagggca gaatcagcaa gaccaagaaa    2880
gagtatctgc tggaagaacg ggacatcaac aggttctccg tgcagaaaga cttcatcaac    2940
cggaacctgg tggataccag atacgccacc agaggcctga tgaacctgct gcggagctac    3000
ttcagagtga caacctgga cgtgaaagtg aagtccatca tggcggctt caccagcttt    3060 ctgcggcgga gtggaagtt taagaaagag cggaacaagg gtacaagca ccacgccgag    3120 gacgccctga tcattgccaa cgccgatttc atcttcaaag agtggaagaa actggacaag    3180
gccaaaaaag tgatggaaaa ccagatgttc gaggaaaagc aggccgagag catgcccgag    3240
atcgaaaccg agcaggagta caaagagatc ttcatcaccc cccaccagat caagcacatt    3300
aaggacttca aggactacaa gtacagccac cgggtggaca gaagcctaa tagagagctg    3360 attaacgaca ccctgtactc cacccggaag gacgacaagg gcaacaccct gatcgtgaac    3420
aatctgaacg gcctgtacga caaggacaat gacaagctga aaaagctgat caacaagagc    3480
cccgaaaagc tgctgatgta ccaccacgac ccccagacct accagaaact gaagctgatt    3540
atggaacagt acggcgacga gaagaatccc ctgtacaagt actacgagga aaccgggaac    3600
tacctgacca agtactccaa aaaggacaac ggccccgtga tcaagaagat taagtattac    3660
```

-continued

```
ggcaacaaac tgaacgccca tctggacatc accgacgact accccaacag cagaaacaag  3720
gtcgtgaagc tgtccctgaa gccctacaga ttcgacgtgt acctggacaa tggcgtgtac  3780
aagttcgtga ccgtgaagaa tctggatgtg atcaaaaaag aaaactacta cgaagtgaat  3840
agcaagtgct atgaggaagc taagaagctg aagaagatca gcaaccaggc cgagtttatc  3900
gcctccttct acaacaacga tctgatcaag atcaacggcg agctgtatag agtgatcggc  3960
gtgaacaacg acctgctgaa ccggatcgaa gtgaacatga tcgacatcac ctaccgcgag  4020
tacctggaaa acatgaacga caagaggccc cccaggatca ttaagacaat cgcctccaag  4080
acccagagca ttaagaagta cagcacagac attctgggca acctgtatga agtgaaatct  4140
aagaagcacc ctcagatcat caaaaagggc aaaaggccgg cggccacgaa aaaggccggc  4200
caggcaaaaa agaaaaaggg atcctaccca tacgatgttc cagattacgc ttacccatac  4260
gatgttccag attacgctta cccatacgat gttccagatt acgcttaaga attctagcaa  4320
taaaggatcg tttattttca ttggaagcgt gtgttggttt tttgatcagg cgcgggtacc  4380
gaacgctgac gtcatcaacc cgctccaagg aatcgcgggc ccagtgtcac taggcgggaa  4440
cacccagcgc gcgtgcgccc tggcaggaag atggctgtga gggacagggg agtggcgccc  4500
tgcaatattt gcatgtcgct atgtgttctg ggaaatcacc ataaacgtga aatgtctttg  4560
gatttgggaa tcttataagt tctgtatgag accacatata gtaatgaaat tattggcacg  4620
ttttagtact ctggaaacag aatctactaa aacaaggcaa aatgccgtgt ttatctcgtc  4680
aacttgttgg cgagattttt ggtaccagga acccctagtg atggagttgg ccactccctc  4740
tctgcgcgct cgctcgctca ctgaggccgg gcgaccaaag tcgcccgac gcccgggctt  4800 tgcccgggcg gcctcagtga gcgagcgagc gcgcagctgc ctgcaggggc gcctgatgcg  4860
gtattttctc cttacgcatc tgtgcggtat ttcacaccgc atacgtcaaa gcaaccatag  4920
tacgcgccct gtagcggcgc attaagcgcg gcgggtgtgg tggttacgcg cagcgtgacc  4980
gctacacttg ccagcgccct agcgcccgct cctttcgctt tcttcccttc ctttctcgcc  5040
acgttcgccg gctttccccg tcaagctcta atcggggggc tccctttagg gttccgattt  5100
agtgctttac ggcacctcga ccccaaaaaa cttgatttgg gtgatggttc acgtagtggg  5160
ccatcgccct gatagacggt ttttcgccct ttgacgttgg agtccacgtt ctttaatagt  5220
ggactcttgt tccaaactgg aacaacactc aaccctatct cgggctattc ttttgattta  5280
taagggattt tgccgatttc ggcctattgg ttaaaaaatg agctgattta acaaaaattt  5340
aacgcgaatt ttaacaaaat attaacgttt acaattttat ggtgcactct cagtacaatc  5400
tgctctgatg ccgcatagtt aagccagccc cgacacccgc caacacccgc tgacgcgccc  5460
tgacgggctt gtctgctccc ggcatccgct tacagacaag ctgtgaccgt ctccgggagc  5520
tgcatgtgtc agaggttttc accgtcatca ccgaaacgcg cgagacgaaa gggcctcgtg  5580
atacgcctat ttttataggt taatgtcatg ataataatgg tttcttagac gtcaggtggc  5640
acttttcggg gaaatgtgcg cggaacccct atttgtttat ttttctaaat acattcaaat  5700
atgtatccgc tcatgagaca ataaccctga taaatgcttc aataatattg aaaaaggaag  5760
agtatgagta ttcaacattt ccgtgtcgcc cttattccct tttttgcggc attttgcctt  5820
cctgtttttg ctcacccaga aacgctggtg aaagtaaaag atgctgaaga tcagttgggt  5880
gcacgagtgg gttacatcga actggatctc aacagcggta agatccttga gagttttcgc  5940
cccgaagaac gttttccaat gatgagcact tttaaagttc tgctatgtgg cgcggtatta  6000
tcccgtattg acgccgggca agagcaactc ggtcgccgca tacactattc tcagaatgac  6060
```

```
ttggttgagt actcaccagt cacagaaaag catcttacgg atggcatgac agtaagagaa    6120
ttatgcagtg ctgccataac catgagtgat aacactgcgg ccaacttact tctgacaacg    6180
atcggaggac cgaaggagct aaccgctttt ttgcacaaca tgggggatca tgtaactcgc    6240
cttgatcgtt gggaaccgga gctgaatgaa gccataccaa acgacgagcg tgacaccacg    6300
atgcctgtag caatggcaac aacgttgcgc aaactattaa ctggcgaact acttactcta    6360
gcttcccggc aacaattaat agactggatg gaggcggata aagttgcagg accacttctg    6420
cgctcggccc ttccggctgg ctggtttatt gctgataaat ctggagccgg tgagcgtgga    6480
agccgcggta tcattgcagc actggggcca gatggtaagc cctcccgtat cgtagttatc    6540
tacacgacgg ggagtcaggc aactatggat gaacgaaata gacagatcgc tgagataggt    6600
gcctcactga ttaagcattg gtaactgtca gaccaagttt actcatatat actttagatt    6660
gatttaaaac ttcattttta atttaaaagg atctaggtga agatcctttt tgataatctc    6720
atgaccaaaa tcccttaacg tgagttttcg ttccactgag cgtcagaccc cgtagaaaag    6780
atcaaaggat cttcttgaga tcctttttttt ctgcgcgtaa tctgctgctt gcaaacaaaa    6840
aaaccaccgc taccagcggt ggtttgtttg ccggatcaag agctaccaac tctttttccg    6900
aaggtaactg gcttcagcag agcgcagata ccaaatactg tccttctagt gtagccgtag    6960
ttaggccacc acttcaagaa ctctgtagca ccgcctacat acctcgctct gctaatcctg    7020
ttaccagtgg ctgctgccag tggcgataag tcgtgtctta ccgggttgga ctcaagacga    7080
tagttaccgg ataaggcgca gcggtcgggc tgaacggggg gttcgtgcac acagcccagc    7140
ttggagcgaa cgacctacac cgaactgaga tacctacagc gtgagctatg agaaagcgcc    7200
acgcttcccg aagggagaaa ggcggacagg tatccggtaa gcggcagggt cggaacagga    7260
gagcgcacga gggagcttcc agggggaaac gcctggtatc tttatagtcc tgtcgggttt    7320
cgccacctct gacttgagcg tcgatttttg tgatgctcgt cagggggcg gagcctatgg    7380 aaaaacgcca gcaacgcggc ctttttacgg ttcctggcct tttgctggcc ttttgctcac    7440
atgt                                                                 7444
```

```
<210> SEQ ID NO 16
<211> LENGTH: 7236
<212> TYPE: DNA
<213> ORGANISM: Artificial Sequence
<220> FEATURE:
<223> OTHER INFORMATION: Synthetic

<400> SEQUENCE: 16
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gaaaaaatct cgccaacaag ttgacgagat aaacacggca    180
ttttgccttg ttttagtaga ttctgtttcc agagtactaa aacacatttc tctctatac     240 aaatgcggtg tttcgtcctt tccacaagat atataaagcc aagaaatcga atactttca     300 agttacggta agcatatgat agtccatttt aaaacataat tttaaaactg caaactaccc    360
aagaaattat tactttctac gtcacgtatt ttgtactaat atctttgtgt ttacagtcaa    420
attaattcca attatctctc taacagcctt gtatcgtata tgcaaatatg aaggaatcat    480
gggaaatagg ccctcctcga gtcgagtggc tccggtgccc gtcagtgggc agagcgcaca    540
tcgcccacag tccccgagaa gttggggggga ggggtcggca attgaaccgg tgcctagaga    600
```

```
aggtggcgcg gggtaaactg ggaaagtgat gtcgtgtact ggctccgcct tttttcccgag      660 ggtgggggag aaccgtatat aagtgcagta gtcgccgtga acgttctttt tcgcaacggg      720
tttgccgcca gaacacaggt gtcgtgaccg cggccatggc cccaaagaag aagcggaagg      780
tcggtatcca cggagtccca gcagccaagc ggaactacat cctgggcctg gacatcggca      840
tcaccagcgt gggctacggc atcatcgact acgagacacg ggacgtgatc gatgccggcg      900
tgcggctgtt caaagaggcc aacgtggaaa caacgaggg caggcggagc aagagaggcg      960
ccagaaggct gaagcggcgg aggcggcata gaatccagag agtgaagaag ctgctgttcg     1020
actacaacct gctgaccgac cacagcgagc tgagcggcat caacccctac gaggccagag     1080
tgaagggcct gagccagaag ctgagcgagg aagagttctc tgccgccctg ctgcacctgg     1140
ccaagagaag aggcgtgcac aacgtgaacg aggtggaaga ggacaccggc aacgagctgt     1200
ccaccaaaga gcagatcagc cggaacagca aggccctgga agagaaatac gtggccgaac     1260
tgcagctgga acggctgaag aaagacggcg aagtgcgggg cagcatcaac agattcaaga     1320
ccagcgacta cgtgaaagaa gccaaacagc tgctgaaggt gcagaaggcc taccaccagc     1380
tggaccagag cttcatcgac acctacatcg acctgctgga aacccggcgg acctactatg     1440
agggacctgg cgagggcagc cccttcggct ggaaggacat caaagaatgg tacgagatgc     1500
tgatgggcca ctgcacctac ttccccgagg aactgcggag cgtgaagtac gcctacaacg     1560
ccgacctgta caacgccctg aacgacctga caatctcgt gatcaccagg gacgagaacg     1620
agaagctgga atattacgag aagttccaga tcatcgagaa cgtgttcaag cagaagaaga     1680
agcccaccct gaagcagatc gccaaagaaa tcctcgtgaa cgaagaggat attaagggct     1740
acagagtgac cagcaccggc aagcccgagt tcaccaacct gaaggtgtac cacgacatca     1800
aggacattac cgcccggaaa gagattattg agaacgccga gctgctggat cagattgcca     1860
agatcctgac catctaccag agcagcgagg acatccagga agaactgacc aatctgaact     1920
ccgagctgac ccaggaagag atcgagcaga tctctaatct gaagggctat accggcaccc     1980
acaacctgag cctgaaggcc atcaacctga tcctggacga gctgtggcac accaacgaca     2040
accagatcgc tatcttcaac cggctgaagc tggtgcccaa gaaggtggac ctgtcccagc     2100
agaaagagat ccccaccacc ctggtggacg acttcatcct gagccccgtc gtgaagagaa     2160
gcttcatcca gagcatcaaa gtgatcaacg ccatcatcaa gaagtacggc ctgcccaacg     2220
acatcattat cgagctggcc cgcgagaaga actccaagga cgcccagaaa atgatcaacg     2280
agatgcagaa gcggaaccgg cagaccaacg agcggatcga ggaaatcatc cggaccaccg     2340
gcaaagagaa cgccaagtac ctgatcgaga agatcaagct gcacgacatg caggaaggca     2400
agtgcctgta cagcctggaa gccatccctc tggaagatct gctgaacaac cccttcaact     2460
atgaggtgga ccacatcatc cccagaagcg tgtccttcga caacagcttc aacaacaagg     2520
tgctcgtgaa gcaggaagaa aacagcaaga gggcaaccg acccccattc cagtacctga     2580
gcagcagcga cagcaagatc agctacgaaa ccttcaagaa gcacatcctg aatctggcca     2640
agggcaaggg cagaatcagc aagaccaaga aagagtatct gctggaagaa cgggacatca     2700
acaggttctc cgtgcagaaa gacttcatca accggaacct ggtggatacc agatacgcca     2760
ccagaggcct gatgaacctg ctgcggagct acttcagagt gaacaacctg gacgtgaaag     2820
tgaagtccat caatggcggc ttcaccagct ttctgcggcg gaagtggaag tttaagaaag     2880
agcggaacaa ggggtacaag caccacgccg aggacgccct gatcattgcc aacgccgatt     2940
tcatcttcaa agagtggaag aaactggaca aggccaaaaa agtgatggaa aaccagatgt     3000
```

-continued

```
tcgaggaaaa gcaggccgag agcatgcccg agatcgaaac cgagcaggag tacaaagaga   3060
tcttcatcac cccccaccag atcaagcaca ttaaggactt caaggactac aagtacagcc   3120
accgggtgga caagaagcct aatagagagc tgattaacga caccctgtac tccacccgga   3180
aggacgacaa gggcaacacc ctgatcgtga acaatctgaa cggcctgtac gacaaggaca   3240
atgacaagct gaaaaagctg atcaacaaga gccccgaaaa gctgctgatg taccaccacg   3300 accccccagac ctaccagaaa ctgaagctga ttatggaaca gtacggcgac gagaagaatc   3360
ccctgtacaa gtactacgag gaaaccggga actacctgac caagtactcc aaaaaggaca   3420
acggccccgt gatcaagaag attaagtatt acggcaacaa actgaacgcc catctggaca   3480
tcaccgacga ctaccccaac agcagaaaca aggtcgtgaa gctgtccctg aagccctaca   3540
gattcgacgt gtacctggac aatggcgtgt acaagttcgt gaccgtgaag aatctggatg   3600
tgatcaaaaa agaaaactac tacgaagtga atagcaagtg ctatgaggaa gctaagaagc   3660
tgaagaagat cagcaaccag gccgagttta tcgcctcctt ctacaacaac gatctgatca   3720
agatcaacgg cgagctgtat agagtgatcg gcgtgaacaa cgacctgctg aaccggatcg   3780
aagtgaacat gatcgacatc acctaccgcg agtacctgga aaacatgaac gacaagaggc   3840
cccccaggat cattaagaca atcgcctcca gacccagag cattaagaag tacagcacag   3900
acattctggg caacctgtat gaagtgaaat ctaagaagca ccctcagatc atcaaaaagg   3960
gcaaaaggcc ggcggccacg aaaaaggccg gccaggcaaa aagagaaaag ggatcctacc   4020
catacgatgt tccagattac gcttaccat acgatgttcc agattacgct tacccatacg   4080
atgttccaga ttacgcttaa gaattctagc aataaaggat cgtttatttt cattggaagc   4140
gtgtgttggt tttttgatca ggcgcgggta ccgaacgctg acgtcatcaa cccgctccaa   4200
ggaatcgcgg gcccagtgtc actaggcggg aacacccagc gcgcgtgcgc cctggcagga   4260
agatggctgt gagggacagg ggagtggcgc cctgcaatat ttgcatgtcg ctatgtgttc   4320
tgggaaatca ccataaacgt gaaatgtctt tggatttggg aatcttataa gttctgtatg   4380
agaccacata tagtaatgaa attattggca cgttttagta ctctggaaac agaatctact   4440
aaaacaaggc aaaatgccgt gtttatctcg tcaacttgtt ggcgagattt ttggtaccag   4500
gaacccctag tgatggagtt ggccactccc tctctgcgcg ctcgctcgct cactgaggcc   4560
gggcgaccaa aggtcgcccg acgcccgggc tttgcccggg cggcctcagt gagcgagcga   4620
gcgcgcagct gcctgcaggg gcgcctgatg cggtattttc tccttacgca tctgtgcggt   4680
atttcacacc gcatacgtca aagcaaccat agtacgcgcc ctgtagcggc gcattaagcg   4740
cggcgggtgt ggtggttacg cgcagcgtga ccgctacact tgccagcgcc ctagcgcccg   4800
ctcctttcgc tttcttccct tcctttctcg ccacgttcgc cggctttccc cgtcaagctc   4860
taaatcgggg gctcccttta gggttccgat ttagtgcttt acggcacctc gaccccaaaa   4920
aacttgattt gggtgatggt tcacgtagtg gccatcgcc ctgatagacg ttttttcgcc   4980
ctttgacgtt ggagtccacg ttctttaata gtggactctt gttccaaact ggaacaacac   5040
tcaaccctat ctcgggctat tcttttgatt tataagggat tttgccgatt tcggcctatt   5100
ggttaaaaaa tgagctgatt taacaaaaat ttaacgcgaa ttttaacaaa atattaacgt   5160
ttacaatttt atggtgcact ctcagtacaa tctgctctga tgccgcatag ttaagccagc   5220
cccgacaccc gccaacaccc gctgacgcgc cctgacgggc ttgtctgctc ccggcatccg   5280
cttacagaca agctgtgacc gtctccggga gctgcatgtg tcagaggttt tcaccgtcat   5340
```

-continued

```
caccgaaacg cgcgagacga aagggcctcg tgatacgcct attttttatag gttaatgtca        5400 tgataataat ggtttcttag acgtcaggtg gcacttttcg gggaaatgtg cgcggaaccc        5460
ctatttgttt attttttctaa atacattcaa atatgtatcc gctcatgaga caataaccct       5520
gataaatgct tcaataatat tgaaaaagga agagtatgag tattcaacat ttccgtgtcg        5580
cccttattcc cttttttgcg gcattttgcc ttcctgtttt tgctcaccca gaaacgctgg        5640
tgaaagtaaa agatgctgaa gatcagttgg gtgcacgagt gggttacatc gaactggatc        5700
tcaacagcgg taagatcctt gagagttttc gccccgaaga acgttttcca atgatgagca        5760
cttttaaagt tctgctatgt ggcgcggtat tatcccgtat tgacgccggg caagagcaac       5820
tcggtcgccg catacactat tctcagaatg acttggttga gtactcacca gtcacagaaa       5880
agcatcttac ggatggcatg acagtaagag aattatgcag tgctgccata accatgagtg       5940
ataacactgc ggccaactta cttctgacaa cgatcggagg accgaaggag ctaaccgctt       6000
ttttgcacaa catgggggat catgtaactc gccttgatcg ttgggaaccg gagctgaatg      6060
aagccatacc aaacgacgag cgtgacacca cgatgcctgt agcaatggca acaacgttgc       6120
gcaaactatt aactggcgaa ctacttactc tagcttcccg gcaacaatta atagactgga       6180
tggaggcgga taaagttgca ggaccacttc tgcgctcggc ccttccggct ggctggttta       6240
ttgctgataa atctggagcc ggtgagcgtg gaagccgcgg tatcattgca gcactggggc       6300
cagatggtaa gccctcccgt atcgtagtta tctacacgac ggggagtcag gcaactatgg       6360
atgaacgaaa tagacagatc gctgagatag gtgcctcact gattaagcat tggtaactgt       6420
cagaccaagt ttactcatat atactttaga ttgatttaaa acttcatttt taatttaaaa       6480
ggatctaggt gaagatcctt tttgataatc tcatgaccaa aatcccttaa cgtgagtttt       6540
cgttccactg agcgtcagac cccgtagaaa agatcaaagg atcttcttga tcctttttt       6600 ttctgcgcgt aatctgctgc ttgcaaacaa aaaaaccacc gctaccagcg gtggtttgtt       6660
tgccggatca gagctacca actctttttc cgaaggtaac tggcttcagc agagcgcaga       6720
taccaaatac tgtccttcta gtgtagccgt agttaggcca ccacttcaag aactctgtag       6780
caccgcctac atacctcgct ctgctaatcc tgttaccagt ggctgctgcc agtggcgata       6840
agtcgtgtct taccgggttg gactcaagac gatagttacc ggataaggcg cagcggtcgg       6900
gctgaacggg gggttcgtgc acacagccca gcttggagcg aacgacctac accgaactga       6960
gatacctaca gcgtgagcta tgagaaagcg ccacgcttcc cgaagggaga aaggcggaca       7020
ggtatccggt aagcggcagg gtcggaacag gagagcgcac gagggagctt ccaggggaa       7080 acgcctggta tctttatagt cctgtcgggt ttcgccacct ctgacttgag cgtcgatttt       7140
tgtgatgctc gtcaggggg cggagcctat ggaaaaacgc cagcaacgcg gcctttttac        7200
ggttcctggc cttttgctgg cctttttgctc acatgt                                7236
```

<210> SEQ ID NO 17
<211> LENGTH: 7444
<212> TYPE: DNA
<213> ORGANISM: Artificial Sequence
<220> FEATURE:
<223> OTHER INFORMATION: Synthetic

<400> SEQUENCE: 17

```
cctgcaggca gctgcgcgct cgctcgctca ctgaggccgc ccgggcgtcg ggcgaccttt          60
ggtcgcccgg cctcagtgag cgagcgagcg cgcagagagg gagtggccaa ctccatcact        120
aggggttcct gcggcctcta gaaaaaatct cgccaacaag ttgacgagat aaacacggca         180
```

-continued

```
ttttgccttg ttttagtaga ttctgtttcc agagtactaa aacacatttc ctctctatac    240
aaatgcggtg tttcgtcctt tccacaagat atataaagcc aagaaatcga aatactttca    300
agttacggta agcatatgat agtccatttt aaaacataat tttaaaactg caaactaccc    360
aagaaattat tactttctac gtcacgtatt ttgtactaat atctttgtgt ttacagtcaa    420
attaattcca attatctctc taacagcctt gtatcgtata tgcaaatatg aaggaatcat    480
gggaaatagg ccctcctcga gctagactag catgctgccc atgtaaggag gcaaggcctg    540
gggacacccg agatgcctgg ttataattaa cccagacatg tggctgcccc cccccccca    600 acacctgctg cctctaaaaa taaccctgca tgccatgttc ccggcgaagg gccagctgtc    660
ccccgccagc tagactcagc acttagttta ggaaccagtg agcaagtcag cccttggggc    720
agcccataca aggccatggg gctgggcaag ctgcacgcct gggtccgggg tgggcacggt    780
gcccgggcaa cgagctgaaa gctcatctgc tctcaggggc ccctccctgg ggacagcccc    840
tcctggctag tcacaccctg taggctcctc tatataaccc aggggcacag gggctgccct    900
cattctacca ccacctccac agcacagaca gacactcagg agccagccag caccggtgcc    960
accatggccc caaagaagaa gcggaaggtc ggtatccacg gagtcccagc agccaagcgg   1020
aactacatcc tgggcctgga catcggcatc accagcgtgg gctacggcat catcgactac   1080
gagacacggg acgtgatcga tgccggccgtg cggctgttca agagggccaa cgtggaaaac   1140
aacgagggca ggcggagcaa gagaggcgcc agaaggctga gcggcggag gcggcataga   1200 atccagagag tgaagaagct gctgttcgac tacaacctgc tgaccgacca cagcgagctg   1260
agcggcatca acccctacga ggccagagtg aagggcctga gccagaagct gagcgaggaa   1320
gagttctctg ccgccctgct gcacctggcc aagagaagag gcgtgcacaa cgtgaacgag   1380
gtggaagagg acaccggcaa cgagctgtcc accaaagagc agatcagccg gaacagcaag   1440
gccctggaag agaaatacgt ggccgaactg cagctggaac ggctgaagaa agacggcgaa   1500
gtgcggggca gcatcaacag attcaagacc agcgactacg tgaaagaagc caaacagctg   1560
ctgaaggtgc agaaggccta ccaccagctg gaccagagct tcatcgacac ctacatcgac   1620
ctgctggaaa cccggcggac ctactatgag ggacctggcg agggcagccc cttcggctgg   1680
aaggacatca agaatggta cgagatgctg atgggccact gcacctactt ccccgaggaa   1740
ctgcggagcg tgaagtacgc ctacaacgcc gacctgtaca cgccctgaa cgacctgaac   1800 aatctcgtga tcaccaggga cgagaacgag aagctggaat attacgagaa gttccagatc   1860
atcgagaacg tgttcaagca gaagaagaag cccaccctga gcagatcgc caaagaaatc   1920 ctcgtgaacg aagaggatat taagggctac agagtgacca gcaccggcaa gcccgagttc   1980
accaacctga aggtgtacca cgacatcaag gacattaccg cccggaaaga gattattgag   2040
aacgccgagc tgctggatca gattgccaag atcctgacca tctaccagag cagcgaggac   2100
atccaggaag aactgaccaa tctgaactcc gagctgaccc aggaagagat cgagcagatc   2160
tctaatctga agggctatac cggcacccac aacctgagcc tgaaggccat caacctgatc   2220
ctggacgagc tgtggcacac caacgacaac cagatcgcta tcttcaaccg gctgaagctg   2280
gtgcccaaga aggtggacct gtcccagcag aaagagatcc ccaccaccct ggtggacgac   2340
ttcatcctga gccccgtcgt gaagagaagc ttcatccaga gcatcaaagt gatcaacgcc   2400
atcatcaaga agtacggcct gcccaacgac atcattatcg agctggccg cgagaagaac   2460 tccaaggacg cccagaaaat gatcaacgag atgcagaagc ggaaccggca gaccaacgag   2520
```

-continued

```
cggatcgagg aaatcatccg gaccaccggc aaagagaacg ccaagtacct gatcgagaag   2580
atcaagctgc acgacatgca ggaaggcaag tgcctgtaca gcctggaagc catccctctg   2640
gaagatctgc tgaacaaccc cttcaactat gaggtggacc acatcatccc cagaagcgtg   2700
tccttcgaca acagcttcaa caacaaggtg ctcgtgaagc aggaagaaaa cagcaagaag   2760
ggcaaccgga ccccattcca gtacctgagc agcagcgaca gcaagatcag ctacgaaacc   2820
ttcaagaagc acatcctgaa tctggccaag ggcaagggca gaatcagcaa gaccaagaaa   2880
gagtatctgc tggaagaacg ggacatcaac aggttctccg tgcagaaaga cttcatcaac   2940
cggaacctgg tggataccag atacgccacc agaggcctga tgaacctgct gcggagctac   3000
ttcagagtga acaacctgga cgtgaaagtg aagtccatca tggcggctt caccagcttt   3060 ctgcggcgga agtggaagtt taagaaagag cggaacaagg ggtacaagca ccacgccgag   3120
gacgccctga tcattgccaa cgccgatttc atcttcaaag agtggaagaa actggacaag   3180
gccaaaaaag tgatggaaaa ccagatgttc gaggaaaagc aggccgagag catgcccgag   3240
atcgaaaccg agcaggagta caaagagatc ttcatcaccc cccaccagat caagcacatt   3300
aaggacttca aggactacaa gtacagccac cgggtggaca agaagcctaa tagagagctg   3360
attaacgaca ccctgtactc cacccggaag gacgacaagg caacaccct gatcgtgaac   3420 aatctgaacg gcctgtacga caaggacaat gacaagctga aaaagctgat caacaagagc   3480
cccgaaaagc tgctgatgta ccaccacgac ccccagacct accagaaact gaagctgatt   3540
atggaacagt acggcgacga gaagaatccc ctgtacaagt actacgagga aaccgggaac   3600
tacctgacca agtactccaa aaaggacaac ggccccgtga tcaagaagat taagtattac   3660
ggcaacaaac tgaacgccca tctggacatc accgacgact accccaacag cagaaacaag   3720
gtcgtgaagc tgtccctgaa gccctacaga ttcgacgtgt acctggacaa tggcgtgtac   3780
aagttcgtga ccgtgaagaa tctggatgtg atcaaaaaag aaaactacta cgaagtgaat   3840
agcaagtgct atgaggaagc taagaagctg aagaagatca gcaaccaggc cgagtttatc   3900
gcctccttct acaacaacga tctgatcaag atcaacggcg agctgtatag agtgatcggc   3960
gtgaacaacg acctgctgaa ccggatcgaa gtgaacatga tcgacatcac ctaccgcgag   4020
tacctggaaa acatgaacga caagaggccc cccaggatca ttaagacaat cgcctccaag   4080
acccagagca ttaagaagta cagcacagac attctgggca acctgtatga agtgaaatct   4140
aagaagcacc ctcagatcat caaaaagggc aaaaggccgg cggccacgaa aaaggccggc   4200
caggcaaaaa agaaaaaggg atcctaccca tacgatgttc cagattacgc ttacccatac   4260
gatgttccag attacgctta cccatacgat gttccagatt acgcttaaga attctagcaa   4320
taaaggatcg tttattttca ttggaagcgt gtgttggttt tttgatcagg cgcgggtacc   4380
gaacgctgac gtcatcaacc cgctccaagg aatcgcgggc ccagtgtcac taggcgggaa   4440
cacccagcgc gcgtgcgccc tggcaggaag atggctgtga gggacagggg agtggcgccc   4500
tgcaatattt gcatgtcgct atgtgttctg ggaaatcacc ataaacgtga atgtctttg   4560 gatttgggaa tcttataagt tctgtatgag accacatata gtaatgaaat tattggcacg   4620
ttttagtact ctggaaacag aatctactaa aacaaggcaa aatgccgtgt ttatctcgtc   4680
aacttgttgg cgagattttt ggtaccagga acccctagtg atggagttgg ccactccctc   4740
tctgcgcgct cgctcgctca ctgaggccgg gcgaccaaag gtcgcccgac gcccgggctt   4800
tgcccgggcg gcctcagtga gcgagcgagc gcgcagctgc ctgcaggggc gcctgatgcg   4860
gtattttctc cttacgcatc tgtgcggtat ttcacaccgc atacgtcaaa gcaaccatag   4920
```

-continued

```
tacgcgccct gtagcggcgc attaagcgcg gcgggtgtgg tggttacgcg cagcgtgacc    4980
gctacacttg ccagcgccct agcgcccgct cctttcgctt tcttcccttc ctttctcgcc    5040
acgttcgccg gctttccccg tcaagctcta aatcgggggc tcccttttagg gttccgattt   5100 agtgctttac ggcacctcga ccccaaaaaa cttgatttgg gtgatggttc acgtagtggg    5160
ccatcgccct gatagacggt ttttcgccct ttgacgttgg agtccacgtt ctttaatagt    5220
ggactcttgt tccaaactgg aacaacactc aaccctatct cgggctattc tttttgattta   5280 taagggattt tgccgatttc ggcctattgg ttaaaaaatg agctgattta acaaaaattt    5340
aacgcgaatt ttaacaaaat attaacgttt acaattttat ggtgcactct cagtacaatc    5400
tgctctgatg ccgcatagtt aagccagccc cgacacccgc caacacccgc tgacgcgccc    5460
tgacgggctt gtctgctccc ggcatccgct tacagacaag ctgtgaccgt ctccgggagc    5520
tgcatgtgtc agaggttttc accgtcatca ccgaaacgcg cgagacgaaa gggcctcgtg    5580
atacgcctat ttttataggt taatgtcatg ataataatgg tttcttagac gtcaggtggc    5640
acttttcggg gaaatgtgcg cggaacccct atttgtttat ttttctaaat acattcaaat    5700
atgtatccgc tcatgagaca ataaccctga taaatgcttc aataatattg aaaaaggaag    5760
agtatgagta ttcaacattt ccgtgtcgcc cttattccct tttttgcggc attttgcctt    5820
cctgtttttg ctcacccaga aacgctggtg aaagtaaaag atgctgaaga tcagttgggt    5880
gcacgagtgg gttacatcga actggatctc aacagcggta agatccttga gagttttcgc    5940
cccgaagaac gttttccaat gatgagcact tttaaagttc tgctatgtgg cgcggtatta    6000
tcccgtattg acgccgggca agagcaactc ggtcgccgca tacactattc tcagaatgac    6060
ttggttgagt actcaccagt cacagaaaag catcttacgg atggcatgac agtaagagaa    6120
ttatgcagtg ctgccataac catgagtgat aacactgcgg ccaacttact tctgacaacg    6180
atcggaggac cgaaggagct aaccgctttt ttgcacaaca tggggggatca tgtaactcgc    6240 cttgatcgtt gggaaccgga gctgaatgaa gccataccaa acgacgagcg tgacaccacg    6300
atgcctgtag caatggcaac aacgttgcgc aaactattaa ctggcgaact acttactcta    6360
gcttcccggc aacaattaat agactggatg gaggcggata aagttgcagg accacttctg    6420
cgctcggccc ttccggctgg ctggtttatt gctgataaat ctggagccgg tgagcgtgga    6480
agccgcggta tcattgcagc actgggggcca gatggtaagc cctcccgtat cgtagttatc    6540
tacacgacgg ggagtcaggc aactatggat gaacgaaata gacagatcgc tgagataggt    6600
gcctcactga ttaagcattg gtaactgtca gaccaagttt actcatatat actttagatt    6660
gatttaaaac ttcattttta atttaaaagg atctaggtga agatcctttt tgataatctc    6720
atgaccaaaa tcccttaacg tgagttttcg ttccactgag cgtcagaccc cgtagaaaag    6780
atcaaaggat cttcttgaga tccttttttt ctgcgcgtaa tctgctgctt gcaaacaaaa    6840
aaaccaccgc taccagcggt ggtttgtttg ccggatcaag agctaccaac tctttttccg    6900
aaggtaactg gcttcagcag agcgcagata ccaaatactg tccttctagt gtagccgtag    6960
ttaggccacc acttcaagaa ctctgtagca ccgcctacat acctcgctct gctaatcctg    7020
ttaccagtgg ctgctgccag tggcgataag tcgtgtctta ccgggttgga ctcaagacga    7080
tagttaccgg ataaggcgca gcggtcgggc tgaacggggg gttcgtgcac acagcccagc    7140
ttggagcgaa cgacctacac cgaactgaga tacctacagc gtgagctatg agaaagcgcc    7200
acgcttcccg aagggagaaa ggcggacagg tatccggtaa gcggcagggt cggaacagga    7260
```

-continued

```
gagcgcacga gggagcttcc agggggaaac gcctggtatc tttatagtcc tgtcgggttt    7320
cgccacctct gacttgagcg tcgatttttg tgatgctcgt caggggggcg gagcctatgg    7380
aaaaacgcca gcaacgcggc ctttttacgg ttcctggcct tttgctggcc ttttgctcac    7440
atgt                                                                 7444
```

<210> SEQ ID NO 18
<211> LENGTH: 7381
<212> TYPE: DNA
<213> ORGANISM: Artificial Sequence
<220> FEATURE:
<223> OTHER INFORMATION: Synthetic

<400> SEQUENCE: 18

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaaaatct cgccaacaag ttgacgagat aaacacggca     180
ttttgccttg ttttagtaga ttctgtttcc agagtactaa aacacatttc ctctctatac     240
aaatgcggtg tttcgtcctt tccacaagat atataaagcc aagaaatcga aatactttca     300
agttacggta agcatatgat agtccatttt aaaacataat tttaaaactg caaactaccc     360
aagaaattat tactttctac gtcacgtatt ttgtactaat atctttgtgt ttacagtcaa     420
attaattcca attatctctc taacagcctt gtatcgtata tgcaaatatg aaggaatcat     480
gggaaatagg ccctcctcga ggagctccac cgcggtggcg gccgtccgcc ttcggcacca     540
tcctcacgac acccaaatat ggcgacgggt gaggaatggt ggggagttat ttttagagcg     600
gtgaggaagg tgggcaggca gcaggtgttg gcgctctaaa ataactcccc gggagttatt     660
tttagagcgg aggaatggtg gacacccaaa tatggcgacg gttcctcacc cgtcgccata     720
tttgggtgtc cgccctcggc cggggccgca ttcctggggg ccgggcggtg ctcccgcccg     780
cctcgataaa aggctccggg gccggcggcg gcccacgagc tacccggagg agcgggaggc     840
gccaagctct agaactagtg gatcccccgg gctgcaggaa ttcgatatac cggtgccacc     900
atggccccaa agaagaagcg gaaggtcggt atccacggag tcccagcagc caagcggaac     960
tacatcctgg gcctggacat cggcatcacc agcgtgggct acggcatcat cgactacgag    1020
acacgggacg tgatcgatgc cggcgtgcgg ctgttcaaag aggccaacgt ggaaaacaac    1080
gagggcaggc ggagcaagag aggcgccaga aggctgaagc ggcggaggcg gcatagaatc    1140
cagagagtga gaagctgct gttcgactac aacctgctga ccgaccacag cgagctgagc    1200
ggcatcaacc cctacgaggc cagagtgaag ggcctgagcc agaagctgag cgaggaagag    1260
ttctctgccg ccctgctgca cctggccaag agaagaggcg tgcacaacgt gaacgaggtg    1320
gaagaggaca ccggcaacga gctgtccacc aaagagcaga tcagccggaa cagcaaggcc    1380
ctggaagaga atacgtggc cgaactgcag ctggaacggc tgaagaaaga cggcgaagtg    1440
cggggcagca tcaacagatt caagaccagc gactacgtga agaagccaa acagctgctg    1500 aaggtgcaga aggcctacca ccagctggac cagagcttca tcgacaccta catcgacctg    1560
ctggaaaccc ggcggaccta ctatgaggga cctggcgagg gcagcccctt cggctggaag    1620
gacatcaaag aatggtacga gatgctgatg ggccactgca cctacttccc cgaggaactg    1680
cggagcgtga gtacgcccta caacgccgac ctgtacaacg ccctgaacga cctgaacaat    1740
ctcgtgatca ccaggggacga gaacgagaag ctggaatatt acgagaagtt ccagatcatc    1800
gagaacgtgt tcaagcagaa gaagaagccc accctgaagc agatcgccaa agaaatcctc    1860
```

```
gtgaacgaag aggatattaa gggctacaga gtgaccagca ccggcaagcc cgagttcacc    1920
aacctgaagg tgtaccacga catcaaggac attaccgccc ggaaagagat tattgagaac    1980
gccgagctgc tggatcagat tgccaagatc ctgaccatct accagagcag cgaggacatc    2040
caggaagaac tgaccaatct gaactccgag ctgacccagg aagagatcga gcagatctct    2100
aatctgaagg gctataccgg cacccacaac ctgagcctga aggccatcaa cctgatcctg    2160
gacgagctgt ggcacaccaa cgacaaccag atcgctatct tcaaccggct gaagctggtg    2220
cccaagaagg tggacctgtc ccagcagaaa gagatcccca ccaccctggt ggacgacttc    2280
atcctgagcc ccgtcgtgaa gagaagcttc atccagagca tcaaagtgat caacgccatc    2340
atcaagaagt acggcctgcc caacgacatc attatcgagc tggcccgcga gaagaactcc    2400
aaggacgccc agaaaatgat caacgagatg cagaagcgga accggcagac caacgagcgg    2460
atcgaggaaa tcatccggac caccggcaaa gagaacgcca agtacctgat cgagaagatc    2520
aagctgcacg acatgcagga aggcaagtgc ctgtacagcc tggaagccat ccctctggaa    2580
gatctgctga caacccctt caactatgag gtggaccaca tcatccccag aagcgtgtcc    2640
ttcgacaaca gcttcaacaa caaggtgctc gtgaagcagg aagaaaacag caagaagggc    2700
aaccggaccc cattccagta cctgagcagc agcgacagca agatcagcta cgaaaccttc    2760
aagaagcaca tcctgaatct ggccaagggc aagggcagaa tcagcaagac caagaaagag    2820
tatctgctgg aagaacggga catcaacagg ttctccgtgc agaaagactt catcaaccgg    2880
aacctggtgg ataccagata cgccaccaga ggcctgatga acctgctgcg gagctacttc    2940
agagtgaaca acctggacgt gaaagtgaag tccatcaatg gcggcttcac cagctttctg    3000
cggcggaagt ggaagtttaa aaagagcgg aacaaggggt acaagcacca cgccgaggac    3060
gccctgatca ttgccaacgc cgatttcatc ttcaaagagt ggaagaaact ggacaaggcc    3120
aaaaaagtga tggaaaacca gatgttcgag gaaaagcagg ccgagagcat gcccgagatc    3180
gaaaccgagc aggagtacaa agagatcttc atcacccccc accagatcaa gcacattaag    3240
gacttcaagg actacaagta cagccaccgg gtggacaaga gcctaatag agagctgatt    3300 aacgacaccc tgtactccac ccggaaggac gacaagggca cacccctgat cgtgaacaat    3360
ctgaacggcc tgtacgacaa ggacaatgac aagctgaaaa agctgatcaa caagagcccc    3420
gaaaagctgc tgatgtacca ccacgacccc cagacctacc agaaactgaa gctgattatg    3480
gaacagtacg gcgacgagaa gaatcccctg tacaagtact acgaggaaac cgggaactac    3540
ctgaccaagt actccaaaaa ggacaacggc cccgtgatca agaagattaa gtattacggc    3600
aacaaactga cgccatct ggacatcacc gacgactacc ccaacagcag aaacaaggtc    3660
gtgaagctgt ccctgaagcc ctacagattc gacgtgtacc tggacaatgg cgtgtacaag    3720
ttcgtgaccg tgaagaatct ggatgtgatc aaaaagaaa actactacga agtgaatagc    3780
aagtgctatg aggaagctaa gaagctgaag aagatcagca accaggccga gtttatcgcc    3840
tccttctaca caacgatct gatcaagatc aacggcgagc tgtatagagt gatcggcgtg    3900
aacaacgacc tgctgaaccg gatcgaagtg aacatgatcg acatcaccta ccgcgagtac    3960
ctggaaaaca tgaacgacaa gaggcccccc aggatcatta agacaatcgc ctccaagacc    4020
cagagcatta agaagtacag cacagacatt ctgggcaacc tgtatgaagt gaaatctaag    4080
aagcaccctc agatcatcaa aaagggcaaa aggccggcgg ccacgaaaaa ggccggccag    4140
gcaaaaaaga aaaagggatc ctacccatac gatgttccag attacgctta cccatacgat    4200
```

-continued

```
gttccagatt acgcttaccc atacgatgtt ccagattacg cttaagaatt ctagcaataa    4260
aggatcgttt attttcattg gaagcgtgtg ttggtttttt gatcaggcgc gggtaccgaa    4320
cgctgacgtc atcaacccgc tccaaggaat cgcgggccca gtgtcactag gcgggaacac    4380
ccagcgcgcg tgcgccctgg caggaagatg gctgtgaggg acaggggagt ggcgccctgc    4440
aatatttgca tgtcgctatg tgttctggga aatcaccata aacgtgaaat gtctttggat    4500
ttgggaatct tataagttct gtatgagacc acatatagta atgaaattat tggcacgttt    4560
tagtactctg gaaacagaat ctactaaaac aaggcaaaat gccgtgttta tctcgtcaac    4620
ttgttggcga gattttttggt accaggaacc cctagtgatg gagttggcca ctccctctct    4680
gcgcgctcgc tcgctcactg aggccgggcg accaaaggtc gcccgacgcc cgggctttgc    4740
ccggccggcc tcagtgagcg agcgagcgcg cagctgcctg caggggcgcc tgatgcggta    4800
ttttctcctt acgcatctgt gcggtatttc acaccgcata cgtcaaagca accatagtac    4860
gcgccctgta gcggcgcatt aagcgcggcg ggtgtggtgg ttacgcgcag cgtgaccgct    4920
acacttgcca gcgccctagc gcccgctcct ttcgctttct tcccttcctt tctcgccacg    4980
ttcgccggct ttccccgtca agctctaaat cggggggctcc ctttagggtt ccgatttagt    5040
gctttacggc acctcgaccc caaaaaactt gatttgggtg atggttcacg tagtgggcca    5100
tcgccctgat agacggtttt tcgccctttg acgttggagt ccacgttctt taatagtgga    5160
ctcttgttcc aaactggaac aacactcaac cctatctcgg gctattcttt tgatttataa    5220
gggattttgc cgatttcggc ctattggtta aaaaatgagc tgatttaaca aaaatttaac    5280
gcgaatttta acaaaatatt aacgtttaca attttatggt gcactctcag tacaatctgc    5340
tctgatgccg catagttaag ccagccccga cacccgccaa cacccgctga cgcgccctga    5400
cgggcttgtc tgctcccggc atccgcttac agacaagctg tgaccgtctc cgggagctgc    5460
atgtgtcaga ggttttcacc gtcatcaccg aaacgcgcga gacgaaaggg cctcgtgata    5520
cgcctatttt tataggttaa tgtcatgata ataatggttt cttagacgtc aggtggcact    5580
tttcggggaa atgtgcgcgg aacccctatt tgtttatttt tctaaataca ttcaaatatg    5640
tatccgctca tgagacaata accctgataa atgcttcaat aatattgaaa aaggaagagt    5700
atgagtattc aacatttccg tgtcgccctt attcccttttt ttgcggcatt ttgccttcct    5760 gttttttgctc acccagaaac gctggtgaaa gtaaaagatg ctgaagatca gttgggtgca    5820
cgagtgggtt acatcgaact ggatctcaac agcggtaaga tccttgagag ttttcgcccc    5880
gaagaacgtt ttccaatgat gagcactttt aaagttctgc tatgtggcgc ggtattatcc    5940
cgtattgacg ccgggcaaga gcaactcggt cgccgcatac actattctca gaatgacttg    6000
gttgagtact caccagtcac agaaaagcat cttacggatg gcatgacagt aagagaatta    6060
tgcagtgctg ccataaccat gagtgataac actgcggcca acttacttct gacaacgatc    6120
ggaggaccga aggagctaac cgcttttttg cacaacatgg gggatcatgt aactcgcctt    6180
gatcgttggg aaccggagct gaatgaagcc ataccaaacg acgagcgtga caccacgatg    6240
cctgtagcaa tggcaacaac gttgcgcaaa ctattaactg gcgaactact tactctagct    6300
tcccggcaac aattaataga ctggatggag gcggataaag ttgcaggacc acttctgcgc    6360
tcggcccttc cggctggctg gtttattgct gataaatctg gagccggtga gcgtggaagc    6420
cgcggtatca ttgcagcact ggggccagat ggtaagccct cccgtatcgt agttatctac    6480
acgacgggga gtcaggcaac tatggatgaa cgaaatagac agatcgctga gataggtgcc    6540
tcactgatta agcattggta actgtcagac caagtttact catatatact ttagattgat    6600
```

-continued

```
ttaaaacttc attttttaatt taaaaggatc taggtgaaga tcctttttga taatctcatg    6660
accaaaatcc cttaacgtga gttttcgttc cactgagcgt cagaccccgt agaaaagatc    6720
aaaggatctt cttgagatcc ttttttttctg cgcgtaatct gctgcttgca aacaaaaaaa    6780
ccaccgctac cagcggtggt ttgtttgccg gatcaagagc taccaactct ttttccgaag    6840
gtaactggct tcagcagagc gcagatacca aatactgtcc ttctagtgta gccgtagtta    6900
ggccaccact tcaagaactc tgtagcaccg cctacatacc tcgctctgct aatcctgtta    6960
ccagtggctg ctgccagtgg cgataagtcg tgtcttaccg ggttggactc aagacgatag    7020
ttaccggata aggcgcagcg gtcgggctga acggggggtt cgtgcacaca gcccagcttg    7080
gagcgaacga cctacaccga actgagatac ctacagcgtg agctatgaga aagcgccacg    7140
cttcccgaag ggagaaaggc ggacaggtat ccggtaagcg gcagggtcgg aacaggagag    7200
cgcacgaggg agcttccagg gggaaacgcc tggtatcttt atagtcctgt cgggtttcgc    7260
cacctctgac ttgagcgtcg attttttgtga tgctcgtcag ggggggcggag cctatggaaa    7320 aacgccagca acgcggcctt tttacggttc ctggccttttt gctggccttttt tgctcacatg    7380 t                                                                    7381

<210> SEQ ID NO 19
<211> LENGTH: 7804
<212> TYPE: DNA
<213> ORGANISM: Artificial Sequence
<220> FEATURE:
<223> OTHER INFORMATION: Synthetic

<400> SEQUENCE: 19
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggcctcta gaaaaaatct cgccaacaag ttgacgagat aaacacggca    180
ttttgccttg ttttagtaga ttctgtttcc agagtactaa aacacatttc ctctctatac    240
aaatgcggtg tttcgtcctt tccacaagat atataaagcc aagaaatcga aatactttca    300
agttacggta agcatatgat agtccatttt aaaacataat tttaaaactg caaactaccc    360
aagaaattat tactttctac gtcacgtatt ttgtactaat atctttgtgt ttacagtcaa    420
attaattcca attatctctc taacagcctt gtatcgtata tgcaaatatg aaggaatcat    480
gggaaatagg ccctcctcga ggtttaaaca agcttgcatg tctaagctag acccttcaga    540
ttaaaaataa ctgaggtaag ggcctgggta ggggaggtgg tgtgagacgc tcctgtctct    600
cctctatctg cccatcggcc ctttggggag gaggaatgtg cccaaggact aaaaaaaggc    660
catggagcca gaggggcgag ggcaacagac ctttcatggg caaaccttgg ggccctgctg    720
tctagcatgc cccactacgg gtctaggctg cccatgtaag gaggcaaggc ctggggacac    780
ccgagatgcc tggttataat taacccagac atgtggctgc ccccccccc ccaacacctg    840 ctgcctctaa aaataaccct gtccctggtg gatccctgc atgcgaagat cttcgaacaa    900
ggctgtgggg gactgagggc aggctgtaac aggcttgggg gccagggctt atacgtgcct    960
gggactccca aagtattact gttccatgtt cccggcgaag ggccagctgt cccccgccag   1020
ctagactcag cacttagttt aggaaccagt gagcaagtca gcccttgggg cagcccatac   1080
aaggccatgg ggctgggcaa gctgcacgcc tgggtccggg gtgggcacgg tgcccgggca   1140
acgagctgaa agctcatctg ctctcagggg ccctccctg gggacagccc ctcctggcta   1200
```

-continued

```
gtcacaccct gtaggctcct ctatataacc caggggcaca ggggctgccc tcattctacc    1260
accacctcca cagcacagac agacactcag gagccagcca gcggcgcgcc caccggtgcc    1320
accatggccc caaagaagaa gcggaaggtc ggtatccacg gagtcccagc agccaagcgg    1380
aactacatcc tgggcctgga catcggcatc accagcgtgg gctacggcat catcgactac    1440
gagacacggg acgtgatcga tgccggcgtg cggctgttca agaggccaa cgtggaaaac    1500 aacgagggca ggcggagcaa gagaggcgcc agaaggctga agcggcggag gcggcataga    1560
atccagagag tgaagaagct gctgttcgac tacaacctgc tgaccgacca cagcgagctg    1620
agcggcatca acccctacga ggccagagtg aagggcctga ccagaagct gagcgaggaa    1680 gagttctctg ccgccctgct gcacctggcc aagagaagag gcgtgcacaa cgtgaacgag    1740
gtggaagagg acaccggcaa cgagctgtcc accaaagagc agatcagccg gaacagcaag    1800
gccctggaag agaaatacgt ggccgaactg cagctggaac ggctgaagaa agacggcgaa    1860
gtgcggggca gcatcaacag attcaagacc agcgactacg tgaaagaagc caaacagctg    1920
ctgaaggtgc agaaggccta ccaccagctg gaccagagct tcatcgacac ctacatcgac    1980
ctgctggaaa cccggcggac ctactatgag ggacctggcg agggcagccc cttcggctgg    2040
aaggacatca agaatggta cgagatgctg atgggccact gcacctactt ccccgaggaa    2100
ctgcggagcg tgaagtacgc ctacaacgcc gacctgtaca acgccctgaa cgacctgaac    2160
aatctcgtga tcaccaggga cgagaacgag aagctggaat attacgagaa gttccagatc    2220
atcgagaacg tgttcaagca gaagaagaag cccaccctga agcagatcgc caaagaaatc    2280
ctcgtgaacg aagaggatat taagggctac agagtgacca gcaccggcaa gcccgagttc    2340
accaacctga aggtgtacca cgacatcaag gacattaccg cccggaaaga gattattgag    2400
aacgccgagc tgctggatca gattgccaag atcctgacca tctaccagag cagcgaggac    2460
atccaggaag aactgaccaa tctgaactcc gagctgaccc aggaagagat cgagcagatc    2520
tctaatctga agggctatac cggcacccac aacctgagcc tgaaggccat caacctgatc    2580
ctggacgagc tgtggcacac caacgacaac cagatcgcta tcttcaaccg gctgaagctg    2640
gtgcccaaga aggtggacct gtcccagcag aaagagatcc ccaccaccct ggtggacgac    2700
ttcatcctga gccccgtcgt gaagagaagc ttcatccaga gcatcaaagt gatcaacgcc    2760
atcatcaaga agtacggcct gcccaacgac atcattatcg agctggcccg cgagaagaac    2820
tccaaggacg cccagaaaat gatcaacgag atgcagaagc ggaaccggca gaccaacgag    2880
cggatcgagg aaatcatccg gaccaccggc aaagagaacg ccaagtacct gatcgagaag    2940
atcaagctgc acgacatgca ggaaggcaag tgcctgtaca gcctggaagc catccctctg    3000
gaagatctgc tgaacaaccc cttcaactat gaggtggacc acatcatccc cagaagcgtg    3060
tccttcgaca acagcttcaa caacaaggtg ctcgtgaagc aggaagaaaa cagcaagaag    3120
ggcaaccgga ccccattcca gtacctgagc agcagcgaca gcaagatcag ctacgaaacc    3180
ttcaagaagc acatcctgaa tctggccaag ggcaagggca gaatcagcaa gaccaagaaa    3240
gagtatctgc tggaagaacg ggacatcaac aggttctccg tgcagaaaga cttcatcaac    3300
cggaacctgg tggataccag atacgccacc agaggcctga tgaacctgct gcggagctac    3360
ttcagagtga caacctgga cgtgaaagtg aagtccatca tggcggctt caccagcttt    3420 ctgcggcgga gtggaagtt taagaaagag cggaacaagg ggtacaagca ccacgccgag    3480
gacgccctga tcattgccaa cgccgatttc atcttcaaag agtggaagaa actggacaag    3540
gccaaaaaag tgatggaaaa ccagatgttc gaggaaaagc aggccgagag catgcccgag    3600
```

-continued

```
atcgaaaccg agcaggagta caaagagatc ttcatcaccc cccaccagat caagcacatt    3660
aaggacttca aggactacaa gtacagccac cgggtggaca agaagcctaa tagagagctg    3720
attaacgaca ccctgtactc cacccggaag gacgacaagg gcaacaccct gatcgtgaac    3780
aatctgaacg gcctgtacga caaggacaat gacaagctga aaaagctgat caacaagagc    3840
cccgaaaagc tgctgatgta ccaccacgac ccccagacct accagaaact gaagctgatt    3900
atggaacagt acggcgacga gaagaatccc ctgtacaagt actacgagga aaccgggaac    3960
tacctgacca agtactccaa aaaggacaac ggccccgtga tcaagaagat taagtattac    4020
ggcaacaaac tgaacgccca tctgacatcc accgacgact accccaacag cagaaacaag    4080
gtcgtgaagc tgtccctgaa gccctacaga ttcgacgtgt acctggacaa tggcgtgtac    4140
aagttcgtga ccgtgaagaa tctggatgtg atcaaaaaag aaaactacta cgaagtgaat    4200
agcaagtgct atgaggaagc taagaagctg aagaagatca gcaaccaggc cgagtttatc    4260
gcctccttct acaacaacga tctgatcaag atcaacggcg agctgtatag agtgatcggc    4320
gtgaacaacg acctgctgaa ccggatcgaa gtgaacatga tcgacatcac ctaccgcgag    4380
tacctggaaa acatgaacga caagaggccc cccaggatca ttaagacaat cgcctccaag    4440
acccagagca ttaagaagta cagcacagac attctgggca acctgtatga agtgaaatct    4500
aagaagcacc ctcagatcat caaaaagggc aaaaggccgg cggccacgaa aaaggccggc    4560
caggcaaaaa agaaaaaggg atcctaccca tacgatgttc cagattacgc ttacccatac    4620
gatgttccag attacgctta cccatacgat gttccagatt acgcttaaga attctagcaa    4680
taaaggatcg tttattttca ttggaagcgt gtgttggttt tttgatcagg cgcgggtacc    4740
gaacgctgac gtcatcaacc cgctccaagg aatcgcgggc ccagtgtcac taggcgggaa    4800
cacccagcgc gcgtgcgccc tggcaggaag atggctgtga gggacagggg agtggcgccc    4860
tgcaatattt gcatgtcgct atgtgttctg ggaaatcacc ataaacgtga aatgtctttg    4920
gatttgggaa tcttataagt tctgtatgag accacatata gtaatgaaat tattggcacg    4980
ttttagtact ctggaaacag aatctactaa aacaaggcaa aatgccgtgt ttatctcgtc    5040
aacttgttgg cgagattttt ggtaccagga acccctagtg atggagttgg ccactccctc    5100
tctgcgcgct cgctcgctca ctgaggccgg gcgaccaaag gtcgcccgac gcccgggctt    5160
tgcccgggcg gcctcagtga gcgagcgagc gcgcagctgc ctgcaggggc gcctgatgcg    5220 gtatttctc cttacgcatc tgtgcggtat ttcacaccgc atacgtcaaa gcaaccatag    5280
tacgcgccct gtagcggcgc attaagcgcg gcgggtgtgg tggttacgcg cagcgtgacc    5340
gctacacttg ccagcgccct agcgcccgct cctttcgctt tcttcccttc ctttctcgcc    5400
acgttcgccg gctttccccg tcaagctcta atcgggggc tccctttagg gttccgattt    5460
agtgctttac ggcacctcga ccccaaaaaa cttgatttgg gtgatggttc acgtagtggg    5520
ccatcgccct gatagacggt ttttcgccct ttgacgttgg agtccacgtt ctttaatagt    5580
ggactcttgt tccaaactgg aacaacactc aaccctatct cgggctattc ttttgattta    5640
taagggattt tgccgatttc ggcctattgg ttaaaaaatg agctgattta acaaaaattt    5700
aacgcgaatt ttaacaaaat attaacgttt acaatttat ggtgcactct cagtacaatc    5760
tgctctgatg ccgcatagtt aagccagccc cgacacccgc caacacccgc tgacgcgccc    5820
tgacgggctt gtctgctccc ggcatccgct tacagacaag ctgtgaccgt ctccgggagc    5880
tgcatgtgtc agaggttttc accgtcatca ccgaaacgcg cgagacgaaa gggcctcgtg    5940
```

-continued

```
atacgcctat ttttataggt taatgtcatg ataataatgg tttcttagac gtcaggtggc    6000
acttttcggg gaaatgtgcg cggaacccct atttgtttat ttttctaaat acattcaaat    6060
atgtatccgc tcatgagaca ataaccctga taaatgcttc aataatattg aaaaaggaag    6120
agtatgagta ttcaacattt ccgtgtcgcc cttattccct tttttgcggc attttgcctt    6180
cctgtttttg ctcacccaga aacgctggtg aaagtaaaag atgctgaaga tcagttgggt    6240
gcacgagtgg gttacatcga actggatctc aacagcggta agatccttga gagttttcgc    6300
cccgaagaac gttttccaat gatgagcact tttaaagttc tgctatgtgg cgcggtatta    6360
tcccgtattg acgccgggca agagcaactc ggtcgccgca tacactattc tcagaatgac    6420
ttggttgagt actcaccagt cacagaaaag catcttacgg atggcatgac agtaagagaa    6480
ttatgcagtg ctgccataac catgagtgat aacactgcgg ccaacttact tctgacaacg    6540
atcggaggac cgaaggagct aaccgctttt ttgcacaaca tgggggatca tgtaactcgc    6600
cttgatcgtt gggaaccgga gctgaatgaa gccataccaa acgacgagcg tgacaccacg    6660
atgcctgtag caatggcaac aacgttgcgc aaactattaa ctggcgaact acttactcta    6720
gcttcccggc aacaattaat agactggatg gaggcggata aagttgcagg accacttctg    6780
cgctcggccc ttccggctgg ctggtttatt gctgataaat ctggagccgg tgagcgtgga    6840
agccgcggta tcattgcagc actggggcca gatggtaagc cctcccgtat cgtagttatc    6900
tacacgacgg ggagtcaggc aactatggat gaacgaaata gacagatcgc tgagataggt    6960
gcctcactga ttaagcattg gtaactgtca gaccaagttt actcatatat actttagatt    7020
gatttaaaac ttcattttta atttaaaagg atctaggtga agatcctttt tgataatctc    7080
atgaccaaaa tcccttaacg tgagttttcg ttccactgag cgtcagaccc cgtagaaaag    7140
atcaaaggat cttcttgaga tccttttttt ctgcgcgtaa tctgctgctt gcaaacaaaa    7200
aaaccaccgc taccagcggt ggtttgtttg ccggatcaag agctaccaac tctttttccg    7260
aaggtaactg gcttcagcag agcgcagata ccaaatactg tccttctagt gtagccgtag    7320
ttaggccacc acttcaagaa ctctgtagca ccgcctacat acctcgctct gctaatcctg    7380
ttaccagtgg ctgctgccag tggcgataag tcgtgtctta ccgggttgga ctcaagacga    7440
tagttaccgg ataaggcgca gcggtcgggc tgaacggggg gttcgtgcac acagcccagc    7500
ttggagcgaa cgacctacac cgaactgaga tacctacagc gtgagctatg agaaagcgcc    7560
acgcttcccg aagggagaaa ggcggacagg tatccggtaa gcggcagggt cggaacagga    7620
gagcgcacga gggagcttcc aggggggaaac gcctggtatc tttatagtcc tgtcgggttt    7680
cgccacctct gacttgagcg tcgatttttg tgatgctcgt caggggggcg gagcctatgg    7740
aaaaacgcca gcaacgcggc cttttttacgg ttcctggcct tttgctggcc ttttgctcac    7800
atgt                                                              7804
```

<210> SEQ ID NO 20
<211> LENGTH: 7408
<212> TYPE: DNA
<213> ORGANISM: Artificial Sequence
<220> FEATURE:
<223> OTHER INFORMATION: Sythetic

<400> SEQUENCE: 20

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaaaatct cgccaacaag ttgacgagat aaacacggca     180
```

```
ttttgccttg ttttagtaga ttctgtttcc agagtactaa aacacatttc ctctctatac    240
aaatgcggtg tttcgtcctt tccacaagat atataaagcc aagaaatcga aatactttca    300
agttacggta agcatatgat agtccatttt aaaacataat tttaaaactg caaactaccc    360
aagaaattat tactttctac gtcacgtatt ttgtactaat atctttgtgt ttacagtcaa    420
attaattcca attatctctc taacagcctt gtatcgtata tgcaaatatg aaggaatcat    480
gggaaatagg ccctcctcga gtcgagtggc tccggtgccc gtcagtgggc agagcgcaca    540
tcgcccacag tccccgagaa gttgggggga ggggtcggca attgaaccgg tgcctagaga    600
aggtggcgcg gggtaaactg ggaaagtgat gtcgtgtact ggctccgcct ttttcccgag    660
ggtgggggag aaccgtatat aagtgcagta gtcgccgtga acgttctttt tcgcaacggg    720
tttgccgcca gaacacaggt gtcgtgaccg cggccatggc cccaaagaag aagcggaagg    780
tcggtatcca cggagtccca gcagccaagc ggaactacat cctgggcctg gacatcggca    840
tcaccagcgt gggctacggc atcatcgact acgagacacg ggacgtgatc gatgccggcg    900
tgcggctgtt caaagaggcc aacgtggaaa acaacgaggg caggcggagc aagagaggcg    960
ccagaaggct gaagcggcgg aggcggcata gaatccagag agtgaagaag ctgctgttcg    1020
actacaacct gctgaccgac cacagcgagc tgagcggcat caacccctac gaggccagag    1080
tgaagggcct gagccagaag ctgagcgagg aagagttctc tgccgccctg ctgcacctgg    1140
ccaagagaag aggcgtgcac aacgtgaacg aggtggaaga ggacaccggc aacgagctgt    1200
ccaccaaaga gcagatcagc cggaacagca aggccctgga agagaaatac gtggccgaac    1260
tgcagctgga acggctgaag aaagacggcg aagtgcgggg cagcatcaac agattcaaga    1320
ccagcgacta cgtgaaagaa gccaaacagc tgctgaaggt gcagaaggcc taccaccagc    1380
tggaccagag cttcatcgac acctacatcg acctgctgga aacccggcgg acctactatg    1440
agggacctgg cgagggcagc cccttcggct ggaaggacat caaagaatgg tacgagatgc    1500
tgatgggcca ctgcacctac ttccccgagg aactgcggag cgtgaagtac gcctacaacg    1560
ccgacctgta caacgccctg aacgacctga acaatctcgt gatcaccagg acgagaacg    1620 agaagctgga atattacgag aagttccaga tcatcgaaga cgtgttcaag cagaagaaga    1680
agcccaccct gaagcagatc gccaaagaaa tcctcgtgaa cgaagaggat attaagggct    1740
acagagtgac cagcaccggc aagcccgagt tcaccaacct gaaggtgtac cacgacatca    1800
aggacattac cgcccggaaa gagattattg agaacgccga gctgctggat cagattgcca    1860
agatcctgac catctaccag agcagcgagg acatccagga agaactgacc aatctgaact    1920
ccgagctgac ccaggaagag atcgagcaga tctctaatct gaagggctat accggcaccc    1980
acaacctgag cctgaaggcc atcaacctga tcctggacga gctgtggcac accaacgaca    2040
accagatcgc tatcttcaac cggctgaagc tggtgcccaa gaaggtggac ctgtcccagc    2100
agaaagagat ccccaccacc ctggtggacg acttcatcct gagccccgtc gtgaagagaa    2160
gcttcatcca gagcatcaaa gtgatcaacg ccatcatcaa gaagtacggc ctgcccaacg    2220
acatcattat cgagctggcc cgcgagaaga actccaagga cgcccagaaa atgatcaacg    2280
agatgcagaa gcggaaccgg cagaccaacg agcggatcga ggaaatcatc cggaccaccg    2340
gcaaagagaa cgccaagtac ctgatcgaga agatcaagct gcacgacatg caggaaggca    2400
agtgcctgta cagcctggaa gccatccctc tggaagatct gctgaacaac cccttcaact    2460
atgaggtgga ccacatcatc cccagaagcg tgtccttcga caacagcttc aacaacaagg    2520
```

-continued

```
tgctcgtgaa gcaggaagaa aacagcaaga agggcaaccg gaccccattc cagtacctga    2580
gcagcagcga cagcaagatc agctacgaaa ccttcaagaa gcacatcctg aatctggcca    2640
agggcaaggg cagaatcagc aagaccaaga aagagtatct gctggaagaa cgggacatca    2700
acaggttctc cgtgcagaaa gacttcatca accggaacct ggtggatacc agatacgcca    2760
ccagaggcct gatgaacctg ctgcggagct acttcagagt gaacaacctg gacgtgaaag    2820
tgaagtccat caatggcggc ttcaccagct ttctgcggcg gaagtggaag tttaagaaag    2880
agcggaacaa ggggtacaag caccacgccg aggacgccct gatcattgcc aacgccgatt    2940
tcatcttcaa agagtggaag aaactggaca aggccaaaaa agtgatggaa aaccagatgt    3000
tcgaggaaaa gcaggccgag agcatgcccg agatcgaaac cgagcaggag tacaaagaga    3060
tcttcatcac ccccaccag atcaagcaca ttaaggactt caaggactac aagtacagcc    3120
accgggtgga caagaagcct aatagagagc tgattaacga caccctgtac tccacccgga    3180
aggacgacaa gggcaacacc ctgatcgtga caatctgaa cggcctgtac gacaaggaca    3240
atgacaagct gaaaaagctg atcaacaaga gccccgaaaa gctgctgatg taccaccacg    3300
acccccagac ctaccagaaa ctgaagctga ttatggaaca gtacggcgac gagaagaatc    3360
ccctgtacaa gtactacgag gaaaccggga actacctgac caagtactcc aaaaaggaca    3420
acggccccgt gatcaagaag attaagtatt acggcaacaa actgaacgcc catctggaca    3480
tcaccgacga ctaccccaac agcagaaaca aggtcgtgaa gctgtccctg aagccctaca    3540
gattcgacgt gtacctggac aatggcgtgt acaagttcgt gaccgtgaag aatctggatg    3600
tgatcaaaaa agaaaactac tacgaagtga atagcaagtg ctatgaggaa gctaagaagc    3660
tgaagaagat cagcaaccag gccgagttta tcgcctcctt ctacaacaac gatctgatca    3720
agatcaacgg cgagctgtat agagtgatcg gcgtgaacaa cgacctgctg aaccggatcg    3780
aagtgaacat gatcgacatc acctaccgcg agtacctgga aaacatgaac gacaagaggc    3840
cccccaggat cattaagaca atcgcctcca gacccagag cattaagaag tacagcacag    3900
acattctggg caacctgtat gaagtgaaat ctaagaagca ccctcagatc atcaaaaagg    3960
gcaaaaggcc ggcggccacg aaaaaggccg gccaggcaaa aagaaaaag ggatcctacc    4020 catacgatgt tccagattac gcttacccat acgatgttcc agattacgct tacccatacg    4080
atgttccaga ttacgcttaa gaattcctag agctcgctga tcagcctcga ctgtgccttc    4140
tagttgccag ccatctgttg tttgcccctc ccccgtgcct tccttgaccc tggaaggtgc    4200
cactcccact gtcctttcct aataaaatga ggaaattgca tcgcattgtc tgagtaggtg    4260
tcattctatt ctggggggtg gggtggggca ggacagcaag ggggaggatt gggaagagaa    4320
tagcaggcat gctggggagg taccgaacgc tgacgtcatc aacccgctcc aaggaatcgc    4380
gggcccagtg tcactaggcg ggaacaccca gcgcgcgtgc gccctggcag gaagatggct    4440
gtgagggaca ggggagtggc gccctgcaat atttgcatgt cgctatgtgt tctgggaaat    4500
caccataaac gtgaaatgtc tttggatttg ggaatcttat aagttctgta tgagaccaca    4560
tatagtaatg aaattattgg cacgttttag tactctggaa acagaatcta ctaaaacaag    4620
gcaaaatgcc gtgtttatct cgtcaacttg ttggcgagat ttttggtacc aggaacccct    4680
agtgatggag ttggccactc cctctctgcg cgctcgctcg ctcactgagg ccgggcgacc    4740
aaaggtcgcc cgacgcccgg gctttgcccg ggcggcctca gtgagcgagc gagcgcgcag    4800
ctgcctgcag gggcgcctga tgcggtattt tctccttacg catctgtgcg gtatttcaca    4860
ccgcatacgt caaagcaacc atagtacgcg ccctgtagcg gcgcattaag cgcggcgggt    4920
```

-continued

```
gtggtggtta cgcgcagcgt gaccgctaca cttgccagcg ccctagcgcc cgctcctttc    4980
gctttcttcc cttcctttct cgccacgttc gccggctttc cccgtcaagc tctaaatcgg    5040
gggctccctt tagggttccg atttagtgct ttacggcacc tcgaccccaa aaaacttgat    5100
ttgggtgatg gttcacgtag tgggccatcg ccctgataga cggttttttcg ccctttgacg    5160 ttggagtcca cgttctttaa tagtggactc ttgttccaaa ctggaacaac actcaaccct    5220
atctcgggct attcttttga tttataaggg attttgccga tttcggccta ttggttaaaa    5280
aatgagctga tttaacaaaa atttaacgcg aattttaaca aaatattaac gtttacaatt    5340
ttatggtgca ctctcagtac aatctgctct gatgccgcat agttaagcca gccccgacac    5400
ccgccaacac ccgctgacgc gccctgacgg gcttgtctgc tcccggcatc cgcttacaga    5460
caagctgtga ccgtctccgg gagctgcatg tgtcagaggt tttcaccgtc atcaccgaaa    5520
cgcgcgagac gaaagggcct cgtgatacgc ctattttttat aggttaatgt catgataata    5580
atggtttctt agacgtcagg tggcactttt cggggaaatg tgcgcggaac ccctatttgt    5640
ttatttttct aaatacattc aaatatgtat ccgctcatga dacaataacc ctgataaatg    5700
cttcaataat attgaaaaag gaagagtatg agtattcaac atttccgtgt cgcccttatt    5760 ccctttttttg cggcattttg ccttcctgtt tttgctcacc cagaaacgct ggtgaaagta    5820
aaagatgctg aagatcagtt gggtgcacga gtgggttaca tcgaactgga tctcaacagc    5880
ggtaagatcc ttgagagttt tcgccccgaa gaacgttttc caatgatgag cacttttaaa    5940
gttctgctat gtggcgcggt attatcccgt attgacgccg ggcaagagca actcggtcgc    6000
cgcatacact attctcagaa tgacttggtt gagtactcac cagtcacaga aaagcatctt    6060
acggatggca tgacagtaag agaattatgc agtgctgcca taaccatgag tgataacact    6120
gcggccaact tacttctgac aacgatcgga ggaccgaagg agctaaccgc ttttttgcac    6180
aacatggggg atcatgtaac tcgccttgat cgttgggaac cggagctgaa tgaagccata    6240
ccaaacgacg agcgtgacac cacgatgcct gtagcaatgg caacaacgtt gcgcaaacta    6300
ttaactggcg aactacttac tctagcttcc cggcaacaat taatagactg gatggaggcg    6360
gataaagttg caggaccact tctgcgctcg gcccttccgg ctggctggtt tattgctgat    6420
aaatctggag ccggtgagcg tggaagccgc ggtatcattg cagcactggg gccagatggt    6480
aagccctccc gtatcgtagt tatctacacg acggggagtc aggcaactat ggatgaacga    6540
aatagacaga tcgctgagat aggtgcctca ctgattaagc attggtaact gtcagaccaa    6600
gtttactcat atatacttta gattgattta aaacttcatt tttaatttaa aaggatctag    6660
gtgaagatcc tttttgataa tctcatgacc aaaatccctt aacgtgagtt ttcgttccac    6720
tgagcgtcag accccgtaga aaagatcaaa ggatcttctt gagatccttt ttttctgcgc    6780
gtaatctgct gcttgcaaac aaaaaaacca ccgctaccag cggtggtttg tttgccggat    6840
caagagctac caactctttt tccgaaggta actggcttca gcagagcgca gataccaaat    6900
actgtccttc tagtgtagcc gtagttaggc caccacttca agaactctgt agcaccgcct    6960
acatacctcg ctctgctaat cctgttacca gtggctgctg ccagtggcga taagtcgtgt    7020
cttaccgggt tggactcaag acgatagtta ccggataagg cgcagcggtc gggctgaacg    7080
gggggttcgt gcacacagcc cagcttggag cgaacgacct acaccgaact gagatacctca    7140 cagcgtgagc tatgagaaag cgccacgctt cccgaaggga gaaaggcgga caggtatccg    7200
gtaagcggca gggtcggaac aggagagcgc acgagggagc ttccaggggg aaacgcctgg    7260
```

```
tatctttata gtcctgtcgg gtttcgccac ctctgacttg agcgtcgatt tttgtgatgc    7320
tcgtcagggg ggcggagcct atggaaaaac gccagcaacg cggcctttt acggttcctg     7380 gccttttgct ggccttttgc tcacatgt                                       7408

<210> SEQ ID NO 21
<211> LENGTH: 7616
<212> TYPE: DNA
<213> ORGANISM: Artificial Sequence
<220> FEATURE:
<223> OTHER INFORMATION: Synthetic

<400> SEQUENCE: 21
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaaaatct cgccaacaag ttgacgagat aaacacggca     180
ttttgccttg ttttagtaga ttctgtttcc agagtactaa aacacatttc ctctctatac     240
aaatgcggtg tttcgtcctt tccacaagat atataaagcc aagaaatcga aatactttca     300
agttacggta agcatatgat agtccatttt aaaacataat tttaaaactg caaactaccc     360
aagaaattat tactttctac gtcacgtatt ttgtactaat atctttgtgt ttacagtcaa     420
attaattcca attatctctc taacagcctt gtatcgtata tgcaaatatg aaggaatcat     480
gggaaatagg ccctcctcga gctagactag catgctgccc atgtaaggag gcaaggcctg     540
gggacacccg agatgcctgg ttataattaa cccagacatg tggctgcccc cccccccca     600 acacctgctg cctctaaaaa taaccctgca tgccatgttc ccggcgaagg gccagctgtc     660
ccccgccagc tagactcagc acttagttta ggaaccagtg agcaagtcag cccttggggc     720
agcccataca aggccatggg gctgggcaag ctgcacgcct gggtccgggg tgggcacggt     780
gcccgggcaa cgagctgaaa gctcatctgc tctcaggggc ccctccctgg gacagcccc      840 tcctggctag tcacaccctg taggctcctc tatataaccc aggggcacag gggctgccct     900
cattctacca ccacctccac agcacagaca gacactcagg agccagccag caccggtgcc     960
accatggccc caaagaagaa gcggaaggtc ggtatccacg gagtcccagc agccaagcgg    1020
aactacatcc tgggcctgga catcggcatc accagcgtgg gctacggcat catcgactac    1080
gagacacggg acgtgatcga tgccggcgtg cggctgttca agaggccaa cgtggaaaac     1140 aacgagggca ggcggagcaa gagaggcgcc agaaggctga gcggcggag gcggcataga     1200 atccagagag tgaagaagct gctgttcgac tacaacctgc tgaccgacca cagcgagctg    1260
agcggcatca acccctacga ggccagagtg aagggcctga gccagaagct gagcgaggaa    1320
gagttctctg ccgccctgct gcacctggcc aagagaagag gcgtgcacaa cgtgaacgag    1380
gtggaagagg acaccggcaa cgagctgtcc accaaagagc agatcagccg gaacagcaag    1440
gccctggaag agaaatacgt ggccgaactg cagctggaac ggctgaagaa agacggcgaa    1500
gtgcggggca gcatcaacag attcaagacc agcgactacg tgaaagaagc caaacagctg    1560
ctgaaggtgc agaaggccta ccaccagctg gaccagagct tcatcgacac ctacatcgac    1620
ctgctggaaa cccggcggac ctactatgag ggacctggcg agggcagccc cttcggctgg    1680
aaggacatca agaatggta cgagatgctg atgggccact gcacctactt ccccgaggaa    1740
ctgcggagcg tgaagtacgc ctacaacgcc gacctgtaca cgccctgaa cgacctgaac    1800 aatctcgtga tcaccaggga cgagaacgag aagctggaat attacgagaa gttccagatc    1860
atcgagaacg tgttcaagca gaagaagaag cccaccctga gcagatcgc caaagaaatc    1920
```

```
ctcgtgaacg aagaggatat taagggctac agagtgacca gcaccggcaa gcccgagttc      1980
accaacctga aggtgtacca cgacatcaag gacattaccg cccggaaaga gattattgag      2040
aacgccgagc tgctggatca gattgccaag atcctgacca tctaccagag cagcgaggac      2100
atccaggaag aactgaccaa tctgaactcc gagctgaccc aggaagagat cgagcagatc      2160
tctaatctga agggctatac cggcacccac aacctgagcc tgaaggccat caacctgatc      2220
ctggacgagc tgtggcacac caacgacaac cagatcgcta tcttcaaccg gctgaagctg      2280
gtgcccaaga aggtggacct gtcccagcag aaagagatcc ccaccaccct ggtggacgac      2340
ttcatcctga gccccgtcgt gaagagaagc ttcatccaga gcatcaaagt gatcaacgcc      2400
atcatcaaga agtacggcct gcccaacgac atcattatcg agctggcccg cgagaagaac      2460
tccaaggacg cccagaaaat gatcaacgag atgcagaagc ggaaccggca gaccaacgag      2520
cggatcgagg aaatcatccg gaccaccggc aaagagaacg ccaagtacct gatcgagaag      2580
atcaagctgc acgacatgca ggaaggcaag tgcctgtaca gcctggaagc catccctctg      2640
gaagatctgc tgaacaaccc cttcaactat gaggtggacc acatcatccc cagaagcgtg      2700
tccttcgaca acagcttcaa caacaaggtg ctcgtgaagc aggaagaaaa cagcaagaag      2760
ggcaaccgga ccccattcca gtacctgagc agcagcgaca gcaagatcag ctacgaaacc      2820
ttcaagaagc acatcctgaa tctggccaag ggcaagggca gaatcagcaa gaccaagaaa      2880
gagtatctgc tggaagaacg ggacatcaac aggttctccg tgcagaaaga cttcatcaac      2940
cggaacctgg tggataccag atacgccacc agaggcctga tgaacctgct gcggagctac      3000
ttcagagtga caacctgga cgtgaaagtg aagtccatca tggcggctt caccagcttt      3060 ctgcggcgga gtggaagtt taagaaagag cggaacaagg ggtacaagca ccacgccgag      3120
gacgccctga tcattgccaa cgccgatttc atcttcaaag agtggaagaa actggacaag      3180
gccaaaaaag tgatggaaaa ccagatgttc gaggaaaagc aggccgagag catgcccgag      3240
atcgaaaccg agcaggagta caaagagatc ttcatcaccc cccaccagat caagcacatt      3300
aaggacttca aggactacaa gtacagccac cgggtggaca agaagcctaa tagagagctg      3360
attaacgaca ccctgtactc caccccggaag gacgacaagg gcaacaccct gatcgtgaac      3420
aatctgaacg gcctgtacga caaggacaat gacaagctga aaagctgat caacaagagc      3480 cccgaaaagc tgctgatgta ccaccacgac ccccagacct accagaaact gaagctgatt      3540
atggaacagt acggcgacga gaagaatccc ctgtacaagt actacgagga aaccgggaac      3600
tacctgacca agtactccaa aaaggacaac ggcccccgtga tcaagaagat taagtattac      3660
ggcaacaaac tgaacgccca tctggacatc accgacgact accccaacag cagaaacaag      3720
gtcgtgaagc tgtccctgaa gcccctacaga ttcgacgtgt acctggacaa tggcgtgtac      3780
aagttcgtga ccgtgaagaa tctggatgtg atcaaaaaag aaaactacta cgaagtgaat      3840
agcaagtgct atgaggaagc taagaagctg aagaagatca gcaaccaggc cgagtttatc      3900
gcctccttct acaacaacga tctgatcaag atcaacggcg agctgtatag agtgatcggc      3960
gtgaacaacg acctgctgaa ccggatcgaa gtgaacatga tcgacatcac ctaccgcgag      4020
tacctggaaa acatgaacga caagaggccc cccaggatca ttaagacaat cgcctccaag      4080
acccagagca ttaagaagta cagcacagac attctgggca acctgtatga agtgaaatct      4140
aagaagcacc tcagatcat caaaaagggc aaaaggccgg cggccacgaa aaaggccggc      4200
caggcaaaaa agaaaaaggg atcctaccca tacgatgttc cagattacgc ttacccatac      4260
```

```
gatgttccag attacgctta cccatacgat gttccagatt acgcttaaga attcctagag      4320
ctcgctgatc agcctcgact gtgccttcta gttgccagcc atctgttgtt tgcccctccc      4380
ccgtgccttc cttgaccctg gaaggtgcca ctcccactgt cctttcctaa taaaatgagg      4440
aaattgcatc gcattgtctg agtaggtgtc attctattct ggggggtggg gtggggcagg      4500
acagcaaggg ggaggattgg gaagagaata gcaggcatgc tggggaggta ccgaacgctg      4560
acgtcatcaa cccgctccaa ggaatcgcgg gcccagtgtc actaggcggg aacacccagc      4620
gcgcgtgcgc cctggcagga agatggctgt gagggacagg ggagtggcgc cctgcaatat      4680
ttgcatgtcg ctatgtgttc tgggaaatca ccataaacgt gaaatgtctt tggatttggg      4740
aatcttataa gttctgtatg agaccacata tagtaatgaa attattggca cgttttagta      4800
ctctggaaac agaatctact aaaacaaggc aaaatgccgt gtttatctcg tcaacttgtt      4860
ggcgagattt ttggtaccag gaacccctag tgatggagtt ggccactccc tctctgcgcg      4920
ctcgctcgct cactgaggcc gggcgaccaa aggtcgcccg acgcccgggc tttgcccggg      4980
cggcctcagt gagcgagcga gcgcgcagct gcctgcaggg gcgcctgatg cggtattttc      5040
tccttacgca tctgtgcggt atttcacacc gcatacgtca aagcaaccat agtacgcgcc      5100
ctgtagcggc gcattaagcg cggcgggtgt ggtggttacg cgcagcgtga ccgctacact      5160
tgccagcgcc ctagcgcccg ctcctttcgc tttcttccct tcctttctcg ccacgttcgc      5220
cggctttccc cgtcaagctc taaatcgggg gctcccttta gggttccgat ttagtgcttt      5280
acggcacctc gaccccaaaa aacttgattt gggtgatggt tcacgtagtg ggccatcgcc      5340
ctgatagacg gtttttcgcc ctttgacgtt ggagtccacg ttctttaata gtggactctt      5400
gttccaaact ggaacaacac tcaaccctat ctcgggctat tcttttgatt tataagggat      5460
tttgccgatt tcggcctatt ggttaaaaaa tgagctgatt taacaaaaat ttaacgcgaa      5520
ttttaacaaa atattaacgt ttacaatttt atggtgcact ctcagtacaa tctgctctga      5580
tgccgcatag ttaagccagc cccgacaccc gccaacaccc gctgacgcgc cctgacgggc      5640
ttgtctgctc ccggcatccg cttacagaca agctgtgacc gtctccggga ctgcatgtg      5700 tcagaggttt tcaccgtcat caccgaaacg cgcgagacga agggcctcg tgatacgcct      5760 attttttatag gttaatgtca tgataataat ggtttcttag acgtcaggtg gcacttttcg      5820
gggaaatgtg cgcggaaccc ctatttgttt attttttctaa atacattcaa atatgtatcc      5880
gctcatgaga caataaccct gataaatgct tcaataatat tgaaaaagga agagtatgag      5940
tattcaacat ttccgtgtcg cccttattcc cttttttgcg gcattttgcc ttcctgtttt      6000
tgctcaccca gaaacgctgg tgaaagtaaa agatgctgaa gatcagttgg gtgcacgagt      6060
gggttacatc gaactggatc tcaacagcgg taagatcctt gagagttttc gccccgaaga      6120
acgttttcca atgatgagca cttttaaagt tctgctatgt ggcgcggtat tatcccgtat      6180
tgacgccggg caagagcaac tcggtcgccg catacactat tctcagaatg acttggttga      6240
gtactcacca gtcacagaaa agcatcttac ggatggcatg acagtaagag aattatgcag      6300
tgctgccata accatgagtg ataacactgc ggccaactta cttctgacaa cgatcggagg      6360
accgaaggag ctaaccgctt ttttgcacaa catgggggat catgtaactc gccttgatcg      6420
ttgggaaccg gagctgaatg aagccatacc aaacgacgag cgtgacacca cgatgcctgt      6480
agcaatggca acaacgttgc gcaaactatt aactggcgaa ctacttactc tagcttcccg      6540
gcaacaatta atagactgga tggaggcgga taaagttgca ggaccacttc tgcgctcggc      6600
ccttccggct ggctggttta ttgctgataa atctggagcc ggtgagcgtg gaagccgcgg      6660
```

-continued

```
tatcattgca gcactggggc cagatggtaa gccctcccgt atcgtagtta tctacacgac    6720
ggggagtcag gcaactatgg atgaacgaaa tagacagatc gctgagatag gtgcctcact    6780
gattaagcat tggtaactgt cagaccaagt ttactcatat atactttaga ttgatttaaa    6840
acttcatttt taatttaaaa ggatctaggt gaagatcctt tttgataatc tcatgaccaa    6900
aatcccttaa cgtgagtttt cgttccactg agcgtcagac cccgtagaaa agatcaaagg    6960
atcttcttga gatccttttt ttctgcgcgt aatctgctgc ttgcaaacaa aaaaaccacc    7020
gctaccagcg gtggtttgtt tgccggatca gagctacca actctttttc cgaaggtaac     7080
tggcttcagc agagcgcaga taccaaatac tgtccttcta gtgtagccgt agttaggcca    7140
ccacttcaag aactctgtag caccgcctac atacctcgct ctgctaatcc tgttaccagt    7200
ggctgctgcc agtggcgata agtcgtgtct taccgggttg gactcaagac gatagttacc    7260
ggataaggcg cagcggtcgg gctgaacggg gggttcgtgc acacagccca gcttggagcg    7320
aacgacctac accgaactga gatacctaca gcgtgagcta tgagaaagcg ccacgcttcc    7380
cgaagggaga aaggcggaca ggtatccggt aagcggcagg gtcggaacag gagagcgcac    7440
gagggagctt ccagggggaa acgcctggta tctttatagt cctgtcgggt ttcgccacct    7500
ctgacttgag cgtcgatttt tgtgatgctc gtcaggggg cggagcctat ggaaaaacgc     7560
cagcaacgcg gcctttttac ggttcctggc cttttgctgg ccttttgctc acatgt        7616
```

```
<210> SEQ ID NO 22
<211> LENGTH: 7553
<212> TYPE: DNA
<213> ORGANISM: Artificial Sequence
<220> FEATURE:
<223> OTHER INFORMATION: Synthetic

<400> SEQUENCE: 22
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaaaatct cgccaacaag ttgacgagat aaacacggca     180
ttttgccttg ttttagtaga ttctgtttcc agagtactaa aacacatttc ctctctatac     240
aaatgcggtg tttcgtcctt tccacaagat atataaagcc aagaaatcga aatactttca     300
agttacggta agcatatgat agtccatttt aaaacataat tttaaaactg caaactaccc     360
aagaaattat tactttctac gtcacgtatt ttgtactaat atctttgtgt ttacagtcaa     420
attaattcca attatctctc taacagcctt gtatcgtata tgcaaatatg aaggaatcat     480
gggaaatagg ccctcctcga ggagctccac cgcggtggcg ccgtccgcc ttcggcacca      540 tcctcacgac acccaaatat ggcgacgggt gaggaatggt ggggagttat ttttagagcg     600
gtgaggaagg tgggcaggca gcaggtgttg gcgctctaaa aataactccc gggagttatt     660
tttagagcgg aggaatggtg gacacccaaa tatggcgacg gttcctcacc cgtcgccata     720
tttgggtgtc cgccctcggc cggggccgca ttcctggggg ccggcggtg ctcccgcccg      780 cctcgataaa aggctccggg gccggcggcg gcccacgagc tacccggagg agcgggaggc     840
gccaagctct agaactagtg gatccccgg gctgcaggaa ttcgatatac cggtgccacc      900
atggccccaa agaagaagcg gaaggtcggt atccacggag tcccagcagc caagcggaac     960
tacatcctgg gcctggacat cggcatcacc agcgtgggct acggcatcat cgactacgag    1020
acacgggacg tgatcgatgc cggcgtgcgg ctgttcaaag aggccaacgt ggaaaacaac    1080
```

-continued

```
gagggcaggc ggagcaagag aggcgccaga aggctgaagc ggcggaggcg gcatagaatc   1140
cagagagtga agaagctgct gttcgactac aacctgctga ccgaccacag cgagctgagc   1200
ggcatcaacc cctacgaggc cagagtgaag ggcctgagcc agaagctgag cgaggaagag   1260
ttctctgccg ccctgctgca cctggccaag agaagaggcg tgcacaacgt gaacgaggtg   1320
gaagaggaca ccggcaacga gctgtccacc aaagagcaga tcagccggaa cagcaaggcc   1380
ctggaagaga aatacgtggc cgaactgcag ctggaacggc tgaagaaaga cggcgaagtg   1440
cggggcagca tcaacagatt caagaccagc gactacgtga aagaagccaa acagctgctg   1500
aaggtgcaga aggcctacca ccagctggac cagagcttca tcgacaccta catcgacctg   1560
ctggaaaccc ggcggaccta ctatgaggga cctggcgagg gcagcccctt cggctggaag   1620
gacatcaaag aatggtacga gatgctgatg ggccactgca cctacttccc cgaggaactg   1680
cggagcgtga agtacgccta caacgccgac ctgtacaacg ccctgaacga cctgaacaat   1740
ctcgtgatca ccagggacga gaacgagaag ctggaatatt acgagaagtt ccagatcatc   1800
gagaacgtgt tcaagcagaa gaagaagccc accctgaagc agatcgccaa agaaatcctc   1860
gtgaacgaag aggatattaa gggctacaga gtgaccagca ccggcaagcc cgagttcacc   1920
aacctgaagg tgtaccacga catcaaggac attaccgccc ggaaagagat tattgagaac   1980
gccgagctgc tggatcagat tgccaagatc ctgaccatct accagagcag cgaggacatc   2040
caggaagaac tgaccaatct gaactccgag ctgacccagg aagagatcga gcagatctct   2100
aatctgaagg gctataccgg cacccacaac ctgagcctga aggccatcaa cctgatcctg   2160
gacgagctgt ggcacaccaa cgacaaccag atcgctatct tcaaccggct gaagctggtg   2220
cccaagaagg tggacctgtc ccagcagaaa gagatcccca ccaccctggt ggacgacttc   2280
atcctgagcc ccgtcgtgaa gagaagcttc atccagagca tcaaagtgat caacgccatc   2340
atcaagaagt acggcctgcc caacgacatc attatcgagc tggcccgcga gaagaactcc   2400
aaggacgccc agaaaatgat caacgagatg cagaagcgga accggcagac caacgagcgg   2460
atcgaggaaa tcatccggac caccggcaaa gagaacgcca agtacctgat cgagaagatc   2520
aagctgcacg acatgcagga aggcaagtgc ctgtacagcc tggaagccat ccctctggaa   2580
gatctgctga caaccccctt caactatgag gtggaccaca tcatccccag aagcgtgtcc   2640
ttcgacaaca gcttcaacaa caaggtgctc gtgaagcagg aagaaaacag caagaagggc   2700
aaccggaccc cattccagta cctgagcagc agcgacagca agatcagcta cgaaaccttc   2760
aagaagcaca tcctgaatct ggccaagggc aagggcagaa tcagcaagac caagaaagag   2820
tatctgctgg aagaacggga catcaacagg ttctccgtgc agaaagactt catcaaccgg   2880
aacctggtgg ataccagata cgccaccaga ggcctgatga acctgctgcg gagctacttc   2940
agagtgaaca acctggacgt gaaagtgaag tccatcaatg gcggcttcac cagctttctg   3000
cggcggaagt ggaagtttaa aaagagcggg aacaaggggt acaagcacca cgccgaggac   3060
gccctgatca ttgccaacgc cgatttcatc ttcaaagagt ggaagaaact ggacaaggcc   3120
aaaaaagtga tggaaaacca gatgttcgag gaaaagcagg ccgagagcat gcccgagatc   3180
gaaaccgagc aggagtacaa agagatcttc atcacccccc accagatcaa gcacattaag   3240
gacttcaagg actacaagta cagccaccgg gtggacaaga gcctaatag agagctgatt   3300 aacgacaccc tgtactccac ccggaaggac gacaagggca caccctgat cgtgaacaat   3360 ctgaacggcc tgtacgacaa ggacaatgac aagctgaaaa agctgatcaa caagagcccc   3420
gaaaagctgc tgatgtacca ccacgacccc cagacctacc agaaactgaa gctgattatg   3480
```

-continued

```
gaacagtacg gcgacgagaa gaatcccctg tacaagtact acgaggaaac cgggaactac   3540
ctgaccaagt actccaaaaa ggacaacggc cccgtgatca agaagattaa gtattacggc   3600
aacaaactga cgcccatctt ggacatcacc gacgactacc ccaacagcag aaacaaggtc   3660
gtgaagctgt ccctgaagcc ctacagattc gacgtgtacc tggacaatgg cgtgtacaag   3720
ttcgtgaccg tgaagaatct ggatgtgatc aaaaagaaa actactacga agtgaatagc   3780
aagtgctatg aggaagctaa gaagctgaag aagatcagca accaggccga gtttatcgcc   3840
tccttctaca caacgatct gatcaagatc aacggcgagc tgtatagagt gatcggcgtg   3900
aacaacgacc tgctgaaccg gatcgaagtg aacatgatcg acatcaccta ccgcgagtac   3960
ctggaaaaca tgaacgacaa gaggcccccc aggatcatta agacaatcgc ctccaagacc   4020
cagagcatta gaagtacag cacagacatt ctgggcaacc tgtatgaagt gaaatctaag   4080
aagcaccctc agatcatcaa aaagggcaaa aggccggcgg ccacgaaaaa ggccggccag   4140
gcaaaaaaga aaaagggatc ctacccatac gatgttccag attacgctta cccatacgat   4200
gttccagatt acgcttaccc atacgatgtt ccagattacg cttaagaatt cctagagctc   4260
gctgatcagc ctcgactgtg ccttctagtt gccagccatc tgttgtttgc ccctcccccg   4320
tgccttcctt gaccctggaa ggtgccactc ccactgtcct ttcctaataa aatgaggaaa   4380
ttgcatcgca ttgtctgagt aggtgtcatt ctattctggg gggtggggtg gggcaggaca   4440 gcaagggga ggattgggaa gagaatagca ggcatgctgg ggaggtaccg aacgctgacg   4500
tcatcaaccc gctccaagga atcgcgggcc cagtgtcact aggcgggaac acccagcgcg   4560
cgtgcgccct ggcaggaaga tggctgtgag ggacagggga gtggcgccct gcaatatttg   4620
catgtcgcta tgtgttctgg gaaatcacca taaacgtgaa atgtctttgg atttgggaat   4680
cttataagtt ctgtatgaga ccacatatag taatgaaatt attggcacgt tttagtactc   4740
tggaaacaga atctactaaa acaaggcaaa atgccgtgtt tatctcgtca acttgttggc   4800 gagattttttg gtaccaggaa cccctagtga tggagttggc cactccctct ctgcgcgctc   4860
gctcgctcac tgaggccggg cgaccaaagg tcgcccgacg cccgggcttt gcccgggcgg   4920
cctcagtgag cgagcgagcg cgcagctgcc tgcaggggcg cctgatgcgg tattttctcc   4980
ttacgcatct gtgcggtatt tcacaccgca tacgtcaaag caaccatagt acgcgccctg   5040
tagcggcgca ttaagcgcgg cgggtgtggt ggttacgcgc agcgtgaccg ctacacttgc   5100
cagcgcccta gcgcccgctc ctttcgcttt cttcccttcc tttctcgcca cgttcgccgg   5160
ctttccccgt caagctctaa atcggggggct ccctttaggg ttccgattta gtgctttacg   5220
gcacctcgac cccaaaaaac ttgatttggg tgatggttca cgtagtgggc catcgccctg   5280
atagacggtt tttcgccctt tgacgttgga gtccacgttc tttaatagtg gactcttgtt   5340
ccaaactgga acaacactca accctatctc gggctattct tttgatttat aagggatttt   5400
gccgatttcg gcctattggt taaaaaatga gctgatttaa caaaaattta cgcgaatttt   5460
taacaaaata ttaacgttta caattttatg gtgcactctc agtacaatct gctctgatgc   5520
cgcatagtta agccagcccc gacacccgcc aacacccgct gacgcgccct gacgggcttg   5580
tctgctcccg gcatccgctt acagacaagc tgtgaccgtc tccgggagct gcatgtgtca   5640
gaggttttca ccgtcatcac cgaaacgcgc gagacgaaag ggcctcgtga tacgcctatt   5700
tttataggtt aatgtcatga taataatggt ttcttagacg tcaggtggca cttttcgggg   5760
aaatgtgcgc ggaacccceta tttgtttatt tttctaaata cattcaaata tgtatccgct   5820
```

```
catgagacaa taaccctgat aaatgcttca ataatattga aaaaggaaga gtatgagtat    5880
tcaacatttc cgtgtcgccc ttattccctt ttttgcggca ttttgccttc ctgttttttgc   5940 tcacccagaa acgctggtga aagtaaaaga tgctgaagat cagttgggtg cacgagtggg    6000
ttacatcgaa ctggatctca acagcggtaa gatccttgag agttttcgcc ccgaagaacg    6060
ttttccaatg atgagcactt ttaaagttct gctatgtggc gcggtattat cccgtattga    6120
cgccgggcaa gagcaactcg gtcgccgcat acactattct cagaatgact tggttgagta    6180
ctcaccagtc acagaaaagc atcttacgga tggcatgaca gtaagagaat tatgcagtgc    6240
tgccataacc atgagtgata acactgcggc caacttactt ctgacaacga tcggaggacc    6300
gaaggagcta accgcttttt tgcacaacat ggggggatcat gtaactcgcc ttgatcgttg   6360
ggaaccggag ctgaatgaag ccataccaaa cgacgagcgt gacaccacga tgcctgtagc    6420
aatggcaaca acgttgcgca aactattaac tggcgaacta cttactctag cttcccggca    6480
acaattaata gactggatgg aggcggataa agttgcagga ccacttctgc gctcggccct    6540
tccggctggc tggtttattg ctgataaatc tggagccggt gagcgtggaa gccgcggtat    6600
cattgcagca ctggggccag atggtaagcc ctcccgtatc gtagttatct acacgacggg    6660
gagtcaggca actatggatg aacgaaatag acagatcgct gagataggtg cctcactgat    6720
taagcattgg taactgtcag accaagttta ctcatatata ctttagattg atttaaaact    6780
tcattttaaa tttaaaagga tctaggtgaa gatcctttt gataatctca tgaccaaaat     6840
cccttaacgt gagttttcgt tccactgagc gtcagacccc gtagaaaaga tcaaaggatc    6900
ttcttgagat cctttttttc tgcgcgtaat ctgctgcttg caaacaaaaa aaccaccgct    6960
accagcggtg gtttgtttgc cggatcaaga gctaccaact ctttttccga aggtaactgg    7020
cttcagcaga gcgcagatac caaatactgt ccttctagtg tagccgtagt taggccacca    7080
cttcaagaac tctgtagcac cgcctacata cctcgctctg ctaatcctgt taccagtggc    7140
tgctgccagt ggcgataagt cgtgtcttac cgggttggac tcaagacgat agttaccgga    7200
taaggcgcag cggtcgggct gaacgggggg ttcgtgcaca cagcccagct tggagcgaac    7260
gacctacacc gaactgagat acctacagcg tgagctatga aaagcgcca cgcttcccga     7320 agggagaaag gcggacaggt atccggtaag cggcagggtc ggaacaggag agcgcacgag    7380
ggagcttcca gggggaaacg cctggtatct ttatagtcct gtcgggtttc gccacctctg    7440
acttgagcgt cgatttttgt gatgctcgtc ggggggcgg agcctatgga aaaacgccag     7500
caacgcggcc tttttacggt tcctggcctt ttgctggcct tttgctcaca tgt          7553
```

```
<210> SEQ ID NO 23
<211> LENGTH: 7976
<212> TYPE: DNA
<213> ORGANISM: Artificial Sequence
<220> FEATURE:
<223> OTHER INFORMATION: Synthetic

<400> SEQUENCE: 23
```

```
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaaaatct cgccaacaag ttgacgagat aaacacggca      180
ttttgccttg ttttagtaga ttctgtttcc agagtactaa aacacatttc ctctctatac      240
aaatgcggtg tttcgtcctt tccacaagat atataaagcc aagaaatcga atactttca       300 agttacggta agcatatgat agtccatttt aaaacataat tttaaaactg caaactaccc      360
```

-continued

```
aagaaattat tactttctac gtcacgtatt ttgtactaat atctttgtgt ttacagtcaa    420
attaattcca attatctctc taacagcctt gtatcgtata tgcaaatatg aaggaatcat    480
gggaaatagg ccctcctcga ggtttaaaca agcttgcatg tctaagctag accttcaga    540 ttaaaaataa ctgaggtaag ggcctgggta ggggaggtgg tgtgagacgc tcctgtctct    600
cctctatctg cccatcggcc ctttggggag gaggaatgtg cccaaggact aaaaaaaggc    660
catggagcca gaggggcgag ggcaacagac ctttcatggg caaaccttgg ggccctgctg    720
tctagcatgc cccactacgg gtctaggctg cccatgtaag gaggcaaggc ctggggacac    780
ccgagatgcc tggttataat taacccagac atgtggctgc cccccccccc ccaacacctg    840
ctgcctctaa aaataacct gtccctggtg gatcccctgc atgcgaagat cttcgaacaa    900
ggctgtgggg gactgagggc aggctgtaac aggcttgggg gccagggctt atacgtgcct    960
gggactccca aagtattact gttccatgtt cccggcgaag ggccagctgt cccccgccag   1020
ctagactcag cacttagttt aggaaccagt gagcaagtca gcccttgggg cagcccatac   1080
aaggccatgg ggctgggcaa gctgcacgcc tgggtccggg gtgggcacgg tgcccgggca   1140
acgagctgaa agctcatctg ctctcagggg cccctccctg gggacagccc ctcctggcta   1200
gtcacaccct gtaggctcct ctatataacc caggggcaca ggggctgccc tcattctacc   1260
accacctcca cagcacagac agacactcag gagccagcca gcggcgcgcc caccggtgcc   1320
accatggccc caaagaagaa gcggaaggtc ggtatccacg gagtcccagc agccaagcgg   1380
aactacatcc tgggcctgga catcggcatc accagcgtgg gctacggcat catcgactac   1440
gagacacggg acgtgatcga tgccggcgtg cggctgttca agagggccaa cgtggaaaac   1500
aacgagggca ggcggagcaa gagaggcgcc agaaggctga gcggcggag gcggcataga   1560 atccagagag tgaagaagct gctgttcgac tacaacctgc tgaccgacca cagcgagctg   1620
agcggcatca accctacga ggccagagtg aagggcctga ccagaagct gagcgaggaa   1680 gagttctctg ccgccctgct gcacctggcc aagagaagag gcgtgcacaa cgtgaacgag   1740
gtggaagagg acaccggcaa cgagctgtcc accaaagagc agatcagccg gaacagcaag   1800
gccctggaag agaaatacgt ggccgaactg cagctggaac ggctgaagaa agacggcgaa   1860
gtgcggggca gcatcaacag attcaagacc agcgactacg tgaaagaagc caaacagctg   1920
ctgaaggtgc agaaggccta ccaccagctg gaccagagct tcatcgacac ctacatcgac   1980
ctgctggaaa cccggcggac ctactatgag ggacctggcg agggcagccc cttcggctgg   2040
aaggacatca agaatggta cgagatgctg atgggccact gcacctactt ccccgaggaa   2100
ctgcggagcg tgaagtacgc ctacaacgcc gacctgtaca cgccctgaa cgacctgaac   2160 aatctcgtga tcaccaggga cgagaacgag aagctggaat attacgagaa gttccagatc   2220
atcgagaacg tgttcaagca gaagaagaag cccaccctga gcagatcgc caaagaaatc   2280 ctcgtgaacg aagaggatat taagggctac agagtgacca gcaccggcaa gcccgagttc   2340
accaacctga aggtgtacca cgacatcaag gacattaccg cccggaaaga gattattgag   2400
aacgccgagc tgctggatca gattgccaag atcctgacca tctaccagag cagcgaggac   2460
atccaggaag aactgaccaa tctgaactcc gagctgaccc aggaagagat cgagcagatc   2520
tctaatctga gggctatac cggcacccac aacctgagcc tgaaggccat caacctgatc   2580
ctggacgagc tgtggcacac caacgacaac cagatcgcta tcttcaaccg gctgaagctg   2640
gtgcccaaga aggtggacct gtcccagcag aaagagatcc ccaccaccct ggtggacgac   2700
```

-continued

```
ttcatcctga gccccgtcgt gaagagaagc ttcatccaga gcatcaaagt gatcaacgcc      2760
atcatcaaga agtacggcct gcccaacgac atcattatcg agctggcccg cgagaagaac      2820
tccaaggacg cccagaaaat gatcaacgag atgcagaagc ggaaccggca gaccaacgag      2880
cggatcgagg aaatcatccg gaccaccggc aaagagaacg ccaagtacct gatcgagaag      2940
atcaagctgc acgacatgca ggaaggcaag tgcctgtaca gcctggaagc catccctctg      3000
gaagatctgc tgaacaaccc cttcaactat gaggtggacc acatcatccc cagaagcgtg      3060
tccttcgaca acagcttcaa caacaaggtg ctcgtgaagc aggaagaaaa cagcaagaag      3120
ggcaaccgga ccccattcca gtacctgagc agcagcgaca gcaagatcag ctacgaaacc      3180
ttcaagaagc acatcctgaa tctggccaag ggcaagggca gaatcagcaa gaccaagaaa      3240
gagtatctgc tggaagaacg ggacatcaac aggttctccg tgcagaaaga cttcatcaac      3300
cggaacctgg tggataccag atacgccacc agaggcctga tgaacctgct gcggagctac      3360
ttcagagtga acaacctgga cgtgaaagtg aagtccatca atggcggctt caccagcttt      3420
ctgcggcgga agtggaagtt taagaaagag cggaacaagg ggtacaagca ccacgccgag      3480
gacgccctga tcattgccaa cgccgatttc atcttcaaag agtggaagaa actggacaag      3540
gccaaaaaag tgatggaaaa ccagatgttc gaggaaaagc aggccgagag catgcccgag      3600
atcgaaaccg agcaggagta caaagagatc ttcatcaccc cccaccagat caagcacatt      3660
aaggacttca ggactacaa gtacagccac cgggtggaca agaagcctaa tagagagctg      3720
attaacgaca ccctgtactc caccggaag gacgacaagg gcaacaccct gatcgtgaac      3780
aatctgaacg gcctgtacga caaggacaat gacaagctga aaaagctgat caacaagagc      3840
cccgaaaagc tgctgatgta ccaccacgac ccccagacct accagaaact gaagctgatt      3900
atggaacagt acggcgacga gaagaatccc ctgtacaagt actacgagga aaccgggaac      3960
tacctgacca gtactccaa aaaggacaac ggccccgtga tcaagaagat taagtattac      4020
ggcaacaaac tgaacgccca tctggacatc accgacgact accccaacag cagaaacaag      4080
gtcgtgaagc tgtccctgaa gcccctacaga ttcgacgtgt acctggacaa tggcgtgtac      4140
aagttcgtga ccgtgaagaa tctggatgtg atcaaaaaag aaaactacta cgaagtgaat      4200
agcaagtgct atgaggaagc taagaagctg aagaagatca gcaaccaggc cgagtttatc      4260
gcctccttct acaacaacga tctgatcaag atcaacggcg agctgtatag agtgatcggc      4320
gtgaacaacg acctgctgaa ccggatcgaa gtgaacatga tcgacatcac ctaccgcgag      4380
tacctggaaa acatgaacga caagaggccc cccaggatca ttaagacaat cgcctccaag      4440
acccagagca ttaagaagta cagcacagac attctgggca acctgtatga agtgaaatct      4500
aagaagcacc ctcagatcat caaaaagggc aaaaggccgg cggccacgaa aaaggccggc      4560
caggcaaaaa agaaaaaggg gatcctaccca tacgatgttc cagattacgc ttacccatac      4620
gatgttccag attacgctta cccatacgat gttccagatt acgcttaaga attcctagag      4680
ctcgctgatc agcctcgact gtgccttcta gttgccagcc atctgttgtt tgcccctccc      4740
ccgtgccttc cttgaccctg gaaggtgcca ctcccactgt cctttcctaa taaaatgagg      4800
aaattgcatc gcattgtctg agtaggtgtc attctattct ggggggtggg gtggggcagg      4860
acagcaaggg ggaggattgg gaagagaata gcaggcatgc tggggaggta ccgaacgctg      4920
acgtcatcaa cccgctccaa ggaatcgcgg gcccagtgtc actaggcggg aacacccagc      4980
gcgcgtgcgc cctggcagga agatggctgt gagggacagg ggagtggcgc cctgcaatat      5040
ttgcatgtcg ctatgtgttc tgggaaatca ccataaacgt gaaatgtctt tggatttggg      5100
```

-continued

```
aatcttataa gttctgtatg agaccacata tagtaatgaa attattggca cgtttttagta   5160 ctctggaaac agaatctact aaaacaaggc aaaatgccgt gtttatctcg tcaacttgtt   5220
ggcgagattt ttggtaccag gaacccctag tgatggagtt ggccactccc tctctgcgcg   5280
ctcgctcgct cactgaggcc gggcgaccaa aggtcgcccg acgcccgggc tttgcccggg   5340
cggcctcagt gagcgagcga gcgcgcagct gcctgcaggg gcgcctgatg cggtattttc   5400
tccttacgca tctgtgcggt atttcacacc gcatacgtca aagcaaccat agtacgcgcc   5460
ctgtagcggc gcattaagcg cggcgggtgt ggtggttacg cgcagcgtga ccgctacact   5520
tgccagcgcc ctagcgcccg ctcctttcgc tttcttccct tcctttctcg ccacgttcgc   5580
cggctttccc cgtcaagctc taaatcgggg gctcccttta gggttccgat ttagtgcttt   5640
acggcacctc gaccccaaaa aacttgattt gggtgatggt tcacgtagtg ggccatcgcc   5700
ctgatagacg gttttttcgcc ctttgacgtt ggagtccacg ttctttaata gtggactctt   5760
gttccaaact ggaacaacac tcaaccctat ctcgggctat tcttttgatt tataagggat   5820
tttgccgatt tcggcctatt ggttaaaaaa tgagctgatt taacaaaaat ttaacgcgaa   5880
ttttaacaaa atattaacgt ttacaatttt atggtgcact ctcagtacaa tctgctctga   5940
tgccgcatag ttaagccagc cccgacaccc gccaacaccc gctgacgcgc cctgacgggc   6000
ttgtctgctc ccggcatccg cttacagaca agctgtgacc gtctccggga gctgcatgtg   6060
tcagaggttt tcaccgtcat caccgaaacg cgcgagacga aagggcctcg tgatacgcct   6120 attttttatag gttaatgtca tgataataat ggtttcttag acgtcaggtg cactttttcg   6180
gggaaatgtg cgcggaaccc ctatttgttt attttttctaa atacattcaa atatgtatcc   6240
gctcatgaga caataaccct gataaatgct tcaataatat tgaaaaagga agagtatgag   6300
tattcaacat ttccgtgtcg cccttattcc cttttttgcg gcattttgcc ttcctgtttt   6360
tgctcaccca gaaacgctgg tgaaagtaaa agatgctgaa gatcagttgg gtgcacgagt   6420
gggttacatc gaactggatc tcaacagcgg taagatcctt gagagttttc gccccgaaga   6480
acgttttcca atgatgagca cttttaaagt tctgctatgt ggcgcggtat tatcccgtat   6540
tgacgccggg caagagcaac tcggtcgccg catacactat tctcagaatg acttggttga   6600
gtactcacca gtcacagaaa agcatcttac ggatggcatg acagtaagag aattatgcag   6660
tgctgccata accatgagtg ataacactgc ggccaactta cttctgacaa cgatcggagg   6720
accgaaggag ctaaccgctt ttttgcacaa catgggggat catgtaactc gccttgatcg   6780
ttgggaaccg gagctgaatg aagccatacc aaacgacgag cgtgacacca cgatgcctgt   6840
agcaatggca acaacgttgc gcaaactatt aactggcgaa ctacttactc tagcttcccg   6900
gcaacaatta atagactgga tggaggcgga taaagttgca ggaccacttc tgcgctcggc   6960
ccttccggct ggctggttta ttgctgataa atctggagcc ggtgagcgtg gaagccgcgg   7020
tatcattgca gcactggggc cagatggtaa gccctcccgt atcgtagtta tctacacgac   7080
ggggagtcag gcaactatgg atgaacgaaa tagacagatc gctgagatag gtgcctcact   7140
gattaagcat tggtaactgt cagaccaagt ttactcatat atactttaga ttgatttaaa   7200
acttcatttt taatttaaaa ggatctaggt gaagatcctt tttgataatc tcatgaccaa   7260
aatcccttaa cgtgagtttt cgttccactg agcgtcagac cccgtagaaa agatcaaagg   7320
atcttcttga tcctttttt ttctgcgcgt aatctgctgc ttgcaaacaa aaaaaccacc   7380
gctaccagcg gtggtttgtt tgccggatca agagctacca actctttttc cgaaggtaac   7440
```

-continued

```
tggcttcagc agagcgcaga taccaaatac tgtccttcta gtgtagccgt agttaggcca      7500
ccacttcaag aactctgtag caccgcctac atacctcgct ctgctaatcc tgttaccagt      7560
ggctgctgcc agtggcgata agtcgtgtct taccgggttg gactcaagac gatagttacc      7620
ggataaggcg cagcggtcgg gctgaacggg gggttcgtgc acacagccca gcttggagcg      7680
aacgacctac accgaactga gatacctaca gcgtgagcta tgagaaagcg ccacgcttcc      7740
cgaagggaga aaggcggaca ggtatccggt aagcggcagg gtcggaacag gagagcgcac      7800
gagggagctt ccaggggaa acgcctggta tctttatagt cctgtcgggt ttcgccacct       7860
ctgacttgag cgtcgatttt tgtgatgctc gtcaggggg cggagcctat ggaaaaacgc       7920
cagcaacgcg gccttttac ggttcctggc cttttgctgg ccttttgctc acatgt          7976
```

```
<210> SEQ ID NO 24
<211> LENGTH: 164
<212> TYPE: DNA
<213> ORGANISM: Artificial Sequence
<220> FEATURE:
<223> OTHER INFORMATION: Synthetic

<400> SEQUENCE: 24
tctagaggat ccggtactcg aggaactgaa aaaccagaaa gttaactggt aagtttagtc       60
tttttgtctt ttatttcagg tcccggatcc ggtggtggtg caaatcaaag aactgctcct      120
cagtggatgt tgcctttact tctaggcctg tacggaagtg ttac                       164
```

```
<210> SEQ ID NO 25
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, g, c, or t
<220> FEATURE:
<221> NAME/KEY: r
<222> LOCATION: (4)..(4)
<223> OTHER INFORMATION: r is a, or g
<220> FEATURE:
<221> NAME/KEY: r
<222> LOCATION: (5)..(5)
<223> OTHER INFORMATION: r is a, or g

<400> SEQUENCE: 25 nngrr                                                                    5
```

```
<210> SEQ ID NO 26
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: r
<222> LOCATION: (4)..(4)
<223> OTHER INFORMATION: r is a, or g
<220> FEATURE:
<221> NAME/KEY: r
<222> LOCATION: (5)..(5)
<223> OTHER INFORMATION: r is a, or g
<220> FEATURE:
<221> NAME/KEY: misc_feature
```

<222> LOCATION: (6)..(6)
<223> OTHER INFORMATION: n is a, g, c, or t

<400> SEQUENCE: 26 nngrrn                                                              6

<210> SEQ ID NO 27
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, g, c, or t
<220> FEATURE:
<221> NAME/KEY: r
<222> LOCATION: (4)..(4)
<223> OTHER INFORMATION: r is a, or g
<220> FEATURE:
<221> NAME/KEY: r
<222> LOCATION: (5)..(5)
<223> OTHER INFORMATION: r is a, or g

<400> SEQUENCE: 27 nngrrt                                                              6

<210> SEQ ID NO 28
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, g, c, or t
<220> FEATURE:
<221> NAME/KEY: r
<222> LOCATION: (4)..(4)
<223> OTHER INFORMATION: r is a, or g
<220> FEATURE:
<221> NAME/KEY: r
<222> LOCATION: (5)..(5)
<223> OTHER INFORMATION: r is a, or g

<400> SEQUENCE: 28 nngrrv                                                              6

<210> SEQ ID NO 29
<211> LENGTH: 7508
<212> TYPE: DNA
<213> ORGANISM: Artificial Sequence
<220> FEATURE:
<223> OTHER INFORMATION: Synthetic

<400> SEQUENCE: 29
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gactcgagga gctccaccgc ggtggcggcc gtccgccttc     180
ggcaccatcc tcacgacacc caaatatggc gacgggtgag gaatggtggg gagttatttt     240
tagagcggtg aggaaggtgg gcaggcagca ggtgttggcg ctctaaaaat aactcccggg     300
agttattttt agagcggagg aatggtggac acccaaatat ggcgacggtt cctcacccgt     360
cgccatattt gggtgtccgc cctcggccgg ggccgcattc ctgggggccg ggcggtgctc     420

-continued

```
ccgcccgcct cgataaaagg ctccgggggcc ggcggcggcc cacgagctac ccggaggagc    480
gggaggcgcc aagctctaga actagtggat cccccgggct gcaggaattc gatatccatg    540
gtctagagga tccggtactc gaggaactga aaaaccagaa agttaactgg taagtttagt    600 cttttttgtct tttatttcag gtcccggatc cggtggtggt gcaaatcaaa gaactgctcc    660
tcagtggatg ttgcctttac ttctaggcct gtacggaagt gttacgccac catggcccca    720
aagaagaagc ggaaggtcgg tatccacgga gtcccagcag ccaagcggaa ctacatcctg    780
ggcctggaca tcggcatcac cagcgtgggc tacggcatca tcgactacga gacacgggac    840
gtgatcgatg ccggcgtgcg gctgttcaaa gaggccaacg tggaaaacaa cgagggcagg    900
cggagcaaga gaggcgccag aaggctgaag cggcggaggc ggcatagaat ccagagagtg    960
aagaagctgc tgttcgacta caacctgctg accgaccaca gcgagctgag cggcatcaac    1020
ccctacgagg ccagagtgaa gggcctgagc cagaagctga gcgaggaaga gttctctgcc    1080
gccctgctgc acctggccaa gagaagaggc gtgcacaacg tgaacgaggt ggaagaggac    1140
accggcaacg agctgtccac caaagagcag atcagccgga acagcaaggc cctggaaagag    1200 aaatacgtgg ccgaactgca gctggaacgg ctgaagaaag acggcgaagt gcggggcagc    1260
atcaacagat tcaagaccag cgactacgtg aaagaagcca aacagctgct gaaggtgcag    1320
aaggcctacc accagctgga ccagagcttc atcgacacct acatcgacct gctggaaacc    1380
cggcggacct actatgaggg acctggcgag ggcagcccct cggctggaa ggacatcaaa    1440 gaatggtacg agatgctgat gggccactgc acctacttcc ccgaggaact gcggagcgtg    1500
aagtacgcct acaacgccga cctgtacaac gccctgaacg acctgaacaa tctcgtgatc    1560
accagggacg agaacgagaa gctggaatat tacgagaagt tccagatcat cgagaacgtg    1620
ttcaagcaga gaagaagcc caccctgaag cagatcgcca agaaatcct cgtgaacgaa    1680 gaggatatta agggctacag agtgaccagc accggcaagc ccgagttcac caacctgaag    1740
gtgtaccacg acatcaagga cattaccgcc cggaaagaga ttattgagaa cgccgagctg    1800
ctggatcaga ttgccaagat cctgaccatc taccagagca gcgaggacat ccaggaagaa    1860
ctgaccaatc tgaactccga gctgacccag aagagatcg agcagatctc taatctgaag    1920
ggctataccg gcacccacaa cctgagcctg aaggccatca cctgatcct ggacgagctg    1980 tggcacacca cgacaacca gatcgctatc ttcaaccggc tgaagctggt gcccaagaag    2040
gtggacctgt cccagcagaa agagatcccc accaccctgg tggacgactt catcctgagc    2100
cccgtcgtga agagaagctt catccagagc atcaaagtga tcaacgccat catcaagaag    2160
tacggcctgc ccaacgacat cattatcgag ctggcccgcg agaagaactc caaggacgcc    2220
cagaaaatga tcaacgagat gcagaagcgg aaccggcaga ccaacgagcg gatcgaggaa    2280
atcatccgga ccaccggcaa agagaacgcc aagtacctga tcgagaagat caagctgcac    2340
gacatgcagg aaggcaagtg cctgtacagc ctggaagcca tccctctgga agatctgctg    2400
aacaacccct tcaactatga ggtggaccac atcatcccca aagcgtgtc cttcgacaac    2460 agcttcaaca caaaggtgct cgtgaagcag aagaaaaca gcaagaaggg caaccggacc    2520
ccattccagt acctgagcag cagcgacagc aagatcagct acgaaaacctt caagaagcac    2580 atcctgaatc tggccaaggg caagggcaga atcagcaaga ccaagaaaga gtatctgctg    2640
gaagaacggg acatcaacag gttctccgtg cagaaagact tcatcaaccg gaacctggtg    2700
gataccagat acgccaccag aggcctgatg aacctgctgc ggagctactt cagagtgaac    2760
aacctggacg tgaaagtgaa gtccatcaat ggcggcttca ccagctttct gcggcggaag    2820
```

-continued

```
tggaagttta agaaagagcg gaacaagggg tacaagcacc acgccgagga cgccctgatc   2880
attgccaacg ccgatttcat cttcaaagag tggaagaaac tggacaaggc caaaaaagtg   2940
atggaaaacc agatgttcga ggaaaagcag gccgagagca tgcccgagat cgaaaccgag   3000
caggagtaca aagagatctt catcaccccc caccagatca agcacattaa ggacttcaag   3060
gactacaagt acagccaccg ggtggacaag aagcctaata gagagctgat taacgacacc   3120
ctgtactcca cccggaagga cgacaagggc aacaccctga tcgtgaacaa tctgaacggc   3180
ctgtacgaca aggacaatga caagctgaaa aagctgatca acaagagccc cgaaaagctg   3240
ctgatgtacc accacgaccc ccagacctac cagaaactga agctgattat ggaacagtac   3300
ggcgacgaga agaatcccct gtacaagtac tacgaggaaa ccgggaacta cctgaccaag   3360
tactccaaaa aggacaacgg ccccgtgatc aagaagatta gtattacggg caacaaactg   3420
aacgcccatc tggacatcac cgacgactac cccaacagca gaaacaaggt cgtgaagctg   3480
tccctgaagc cctacagatt cgacgtgtac ctggacaatg gcgtgtacaa gttcgtgacc   3540
gtgaagaatc tggatgtgat caaaaaagaa aactactacg aagtgaatag caagtgctat   3600
gaggaagcta agaagctgaa gaagatcagc aaccaggccg agtttatcgc ctccttctac   3660
aacaacgatc tgatcaagat caacggcgag ctgtatagag tgatcggcgt gaacaacgac   3720
ctgctgaacc ggatcgaagt gaacatgatc gacatcacct accgcgagta cctggaaaac   3780
atgaacgaca agaggccccc caggatcatt aagacaatcg cctccaagac ccagagcatt   3840
aagaagtaca gcacagacat tctgggcaac ctgtatgaag tgaaatctaa gaagcaccct   3900
cagatcatca aaaagggcaa aaggccggcg gccacgaaaa aggccggcca ggcaaaaaag   3960
aaaaagggat ccgaattcta gcaataaagg atcgtttatt ttcattggaa gcgtgtgttg   4020 gtttttttgat caggcgcggg taccaaaaat ctcgccaaca agttgacgag ataaacacgg   4080
cattttgcct tgtttttagta gattctgttt ccagagtact aaaacacatt tcctctctat   4140
acaaatgcgg tgtttcgtcc tttccacaag atatataaag ccaagaaatc gaaatacttt   4200
caagttacgg taagcatatg atagtccatt ttaaaacata attttaaaac tgcaaactac   4260
ccaagaaatt attactttct acgtcacgta ttttgtacta atatctttgt gtttacagtc   4320
aaattaattc caattatctc tctaacagcc ttgtatcgta tatgcaaata tgaaggaatc   4380
atgggaaata ggccctcctc gactagtaga aaaatctcgc caacaagttg acgagataaa   4440
cacggcattt tgccttgttt tagtagattc tgtttccaga gtactaaaac gtgccaataa   4500
tttcattact atatcggtgt ttcgtccttt ccacaagata tataaagcca agaaatcgaa   4560
atactttcaa gttacggtaa gcatatgata gtccatttta aaacataatt ttaaaactgc   4620
aaactaccca agaaattatt actttctacg tcacgtattt tgtactaata tctttgtgtt   4680
tacagtcaaa ttaattccaa ttatctctct aacagccttg tatcgtatat gcaaatatga   4740
aggaatcatg ggaaataggc cctcggtacc aggaacccct agtgatggag ttggccactc   4800
cctctctgcg cgctcgctcg ctcactgagg ccgggcgacc aaaggtcgcc cgacgcccgg   4860
gctttgcccg ggcggcctca gtgagcgagc gagcgcgcag ctgcctgcag gggcgcctga   4920
tgcggtattt tctccttacg catctgtgcg gtatttcaca ccgcatacgt caaagcaacc   4980
atagtacgcg ccctgtagcg gcgcattaag cgcggcgggt gtggtggtta cgcgcagcgt   5040
gaccgctaca cttgccagcg ccctagcgcc cgctcctttc gctttcttcc cttcctttct   5100
cgccacgttc gccggctttc cccgtcaagc tctaaatcgg gggctccctt tagggttccg   5160
```

-continued

```
atttagtgct ttacggcacc tcgaccccaa aaaacttgat ttgggtgatg gttcacgtag    5220
tgggccatcg ccctgataga cggttttttcg ccctttgacg ttggagtcca cgttctttaa    5280
tagtggactc ttgttccaaa ctggaacaac actcaaccct atctcgggct attctttttga    5340 tttataaggg attttgccga tttcggccta ttggttaaaa aatgagctga tttaacaaaa    5400
atttaacgcg aattttaaca aaatattaac gtttacaatt ttatggtgca ctctcagtac    5460
aatctgctct gatgccgcat agttaagcca gccccgacac ccgccaacac ccgctgacgc    5520
gccctgacgg gcttgtctgc tcccggcatc cgcttacaga caagctgtga ccgtctccgg    5580
gagctgcatg tgtcagaggt tttcaccgtc atcaccgaaa cgcgcgagac gaaagggcct    5640
cgtgatacgc ctatttttat aggttaatgt catgataata atggtttctt agacgtcagg    5700
tggcactttt cggggaaatg tgcgcggaac ccctatttgt ttattttttct aaatacattc    5760 aaatatgtat ccgctcatga gacaataacc ctgataaatg cttcaataat attgaaaaag    5820
gaagagtatg agtattcaac atttccgtgt cgcccttatt cccttttttg cggcattttg    5880
ccttcctgtt tttgctcacc cagaaacgct ggtgaaagta aaagatgctg aagatcagtt    5940
gggtgcacga gtgggttaca tcgaactgga tctcaacagc ggtaagatcc ttgagagttt    6000
tcgccccgaa gaacgttttc caatgatgag cacttttaaa gttctgctat gtggcgcggt    6060
attatcccgt attgacgccg ggcaagagca actcggtcgc cgcatacact attctcagaa    6120
tgacttggtt gagtactcac cagtcacaga aaagcatctt acggatggca tgacagtaag    6180
agaattatgc agtgctgcca taaccatgag tgataacact gcggccaact tacttctgac    6240
aacgatcgga ggaccgaagg agctaaccgc tttttttgcac aacatggggg atcatgtaac    6300
tcgccttgat cgttgggaac cggagctgaa tgaagccata ccaaacgacg agcgtgacac    6360
cacgatgcct gtagcaatgg caacaacgtt gcgcaaacta ttaactggcg aactacttac    6420
tctagcttcc cggcaacaat taatagactg gatggaggcg gataaagttg caggaccact    6480
tctgcgctcg gcccttccgg ctggctggtt tattgctgat aaatctggag ccggtgagcg    6540
tggaagccgc ggtatcattg cagcactggg gccagatggt aagccctccc gtatcgtagt    6600
tatctacacg acggggagtc aggcaactat ggatgaacga atagacaga tcgctgagat    6660 aggtgcctca ctgattaagc attggtaact gtcagaccaa gtttactcat atatacttta    6720
gattgattta aaacttcatt tttaatttaa aaggatctag gtgaagatcc tttttgataa    6780
tctcatgacc aaaatccctt aacgtgagtt ttcgttccac tgagcgtcag accccgtaga    6840
aaagatcaaa ggatcttctt gagatccttt ttttctgcgc gtaatctgct gcttgcaaac    6900
aaaaaaacca ccgctaccag cggtggtttg tttgccggat caagagctac caactctttt    6960
tccgaaggta actggcttca gcagagcgca gataccaaat actgtccttc tagtgtagcc    7020
gtagttaggc caccacttca agaactctgt agcaccgcct acatacctcg ctctgctaat    7080
cctgttacca gtggctgctg ccagtggcga taagtcgtgt cttaccgggt tggactcaag    7140
acgatagtta ccggataagg cgcagcggtc gggctgaacg gggggttcgt gcacacagcc    7200
cagcttggag cgaacgacct acaccgaact gagataccta cagcgtgagc tatgagaaag    7260
cgccacgctt cccgaaggga gaaaggcgga caggtatccg gtaagcggca gggtcggaac    7320
aggagagcgc acgagggagc ttccagggggg aaacgcctgg tatctttata gtcctgtcgg    7380
gtttcgccac ctctgacttg agcgtcgatt tttgtgatgc tcgtcagggg ggcggagcct    7440
atggaaaaac gccagcaacg cggcctttttt acggttcctg gccttttgct ggcctttttgc    7500 tcacatgt                                                             7508
```

<210> SEQ ID NO 30
<211> LENGTH: 7913
<212> TYPE: DNA
<213> ORGANISM: Artificial Sequence
<220> FEATURE:
<223> OTHER INFORMATION: Synthetic

<400> SEQUENCE: 30
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gactcgagag cttgcatgtc taagctagac ccttcagatt     180
aaaaataact gaggtaaggg cctgggtagg ggaggtggtg tgagacgctc ctgtctctcc     240
tctatctgcc catcggccct ttggggagga ggaatgtgcc caaggactaa aaaaaggcca     300
tggagccaga ggggcgaggg caacagacct tcatgggca aaccttgggg ccctgctgtc      360
tagcatgccc cactacgggt ctaggctgcc catgtaagga ggcaaggcct ggggacaccc     420
gagatgcctg gttataatta acccagacat gtggctgccc cccccccccc aacacctgct     480
gcctctaaaa ataaccctgt ccctggtgga tccctgcat gcgaagatct tcgaacaagg      540 ctgtgggggga ctgagggcag gctgtaacag gcttgggggc cagggcttat acgtgcctgg    600
gactcccaaa gtattactgt tccatgttcc cggcgaaggg ccagctgtcc cccgccagct     660
agactcagca cttagtttag gaaccagtga gcaagtcagc ccttgggggca gcccatacaa    720 ggccatggg g ctgggcaagc tgcacgcctg ggtccggggt gggcacggtg cccgggcaac    780
gagctgaaag ctcatctgct ctcagggggcc cctccctggg gacagcccct cctggctagt    840
cacaccctgt aggctcctct atataaccca ggggcacagg ggctgccctc attctaccac     900
cacctccaca gcacagacag acactcagga gccagccagc ccatggtcta gaggatccgg     960
tactcgagga actgaaaaac cagaaagtta actggtaagt ttagtctttt tgtcttttat    1020
ttcaggtccc ggatccggtg gtggtgcaaa tcaaagaact gctcctcagt ggatgttgcc   1080
tttacttcta ggcctgtacg gaagtgttac gccaccatgg ccccaaagaa gaagcggaag   1140
gtcggtatcc acggagtccc agcagccaag cggaactaca tcctgggcct ggacatcggc   1200
atcaccagcg tgggctacgg catcatcgac tacgagacac gggacgtgat cgatgccggc   1260
gtgcggctgt tcaaagaggc caacgtggaa aacaacgagg gcaggcggag caagagaggc   1320
gccagaaggc tgaagcggcg gaggcggcat agaatccaga gagtgaagaa gctgctgttc   1380
gactacaacc tgctgaccga ccacagcgag ctgagcggca tcaaccccta cgaggccaga   1440
gtgaagggcc tgagccagaa gctgagcgag gaagagttct ctgccgccct gctgcacctg   1500
gccaagagaa gaggcgtgca caacgtgaac gaggtggaag aggacaccgg caacgagctg   1560
tccaccaaag agcagatcag ccggaacagc aaggccctgg aagagaaata cgtggccgaa   1620
ctgcagctgg aacggctgaa gaaagacggc gaagtgcggg gcagcatcaa cagattcaag   1680
accagcgact acgtgaaaga agccaaacag ctgctgaagg tgcagaaggc ctaccaccag   1740
ctggaccaga gcttcatcga cacctacatc gacctgctgg aaacccggcg gacctactat   1800
gagggacctg cgagggcag ccccttcggc tggaaggaca tcaagaatg gtacgagatg    1860 ctgatgggcc actgcaccta cttccccgag gaactgcgga gcgtgaagta cgcctacaac   1920
gccgacctgt acaacgccct gaacgacctg aacaatctcg tgatcaccag ggacgagaac   1980
gagaagctgg aatattacga gaagttccag atcatcgaga acgtgttcaa gcagaagaag   2040

-continued

```
aagcccaccc tgaagcagat cgccaaagaa atcctcgtga acgaagagga tattaagggc   2100
tacagagtga ccagcaccgg caagcccgag ttcaccaacc tgaaggtgta ccacgacatc   2160
aaggacatta ccgcccggaa agagattatt gagaacgccg agctgctgga tcagattgcc   2220
aagatcctga ccatctacca gagcagcgag gacatccagg aagaactgac caatctgaac   2280
tccgagctga cccaggaaga gatcgagcag atctctaatc tgaagggcta taccggcacc   2340
cacaacctga gcctgaaggc catcaacctg atcctggacg agctgtggca caccaacgac   2400
aaccagatcg ctatcttcaa ccggctgaag ctggtgccca agaaggtgga cctgtcccag   2460
cagaaagaga tccccaccac cctggtggac gacttcatcc tgagccccgt cgtgaagaga   2520
agcttcatcc agagcatcaa agtgatcaac gccatcatca agaagtacgg cctgcccaac   2580
gacatcatta tcgagctggc ccgcgagaag aactccaagg acgcccagaa aatgatcaac   2640
gagatgcaga agcggaaccg gcagaccaac gagcggatcg aggaaatcat ccggaccacc   2700
ggcaaagaga acgccaagta cctgatcgag aagatcaagc tgcacgacat gcaggaaggc   2760
aagtgcctgt acagcctgga agccatccct ctggaagatc tgctgaacaa ccccttcaac   2820
tatgaggtgg accacatcat ccccagaagc gtgtccttcg acaacagctt caacaacaag   2880
gtgctcgtga gcaggaaga aaacagcaag aagggcaacc ggacccatt ccagtacctg   2940 agcagcagcg acagcaagat cagctacgaa accttcaaga agcacatcct gaatctggcc   3000
aagggcaagg gcagaatcag caagaccaag aaagagtatc tgctggaaga cgggacatc   3060 aacaggttct ccgtgcagaa agacttcatc aaccggaacc tggtggatac cagatacgcc   3120
accagaggcc tgatgaacct gctgcggagc tacttcagag tgaacaacct ggacgtgaaa   3180
gtgaagtcca tcaatggcgg cttcaccagc tttctgcggc ggaagtggaa gtttaagaaa   3240
gagcggaaca aggggtacaa gcaccacgcc gaggacgccc tgatcattgc caacgccgat   3300
ttcatcttca aagagtggaa gaaactggac aaggccaaaa agtgatgga aaaccagatg   3360 ttcgaggaaa agcaggccga gagcatgccc gagatcgaaa ccgagcagga gtacaaagag   3420
atcttcatca ccccccacca gatcaagcac attaaggact tcaaggacta caagtacagc   3480
caccgggtgg acaagaagcc taatagagag ctgattaacg acaccctgta ctccacccgg   3540
aaggacgaca agggcaacac cctgatcgtg aacaatctga cggcctgta cgacaaggac   3600 aatgacaagc tgaaaaagct gatcaacaag agccccgaaa agctgctgat gtaccaccac   3660
gacccccaga cctaccagaa actgaagctg attatggaac agtacggcga cgagaagaat   3720
cccctgtaca gtactacga ggaaaccggg aactacctga ccaagtactc caaaaaggac   3780
aacggccccg tgatcaagaa gattaagtat tacggcaaca aactgaacgc ccatctggac   3840
atcaccgacg actaccccaa cagcagaaac aaggtcgtga agctgtccct gaagccctac   3900
agattcgacg tgtacctgga caatggcgtg tacaagttcg tgaccgtgaa gaatctggat   3960
gtgatcaaaa aagaaaacta ctacgaagtg aatagcaagt gctatgagga agctaagaag   4020
ctgaagaaga tcagcaacca ggccgagttt atcgcctcct tctacaacaa cgatctgatc   4080
aagatcaacg gcgagctgta tagagtgatc ggcgtgaaca cgacctgct gaaccggatc   4140 gaagtgaaca tgatcgacat cacctaccgc gagtacctgg aaaacatgaa cgacaagagg   4200 cccccccagga tcattaagac aatcgcctcc aagacccaga gcattaagaa gtacagcaca   4260
gacattctgg gcaacctgta tgaagtgaaa tctaagaagc accctcagat catcaaaaag   4320
ggcaaaaggc cggcggccac gaaaaaggcc ggccaggcaa aaaagaaaaa gggatccgaa   4380
ttctagcaat aaaggatcgt ttattttcat tggaagcgtg tgttggtttt ttgatcaggc   4440
```

-continued

```
gcgggtacca aaaatctcgc caacaagttg acgagataaa cacggcattt tgccttgttt      4500
tagtagattc tgtttccaga gtactaaaac acatttcctc tctatacaaa tgcggtgttt      4560
cgtcctttcc acaagatata taaagccaag aaatcgaaat actttcaagt tacggtaagc      4620
atatgatagt ccattttaaa acataatttt aaaactgcaa actacccaag aaattattac      4680
tttctacgtc acgtattttg tactaatatc tttgtgttta cagtcaaatt aattccaatt      4740
atctctctaa cagccttgta tcgtatatgc aaatatgaag gaatcatggg aaataggccc      4800
tcctcgacta gtagaaaaat ctcgccaaca agttgacgag ataaacacgg cattttgcct      4860
tgttttagta gattctgttt ccagagtact aaaacgtgcc aataatttca ttactatatc      4920
ggtgtttcgt cctttccaca agatatataa agccaagaaa tcgaaatact ttcaagttac      4980
ggtaagcata tgatagtcca ttttaaaaca taattttaaa actgcaaact acccaagaaa      5040
ttattacttt ctacgtcacg tattttgtac taatatcttt gtgtttacag tcaaattaat      5100
tccaattatc tctctaacag ccttgtatcg tatatgcaaa tatgaaggaa tcatgggaaa      5160
taggccctcg gtaccaggaa cccctagtga tggagttggc cactccctct ctgcgcgctc      5220
gctcgctcac tgaggccggg cgaccaaagg tcgcccgacg cccgggcttt gcccgggcgg      5280
cctcagtgag cgagcgagcg cgcagctgcc tgcaggggcg cctgatgcgg tattttctcc      5340
ttacgcatct gtgcggtatt tcacaccgca tacgtcaaag caaccatagt acgcgccctg      5400
tagcggcgca ttaagcgcgg cgggtgtggt ggttacgcgc agcgtgaccg ctacacttgc      5460
cagcgcccta gcgcccgctc ctttcgcttt cttcccttcc tttctcgcca cgttcgccgg      5520
ctttccccgt caagctctaa atcgggggct ccctttaggg ttccgattta gtgctttacg      5580
gcacctcgac cccaaaaaac ttgatttggg tgatggttca cgtagtgggc catcgccctg      5640
atagacggtt tttcgccctt tgacgttgga gtccacgttc tttaatagtg gactcttgtt      5700
ccaaactgga acaacactca accctatctc gggctattct tttgatttat aagggatttt      5760
gccgatttcg gcctattggt taaaaaatga gctgatttaa caaaaattta acgcgaattt      5820
taacaaaata ttaacgttta caattttatg gtgcactctc agtacaatct gctctgatgc      5880
cgcatagtta agccagcccc gacacccgcc aacacccgct gacgcgccct gacgggcttg      5940
tctgctcccg gcatccgctt acagacaagc tgtgaccgtc tccgggagct gcatgtgtca      6000
gaggttttca ccgtcatcac cgaaacgcgc gagacgaaag ggcctcgtga tacgcctatt      6060
tttataggtt aatgtcatga taataatggt ttcttagacg tcaggtggca cttttcgggg      6120
aaatgtgcgc ggaacccota tttgtttatt tttctaaata cattcaaata tgtatccgct      6180
catgagacaa taaccctgat aaatgcttca ataatattga aaaggaaga gtatgagtat      6240 tcaacatttc cgtgtcgccc ttattccctt ttttgcggca ttttgccttc ctgttttgc      6300 tcacccagaa acgctggtga aagtaaaaga tgctgaagat cagttgggtg cacgagtggg      6360
ttacatcgaa ctggatctca acagcggtaa gatccttgag agttttcgcc ccgaagaacg      6420
ttttccaatg atgagcactt ttaaagttct gctatgtggc gcggtattat cccgtattga      6480
cgccgggcaa gagcaactcg gtcgccgcat acactattct cagaatgact ggtttgagta      6540
ctcaccagtc acagaaaagc atcttacgga tggcatgaca gtaagagaat tatgcagtgc      6600
tgccataacc atgagtgata acactgcggc caacttactt ctgacaacga tcggaggacc      6660
gaaggagcta accgcttttt tgcacaacat ggggggatcat gtaactcgcc ttgatcgttg      6720
ggaaccggag ctgaatgaag ccataccaaa cgacgagcgt gacaccacga tgcctgtagc      6780
```

-continued

```
aatggcaaca acgttgcgca aactattaac tggcgaacta cttactctag cttcccggca    6840
acaattaata gactggatgg aggcggataa agttgcagga ccacttctgc gctcggccct    6900
tccggctggc tggtttattg ctgataaatc tggagccggt gagcgtggaa gccgcggtat    6960
cattgcagca ctggggccag atggtaagcc ctcccgtatc gtagttatct acacgacggg    7020
gagtcaggca actatggatg aacgaaatag acagatcgct gagataggtg cctcactgat    7080
taagcattgg taactgtcag accaagttta ctcatatata ctttagattg atttaaaact    7140 tcattttttaa tttaaaagga tctaggtgaa gatccttttt gataatctca tgaccaaaat    7200
cccttaacgt gagttttcgt tccactgagc gtcagacccc gtagaaaaga tcaaaggatc    7260
ttcttgagat cctttttttc tgcgcgtaat ctgctgcttg caaacaaaaa aaccaccgct    7320
accagcggtg gtttgtttgc cggatcaaga gctaccaact cttttttccga aggtaactgg    7380 cttcagcaga gcgcagatac caaatactgt ccttctagtg tagccgtagt taggccacca    7440
cttcaagaac tctgtagcac cgcctacata cctcgctctg ctaatcctgt taccagtggc    7500
tgctgccagt ggcgataagt cgtgtcttac cgggttggac tcaagacgat agttaccgga    7560
taaggcgcag cggtcgggct gaacggggggg ttcgtgcaca cagcccagct tggagcgaac    7620
gacctacacc gaactgagat acctacagcg tgagctatga gaaagcgcca cgcttcccga    7680
agggagaaag gcggacaggt atccggtaag cggcagggtc ggaacaggag agcgcacgag    7740
ggagcttcca gggggaaacg cctggtatct ttatagtcct gtcgggtttc gccacctctg    7800
acttgagcgt cgatttttgt gatgctcgtc aggggggcgg agcctatgga aaaacgccag    7860
caacgcggcc tttttacggt tcctggcctt ttgctggcct tttgctcaca tgt    7913
```

```
<210> SEQ ID NO 31
<211> LENGTH: 3158
<212> TYPE: DNA
<213> ORGANISM: Artificial Sequence
<220> FEATURE:
<223> OTHER INFORMATION: Synthetic

<400> SEQUENCE: 31
```

```
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca tgagggacg gagaagcaag aggggagcca ggcgcctgaa acgacgggaga     180 aggcacagaa tccagagggt gaagaaactg ctgttcgatt acaacctgct gaccgaccat     240
tctgagctga gtggaattaa tccttatgaa gccagggtga aaggcctgag tcagaagctg     300
tcagaggaag agttttccgc agctctgctg cacctggcta agcgccgagg agtgcataac     360
gtcaatgagg tggaagagga caccggcaac gagctgtcta caaaggaaca gatctcacgc     420
aatagcaaag ctctggaaga agagtatgtc gcagagctgc agctggaacg gctgaagaaa     480
gatggcgagg tgagagggtc aattaatagg ttcaagacaa gcgactacgt caaagaagcc     540
aagcagctgc tgaaagtgca gaaggcttac accagctgg atcagagctt catcgatact      600
tatatcgacc tgctggagac tcggagaacc tactatgagg accaggagag agggagcccc     660
ttcggatgga aagacatcaa ggaatggtac gagatgctga tgggacattg cacctatttt     720
ccagaagagc tgagaagcgt caagtacgct tataacgcag atctgtacaa cgccctgaat     780
gacctgaaca acctggtcat caccaggggat gaaaacgaga aactggaata ctatgagaag     840
ttccagatca tcgaaaacgt gtttaagcag aagaaaaagc ctacactgaa acagattgct     900
aaggagatcc tggtcaacga agaggacatc aagggctacc gggtgacaag cactggaaaa     960
```

```
ccagagttca ccaatctgaa agtgtatcac gatattaagg acatcacagc acggaaagaa      1020
atcattgaga acgccgaact gctggatcag attgctaaga tcctgactat ctaccagagc      1080
tccgaggaca tccaggaaga gctgactaac ctgaacagcg agctgaccca ggaagagatc      1140
gaacagatta gtaatctgaa ggggtacacc ggaacacaca acctgtccct gaaagctatc      1200
aatctgattc tggatgagct gtggcataca aacgacaatc agattgcaat ctttaaccgg      1260
ctgaagctgg tcccaaaaaa ggtggacctg agtcagcaga aagagatccc aaccacactg      1320
gtggacgatt tcattctgtc acccgtggtc aagcggagct tcatccagag catcaaagtg      1380
atcaacgcca tcatcaagaa gtacggcctg cccaatgata tcattatcga gctggctagg      1440
gagaagaaca gcaaggacgc acagaagatg atcaatgaga tgcagaaacg aaaccggcag      1500
accaatgaac gcattgaaga gattatccga actaccggga aagagaacgc aaagtacctg      1560
attgaaaaaa tcaagctgca cgatatgcag gagggaaagt gtctgtattc tctggaggcc      1620
tcccctcgga ggacctgctg aacaatccat tcaactacga ggtcgatcat attatcccca      1680
gaagcgtgtc cttcgacaat tcctttaaca acaaggtgct ggtcaagcag gaagagaact      1740
ctaaaaaggg caataggact cctttccagt acctgtctag ttcagattcc aagatctctt      1800
acgaaacctt taaaaagcac attctgaatc tggccaaagg aaagggccgc atcagcaaga      1860
ccaaaaagga gtacctgctg aagagcgggg acatcaacag attctccgtc cagaaggatt      1920
ttattaaccg gaatctggtg gacacaagat acgctactcg cggcctgatg aatctgctgc      1980
gatcctattt ccgggtgaac aatctggatg tgaaagtcaa gtccatcaac ggcgggttca      2040
catcttttct gaggcgcaaa tggaagtttt aaaaggagcg caacaaaggg tacaagcacc      2100
atgccgaaga tgctctgatt atcgcaaatg ccgacttcat ctttaaggag tggaaaaagc      2160
tggacaaagc caagaaagtg atggagaacc agatgttcga agagaagcag gccgaatcta      2220
tgcccgaaat cgagacagaa caggagtaca aggagatttt catcactcct caccagatca      2280
agcatatcaa ggatttcaag gactacaagt actctcaccg ggtggataaa aagcccaaca      2340
gagagctgat caatgacacc ctgtatagta caagaaaaga cgataagggg aataccctga      2400
ttgtgaacaa tctgaacgga ctgtacgaca agataatga caagctgaaa aagctgatca      2460
acaaaagtcc cgagaagctg ctgatgtacc accatgatcc tcagacatat cagaaactga      2520
agctgattat ggagcagtac ggcgacgaga agaaccccact gtataagtac tatgaagaga      2580
ctgggaacta cctgaccaag tatagcaaaa aggataatgg ccccgtgatc aagaagatca      2640
agtactatgg gaacaagctg aatgcccatc tggacatcac agacgattac cctaacagtc      2700
gcaacaaggt ggtcaagctg tcactgaagc catacagatt cgatgtctat ctggacaacg      2760
gcgtgtataa atttgtgact gtcaagaatc tggatgtcat caaaaaggag aactactatg      2820
aagtgaatag caagtgctac gaagaggcta aaaagctgaa aaagattagc aaccaggcag      2880
agttcatcgc ctcctttac aacaacgacc tgattaagat caatggcgaa ctgtataggg      2940
tcatcggggt gaacaatgat ctgctgaacc gcattgaagt gaatatgatt gacatcactt      3000
accgagagta tctggaaaac atgaatgata agcgccccc tcgaattatc aaaacaattg      3060
cctctaagac tcagagtatc aaaaagtact caaccgacat tctgggaaac ctgtatgagg      3120
tgaagagcaa aaagcaccct cagattatca aaaagggc                             3158
```

<210> SEQ ID NO 32
<211> LENGTH: 3159
<212> TYPE: DNA

<213> ORGANISM: Artificial Sequence
<220> FEATURE:
<223> OTHER INFORMATION: Synthetic

<400> SEQUENCE: 32
atgaagcgga actacatcct gggcctggac atcggcatca ccagcgtggg ctacggcatc      60
atcgactacg agacacggga cgtgatcgat gccggcgtgc ggctgttcaa agaggccaac     120
gtggaaaaca acgagggcag gcggagcaag agaggcgcca gaaggctgaa gcggcggagg     180
cggcatagaa tccagagagt gaagaagctg ctgttcgact acaacctgct gaccgaccac     240
agcgagctga gcggcatcaa cccctacgag gccagagtga agggcctgag ccagaagctg     300
agcgaggaag agttctctgc cgccctgctg cacctggcca agagaagagg cgtgcacaac     360
gtgaacgagg tggaagagga caccggcaac gagctgtcca ccaaagagca gatcagccgg     420
aacagcaagg ccctggaaga gaaatacgtg gccgaactgc agctggaacg gctgaagaaa     480
gacggcgaag tgcggggcag catcaacaga ttcaagacca gcgactacgt gaaagaagcc     540
aaacagctgc tgaaggtgca gaaggcctac caccagctgg accagagctt catcgacacc     600
tacatcgacc tgctggaaac ccggcggacc tactatgagg gacctggcga gggcagcccc     660
ttcggctgga aggacatcaa agaatggtac gagatgctga tgggccactg cacctacttc     720
cccgaggaac tgcggagcgt gaagtacgcc tacaacgccg acctgtacaa cgccctgaac     780
gacctgaaca atctcgtgat caccagggac gagaacgaga gctggaata ttacgagaag     840 ttccagatca tcgagaacgt gttcaagcag aagaagaagc ccaccctgaa gcagatcgcc     900
aaagaaatcc tcgtgaacga agaggatatt aagggctaca gagtgaccag caccggcaag     960
cccgagttca ccaacctgaa ggtgtaccac gacatcaagg acattaccgc ccggaaagag    1020
attattgaga cgccgagct gctggatcag attgccaaga tcctgaccat ctaccagagc    1080
agcgaggaca tccaggaaga actgaccaat ctgaactccg agctgaccca ggaagagatc    1140
gagcagatct ctaatctgaa gggctatacc ggcacccaca acctgagcct gaaggccatc    1200
aacctgatcc tggacgagct gtggcacacc aacgacaacc agatcgctat cttcaaccgg    1260
ctgaagctgg tgcccaagaa ggtggacctg tcccagcaga aagagatccc caccaccctg    1320
gtggacgact tcatcctgag ccccgtcgtg aagagaagct tcatccagag catcaaagtg    1380
atcaacgcca tcatcaagaa gtacggcctg cccaacgaca tcattatcga gctggccgc    1440 gagaagaact ccaaggacgc ccagaaaatg atcaacgaga tgcagaagcg gaaccggcag    1500
accaacgagc ggatcgagga aatcatccgg accaccggca agagaacgc caagtacctg    1560 atcgagaaga tcaagctgca cgacatgcag gaaggcaagt gcctgtacag cctggaagcc    1620
atccctctgg aagatctgct gaacaacccc ttcaactatg aggtggacca catcatcccc    1680
agaagcgtgt ccttcgacaa cagcttcaac aacaaggtgc tcgtgaagca ggaagaaaac    1740
agcaagaagg caaccggac cccattccag tacctgagca gcagcgacag caagatcagc    1800
tacgaaacct tcaagaagca catcctgaat ctggccaagg gcaagggcag aatcagcaag    1860
accaagaaag agtatctgct ggaagaacgg gacatcaaca ggttctccgt gcagaaagac    1920
ttcatcaacc ggaacctggt ggataccaga tacgccacca gaggcctgat gaacctgctg    1980
cggagctact tcagagtgaa caacctggac gtgaaagtga gtccatcaa tggcggcttc    2040 accagctttc tgcggcggaa gtggaagttt aagaaagagc ggaacaaggg gtacaagcac    2100
cacgccgagg acgccctgat cattgccaac gccgatttca tcttcaaaga gtggaagaaa    2160
ctggacaagg ccaaaaaagt gatggaaaac cagatgttcg aggaaaagca ggccgagagc    2220

```
atgcccgaga tcgaaaccga gcaggagtac aaagagatct tcatcacccc ccaccagatc      2280
aagcacatta aggacttcaa ggactacaag tacagccacc gggtggacaa gaagcctaat      2340
agagagctga ttaacgacac cctgtactcc acccggaagg acgacaaggg caacaccctg      2400
atcgtgaaca atctgaacgg cctgtacgac aaggacaatg acaagctgaa aaagctgatc      2460
aacaagagcc ccgaaaagct gctgatgtac caccacgacc cccagaccta ccagaaactg      2520
aagctgatta tggaacagta cggcgacgag aagaatcccc tgtacaagta ctacgaggaa      2580
accgggaact acctgaccaa gtactccaaa aaggacaacg gccccgtgat caagaagatt      2640
aagtattacg gcaacaaact gaacgcccat ctggacatca ccgacgacta ccccaacagc      2700
agaaacaagg tcgtgaagct gtccctgaag ccctacagat tcgacgtgta cctggacaat      2760
ggcgtgtaca agttcgtgac cgtgaagaat ctggatgtga tcaaaaaaga aaactactac      2820
gaagtgaata gcaagtgcta tgaggaagct aagaagctga agaagatcag caaccaggcc      2880
gagtttatcg cctccttcta caacaacgat ctgatcaaga tcaacggcga gctgtataga      2940
gtgatcggcg tgaacaacga cctgctgaac cggatcgaag tgaacatgat cgacatcacc      3000
taccgcgagt acctggaaaa catgaacgac aagaggcccc ccaggatcat taagacaatc      3060
gcctccaaga cccagagcat taagaagtac agcacagaca ttctgggcaa cctgtatgaa      3120
gtgaaatcta agaagcaccc tcagatcatc aaaaagggc                             3159
```

```
<210> SEQ ID NO 33
<211> LENGTH: 3159
<212> TYPE: DNA
<213> ORGANISM: Artificial Sequence
<220> FEATURE:
<223> OTHER INFORMATION: Synthetic

<400> SEQUENCE: 33
atgaagcgca actacatcct cggactggac atcggcatta cctccgtggg atacggcatc        60
atcgattacg aaactaggga tgtgatcgac gctggagtca ggctgttcaa agaggcgaac       120
gtggagaaca cgaggggcg gcgctcaaag aggggggccc gccggctgaa gcgccgccgc       180
agacatagaa tccagcgcgt gaagaagctg ctgttcgact acaaccttct gaccgaccac       240
tccgaacttt ccggcatcaa cccatatgag gctagagtga agggattgtc ccaaaagctg       300
tccgaggaag agttctccgc cgcgttgctc cacctcgcca agcgcagggg agtgcacaat       360
gtgaacgaag tggaagaaga taccggaaac gagctgtcca ccaaggagca gatcagccgg       420
aactccaagg ccctggaaga gaaatacgtg gcggaactgc aactggagcg gctgaagaaa       480
gacggagaag tgcgcggctc gatcaaccgc ttcaagacct cggactacgt gaaggaggcc       540
aagcagctcc tgaaagtgca aaaggcctat caccaacttg accagtcctt tatcgatacc       600
tacatcgatc tgctcgagac tcggcggact tactacgagg gtccagggga gggctcccca       660
tttggttgga aggatattaa ggagtggtac gaaatgctga tgggacactg cacatacttc       720
cctgaggagc tgcggagcgt gaaatacgca tacaacgcag acctgtacaa cgcgctgaac       780
gacctgaaca atctcgtgat cacccgggac gagaacgaaa agctgagta ttacgaaaag       840 ttccagatta ttgagaacgt gttcaaacag aagaagaagc gcacactgaa gcagattgcc       900
aaggaaatcc tcgtgaacga agaggacatc aagggctatc gagtgacctc aacgggaaag       960
ccggagttca ccaatctgaa ggtctaccac gacatcaaag acattaccgc ccggaaggag      1020
atcattgaga acgcggagct gttggaccag attgcgaaga ttctgaccat ctaccaatcc      1080
```

-continued

```
tccgaggata ttcaggaaga actcaccaac ctcaacagcg aactgaccca ggaggagata   1140
gagcaaatct ccaacctgaa gggctacacc ggaactcata acctgagcct gaaggccatc   1200
aacttgatcc tggacgagct gtggcacacc aacgataacc agatcgctat tttcaatcgg   1260
ctgaagctgg tccccaagaa agtggacctc tcacaacaaa aggagatccc tactacccct   1320
gtggacgatt tcattctgtc ccccgtggtc aagagaagct tcatacagtc aatcaaagtg   1380
atcaatgcca ttatcaagaa atacggtctg cccaacgaca ttatcattga gctcgcccgc   1440
gagaagaact cgaaggacgc ccagaagatg attaacgaaa tgcagaagag gaaccgacag   1500
actaacgaac ggatcgaaga aatcatccgg accaccggga aggaaaacgc gaagtacctg   1560
atcgaaaaga tcaagctcca tgacatgcag gaaggaaagt gtctgtactc gctggaggcc   1620
attccgctgg aggacttgct gaacaaccct tttaactacg aagtggatca tatcattccg   1680
aggagcgtgt cattcgacaa ttccttcaac aacaaggtcc tcgtgaagca ggaggaaaac   1740
tcgaagaagg gaaaccgcac gccgttccag tacctgagca gcagcgactc caagatttcc   1800
tacgaaacct tcaagaagca catcctcaac ctggcaaagg ggaagggtcg catctccaag   1860
accaagaagg aatatctgct ggaagaaaga gacatcaaca gattctccgt gcaaaaggac   1920
ttcatcaacc gcaacctcgt ggatactaga tacgctactc ggggtctgat gaacctcctg   1980
agaagctact ttagagtgaa caatctggac gtgaaggtca agtcgattaa cggaggtttc   2040
acctccttcc tgcggcgcaa gtggaagttc aagaaggaac ggaacaaggg ctacaagcac   2100
cacgccgagg acgccctgat cattgccaac gccgacttca tcttcaaaga atggaagaaa   2160
cttgacaagg ctaagaaggt catggaaaac cagatgttcg aagaaaagca ggccgagtct   2220
atgcctgaaa tcgagactga acaggagtac aaggaaatct ttattacgcc acaccagatc   2280
aaacacatca aggatttcaa ggattacaag tactcacatc gcgtggacaa aaagccgaac   2340
agggaactga tcaacgacac cctctactcc acccggaagg atgacaaagg gaataccctc   2400
atcgtcaaca accttaacgg cctgtacgac aaggacaacg ataagctgaa gaagctcatt   2460
aacaagtcgc ccgaaaagtt gctgatgtac caccacgacc ctcagactta ccagaagctc   2520
aagctgatca tggagcagta tgggggacgag aaaaacccgt tgtacaagta ctacgaagaa   2580
actgggaatt atctgactaa gtactccaag aaagataacg gccccgtgat taagaagatt   2640
aagtactacg gcaacaagct gaacgcccat ctggacatca ccgatgacta ccctaattcc   2700
cgcaacaagg tcgtcaagct gagcctcaag ccctaccggt ttgatgtgta ccttgacaat   2760
ggagtgtaca agttcgtgac tgtgaagaac cttgacgtga tcaagaagga gaactactac   2820
gaagtcaact ccaagtgcta cgaggaagca aagaagttga agaagatctc gaaccaggcc   2880
gagttcattg cctccttcta taacaacgac ctgattaaga tcaacggcga actgtaccgc   2940
gtcattggcg tgaacaacga tctcctgaac cgcatcgaag tgaacatgat cgacatcact   3000
taccgggaat acctggagaa tatgaacgac aagcgcccgc cccggatcat taagactatc   3060
gcctcaaaga cccagtcgat caagaagtac agcaccgaca tcctgggcaa cctgtacgag   3120
gtcaaatcga gaagcaccc ccagatcatc aagaaggga                          3159
```

```
<210> SEQ ID NO 34
<211> LENGTH: 3255
<212> TYPE: DNA
<213> ORGANISM: Artificial Sequence
<220> FEATURE:
<223> OTHER INFORMATION: Synthetic

<400> SEQUENCE: 34
```

-continued

```
atggccccaa agaagaagcg gaaggtcggt atccacggag tcccagcagc caagcggaac      60
tacatcctgg gcctggacat cggcatcacc agcgtgggct acggcatcat cgactacgag     120
acacgggacg tgatcgatgc cggcgtgcgg ctgttcaaag aggccaacgt ggaaaacaac     180
gagggcaggc ggagcaagag aggcgccaga aggctgaagc ggcggaggcg gcatagaatc     240
cagagagtga agaagctgct gttcgactac aacctgctga ccgaccacag cgagctgagc     300
ggcatcaacc cctacgaggc cagagtgaag ggcctgagcc agaagctgag cgaggaagag     360
ttctctgccg ccctgctgca cctggccaag agaagaggcg tgcacaacgt gaacgaggtg     420
gaagaggaca ccggcaacga gctgtccacc agagagcaga tcagccggaa cagcaaggcc     480
ctggaagaga aatacgtggc cgaactgcag ctggaacggc tgaagaaaga cggcgaagtg     540
cggggcagca tcaacagatt caagaccagc gactacgtga agaagccaa acagctgctg     600 aaggtgcaga aggcctacca ccagctggac cagagcttca tcgacaccta catcgacctg     660
ctggaaaccc ggcggaccta ctatgaggga cctggcgagg gcagcccctt cggctggaag     720
gacatcaaag aatggtacga gatgctgatg ggccactgca cctacttccc cgaggaactg     780
cggagcgtga agtacgccta caacgccgac ctgtacaacg ccctgaacga cctgaacaat     840
ctcgtgatca ccagggacga gaacgagaag ctggaatatt acgagaagtt ccagatcatc     900
gagaacgtgt tcaagcagaa gaagaagccc accctgaagc agatcgccaa agaaatcctc     960
gtgaacgaag aggatattaa gggctacaga gtgaccagca ccggcaagcc cgagttcacc    1020
aacctgaagg tgtaccacga catcaaggac attaccgccc ggaaagagat tattgagaac    1080
gccgagctgc tggatcagat tgccaagatc ctgaccatct accagagcag cgaggacatc    1140
caggaagaac tgaccaatct gaactccgag ctgacccagg aagagatcga gcagatctct    1200
aatctgaagg gctataccgg cacccacaac ctgagcctga aggccatcaa cctgatcctg    1260
gacgagctgt ggcacaccaa cgacaaccag atcgctatct tcaaccggct gaagctggtg    1320
cccaagaagg tggacctgtc ccagcagaaa gagatcccca ccaccctggt ggacgacttc    1380
atcctgagcc ccgtcgtgaa gagaagcttc atccagagca tcaaagtgat caacgccatc    1440
atcaagaagt acggcctgcc caacgacatc attatcgagc tggcccgcga gaagaactcc    1500
aaggacgccc agaaaatgat caacgagatg cagaagcgga accggcagac caacgagcgg    1560
atcgaggaaa tcatccggac caccggcaaa gagaacgcca agtacctgat cgagaagatc    1620
aagctgcacg acatgcagga aggcaagtgc ctgtacagcc tggaagccat ccctctggaa    1680
gatctgctga acaaccccctt caactatgag gtggaccaca tcatccccag aagcgtgtcc    1740
ttcgacaaca gcttcaacaa caaggtgctc gtgaagcagg aagaaacag caagaagggc    1800 aaccggaccc cattccagta cctgagcagc agcgacagca gatcagcta cgaaaccttc    1860 aagaagcaca tcctgaatct ggccaagggc aagggcagaa tcagcaagac caagaaagag    1920
tatctgctgg aagaacggga catcaacagg ttctccgtgc agaaagactt catcaaccgg    1980
aacctggtgg ataccagata cgccaccaga ggcctgatga acctgctgcg gagctacttc    2040
agagtgaaca acctggacgt gaaagtgaag tccatcaatg gcggcttcac cagctttctg    2100
cggcggaagt ggaagtttaa aaagagcggc aacaagggt acaagcacca cgccgaggac    2160
gccctgatca ttgccaacgc cgatttcatc ttcaaagagt ggaagaaact ggacaaggcc    2220
aaaaaagtga tggaaaacca gatgttcgag gaaaggcagg ccgagagcat gcccgagatc    2280
gaaaccgagc aggagtacaa agagatcttc atcacccccc accagatcaa gcacattaag    2340
```

-continued

```
gacttcaagg actacaagta cagccaccgg gtggacaaga agcctaatag agagctgatt      2400
aacgacaccc tgtactccac ccggaaggac gacaagggca acaccctgat cgtgaacaat      2460
ctgaacggcc tgtacgacaa ggacaatgac aagctgaaaa agctgatcaa caagagcccc      2520
gaaaagctgc tgatgtacca ccacgacccc cagacctacc agaaactgaa gctgattatg      2580
gaacagtacg gcgacgagaa gaatcccctg tacaagtact acgaggaaac cgggaactac      2640
ctgaccaagt actccaaaaa ggacaacggc cccgtgatca agaagattaa gtattacggc      2700
aacaaactga cgcccatct ggacatcacc gacgactacc ccaacagcag aaacaaggtc       2760
gtgaagctgt ccctgaagcc ctacagattc gacgtgtacc tggacaatgg cgtgtacaag      2820
ttcgtgaccg tgaagaatct ggatgtgatc aaaaaagaaa actactacga agtgaatagc      2880
aagtgctatg aggaagctaa gaagctgaag aagatcagca accaggccga gtttatcgcc      2940
tccttctaca caacgatct gatcaagatc aacggcgagc tgtatagagt gatcggcgtg       3000
aacaacgacc tgctgaaccg gatcgaagtg aacatgatcg acatcaccta ccgcgagtac      3060
ctggaaaaca tgaacgacaa gaggcccccc aggatcatta agacaatcgc ctccaagacc      3120
cagagcatta agaagtacag cacagacatt ctgggcaacc tgtatgaagt gaaatctaag      3180
aagcaccctc agatcatcaa aaagggcaaa aggccggcgg ccacgaaaaa ggccggccag      3240
gcaaaaaaga aaaag                                                        3255
```

<210> SEQ ID NO 35
<211> LENGTH: 3242
<212> TYPE: DNA
<213> ORGANISM: Artificial Sequence
<220> FEATURE:
<223> OTHER INFORMATION: Synthetic

<400> SEQUENCE: 35

```
accggtgcca ccatgtaccc atacgatgtt ccagattacg cttcgccgaa gaaaaagcgc        60
aaggtcgaag cgtccatgaa aaggaactac attctggggc tggacatcgg gattacaagc       120
gtggggtatg ggattattga ctatgaaaca agggacgtga tcgacgcagg cgtcagactg       180
ttcaaggagg ccaacgtgga aaacaatgag ggacggagaa gcaagagggg agccaggcgc       240
ctgaaacgac ggagaaggca cagaatccag agggtgaaga aactgctgtt cgattacaac       300
ctgctgaccg accattctga gctgagtgga attaatcctt atgaagccag ggtgaaaggc       360
ctgagtcaga agctgtcaga ggaagagttt tccgcagctc tgctgcacct ggctaagcgc       420
cgaggagtgc ataacgtcaa tgaggtggaa gaggacaccg gcaacgagct gtctacaaag       480
gaacagatct cacgcaatag caaagctctg gaagagaagt atgtcgcaga gctgcagctg       540
gaacggctga agaagatgg cgaggtgaga gggtcaatta ataggttcaa gacaagcgac       600
tacgtcaaag aagccaagca gctgctgaaa gtgcagaagg cttaccacca gctggatcag       660
agcttcatcg atacttatat cgacctgctg gagactcgga gaacctacta tgagggacca      720
ggagaaggga gcccccttcgg atggaaagac atcaaggaat ggtacgagat gctgatggga     780
cattgcacct attttccaga gagctgaga agcgtcaagt acgcttataa cgcagatctt        840
acaacgccct gaatgacctg aacaacctgg tcatcaccag ggatgaaaac gagaaactgg      900
aatactatga gaagttccag atcatcgaaa acgtgtttaa gcagaagaaa aagcctacac      960
tgaaacagat tgctaaggag atcctggtca cgaagagga catcaagggc taccgggtga      1020
caagcactgg aaaaccagag ttcaccaatc tgaaagtgta tcacgatatt aaggacatca     1080
cagcacggaa agaaatcatt gagaacgccg aactgctgga tcagattgct aagatcctga     1140
```

```
ctatctacca gagctccgag gacatccagg aagagctgac taacctgaac agcgagctga        1200
cccaggaaga gatcgaacag attagtaatc tgaaggggta caccggaaca cacaacctgt        1260
ccctgaaagc tatcaatctg attctggatg agctgtggca tacaaacgac aatcagattg        1320
caatctttaa ccggctgaag ctggtcccaa aaaaggtgga cctgagtcag cagaaagaga        1380
tcccaaccac actggtggac gatttcattc tgtcacccgt ggtcaagcgg agcttcatcc        1440
agagcatcaa agtgatcaac gccatcatca agaagtacgg cctgcccaat gatatcatta        1500
tcgagctggc tagggagaag aacagcaagg acgcacagaa gatgatcaat gagatgcaga        1560
aacgaaaccg gcagaccaat gaacgcattg aagagattat ccgaactacc gggaaagaga        1620
acgcaaagta cctgattgaa aaaatcaagc tgcacgatat gcaggaggga aagtgtctgt        1680
attctctgga ggccatcccc ctggaggacc tgctgaacaa tccattcaac tacgaggtcg        1740
atcatattat ccccagaagc gtgtccttcg acaattcctt taacaacaag gtgctggtca        1800
agcaggaaga gaactctaaa aagggcaata ggactccttt ccagtacctg tctagttcag        1860
attccaagat ctcttacgaa acctttaaaa agcacattct gaatctggcc aaaggaaagg        1920
gccgcatcag caagaccaaa aaggagtacc tgctggaaga gcgggacatc aacagattct        1980
ccgtccagaa ggatttttatt aaccggaatc tggtggacac aagatacgct actcgcggcc       2040
tgatgaatct gctgcgatcc tatttccggg tgaacaatct ggatgtgaaa gtcaagtcca        2100
tcaacggcgg gttcacatct tttctgaggc gcaaatggaa gtttaaaaag gagcgcaaca        2160
aagggtacaa gcaccatgcc gaagatgctc tgattatcgc aaatgccgac ttcatcttta        2220
aggagtggaa aaagctggac aaagccaaga agtgatgga gaaccagatg ttcgaagaga         2280
agcaggccga atctatgccc gaaatcgaga cagaacagga gtacaaggag attttcatca        2340
ctcctcacca gatcaagcat atcaaggatt tcaaggacta caagtactct caccgggtgg        2400
ataaaaagcc caacagagag ctgatcaatg acaccctgta tagtacaaga aaagacgata        2460
aggggaatac cctgattgtg aacaatctga acggactgta cgacaaagat aatgacaagc        2520
tgaaaaagct gatcaacaaa agtcccgaga agctgctgat gtaccaccat gatcctcaga        2580
catatcagaa actgaagctg attatggagc agtacggcga cgagaagaac ccactgtata        2640
agtactatga agagactggg aactacctga ccaagtatag caaaaaggat aatggccccg        2700
tgatcaagaa gatcaagtac tatgggaaca agctgaatgc ccatctggac atcacagacg        2760
attaccctaa cagtcgcaac aaggtggtca agctgtcact gaagccatac agattcgatg        2820
tctatctgga caacggcgtg tataaatttg tgactgtcaa gaatctggat gtcatcaaaa        2880
aggagaacta ctatgaagtg aatagcaagt gctacgaaga ggctaaaaag ctgaaaaaga        2940
ttagcaacca ggcagagttc atcgcctcct tttacaacaa cgacctgatt aagatcaatg        3000
gcgaactgta tagggtcatc ggggtgaaca atgatctgct gaaccgcatt gaagtgaata        3060
tgattgacat cacttaccga gagtatctgg aaaacatgaa tgataagcgc cccctcgaa         3120 ttatcaaaac aattgcctct aagactcaga gtatcaaaaa gtactcaacc gacattctgg        3180
gaaacctgta tgaggtgaag agcaaaaagc accctcagat tatcaaaaag ggctaagaat        3240
tc                                                                       3242
```

<210> SEQ ID NO 36
<211> LENGTH: 3255
<212> TYPE: DNA
<213> ORGANISM: Artificial Sequence
<220> FEATURE:

-continued

<223> OTHER INFORMATION: Synthetic

<400> SEQUENCE: 36

```
atggccccaa agaagaagcg gaaggtcggt atccacggag tcccagcagc caagcggaac      60
tacatcctgg gcctggacat cggcatcacc agcgtgggct acggcatcat cgactacgag     120
acacgggacg tgatcgatgc cggcgtgcgg ctgttcaaag aggccaacgt ggaaaacaac     180
gagggcaggc ggagcaagag aggcgccaga aggctgaagc ggcggaggcg gcatagaatc     240
cagagagtga agaagctgct gttcgactac aacctgctga ccgaccacag cgagctgagc     300
ggcatcaacc cctacgaggc cagagtgaag ggcctgagcc agaagctgag cgaggaagag     360
ttctctgccg ccctgctgca cctggccaag agaagaggcg tgcacaacgt gaacgaggtg     420
gaagaggaca ccggcaacga gctgtccacc aaagagcaga tcagccggaa cagcaaggcc     480
ctggaagaga aatacgtggc cgaactgcag ctggaacggc tgaagaaaga cggcgaagtg     540
cggggcagca tcaacagatt caagaccagc gactacgtga agaagccaa acagctgctg     600 aaggtgcaga aggcctacca ccagctggac cagagcttca tcgacaccta catcgacctg     660
ctggaaaccc ggcggaccta ctatgaggga cctggcgagg gcagcccctt cggctggaag     720
gacatcaaag aatggtacga gatgctgatg ggccactgca cctacttccc cgaggaactg     780
cggagcgtga gtacgcctca aacgccgac ctgtacaacg ccctgaacga cctgaacaat     840
ctcgtgatca ccagggacga gaacgagaag ctggaatatt acgagaagtt ccagatcatc     900
gagaacgtgt tcaagcagaa gaagaagccc accctgaagc agatcgccaa agaaatcctc     960
gtgaacgaag aggatattaa gggctacaga gtgaccagca ccggcaagcc cgagttcacc    1020
aacctgaagg tgtaccacga catcaaggac attaccgccc ggaaagagat tattgagaac    1080
gccgagctgc tggatcagat tgccaagatc ctgaccatct accagagcag cgaggacatc    1140
caggaagaac tgaccaatct gaactccgag ctgacccagg aagagatcga gcagatctct    1200
aatctgaagg gctataccgg cacccacaac ctgagcctga aggccatcaa cctgatcctg    1260
gacgagctgt ggcacaccaa cgacaaccag atcgctatct tcaaccggct gaagctggtg    1320
cccaagaagg tggacctgtc ccagcagaaa gagatcccca ccaccctggt ggacgacttc    1380
atcctgagcc ccgtcgtgaa gagaagcttc atccagagca tcaaagtgat caacgccatc    1440
atcaagaagt acggcctgcc caacgacatc attatcgagc tggcccgcga gaagaactcc    1500
aaggacgccc agaaaatgat caacgagatg cagaagcgga accggcagac caacgagcgg    1560
atcgaggaaa tcatccggac caccggcaaa gagaacgcca gtacctgat cgagaagatc    1620 aagctgcacg acatgcagga aggcaagtgc ctgtacagcc tggaagccat ccctctggaa    1680
gatctgctga caaccccctt caactatgag gtggaccaca tcatccccag aagcgtgtcc    1740
ttcgacaaca gcttcaacaa caaggtgctc gtgaagcagg aagaaaacag caagaagggc    1800
aaccggaccc cattccagta cctgagcagc agcgacagca gatcagcta cgaaaccttc    1860 aagaagcaca tcctgaatct ggccaaggc aagggcagaa tcagcaagac caagaaagag    1920
tatctgctgg aagaacggga catcaacagg ttctccgtgc agaaagactt catcaaccgg    1980
aacctggtgg ataccagata cgccaccaga ggcctgatga acctgctgcg gagctacttc    2040
agagtgaaca acctggacgt gaaagtgaag tccatcaatg gcggcttcac cagctttctg    2100
cggcggaagt ggaagtttaa gaaagagcgg aacaagggt acaagcacca cgccgaggac    2160
gccctgatca ttgccaacgc cgatttcatc ttcaaagagt ggaagaaact ggacaaggcc    2220
aaaaaagtga tggaaaacca gatgttcgag gaaaagcagg ccgagagcat gcccgagatc    2280
```

```
gaaaccgagc aggagtacaa agagatcttc atcacccccc accagatcaa gcacattaag      2340
gacttcaagg actacaagta cagccaccgg gtggacaaga agcctaatag agagctgatt      2400
aacgacaccc tgtactccac ccggaaggac gacaagggca caccctgat cgtgaacaat       2460 ctgaacggcc tgtacgacaa ggacaatgac aagctgaaaa agctgatcaa caagagcccc      2520
gaaaagctgc tgatgtacca ccacgacccc cagacctacc agaaactgaa gctgattatg      2580
gaacagtacg gcgacgagaa gaatcccctg tacaagtact acgaggaaac cgggaactac      2640
ctgaccaagt actccaaaaa ggacaacggc cccgtgatca agaagattaa gtattacggc      2700
aacaaactga cgcccatct ggacatcacc gacgactacc ccaacagcag aaacaaggtc       2760
gtgaagctgt ccctgaagcc ctacagattc gacgtgtacc tggacaatgg cgtgtacaag      2820
ttcgtgaccg tgaagaatct ggatgtgatc aaaaaagaaa actactacga agtgaatagc      2880
aagtgctatg aggaagctaa gaagctgaag aagatcagca accaggccga gtttatcgcc      2940
tccttctaca acaacgatct gatcaagatc aacggcgagc tgtatagagt gatcggcgtg      3000
aacaacgacc tgctgaaccg gatcgaagtg aacatgatcg acatcaccta ccgcgagtac      3060
ctggaaaaca tgaacgacaa gaggcccccc aggatcatta agacaatcgc ctccaagacc      3120
cagagcatta agaagtacag cacagacatt ctgggcaacc tgtatgaagt gaaatctaag      3180
aagcaccctc agatcatcaa aaagggcaaa aggccggcgg ccacgaaaaa ggccggccag      3240
gcaaaaaaga aaaag                                                       3255

<210> SEQ ID NO 37
<211> LENGTH: 3156
<212> TYPE: DNA
<213> ORGANISM: Staphylococcus aureus

<400> SEQUENCE: 37
aagcggaact acatcctggg cctggacatc ggcatcacca gcgtgggcta cggcatcatc        60
gactacgaga cacgggacgt gatcgatgcc ggcgtgcggc tgttcaaaga ggccaacgtg       120
gaaaacaacg agggcaggcg gagcaagaga ggcgccagaa ggctgaagcg gcggaggcgg       180
catagaatcc agagagtgaa gaagctgctg ttcgactaca acctgctgac cgaccacagc       240
gagctgagcg gcatcaaccc ctacgaggcc agagtgaagg gcctgagcca gaagctgagc       300
gaggaagagt tctctgccgc cctgctgcac ctggccaaga agagaggcgt gcacaacgtg       360
aacgaggtgg aagaggacac cggcaacgag ctgtccacca agagcagat cagccggaac        420 agcaaggccc tggaagagaa atacgtggcc gaactgcagc tggaacggct gaagaaagac       480
ggcgaagtgc ggggcagcat caacagattc aagaccagcg actacgtgaa agaagccaaa       540
cagctgctga aggtgcagaa ggcctaccac cagctggacc agagcttcat cgacacctac       600
atcgacctgc tggaaacccg gcggacctac tatgagggac ctggcgaggg cagccccttc       660
ggctggaagg acatcaaaga atggtacgag atgctgatgg gccactgcac ctacttcccc       720
gaggaactgc ggagcgtgaa gtacgcctac aacgccgacc tgtacaacgc cctgaacgac       780
ctgaacaatc tcgtgatcac cagggacgag aacgagaagc tggaatatta cgagaagttc       840
cagatcatcg agaacgtgtt caagcagaag aagaagccca ccctgaagca gatcgccaaa       900
gaaatcctcg tgaacgaaga ggatattaag ggctacagag tgaccagcac cggcaagccc       960
gagttcacca acctgaaggt gtaccacgac atcaaggaca ttaccgcccg gaaagagatt      1020
attgagaacg ccgagctgct ggatcagatt gccaagatcc tgaccatcta ccagagcagc      1080
```

-continued

```
gaggacatcc aggaagaact gaccaatctg aactccgagc tgacccagga agagatcgag    1140
cagatctcta atctgaaggg ctataccggc acccacaacc tgagcctgaa ggccatcaac    1200
ctgatcctgg acgagctgtg gcacaccaac gacaaccaga tcgctatctt caaccggctg    1260
aagctggtgc ccaagaaggt ggacctgtcc cagcagaaag agatccccac caccctggtg    1320
gacgacttca tcctgagccc cgtcgtgaag agaagcttca tccagagcat caaagtgatc    1380
aacgccatca tcaagaagta cggcctgccc aacgacatca ttatcgagct ggcccgcgag    1440
aagaactcca aggacgccca gaaaatgatc aacgagatgc agaagcggaa ccggcagacc    1500
aacgagcgga tcgaggaaat catccggacc accggcaaag agaacgccaa gtacctgatc    1560
gagaagatca agctgcacga catgcaggaa ggcaagtgcc tgtacagcct ggaagccatc    1620
cctctggaag atctgctgaa caacccttc aactatgagg tggaccacat catccccaga    1680
agcgtgtcct cgacaacag cttcaacaac aaggtgctcg tgaagcagga agaaaacagc    1740
aagaagggca accggacccc attccagtac ctgagcagca gcgacagcaa gatcagctac    1800
gaaaccttca gaagcacat cctgaatctg gccaagggca agggcagaat cagcaagacc    1860
aagaaagagt atctgctgga agaacgggac atcaacaggt tctccgtgca gaaagacttc    1920
atcaaccgga acctggtgga taccagatac gccaccagag gcctgatgaa cctgctgcgg    1980
agctacttca gagtgaacaa cctggacgtg aaagtgaagt ccatcaatgg cggcttcacc    2040
agctttctgc ggcggaagtg gaagtttaag aaagagcgga acaaggggta caagcaccac    2100
gccgaggacg ccctgatcat tgccaacgcc gatttcatct tcaaagagtg gaagaaactg    2160
gacaaggcca aaaaagtgat ggaaaaccag atgttcgagg aaaagcaggc cgagagcatg    2220
cccgagatcg aaaccgagca ggagtacaaa gagatcttca tcacccccca ccagatcaag    2280
cacattaagg acttcaagga ctacaagtac agccaccggg tggacaagaa gcctaataga    2340
gagctgatta cgacaccct gtactccacc cggaaggacg acaagggcaa caccctgatc    2400
gtgaacaatc tgaacggcct gtacgacaag gacaatgaca agctgaaaaa gctgatcaac    2460
aagagccccg aaaagctgct gatgtaccac cacgacccc agacctacca gaaactgaag    2520
ctgattatgg aacagtacgg cgacgagaag aatcccctgt acaagtacta cgaggaaacc    2580
gggaactacc tgaccaagta ctccaaaaag gacaacggcc ccgtgatcaa gaagattaag    2640
tattacggca caaactgaa cgcccatctg gacatcaccg acgactaccc caacagcaga    2700
aacaaggtcg tgaagctgtc cctgaagccc tacagattcg acgtgtacct ggacaatggc    2760
gtgtacaagt tcgtgaccgt gaagaatctg gatgtgatca aaaaagaaaa ctactacgaa    2820
gtgaatagca agtgctatga ggaagctaag aagctgaaga agatcagcaa ccaggccgag    2880
tttatcgcct ccttctacaa caacgatctg atcaagatca acggcgagct gtatagagtg    2940
atcggcgtga caacgacct gctgaaccgg atcgaagtga acatgatcga catcacctac    3000
cgcgagtacc tggaaaacat gaacgacaag aggccccccca ggatcattaa gacaatcgcc    3060
tccaagaccc agagcattaa gaagtacagc acagacattc tgggcaacct gtatgaagtg    3120
aaatctaaga agcaccctca gatcatcaaa aagggc                              3156
```

<210> SEQ ID NO 38
<211> LENGTH: 7009
<212> TYPE: DNA
<213> ORGANISM: Artificial Sequence
<220> FEATURE:
<223> OTHER INFORMATION: Synthetic

<400> SEQUENCE: 38

```
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tgggtacctt     660
taattctagt actatgcatg cgttgacatt gattattgac tagttattaa tagtaatcaa     720
ttacggggtc attagttcat agcccatata tggagttccg cgttacataa cttacggtaa     780
atggcccgcc tggctgaccg cccaacgacc cccgcccatt gacgtcaata atgacgtatg     840
ttcccatagt aacgccaata gggactttcc attgacgtca atgggtggag tatttacggt     900
aaactgccca cttggcagta catcaagtgt atcatatgcc aagtacgccc cctattgacg     960
tcaatgacgg taaatggccc gcctggcatt atgcccagta catgacctta tgggactttc    1020
ctacttggca gtacatctac gtattagtca tcgctattac catggtgatg cggttttggc    1080
agtacatcaa tgggcgtgga tagcggtttg actcacgggg atttccaagt ctccacccca    1140
ttgacgtcaa tgggagtttg ttttggcacc aaaatcaacg ggactttcca aaatgtcgta    1200
acaactccgc cccattgacg caaatgggcg gtaggcgtgt acggtgggag gtctatataa    1260
gcagagctct ctggctaact accggtgcca ccatgaaaag gaactacatt ctggggctgg    1320
acatcgggat tacaagcgtg gggtatggga ttattgacta tgaaacaagg gacgtgatcg    1380
acgcaggcgt cagactgttc aaggaggcca acgtggaaaa caatgaggga cggagaagca    1440 agagggggagc caggcgcctg aaacgacgga gaaggcacag aatccagagg gtgaagaaac    1500
tgctgttcga ttacaacctg ctgaccgacc attctgagct gagtggaatt aatccttatg    1560
aagccagggt gaaaggcctg agtcagaagc tgtcagagga agagtttttcc gcagctctgc    1620 tgcacctggc taagcgccga ggagtgcata cgtcaatga ggtggaagag gacaccggca    1680
acgagctgtc tacaaaggaa cagatctcac gcaatagcaa agctctggaa gagaagtatg    1740
tcgcagagct gcagctggaa cggctgaaga agatggcga ggtgagaggg tcaattaata    1800
ggttcaagac aagcgactac gtcaaagaag ccaagcagct gctgaaagtg cagaaggctt    1860
accaccagct ggatcagagc ttcatcgata cttatatcga cctgctggag actcggagaa    1920
cctactatga gggaccagga gaagggagcc ccttcggatg gaaagacatc aaggaatggt    1980
acgagatgct gatgggacat tgcacctatt ttccagaaga gctgagaagc gtcaagtacg    2040
cttataacgc agatctgtac aacgccctga atgacctgaa caacctggtc atcaccaggg    2100
atgaaaacga gaaactggaa tactatgaga gttccagat catcgaaaac gtgtttaagc    2160
agaagaaaaa gcctacactg aaacagattg ctaaggagat cctggtcaac gaagaggaca    2220
tcaagggcta ccgggtgaca agcactggaa aaccagagtt caccaatctg aaagtgtatc    2280
acgatattaa ggacatcaca gcacggaaag aaatcattga gaacgccgaa ctgctggatc    2340
```

-continued

```
agattgctaa gatcctgact atctaccaga gctccgagga catccaggaa gagctgacta    2400
acctgaacag cgagctgacc caggaagaga tcgaacagat tagtaatctg aaggggtaca    2460
ccggaacaca caacctgtcc ctgaaagcta tcaatctgat tctggatgag ctgtggcata    2520
caaacgacaa tcagattgca atctttaacc ggctgaagct ggtcccaaaa aaggtggacc    2580
tgagtcagca gaaagagatc ccaaccacac tggtggacga tttcattctg tcacccgtgg    2640
tcaagcggag cttcatccag agcatcaaag tgatcaacgc catcatcaag aagtacggcc    2700
tgcccaatga tatcattatc gagctggcta gggagaagaa cagcaaggac gcacagaaga    2760
tgatcaatga gatgcagaaa cgaaccggc agaccaatga acgcattgaa gagattatcc    2820
gaactaccgg gaaagagaac gcaaagtacc tgattgaaaa aatcaagctg cacgatatgc    2880
aggagggaaa gtgtctgtat tctctggagg ccatccccct ggaggacctg ctgaacaatc    2940
cattcaacta cgaggtcgat catattatcc ccagaagcgt gtccttcgac aattcctta    3000 acaacaaggt gctggtcaag caggaagaga actctaaaaa gggcaatagg actcctttcc    3060
agtacctgtc tagttcagat tccaagatct cttacgaaac ctttaaaaag cacattctga    3120
atctggccaa aggaaagggc cgcatcagca gaccaaaaa ggagtacctg ctggaagagc    3180
gggacatcaa cagattctcc gtccagaagg attttattaa ccggaatctg gtggacacaa    3240
gatacgctac tcgcggcctg atgaatctgc tgcgatccta tttccgggtg aacaatctgg    3300
atgtgaaagt caagtccatc aacggcgggt tcacatcttt tctgaggcgc aaatggaagt    3360
ttaaaaagga gcgcaacaaa gggtacaagc accatgccga agatgctctg attatcgcaa    3420
atgccgactt catctttaag gagtggaaaa agctggacaa agccaagaaa gtgatggaga    3480
accagatgtt cgaagagaag caggccgaat ctatgcccga aatcgagaca gaacaggagt    3540
acaaggagat tttcatcact cctcaccaga tcaagcatat caaggatttc aaggactaca    3600
agtactctca ccgggtggat aaaaagccca acagagagct gatcaatgac accctgtata    3660
gtacaagaaa agacgataag gggaataccc tgattgtgaa caatctgaac ggactgtacg    3720
acaaagataa tgacaagctg aaaaagctga tcaacaaaag tcccgagaag ctgctgatgt    3780
accaccatga tcctcagaca tatcagaaac tgaagctgat tatggagcag tacggcgacg    3840
agaagaaccc actgtataag tactatgaag agactgggaa ctacctgacc aagtatagca    3900
aaaaggataa tggcccccgtg atcaagaaga tcaagtacta tgggaacaag ctgaatgccc    3960
atctggacat cacagacgat taccctaaca gtcgcaacaa ggtggtcaag ctgtcactga    4020
agccatacag attcgatgtc tatctggaca acggcgtgta taaatttgtg actgtcaaga    4080
atctggatgt catcaaaaag gagaactact atgaagtgaa tagcaagtgc tacgaagagg    4140
ctaaaaagct gaaaaagatt agcaaccagg cagagttcat cgcctccttt tacaacaacg    4200
acctgattaa gatcaatggc gaactgtata gggtcatcgg ggtgaacaat gatctgctga    4260
accgcattga agtgaatatg attgacatca cttaccgaga gtatctggaa aacatgaatg    4320
ataagcgccc ccctcgaatt atcaaaacaa ttgcctctaa gactcagagt atcaaaaagt    4380
actcaaccga cattctggga aacctgtatg aggtgaagag caaaaagcac cctcagatta    4440
tcaaaaaggg gcagcggagc aagcgtcctg ctgctactaa gaaagctggt caagctaaga    4500 aaagaaagg atcctaccca tacgatgttc cagattacgc ttaagaattc ctagagctcg    4560
ctgatcagcc tcgactgtgc cttctagttg ccagccatct gttgtttgcc cctcccccgt    4620
gccttccttg accctggaag gtgccactcc cactgtcctt tcctaataaa atgaggaaat    4680
tgcatcgcat tgtctgagta ggtgtcattc tattctgggg ggtgggggtgg ggcaggacag    4740
```

-continued

```
caaggggggag gattgggaag agaatagcag gcatgctggg gaggtagcgg ccgcccgcgg      4800
tggagctcca gcttttgttc cctttagtga gggttaattg cgcgcttggc gtaatcatgg      4860
tcatagctgt ttcctgtgtg aaattgttat ccgctcacaa ttccacacaa catacgagcc      4920
ggaagcataa agtgtaaagc ctggggtgcc taatgagtga gctaactcac attaattgcg      4980
ttgcgctcac tgcccgcttt ccagtcggga aacctgtcgt gccagctgca ttaatgaatc      5040
ggccaacgcg cggggagagg cggtttgcgt attgggcgct cttccgcttc ctcgctcact      5100
gactcgctgc gctcggtcgt tcggctgcgg cgagcggtat cagctcactc aaaggcggta      5160
atacggttat ccacagaatc aggggataac gcaggaaaga acatgtgagc aaaaggccag      5220
caaaaggcca ggaaccgtaa aaaggccgcg ttgctggcgt ttttccatag gctccgcccc      5280
cctgacgagc atcacaaaaa tcgacgctca agtcagaggt ggcgaaaccc gacaggacta      5340
taaagatacc aggcgtttcc ccctggaagc tccctcgtgc gctctcctgt tccgaccctg      5400
ccgcttaccg gatacctgtc cgcctttctc ccttcgggaa gcgtggcgct ttctcatagc      5460
tcacgctgta ggtatctcag ttcggtgtag tcgttcgct ccaagctggg ctgtgtgcac      5520
gaaccccccg ttcagcccga ccgctgcgcc ttatccggta actatcgtct tgagtccaac      5580
ccggtaagac acgacttatc gccactggca gcagccactg gtaacaggat tagcagagcg      5640
aggtatgtag gcggtgctac agagttcttg aagtggtggc ctaactacgg ctacactaga      5700
aggacagtat ttggtatctg cgctctgctg aagccagtta ccttcggaaa aagagttggt      5760
agctcttgat ccggcaaaca aaccaccgct ggtagcggtg gttttttgt ttgcaagcag      5820 cagattacgc gcagaaaaaa aggatctcaa gaagatcctt tgatctttc tacggggtct      5880 gacgctcagt ggaacgaaaa ctcacgttaa gggattttgg tcatgagatt atcaaaaagg      5940
atcttcacct agatcctttt aaattaaaaa tgaagtttta aatcaatcta agtatatat       6000 gagtaaactt ggtctgacag ttaccaatgc ttaatcagtg aggcacctat ctcagcgatc      6060
tgtctatttc gttcatccat agttgcctga ctccccgtcg tgtagataac tacgatacgg      6120
gagggcttac catctggccc cagtgctgca atgataccgc gagacccacg ctcaccggct      6180
ccagatttat cagcaataaa ccagccagcc ggaagggccg agcgcagaag tggtcctgca      6240
actttatccg cctccatcca gtctattaat tgttgccggg aagctagagt aagtagttcg      6300
ccagttaata gtttgcgcaa cgttgttgcc attgctacag gcatcgtggt gtcacgctcg      6360
tcgtttggta tggcttcatt cagctccggt tcccaacgat caaggcgagt tacatgatcc      6420
cccatgttgt gcaaaaaagc ggttagctcc ttcggtcctc cgatcgttgt cagaagtaag      6480
ttggccgcag tgttatcact catggttatg gcagcactgc ataattctct tactgtcatg      6540
ccatccgtaa gatgcttttc tgtgactggt gagtactcaa ccaagtcatt ctgagaatag      6600
tgtatgcggc gaccgagttg ctcttgcccg gcgtcaatac gggataatac cgcgccacat      6660
agcagaactt taaaagtgct catcattgga aaacgttctt cggggcgaaa actctcaagg      6720
atcttaccgc tgttgagatc cagttcgatg taacccactc gtgcacccaa ctgatcttca      6780
gcatctttta ctttcaccag cgtttctggg tgagcaaaaa caggaaggca aaatgccgca      6840
aaaaagggaa taagggcgac acggaaatgt tgaatactca tactcttcct ttttcaatat      6900
tattgaagca tttatcaggg ttattgtctc atgagcggat acatatttga atgtatttag      6960
aaaaataaac aaataggggt tccgcgcaca tttccccgaa aagtgccac                   7009
```

<210> SEQ ID NO 39

<211> LENGTH: 1053
<212> TYPE: PRT
<213> ORGANISM: Staphylococcus aureus

<400> SEQUENCE: 39

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
```

```
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
                450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
                530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
                610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
                690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
                770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815
```

-continued

```
Lys Lys Leu Ile Asn Lys Ser Pro Glu Lys Leu Leu Met Tyr His His
        820              825              830

Asp Pro Gln Thr Tyr Gln Lys Leu Lys Leu Ile Met Glu Gln Tyr Gly
        835              840              845

Asp Glu Lys Asn Pro Leu Tyr Lys Tyr Tyr Glu Glu Thr Gly Asn Tyr
        850              855              860

Leu Thr Lys Tyr Ser Lys Lys Asp Asn Gly Pro Val Ile Lys Lys Ile
865              870              875              880

Lys Tyr Tyr Gly Asn Lys Leu Asn Ala His Leu Asp Ile Thr Asp Asp
                885              890              895

Tyr Pro Asn Ser Arg Asn Lys Val Val Lys Leu Ser Leu Lys Pro Tyr
                900              905              910

Arg Phe Asp Val Tyr Leu Asp Asn Gly Val Tyr Lys Phe Val Thr Val
        915              920              925

Lys Asn Leu Asp Val Ile Lys Lys Glu Asn Tyr Tyr Glu Val Asn Ser
    930              935              940

Lys Cys Tyr Glu Glu Ala Lys Lys Leu Lys Lys Ile Ser Asn Gln Ala
945              950              955              960

Glu Phe Ile Ala Ser Phe Tyr Asn Asn Asp Leu Ile Lys Ile Asn Gly
                965              970              975

Glu Leu Tyr Arg Val Ile Gly Val Asn Asn Asp Leu Leu Asn Arg Ile
                980              985              990

Glu Val Asn Met Ile Asp Ile Thr  Tyr Arg Glu Tyr Leu  Glu Asn Met
        995              1000              1005

Asn Asp  Lys Arg Pro Pro Arg  Ile Ile Lys Thr Ile  Ala Ser Lys
    1010              1015              1020

Thr Gln  Ser Ile Lys Lys Tyr  Ser Thr Asp Ile Leu  Gly Asn Leu
    1025              1030              1035

Tyr Glu  Val Lys Ser Lys Lys  His Pro Gln Ile Ile  Lys Lys Gly
    1040              1045              1050
```

<210> SEQ ID NO 40
<211> LENGTH: 1052
<212> TYPE: PRT
<213> ORGANISM: Staphylococcus aureus

<400> SEQUENCE: 40

```
Lys Arg Asn Tyr Ile Leu Gly Leu Asp Ile Gly Ile Thr Ser Val Gly
1               5               10              15

Tyr Gly Ile Ile Asp Tyr Glu Thr Arg Asp Val Ile Asp Ala Gly Val
        20              25              30

Arg Leu Phe Lys Glu Ala Asn Val Glu Asn Asn Glu Gly Arg Arg Ser
        35              40              45

Lys Arg Gly Ala Arg Arg Leu Lys Arg Arg Arg His Arg Ile Gln
    50              55              60

Arg Val Lys Lys Leu Leu Phe Asp Tyr Asn Leu Leu Thr Asp His Ser
65              70              75              80

Glu Leu Ser Gly Ile Asn Pro Tyr Glu Ala Arg Val Lys Gly Leu Ser
                85              90              95

Gln Lys Leu Ser Glu Glu Glu Phe Ser Ala Ala Leu Leu His Leu Ala
        100              105              110

Lys Arg Arg Gly Val His Asn Val Asn Glu Val Glu Glu Asp Thr Gly
        115              120              125

Asn Glu Leu Ser Thr Lys Glu Gln Ile Ser Arg Asn Ser Lys Ala Leu
```

```
          130                135                140

Glu Glu Lys Tyr Val Ala Glu Leu Gln Leu Glu Arg Leu Lys Lys Asp
145                150                155                160

Gly Glu Val Arg Gly Ser Ile Asn Arg Phe Lys Thr Ser Asp Tyr Val
               165                170                175

Lys Glu Ala Lys Gln Leu Leu Lys Val Gln Lys Ala Tyr His Gln Leu
               180                185                190

Asp Gln Ser Phe Ile Asp Thr Tyr Ile Asp Leu Leu Glu Thr Arg Arg
               195                200                205

Thr Tyr Tyr Glu Gly Pro Gly Glu Gly Ser Pro Phe Gly Trp Lys Asp
       210                215                220

Ile Lys Glu Trp Tyr Glu Met Leu Met Gly His Cys Thr Tyr Phe Pro
225                230                235                240

Glu Glu Leu Arg Ser Val Lys Tyr Ala Tyr Asn Ala Asp Leu Tyr Asn
               245                250                255

Ala Leu Asn Asp Leu Asn Asn Leu Val Ile Thr Arg Asp Glu Asn Glu
               260                265                270

Lys Leu Glu Tyr Tyr Glu Lys Phe Gln Ile Ile Glu Asn Val Phe Lys
               275                280                285

Gln Lys Lys Lys Pro Thr Leu Lys Gln Ile Ala Lys Glu Ile Leu Val
       290                295                300

Asn Glu Glu Asp Ile Lys Gly Tyr Arg Val Thr Ser Thr Gly Lys Pro
305                310                315                320

Glu Phe Thr Asn Leu Lys Val Tyr His Asp Ile Lys Asp Ile Thr Ala
               325                330                335

Arg Lys Glu Ile Ile Glu Asn Ala Glu Leu Leu Asp Gln Ile Ala Lys
               340                345                350

Ile Leu Thr Ile Tyr Gln Ser Ser Glu Asp Ile Gln Glu Glu Leu Thr
               355                360                365

Asn Leu Asn Ser Glu Leu Thr Gln Glu Glu Ile Glu Gln Ile Ser Asn
       370                375                380

Leu Lys Gly Tyr Thr Gly Thr His Asn Leu Ser Leu Lys Ala Ile Asn
385                390                395                400

Leu Ile Leu Asp Glu Leu Trp His Thr Asn Asp Asn Gln Ile Ala Ile
               405                410                415

Phe Asn Arg Leu Lys Leu Val Pro Lys Lys Val Asp Leu Ser Gln Gln
               420                425                430

Lys Glu Ile Pro Thr Thr Leu Val Asp Asp Phe Ile Leu Ser Pro Val
               435                440                445

Val Lys Arg Ser Phe Ile Gln Ser Ile Lys Val Ile Asn Ala Ile Ile
       450                455                460

Lys Lys Tyr Gly Leu Pro Asn Asp Ile Ile Ile Glu Leu Ala Arg Glu
465                470                475                480

Lys Asn Ser Lys Asp Ala Gln Lys Met Ile Asn Glu Met Gln Lys Arg
               485                490                495

Asn Arg Gln Thr Asn Glu Arg Ile Glu Glu Ile Ile Arg Thr Thr Gly
               500                505                510

Lys Glu Asn Ala Lys Tyr Leu Ile Glu Lys Ile Lys Leu His Asp Met
               515                520                525

Gln Glu Gly Lys Cys Leu Tyr Ser Leu Glu Ala Ile Pro Leu Glu Asp
       530                535                540

Leu Leu Asn Asn Pro Phe Asn Tyr Glu Val Asp His Ile Ile Pro Arg
545                550                555                560
```

-continued

```
Ser Val Ser Phe Asp Asn Ser Phe Asn Asn Lys Val Leu Val Lys Gln
            565             570             575

Glu Glu Asn Ser Lys Lys Gly Asn Arg Thr Pro Phe Gln Tyr Leu Ser
            580             585             590

Ser Ser Asp Ser Lys Ile Ser Tyr Glu Thr Phe Lys Lys His Ile Leu
            595             600             605

Asn Leu Ala Lys Gly Lys Gly Arg Ile Ser Lys Thr Lys Lys Glu Tyr
    610             615             620

Leu Leu Glu Glu Arg Asp Ile Asn Arg Phe Ser Val Gln Lys Asp Phe
625             630             635             640

Ile Asn Arg Asn Leu Val Asp Thr Arg Tyr Ala Thr Arg Gly Leu Met
            645             650             655

Asn Leu Leu Arg Ser Tyr Phe Arg Val Asn Asn Leu Asp Val Lys Val
            660             665             670

Lys Ser Ile Asn Gly Gly Phe Thr Ser Phe Leu Arg Arg Lys Trp Lys
    675             680             685

Phe Lys Lys Glu Arg Asn Lys Gly Tyr Lys His His Ala Glu Asp Ala
    690             695             700

Leu Ile Ile Ala Asn Ala Asp Phe Ile Phe Lys Glu Trp Lys Lys Leu
705             710             715             720

Asp Lys Ala Lys Lys Val Met Glu Asn Gln Met Phe Glu Glu Lys Gln
            725             730             735

Ala Glu Ser Met Pro Glu Ile Glu Thr Glu Gln Glu Tyr Lys Glu Ile
            740             745             750

Phe Ile Thr Pro His Gln Ile Lys His Ile Lys Asp Phe Lys Asp Tyr
            755             760             765

Lys Tyr Ser His Arg Val Asp Lys Lys Pro Asn Arg Glu Leu Ile Asn
    770             775             780

Asp Thr Leu Tyr Ser Thr Arg Lys Asp Asp Lys Gly Asn Thr Leu Ile
785             790             795             800

Val Asn Asn Leu Asn Gly Leu Tyr Asp Lys Asp Asn Asp Lys Leu Lys
            805             810             815

Lys Leu Ile Asn Lys Ser Pro Glu Lys Leu Leu Met Tyr His His Asp
            820             825             830

Pro Gln Thr Tyr Gln Lys Leu Lys Leu Ile Met Glu Gln Tyr Gly Asp
            835             840             845

Glu Lys Asn Pro Leu Tyr Lys Tyr Tyr Glu Glu Thr Gly Asn Tyr Leu
    850             855             860

Thr Lys Tyr Ser Lys Lys Asp Asn Gly Pro Val Ile Lys Lys Ile Lys
865             870             875             880

Tyr Tyr Gly Asn Lys Leu Asn Ala His Leu Asp Ile Thr Asp Asp Tyr
            885             890             895

Pro Asn Ser Arg Asn Lys Val Val Lys Leu Ser Leu Lys Pro Tyr Arg
            900             905             910

Phe Asp Val Tyr Leu Asp Asn Gly Val Tyr Lys Phe Val Thr Val Lys
            915             920             925

Asn Leu Asp Val Ile Lys Lys Glu Asn Tyr Tyr Glu Val Asn Ser Lys
    930             935             940

Cys Tyr Glu Glu Ala Lys Lys Leu Lys Lys Ile Ser Asn Gln Ala Glu
945             950             955             960

Phe Ile Ala Ser Phe Tyr Asn Asn Asp Leu Ile Lys Ile Asn Gly Glu
            965             970             975
```

```
Leu Tyr Arg Val Ile Gly Val Asn Asn Asp Leu Leu Asn Arg Ile Glu
        980                 985                 990

Val Asn Met Ile Asp Ile Thr Tyr  Arg Glu Tyr Leu Glu  Asn Met Asn
        995                 1000                1005

Asp Lys  Arg Pro Pro Arg Ile  Ile Lys Thr Ile Ala  Ser Lys Thr
    1010                1015                1020

Gln Ser  Ile Lys Lys Tyr Ser  Thr Asp Ile Leu Gly  Asn Leu Tyr
    1025                1030                1035

Glu Val  Lys Ser Lys Lys His  Pro Gln Ile Ile Lys  Lys Gly
    1040                1045                1050

<210> SEQ ID NO 41
<211> LENGTH: 7373
<212> TYPE: DNA
<213> ORGANISM: Artificial Sequence
<220> FEATURE:
<223> OTHER INFORMATION: Synthetic

<400> SEQUENCE: 41
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gactcgagtc gagtggctcc ggtgcccgtc agtgggcaga     180
gcgcacatcg cccacagtcc ccgagaagtt ggggggaggg gtcggcaatt gaaccggtgc     240
ctagagaagg tggcgcgggg taaactggga aagtgatgtc gtgtactggc tccgcctttt     300
tcccgagggt gggggagaac cgtatataag tgcagtagtc gccgtgaacg ttctttttcg     360
caacgggttt gccgccagaa cacaggtgtc gtgaccgcgg ccatggtcta gaggatccgg     420
tactcgagga actgaaaaac cagaaagtta actggtaagt ttagtctttt tgtctttat     480 ttcaggtccc ggatccggtg gtggtgcaaa tcaaagaact gctcctcagt ggatgttgcc     540
tttacttcta ggcctgtacg gaagtgttac gccaccatgg ccccaaagaa gaagcggaag     600
gtcggtatcc acggagtccc agcagccaag cggaactaca tcctgggcct ggacatcggc     660
atcaccagcg tgggctacgg catcatcgac tacgagacac gggacgtgat cgatgccggc     720
gtgcggctgt tcaaagaggc caacgtggaa aacaacgagg gcaggcggag caagagaggc     780
gccagaaggc tgaagcggcg gaggcggcat agaatccaga gagtgaagaa gctgctgttc     840
gactacaacc tgctgaccga ccacagcgag ctgagcggca tcaacccta cgaggccaga     900 gtgaagggcc tgagccagaa gctgagcgag gaagagttct ctgccgccct gctgcacctg     960
gccaagagaa gaggcgtgca caacgtgaac gaggtggaag aggacaccgg caacgagctg     1020
tccaccaaag agcagatcag ccggaacagc aaggccctgg aagagaaata cgtggccgaa     1080
ctgcagctgg aacggctgaa gaaagacggc gaagtgcggg gcagcatcaa cagattcaag     1140
accagcgact acgtgaaaga agccaaacag ctgctgaagg tgcagaaggc ctaccaccag     1200
ctggaccaga gcttcatcga cacctacatc gacctgctgg aaacccggcg gacctactat     1260
gagggacctg gcgagggcag ccccttcggc tggaaggaca tcaaagaatg gtacgagatg     1320
ctgatgggcc actgcaccta cttccccgag gaactgcgga gcgtgaagta cgcctacaac     1380
gccgacctgt acaacgccct gaacgacctg aacaatctcg tgatcaccag ggacgagaac     1440
gagaagctgg aatattacga gaagttccag atcatcgaga acgtgttcaa gcagaagaag     1500
aagcccaccc tgaagcagat cgccaaagaa atcctcgtga cgaagaggga tattaagggc     1560
tacagagtga ccagcaccgg caagcccgag ttcaccaacc tgaaggtgta ccacgacatc     1620
```

```
aaggacatta ccgcccggaa agagattatt gagaacgccg agctgctgga tcagattgcc   1680
aagatcctga ccatctacca gagcagcgag gacatccagg aagaactgac caatctgaac   1740
tccgagctga cccaggaaga gatcgagcag atctctaatc tgaagggcta taccggcacc   1800
cacaacctga gcctgaaggc catcaacctg atcctggacg agctgtggca caccaacgac   1860
aaccagatcg ctatcttcaa ccggctgaag ctggtgccca agaaggtgga cctgtcccag   1920
cagaaagaga tccccaccac cctggtggac gacttcatcc tgagccccgt cgtgaagaga   1980
agcttcatcc agagcatcaa agtgatcaac gccatcatca agaagtacgg cctgcccaac   2040
gacatcatta tcgagctggc ccgcgagaag aactccaagg acgcccagaa aatgatcaac   2100
gagatgcaga agcggaaccg gcagaccaac gagcggatcg aggaaatcat ccggaccacc   2160
ggcaaagaga acgccaagta cctgatcgag aagatcaagc tgcacgacat gcaggaaggc   2220
aagtgcctgt acagcctgga agccatccct ctggaagatc tgctgaacaa ccccttcaac   2280
tatgaggtgg accacatcat ccccagaagc gtgtccttcg acaacagctt caacaacaag   2340
gtgctcgtga agcaggaaga aaacagcaag aagggcaacc ggaccccatt ccagtacctg   2400
agcagcagcg acagcaagat cagctacgaa accttcaaga agcacatcct gaatctggcc   2460
aagggcaagg gcagaatcag caagaccaag aaagagtatc tgctggaaga acgggacatc   2520
aacaggttct ccgtgcagaa agacttcatc aaccggaacc tggtggatac cagatacgcc   2580
accagaggcc tgatgaacct gctgcggagc tacttcagag tgaacaacct ggacgtgaaa   2640
gtgaagtcca tcaatggcgg cttcaccagc tttctgcggc ggaagtggaa gtttaagaaa   2700
gagcggaaca aggggtacaa gcaccacgcc gaggacgccc tgatcattgc caacgccgat   2760
ttcatcttca aagagtggaa gaaactggac aaggccaaaa agtgatggaa aaaccagatg   2820
ttcgaggaaa agcaggccga gagcatgccc gagatcgaaa ccgagcagga gtacaaagag   2880
atcttcatca ccccccacca gatcaagcac attaaggact tcaaggacta caagtacagc   2940
caccgggtgg acaagaagcc taatagagag ctgattaacg acaccctgta ctccacccgg   3000
aaggacgaca agggcaacac cctgatcgtg aacaatctga acggcctgta cgacaaggac   3060
aatgacaagc tgaaaaagct gatcaacaag agccccgaaa agctgctgat gtaccaccac   3120
gacccccaga cctaccagaa actgaagctg attatggaac agtacggcga cgagaagaat   3180
cccctgtaca gtactacga ggaaaccggg aactacctga ccaagtactc caaaaaggac   3240
aacggccccg tgatcaagaa gattaagtat tacggcaaca aactgaacgc ccatctggac   3300
atcaccgacg actaccccaa cagcagaaac aaggtcgtga agctgtccct gaagccctac   3360
agattcgacg tgtacctgga caatggcgtg tacaagttcg tgaccgtgaa gaatctggat   3420
gtgatcaaaa aagaaaacta ctacgaagtg aatagcaagt gctatgagga agctaagaag   3480
ctgaagaaga tcagcaacca ggccgagttt atcgcctcct tctacaacaa cgatctgatc   3540
aagatcaacg gcgagctgta tagagtgatc ggcgtgaaca cgacctgct gaaccggatc   3600 gaagtgaaca tgatcgacat cacctaccgc gagtacctgg aaaacatgaa cgacaagagg   3660
cccccaggga tcattaagac aatcgcctcc aagacccaga gcattaagaa gtacagcaca   3720
gacattctgg gcaacctgta tgaagtgaaa tctaagaagc accctcagat catcaaaaag   3780
ggcaaaaggc cggcggccac gaaaaaggcc ggccaggcaa aaagaaaaa gggatccgaa   3840 ttctagcaat aaaggatcgt ttattttcat tggaagcgtg tgttggtttt ttgatcaggc   3900
gcgggtacca aaaatctcgc caacaagttg acgagataaa cacggcattt tgccttgttt   3960
tagtagattc tgtttccaga gtactaaaac acatttcctc tctatacaaa tgcggtgttt   4020
```

-continued

```
cgtcctttcc acaagatata taaagccaag aaatcgaaat actttcaagt tacggtaagc    4080
atatgatagt ccattttaaa acataatttt aaaactgcaa actacccaag aaattattac    4140
tttctacgtc acgtattttg tactaatatc tttgtgttta cagtcaaatt aattccaatt    4200
atctctctaa cagccttgta tcgtatatgc aaatatgaag gaatcatggg aaataggccc    4260
tcctcgacta gtagaaaaat ctcgccaaca agttgacgag ataaacacgg cattttgcct    4320
tgttttagta gattctgttt ccagagtact aaaacgtgcc aataatttca ttactatatc    4380
ggtgtttcgt cctttccaca agatatataa agccagaaaa tcgaaatact ttcaagttac    4440
ggtaagcata tgatagtcca ttttaaaaca taattttaaa actgcaaact acccaagaaa    4500
ttattacttt ctacgtcacg tattttgtac taatatcttt gtgtttacag tcaaattaat    4560
tccaattatc tctctaacag ccttgtatcg tatatgcaaa tatgaaggaa tcatgggaaa    4620
taggccctcg gtaccaggaa cccctagtga tggagttggc cactccctct ctgcgcgctc    4680
gctcgctcac tgaggccggg cgaccaaagg tcgcccgacg cccgggcttt gcccgggcgg    4740
cctcagtgag cgagcgagcg cgcagctgcc tgcaggggcg cctgatgcgg tattttctcc    4800
ttacgcatct gtgcggtatt tcacaccgca tacgtcaaag caaccatagt acgcgccctg    4860
tagcggcgca ttaagcgcgg cgggtgtggt ggttacgcgc agcgtgaccg ctacacttgc    4920
cagcgcccta gcgcccgctc ctttcgcttt cttcccttcc tttctcgcca cgttcgccgg    4980
ctttccccgt caagctctaa atcggggget ccctttaggg ttccgattta gtgctttacg    5040
gcacctcgac cccaaaaaac ttgatttggg tgatggttca cgtagtgggc catcgccctg    5100
atagacggtt tttcgccctt tgacgttgga gtccacgttc tttaatagtg gactcttgtt    5160
ccaaactgga acaacactca accctatctc gggctattct tttgatttat aagggatttt    5220
gccgatttcg gcctattggt taaaaaatga gctgatttaa caaaaattta acgcgaattt    5280
taacaaaata ttaacgttta caattttatg gtgcactctc agtacaatct gctctgatgc    5340
cgcatagtta agccagcccc gacacccgcc aacacccgct gacgcgccct gacgggcttg    5400
tctgctcccg gcatccgctt acagacaagc tgtgaccgtc tccgggagct gcatgtgtca    5460
gaggttttca ccgtcatcac cgaaacgcgc gagacgaaag ggcctcgtga tacgcctatt    5520
tttataggtt aatgtcatga taataatggt ttcttagacg tcaggtggca cttttcgggg    5580
aaatgtgcgc ggaaccccta tttgtttatt tttctaaata cattcaaata tgtatccgct    5640
catgagacaa taaccctgat aaatgcttca ataatattga aaaaggaaga gtatgagtat    5700
tcaacatttc cgtgtcgccc ttattccctt ttttgcggca ttttgccttc ctgttttgc    5760 tcacccagaa acgctggtga agtaaaaga tgctgaagat cagttgggtg cacgagtggg    5820
ttacatcgaa ctggatctca acagcggtaa gatccttgag agttttcgcc ccgaagaacg    5880
ttttccaatg atgagcactt ttaaagttct gctatgtggc gcggtattat cccgtattga    5940
cgccgggcaa gagcaactcg gtcgccgcat acactattct cagaatgact tggttgagta    6000
ctcaccagtc acagaaaagc atcttacgga tggcatgaca gtaagagaat tatgcagtgc    6060
tgccataacc atgagtgata acactgcggc caacttactt ctgacaacga tcggaggacc    6120
gaaggagcta accgcttttt tgcacaacat ggggatcat gtaactcgcc ttgatcgttg    6180
ggaaccggag ctgaatgaag ccataccaaa cgacgagcgt gacaccacga tgcctgtagc    6240
aatggcaaca acgttgcgca aactattaac tggcgaacta cttactctag cttcccggca    6300
acaattaata gactggatgg aggcggataa agttgcagga ccacttctgc gctcggccct    6360
```

-continued

```
tccggctggc tggtttattg ctgataaatc tggagccggt gagcgtggaa gccgcggtat    6420
cattgcagca ctggggccag atggtaagcc ctcccgtatc gtagttatct acacgacggg    6480
gagtcaggca actatggatg aacgaaatag acagatcgct gagataggtg cctcactgat    6540
taagcattgg taactgtcag accaagttta ctcatatata ctttagattg atttaaaact    6600
tcatttttaa tttaaaagga tctaggtgaa gatccttttt gataatctca tgaccaaaat    6660
cccttaacgt gagttttcgt tccactgagc gtcagacccc gtagaaaaga tcaaaggatc    6720
ttcttgagat cctttttttc tgcgcgtaat ctgctgcttg caaacaaaaa aaccaccgct    6780
accagcggtg gtttgtttgc cggatcaaga gctaccaact ctttttccga aggtaactgg    6840
cttcagcaga gcgcagatac caaatactgt ccttctagtg tagccgtagt taggccacca    6900
cttcaagaac tctgtagcac cgcctacata cctcgctctg ctaatcctgt taccagtggc    6960
tgctgccagt ggcgataagt cgtgtcttac cgggttggac tcaagacgat agttaccgga    7020
taaggcgcag cggtcgggct gaacggggg ttcgtgcaca cagcccagct tggagcgaac    7080
gacctacacc gaactgagat acctacagcg tgagctatga aaagcgcca cgcttcccga    7140 agggagaaag gcggacaggt atccggtaag cggcagggtc ggaacaggag agcgcacgag    7200
ggagcttcca gggggaaacg cctggtatct ttatagtcct gtcgggtttc gccacctctg    7260
acttgagcgt cgatttttgt gatgctcgtc aggggggcgg agcctatgga aaaacgccag    7320
caacgcggcc ttttacggt tcctggcctt ttgctggcct tttgctcaca tgt            7373
```

<210> SEQ ID NO 42
<211> LENGTH: 7570
<212> TYPE: DNA
<213> ORGANISM: Artificial Sequence
<220> FEATURE:
<223> OTHER INFORMATION: Synthetic

<400> SEQUENCE: 42

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gactcgagct agactagcat gctgcccatg taaggaggca     180
aggcctgggg acacccgaga tgcctggtta taattaaccc agacatgtgg ctgcccccc      240 cccccaaca cctgctgcct ctaaaaataa ccctgcatgc catgttcccg gcgaagggcc      300
agctgtcccc cgccagctag actcagcact tagtttagga accagtgagc aagtcagccc     360
ttggggcagc ccatacaagg ccatggggct gggcaagctg cacgcctggg tccggggtgg     420
gcacggtgcc cggcaacga gctgaaagct catctgctct caggggcccc tccctgggga     480
cagcccctcc tggctagtca caccctgtag gctcctctat ataacccagg gcacagggg       540 ctgccctcat tctaccacca cctccacagc acagacagac actcaggagc cagccagcca     600
tggtctagag gatccggtac tcgaggaact gaaaaaccag aaagttaact ggtaagttta     660 gtcttttgt cttttatttc aggtcccgga tccggtggtg gtgcaaatca aagaactgct      720
cctcagtgga tgttgccttt acttctaggc ctgtacggaa gtgttacgcc accatggccc     780
caaagaagaa gcggaaggtc ggtatccacg agtcccagc agccaagcgg aactacatcc       840
tgggcctgga catcggcatc accagcgtgg gctacggcat catcgactac gagacacggg     900
acgtgatcga tgccggcgtg cggctgttca agagggccaa cgtggaaaac aacgagggca     960
ggcggagcaa gagaggcgcc agaaggctga agcggcggag gcggcataga atccagagag    1020
tgaagaagct gctgttcgac tacaacctgc tgaccgacca cagcgagctg agcggcatca    1080
```

-continued

```
acccctacga ggccagagtg aagggcctga gccagaagct gagcgaggaa gagttctctg    1140
ccgccctgct gcacctggcc aagagaagag gcgtgcacaa cgtgaacgag gtggaagagg    1200
acaccggcaa cgagctgtcc accaaagagc agatcagccg gaacagcaag gccctggaag    1260
agaaatacgt ggccgaactg cagctggaac ggctgaagaa agacggcgaa gtgcggggca    1320
gcatcaacag attcaagacc agcgactacg tgaaagaagc caaacagctg ctgaaggtgc    1380
agaaggccta ccaccagctg gaccagagct tcatcgacac ctacatcgac ctgctggaaa    1440
cccggcggac ctactatgag ggacctggcg agggcagccc cttcggctgg aaggacatca    1500
aagaatggta cgagatgctg atgggccact gcacctactt ccccgaggaa ctgcggagcg    1560
tgaagtacgc ctacaacgcc gacctgtaca cgccctgaa cgacctgaac aatctcgtga    1620
tcaccaggga cgagaacgag aagctggaat attacgagaa gttccagatc atcgagaacg    1680
tgttcaagca gaagaagaag cccaccctga gcagatcgc caaagaaatc ctcgtgaacg    1740
aagaggatat taagggctac agagtgacca gcaccggcaa gcccgagttc accaacctga    1800
aggtgtacca cgacatcaag gacattaccg cccggaaaga gattattgag aacgccgagc    1860
tgctggatca gattgccaag atcctgacca tctaccagag cagcgaggac atccaggaag    1920
aactgaccaa tctgaactcc gagctgaccc aggaagagat cgagcagatc tctaatctga    1980
agggctatac cggcacccac aacctgagcc tgaaggccat caacctgatc ctggacgagc    2040
tgtggcacac caacgacaac cagatcgcta tcttcaaccg gctgaagctg gtgcccaaga    2100
aggtggacct gtcccagcag aaagagatcc ccaccaccct ggtggacgac ttcatcctga    2160
gccccgtcgt gaagagaagc ttcatccaga gcatcaaagt gatcaacgcc atcatcaaga    2220
agtacggcct gcccaacgac atcattatcg agctggcccg cgagaagaac tccaaggacg    2280
cccagaaaat gatcaacgag atgcagaagc ggaaccggca gaccaacgag cggatcgagg    2340
aaatcatccg gaccaccggc aaagagaacg ccaagtacct gatcgagaag atcaagctgc    2400
acgacatgca ggaaggcaag tgcctgtaca gcctggaagc catccctctg gaagatctgc    2460
tgaacaaccc cttcaactat gaggtggacc acatcatccc cagaagcgtg tccttcgaca    2520
acagcttcaa caacaaggtg ctcgtgaagc aggaagaaaa cagcaagaag ggcaaccgga    2580
ccccattcca gtacctgagc agcagcgaca gcaagatcag ctacgaaacc ttcaagaagc    2640
acatcctgaa tctggccaag ggcaagggca gaatcagcaa gaccaagaaa gagtatctgc    2700
tggaagaacg ggacatcaac aggttctccg tgcagaaaga cttcatcaac cggaacctgg    2760
tggataccag atacgccacc agaggcctga tgaacctgct gcggagctac ttcagagtga    2820
acaacctgga cgtgaaagtg aagtccatca tggcggctt caccagcttt ctgcggcgga    2880
agtggaagtt taagaaagag cggaacaagg ggtacaagca ccacgccgag gacgccctga    2940
tcattgccaa cgccgatttc atcttcaaag agtggaagaa actggacaag gccaaaaaag    3000
tgatggaaaa ccagatgttc gaggaaaagc aggccgagag catgcccgag atcgaaaccg    3060
agcaggagta caaagagatc ttcatcaccc cccaccagat caagcacatt aaggacttca    3120
aggactacaa gtacagccac cgggtggaca agaagcctaa tagagagctg attaacgaca    3180
ccctgtactc caccccggaag gacgacaagg gcaacaccct gatcgtgaac aatctgaacg    3240
gcctgtacga caaggacaat gacaagctga aaaagctgat caacaagagc cccgaaaagc    3300
tgctgatgta ccaccacgac ccccagacct accagaaact gaagctgatt atggaacagt    3360
acggcgacga gaagaatccc ctgtacaagt actacgagga aaccgggaac tacctgacca    3420
```

-continued

```
agtactccaa aaaggacaac ggccccgtga tcaagaagat taagtattac ggcaacaaac    3480
tgaacgccca tctggacatc accgacgact accccaacag cagaaacaag gtcgtgaagc    3540
tgtccctgaa gccctacaga ttcgacgtgt acctggacaa tggcgtgtac aagttcgtga    3600
ccgtgaagaa tctggatgtg atcaaaaaag aaaactacta cgaagtgaat agcaagtgct    3660
atgaggaagc taagaagctg aagaagatca gcaaccaggc cgagtttatc gcctccttct    3720
acaacaacga tctgatcaag atcaacggcg agctgtatag agtgatcggc gtgaacaacg    3780
acctgctgaa ccggatcgaa gtgaacatga tcgacatcac ctaccgcgag tacctggaaa    3840
acatgaacga caagaggccc cccaggatca ttaagacaat cgcctccaag acccagagca    3900
ttaagaagta cagcacagac attctgggca acctgtatga agtgaaatct aagaagcacc    3960
ctcagatcat caaaaagggc aaaaggccgg cggccacgaa aaaggccggc caggcaaaaa    4020
agaaaaaggg atccgaattc tagcaataaa ggatcgttta ttttcattgg aagcgtgtgt    4080 tggtttttg atcaggcgcg ggtaccaaaa atctcgccaa caagttgacg agataaacac    4140
ggcattttgc cttgtttag tagattctgt ttccagagta ctaaaacaca tttcctctct    4200
atacaaatgc ggtgtttcgt cctttccaca agatatataa agccaagaaa tcgaaatact    4260
ttcaagttac ggtaagcata tgatagtcca ttttaaaaca taattttaaa actgcaaact    4320
acccaagaaa ttattacttt ctacgtcacg tattttgtac taatatcttt gtgtttacag    4380
tcaaattaat tccaattatc tctctaacag ccttgtatcg tatatgcaaa tatgaaggaa    4440
tcatgggaaa taggccctcc tcgactagta gaaaaatctc gccaacaagt tgacgagata    4500
aacacggcat tttgccttgt tttagtagat tctgttccca gagtactaaa acgtgccaat    4560
aatttcatta ctatatcggt gtttcgtcct ttccacaaga tatataaagc caagaaatcg    4620
aaatactttc aagttacggt aagcatatga tagtccattt taaaacataa ttttaaaact    4680
gcaaactacc caagaaatta ttactttcta cgtcacgtat tttgtactaa tatctttgtg    4740
tttacagtca aattaattcc aattatctct ctaacagcct tgtatcgtat atgcaaatat    4800
gaaggaatca tgggaaatag gccctcggta ccaggaaccc ctagtgatgg agttggccac    4860
tccctctctg cgcgctcgct cgctcactga ggccgggcga ccaaaggtcg cccgacgccc    4920
gggctttgcc cgggcggcct cagtgagcga gcgagcgcgc agctgcctgc aggggcgcct    4980
gatgcggtat tttctcctta cgcatctgtg cggtatttca caccgcatac gtcaaagcaa    5040
ccatagtacg cgccctgtag cggcgcatta agcgcggcgg gtgtggtggt tacgcgcagc    5100
gtgaccgcta cacttgccag cgccctagcg cccgctcctt cgctttctt cccttccttt    5160 ctcgccacgt tcgccggctt tccccgtcaa gctctaaatc gggggctccc tttagggttc    5220
cgatttagtg ctttacggca cctcgacccc aaaaaacttg atttgggtga tggttcacgt    5280
agtgggccat cgccctgata gacggttttt cgccctttga cgttggagtc cacgttcttt    5340
aatagtggac tcttgttcca aactggaaca cactcaacc ctatctcggg ctattctttt    5400
gatttataag ggattttgcc gatttcggcc tattggttaa aaaatgagct gatttaacaa    5460
aaatttaacg cgaattttaa caaaatatta cgtttacaa ttttatggtg cactctcagt    5520
acaatctgct ctgatgccgc atagttaagc cagccccgac acccgccaac acccgctgac    5580
gcgccctgac gggcttgtct gctcccggca tccgcttaca gacaagctgt gaccgtctcc    5640
gggagctgca tgtgtcagag gttttcaccg tcatcaccga aacgcgcgag acgaaagggc    5700
ctcgtgatac gcctattttt ataggttaat gtcatgataa taatggtttc ttagacgtca    5760
ggtggcactt ttcggggaaa tgtgcgcgga accctatttt gtttattttt ctaaatacat    5820
```

-continued

```
tcaaatatgt atccgctcat gagacaataa ccctgataaa tgcttcaata atattgaaaa    5880
aggaagagta tgagtattca acatttccgt gtcgccctta ttcccttttt tgcggcattt    5940
tgccttcctg tttttgctca cccagaaacg ctggtgaaag taaaagatgc tgaagatcag    6000
ttgggtgcac gagtgggtta catcgaactg gatctcaaca gcggtaagat ccttgagagt    6060
tttcgccccg aagaacgttt tccaatgatg agcactttta aagttctgct atgtggcgcg    6120
gtattatccc gtattgacgc cgggcaagag caactcggtc gccgcataca ctattctcag    6180
aatgacttgg ttgagtactc accagtcaca gaaaagcatc ttacggatgg catgacagta    6240
agagaattat gcagtgctgc cataaccatg agtgataaca ctgcggccaa cttacttctg    6300
acaacgatcg gaggaccgaa ggagctaacc gcttttttgc acaacatggg ggatcatgta    6360
actcgccttg atcgttggga accggagctg aatgaagcca taccaaacga cgagcgtgac    6420
accacgatgc ctgtagcaat ggcaacaacg ttgcgcaaac tattaactgg cgaactactt    6480
actctagctt cccggcaaca attaatagac tggatggagg cggataaagt tgcaggacca    6540
cttctgcgct cggcccttcc ggctggctgg tttattgctg ataaatctgg agccggtgag    6600
cgtggaagcc gcggtatcat tgcagcactg gggccagatg gtaagccctc ccgtatcgta    6660
gttatctaca cgacggggag tcaggcaact atggatgaac gaaatagaca gatcgctgag    6720
ataggtgcct cactgattaa gcattggtaa ctgtcagacc aagtttactc atatatactt    6780
tagattgatt taaaacttca tttttaattt aaaaggatct aggtgaagat cctttttgat    6840
aatctcatga ccaaaatccc ttaacgtgag ttttcgttcc actgagcgtc agaccccgta    6900
gaaaagatca aggatcttc ttgagatcct ttttttctgc gcgtaatctg ctgcttgcaa    6960
acaaaaaaac caccgctacc agcggtggtt tgtttgccgg atcaagagct accaactctt    7020
tttccgaagg taactggctt cagcagagcg cagataccaa atactgtcct tctagtgtag    7080
ccgtagttag gccaccactt caagaactct gtagcaccgc ctacatacct cgctctgcta    7140
atcctgttac cagtggctgc tgccagtggc gataagtcgt gtcttaccgg gttggactca    7200
agacgatagt taccggataa ggcgcagcgg tcgggctgaa cggggggttc gtgcacacag    7260
cccagcttgg agcgaacgac ctacaccgaa ctgagatacc tacagcgtga gctatgagaa    7320
agcgccacgc ttcccgaagg gagaaaggcg gacaggtatc cggtaagcgg cagggtcgga    7380
acaggagagc gcacgaggga gcttccaggg ggaaacgcct ggtatcttta tagtcctgtc    7440
gggtttcgcc acctctgact tgagcgtcga tttttgtgat gctcgtcagg ggggcggagc    7500
ctatggaaaa acgccagcaa cgcggccttt ttacggttcc tggccttttg ctggcctttt    7560
gctcacatgt                                                           7570
```

AAV VECTOR-MEDIATED DELETION OF LARGE MUTATIONAL HOTSPOT FOR TREATMENT OF DUCHENNE MUSCULAR DYSTROPHY

CROSS-REFERENCE TO RELATED APPLICATIONS

This patent application is the U.S. national stage entry, under 35 U.S.C. § 371, of International Application Number PCT/US2020/028148, filed Apr. 14, 2020, which claims priority to U.S. Provisional Patent Application No. 62/833, 760, filed Apr. 14, 2019, the entire contents of each of which are hereby incorporated by reference.

STATEMENT REGARDING FEDERALLY SPONSORED RESEARCH

This invention was made with government support under grant R01AR069085 awarded by the National Institutes of Health. The government has certain rights in the invention.

SEQUENCE LISTING

This instant application includes a Sequence Listing which has been submitted electronically in ASCII format and is hereby incorporated by reference in its entirety. Said ASCII copy created on Jun. 5, 2020, is named "028193-9324-WO01_As_Filed_Sequence_Listing.txt" and is 208, 630 bytes in size.

FIELD

The present disclosure relates to the field of gene expression alteration, genome engineering, and genomic alteration of genes using Clustered Regularly Interspaced Short Palindromic Repeats (CRISPR)/CRISPR-associated (Cas) 9-based systems and viral delivery systems. The present disclosure also relates to the field of genome engineering and genomic alteration of genes in muscle, such as skeletal muscle and cardiac muscle.

INTRODUCTION

CRISPR/Cas9-based gene editing systems can be used to introduce site-specific double strand breaks at targeted genomic loci. This DNA cleavage stimulates the natural DNA-repair machinery, leading to one of two possible repair pathways. In the absence of a donor template, the break will be repaired by non-homologous end joining (NHEJ), an error-prone repair pathway that leads to small insertions or deletions of DNA. This method can be used to intentionally disrupt, delete, or alter the reading frame of targeted gene sequences. However, if a donor template is provided along with the nucleases, then the cellular machinery will repair the break by homologous recombination, which is enhanced several orders of magnitude in the presence of DNA cleavage. This method can be used to introduce specific changes in the DNA sequence at target sites. Engineered nucleases have been used for gene editing in a variety of human stem cells and cell lines, and for gene editing in the mouse liver. However, the major hurdle for implementation of these technologies is delivery to particular tissues in vivo in a way that is effective, efficient, and facilitates successful genome modification.

Hereditary genetic diseases have devastating effects on children in the United States. These diseases currently have no cure and can only be managed by attempts to alleviate the symptoms. For decades, the field of gene therapy has promised a cure to these diseases. However technical hurdles regarding the safe and efficient delivery of therapeutic genes to cells and patients have limited this approach. Duchenne muscular dystrophy (DMD) is a fatal genetic disease, clinically characterized by muscle wasting, loss of ambulation, and death typically in the third decade of life due to the loss of functional dystrophin. DMD is the result of inherited or spontaneous mutations in the dystrophin gene. Most mutations causing DMD are a result of deletions of exon(s), pushing the translational reading frame out of frame. The majority of DMD mutations are deletions (~68%) of one or more of its 79 exons that shift the reading frame and terminate expression of the full-length transcript. Deletions mostly occur in two "hotspots" of the gene, which encompass exons 2 through 20 (~⅓ of all deletions) and exons 45 through 55 (~⅔ of all deletions). Becker muscular dystrophy (BMD) patients with naturally occurring in-frame deletions of the entire 45 to 55 region of the dystrophin gene exhibit delayed disease onset and minimal skeletal muscle pathology.

Dystrophin is a key component of a protein complex that is responsible for regulating muscle cell integrity and function. DMD patients typically lose the ability to physically support themselves during childhood, become progressively weaker during the teenage years, and die in their twenties. Current experimental gene therapy strategies for DMD require repeated administration of transient gene delivery vehicles or rely on permanent integration of foreign genetic material into the genomic DNA. Both of these methods have serious safety concerns. Furthermore, these strategies have been limited by an inability to deliver the large and complex dystrophin gene sequence. There remains a need for more precise and efficient gene editing tools for correcting and treating patients with mutations in the dystrophin gene.

SUMMARY

In an aspect, the disclosure relates to a CRISPR-Cas system. The CRISPR-Cas system may include one or more vectors encoding a composition, the composition comprising: (a) a first guide RNA (gRNA) molecule targeting intron 44 of dystrophin; (b) a second gRNA molecule targeting intron 55 of dystrophin; and (c) a Cas9 protein; and (d) one or more Cas9 gRNA scaffolds. In some embodiments, the system comprises a single vector. In some embodiments, the system comprises two or more vectors, wherein the two or more vectors comprises a first vector and a second vector. In some embodiments, (a) the first vector encodes the first gRNA molecule and the second gRNA molecule; and (b) the second vector encodes the Cas9 protein. In some embodiments, (a) the first vector encodes the first gRNA molecule; and (b) the second vector encodes the second gRNA molecule. In some embodiments, the first vector further encodes the Cas9 protein. In some embodiments, the second vector further encodes the Cas9 protein. In some embodiments, the expression of the Cas9 protein is driven by a constitutive promoter or a muscle-specific promoter. In some embodiments, the muscle-specific promoter comprises a MHCK7 promoter, a CK8 promoter, or a Spc512 promoter. In some embodiments, the single vector encodes the first gRNA molecule, the second gRNA molecule, and the Cas9 protein. In some embodiments, the vector comprises at least one bidirectional promoter. In some embodiments, the bidirectional promoter comprises: a first promoter driving expression of the first gRNA molecule and/or the second gRNA molecule; and a second promoter driving expression of the Cas9 protein. In some embodiments, the first gRNA targets the polynucleotide of SEQ ID NO:2 or a 5' truncation thereof. In some embodiments, the second gRNA targets the polynucleotide of SEQ ID NO:3 or a 5' truncation thereof. In some embodiments, the Cas9 protein is SpCas9, SaCas9, or St1Cas9 protein. In some embodiments, the Cas9 gRNA scaffold is a SaCas9 gRNA scaffold. In some embodiments, the SaCas9 gRNA scaffold comprises or is encoded by the polynucleotide of SEQ ID NO:4. In some embodiments, the Cas9 protein is a SaCas9 protein encoded by the polynucleotide of SEQ ID NO:11. In some embodiments, the vector comprises at least one polynucleotide selected from SEQ ID NOs: 1-13 and 24. In some embodiments, the vector comprises the polynucleotide sequence of SEQ ID NO: 24. In some embodiments, the vector comprises a polynucleotide sequence that is selected from SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 41, SEQ ID NO: 42, SEQ ID NO: 29, and SEQ ID NO: 30. In some embodiments, the vector is a viral vector. In some embodiments, the vector is an Adeno-associated virus (AAV) vector. In some embodiments, the AAV vector is AAV1, AAV2, AAV3, AAV4, AAV5, AAV6, AAV7, AAV8, AAV9, AAV-10, AAV-11, AAV-12, AAV-13, or AAVrh.74. In some embodiments, the vector comprises a ubiquitous promoter or a tissue-specific promoter operably linked to the polynucleotide sequence encoding the first gRNA molecule, the second gRNA molecule, and/or the Cas9 protein. In some embodiments, the tissue-specific promoter is a muscle specific promoter.

In a further aspect, the disclosure relates to a cell comprising the herein described system.

Another aspect of the disclosure provides a kit comprising the herein described system.

Another aspect of the disclosure provides a method of correcting a mutant dystrophin gene in a cell. The method may include administering to a cell the herein described system.

Another aspect of the disclosure provides a method of genome editing a mutant dystrophin gene in a subject. The method may include administering to the subject a herein described system or cell. The system or cell may be administered to the subject intramuscularly, intravenously, or a combination thereof.

Another aspect of the disclosure provides a method of treating a subject having a mutant dystrophin gene. The method may include administering to the subject the herein described system or cell. The system or cell may be administered to the subject intramuscularly, intravenously, or a combination thereof.

The disclosure provides for other aspects and embodiments that will be apparent in light of the following detailed description and accompanying figures.

DETAILED DESCRIPTION

Figure 1:
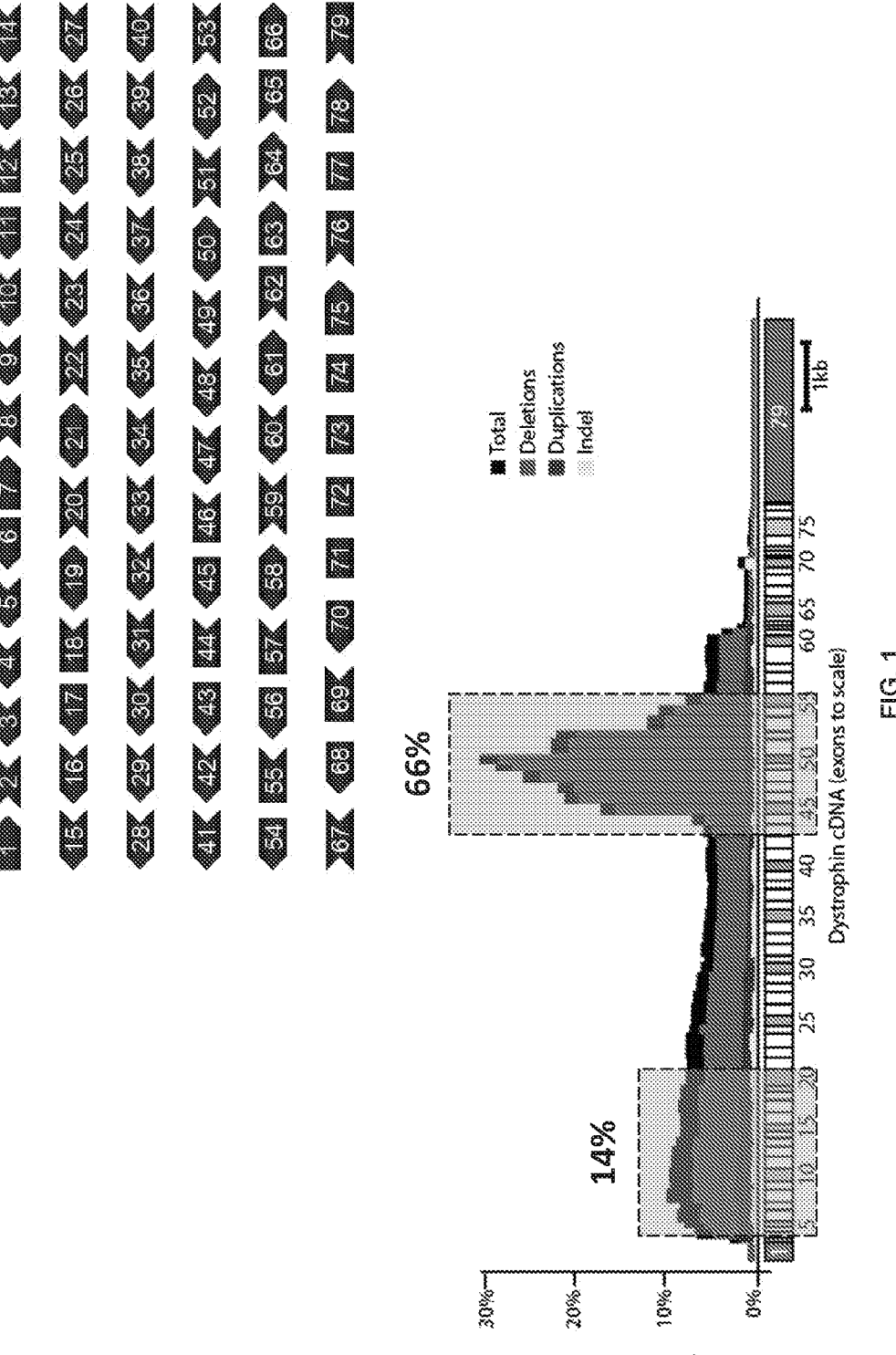
FIG. 1 shows the two deletion prone hotspots in dystrophin. The dystrophin gene (which may be referred to as DMD) is the largest known gene in humans (2.3 Mbp). Approximately, 68% of mutations are large exon deletions that lead to frameshift errors.

As described herein, certain methods and engineered gRNAs have been discovered to be useful with CRISPR/CRISPR-associated (Cas) 9-based gene editing systems for altering the expression, genome engineering, and correcting or reducing the effects of mutations in the dystrophin gene involved in genetic diseases, such as DMD. The disclosed gRNAs were generated to target sites that are more amenable to clinical translation. For example, the gene encoding *S. pyogenes* Cas9 (SpCas9) is too large to be delivered by adeno-associated virus (AAV), a vector used for the systemic gene delivery to muscle when all other necessary regulatory sequences are included. Instead, the disclosed gRNAs were selected and screened for use with *S. aureus* Cas9 (SaCas9), which is about 1 kb smaller than SpCas9. The disclosed gRNAs, which target human dystrophin gene sequences, can be used with the CRISPR/Cas9-based system to target exons 45 to 55 of the human dystrophin gene, causing genomic deletions of this region in order to restore expression of functional dystrophin in cells from DMD patients.

Also described herein are genetic constructs, compositions, and methods for delivering CRISPR/Cas9-based gene editing system and multiple gRNAs to target the dystrophin gene. The presently disclosed subject matter also provides for methods for delivering the genetic constructs (e.g., vectors) or compositions comprising thereof to skeletal muscle and cardiac muscle. The vector can be an AAV, including modified AAV vectors. The presently disclosed subject matter describes a way to deliver active forms of this class of therapeutics to skeletal muscle or cardiac muscle that is effective, efficient, and facilitates successful genome modification, as well as provide a means to rewrite the human genome for therapeutic applications and target model species for basic science applications. The methods may relate to the use of a single AAV vector for the delivery of all of the editing components necessary for the excision of exons 45 through 55 of dystrophin.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6,2, 6.3, 6.4, 6.5, 6.6, 6.7, 6.8, 6.9, and 7.0 are explicitly contemplated.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, particularly with respect to biological systems or processes, the term can mean within an order of magnitude, preferably within 5-fold, and more preferably within 2-fold, of a value.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Cardiac muscle" or "heart muscle" as used interchangeably herein means a type of involuntary striated muscle found in the walls and histological foundation of the heart, the myocardium. Cardiac muscle is made of cardiomyocytes or myocardiocytes. Myocardiocytes show striations similar to those on skeletal muscle cells but contain only one, unique nucleus, unlike the multinucleated skeletal cells. In certain embodiments, "cardiac muscle condition" refers to a condition related to the cardiac muscle, such as cardiomyopathy, heart failure, arrhythmia, and inflammatory heart disease.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing," and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site, or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

The term "directional promoter" refers to two or more promoters that are capable of driving transcription of two separate sequences in both directions. In one embodiment, one promoter drives transcription from 5' to 3' and the other promoter drives transcription from 3' to 5'. In one embodiment, bidirectional promoters are double-strand transcription control elements that can drive expression of at least two separate sequences, for example, coding or non-coding sequences, in opposite directions. Such promoter sequences may be composed of two individual promoter sequences acting in opposite directions, such as one nucleotide sequence linked to the other (complementary) nucleotide sequence, including packaging constructs comprising the two promoters in opposite directions, for example, by hybrid, chimeric or fused sequences comprising the two individual promoter sequences, or at least core sequences thereof, or else by only one transcription regulating sequence that can initiate the transcription in both directions. The two individual promoter sequences, in some embodiments, may be juxtaposed or a linker sequence can be located between the first and second sequences. A promoter sequence may be reversed to be combined with another promoter sequence in the opposite orientation. Genes located on both sides of a bidirectional promoter can be operably linked to a single transcription control sequence or region that drives the transcription in both directions. In other embodiments, the bidirectional promoters are not juxtaposed. For example, one promoter may drive transcription on the 5' end of a nucleotide fragment, and another promoter may drive transcription from the 3' end of the same fragment. In another embodiment, a first gene can be operably linked to the bidirectional promoter with or without further regulatory elements, such as a reporter or terminator elements, and a second gene can be operably linked to the bidirectional promoter in the opposite direction and by the complementary promoter sequence, again with or without further regulatory elements.

"Donor DNA", "donor template," and "repair template" as used interchangeably herein refers to a double-stranded DNA fragment or molecule that includes at least a portion of the gene of interest. The donor DNA may encode a full-functional protein or a partially-functional protein.

"Duchenne Muscular Dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exons 45 through 55" of dystrophin as used herein refers to an area where roughly 45% of all dystrophin mutations are located. Exon 45-55 deletions are associated with very mild Becker phenotypes and have even been found in asymptomatic individuals. Exon 45-55 multiexon skipping would be beneficial for roughly 50% of all DMD patients.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operably linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, Becker Muscular Dystrophy (BMD), hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the CRISPR/Cas9-based gene editing system, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression. For example, a normal gene may be a wild-type gene.

"Nuclease mediated NHEJ" as used herein refers to NHEJ that is initiated after a nuclease, such as a Cas9 molecule, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a nonfunctional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively (constitutive promoter), or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, human U6 (hU6) promoter, and CMV IE promoter. Examples of muscle-specific promoters may include a MHCK7 promoter, a CK8 promoter, and a Spc512 promoter.

"Skeletal muscle" as used herein refers to a type of striated muscle, which is under the control of the somatic nervous system and attached to bones by bundles of collagen fibers known as tendons. Skeletal muscle is made up of individual components known as myocytes, or "muscle cells", sometimes colloquially called "muscle fibers," Myocytes are formed from the fusion of developmental myoblasts (a type of embryonic progenitor cell that gives rise to a muscle cell) in a process known as myogenesis. These long, cylindrical, multinucleated cells are also called myofibers.

"Skeletal muscle condition" as used herein refers to a condition related to the skeletal muscle, such as muscular dystrophies, aging, muscle degeneration, wound healing, and muscle weakness or atrophy.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be a mutated gene involved in a genetic disease. In certain embodiments, the target gene is a human dystrophin gene. In certain embodiments, the target gene is a mutant human dystrophin gene.

"Target region" as used herein refers to the region of the target gene to which the CRISPR/Cas9-based gene editing system is designed to bind and cleave.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Genetic Constructs for Genome Editing of Dystrophin Gene

Provided herein are genetic constructs for genome editing, genomic alteration, and/or altering gene expression of a dystrophin gene. The dystrophin gene may be a human dystrophin gene. The genetic constructs include at least one gRNA that targets a dystrophin gene sequence(s). The at least one gRNA may target human and/or rhesus monkey dystrophin gene sequences and may be SaCas9-compatible targets. The disclosed gRNAs can be included in a CRISPR/Cas9-based gene editing system, including systems that use SaCas9, to target exons 45 through 55 of the human dystrophin gene. The disclosed gRNAs, which may be included in a CRISPR/Cas9-based gene editing system, can cause genomic deletions of the region of exons 45 through 55 of the human dystrophin gene in order to restore expression of functional dystrophin in cells from DMD patients.

a. Dystrophin Gene

Dystrophin is a rod-shaped cytoplasmic protein that is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being approximately 14 kb. 79 exons code for the protein, which is over 3500 amino acids. Normal skeleton muscle tissue contains only small amounts of dystrophin, but its absence of abnormal expression leads to the development of severe and incurable symptoms. Some mutations in the dystrophin gene lead to the production of defective dystrophin and severe dystrophic phenotype in affected patients. Some mutations in the dystrophin gene lead to partially functional dystrophin protein and a much milder dystrophic phenotype in affected patients.

Figure 2:
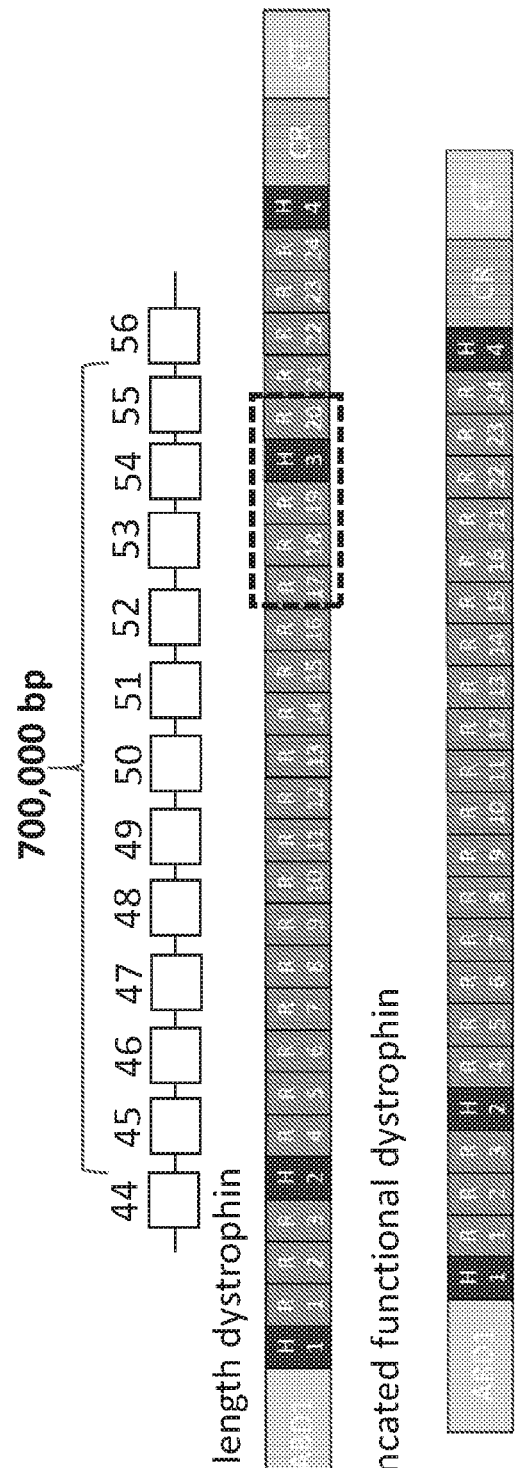
FIG. 2 details relating to the exon 45 through exon 55 mutational hotspot. Approximately 45% of all DMD mutations, and many commonly deleted single exons, are located in this region. Patients with exon 45 to 55 in-frame deletion display milder dystrophic phenotype. AONs (antisense oligonucleotides) have been used to induce exon skipping in this region.

DMD is the result of inherited or spontaneous mutations that cause nonsense or frame shift mutations in the dystrophin gene. Naturally occurring mutations and their consequences are relatively well understood for DMD. In-frame deletions that occur in the axon 45-55 regions (FIG. 1, FIG. 2) contained within the rod domain can produce highly functional dystrophin proteins, and many carriers are asymptomatic or display mild symptoms. Furthermore, more than 60% of patients may theoretically be treated by targeting this region as a whole (exons 45 through 55) or specific exons in this region of the dystrophin gene (for example, targeting exon 51 only). Efforts have been made to restore the disrupted dystrophin reading frame in DMD patients by skipping non-essential exon(s) (for example, exon 51 skipping) during mRNA splicing to produce internally deleted but functional dystrophin proteins. The deletion of internal dystrophin exon(s) (for example, deletion of exon 51) retains the proper reading frame but cause the less severe Becker muscular dystrophy (BMD). The BMD genotype is similar to DMD in that deletions are present in the dystrophin gene. However, the deletions in BMD leave the reading frame intact. Thus an internally truncated but partially functional dystrophin protein is created. BMD has a wide array of phenotypes, but often if deletions are between exons 45-55 of dystrophin, the phenotype is much milder compared to DMD. Thus changing a DMD genotype to a BMD genotype is a common strategy to correct dystrophin. There are many strategies to correct dystrophin, many of which rely on restoring the reading frame of the endogenous dystrophin. This shifts the disease genotype from DMD to Becker muscular dystrophy. Many BMD patients have intragenic deletions that maintain the translational reading frame, leading to a shorter but largely functional dystrophin protein.

In certain embodiments, modification of exons 45-55 (such as deletion or excision of axons 45 through 55 by, for example, NHEJ) to restore reading frame ameliorates the phenotype DMD in subjects, including DMD subjects with deletion mutations. Exons 45 through 55 of a dystrophin gene refers to the 45th exon, 46th exon, 47th exon, 48th exon, 49th exon, 50th exon, 51st exon, 52nd exon, 53rd exon, 54th exon, and the 55th exon of the dystrophin gene. Mutations in the 45th through 55th exon region are ideally suited for permanent correction by NHEJ-based genome editing.

The presently disclosed genetic constructs can generate deletions in the dystrophin gene. The dystrophin gene may be a human dystrophin gene. In certain embodiments, the vector is configured to form two double stand breaks (a first double strand break and a second double strand break) in two introns (a first intron and a second intron) flanking a target position of the dystrophin gene, thereby deleting a segment of the dystrophin gene comprising the dystrophin target position. A "dystrophin target position" can be a dystrophin exonic target position or a dystrophin intra-exonic target position, as described herein. Deletion of the dystrophin exonic target position can optimize the dystrophin sequence of a subject suffering from Duchenne muscular dystrophy. For example, it can increase the function or activity of the encoded dystrophin protein, and/or result in an improvement in the disease state of the subject. In certain embodiments, excision of the dystrophin exonic target position restores reading frame. The dystrophin exonic target position can comprise one or more exons of the dystrophin gene. In certain embodiments, the dystrophin target position comprises exon 51 of the dystrophin gene (e.g., human dystrophin gene).

A presently disclosed genetic construct can mediate highly efficient gene editing at the exon 45 through exon 55 region of a dystrophin gene. A presently disclosed genetic construct can restore dystrophin protein expression in cells from DMD patients.

Elimination of exons 45 through 55 from the dystrophin transcript by exon skipping can be used to treat approximately 50% of all DMD patients. This class of dystrophin mutations is suited for permanent correction by NHEJ-based genome editing and HDR. The genetic constructs described herein have been developed for targeted modification of exon 45 through exon 55 in the human dystrophin gene. A presently disclosed genetic construct may be transfected into human DMD cells and mediate efficient gene modification and conversion to the correct reading frame. Protein restoration may be concomitant with frame restoration and detected in a bulk population of CRISPR/Cas9-based gene editing system-treated cells.

b. CRISPR System

A presently disclosed genetic construct may encode a CRISPR/Cas9-based gene editing system that is specific for a dystrophin gene. "Clustered Regularly Interspaced Short Palindromic Repeats" and "CRISPRs", as used interchangeably herein, refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the sgRNA (also referred interchangeably herein as "gRNA"), and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the crRNA, i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 by recognition sequence of the expressed sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II, and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

The Cas9: crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a shod sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9-based gene editing system is the straightforward ability to simultaneously target multiple distinct genomic loci by co-expressing a single Cas9 protein with two or more sgRNAs. For example, the *Streptococcus pyogenes* Type II system naturally prefers to use an "NGG" sequence, where "N" can be any nucleotide, but also accepts other PAM sequences, such as "NAG" in engineered systems (Hsu et al., Nature Biotechnology (2013) doi:10.1038/nbt.2647). Similarly, the Cas9 derived from *Neisseria meningitidis* (NmCas9) normally has a native PAM of NNNNGATT, but has activity across a variety of PAMs, including a highly degenerate NNNNGNNN PAM (Esvelt et al. Nature Methods (2013) doi:10.1038/nmeth.2681).

A Cas9 molecule of *S. aureus* recognizes the sequence motif NNGRR (R=A or G) (SEQ ID NO: 25) and directs cleavage of a target nucleic acid sequence 1 to 10, e.g., 3 to 5, bp upstream from that sequence. In certain embodiments, a Cas9 molecule of *S. aureus* recognizes the sequence motif NNGRRN (R=A or G) (SEQ ID NO: 26) and directs cleavage of a target nucleic acid sequence 1 to 10, e.g., 3 to 5, bp upstream from that sequence. In certain embodiments, a Cas9 molecule of *S. aureus* recognizes the sequence motif NNGRRT (R=A or G) (SEQ ID NO: 27) and directs cleavage of a target nucleic acid sequence 1 to 10, e.g., 3 to 5, bp upstream from that sequence. In certain embodiments, a Cas9 molecule of *S. aureus* recognizes the sequence motif NNGRRV (R=A or G) (SEQ ID NO: 28) and directs cleavage of a target nucleic acid sequence 1 to 10, e.g., 3 to 5, bp upstream from that sequence. In the aforementioned embodiments, N can be any nucleotide residue, e.g., any of A, G, C, or T. Cas9 molecules can be engineered to alter the PAM specificity of the Cas9 molecule.

i) CRISPR/Cas9-based Gene Editing System

An engineered form of the Type II effector system of *Streptococcus pyogenes* was shown to function in human cells for genome engineering. In this system, the Cas9 protein was directed to genomic target sites by a syntheti-cally reconstituted "guide RNA" ("gRNA", also used interchangeably herein as a chimeric single guide RNA ("sgRNA")), which is a crRNA-tracrRNA fusion that obviates the need for RNase III and crRNA processing in general. Provided herein are CRISPR/Cas9-based engineered systems for use in genome editing and treating genetic diseases. The CRISPR/Cas9-based engineered systems can be designed to target any gene, including genes involved in a genetic disease, aging, tissue regeneration, or wound healing. The CRISPR/Cas9-based gene editing systems can include a Cas9 protein or Cas9 fusion protein and at least one gRNA. In certain embodiments, the system comprises two gRNA molecules. The Cas9 fusion protein may, for example, include a domain that has a different activity that what is endogenous to Cas9, such as a trans-activation domain.

The target gene (e.g., a dystrophin gene, e.g., human dystrophin gene) can be involved in differentiation of a cell or any other process in which activation of a gene can be desired, or can have a mutation such as a frameshift mutation or a nonsense mutation. If the target gene has a mutation that causes a premature stop codon, an aberrant splice acceptor site or an aberrant splice donor site, the CRISPR/Cas9-based gene editing system can be designed to recognize and bind a nucleotide sequence upstream or downstream from the premature stop codon, the aberrant splice acceptor site or the aberrant splice donor site. The CRISPR-Cas9-based system can also be used to disrupt normal gene splicing by targeting splice acceptors and donors to induce skipping of premature stop codons or restore a disrupted reading frame. The CRISPR/Cas9-based gene editing system may or may not mediate off-target changes to protein-coding regions of the genome.

(1) Cas9 Molecules and Cas9 Fusion Proteins

The CRISPR/Cas9-based gene editing system can include a Cas9 protein or a Cas9 fusion protein. Cas9 protein is an endonuclease that cleaves nucleic acid and is encoded by the CRISPR loci and is involved in the Type II CRISPR system. The Cas9 protein can be from any bacterial or archaea species, including, but not limited to, *Streptococcus pyogenes, Staphylococcus aureus (S. aureus), Acidovorax avenae, Actinobacillus pleuropneumoniae, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocyslis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*. In certain embodiments, the Cas9 molecule is a *Streptococcus pyo-*

*genes* Cas9 molecule (also referred herein as "SpCas9"). In certain embodiments, the Cas9 molecule is a *Staphylococcus aureus* Cas9 molecule (also referred herein as "SaCas9").

A Cas9 molecule or a Cas9 fusion protein can interact with one or more gRNA molecule and, in concert with the gRNA molecule(s), localizes to a site which comprises a target domain, and in certain embodiments, a PAM sequence. The ability of a Cas9 molecule or a Cas9 fusion protein to recognize a PAM sequence can be determined, for example, using a transformation assay as known in the art.

In certain embodiments, the ability of a Cas9 molecule or a Cas9 fusion protein to interact with and cleave a target nucleic acid is PAM sequence dependent. A PAM sequence is a sequence in the target nucleic acid. In certain embodiments, cleavage of the target nucleic acid occurs upstream from the PAM sequence. Cas9 molecules from different bacterial species can recognize different sequence motifs (e.g., PAM sequences). In certain embodiments, a Cas9 molecule of *S. aureus* recognizes the sequence motif NNGRR (R=A or G) (SEQ ID NO: 25) and directs cleavage of a target nucleic acid sequence 1 to 10, e.g., 3 to 5, bp upstream from that sequence. In certain embodiments, a Cas9 molecule of *S. aureus* recognizes the sequence motif NNGRRN (R=A or G) (SEQ ID NO: 26) and directs cleavage of a target nucleic acid sequence 1 to 10, e.g., 3 to 5, bp upstream from that sequence. In certain embodiments, a Cas9 molecule of *S. aureus* recognizes the sequence motif NNGRRT (R=A or G) (SEQ ID NO: 27) and directs cleavage of a target nucleic acid sequence 1 to 10, e.g., 3 to 5, bp upstream from that sequence. In certain embodiments, a Cas9 molecule of *S. aureus* recognizes the sequence motif NNGRRV (R=A or G; V=A or C or G) (SEQ ID NO: 28) and directs cleavage of a target nucleic acid sequence 1 to 10, e.g., 3 to 5, bp upstream from that sequence. In the aforementioned embodiments, N can be any nucleotide residue, e.g., any of A, G, C, or T. Cas9 molecules can be engineered to alter the PAM specificity of the Cas9 molecule.

In certain embodiments, the vector encodes at least one Cas9 molecule that recognizes a Protospacer Adjacent Motif (PAM) of either NNGRRT (SEQ ID NO: 27) or NNGRRV (SEQ ID NO: 28). In certain embodiments, the at least one Cas9 molecule is an *S. aureus* Cas9 molecule. In certain embodiments, the at least one Cas9 molecule is a mutant *S. aureus* Cas9 molecule.

Additionally or alternatively, a nucleic acid encoding a Cas9 molecule or Cas9 polypeptide may comprise a nuclear localization sequence (NLS). Nuclear localization sequences are known in the art.

Exemplary codon optimized nucleic acid sequences encoding a Cas9 molecule of *S. aureus*, and optionally containing nuclear localization sequences (NLSs), are set forth in SEQ ID NOs: 31-37. Another exemplary codon optimized nucleic acid sequence encoding a Cas9 molecule of *S. aureus* comprises the nucleotides 1293-4451 of SEQ ID NO: 38.

In some embodiments, the nucleotide sequence encoding a *S. aureus* Cas9 molecule includes the polynucleotide sequence of SEQ ID NO: 37. An amino acid sequence of an *S. aureus* Cas9 molecule is set forth in SEQ ID NO: 39. An amino acid sequence of an *S. aureus* Cas9 molecule is set forth in SEQ ID NO: 40.

Alternatively or additionally, the CRISPR/Cas9-based gene editing system can include a fusion protein. The fusion protein can comprise two heterologous polypeptide domains, wherein the first polypeptide domain comprises a Cas protein and the second polypeptide domain has an activity such as transcription activation activity, transcription repression activity, transcription release factor activity, histone modification activity, nuclease activity, nucleic acid association activity, methylase activity, or demethylase activity. The fusion protein can include a Cas9 protein or a mutated Cas9 protein, fused to a second polypeptide domain that has an activity such as transcription activation activity, transcription repression activity, transcription release factor activity, histone modification activity, nuclease activity, nucleic acid association activity, methylase activity, or demethylase activity.

(a) Transcription Activation Activity

The second polypeptide domain can have transcription activation activity, i.e., a transactivation domain. For example, gene expression of endogenous mammalian genes, such as human genes, can be achieved by targeting a fusion protein of iCas9 and a transactivation domain to mammalian promoters via combinations of gRNAs. The transactivation domain can include a p300 protein, VP16 protein, multiple VP16 proteins, such as a VP48 domain or VP64 domain, or p65 domain of NF kappa B transcription activator activity. For example, the fusion protein may be dCas9-VP64 or dCas9-p300.

(b) Transcription Repression Activity

The second polypeptide domain can have transcription repression activity. The second polypeptide domain can have a Kruppel associated box activity, such as a KRAB domain, ERF repressor domain activity, Mxil repressor domain activity, SID4X repressor domain activity, Mad-SID repressor domain activity or TATA box binding protein activity. For example, the fusion protein may be dCas9-KRAB.

(c) Transcription Release Factor Activity

The second polypeptide domain can have transcription release factor activity. The second polypeptide domain can have eukaryotic release factor 1 (ERF1) activity or eukaryotic release factor 3 (ERF3) activity.

(d) Histone Modification Activity

The second polypeptide domain can have histone modification activity. The second polypeptide domain can have histone deacetylase, histone acetyltransferase, histone demethylase, or histone methyltransferase activity. The histone acetyltransferase may be p300 or CREB-binding protein (CBP) protein, or fragments thereof. For example, the fusion protein may be dCas9-p300.

(e) Nuclease Activity

The second polypeptide domain can have nuclease activity that is different from the nuclease activity of the Cas9 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

(f) Nucleic Acid Association Activity

The second polypeptide domain can have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

(g) Methylase Activity

The second polypeptide domain can have methylase activity, which involves transferring a methyl group to DNA, RNA, protein, small molecule, cytosine or adenine. The second polypeptide domain may include a DNA methyltransferase.

(h) Demethylase Activity

The second polypeptide domain can have demethylase activity. The second polypeptide domain can include an enzyme that remove methyl (CH3-) groups from nucleic acids, proteins (in particular histones), and other molecules. Alternatively, the second polypeptide can covert the methyl group to hydroxymethylcytosine in a mechanism for demethylating DNA. The second polypeptide can catalyze this reaction. For example, the second polypeptide that catalyzes this reaction can be Tet1.

(2) gRNA Targeting the Dystrophin Gene

The CRISPR/Cas9-based gene editing system includes at least one gRNA molecule, for example, two gRNA molecules. The gRNA provides the targeting of a CRISPR/Cas9-based gene editing system. The gRNA is a fusion of two noncoding RNAs: a crRNA and a tracrRNA. The sgRNA may target any desired DNA sequence by exchanging the sequence encoding a 20 by protospacer which confers targeting specificity through complementary base pairing with the desired DNA target. The gRNA mimics the naturally occurring crRNA:tracrRNA duplex involved in the Type II Effector system. This duplex, which may include, for example, a 42-nucleotide crRNA and a 75-nucleotide tracrRNA, acts as a guide for the Cas9 to cleave the target nucleic acid. The "target region", "target sequence," or "protospacer" may be used interchangeably herein and refers to the region of the target gene (e.g., a dystrophin gene) to which the CRISPR/Cas9-based gene editing system targets. The CRISPR/Cas9-based gene editing system may include at least one gRNA, wherein each gRNA targets a different DNA sequence. The target DNA sequences may be overlapping. The target sequence or protospacer is followed by a PAM sequence at the 3' end of the protospacer. Different Type II systems have differing PAM requirements. For example, the *Streptococcus pyogenes* Type II system uses an "NGG" sequence, where "N" can be any nucleotide. In some embodiments, the PAM sequence may be "NGG", where "N" can be any nucleotide. In some embodiments, the PAM sequence may be NNGRRT (SEQ ID NO: 27) or NNGRRV (SEQ ID NO: 28).

The number of gRNA molecules encoded by a presently disclosed genetic construct (e.g., an AAV vector) can be at least 1 gRNA, at least 2 different gRNAs, at least 3 different gRNAs, at least 4 different gRNAs, at least 5 different gRNAs, at least 6 different gRNAs, at least 7 different gRNAs, at least 8 different gRNAs, at least 9 different gRNAs, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA molecules encoded by a presently disclosed genetic construct can be less than 50 gRNAs, less than 45 different gRNAs, less than 40 different gRNAs, less than 35 different gRNAs, less than 30 different gRNAs, less than 25 different gRNAs, less than 20 different gRNAs, less than 19 different gRNAs, less than 18 different gRNAs, less than 17 different gRNAs, less than 16 different gRNAs, less than 15 different gRNAs, less than 14 different gRNAs, less than 13 different gRNAs less than 12 different gRNAs, less than 11 different gRNAs, less than 10 different gRNAs, less than 9 different gRNAs, less than 8 different gRNAs, less than 7 different gRNAs, less than 6 different gRNAs, less than 5 different gRNAs, less than 4 different gRNAs, or less than 3 different gRNAs. The number of gRNAs encoded by a presently disclosed genetic construct can be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs. In certain embodiments, the genetic construct (e.g., an AAV vector) encodes one gRNA molecule, i.e., a first gRNA molecule, and optionally a Cas9 molecule. In certain embodiments, a first genetic construct (e.g., a first AAV vector) encodes one gRNA molecule, i.e., a first gRNA molecule, and optionally a Cas9 molecule, and a second genetic construct (e.g., a second AAV vector) encodes one gRNA molecule, i.e., a second gRNA molecule, and optionally a Cas9 molecule.

The gRNA molecule comprises a targeting domain (also referred to as a targeting sequence), which is a complementary polynucleotide sequence of the target DNA sequence followed by a PAM sequence. The gRNA may comprise a "G" at the 5' end of the targeting domain or complementary polynucleotide sequence. The targeting domain of a gRNA molecule may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. The targeting domain of a gRNA molecule may comprise less than a 40 base pair, less than a 35 base pair, less than a 30 base pair, less than a 25 base pair, less than a 20 base pair, less than a 19 base pair, less than a 18 base pair, less than a 17 base pair, less than a 16 base pair, less than a 15 base pair, less than a 14 base pair, less than a 13 base pair, less than a 12 base pair, less than a 11 base pair, or less than a 10 base pair complementary polynucleotide sequence of the target DNA sequence followed by a PAM sequence. In certain embodiments, the targeting domain of a gRNA molecule has 19-25 nucleotides in length. In certain embodiments, the targeting domain of a gRNA molecule is 20 nucleotides in length. In certain embodiments, the targeting domain of a gRNA molecule is 21 nucleotides in length. In certain embodiments, the targeting domain of a gRNA molecule is 22 nucleotides in length. In certain embodiments, the targeting domain of a gRNA molecule is 23 nucleotides in length.

The gRNA may target a region of the dystrophin gene (DMD) In certain embodiments, the gRNA can target at least one of exons, introns, the promoter region, the enhancer region, the transcribed region of the dystrophin gene. In certain embodiments, the gRNA molecule targets intron 44 of the human dystrophin gene. In certain embodiments, the gRNA molecule targets intron 55 of the human dystrophin gene. In some embodiments, a first gRNA and a second gRNA each target an intron of a human dystrophin gene such that exons 45 through 55 are deleted. A gRNA may bind and target a polynucleotide sequence corresponding to SEQ ID NO: 2 or a fragment thereof or a complement thereof. A gRNA may be encoded by a polynucleotide sequence comprising SEQ ID NO: 2 or a fragment thereof or a complement thereof. The targeting sequence of the gRNA may comprise the polynucleotide of SEQ ID NO: 2 or a fragment thereof, such as a 5' truncation thereof, or a complement thereof. Truncations may be, for example, 1, 2, 3, 4, 5, 6, 7, 8, 9, 10, 11, 12, 13, 14, or 15 nucleotides shorter than SEQ ID NO: 2. In some embodiments, the gRNA may bind and target the polynucleotide of SEQ ID NO: 2. In some embodiments, the gRNA may bind and target a 5' truncation of the polynucleotide of SEQ ID NO: 2. A gRNA may bind and target a polynucleotide sequence corresponding to SEQ ID NO: 3 or a fragment thereof or a complement thereof. A gRNA may be encoded by a polynucleotide sequence comprising SEQ ID NO: 3 or a fragment thereof or a complement thereof. The targeting sequence of the gRNA may comprise the polynucleotide of SEQ ID NO: 3 or a fragment thereof, such as a 5' truncation thereof, or a complement thereof. Truncations may be, for example, 1, 2, 3, 4, 5, 6, 7, 8, 9, 10, 11, 12, 13, 14, or 15 nucleotides shorter than SEQ ID NO: 3. In some embodiments, the gRNA may bind and target the polynucleotide of SEQ ID NO: 3. In some embodiments, the gRNA may bind and target a 5' truncation of the polynucleotide of SEQ ID NO: 3. In some embodiments, a gRNA that binds and targets or is encoded by a polynucleotide sequence comprising or corresponding to SEQ ID NO: 2 or truncation thereof is paired with a gRNA that binds and targets or is encoded by a polynucleotide sequence comprising or corresponding to SEQ ID NO: 3 or truncation thereof.

Single or multiplexed gRNAs can be designed to restore the dystrophin reading frame by targeting the mutational hotspot in exons 45-55 of dystrophin. Following treatment with a presently disclosed vector, dystrophin expression can be restored in Duchenne patient muscle cells in vitro. Human dystrophin was detected in vivo following transplantation of genetically corrected patient cells into immunodeficient mice. Significantly, the unique multiplex gene editing capabilities of the CRISPR/Cas9-based gene editing system enable efficiently generating large deletions of this mutational hotspot region that can correct up to 62% of patient mutations by universal or patient-specific gene editing approaches. In some embodiments, candidate gRNAs are evaluated and chosen based on off-target activity, on-target activity as measured by surveyor, and distance from the exon, (3) gRNA Scaffold The CRISPR/Cas9-based gene editing system includes at least one gRNA scaffold. The gRNA scaffold facilitates Cas9 binding to the gRNA and endonuclease activity. The gRNA scaffold is a polynucleotide sequence that follows the gRNA targeting sequence. Together, the gRNA targeting sequence and gRNA scaffold form one polynucleotide. In some embodiments, the gRNA scaffold comprises the polynucleotide sequence of SEQ ID NO: 4, or a complement thereof. In some embodiments, the gRNA scaffold is encoded by the polynucleotide sequence of SEQ ID NO: 4, or a complement thereof. In some embodiments, the gRNA comprises a polynucleotide that targets a sequence of SEQ ID NO: 2 or SEQ ID NO: 3 or a truncation thereof, and a polynucleotide corresponding to or encoded by the gRNA scaffold of SEQ ID NO: 4.

3. DNA Targeting Compositions

Further disclosed herein are DNA targeting compositions that comprise such genetic constructs. The DNA targeting compositions include at least one gRNA molecule (for example, two gRNA molecules) that targets a dystrophin gene (for example, human dystrophin gene), as described above. The at least one gRNA molecule can bind and recognize a target region. The target regions can be chosen immediately upstream of possible out-of-frame stop codons such that insertions or deletions during the repair process restore the dystrophin reading frame by frame conversion. Target regions can also be splice acceptor sites or splice donor sites, such that insertions or deletions during the repair process disrupt splicing and restore the dystrophin reading frame by splice site disruption and exon exclusion. Target regions can also be aberrant stop codons such that insertions or deletions during the repair process restore the dystrophin reading frame by eliminating or disrupting the stop codon.

In certain embodiments, the presently disclosed DNA targeting composition includes a first gRNA and a second gRNA. The first gRNA molecule and the second gRNA molecule may bind or target a polynucleotide of SEQ ID NO:2 and SEQ ID NO:3, respectively, or a truncation or a complement thereof. The first gRNA molecule and the second gRNA molecule may comprise a polynucleotide corresponding to SEQ ID NO:2 and SEQ ID NO:3, respectively, or a truncation or a complement thereof.

The deletion efficiency of the presently disclosed vectors can be related to the deletion size, i.e., the size of the segment deleted by the vectors. In certain embodiments, the length or size of specific deletions is determined by the distance between the PAM sequences in the gene being targeted (e.g., a dystrophin gene). In certain embodiments, a specific deletion of a segment of the dystrophin gene, which is defined in terms of its length and a sequence it comprises (e.g., exon 51), is the result of breaks made adjacent to specific PAM sequences within the target gene (e.g., a dystrophin gene).

In certain embodiments, the deletion size is about 50 to about 2,000 base pairs (bp), e.g., about 50 to about 1999 bp, about 50 to about 1900 bp, about 50 to about 1800 bp, about 50 to about 1700 bp, about 50 to about 1650 bp, about 50 to about 1600 bp, about 50 to about 1500 bp, about 50 to about 1400 bp, about 50 to about 1300 bp, about 50 to about 1200 bp, about 50 to about 1150 bp, about 50 to about 1100 bp, about 50 to about 1000 bp, about 50 to about 900 bp, about 50 to about 850 bp, about 50 to about 800 bp, about 50 to about 750 bp, about 50 to about 700 bp, about 50 to about 600 bp, about 50 to about 500 bp, about 50 to about 400 bp, about 50 to about 350 bp, about 50 to about 300 bp, about 50 to about 250 bp, about 50 to about 200 bp, about 50 to about 150 bp, about 50 to about 100 bp, about 100 to about 1999 bp, about 100 to about 1900 bp, about 100 to about 1800 bp, about 100 to about 1700 bp, about 100 to about 1650 bp, about 100 to about 1600 bp, about 100 to about 1500 bp, about 100 to about 1400 bp, about 100 to about 1300 bp, about 100 to about 1200 bp, about 100 to about 1150 bp, about 100 to about 1100 bp, about 100 to about 1000 bp, about 100 to about 900 bp, about 100 to about 850 bp, about 100 to about 800 bp, about 100 to about 750 bp, about 100 to about 700 bp, about 100 to about 600 bp, about 100 to about 1000 bp, about 100 to about 400 bp, about 100 to about 350 bp, about 100 to about 300 bp, about 100 to about 250 bp, about 100 to about 200 bp, about 100 to about 150 bp, about 200 to about 1999 bp, about 200 to about 1900 bp, about 200 to about 1800 bp, about 200 to about 1700 bp, about 200 to about 1650 bp, about 200 to about 1600 bp, about 200 to about 1500 bp, about 200 to about 1400 bp, about 200 to about 1300 bp, about 200 to about 1200 bp, about 200 to about 1150 bp, about 200 to about 1100 bp, about 200 to about 1000 bp, about 200 to about 900 bp, about 200 to about 850 bp, about 200 to about 800 bp, about 200 to about 750 bp, about 200 to about 700 bp, about 200 to about 600 bp, about 200 to about 2000 bp, about 200 to about 400 bp, about 200 to about 350 bp, about 200 to about 300 bp, about 200 to about 250 bp, about 300 to about 1999 bp, about 300 to about 1900 bp, about 300 to about 1800 bp, about 300 to about 1700 bp, about 300 to about 1650 bp, about 300 to about 1600 bp, about 300 to about 1500 bp, about 300 to about 1400 bp, about 300 to about 1300 bp, about 300 to about 1200 bp, about 300 to about 1150 bp, about 300 to about 1100 bp, about 300 to about 1000 bp, about 300 to about 900 bp, about 300 to about 850 bp, about 300 to about 800 bp, about 300 to about 750 bp, about 300 to about 700 bp, about 300 to about 600 bp, about 300 to about 3000 bp, about 300 to about 400 bp, or about 300 to about 350 bp. In certain embodiments, the deletion size can be about 118 base pairs, about 233 base pairs, about 326 base pairs, about 766 base pairs, about 805 base pairs, or about 1611 base pairs.

4. Compositions for Genome Editing in Muscle

Disclosed herein is a genetic construct or a composition thereof for genome editing a target gene in a subject, such as, for example, a target gene in skeletal muscle and/or cardiac muscle of a subject. The genetic construct may be a vector. The vector may be a modified AAV vector. The composition may include a polynucleotide sequence encoding a CRISPR/Cas9-based gene editing system. The composition may deliver active forms of CRISPR/Cas9-based gene editing systems to skeletal muscle or cardiac muscle. The presently disclosed genetic constructs can be used in correcting or reducing the effects of mutations in the dystrophin gene involved in genetic diseases and/or other skeletal or cardiac muscle conditions, such as, for example, DMD. The composition may further comprise a donor DNA or a transgene. These compositions may be used in genome editing, genome engineering, and correcting or reducing the effects of mutations in genes involved in genetic diseases and/or other skeletal and/or cardiac muscle conditions.

a. CRISPR/Cas9-Based Gene Editing System for Targeting Dystrophin

A CRISPR/Cas9-based gene editing system specific for dystrophin gene is disclosed herein. The CRISPR/Cas9-based gene editing system may include Cas9 and at least one gRNA to target the dystrophin gene. The CRISPR/Cas9-based gene editing system may bind and recognize a target region. The target regions may be chosen immediately upstream of possible out-of-frame stop codons such that insertions or deletions during the repair process restore the dystrophin reading frame by frame conversion. Target regions may also be splice acceptor sites or splice donor sites, such that insertions or deletions during the repair process disrupt splicing and restore the dystrophin reading frame by splice site disruption and exon exclusion. Target regions may also be aberrant stop codons such that insertions or deletions during the repair process restore the dystrophin reading frame by eliminating or disrupting the stop codon. Target regions may include an intron of the dystrophin gene. Target regions may include an exon of the dystrophin gene.

b. Adeno-Associated Virus Vectors

The composition may also include a viral delivery system. In certain embodiments, the vector is an adeno-associated virus (AAV) vector. The AAV vector is a small virus belonging to the genus Dependovirus of the Parvoviridae family that infects humans and some other primate species. AAV vectors may be used to deliver CRISPR/Cas9-based gene editing systems using various construct configurations. For example, AAV vectors may deliver Cas9 and gRNA expression cassettes on separate vectors or on the same vector. Alternatively, if the small Cas9 proteins, derived from species such as *Staphylococcus aureus* or *Neisseria meningitidis*, are used then both the Cas9 and up to two gRNA expression cassettes may be combined in a single AAV vector within the 4.7 kb packaging limit.

In certain embodiments, the AAV vector is a modified AAV vector. The modified AAV vector may have enhanced cardiac and skeletal muscle tissue tropism. The modified AAV vector may be capable of delivering and expressing the CRISPR/Cas9-based gene editing system in the cell of a mammal. For example, the modified AAV vector may be an AAV-SASTG vector (Piacentino et al. (2012) Human Gene Therapy 23:635-646). The modified AAV vector may deliver nucleases to skeletal and cardiac muscle in vivo. The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5, and AAV/SASTG vectors that efficiently transduce skeletal muscle or cardiac muscle by systemic and local delivery (Seto et al. Current Gene Therapy (2012) 12:139-151). The modified AAV vector may be AAV2i8G9 (Shen et al. J. Biol. Chem. (2013) 288:28814-28823). The AAV vector may be AAVrh74.

5. Methods a. Methods of Genome Editing in Muscle

Disclosed herein are methods of genome editing in subject. The genome editing may be in a skeletal muscle and/or cardiac muscle of a subject. The method may comprise administering to the skeletal muscle and/or cardiac muscle of the subject the system or composition for genome editing, as described above. The genome editing may include correcting a mutant gene or inserting a transgene. Correcting the mutant gene may include deleting, rearranging, or replacing the mutant gene. Correcting the mutant gene may include nuclease-mediated NHEJ or HDR.

b. Methods of Correcting a Mutant Gene and Treating a Subject

Disclosed herein are methods of correcting a mutant gene (e.g., a mutant dystrophin gene, e.g., a mutant human dystrophin gene) in a cell and treating a subject suffering from a genetic disease, such as DMD. The method can include administering to a cell or a subject a presently disclosed system or genetic construct (e.g., a vector) or a composition comprising thereof as described above. The method can comprise administering to the skeletal muscle and/or cardiac muscle of the subject the presently disclosed system or genetic construct (e.g., a vector) or a composition comprising the same for genome editing in skeletal muscle and/or cardiac muscle, as described above. Use of the presently disclosed system or genetic construct (e.g., a vector) or a composition comprising the same to deliver the CRISPR/Cas9-based gene editing system to the skeletal muscle or cardiac muscle may restore the expression of a fully-functional or partially-functional protein with a repair template or donor DNA, which can replace the entire gene or the region containing the mutation. The CRISPR/Cas9-based gene editing system may be used to introduce site-specific double strand breaks at targeted genomic loci. Site-specific double-strand breaks are created when the CRISPR/Cas9-based gene editing system binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

Provided herein is genome editing with a CRISPR/Cas9-based gene editing system without a repair template, which can efficiently correct the reading frame and restore the expression of a functional protein involved in a genetic disease. The disclosed CRISPR/Cas9-based gene editing systems may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cas9-based gene editing systems with an efficient gene editing method for the treatment of genetic diseases caused by mutations in nonessential coding regions that cause frameshifts, premature stop codons, aberrant splice donor sites or aberrant splice acceptor sites.

i) Nuclease Mediated Non-Homologous End Joining

Restoration of protein expression from an endogenous mutated gene may be through template-free NHEJ-mediated DNA repair. In contrast to a transient method targeting the target gene RNA, the correction of the target gene reading frame in the genome by a transiently expressed CRISPR/Cas9-based gene editing system may lead to permanently restored target gene expression by each modified cell and all of its progeny. In certain embodiments, NHEJ is a nuclease mediated NHEJ, which in certain embodiments, refers to NHEJ that is initiated a Cas9 molecule, cuts double stranded DNA. The method comprises administering a presently disclosed genetic construct (e.g., a vector) or a composition comprising thereof to the skeletal muscle or cardiac muscle of the subject for genome editing in skeletal muscle or cardiac muscle.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment, NHEJ-based gene correction using a CRISPR/Cas9-based gene editing system, as well as other engineered nucleases including meganucleases and zinc finger nucleases, may be combined with other existing ex vivo and in vivo platforms for cell- and gene-based therapies, in addition to the plasmid electroporation approach described here. For example, delivery of a CRISPR/Cas9-based gene editing system by mRNA-based gene transfer or as purified cell permeable proteins could enable a DNA-free genome editing approach that would circumvent any possibility of insertional mutagenesis.

ii) Homology-Directed Repair

Restoration of protein expression from an endogenous mutated gene may involve homology-directed repair. The method as described above further includes administrating a donor template to the cell. The donor template may include a nucleotide sequence encoding a full-functional protein or a partially-functional protein. For example, the donor template may include a miniaturized dystrophin construct, termed minidystrophin ("minidys"), a full-functional dystrophin construct for restoring a mutant dystrophin gene, or a fragment of the dystrophin gene that after homology-directed repair leads to restoration of the mutant dystrophin gene.

iii) Methods of Correcting a Mutant Gene and Treating a Subject Using CRISPR/Cas9

The present disclosure is also directed to genome editing with the CRISPR/Cas9-based gene editing system to restore the expression of a full-functional or partially-functional protein with a repair template or donor DNA, which can replace the entire gene or the region containing the mutation. The CRISPR/Cas9-based gene editing system may be used to introduce site-specific double strand breaks at targeted genomic loci. Site-specific double-strand breaks are created when the CRISPR/Cas9-based gene editing system binds to a target DNA sequences using the gRNA, thereby permitting cleavage of the target DNA. The CRISPR/Cas9-based gene editing system has the advantage of advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with CRISPR/Cas9-based gene editing system without a repair template, which can efficiently correct the reading frame and restore the expression of a functional protein involved in a genetic disease. The disclosed CRISPR/Cas9-based gene editing system and methods may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cas9-based gene editing system with an efficient gene editing method for the treatment of genetic diseases caused by mutations in nonessential coding regions that cause frameshifts, premature stop codons, aberrant splice donor sites or aberrant splice acceptor sites.

The present disclosure provides methods of correcting a mutant gene in a cell and treating a subject suffering from a genetic disease, such as DMD. The method may include administering to a cell or subject a CRISPR/Cas9-based gene editing system, a polynucleotide or vector encoding said CRISPR/Cas9-based gene editing system, or composition of said CRISPR/Cas9-based gene editing system as described above. The method may include administering a CRISPR/Cas9-based gene editing system, such as administering a Cas9 protein or Cas9 fusion protein containing a second domain having nuclease activity, a nucleotide sequence encoding said Cas9 protein or Cas9 fusion protein, and/or at least one gRNA, wherein the gRNAs target different DNA sequences. The target DNA sequences may be overlapping. The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNA, at least 15 different gRNA, at least 20 different gRNA, at least 30 different gRNA, or at least 50 different gRNA, as described above. The method may involve homology-directed repair or non-homologous end joining.

c. Methods of Treating Disease

The present disclosure is directed to a method of treating a subject in need thereof. The method comprises administering to a tissue of a subject the presently disclosed system or genetic construct (e.g., a vector) or a composition comprising thereof, as described above. In certain embodiments, the method may comprise administering to the skeletal muscle or cardiac muscle of the subject the presently disclosed system or genetic construct (e.g., a vector) or composition comprising thereof, as described above. In certain embodiments, the method may comprise administering to a vein of the subject the presently disclosed system or genetic construct (e.g., a vector) or composition comprising thereof, as described above. In certain embodiments, the subject is suffering from a skeletal muscle or cardiac muscle condition causing degeneration or weakness or a genetic disease. For example, the subject may be suffering from Duchenne muscular dystrophy, as described above.

i) Duchenne Muscular Dystrophy

The method, as described above, may be used for correcting the dystrophin gene and recovering full-functional or partially-functional protein expression of said mutated dystrophin gene. In some aspects and embodiments the disclosure provides a method for reducing the effects (e.g., clinical symptoms/indications) of DMD in a patient. In some aspects and embodiments the disclosure provides a method for treating DMD in a patient. In some aspects and embodiments the disclosure provides a method for preventing DMD in a patient. In some aspects and embodiments the disclosure provides a method for preventing further progression of DMD in a patient.

6. Constructs and Plasmids

The compositions, as described above, may comprise one or more genetic constructs that encode the CRISPR/Cas9-based gene editing system, as disclosed herein. The genetic construct, such as a plasmid, may comprise a nucleic acid that encodes the CRISPR/Cas9-based gene editing system, such as the Cas9 protein and/or Cas9 fusion proteins and/or at least one of the gRNAs. The compositions, as described above, may comprise genetic constructs that encodes the modified AAV vector and a nucleic acid sequence that encodes the CRISPR/Cas9-based gene editing system, as disclosed herein. The genetic construct, such as a plasmid, may comprise a nucleic acid that encodes the CRISPR/Cas9-based gene editing system. The compositions, as described above, may comprise genetic constructs that encodes the modified lentiviral vector, as disclosed herein.

The genetic construct, such as a recombinant plasmid or recombinant viral particle, may comprise a nucleic acid that encodes the Cas9-fusion protein and at least one gRNA. In some embodiments, the genetic construct may comprise a nucleic acid that encodes the Cas9-fusion protein and at least two different gRNAs. In some embodiments, the genetic construct may comprise a nucleic acid that encodes the Cas9-fusion protein and more than two different gRNAs. In some embodiments, the genetic construct may comprise a promoter that operably linked to the nucleotide sequence encoding the at least one gRNA molecule and/or a Cas9 molecule. In some embodiments, the promoter is operably linked to the nucleotide sequence encoding a first gRNA molecule, a second gRNA molecule, and/or a Cas9 molecule. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation In certain embodiments, the genetic construct is a vector. The vector can be an Adeno-associated virus (AAV) vector, which encode at least one Cas9 molecule and at least one gRNA molecule; the vector is capable of expressing the at least one Cas9 molecule and the at least gRNA molecule, in the cell of a mammal. The vector can be a plasmid. The vectors can be used for in vivo gene therapy. The vector may be recombinant. The vector may comprise heterologous nucleic acid encoding the fusion protein, such as the Cas9-fusion protein or CRISPR/Cas9-based gene editing system. The vector may be a plasmid. The vector may be useful for transfecting cells with nucleic acid encoding the Cas9-fusion protein or CRISPR/Cas9-based gene editing system, which the transformed host cell is cultured and maintained under conditions wherein expression of the Cas9-fusion protein or the CRISPR/Cas9-based gene editing system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based gene editing system and may further comprise an initiation codon, which may be upstream of the CRISPR/Cas9-based gene editing system coding sequence, and a stop codon, which may be downstream of the CRISPR/Cas9-based gene editing system coding sequence. The initiation and termination codon may be in frame with the CRISPR/Cas9-based gene editing system coding sequence. The vector may also comprise a promoter that is operably linked to the CRISPR/Cas9-based gene editing system coding sequence. The promoter that is operably linked to the CRISPR/Cas9-based gene editing system coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, a U6 promoter, such as the human U6 promoter, or a Rous sarcoma virus (RSV) promoter. The promoter may also be a promoter from a human gene such as human ubiquitin C (hUbC), human actin, human myosin, human hemoglobin, human muscle creatine, or human metallothionein. The promoter may also be a tissue specific promoter, such as a muscle or skin specific promoter, natural or synthetic. Examples of such promoters are described in US Patent Application Publication Nos. US20040175727 and US20040192593, the contents of which are incorporated herein in their entirety. Examples of muscle-specific promoters include a Spc5-12 promoter (described in US Patent Application Publication No. US 20040192593, which is incorporated by reference herein in its entirety: Hakim et al. Mol. Ther. Methods Clin. Dev. (2014) 1:14002; and Lai et al. Hum Mol Genet. (2014) 23(12): 3189-3199), a MHCK7 promoter (described in Salva et al., Mol. Ther. (2007) 15:320-329), a CK8 promoter (described in Park et al. PLoS ONE (2015) 10(4): e0124914), and a CK8e promoter (described in Muir et al., Mol. Ther. Methods Clin. Dev. (2014) 1:14025). In some embodiments, the expression of the gRNA and/or Cas9 protein is driven by tRNAs.

Each of the polynucleotide sequences encoding the gRNA molecule and/or Cas9 molecule may each be operably linked to a promoter. The promoters that are operably linked to the gRNA molecule and/or Cas9 molecule may be the same promoter. The promoters that are operably linked to the gRNA molecule and/or Cas9 molecule may be different promoters. The promoter may be a constitutive promoter, an inducible promoter, a repressible promoter, or a regulatable promoter. The promoter may be a tissue specific promoter. The tissue specific promoter may be a muscle specific promoter. Examples of muscle-specific promoters may include a MHCK7 promoter, a CK8 promoter, and a Spc512 promoter. The promoter may be a CK8 promoter, a Spc512 promoter, a MHCK7 promoter, for example.

The vector may also comprise a polyadenylation signal, which may be downstream of the CRISPR/Cas9-based gene editing system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, CA).

The vector may also comprise an enhancer upstream of the CRISPR/Cas9-based gene editing system, i.e., the Cas9 protein or Cas9 fusion protein coding sequence or sgRNAs, or the CRISPR/Cas9-based gene editing system. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based gene editing system, including the nucleic acid sequence encoding the Cas9 protein or Cas9 fusion protein and the nucleic acid sequence encoding the at least one gRNA.

7. Pharmaceutical Compositions

The presently disclosed subject matter provides for compositions comprising the above-described genetic constructs. The pharmaceutical compositions as detailed herein can be formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing in skeletal muscle or cardiac muscle at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example International Patent Publication No. WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

8. Methods of Delivery

Provided herein is a method for delivering the presently disclosed genetic construct (e.g., a vector) or a composition thereof to a cell. The delivery of the compositions may be the transfection or electroporation of the composition as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product #D8537 (PBS), Invitrogen OptiMEM I (OM), or Amaxa Nucleofector solution V (N.V.). Transfections may include a transfection reagent, such as Lipofectamine 2000.

Upon delivery of the presently disclosed genetic construct or composition to the tissue, and thereupon the vector into the cells of the mammal, the transfected cells will express the gRNA molecule(s) and the Cas9 molecule. The genetic construct or composition may be administered to a mammal to alter gene expression or to re-engineer or alter the genome. For example, the genetic construct or composition may be administered to a mammal to correct the dystrophin gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

The genetic construct (e.g., a vector) encoding the gRNA molecule(s) and the Cas9 molecule can be delivered to the mammal by DNA injection (also referred to as DNA vaccination) with and without in vivo electroporation, liposome mediated, nanoparticle facilitated, and/or recombinant vectors. The recombinant vector can be delivered by any viral mode. The viral mode can be recombinant lentivirus, recombinant adenovirus, and/or recombinant adeno-associated virus.

A presently disclosed genetic construct (e.g., a vector) or a composition comprising thereof can be introduced into a cell to genetically correct a dystrophin gene (e.g., human dystrophin gene). In certain embodiments, a presently disclosed genetic construct (e.g., a vector) or a composition comprising thereof is introduced into a myoblast cell from a DMD patient. In certain embodiments, the genetic construct (e.g., a vector) or a composition comprising thereof is introduced into a fibroblast cell from a DMD patient, and the genetically corrected fibroblast cell can be treated with MyoD to induce differentiation into myoblasts, which can be implanted into subjects, such as the damaged muscles of a subject to verify that the corrected dystrophin protein is functional and/or to treat the subject. The modified cells can also be stem cells, such as induced pluripotent stem cells, bone marrow-derived progenitors, skeletal muscle progenitors, human skeletal myoblasts from DMD patients, CD 133+ cells, mesoangioblasts, and MyoD- or Pax7-transduced cells, or other myogenic progenitor cells. For example, the CRISPR/Cas9-based gene editing system may cause neuronal or myogenic differentiation of an induced pluripotent stem cell.

9. Routes of Administration

The presently disclosed genetic constructs (e.g., vectors) or a composition comprising thereof may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. In certain embodiments, the presently disclosed genetic construct (e.g., a vector) or a composition is administered to a subject (e.g., a subject suffering from DMD) intramuscularly, intravenously or a combination thereof. For veterinary use, the presently disclosed genetic constructs (e.g., vectors) or compositions may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The presently disclosed genetic construct (e.g., a vector) or a composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus. The composition may be injected into the skeletal muscle or cardiac muscle. For example, the composition may be injected into the tibialis anterior muscle or tail.

In some embodiments, the presently disclosed genetic construct (e.g., a vector) or a composition thereof is administered by 1) tail vein injections (systemic) into adult mice; 2) intramuscular injections, for example, local injection into a muscle such as the TA or gastrocnemius in adult mice; 3) intraperitoneal injections into P2 mice; or 4) facial vein injection (systemic) into P2 mice.

10. Cell Types

Any of these delivery methods and/or routes of administration can be utilized with a myriad of cell types. Cell types may include, but are not limited to, immortalized myoblast cells, such as wild-type and DMD patient derived lines, for example Δ48-50 DMD, DMD 6594 (del48-50), DMD 8036 (del48-50), C25C14 and DMD-7796 cell lines, primal DMD dermal fibroblasts, induced pluripotent stem cells, bone marrow-derived progenitors, skeletal muscle progenitors, human skeletal myoblasts from DMD patients, CD 133+ cells, mesoangioblasts, cardiomyocytes, hepatocytes, chondrocytes, mesenchymal progenitor cells, hematopoietic stem cells, smooth muscle cells, and MyoD- or Pax7-transduced cells, or other myogenic progenitor cells. Immortalization of human myogenic cells can be used for clonal derivation of genetically corrected myogenic cells. Cells can be modified ex vivo to isolate and expand clonal populations of immortalized DMD myoblasts that include a genetically corrected dystrophin gene and are free of other nuclease-introduced mutations in protein coding regions of the genome. Alternatively, transient in vivo delivery of CRISPR/Cas9-based systems by non-viral or non-integrating viral gene transfer, or by direct delivery of purified proteins and gRNAs containing cell-penetrating motifs may enable highly specific correction in situ with minimal or no risk of exogenous DNA integration.

11. Kits

Provided herein is a kit, which may be used to correct a mutated dystrophin gene. The kit comprises at least a gRNA for correcting a mutated dystrophin gene and instructions for using the CRISPR/Cas9-based gene editing system. Also provided herein is a kit, which may be used for genome editing of a dystrophin gene in skeletal muscle or cardiac muscle. The kit may comprise genetic constructs (e.g., vectors) or a composition comprising thereof for genome editing in skeletal muscle or cardiac muscle, as described above, and instructions for using said composition.

Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an Internet site that provides the instructions.

The genetic constructs (e.g., vectors) or a composition comprising thereof for correcting a mutated dystrophin or genome editing of a dystrophin gene in skeletal muscle or cardiac muscle may include a modified AAV vector that includes a gRNA molecule(s) and a Cas9 molecule, as described above, that specifically binds and cleaves a region of the dystrophin gene. The CRISPR/Cas9-based gene editing system, as described above, may be included in the kit to specifically bind and target a particular region in the mutated dystrophin gene. The kit may further include donor DNA, a different gRNA, or a transgene, as described above.

12. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure details multiple embodiments and aspects, illustrated by the following non-limiting examples.

Example 1

Dual Vector System

Figure 6:
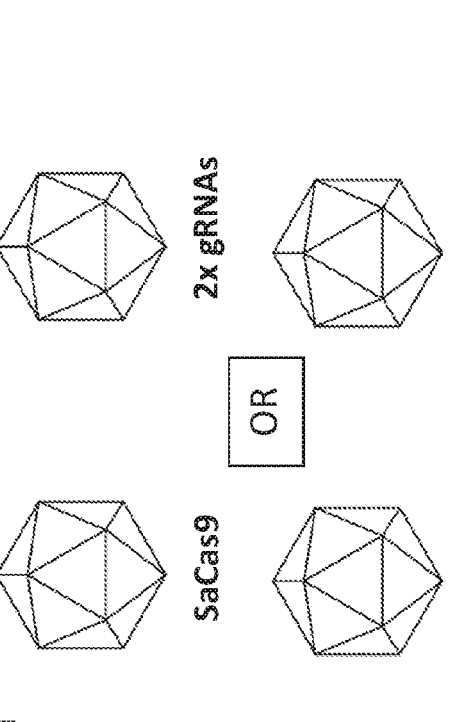
FIG. 6 shows the traditional two vector system as compared to the one vector system. Advantages to the one vector system may include: having all necessary editing components on a single vector, ability to increase effective dose, streamlining of other vector production (single therapeutic agent), use/incorporation of muscle-specific promoters (CK8, Spc512, MHCK7), and ability to target combinations of exons and large deletions (by changing guide sequences).
Figure 6:
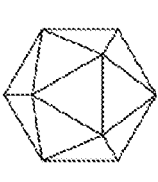
Figure 7:
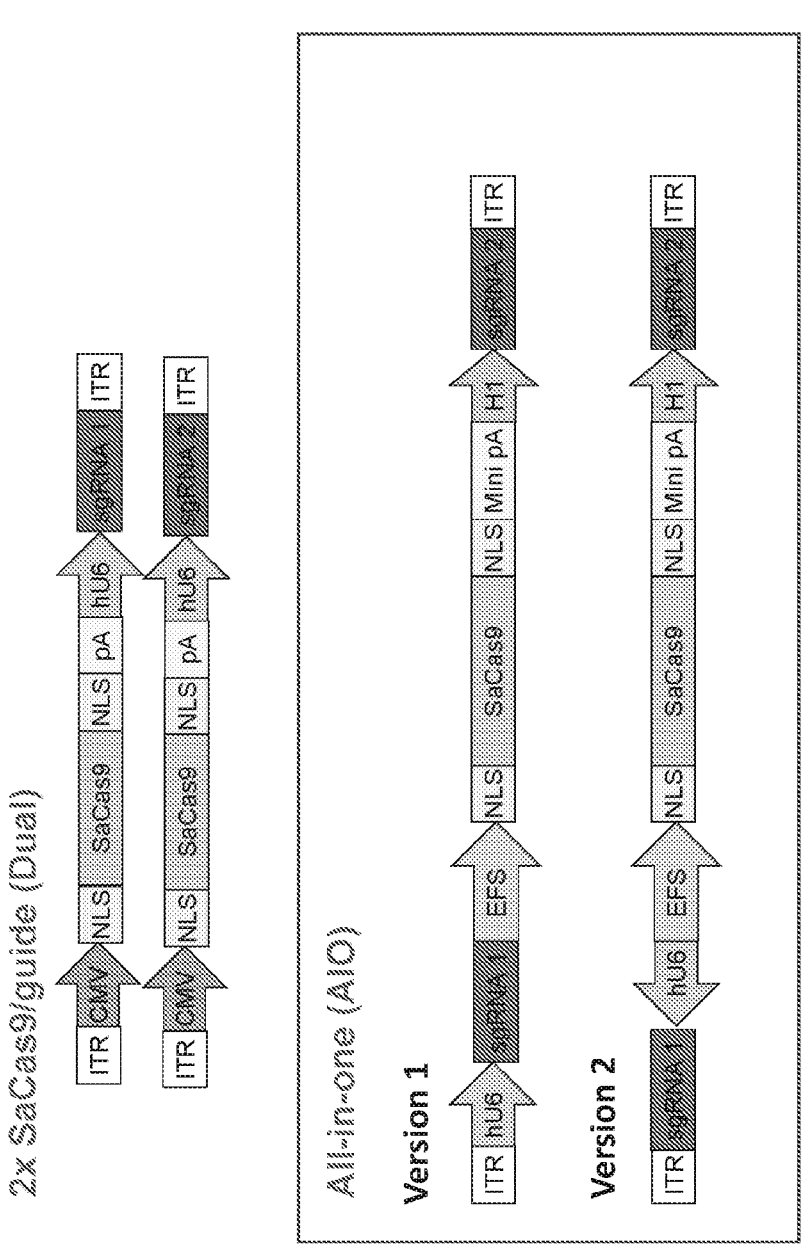
FIG. 7 shows a vector design comparison. The all-in-one vector components (total packaged DNA<4.8 kb include: SaCas7 (~3.2 kb); mini polyadenylation signal (60 bp) or bGH polyadenylation signal (232 bp); constitutive EFS promoter (252 bp) or muscle specific promoter).

Conventional CRISPR/Cas9 systems for the treatment of DMD typically include more than one vector (FIG. 6, FIG. 7). For example, one vector may encode a Cas9 protein, and a second vector may encode two gRNAs. As another example, one vector may encode a Cas9 protein and a first gRNA, and a second vector may encode a Cas9 protein and a second gRNA.

Figure 3:
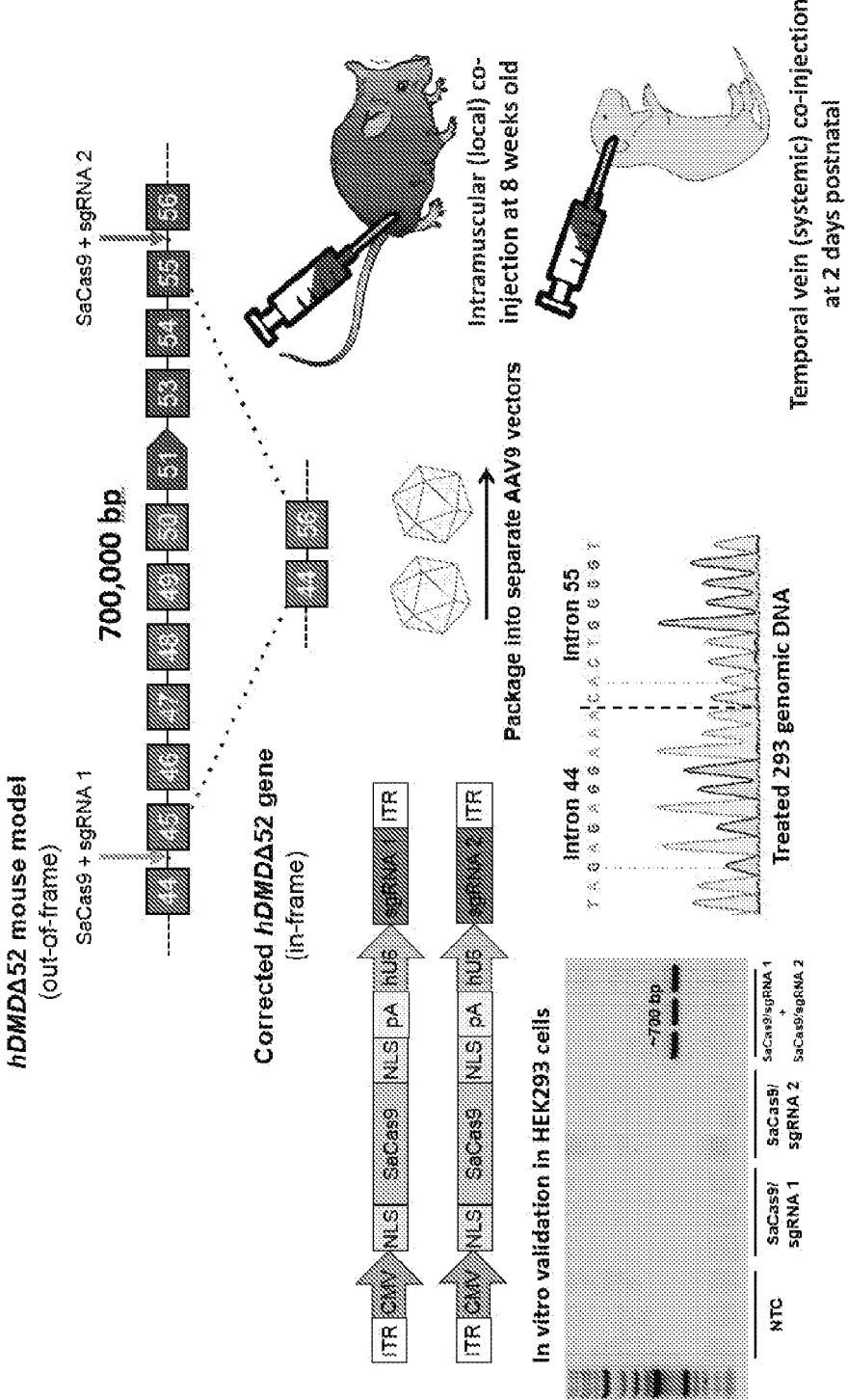
FIG. 3 shows excision of exons 45 through 55 of dystrophin. This system is being tested in a humanized mouse carrying the human gene with a deletion of exon 52.
Figure 4:
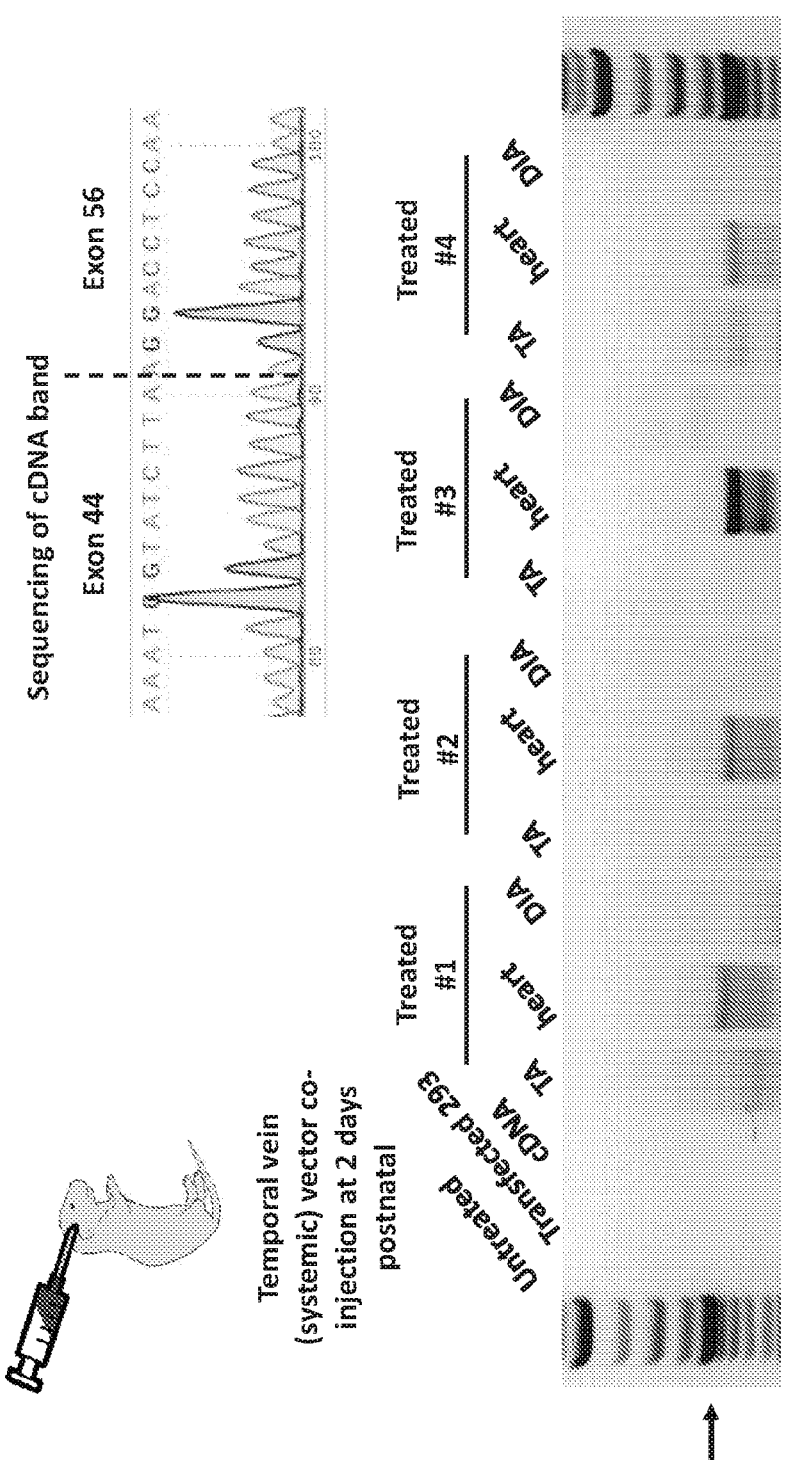
FIG. 4 shows injection of a system to excise exons 45 through 55 of dystrophin in neonatal mice. Neonatal mice were systemically injected at 2 days postnatal (P2). Muscles were harvested 8 weeks post-treatment. PCR bands show the intended deletion.
Figure 5:
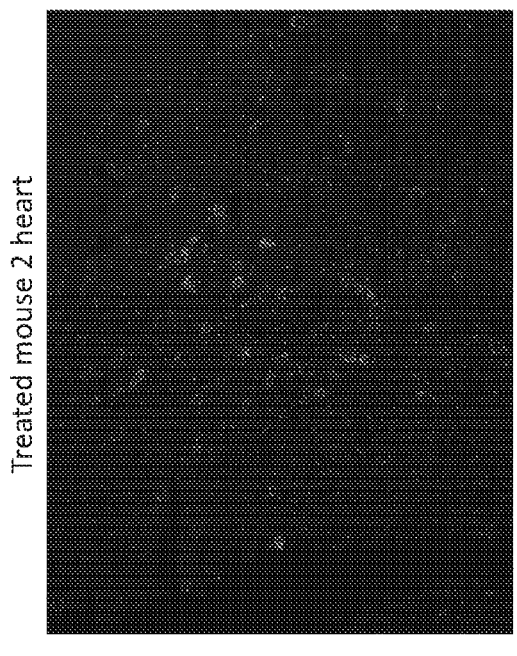
FIG. 5 shows dystrophin expression in systemically treated mice. 10× magnification, dual vector P2 injected, 8 weeks post-treatment.
Figure 5:
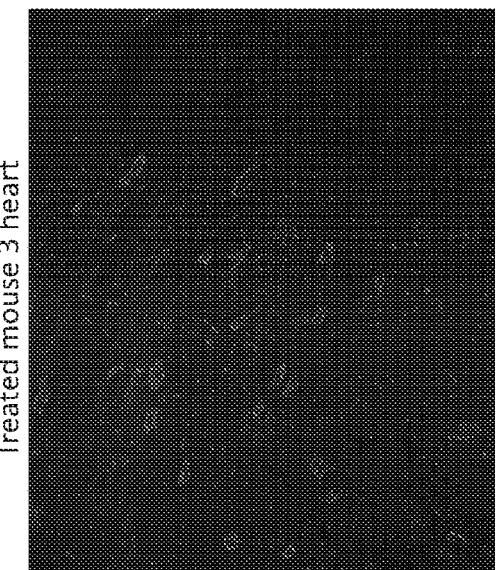
Figure 5:
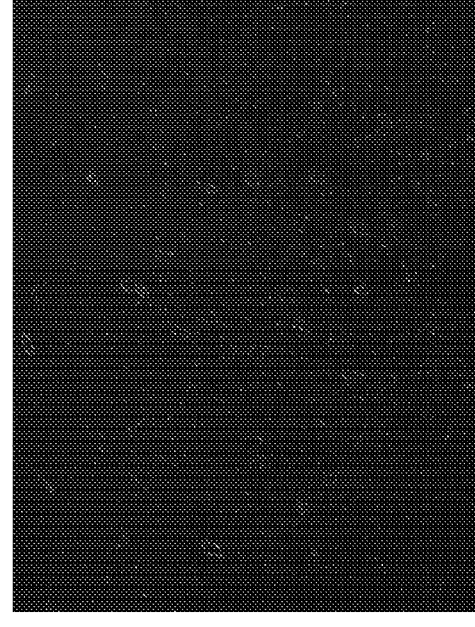
Figure 10:
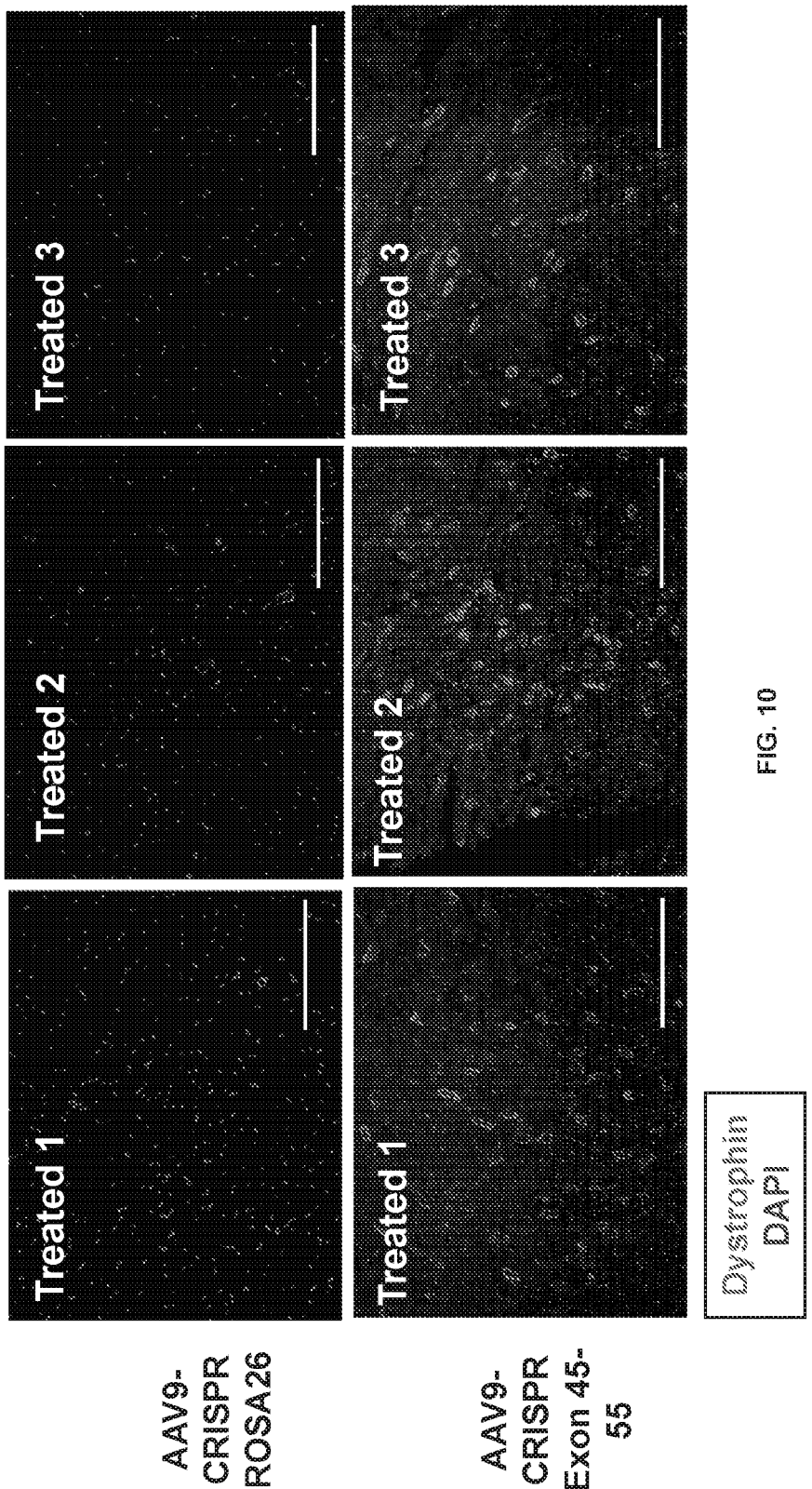
FIG. 10 are images of cardiac muscle cells from neonatal hDMDΔ52/mdx mice injected with either AAV-CRISPR targeting a control locus (top panel) or targeting exon 45-55 (bottom panel). Cells were harvested 8 weeks post injection. Cells were stained with DAPI or for dystrophin. 10× magnification, scale bar=200 μm.

A schematic of an experiment that uses multiple vectors to excise exons 45-55 of dystrophin in mice is shown in FIG. 3 with results shown in FIG. 4, FIG. 5, and FIG. 10. Neonatal mice were treated with the dual vector system via systemic/temporal vein injection. At 8 weeks post-treatment, tissue was harvested. As shown in FIG. 4, PCR and sequencing confirmed the deletion of the mutational hotspot exon 45-55. Additional results are shown in FIG. 10 with either AAV-CRISPR targeting a control locus (FIG. 10, top panel) or targeting exon 45-55 (FIG. 10, bottom panel),showing that widespread dystrophin expression was observed in cardiac muscle after deletion of exon 45-55, but not in sham vector-treated mice.

Example 2

Validation of Therapeutic Approach for Dual Vector System

Figure 9A:
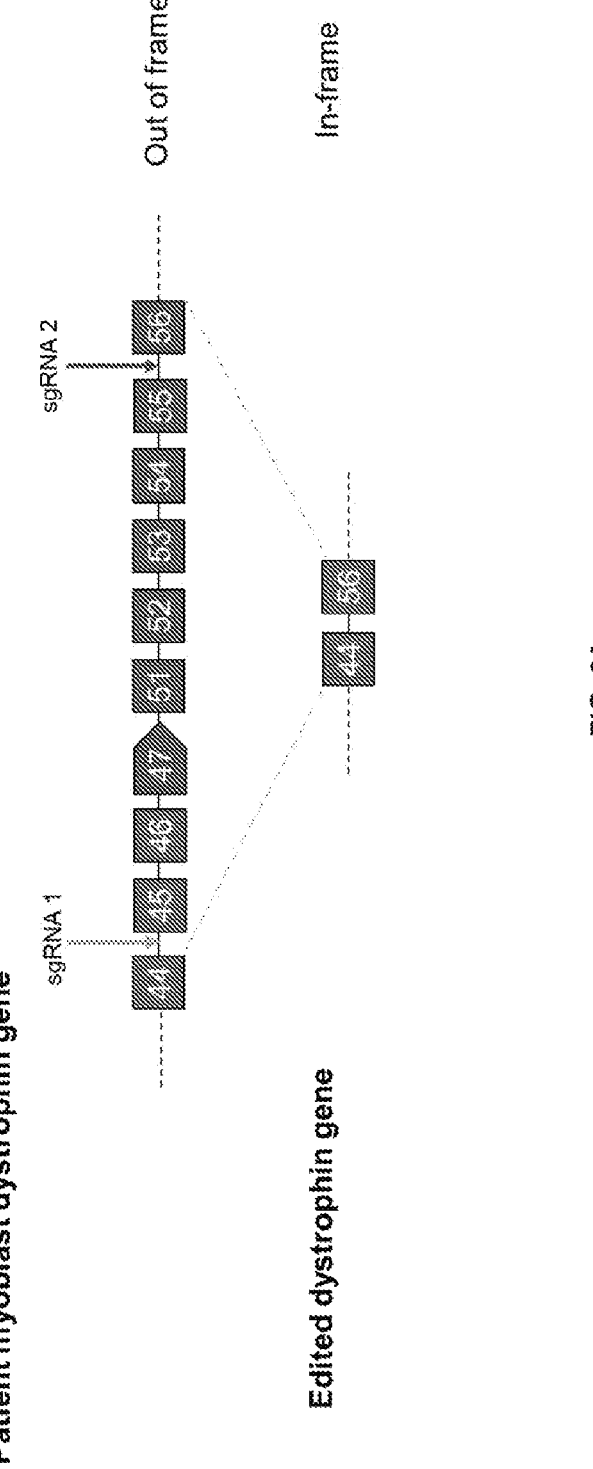
FIG. 9A is a schematic diagram of the dystrophin gene from immortalized myoblasts isolated from a DMD patient, showing the deletion of exons 48-50.

Additional validation of the CRISPR-based approach to restore functional dystrophin gene with the dual vectors of Example 1 was performed using immortalized myoblasts isolated from a DMD patient. The immortalized myoblasts contained a deletion of exons 48-50, creating an out-of-frame mutation (FIG. 9A). Patient myoblasts were transfected with the same AAV plasmids used in the HEK293 in vitro experiment in Example 1.

Figure 9B:
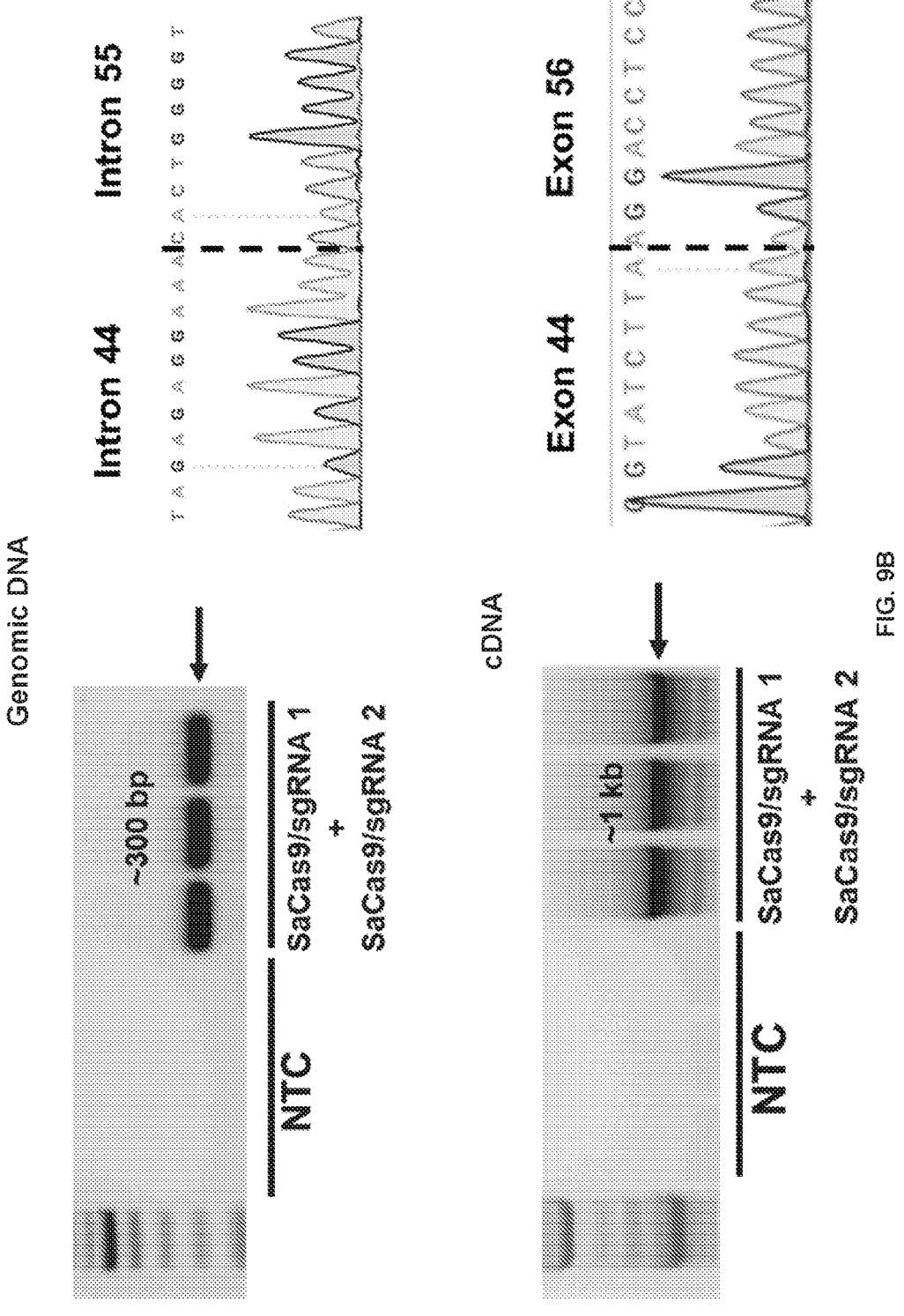
FIG. 9B shows results from deletion PCR of genomic DNA and cDNA from treated DMD patients, indicating that exon 45-55 was effectively deleted with vectors as detailed herein.
Figure 9C:
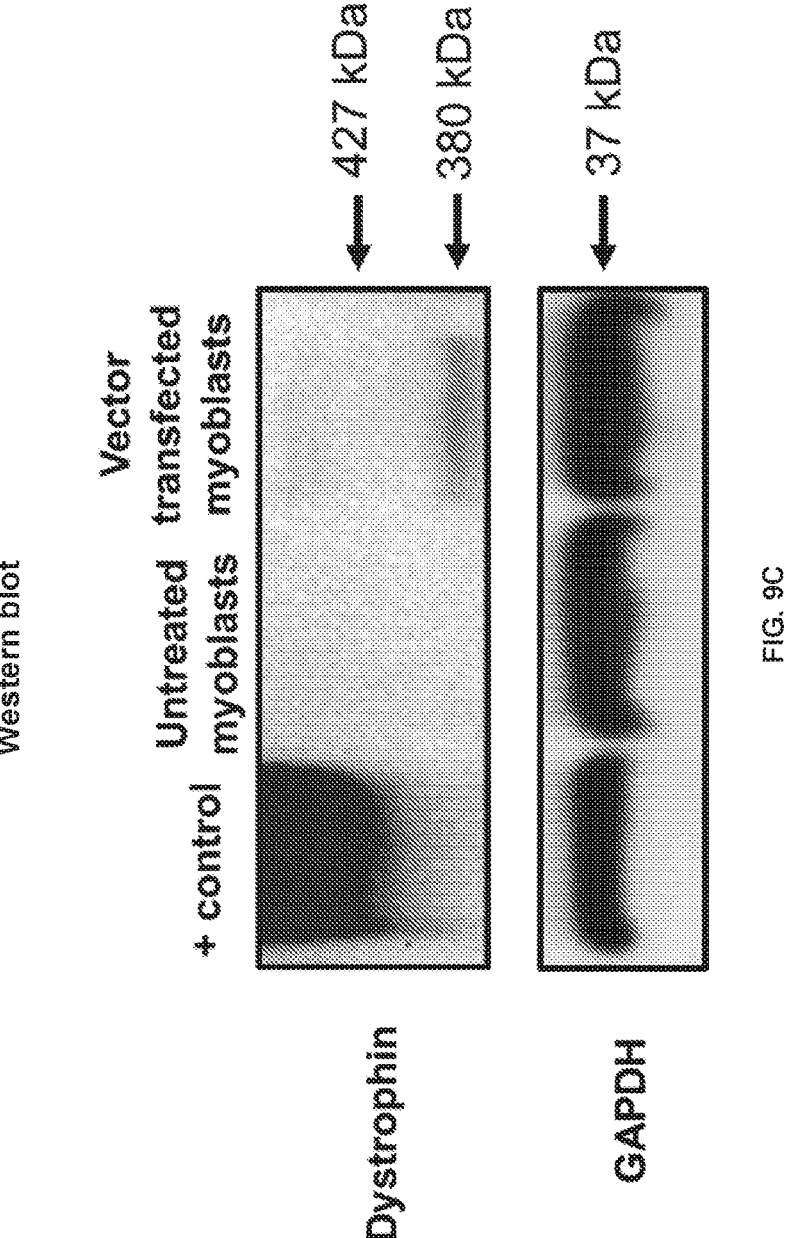
FIG. 9C is a Western blot of cell lysates, showing that untreated myoblasts produced no dystrophin protein, while transfected myoblasts expressed a smaller dystrophin protein compared to the positive control, consistent with hotspot deletion.

Deletion PCR of genomic DNA and cDNA revealed that exon 45-55 was effectively deleted, which was confirmed by Sanger sequencing (FIG. 9B). Western blot of cell lysates showed that untreated myoblasts produced no dystrophin protein, while transfected myoblasts expressed a smaller dystrophin protein compared to the positive control, consistent with hotspot deletion (FIG. 9C). These results additionally provided in vitro validation that the dual vector constructs can be used to edit a human mutation and restore dystrophin expression.

Example 3

Components for An-in-One Vectors

Figure 8:
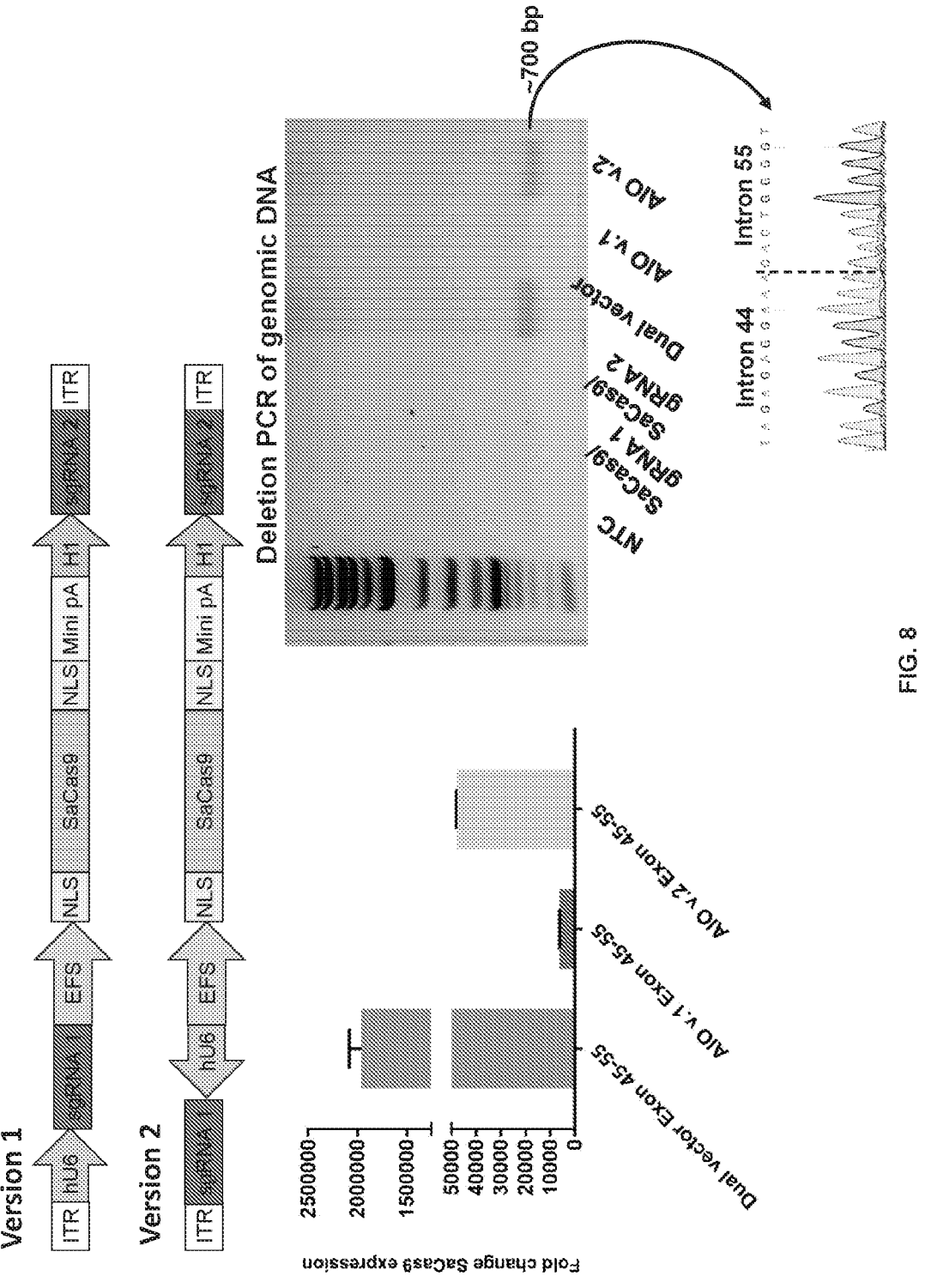
FIG. 8 shows the all-in-one vector for deletion of exons 45-55 and in vitro analyses in HEK293s.
Figure 12:
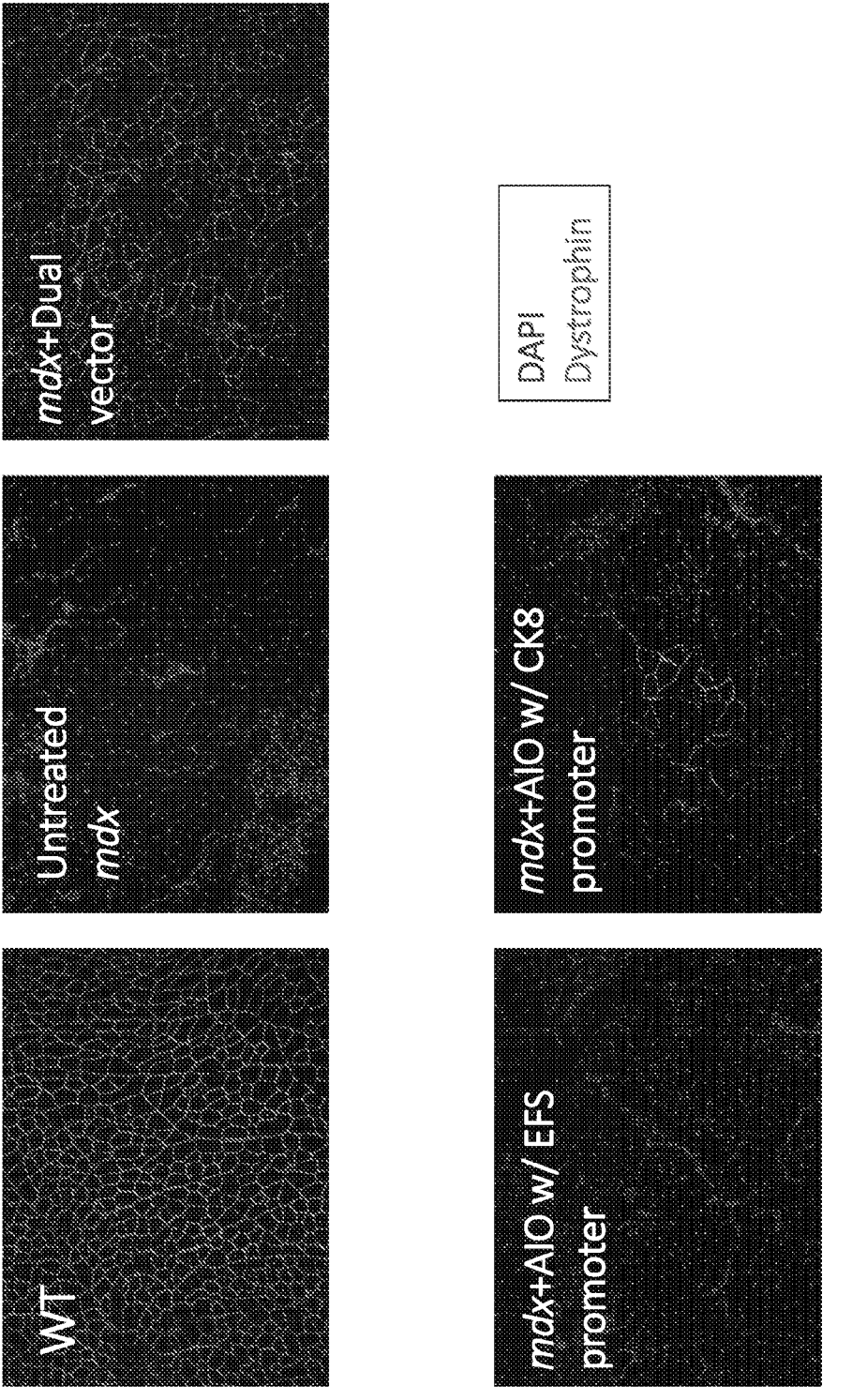
FIG. 12 are images of TA muscle cells 8 weeks after injection with the vectors as indicated, at 10× magnification.
Figure 13:
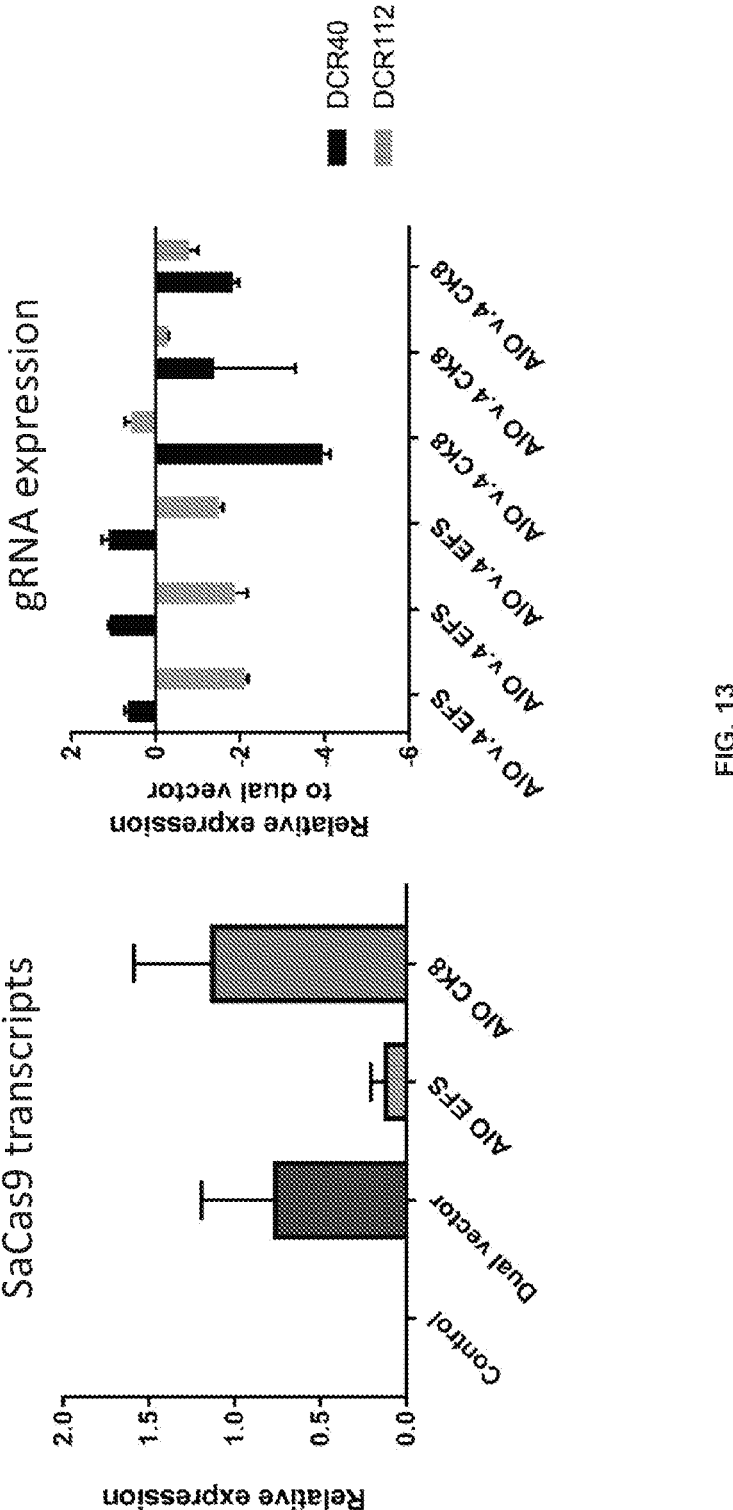
FIG. 13 are graphs showing SaCas9 and gRNA in vivo expression resulting from treatment with the indicated all-in-one vectors, as determined by qRT-PCR using TA samples 8 weeks post-injection, N=3-4.
Figure 14:
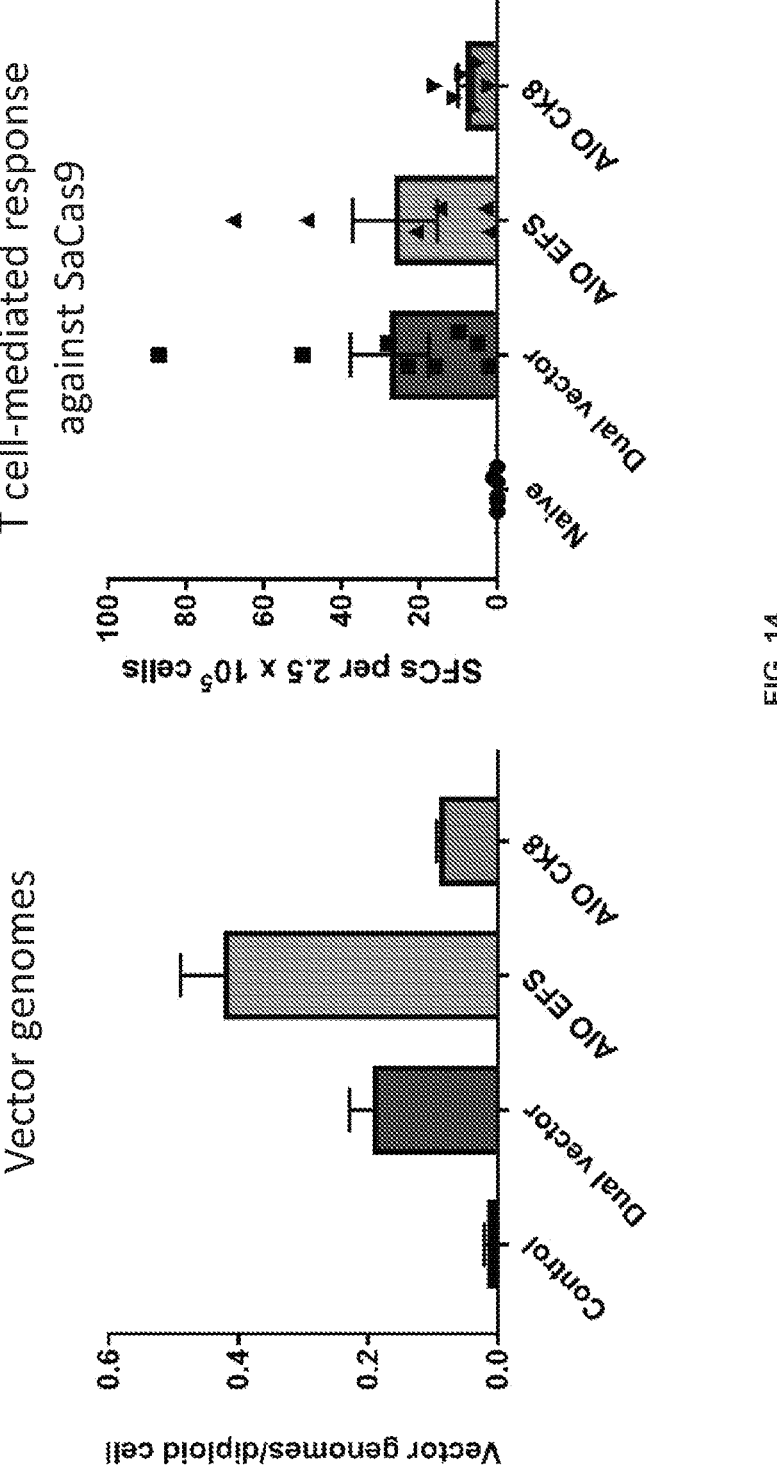
FIG. 14 are graphs showing the stability of all-in-one (AIO) vectors in vivo. The left graph are results from qPCR using TA samples 8 weeks post-injection. The right graphs are results from IFN-gamma ELISpot assay against SaCas9. N=3-4 for both.

A one-vector CRISPR/Cas9 system was developed for the treatment of DMD (FIG. 6, FIG. 7). Advantages to a one vector system may include having all necessary editing components on a single vector, ability to increase effective dose, streamlining of other vector production (single therapeutic agent), use/incorporation of muscle-specific promoters (for example, CK8, Spc512, MHCK7), and ability to target combinations of exons and large deletions (for example, by changing guide sequences). A schematic diagram of the all-in-one vectors developed is shown in FIG. 8. Sequences included in some or all of the herein described all-in-one vectors are shown in TABLE 1. FIG. 12, FIG. 13, and FIG. 14 show results from testing these constructs in the mdx mouse. The all-in-one vectors are further detailed in Examples 4-7.

TABLE 1

| Component | Sequence |
| --- | --- |
| AAV ITR | CCTGCAGGCAGCTGCGCGCTCGCTCGCTCACTGAGGCCGCCC GGGCGTCGGGCGACCTTTGGTCGCCCGGCCTCAGTGAGCGAG CGAGCGCGCAGAGAGGGAGTGGCCAACTCCATCACTAGGGGT TCCT (SEQ ID NO: 1) |

TABLE 1-continued

| Component | Sequence |
|-----------|----------|
| JCR143: guide sequence RNA targeting human dystrophin intron 44 region | ACATTTCCTCTCTATACAAATG (SEQ ID NO: 2) |
| JCR120: guide sequence RNA targeting human dystrophin intron 55 region | ATATAGTAATGAAATTATTGGCAC (SEQ ID NO: 3) |
| SaCas9 guide RNA scaffold | TCTCGCCAACAAGTTGACGAGATAAACACGGCATTTTGCCTTGT TTTAGTAGATTCTGTTTCCAGAGTACTAAAAC (SEQ ID NO: 4) |
| U6 promoter | GGTGTTTCGTCCTTTCCACAAGATATATAAAGCCAAGAAATCGA AATACTTTCAAGTTACGGTAAGCATATGATAGTCCATTTTAAAAC ATAATTTTAAAACTGCAAACTACCCAAGAAATTATTACTTTCTAC GTCACGTATTTTGTACTAATATCTTTGTGTTTACAGTCAAATTAA TTCCAATTATCTCTCTAACAGCCTTGTATCGTATATGCAAATATG AAGGAATCATGGGAAATAGGCCCTC (SEQ ID NO: 5) |
| H1 promoter | GAACGCTGACGTCATCAACCCGCTCCAAGGAATCGCGGGCCC AGTGTCACTAGGCGGGAACACCCAGCGCGCGTGCGCCCTGGC AGGAAGATGGCTGTGAGGGACAGGGGAGTGGCGCCCTGCAAT ATTTGCATGTCGCTATGTGTTCTGGGAAATCACCATAAACGTGA AATGTCTTTGGATTTGGGAATCTTATAAGTTCTGTATGAGACCA C (SEQ ID NO: 6) |
| EFS promoter | TCGAGTGGCTCCGGTGCCCGTCAGTGGGCAGAGCGCACATCG CCCACAGTCCCCGAGAAGTTGGGGGGAGGGGTCGGCAATTGA ACCGGTGCCTAGAGAAGGTGGCGCGGGGTAAACTGGGAAAGT GATGTCGTGTACTGGCTCCGCCTTTTTCCCGAGGGTGGGGGAG AACCGTATATAAGTGCAGTAGTCGCCGTGAACGTTCTTTTTCGC AACGGGTTTGCCGCCAGAACACAGGTGTCGTGACCGCGG C (SEQ ID NO: 7) |
| CK8 promoter | CTAGACTAGCATGCTGCCCATGTAAGGAGGCAAGGCCTGGGG ACACCCGAGATGCCTGGTTATAATTAACCCAGACATGTGGCTG CCCCCCCCCCCCAACACCTGCTGCCTCTAAAAATAACCCTGC ATGCCATGTTCCCGGCGAAGGGCCAGCTGTCCCCGCCAGCT AGACTCAGCACTTAGTTTAGGAACCAGTGAGCAAGTCAGCCCT TGGGGCAGCCCATACAAGGCCATGGGGCTGGGCAAGCTGCAC GCCTGGGTCCGGGGTGGGCACGGTGCCCGGGCAACGAGCTG AAAGCTCATCTGCTCTCAGGGGCCCCTCCCTGGGGACAGCCC CTCCTGGCTAGTCACACCCTGTAGGCTCCTCTATATAACCCAG GGGCACAGGGGCTGCCCTCATTCTACCACCACCTCCACAGCAC AGACAGACACTCAGGAGCCAGCCAG (SEQ ID NO: 8) |
| Spc512 promoter | GAGCTCCACCGCGGTGGCGGCCGTCCGCCTTCGGCACCATCC TCACGACACCCAAATATGGCGACGGGTGAGGAATGGTGGGGA GTTATTTTTAGAGCGGTGAGGAAGGTGGGCAGGCAGCAGGTGT TGGCGCTCTAAAAATAACTCCCGGGAGTTATTTTTAGAGCGGAG GAATGGTGGACACCCAAATATGGCGACGGTTCCTCACCCGTCG CCATATTTGGGTGTCCGCCCTCGGCCGGGGCCGCATTCCTGG GGGCCGGGCGGTGCTCCCGCCCGCCTCGATAAAAGGCTCCGG GGCCGGCGGCGGCCCACGAGCTACCCGGAGGAGCGGGAGGC GCCAAGCTCTAGAACTAGTGGATCCCCCGGGCTGCAGGAATTC GATAT (SEQ ID NO: 9) |
| MHCK7 promoter | GTTTAAACAAGCTTGCATGTCTAAGCTAGACCCTTCAGATTAAA AATAACTGAGGTAAGGGCCTGGGTAGGGGAGGTGGTGTGAGA CGCTCCTGTCTCTCCTCTATCTGCCCATCGGCCCTTTGGGGAG GAGGAATGTGCCCAAGGACTAAAAAAAGGCCATGGAGCCAGAG GGGCGAGGGCAACAGACCTTTCATGGGCAAACCTTGGGGCCC TGCTGTCTAGCATGCCCCACTACGGGTCTAGGCTGCCCATGTA AGGAGGCAAGGCCTGGGGACACCCGAGATGCCTGGTTATAATT AACCCAGACATGTGGCTGCCCCCCCCCCCCCCAACACCTGCTGC CTCTAAAAATAACCCTGTCCCTGGTGGATCCCCTGCATGCGAA GATCTTCGAACAAGGCTGTGGGGGACTGAGGGCAGGCTGTAA CAGGCTTGGGGGCCAGGGCTTATACGTGCCTGGGACTCCCAA AGTATTACTGTTCCATGTTCCCGGCGAAGGGCCAGCTGTCCCC CGCCAGCTAGACTCAGCACTTAGTTTAGGAACCAGTGAGCAAG TCAGCCCTTGGGGCAGCCCATACAAGGCCATGGGGCTGGGCA AGCTGCACGCCTGGGTCCGGGGTGGGCACGGTGCCCGGGCA |

TABLE 1-continued

| Component | Sequence |
|---|---|
| | ACGAGCTGAAAGCTCATCTGCTCTCAGGGGCCCCTCCCTGGG GACAGCCCCTCCTGGCTAGTCACACCCTGTAGGCTCCTCTATA TAACCCAGGGGCACAGGGGCTGCCCTCATTCTACCACCACCTC CACAGCACAGACAGACACTCAGGAGCCAGCCAGCGGCGCGCC C (SEQ ID NO: 10) |
| SaCas9 | AAGCGGAACTACATCCTGGGCCTGGACATCGGCATCACCAGCG TGGGCTACGGCATCATCGACTACGAGACACGGGACGTGATCGA TGCCGGCGTGCGGCTGTTCAAAGAGGCCAACGTGGAAAACAA CGAGGGCAGGCGGAGCAAGAGAGGCGCCAGAAGGCTGAAGC GGCGGAGGCGGCATAGAATCCAGAGAGTGAAGAAGCTGCTGT TCGACTACAACCTGCTGACCGACCACAGCGAGCTGAGCGGCAT CAACCCCTACGAGGCCAGAGTGAAGGGCCTGAGCCAGAAGCT GAGCGAGGAAGAGTTCTCTGCCGCCCTGCTGCACCTGGCCAA GAGAAGAGGCGTGCACAACGTGAACGAGGTGGAAGAGGACAC CGGCAACGAGCTGTCCACCAAAGAGCAGATCAGCCGGAACAG CAAGGCCCTGGAAGAGAAATACGTGGCCGAACTGCAGCTGGA ACGGCTGAAGAAAGACGGCGAAGTGCGGGGCAGCATCAACAG ATTCAAGACCAGCGACTACGTGAAAGAAGCCAAACAGCTGCTG AAGGTGCAGAAGGCCTACCACCAGCTGGACCAGAGCTTCATCG ACACCTACATCGACCTGCTGGAAACCCGGCGGACCTACTATGA GGGACCTGGCGAGGGCAGCCCCTTCGGCTGGAAGGACATCAA AGAATGGTACGAGATGCTGATGGGCCACTGCACCTACTTCCCC GAGGAACTGCGGAGCGTGAAGTACGCCTACAACGCCGACCTG TACAACGCCCTGAACGACCTGAACAATCTCGTGATCACCAGGG ACGAGAACGAGAAGCTGGAATATTACGAGAAGTTCCAGATCAT CGAGAACGTGTTCAAGCAGAAGAAGAAGCCCACCCTGAAGCAG ATCGCCAAAGAAATCCTCGTGAACGAAGAGGATATTAAGGGCT ACAGAGTGACCAGCACCGGCAAGCCCGAGTTCACCAACCTGAA GGTGTACCACGACATCAAGGACATTACCGCCCGGAAAGAGATT ATTGAGAACGCCGAGCTGCTGGATCAGATTGCCAAGATCCTGA CCATCTACCAGAGCAGCGAGGACATCCAGGAAGAACTGACCAA TCTGAACTCCGAGCTGACCCAGGAAGAGATCGAGCAGATCTCT AATCTGAAGGGCTATACCGGCACCCACAACCTGAGCCTGAAGG CCATCAACCTGATCCTGGACGAGCTGTGGCACACCAACGACAA CCAGATCGCTATCTTCAACCGGCTGAAGCTGGTGCCCAAGAAG GTGGACCTGTCCCAGCAGAAAGAGATCCCCACCACCCTGGTG GACGACTTCATCCTGAGCCCCGTCGTGAAGAGAAGCTTCATCC AGAGCATCAAAGTGATCAACGCCATCATCAAGAAGTACGGCCT GCCCAACGACATCATTATCGAGCTGGCCCGCGAGAAGAACTCC AAGGACGCCCAGAAAATGATCAACGAGATGCAGAAGCGGAACC GGCAGACCAACGAGCGGATCGAGGAAATCATCCGGACCACCG GCAAAGAGAACGCCAAGTACCTGATCGAGAAGATCAAGCTGCA CGACATGCAGGAAGGCAAGTGCCTGTACAGCCTGGAAGCCATC CCTCTGGAAGATCTGCTGAACAACCCCTTCAACTATGAGGTGG ACCACATCATCCCCAGAAGCGTGTCCTTCGACAACAGCTTCAA CAACAAGGTGCTCGTGAAGCAGGAAGAAAACAGCAAGAAGGG CAACCGGACCCCATTCCAGTACCTGAGCAGCAGCGACAGCAAG ATCAGCTACGAAACCTTCAAGAAGCACATCCTGAATCTGGCCAA GGGCAAGGGCAGAATCAGCAAGACCAAGAAAGAGTATCTGCTG GAAGAACGGGACATCAACAGGTTCTCCGTGCAGAAAGACTTCA TCAACCGGAACCTGGTGGATACCAGATACGCCACCAGAGGCCT GATGAACCTGCTGCGGAGCTACTTCAGAGTGAACAACCTGGAC GTGAAAGTGAAGTCCATCAATGGCGGCTTCACCAGCTTTCTG GGCGGAAGTGGAAGTTTAAGAAAGAGCGGAACAAGGGGTACA AGCACCACGCCGAGGACGCCCTGATCATTGCCAACGCCGATTT CATCTTCAAAGAGTGGAAGAAACTGGACAAGGCCAAAAAAGTG ATGGAAAACCAGATGTTCGAGGAAAAGCAGGCCGAGAGCATGC CCGAGATCGAAACCGAGCAGGAGTACAAAGAGATCTTCATCAC CCCCCACCAGATCAAGCACATTAAGGACTTCAAGGACTACAAG TACAGCCACCGGGTGGACAAGAAGCCTAATAGAGAGCTGATTA ACGACACCCTGTACTCCACCCGGAAGGACGACAAGGGCAACA CCCTGATCGTGAACAATCTGAACGGCCTGTACGACAAGGACAA TGACAAGCTGAAAAAGCTGATCAACAAGAGCCCCGAAAAGCTG CTGATGTACCACCACGACCCCCAGACCTACCAGAAACTGAAGC TGATTATGGAACAGTACGGCGACGAGAAGAATCCCCTGTACAA GTACTACGAGGAAACCGGGAACTACCTGACCAAGTACTCCAAA AAGGACAACGGCCCCGTGATCAAGAAGATTAAGTATTACGGCA ACAAACTGAACGCCCATCTGGACATCACCGACGACTACCCCAA CAGCAGAAACAAGGTCGTGAAGCTGTCCCTGAAGCCCTACAGA TTCGACGTGTACCTGGACAATGGCGTGTACAAGTTCGTGACCG TGAAGAATCTGGATGTGATCAAAAAAGAAAACTACTACGAAGTG AATAGCAAGTGCTATGAGGAAGCTAAGAAGCTGAAGAAGATCA GCAACCAGGCCGAGTTTATCGCCTCCTTCTACAACAACGATCT GATCAAGATCAACGGCGAGCTGTATAGAGTGATCGGCGTGAAC |

TABLE 1-continued

| Component | Sequence |
|---|---|
|  | AACGACCTGCTGAACCGGATCGAAGTGAACATGATCGACATCA<br>CCTACCGCGAGTACCTGGAAAACATGAACGACAAGAGGCCCCC<br>CAGGATCATTAAGACAATCGCCTCCAAGACCCAGAGCATTAAG<br>AAGTACAGCACAGACATTCTGGGCAACCTGTATGAAGTGAAATC<br>TAAGAAGCACCCTCAGATCATCAAAAAGGGC (SEQ ID NO: 11) |
| Mini<br>polyadenylation<br>signal | TAGCAATAAAGGATCGTTTATTTTCATTGGAAGCGTGTGTTGGT<br>TTTTTGATCAGGCGCG (SEQ ID NO: 12) |
| bGH<br>polyadenylation<br>signal | CTAGAGCTCGCTGATCAGCCTCGACTGTGCCTTCTAGTTGCCA<br>GCCATCTGTTGTTTGCCCCTCCCCCGTGCCTTCCTTGACCCTG<br>GAAGGTGCCACTCCCACTGTCCTTTCCTAATAAAATGAGGAAAT<br>TGCATCGCATTGTCTGAGTAGGTGTCATTCTATTCTGGGGGGT<br>GGGGTGGGGCAGGACAGCAAGGGGGAGGATTGGGAAGAGAA<br>TAGCAGGCATGCTGGGGA (SEQ ID NO: 13) |
| SV40 intron | TCTAGAGGATCCGGTACTCGAGGAACTGAAAAACCAGAAAGTT<br>AACTGGTAAGTTTAGTCTTTTTGTCTTTTATTTCAGGTCCCGGAT<br>CCGGTGGTGGTGCAAATCAAAGAACTGCTCCTCAGTGGATGTT<br>GCCTTTACTTCTAGGCCTGTACGGAAGTGTTAC (SEQ ID NO:<br>24) |

Example 4

All-in-One Vector 1 (Versions 1 and 2)

Two versions of vector 1 were generated. Vector 1 contained exon 45-55 targeted gRNAs with all promoters (U6, H1, and SaCas9-driving) in forward direction and mini polyadenylation signal for SaCas9.

Version 1 of vector 1 contained an EFS constitutive promoter. The sequence for version 1 of vector 1 is in SEQ ID NO:14.

Version 2 of vector 1 contained a CK8 constitutive promoter. The sequence for version 2 of vector 1 is in SEQ ID NO:15.

Example 5

All-in-One Vector 2 (Versions 1-4)

Four versions of vector 2 were generated. Vector 2 contained exon 45-55 targeted gRNAs with U6 promoter in reverse direction facing away from SaCas9-driving promoter and mini polyadenylation signal for SaCas9.

Version 1 of vector 2 contained an EFS constitutive promoter. The sequence for version 1 of vector 2 is in SEQ ID NO:16.

Version 2 of vector 2 contained a CK8 constitutive promoter. The sequence for version 2 of vector 2 is as in SEQ ID NO:17.

Version 3 of vector 2 contained a Spc512 promoter. The sequence for version 3 of vector 2 is as in SEQ ID NO:18.

Version 4 of vector 2 contained a MHCK7 promoter. The sequence for version 4 of vector 2 is as in SEQ ID NO:19.

Example 6

All-in-One Vector 3 (Versions 1-4)

Four versions of vector 3 were generated. Vector 3 contained exon 45-55 targeted gRNAs with U6 promoter in reverse direction facing away from SaCas9-driving promoter and mini polyadenylation signal for SaCas9.

Version 1 of vector 3 contained an EFS constitutive promoter. The sequence for version 1 of vector 3 is as in SEQ ID NO:20.

Version 2 of vector 3 contained a CK8 promoter. The sequence for version 2 of vector 3 is as in SEQ ID NO:21

Version 3 of vector 3 contained a Spc512 promoter. The sequence for version 3 of vector 3 is as in SEQ ID NO:22.

Version 4 of vector 3 contained a MHCK7 promoter. The sequence for version 4 of vector 3 is as in SEQ ID NO:23.

Example 7

All-in-One Vector 5 (Versions 1-4)

Figure 11:
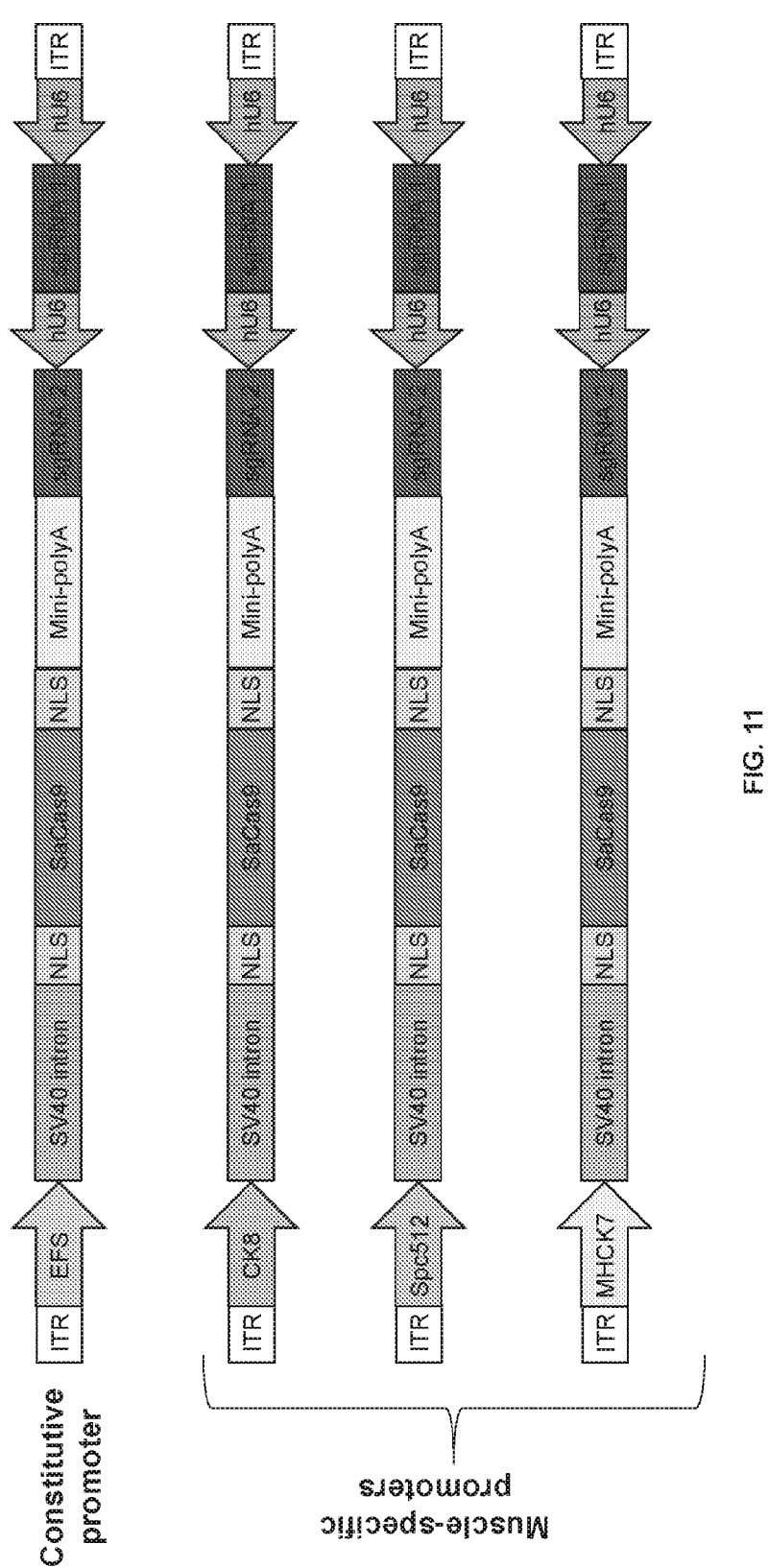
FIG. 11 is a schematic diagram of the versions of all-in-one vector 5.

After screening a panel of all-in-one vector designs to determine the effect of guide placement, regulatory elements, and promoters, a new set of all-in-one vectors was created with constitutive and muscle-specific promoters (FIG. 11). Versions of vector 5 of the all-in-one vector included an SV40 intron (see SEQ ID NO: 24) and placement of different elements.

Version 1 of vector 5 included a constitutive promoter. The sequence for version 1 of vector 5 is as in SEQ ID NO: 41.

Version 2 of vector 5 included a CK8 promoter. The sequence for version 2 of vector 5 is as in SEQ ID NO: 42.

Version 3 of vector 5 included a Spc-512 promoter. The sequence for version 3 of vector 5 is as in SEQ ID NO: 29.

Version 4 of vector 5 included a MHCK7 promoter. The sequence for version 4 of vector 5 is as in SEQ ID NO: 30.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the disclosure are set out in the following numbered clauses:

Clause 1. A CRISPR-Cas system comprising one or more vectors encoding a composition, the composition comprising: (a) a first guide RNA (gRNA) molecule targeting intron 44 of dystrophin; (b) a second gRNA molecule targeting intron 55 of dystrophin; and (c) a Cas9 protein; and (d) one or more Cas9 gRNA scaffolds.

Clause 2. The system of clause 1, wherein the system comprises a single vector.

Clause 3. The system of clause 1, wherein the system comprises two or more vectors, wherein the two or more vectors comprises a first vector and a second vector.

Clause 4. The system of clause 3, wherein (a) the first vector encodes the first gRNA molecule and the second gRNA molecule; and (b) the second vector encodes the Cas9 protein.

Clause 5. The system of clause 3, wherein (a) the first vector encodes the first gRNA molecule; and (b) the second vector encodes the second gRNA molecule.

Clause 6. The system of clause 5, wherein the first vector further encodes the Cas9 protein.

Clause 7. The system of clause 5 or 6, wherein the second vector further encodes the Cas9 protein.

Clause 8. The system of any one of clauses 1-7, wherein the expression of the Cas9 protein is driven by a constitutive promoter or a muscle-specific promoter.

Clause 9. The system of clause 8, where the muscle-specific promoter comprises a MHCK7 promoter, a CK8 promoter, or a Spc512 promoter.

Clause 10. The system of clause 2, wherein the single vector encodes the first gRNA molecule, the second gRNA molecule, and the Cas9 protein.

Clause 11. The system of any one of clauses 1-10, wherein the vector comprises at least one bidirectional promoter.

Clause 12. The system of clause 11, wherein the bidirectional promoter comprises: a first promoter driving expression of the first gRNA molecule and/or the second gRNA molecule; and a second promoter driving expression of the Cas9 protein.

Clause 13. The system of any one of clauses 1-12, wherein the first gRNA targets the polynucleotide of SEQ ID NO:2 or a 5' truncation thereof.

Clause 14. The system of any one of clauses 1-13, wherein the second gRNA targets the polynucleotide of SEQ ID NO:3 or a 5' truncation thereof.

Clause 15. The system of any one of clauses 1-14, wherein the Cas9 protein is SpCas9, SaCas9, or St1Cas9 protein.

Clause 16. The system of any one of clauses 1-15, wherein the Cas9 gRNA scaffold is a SaCas9 gRNA scaffold.

Clause 17. The system of clause 16, wherein the SaCas9 gRNA scaffold comprises or is encoded by the polynucleotide of SEQ ID NO:4.

Clause 18. The system of any one of clauses 1-17, wherein the Cas9 protein is a SaCas9 protein encoded by the polynucleotide of SEQ ID NO:11.

Clause 19. The system of any one of clauses 1-18, wherein the vector comprises at least one polynucleotide selected from SEQ ID NOs: 1-13 and 24.

Clause 20. The system of any one of clauses 1-19, wherein the vector comprises the polynucleotide sequence of SEQ ID NO: 24.

Clause 21. The system of any one of clauses 1-20, wherein the vector comprises a polynucleotide sequence that is selected from SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 41, SEQ ID NO: 42, SEQ ID NO: 29, and SEQ ID NO: 30.

Clause 22. The system of any one of clauses 1-21, wherein the vector is a viral vector.

Clause 23. The system of any one of clauses 1-22, wherein the vector is an Adeno-associated virus (AAV) vector.

Clause 24. The system of clause 23, wherein the AAV vector is AAV1, AAV2, AAV3, AAV4, AAV5, AAV6, AAV7, AAV8, AAV9, AAV-10, AAV-11, AAV-12, AAV-13 or AAVrh.74.

Clause 25. The system of any one of clauses 1-24, wherein the vector comprises a ubiquitous promoter or a tissue-specific promoter operably linked to the polynucleotide sequence encoding the first gRNA molecule, the second gRNA molecule, and/or the Cas9 protein.

Clause 26. The system of clause 25, wherein the tissue-specific promoter is a muscle specific promoter.

Clause 27. A cell comprising the system of any one of clauses 1-26.

Clause 28. A kit comprising the system of any one of clauses 1-26.

Clause 29. A method of correcting a mutant dystrophin gene in a cell, the method comprising administering to a cell the system of any one of clauses 1-26.

Clause 30, A method of genome editing a mutant dystrophin gene in a subject, the method comprising administering to the subject the system of any one of clauses 1-26 or the cell of clause 27.

Clause 31. A method of treating a subject having a mutant dystrophin gene, the method comprising administering to the subject the system of any one of clauses 1-26 or the cell of clause 27.

Clause 32. The method of clause 30 or 31, wherein the system or the cell is administered to the subject intramuscularly, intravenously, or a combination thereof.

```
SEQUENCES
SEQ ID NO: 1, AAV ITR
                                                    (SEQ ID NO: 1)
cctgcaggcagctgcgcgctcgctcgctcactgaggccgcccgggcgtcgggcgacctttgg tcgcccggcctcagtgagcgagcgagcgcgcagagagggagtggccaactccatcactaggg gttcct SEQ ID NO: 2, JCR143: DNA target sequence of gRNA targeting
human dystrophin intron 44 region
                                                    (SEQ ID NO: 2)
acatttcctctctatacaaatg
```

-continued

SEQ ID NO: 3, JCR120: DNA target sequence of gRNA targeting
human dystrophin intron 55 region (SEQ ID NO: 3)

atatagtaatgaaattattggcac

SEQ ID NO: 4, SaCas9 guide RNA scaffold, scaffold of gRNAs (SEQ ID NO: 4)

tctcgccaacaagttgacgagataaacacggcattttgccttgttttagtagattctgtttc cagagtactaaaac

SEQ ID NO: 5, U6 promoter (SEQ ID NO: 5)

ggtgtttcgtcctttccacaagatatataaagccaagaaatcgaaatactttcaagttacgg taagcatatgatagtccattttaaaacataattttaaaactgcaaactacccaagaaattat tactttctacgtcacgtattttgtactaatatctttgtgtttacagtcaaattaattccaat tatctctctaacagccttgtatcgtatatgcaaatatgaaggaatcatgggaaataggccct c SEQ ID NO: 6, H1 promoter (SEQ ID NO: 6)

gaacgctgacgtcatcaacccgctccaaggaatcgcgggcccagtgtcactaggcgggaaca cccagcgcgcgtgcgccctggcaggaagatggctgtgagggacaggggagtggcgccctgca atatttgcatgtcgctatgtgttctgggaaatcaccatTaaacgtgaaatgtctttggatttg ggaatcttataagttctgtatgagaccac SEQ ID NO: 7, EPS promoter (SEQ ID NO: 7)

tcgagtggctccggtgcccgtcagtgggcagagcgcacatcgcccacagtccccgagaagtt ggggggaggggtcggcaattgaaccggtgcctagagaaggtggcgcgggtaaactgggaaa gtgatgtcgtgtactggctccgccttttttcccgagggtgggggagaaccgtatataagtgca gtagtcgccgtgaacgttctttttcgcaacgggtttgccgccagaacacaggtgtcgtgacc gcgg SEQ ID NO: 8, CK8 promoter (SEQ ID NO: 8)

ctagactagcatgctgcccatgtaaggaggcaaggcctggggacacccgagatgcctggtta taattaacccagacatgtggctgcccccccccccccaacacctgctgcctctaaaaataacc ctgcatgccatgttcccggcgaagggccagctgtcccccgccagctagactcagcacttagt ttaggaaccagtgagcaagtcagcccttggggcagcccatacaaggccatggggctgggcaa gctgcacgcctgggtccggggtgggcacggtgcccgggcaacgagctgaaagctcatctgct ctcaggggcccctccctggggacagcccctcctggctagtcacaccctgtaggctcctctat ataacccaggggcacaggggctgccctcattctaccaccacctccacagcacagacagacac tcaggagccagccag SEQ ID NO: 9, Spc512 promoter (SEQ ID NO: 9)

gagctccaccgcggtggcggccgtccgccttcggcaccatcctcacgacacccaaatatggc gacgggtgaggaatggtggggagttattttttagagcggtgaggaaggtgggcaggcagcagg tgttggcgctctaaaaataactcccgggagttatttttagagcggaggaatggtggacaccc aaatatggcgacggttcctcacccgtcgccatatttgggtgtccgccctcggccgggggccgc attcctgggggccgggcggtgctcccgcccgcctcgataaaaaggctccgggggccggcggcgg cccacgagctacccggaggagcgggaggcgccaagctctagaactagtggatcccccgggct gcaggaattcgatat -continued SEQ ID NO: 10, MHCK7 promoter (SEQ ID NO: 10)

gtttaaacaagcttgcatgtctaagctagacccttcagattaaaaataactgaggtaagggc ctgggtaggggaggtggtgtgagacgctcctgtctctcctctatctgcccatcggccctttg gggaggaggaatgtgcccaaggactaaaaaaaaggccatggagccagaggggcgagggcaaca gacctttcatgggcaaaccttggggccctgctgtctagcatgccccactacgggtctaggct gcccatgtaaggaggcaaggcctggggacacccgagatgcctggttataattaacccagaca tgtggctgccccccccccccaacacctgctgcctctaaaaataaccctgtccctggtggat cccctgcatgcgaagatcttcgaacaaggctgtgggggactgaggacaggctgtaacaggct tgggggccagggcttatacgtgcctgggactcccaaagtattactgttccatgttcccagcg aagggccagctgtcccccgccagctagactcagcacttagtttaggaaccagtgagcaagtc agcccttggggcagcccatacaaggccatggggctgggcaagctgcacgcctgggtccgggg tgggcacggtgcccgggcaacgagctgaaagctcatctgctctcaggggcccctccctgggg acagcccctcctggctagtcacaccctgtaggctcctctatataacccaggggcacaggggc tgccctcattctaccaccacctccacagcacagacagacactcaggagccagccagcggcgc gccc SEQ ID NO: 11, polynucleotide encoding SaCas9

(SEQ ID NO: 11)

aagcggaactacatcctgggcctggacatcggcatcaccagcgtgggctacggcatcatcga ctacgagacacgggacgtgatcgatgccggcgtgcggctgttcaaagaggccaacgtgaaaa acaacgagggcaggcggagcaagagaagcgccagaaggctgaagcggcggaggcggcataga atccagagagtgaagaagctgctgttcgactacaacctgctgaccgaccacagcgagctgag cggcatcaacccctacgaggccagagtgaagggcctgagccagaagctgagcgaggaagagt tctctgccgccctgctgcacctggccaagagaagaggcgtgcacaacgtgaacgaggtggaa gaggacaccggcaacgagctgtccaccaaagagcagatcagccggaacagcaaggccctgga agagaaatacgtggccgaactgcagctggaacggctgaagaaagacggcgaagtgcggggca gcatcaacagattcaagaccagcgactacgtgaaagaagccaaacagctgctgaaggtgcag aaggcctaccaccagctggaccagagcttcatcgacacctacatcgacctgctggaaacccg gcggacctactatgagggacctggcgagggcagccccttcggctggaaggacatcaaagaat ggtacgagatgctgatgggccactgcacctacttccccgaggaactgcggagcgtgaagtac gcctacaacgccgacctgtacaacgccctgaacgacctgaacaatctcgtgatcaccaggga cgagaacgagaagctggaatattacgagaagttccagatcatcgagaacgtgttcaagcaga agaagaagcccaccctgaagcagatcgccaaagaaatcctcgtgaacgaagaggatattaag ggctacagagtgaccagcaccggcaagcccgagttcaccaacctgaaggtgtaccacgacat caaggacattaccgcccggaaagagattattgagaacgccgagctgctggatcagattgcca agatcctgaccatctaccagagcagcgaggacatccaggaagaactgaccaatctgaactcc gagctgacccaggaagagatcgagcagatctctaatctgaagggctataccggcacccacaa cctgagcctgaaggccatcaacctgatcctggacgagctgtggcacaccaacgacaaccaga tcgctatcttcaaccggctgaagctggtgcccaagaaggtggacctgtcccagcagaaagag atccccaccaccctggtggacgacttcatcctgagccccgtcgtgaagagaagcttcatcca gagcatcaaagtgatcaacgccatcatcaagaagtacggcctgcccaacgacatcattatcg agctggcccgcgagaagaactccaaggacgcccagaaaatgatcaacgagatgcagaagcgg aaccggcagaccaacgagcggatcgaggaaatcatccggaccaccggcaaagagaacgccaa -continued

```
gtacctgatcgagaagatcaagctgcacgacatgcaggaaggcaagtgcctgtacagcctgg aagccatccctctggaagatctgctgaacaaccccttcaactatgaggtggaccacatcatc cccagaagcgtgtccttcgacaacagcttcaacaacaaggtgctcgtgaagcaggaagaaaa cagcaagaagggcaaccggaccccattccagtacctgagcagcagcgacagcaagatcagct acgaaaccttcaagaagcacatcctgaatctggccaagggcaagggcagaatcagcaagacc aagaaagagtatctgctggaagaacgggacatcaacaggttctccgtgcagaaagacttcat caaccggaacctggtggataccagatacgccaccagaggcctgatgaacctgctgcggagct acttcagagtgaacaacctggacgtgaaagtgaagtccatcaatggcggcttcaccagcttt ctgcggcggaagtggaagtttaagaaagagcggaacaaggggtacaagcaccacgccgagga cgccctgatcattgccaacgccgatttcatcttcaaagagtggaagaaactggacaaggcca aaaaagtgatggaaaaccagatgttcgaggaaaagcaggccgagagcatgcccgagatcgaa accaagcaggagtacaaagagatcttcatcacccccaccagatcaagcacattaaggactt caaggactacaagtacagccaccgggtggacaagaagcctaatagagagctgattaacgaca ccctgtactccacccggaaggacgacaagggcaacacccctgatcgtgaacaatctgaacggc ctgtacgacaaggacaatgacaagctgaaaaagctgatcaacaagagccccgaaaagctgct gatgtaccaccacgaccccagacctaccagaaactgaagctgattatggaacagtacggcg acgagaagaatcccctgtacaagtactacgaggaaaccgggaactacctgaccaagtactcc aaaaaggacaacggccccgtgatcaagaagattaagtattacggcaacaaactgaacgccca tctggacatcaccgacgactacccccaacagcagaaacaaggtcgtgaagctgtccctgaagc cctacagattcgacgtgtacctggacaatggcgtgtacaagttcgtgaccgtgaagaatctg gatgtgatcaaaaaagaaaactactacgaagtgaatagcaagtgctatgaggaagctaagaa gctgaagaagatcagcaaccaggccgagtttatcgcctccttctacaacaacgatctgatca agatcaacggcgagctgtatagagtgatcggcgtgaacaacgacctgctgaaccggatcgaa gtgaacatgatcgacatcaccaccgcgagtacctggaaaacatgaacgacaaaaggccccc tgggcaacctgtatgaagtgaaatctaagaagcaccctcagatcatcaaaaagggc
```

SEQ ID NO: 12, Mini polyadenylation signal (SEQ ID NO: 12)
```
tagcaataaaggatcgtttattttcattggaagcgtgtgttggttttttgatcaggcgcg
```

SEQ ID NO: 13, bGH polyadenylation signal (SEQ ID NO: 13)
```
ctagagctcgctgatcagcctcgactgtgccttctagttgccagccatctgttgtttgcccc tcccccgtgccttccttgaccctggaaggtgccactcccactgtcctttcctaataaaatga ggaaattgcatcgcattgtctgagtaggtgtcattctattctggggggtggggtggggcagg acagcaaggggggaggattgggaagagaatagcaggcatgctgggga
```

SEQ ID NO: 14, Version 1 of vector 1
```
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc

TCTAGAGAGGGCCTATTTCCCATGATTCCTTCATATTTGCATATACGATACAAGGCTGTTAGAGAGAT

AATTGGAATTAATTTGACTGTAAACACAAAGATATTAGTACAAAATACGTGACGTAGAAAGTAATAAT

TTCTTGGGTAGTTTGCAGTTTTAAAATTATGTTTTAAAATGGACTATCATATGCTTACCGTAACTTGA

AAGTATTTCGATTTCTTGGCTTTATATATCTTGTGGAAAGGACGAAACACCGcatttgtatagagagg aaatgtgttttagtactctggaaacagaatctactaaaacaaggcaaaatgccgtgtttatctcgtca acttgttggcgagattttttCTCGAGTCGAGTGGCTCCGGTGCCCGTCAGTGGGCAGAGCGCACATCGC
```

-continued

```
CCACAGTCCCCGAGAAGTTGGGGGGAGGGGTCGGCAATTGAACCGGTGCCTAGAGAAGGTGGCGCGGG

GTAAACTGGGAAAGTGATGTCGTGTACTGGCTCCGCCTTTTTCCCGAGGGTGGGGGAGAACCGTATAT

AAGTGCAGTAGTCGCCGTGAACGTTCTTTTTCGCAACGGGTTTGCCGCCAGAACACAGGTGTCGTGAC

CGCGGCCATGGCCCCAAAGAAGAAGCGGAAGGTCGGTATCCACGGAGTCCCAGCAGCCAAGCGGAACT

ACATCCTGGGCCTGGACATCGGCATCACCAGCGTGGGCTACGGCATCATCGACTACGAGACACGGGAC

GTGATCGATGCCGGCGTGCGGCTGTTCAAAGAGGCCAACGTGGAAAACAACGAGGGCAGGCGGAGCAA

GAGAGGCGCCAGAAGGCTGAAGCGGCGGAGGCGGCATAGAATCCAGAGAGTGAAGAAGCTGCTGTTCG

ACTACAACCTGCTGACCGACCACAGCGAGCTGAGCGGCATCAACCCCTACGAGGCCAGAGTGAAGGGC

CTGAGCCAGAAGCTGAGCGAGGAAGAGTTCTCTGCCGCCCTGCTGCACCTGGCCAAGAGAAGAGGCGT

GCACAACGTGAACGAGGTGGAAGAGGACACCGGCAACGAGCTGTCCACCAAAGAGCAGATCAGCCGGA

ACAGCAAGGCCCTGGAAGAGAAATACGTGGCCGAACTGCAGCTGGAACGGCTGAAGAAAGACGGCGAA

GTGCGGGGCAGCATCAACAGATTCAAGACCAGCGACTACGTGAAAGAAGCCAAACAGCTGCTGAAGGT

GCAGAAGGCCTACCACCAGCTGGACCAGAGCTTCATCGACACCTACATCGACCTGCTGGAAACCCGGC

GGACCTACTATGAGGGACCTGGCGAGGGCAGCCCCTTCGGCTGGAAGGACATCAAAGAATGGTACGAG

ATGCTGATGGGCCACTGCACCTACTTCCCCGAGGAACTGCGGAGCGTGAAGTACGCCTACAACGCCGA

CCTGTACAACGCCCTGAACGACCTGAACAATCTCGTGATCACCAGGGACGAGAACGAGAAGCTGGAAT

ATTACGAGAAGTTCCAGATCATCGAGAACGTGTTCAAGCAGAAGAAGAAGCCCACCCTGAAGCAGATC

GCCAAAGAAATCCTCGTGAACGAAGAGGATATTAAGGGCTACAGAGTGACCAGCACCGGCAAGCCCGA

GTTCACCAACCTGAAGGTGTACCACGACATCAAGGACATTACCGCCCGGAAAGAGATTATTGAGAACG

CCGAGCTGCTGGATCAGATTGCCAAGATCCTGACCATCTACCAGAGCAGCGAGGACATCCAGGAAGAA

CTGACCAATCTGAACTCCGAGCTGACCCAGGAAGAGATCGAGCAGATCTCTAATCTGAAGGGCTATAC

CGGCACCCACAACCTGAGCCTGAAGGCCATCAACCTGATCCTGGACGAGCTGTGGCACACCAACGACA

ACCAGATCGCTATCTTCAACCGGCTGAAGCTGGTGCCCAAGAAGGTGGACCTGTCCCAGCAGAAAGAG

ATCCCCACCACCCTGGTGGACGACTTCATCCTGAGCCCCGTCGTGAAGAGAAGCTTCATCCAGAGCAT

CAAAGTGATCAACGCCATCATCAAGAAGTACGGCCTGCCCAACGACATCATTATCGAGCTGGCCCGCG

AGAAGAACTCCAAGGACGCCCAGAAAATGATCAACGAGATGCAGAAGCGGAACCGGCAGACCAACGAG

CGGATCGAGGAAATCATCCGGAGCACCGGCAAAGAGAACGCCAAGTACCTGATCGAGAAGATCAAGCT

GCACGACATGCAGGAAGGCAAGTGCCTGTACAGCCTGGAAGCCATCCCTCTGGAAGATCTGCTGAACA

ACCCCTTCAACTATGAGGTGGACCACATCATCCCCAGAAGCGTGTCCTTCGACAAGAGCTTCAACAAC

AAGGTGCTCGTGAAGCAGGAAGAAAACAGCAAGAAGGGCAACCGGACCCCATTCCAGTACCTGAGCAG

CAGCGACAGCAAGATCAGCTACGAAACCTTCAAGAAGCACATCCTGAATCTGGCCAAGGGCAAGGGCA

GAATCAGCAAGACCAAGAAAGAGTATCTGCTGGAAGAACGGGACATCAACAGGTTCTCCGTGCAGAAA

GACTTCATCAACCGGAACCTGGTGGATACCAGATACGCCACCAGAGGCCTGATGAACCTGCTGCGGAG

CTACTTCAGAGTGAACAACCTGGACGTGAAAGTGAAGTCCATCAATGGCGGCTTCACCAGCTTTCTGC

GGCGGAAGTGGAAGTTTAAGAAAGAGCGGAACAAGGGGTACAAGCACCACGCCGAGGACGCCCTGATC

ATTGCCAACGCCGATTTCATCTTCAAAGAGTGGAAGAAACTGGACAAGGCCAAAAAAGTGATGGAAAA

CCAGATGTTCGAGGAAAAGCAGGCCGAGAGCATGCCCGAGATCGAAACCGAGCAGGAGTACAAAGAGA

TCTTCATCACCCCCCACCAGATCAAGCACATTAAGGACTTCAAGGACTACAAGTACAGCCACCGGGTG

GACAAGAAGCCTAATAGAGAGCTGATTAACGACACCCTGTACTCCACCCGGAAGGACGACAAGGGCAA

CACCCTGATCGTGAACAATCTGAACGGCCTGTACGACAAGGACAATGACAAGCTGAAAAAGCTGATCA
```

-continued

```
ACAAGAGCCCCGAAAAGCTGCTGATGTACCACCACGACCCCCAGACCTACCAGAAACTGAAGCTGATT

ATGGAACAGTACGGCGACGAGAAGAATCCCCTGTACAAGTACTACGAGGAAACCGGGAACTACCTGAC

CAAGTACTCCAAAAAGGACAACGGCCCCGTGATCAAGAAGATTAAGTATTACGGCAACAAACTGAACG

CCCATCTGGACATCACCGACGACTACCCCAACAGCAGAAACAAGGTCGTGAAGCTGTCCCTGAAGCCC

TACAGATTCGACGTGTACCTGGACAATGGCGTGTACAAGTTCGTGACCGTGAAGAATCTGGATGTGAT

CAAAAAAGAAAACTACTACGAAGTGAATAGCAAGTGCTATGAGGAAGCTAAGAAGCTGAAGAAGATCA

GCAACCAGGCCGAGTTTATCGCCTCCTTCTACAACAACGATCTGATCAAGATCAACGGCGAGCTGTAT

AGAGTGATCGGCGTGAACAACGACCTGCTGAACCGGATCGAAGTGAACATGATCGACATCACCTACCG

CGAGTACCTGGAAAACATGAACGACAAGAGGCCCCCCAGGATCATTAAGACAATCGCCTCCAAGACCC

AGAGCATTAAGAAGTACAGCACAGACATTCTGGGCAACCTGTATGAAGTGAAATCTAAGAAGCACCCT

CAGATCATCAAAAAGGGCAAAAGGCCGGCGGCCACGAAAAAGGCCGGCCAGGCAAAAAAGAAAAAGgg atcctacccatacgatgttccagattacgcttacccatacgatgttccagattacgcttaccCatacg atgttccagattacgcttaaGaattctagcaataaaggatcgtttattttcattggaagcgtgtgttg gtttttgatcaggcgcgGGTACCGAACGCTGACGTCATCAACCCGCTCCAAGGAATCGCGGGCCCAG

TGTCACTAGGCGGGAACACCCAGCGCGCGTGCGCCCTGGCAGGAAGATGGCTGTGAGGGACAGGGGAG

TGGCGCCCTGCAATATTTGCATGTCGCTATGTGTTCTGGGAAATCACCATAAACGTGAAATGTCTTTG

GATTTGGGAATCTTATAAGTTCTGTATGAGACCACATATAGTAATGAAATTATTGGCACGTTTTAGTA

CTCTGGAAACAGAATCTACTAAAACAAGGCAAAATGCCGTGTTTATCTCGTCAACTTGTTGGCGAGAT

TTTTGGTACCaggaacccctagtgatggagttggccactccctctctgcgcgctcgctcgctcactga ggccgggcgaccaaaggtcgcccgacgcccgggctttgcccgggcggcctcagtgagcgagcgagcgc gcagctgcctgcaggggcgcctgatgcggtattttctccttacgcatctgtgcggtatttcacaccgc atacgtcaaagcaaccatagtacgcgccctgtagcggcgcattaagcgcggcgggtgtggtggttacg cgcagcgtgaccgctacacttgccagcgccctagcgcccgctcctttcgctttcttcccttcctttct cgccacgttcgccggctttccccgtcaagctctaaatcggggggctcccctttagggttccgatttagtg ctttacggcacctcgaccccaaaaaacttgatttgggtgatggttcacgtagtgggccatcgccctga tagacggtttttcgccctttgacgttggagtccacgttctttaatagtggactcttgttccaaactgg aacaacactcaaccctatctcgggctattcttttgatttataagggattttgccgatttcggcctatt ggttaaaaaatgagctgatttaacaaaaatttaacgcgaattttaacaaaatattaacgtttacaatt ttatggtgcactctcagtacaatctgctctgatgccgcatagttaagccagccccgacaccgccaac acccgctgacgcgccctgacgggcttgtctgctcccggcatccgcttacagacaagctgtgaccgtct ccgggagctgcatgtgtcagaggttttcaccgtcatcaccgaaacgcgcgagacgaaagggcctcgtg atacgcctattttttataggttaatgtcatgataataatggtttcttagacgtcaggtggcacttttcg gggaaatgtgcgcggaacccctatttgtttatttttctaaatacattcaaatatgtatccgctcatga gacaataaccctgataaatgcttcaataatattgaaaaaggaagagtatgagtattcaacatttccgt gtcgcccttattccctttttgcggcattttgccttcctgttttgctcacccagaaacgctggtgaa agtaaaagatgctgaagatcagttgggtgcacgagtgggttacatcgaactggatctcaacagcggta agatccttgagagttttcgccccgaagaacgttttccaatgatgagcacttttaaagttctgctatgt ggcgcggtattatcccgtattgacgccgggcaagagcaactcggtcgccgcatacactattctcagaa tgacttggttgagtactcaccagtcacagaaaagcatcttacggatggcatgacagtaagagaattat gcagtgctgccataaccatgagtgataacactgcggccaacttacttctgacaacgatcggaggaccg aaggagctaaccgcttttttgcacaacatgggggatcatgtaactcgccttgatcgttgggaaccgga
```

-continued gctgaatgaagccataccaaacgacgagcgtgacaccacgatgcctgtagcaatggcaacaacgttgc gcaaactattaactggcgaactacttactctagcttcccggcaacaattaatagactggatggaggcg gataaagttgcaggaccacttctgcgctcggcccttccggctggctggtttattgctgataaatctgg agccggtgagcgtggaagccgcggtatcattgcagcactggggccagatggtaagccctcccgtatcg tagttatctacacgacggggagtcaggcaactatggatgaacgaaatagacagatcgctgagataggt gcctcactgattaagcattggtaactgtcagaccaagtttactcatatatactttagattgatttaaa acttcatttttaatttaaaaggatctaggtgaagatcctttttgataatctcatgaccaaaatccctt aacgtgagttttcgttccactgagcgtcagaccccgtagaaaagatcaaaggatcttcttgagatcct tttttttctgcgcgtaatctgctgcttgcaaacaaaaaaaccaccgctaccagcggtggtttgtttgcc ggatcaagagctaccaactcttttttccgaaggtaactggcttcagcagagcgcagataccaaatactg tccttctagtgtagccgtagttaggccaccacttcaagaactctgtagcaccgcctacatacctcgct ctgctaatcctgttaccagtggctgctgccagtggcgataagtcgtgtcttaccgggttggactcaag acgatagttaccggataaggcgcagcggtcgggctgaacggggggttcgtgcacacagcccagcttgg agcgaacgacctacaccgaactgagatacctacagcgtgagctatgagaaagcgccacgcttcccgaa gggagaaaggcggacaggtatccggtaagcggcagggtcggaacaggagagcgcacgagggagcttcc agggggaaacgcctggtatctttatagtcctgtcgggtttcgccacctctgacttgagcgtcgatttt tgtgatgctcgtcaggggggcggagcctatggaaaaacgccagcaacgcggcctttttacggttcctg gcctttgctggccttttgctcacatgt SEQ ID NO: 15, Version 2 of vector 1
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc

TCTAGAGAGGGCCTATTTCCCATGATTCCTTCATATTTGCATATACGATACAAGGCTGTTAGAGAGAT

AATTGGAATTAATTTGACTGTAAACACAAAGATATTAGTACAAAATACGTGACGTAGAAAGTAATAAT

TTCTTGGGTAGTTTGCAGTTTTAAAATTATGTTTTAAAATGGACTATCATATGCTTACCGTAACTTGA

AAGTATTTCGATTTCTTGGCTTTATATATCTTGTGGAAAGGACGAAACACCGcatttgtatagagagg aaatgtgtttagtactctggaaacagaatctactaaaacaaggcaaaatgccgtgtttatctcgtca acttgttggcgagattttttCTCGAGCTAGACTAGCATGCTGCCCATGTAAGGAGGCAAGGCCTGGGGA

CACCCGAGATGCCTGGTTATAATTAACCCAGACATGTGGCTGCCCCCCCCCCCCCCAACACCTGCTGCC

TCTAAAAATAACCCTGCATGCCATGTTCCCGGCGAAGGGCCAGCTGTCCCCCGCCAGCTAGACTCAGC

ACTTAGTTTAGGAACCAGTGAGCAAGTCAGCCCTTGGGGCAGCCCATACAAGGCCATGGGGCTGGGCA

AGCTGCACGCCTGGGTCCGGGGTGGGCACGGTGCCCGGGCAACGAGCTGAAAGCTCATCTGCTCTCAG

GGGCCCCTCCCTGGGGACAGCCCCTCCTGGCTAGTCACACCCTGTAGGCTCCTCTATATAACCCAGGG

GCACAGGGGCTGCCCTCATTCTACCACCACCTCCACAGCACAGACAGACACTCAGGAGCCAGCCAGCa ccggtgccaccATGGCCCCAAAGAAGAAGCGGAAGGTCGGTATCCACGGAGTCCCAGCAGCCAAGCGG

AACTACATCCTGGGCCTGGACATCGGCATCACCAGCGTGGGCTACGGCATCATCGACTACGAGACACG

GGACGTGATCGATGCCGGCGTGCGGCTGTTCAAAGAGGCCAACGTGGAAAACAACGAGGGCAGGCGGA

GCAAGAGAGGCGCCAGAAGGCTGAAGCGGCGGAGGCGGCATAGAATCCAGAGAGTGAAGAAGCTGCTG

TTCGACTACAACCTGCTGACCGACCACAGCGAGCTGAGCGGCATCAACCCCTAGGAGGCCAGAGTGAA

GGGCCTGAGCCAGAAGCTGAGCGAGGAAGAGTTCTCTGCCGCCCTGCTGCACCTGGCCAAGAGAAGAG

GCGTGCACAACGTGAACGAGGTGGAAGAGGACACCGGCAACGAGCTGTCCACCAAAGAGCAGATCAGC

CGGAACAGCAAGGCCCTGGAAGAGAAATACGTGGCCGAACTGCAGCTGGAACGGCTGAAGAAAGACGG

-continued

```
CGAAGTGCGGGGCAGCATCAACAGATTCAAGACCAGCGACTACGTGAAAGAAGCCAAACAGCTGCTGA

AGGTGCAGAAGGCCTACCACCAGCTGGACCAGAGCTTCATCGACACCTACATCGACCTGCTGGAAACC

CGGCGGACCTACTATGAGGGACCTGGCGAGGGCAGCCCCTTCGGCTGGAAGGACATCAAAGAATGGTA

CGAGATGCTGATGGGCCACTGCACCTACTTCCCCGAGGAACTGCGGAGCGTGAAGTACGCCTACAACG

CCGACCTGTACAACGCCCTGAACGACCTGAACAATCTCGTGATCACCAGGGACGAGAACGAGAAGCTG

GAATATTACGAGAAGTTCCAGATCATCGAGAACGTGTTCAAGCAGAAGAAGAAGCCCACCCTGAAGCA

GATCGCCAAAGAAATCCTCGTGAACGAAGAGGATATTAAGGGCTACAGAGTGACCAGCACCGGCAAGC

CCGAGTTCACCAACCTGAAGGTGTACCACGACATCAaGGACATTACCGCCCGGAAAGAGATTATTGAG

AACGCCGAGCTGCTGGATCAGATTGCCAAGATCCTGACCATCTACCAGAGCAGCGAGGACATCCAGGA

AGAACTGACCAATCTGAACTCCGAGCTGACCCAGGAAGAGATCGAGCAGATCTCTAATCTGAAGGGCT

ATACCGGCACCCACAACCTGAGCCTGAAGGCCATCAACCTGATCCTGGACGAGCTGTGGCACACCAAC

GACAACCAGATCGCTATCTTCAACCGGCTGAAGCTGGTGCCCAAGAAGGTGGACCTGTCCCAGCAGAA

AGAGATCCCCACCACCCTGGTGGACGACTTCATCCTGAGCCCCGTCGTGAAGAGAAGCTTCATCCAGA

GCATCAAAGTGATCAACGCCATCATCAAGAAGTACGGCCTGCCCAACGACATCATTATCGAGCTGGCC

CGCGAGAAGAACTCCAAGGACGCCCAGAAAATGATCAACGAGATGCAGAAGCGGAACCGGCAGACCAA

CGAGCGGATCGAGGAAATCATCCGGACCACCGGCAAAGAGAACGCCAAGTACCTGATCGAGAAGATCA

AGCTGCACGACATGCAGGAAGGCAAGTGCCTGTACAGCCTGGAAGCCATCCCTCTGGAAGATCTGCTG

AACAACCCCTTCAACTATGAGGTGGACCACATCATCCCCAGAAGCGTGTCCTTCGACAACAGCTTCAA

CAACAAGGTGCTCGTGAAGCAGGAAGAAAACAGCAAGAAGGGCAACCGGACCCCATTCCAGTACCTGA

GCAGCAGCGACAGCAAGATCAGCTACGAAACCTTCAAGAAGCACATCCTGAATCTGGCCAAGGGCAAG

GGCAGAATCAGCAAGACCAAGAAAGAGTATCTGCTGGAAGAACGGGACATCAACAGGTTCTCCGTGCA

GAAAGACTTCATCAACCGGAACCTGGTGGATACCAGATACGCCACCAGAGGCCTGATGAACCTGCTGC

GGAGCTACTTCAGAGTGAACAACCTGGACGTGAAAGTGAAGTCCATCAATGGCGGCTTCACCAGCTTT

CTGCGGCGGAAGTGGAAGTTTAAGAAAGAGCGGAACAAGGGGTACAAGCACCACGCCGAGGACGCCCT

GATCATTGCCAACGCCGATTTCATCTTCAAAGAGTGGAAGAAACTGGACAAGGCCAAAAAAGTGATGG

AAAACCAGATGTTCGAGGAAAAGCAGGCCGAGAGCATGCCCGAGATCGAAACCGAGCAGGAGTACAAA

GAGATCTTCATCACCCCCCACCAGATCAAGCACATTAAGGACTTCAAGGACTACAAGTACAGCCACCG

GGTGGACAAGAAGCCTAATAGAGAGCTGATTAACGACACCCTGTACTCCACCCGGAAGGACGACAAGG

GCAACACCCTGATCGTGAACAATCTGAACGGCCTGTACGACAAGGACAATGACAAGCTGAAAAAGCTG

ATCAACAAGAGCCCCGAAAAGCTGCTGATGTACCACCACGACCCCCAGACCTACCAGAAACTGAAGCT

GATTATGGAACAGTACGGCGACGAGAAGAATCCCCTGTACAAGTACTACGAGGAAACCGGGAACTACC

TGACCAAGTACTCCAAAAAGGACAACGGCCCCGTGATCAAGAAGATTAAGTATTACGGCAACAAACTG

AACGCCCATCTGGACATCACCGACGACTACCCCAACAGCAGAAACAAGGTCGTGAAGCTGTCCCTGAA

GCCCTACAGATTCGACGTGTACCTGGACAATGGCGTGTACAAGTTCGTGACCGTGAAGAATCTGGATG

TGATCAAAAAAGAAAACTACTACGAAGTGAATAGCAAGTGCTATGAGGAAGCTAAGAAGCTGAAGAAG

ATCAGCAACCAGGCCGAGTTTATCGCCTCCTTCTACAACAACGATCTGATCAAGATCAACGGCGAGCT

GTATAGAGTGATCGGCGTGAACAACGACCTGCTGAACCGGATCGAAGTGAACATGATCGACATCACCT

ACCGCGAGTACCTGGAAAACATGAACGACAAGAGGCCCCCCAGGATCATTAAGACAATCGCCTCCAAG

ACCCAGAGCATTAAGAAGTACAGCACAGACATTCTGGGCAACCTGTATGAAGTGAAATCTAAGAAGCA

CCCTCAGATCATCAAAAAGGGCAAAAGGCCGGCGGCCACGAAAAAGGCCGGCCAGGCAAAAAAGAAAA
```

-continued

```
AGggatcctacccatacgatgttccagattacgcttacccatacgatgttccagattacgcttaccCa tacgatgttccagattacgcttaaGaattctagcaataaaggatcgtttattttcattggaagcgtgt gttggtttttttgatcaggcgcgGGTACCGAACGCTGACGTCATCAACCCGCTCCAAGGAATCGCGGGC

CCAGTGTCACTAGGCGGGAACACCCAGCGCGCGTGCGCCCTGGCAGGAAGATGGCTGTGAGGGACAGG

GGAGTGGCGCCCTGCAATATTTGCATGTCGCTATGTGTTCTGGGAAATCACCATAAACGTGAAATGTC

TTTGGATTTGGGAATCTTATAAGTTCTGTATGAGACCACATATAGTAATGAAATTATTGGCACGTTTT

AGTACTCTGGAAACAGAATCTACTAAAACAAGGCAAAATGCCGTGTTTATCTCGTCAACTTGTTGGCG

AGATTTTTGGTACCaggaacccctagtgatggagttggccactccctctctgcgcgctcgctcgctca ctgaggccgggcgaccaaaggtcgcccgacgcccgggctttgcccgggcggcctcagtgagcgagcga gcgcgcagctgcctgcaggggcgcctgatgcggtattttctccttacgcatctgtgcggtatttcaca ccgcatacgtcaaagcaaccatagtacgcgccctgtagcggcgcattaagcgcggcgggtgtggtggt tacgcgcagcgtgaccgctacacttgccagcgccctagcgcccgctcctttcgctttcttcccttcct ttctcgccacgttcgccggctttccccgtcaagctctaaatcggggggctccctttagggttccgattt agcgctttacggcacctcgaccccaaaaaacttgatttgggtgatggttcacgtagtgggccatcgcc ctgatagacggtttttcgccctttgacgttggagtccacgttctttaatagtggactcttgttccaaa ctggaacaacactcaaccctatctcgggctattcttttgatttataagggattttgccgatttcggcc tattggttaaaaaatgagctgatttaacaaaaatttaacgcgaattttaacaaaatattaacgtttac aattttatggtgcactctcagtacaatctgctctgatgccgcatagttaagccagccccgacacccgc caacacccgctgacgcgccctgacgggcttgtctgctcccggcatccgcttacagacaagctgtgacc gtctccgggagctgcatgtgtcagaggttttcaccgtcatcaccgaaacgcgcgagacgaaagggcct cgtgatacgcctatttttataggttaatgtcatgataataatggtttcttagacgtcaggtggcactt ttcggggaaatgtgcgcggaacccctatttgtttatttttctaaatacattcaaatatgtatccgctc atgagacaataaccctgataaatgcttcaataatattgaaaaaggaagagtatgagtattcaacattt ccgtgtcgcccttattcccttttttgcggcattttgccttcctgtttttgctcacccagaaacgctgg tgaaagtaaaagatgctgaagatcagttgggtgcacgagtgggttacatcgaactggatctcaacagc ggtaagatccttgagagttttcgccccgaagaacgttttccaatgatgagcacttttaaagttctgct atgtggcgcggtattatcccgtattgacgccgggcaagagcaactcggtcgccgcatacactattctc agaatgacttggttgagtactcaccagtcacagaaaagcatcttacggatggcatgacagtaagagaa ttatgcagtgctgccataaccatgagtgataacactgcggccaacttacttctgacaacgatcggagg accgaaggagctaaccgcttttttgcacaacatgggggatcatgtaactcgcctcgatcgttgggaac cggagctgaatgaagccataccaaacgacgagcgtgacaccacgatgcctgtagcaatggcaacaacg ttgcgcaaactattaactggcgaactacttactctagcttcccggcaacaattaatagactggatgga ggcggataaagttgcaggaccacttctgcgctcggcccttccggctggctggtttattgctgataaat ctggagccggtgagcgtggaagccgcggtatcattgcagcactggggccagatggtaagccctcccgt atcgtagttatctacacgacggggagtcaggcaactatggatgaacgaaatagacagatcgctgagat aggtgcctcactgattaagcattggtaactgtcagaccaagtttactcatatatactttagattgatt taaaacttcatttttaatttaaaaggatctaggtgaagatcctttttgataatctcatgaccaaaatc ccctaacgtgagttttcgttccactgagcgtcagaccccgtagaaaagatcaaaggatcttcttgaga tcctttttttctgcgcgtaatctgctgcttgcaaacaaaaaaaccaccgctaccagcggtggtttgtt tgccggatcaagagctaccaactctttttccgaaggtaactggcttcagcagagcgcagataccaaat actgtccttctagtgtagccgtagttaggccaccacttcaagaactctgtagcaccgcctacatacct
```

-continued cgctctgctaatcctgttaccagtggctgctgccagtggcgataagtcgtgtcttaccgggttggact caagacgatagttaccggataaggcgcagcggtcgggctgaacggggggttcgtgcacacagcccagc ttggagcgaacgacctacaccgaactgagatacctacagcgtgagctatgagaaagcgccacgcttcc cgaagggagaaaggcggacaggtatccggtaagcggcaggggtcggaacaggagagcgcacgagggagc ttccaggggggaaacgcctggtatctttatagtcctgtcgggtttcgccacctctgacttgagcgtcga tttttgrgatgctcgtcaggggggcggagcctatggaaaaacgccagcaacgcggcctttttacggtt cctggcctttgctggcctttttgctcacatgt SEQ ID NO: 16, Version 1 of vector 2
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGAaaaaatctcgccaacaagttgacgagataaacacggcattttgccttgtttttagtagattct gtttccagagtactaaaacacatttcctctctatacaaatgCGGTGTTTCGTCCTTTCCACAAGATAT

ATAAAGCCAAGAAATCGAAATACTTTCAAGTTACGGTAAGCATATGATAGTCCATTTTAAAACATAAT

TTTAAAACTGCAAACTACCCAAGAAATTATTACTTTCTACGTCACGTATTTTGTACTAATATCTTTGT

GTTTACAGTCAAATTAATTCCAATTATCTCTCTAACAGCCTTGTATCGTATATGCAAATATGAAGGAA

TCATGGGAAATAGGCCCTCCTCGAGTCGAGTGGCTCCGGTGCCCGTCAGTGGGCAGAGCGCACATCGC

CCACAGTCCCCGAGAAGTTGGGGGGAGGGGTCGGCAATTGAACCGGTGCCTAGAGAAGGTGGCGCGGG

GTAAACTGGGAAAGTGATGTCGTGTACTGGCTCCGCCTTTTTCCCGAGGGTGGGGGAGAACCGTATAT

AAGTGCAGTAGTCGCCGTGAACGTTCTTTTTCGCAACGGGTTTGCCGCCAGAACACAGGTGTCGTGAC

CGCGGCCATGGCCCCAAAGAAGAAGCGGAAGGTCGGTATCCACGGAGTCCCAGCAGCCAAGCGGAACT

ACATCCTGGGCCTGGACATCGGCATCACCAGCGTGGGCTACGGCATCATCGACTACGAGACACGGGAC

GTGATCGATGCCGGCGTGCGGCTGTTCAAAGAGGCCAACGTGGAAAACAACGAGGGCAGGCGGAGCAA

GAGAGGCGCCAGAAGGCTGAAGCGGCGGAGGCGGCATAGAATCCAGAGAGTGAAGAAGCTGCTGTTCG

ACTACAACCTGCTGACCGACCACAGCGAGCTGAGCGGCATCAACCCCTACGAGGCCAGAGTGAAGGGC

CTGAGCCAGAAGCTGAGCGAGGAAGAGTTCTCTGCCGCCCTGCTGCACCTGGCCAAGAGAAGAGGCGT

GCACAACGTGAACGAGGTGGAAGAGGACACCGGCAACGAGCTGTCCACCAAAGAGCAGATCAGCCGGA

ACAGCAAGGCCCTGGAAGAGAAATACGTGGCCGAACTGCAGCTGGAACGGCTGAAGAAAGACGGCGAA

GTGCGGGGCAGCATCAACAGATTCAAGACCAGCGACTACGTGAAAGAAGCCAAACAGCTGCTGAAGGT

GCAGAAGGCCTACCACCAGCTGGACCAGAGCTTCATCGACACCTACATCGACCTGCTGGAAACCCGGC

GGACCTACTATGAGGGACCTGGCGAGGGCAGCCCCTTCGGCTGGAAGGACATCAAAGAATGGTACGAG

ATGCTGATGGGCCACTGCACCTACTTCCCCGAGGAACTGCGCGGAGCGTGAAGTACGCCTACAACGCCGA

CCTGTACAACGCCCTGAACGACCTGAACAATCTCGTGATCACCAGGGACGAGAACGAGAAGCTGGAAT

ATTACGAGAAGTTCCAGATCATCGAGAACGTGTTCAAGCAGAAGAAGAAGCCCACCCTGAAGCAGATC

GCCAAAGAAATCCTCGTGAACGAAGAGGATATTAAGGGCTACAGAGTGACCAGCACCGGCAAGCCCGA

GTTCACCAACCTGAAGGTGTACCACGACATCAAGGACATTACCGCCCGGAAAGAGATTATTGAGAACG

CCGAGCTGCTGGATCAGATTGCCAAGATCCTGACCATCTACCAGAGCAGCGAGGACATCCAGGAAGAA

CTGACCAATCTGAACTCCGAGCTGACCCAGGAAGAGATCGAGCAGATCTCTAATCTGAAGGGCTATAC

CGGCACCCACAACCTGAGCCTGAAGGCCATCAACCTGATCCTGGACGAGCTGTGGCACACCAACGACA

ACCAGATCGCTATCTTCAACCGGCTGAAGCTGGTGCCCAAGAAGGTGGACCTGTCCCAGCAGAAAGAG

ATCCCCACCACCCTGGTGGACGACTTCATCCTGAGCCCCGTCGTGAAGAGAAGCTTCATCCAGAGCAT

CAAAGTGATCAACGCCATCATCAAGAAGTACGGCCTGCCCAACGACATCATTATCGAGCTGGCCCGCG

-continued

```
AGAAGAACTCCAAGGACGCCCAGAAAATGATCAACGAGATGCAGAAGCGGAACCGGCAGACCAACGAG

CGGATCGAGGAAATCATCCGGACCACCGGCAAAGAGAACGCCAAGTACCTGATCGAGAAGATCAAGCT

GCACGACATGCAGGAAGGCAAGTGCCTGTACAGCCTGGAAGCCATCCCTCTGGAAGATCTGCTGAACA

ACCCCTTCAACTATGAGGTGGACCAGATCATCCCCAGAAGCGTGTCCTTCGACAACAGCTTCAACAAC

AAGGTGCTCGTGAAGCAGGAAGAAAACAGCAAGAAGGGCAACCGGACCCCATTCCAGTACCTGAGCAG

CAGCGACAGCAAGATCAGCTACGAAACCTTCAAGAAGCACATCCTGAATCTGGCCAAGGGCAAGGGCA

GAATCAGCAAGACCAAGAAAGAGTATCTGCTGGAAGAACGGGACATCAACAGGTTCTCCGTGCAGAAA

GACTTCATCAACCGGAACCTGGTGGATACCAGATACGCCACCAGAGGCCTGATGAACCTGCTGCGGAG

CTACTTCAGAGTGAACAACCTGGACGTGAAAGTGAAGTCCATCAATGGCGGCTTCACCAGCTTTCTGC

GGCGGAAGTGGAAGTTTAAGAAAGAGCGGAACAAGGGGTACAAGCACCACGCCGAGGACGCCCTGATC

ATTGCCAACGCCGATTTCATCTTCAAAGAGTGGAAGAAACTGGACAAGGCCAAAAAAGTGATGGAAAA

CCAGATGTTCGAGGAAAAGCAGGCCGAGAGCATGCCCGAGATCGAAACCGAGCAGGAGTACAAAGAGA

TCTTCATCACCCCCCACCAGATCAAGCACATTAAGGACTTCAAGGACTACAAGTACAGCCACCGGGTG

GACAAGAAGCCTAATAGAGAGCTGATTAACGACACCCTGTACTCCACCCGGAAGGACGACAAGGGCAA

CACCCTGATCGTGAACAATCTGAACGGCCTGTACGACAAGGACAATGACAAGCTGAAAAAGCTGATCA

ACAAGAGCCCCGAAAAGCTGCTGATGTACCACCACGACCCCCAGACCTACCAGAAACTGAAGCTGATT

ATGGAACAGTACGGCGACGAGAAGAATCCCCTGTACAAGTACTACGAGGAAACCGGGAACTACCTGAC

CAAGTACTCCAAAAAGGACAACGGCCCCGTGATCAAGAAGATTAAGTATTACGGCAACAAACTGAACG

CCCATCTGGACATCACCGACGACTACCCCAACAGCAGAAACAAGGTCGTGAAGCTGTCCCTGAAGCCC

TACAGATTCGACGTGTACCTGGACAATGGCGTGTACAAGTTCGTGACCGTGAAGAATCTGGATGTGAT

CAAAAAAGAAAACTACTACGAAGTGAATAGCAAGTGCTATGAGGAAGCTAAGAAGCTGAAGAAGATCA

GCAACCAGGCCGAGTTTATCGCCTCCTTCTACAACAACGATCTGATCAAGATCAACGGCGAGCTGTAT

AGAGTGATCGGCGTGAACAACGACCTGCTGAACCGGATCGAAGTGAACATGATCGACATCACCTACCG

CGAGTACCTGGAAAACATGAACGACAAGAGGCCCCCCAGGATCATTAAGACAATCGCCTCCAAGACCC

AGAGCATTAAGAAGTACAGCACAGACATTCTGGGCAACCTGTATGAAGTGAAATCTAAGAAGCACCCT

CAGATCATCAAAAAGGGCAAAAGGCCGGCGGCCACGAAAAAGGCCGGCCAGGCAAAAAAGAAAAAGgg atcctacccatacgatgttccagattacgcttacccatacgatgttccagattacgcttaccCatacg atgttccagattacgcttaaGaattctagcaataaaggatcgtttattttcattggaagcgtgtgttg gttttttgatcaggcgcgGGTACCGAACGCTGACGTCATCAACCCGCTCCAAGGAATCGCGGGCCCAG

TGTCACTAGGCGGGAACACCCAGCGCGCGTGCGCCCTGGCAGGAAGATGGCTGTGAGGGACAGGGGAG

TGGCGCCCTGCAATATTTGCATGTCGCTATGTGTTCTGGGAAATCACCATAAACGTGAAATGTCTTTG

GATTTGGGAATCTTATAAGTTCTGTATGAGACCACATATAGTAATGAAATTATTGGCACGTTTTAGTA

CTCTGGAAACAGAATCTACTAAAACAAGGCAAAATGCCGTGTTTATCTCGTCAACTTGTTGGCGAGAT

TTTTGGTACCaggaacccctagtgatggagttggccactccctctctgcgcgctcgctcgctcactga ggccgggcgaccaaaggtcgcccgacgcccgggctttgcccgggcggcctcagtgagcgagcgagcgc gcagctgcctgcaggggcgcctgatgcggtattttctccttacgcatctgtgcggtatttcacaccgc atacgtcaaagcaaccatagtacgcgccctgtagcggcgcattaagcgcggcgggtgtggtggttacg cgcagcgtgaccgctacacttgccagcgccctagcgcccgctcctttcgctttcttcccttcctttct cgccacgttcgccggctttccccgtcaagctctaaatcggggggctccctttagggttccgatttagtg ctttacggcacctcgaccccaaaaaacttgatttgggtgatggttcacgtagtgggccatcgccctga
```

-continued

```
tagacggtttttcgccctttgacgttggagtccacgttctttaatagtggactcttgttccaaactgg aacaacactcaaccctatctcgggctattcttttgatttataagggattttgccgatttcggcctatt ggttaaaaaatgagctgatttaacaaaaatttaacgcgaattttaacaaaatattaacgtttacaatt ttatggtgcactctcagtacaatctgctctgatgccgcatagttaagccagccccgacacccgccaac acccgctgacgcgccctgacgggcttgtctgctcccggcatccgcttacagacaagctgtgaccgtct ccgggagctgcatgtgtcagaggttttcaccgtcatcaccgaaacgcgcgagacgaaagggcctcgtg atacgcctatttttataggttaatgtcatgataataatggtttcttagacgtcaggtggcactttttcg gggaaatgtgcgcggaacccctatttgtttatttttctaaatacattcaaatatgtatccgctcatga gacaataaccctgataaatgcttcaataatattgaaaaaggaagagtatgagtattcaacatttccgt gtcgcccttattcccttttttgcggcattttgccttcctgttttttgctcacccagaaacgctggtgaa agtaaaagatgctgaagatcagttgggtgcacgagtgggttacatcgaactggatctcaacagcggta agatccttgagagttttcgccccgaagaacgttttccaatgatgagcacttttaaagttctgctatgt ggcgcggtattatcccgtattgacgccgggcaagagcaactcggtcgccgcatacactattctcagaa tgacttggttgagtactcaccagtcacagaaaagcatcttacggatggcatgacagtaagagaattat gcagtgctgccataaccatgagtgataacactgcggccaacttacttctgacaacgatcggaggaccg aaggagctaaccgcttttttgcacaacatgggggatcatgtaactcgccttgatcgttgggaaccgga gctgaatgaagccataccaaacgacgagcgtgacaccacgatgcctgtagcaatggcaacaacgttgc gcaaactattaactggcgaactacttactctagcttcccggcaacaattaatagactggatggaggcg gataaagttgcaggaccacttctgcgctcggcccttccggctggctggtttattgctgataaatctgg agccggtgagcgtggaagccgcggtatcattgcagcactggggccagatggtaagccctcccgtatcg tagttatctacacgacggggagtcaggcaactatggatgaacgaaatagacagatcgctgagataggt gcctcactgattaagcattggtaactgtcagaccaagtttactcatatatactttagattgatttaaa acttcatttttaatttaaaaggatctaggtgaagatcctttttgataatctcatgaccaaaatccctt aacgtgagttttcgttccactgagcgtcagaccccgtagaaaagatcaaaggatcttcttgagatcct ttttttctgcgcgtaatctgctgcttgcaaacaaaaaaaccaccgctaccagcggtggtttgtttgcc ggatcaagagctaccaactctttttccgaaggtaactggcttcagcagagcgcagataccaaatactg tccttctagtgtagccgtagttaggccaccacttcaagaactctgtagcaccgcctacatacctcgct ctgctaatcctgttaccagtggctgctgccagtggcgataagtcgtgtcttaccgggttggactcaag acgatagttaccggataaggcgcagcggtcgggctgaacggggggttcgtgcacacagcccagcttgg agcgaacgacctacaccgaactgagatacctacagcgtgagctatgagaaagcgccacgcttcccgaa gggagaaaggcggacaggtatccggtaagcggcagggtcggaacaggagagcgcacgagggagcttcc agggggaaacgcctggtatctttatagtcctgtcgggtttcgccacctctgacttgagcgtcgatttt tgtgatgctcgtcaggggggcggagcctatggaaaaacgccagcaacgcggcctttttacggttcctg gccttttgctggccttttgctcacatgt
```

SEQ ID NO: 17, Version 2 of vector 2
```
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGAaaaaatctcgccaacaagttgacgagataaacacggcattttgccttgttttagtagattct gtttccagagtactaaaacacatttcctctctatacaaatgCGGTGTTTCGTCCTTTCCACAAGATAT

ATAAAGCCAAGAAATCGAAATACTTTCAAGTTACGGTAAGCATATGATAGTCCATTTTAAAACATAAT

TTTAAAACTGCAAACTACCCAAGAAATTATTACTTTCTACGTCACGTATTTTGTACTAATATCTTTGT
```

-continued

```
GTTTACAGTCAAATTAATTCCAATTATCTCTCTAACAGCCTTGTATCGTATATGCAAATATGAAGGAA

TCATGGGAAATAGGCCCTCCTCGAGCTAGACTAGCATGCTGCCCATGTAAGGAGGCAAGGCCTGGGGA

CACCCGAGATGCCTGGTTATAATTAACCCAGACATGTGGCTGCCCCCCCCCCCCCCAACACCTGCTGCC

TCTAAAAATAACCCTGCATGCCATGTTCCCGGCGAAGGGCCAGCTGTCCCCCGCCAGCTAGACTCAGC

ACTTAGTTTAGGAACCAGTGAGCAAGTCAGCCCTTGGGGCAGCCCATACAAGGCCATGGGGCTGGGCA

AGCTGCACGCCTGGGTCCGGGGTGGGCACGGTGCCCGGGCAACGAGCTGAAAGCTCATCTGCTCTCAG

GGGCCCCTCCCTGGGGACAGCCCCTCCTGGCTAGTCACACCCTGTAGGCTCCTCTATATAACCCAGGG

GCACAGGGGCTGCCCTCATTCTACCACCACCTCCACAGCACAGACAGACACTCAGGAGCCAGCCAGCa ccggtgccaccATGGCCCCAAAGAAGAAGCGGAAGGTCGGTATCCACGGAGTCCCAGCAGCCAAGCGG

AACTACATCCTGGGCCTGGACATCGGCATCACCAGCGTGGGCTACGGCATCATCGACTACGAGACACG

GGACGTGATCGATGCCGGCGTGCGGCTGTTCAAAGAGGCCAACGTGGAAAACAACGAGGGCAGGCGGA

GCAAGAGAGGCGCCAGAAGGCTGAAGCGGCGGAGGCGGCATAGAATCCAGAGAGTGAAGAAGCTGCTG

TTCGACTACAACCTGCTGACCGACCACAGCGAGCTGAGCGGCATCAACCCCTACGAGGCCAGAGTGAA

GGGCCTGAGCCAGAAGCTGAGCGAGGAAGAGTTCTCTGCCGCCCTGCTGCACCTGGCCAAGAGAAGAG

GCGTGCACAACGTGAACGAGGTGGAAGAGGACACCGGCAACGAGCTGTCCACCAAAGAGCAGATCAGC

CGGAACAGCAAGGCCCTGGAAGAGAAATACGTGGCCGAACTGCAGCTGGAACGGCTGAAGAAAGACGG

CGAAGTGCGGGGCAGCATCAACAGATTCAAGACCAGCGACTACGTGAAAGAAGCCAAACAGCTGCTGA

AGGTGCAGAAGGCCTACCACCAGCTGGACCAGAGCTTCATCGACACCTACATCGACCTGCTGGAAACC

CGGCGGACCTACTATGAGGGACCTGGCGAGGGCAGCCCCTTCGGCTGGAAGGACATCAAAGAATGGTA

CGAGATGCTGATGGGCCACTGCACCTACTTCCCCGAGGAACTGCGGAGCGTGAAGTACGCCTACAACG

CCGACCTGTACAACGCCCTGAACGACCTGAACAATCTCGTGATCACCAGGGAGGAGAACGAGAAGCTG

GAATATTACGAGAAGTTCCAGATCATCGAGAACGTGTTCAAGCAGAAGAAGAAGCCCACCCTGAAGCA

GATCGCCAAAGAAATCCTCGTGAACGAAGAGGATATTAAGGGCTACAGAGTGACCAGCACCGGCAAGC

CCGAGTTCACCAACCTGAAGGTGTACCACGACATCAAGGACATTAGCGCCCGGAAAGAGATTATTGAG

AACGCCGAGCTGCTGGATCAGATTGCCAAGATCCTGACCATCTACCAGAGCAGCGAGGACATCCAGGA

AGAACTGACCAATCTGAACTCCGAGCTGACCCAGGAAGAGATCGAGCAGATCTCTAATCTGAAGGGCT

ATACCGGCACCCACAACCTGAGCCTGAAGGCCATCAACCTGATCCTGGACGAGCTGTGGCACACCAAC

GACAACCAGATCGCTATCTTCAACCGGCTGAAGCTGGTGCCCAAGAAGGTGGACCTGTCCCAGCAGAA

AGAGATCCCCACCACCCTGGTGGACGACTTCATCCTGAGCCCCGTCGTGAAGAGAAGCTTCATCCAGA

GCATCAAAGTGATCAACGCCATCATCAAGAAGTACGGCCTGCCCAACGACATCATTATCGAGCTGGCC

CGCGAGAAGAACTCCAAGGACGCCCAGAAAATGATCAACGAGATGCAGAAGCGGAACCGGCAGACCAA

CGAGCGGATCGAGGAAATCATCCGGACCACCGGCAAAGAGAACGCCAAGTACCTGATCGAGAAGATCA

AGCTGCACGACATGCAGGAAGGCAAGTGCCTGTACAGCCTGGAAGCCATCCCTCTGGAAGATCTGCTG

AACAACCCCTTCAACTATGAGGTGGACCACATCATCCCCAGAAGCGTGTCCTTCGACAACAGCTTCAA

CAACAAGGTGCTCGTGAAGCAGGAAGAAAACAGCAAGAAGGGCAACCGGACCCCATTCCAGTACCTGA

GCAGCAGCGACAGCAAGATCAGCTACGAAACCTTCAAGAAGCACATCCTGAATCTGGCCAAGGGCAAG

GGCAGAATCAGCAAGACCAAGAAAGAGTATCTGCTGGAAGAACGGGACATCAACAGGTTCTCCGTGCA

GAAAGACTTCATCAACCGGAACCTGGTGGATACCAGATACGCCACCAGAGGCCTGATGAACCTGCTGC

GGAGCTACTTCAGAGTGAACAACCTGGACGTGAAAGTGAAGTCCATCAATGGCGGCTTCACCAGCTTT

CTGCGGCGGAAGTGGAAGTTTAAGAAAGAGCGGAACAAGGGGTACAAGCACCACGCCGAGGACGCCCT

GATCATTGCCAACGCCGATTTCATCTTCAAAGAGTGGAAGAAACTGGACAAGGCCAAAAAAGTGATGG
```

-continued

AAAACCAGATGTTCGAGGAAAAGCAGGCCGAGAGCATGCCCGAGATCGAAACCGAGCAGGAGTACAAA

GAGATCTTCATCACCCCCCACCAGATCAAGCACATTAAGGACTTCAAGGACTACAAGTACAGCCACCG

GGTGGACAAGAAGCCTAATAGAGAGCTGATTAACGACACCCTGTACTCCACCCGGAAGGACGACAAGG

GCAACACCCTGATCGTGAACAATCTGAACGGCCTGTACGACAAGGACAATGACAAGCTGAAAAAGCTG

ATCAACAAGAGCCCCGAAAAGCTGCTGATGTACCACCACGACCCCCAGACCTACCAGAAACTGAAGCT

GATTATGGAACAGTACGGCGACGAGAAGAATCCCCTGTACAAGTACTACGAGGAAACCGGGAACTACC

TGACCAAGTACTCCAAAAAGGACAACGGCCCCGTGATCAAGAAGATTAAGTATTACGGCAACAAACTG

AACGCCCATCTGGACATCACCGACGACTACCCCAACAGCAGAAACAAGGTCGTGAAGCTGTCCCTGAA

GCCCTACAGATTCGACGTGTACCTGGACAATGGCGTGTACAAGTTCGTGACCGTGAAGAATCTGGATG

TGATCAAAAAAGAAAACTACTACGAAGTGAATAGCAAGTGCTATGAGGAAGCTAAGAAGCTGAAGAAG

ATCAGCAACCAGGCCGAGTTTATCGCCTCCTTCTACAACAACGATCTGATCAAGATCAACGGCGAGCT

GTATAGAGTGATCGGCGTGAACAACGACCTGCTGAACCGGATCGAAGTGAACATGATCGACATCACCT

ACCGCGAGTACCTGGAAAACATGAACGACAAGAGGCCCCCCAGGATCATTAAGACAATCGCCTCCAAG

ACCCAGAGCATTAAGAAGTACAGCACAGACATTCTGGGCAACCTGTATGAAGTGAAATCTAAGAAGCA

CCCTCAGATCATCAAAAAGGGCAAAAGGCCGGCGGCCACGAAAAAGGCCGGCCAGGCAAAAAAGAAAA

AGggatcctacccatacgatgttccagattacgcttacccatacgatgttccagattacgcttaccCa tacgatgttccagattacgcttaaGaattctagcaataaaggatcgtttattttcattggaagcgtgt gttggtttttttgatcaggcgcgGGTACCGAACGCTGACGTCATCAACCCGCTCCAAGGAATCGCGGGC

CCAGTGTCACTAGGCGGGAACACCCAGCGCGCGTGCGCCCTGGCAGGAAGATGGCTGTGAGGGACAGG

GGAGTGGCGCCCTGCAATATTTGCATGTCGCTATGTGTTCTGGGAAATCACCATAAACGTGAAATGTC

TTTGGATTTGGGAATCTTATAAGTTCTGTATGAGACCACATATAGTAATGAAATTATTGGCACGTTTT

AGTACTCTGGAAACAGAATCTACTAAAACAAGGCAAAATGCCGTGTTTATCTCGTCAACTTGTTGGCG

AGATTTTTGGTACCaggaacccctagtgatggagttggccactccctctctgcgcgctcgctcgctca ctgaggccgggcgaccaaaggtcgcccgacgcccgggctttgcccgggcggcctcagtgagcgagcga gcgcgcagctgcctgcaggggcgcctgatgcggtattttctccttacgcatctgtgcggtatttcaca ccgcatacgtcaaagcaaccatagtacgcgccctgtagcggcgcattaagcgcggcgggtgtggtggt tacgcgcagcgtgaccgctacacttgccagcgccctagcgcccgctcctttcgctttcttcccttcct ttctcgccacgttcgccggctttccccgtcaagctctaaatcggggggctccctttagggttccgattt agtgctttacggcacctcgacccccaaaaaacttgatttgggtgatggttcacgtagtgggccatcgcc ctgatagacggttttttcgccctttgacgttggagtccacgttctttaatagtggactcttgttccaaa ctggaacaacactcaaccctatctcgggctattctttttgatttataagggattttgccgatttcggcc tattggttaaaaaatgagctgatttaacaaaaatttaacgcgaattttaacaaaatattaacgtttac aattttatggtgcactctcagtacaatctgctctgatgccgcatagttaagccagccccgacacccgc caacacccgctgacgcgccctgacgggcttgtctgctcccggcatccgcttacagacaagctgtgacc gtctccgggagctgcatgtgtcagaggttttcaccgtcatcaccgaaacgcgcgagacgaaagggcct cgtgatacgcctatttttataggttaatgtcatgataataatggtttcttagacgtcaggtggcactt ttcggggaaatgtgcgcggaacccctatttgtttatttttctaaatacattcaaatatgtatccgctc atgagacaataaccctgataaatgcttcaataatattgaaaaaggaagagtatgagtattcaacattt ccgtgtcgcccttattcccttttttgcggcattttgccttcctgtttttgctcacccagaaacgctgg tgaaagtaaaagatgctgaagatcagttgggtgcacgagtgggttacatcgaactggatctcaacagc -continued ggtaagatccttgagagttttcgccccgaagaacgttttccaatgatgagcacttttaaagttctgct atgtggcgcggtattatcccgtattgacgccgggcaagagcaactcggtcgccgcatacactattctc agaatgacttggttgagtactcaccagtcacagaaaagcatcttacggatggcatgacagtaagagaa ttatgcagtgctgccataaccatgagtgataacactgcggccaacttacttctgacaacgatcggagg accgaaggagctaaccgcttttttgcacaacatgggggatcatgtaactcgccttgatcgttgggaac cggagctgaatgaagccataccaaacgacgagcgtgacaccacgatgcctgtagcaatggcaacaacg ttgcgcaaactattaactggcgaactacttactctagcttcccggcaacaattaatagactggatgga ggcggataaagttgcaggaccacttctgcgctcggcccttccggctggctggtttattgctgataaat ctggagccggtgagcgtggaagccgcggtatcattgcagcactggggccagatggtaagccctcccgt atcgtagttatctacacgacggggagtcaggcaactatggatgaacgaaatagacagatcgctgagat aggtgcctcactgattaagcattggtaactgtcagaccaagtttactcatatatactttagattgatt taaaacttcatttttaatttaaaaggatctaggtgaagatcctttttgataatctcatgaccaaaatc ccttaacgtgagttttcgttccactgagcgtcagaccccgtagaaaagatcaaaggatcttcttgaga tcctttttttctgcgcgtaatctgctgcttgcaaacaaaaaaaccaccgctaccagcggtggtttgtt tgccggatcaagagctaccaactctttttccgaaggtaactggcttcagcagagcgcagataccaaat actgtccttctagtgtagccgtagttaggccaccacttcaagaactctgtagcaccgcctacatacct cgctctgctaatcctgttaccagtggctgctgccagtggcgataagtcgtgtcttaccgggttggact caagacgatagttaccggataaggcgcagcggtcgggctgaacggggggttcgtgcacacagcccagc ttggagcgaacgacctacaccgaactgagatacctacagcgtgagctatgagaaagcgccacgcttcc cgaagggagaaaggcggacaggtatccggtaagcggcagggtcggaacaggagagcgcacgagggagc ttccaggggaaacgcctggtatctttatagtcctgtcgggtttcgccacctctgacttgagcgtcga tttttgtgatgctcgtcaggggggcggagcctatggaaaaacgccagcaacgcggcctttttacggtt cctggccttttgctggccttttgctcacatgt SEQ ID NO: 18, Version 3 of vector 2
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGAaaaaatctcgccaacaagttgacgagataaacacggcattttgccttgtttttagtagattct gtttccagagtactaaaacacatttcctctctatacaaatgCGGTGTTTCGTCCTTTCCACAAGATAT

ATAAAGCCAAGAAATCGAAATACTTTCAAGTTACGGTAAGCATATGATAGTCCATTTTAAAACATAAT

TTTAAAACTGCAAACTACCCAAGAAATTATTACTTTCTACGTCACGTATTTTGTACTAATATCTTTGT

GTTTACAGTCAAATTAATTCCAATTATCTCTCTAACAGCCTTGTATCGTATATGCAAATATGAAGGAA

TCATGGGAAATAGGCCCTCCTCGAGGAGCTCCACCGCGGTGGCGGCCGTCCGCCtTCGGCACCATCCT

CACGACACCCAAATATGGCGACGGGTGAGGAATGGTGGGGAGTTATTTTTAGAGCGGTGAGGAAGGTG

GGCAGGCAGCAGGTGTTGGCGCTCTAAAAATAACTCCCGGGAGTTATTTTTAGAGCGGAGGAATGGTG

GACACCCAAATATGGCGACGGTTCCTCACCCGTCGCCATATTTGGGTGTCCGCCCTCGGCCGGGGCCG

CATTCCTGGGGGCCGGGCGGTGCTCCCGCCCGCCTCGATAAAAGGCTCCGGGGCCGGCGGCGGCCCAC

GAGCTACCCGGAGGAGCGGGAGGCGCCAAGCTCTAGAACTAGTGGATCCCCCGGGCTGCAGGAATTCG

ATATaccggtgccaccATGGCCCCAAAGAAGAAGCGGAAGGTCGGTATCCACGGAGTCCCAGCAGCCA

AGCGGAACTACATCCTGGGCCTGGACATCGGCATCACCAGCGTGGGCTACGGCATCATCGACTACGAG

ACACGGGACGTGATCGATGCCGGCGTGCGGCTGTTCAAAGAGGCCAACGTGGAAAACAACGAGGGCAG

GCGGAGCAAGAGAGGCGCCAGAAGGCTGAAGCGGCGGAGGCGGCATAGAATCCAGAGAGTGAAGAAGC

```
TGCTGTTCGACTACAACCTGCTGACCGACCACAGCGAGCTGAGCGGCATCAACCCCTACGAGGCCAGA

GTGAAGGGCCTGAGCCAGAAGCTGAGCGAGGAAGAGTTCTCTGCCGCCCTGCTGCACCTGGCCAAGAG

AAGAGGCGTGCACAACGTGAACGAGGTGGAAGAGGACACCGGCAACGAGCTGTCCACCAAAGAGCAGA

TCAGCCGGAACAGCAAGGCCCTGGAAGAGAAATACGTGGCCGAACTGCAGCTGGAACGGCTGAAGAAA

GACGGCGAAGTGCGGGGCAGCATCAACAGATTCAAGACCAGCGACTACGTGAAAGAAGCCAAACAGCT

GCTGAAGGTGCAGAAGGCCTACCACCAGCTGGACCAGAGCTTCATCGACACCTACATCGACCTGCTGG

AAACCCGGCGGACCTACTATGAGGGACCTGGCGAGGGCAGCCCCTTCGGCTGGAAGGACATCAAAGAA

TGGTACGAGATGCTGATGGGCCACTGCACCTACTTCCCCGAGGAACTGCGGAGCGTGAAGTACGCCTA

CAACGCCGAGCTGTACAACGCCCTGAACGACCTGAACAATCTCGTGATCACGAGGGACGAGAACGAGA

AGCTGGAATATTACGAGAAGTTCCAGATCATCGAGAACGTGTTCAAGCAGAAGAAGAAGCCCACCCTG

AAGCAGATCGCCAAAGAAATCCTCGTGAACGAAGAGGATATTAAGGGCTACAGAGTGACCAGCACCGG

CAAGCCCGAGTTCACCAACCTGAAGGTGTACCACGACATCAAGGACATTACCGCCCGGAAAGAGATTA

TTGAGAACGCCGAGCTGCTGGATCAGATTGCCAAGATCCTGACCATCTACCAGAGCAGCGAGGACATC

CAGGAAGAACTGACCAATCTGAACTCCGAGCTGACCCAGGAAGAGATCGAGCAGATCTCTAATCTGAA

GGGCTATACCGGCACCCACAACCTGAGCCTGAAGGCCATCAACCTGATCCTGGACGAGCTGTGGCACA

CCAACGACAACCAGATCGCTATCTTCAACCGGCTGAAGCTGGTGCCCAAGAAGGTGGACCTGTCCCAG

CAGAAAGAGATCCCCACCACCCTGGTGGACGACTTCATCCTGAGCCCCGTCGTGAAGAGAAGCTTCAT

CCAGAGCATCAAAGTGATCAACGCCATCATCAAGAAGTACGGCCTGCCCAACGACATCATTATCGAGC

TGGCCCGCGAGAAGAACTCCAAGGACGCCCAGAAAATGATCAACGAGATGCAGAAGCGGAACCGGCAG

ACCAACGAGCGGATCGAGGAAATCATCCGGACCACCGGCAAAGAGAACGCCAAGTACCTGATCGAGAA

GATCAAGCTGCACGACATGCAGGAAGGCAAGTGCCTGTACAGCCTGGAAGCCATCCCTCTGGAAGATC

TGCTGAACAACCCCTTCAACTATGAGGTGGACCACATCATCCCCAGAAGCGTGTCCTTCGACAACAGC

TTCAACAACAAGGTGCTCGTGAAGCAGGAAGAAACAGCAAGAAGGGCAACCGGACCCCATTCCAGTA

CCTGAGCAGCAGCGACAGCAAGATCAGCTACGAAACCTTCAAGAAGCACATCCTGAATCTGGCCAAGG

GCAAGGGCAGAATCAGCAAGACCAAGAAAGAGTATCTGCTGGAAGAACGGGACATCAACAGGTTCTCC

GTGCAGAAAGACTTCATCAACCGGAACCTGGTGGATACCAGATACGCCACCAGAGGCCTGATGAACCT

GCTGCGGAGCTACTTCAGAGTGAACAACCTGGACGTGAAAGTGAAGTCCATCAATGGCGGCTTCACCA

GCTTTCTGCGGCGGAAGTGGAAGTTTAAGAAAGAGCGGAACAAGGGGTACAAGCACCACGCCGAGGAC

GCCCTGATCATTGCCAACGCCGATTTCATCTTCAAAGAGTGGAAGAAACTGGACAAGGCCAAAAAAGT

GATGGAAAACCAGATGTTCGAGGAAAAGCAGGCCGAGAGCATGCCCGAGATCGAAACCGAGCAGGAGT

ACAAAGAGATCTTCATCACCCCCCCACCAGATCAAGCACATTAAGGACTTCAAGGACTACAAGTACAGC

CACCGGGTGGACAAGAAGCCTAATAGAGAGCTGATTAACGACACCCTGTACTCCACCCGGAAGGACGa

CAAGGGCAACACCCTGATCGTGAACAATCTGAACGGCCTGTACGACAAGGACAATGACAAGCTGAAAA

AGCTGATCAACAAGAGCCCCGAAAAGCTGCTGATGTACCACCACGACCCCCAGACCTACCAGAAACTG

AAGCTGATTATGGAACAGTACGGCGACGAGAAGAATCCCCTGTACAAGTACTACGAGGAAACCGGGAA

CTACCTGACCAAGTACTCCAAAAAGGACAACGGCCCCGTGATCAAGAAGATTAAGTATTACGGCAACA

AACTGAACGCCCATCTGGACATCACCGACGACTACCCCAACAGCAGAAACAAGGTCGTGAAGCTGTCC

CTGAAGCCCTACAGATTCGACGTGTACCTGGACAATGGCGTGTACAAGTTCGTGACCGTGAAGAATCT

GGATGTGATCAAAAAAGAAAACTACTACGAAGTGAATAGCAAGTGCTATGAGGAAGCTAAGAAGCTGA

AGAAGATCAGCAACCAGGCCGAGTTTATCGCCTCCTTCTACAACAACGATCTGATCAAGATCAACGGC

GAGCTGTATAGAGTGATCGGCGTGAACAACGACCTGCTGAACCGGATCGAAGTGAACATGATCGACAT
```

-continued

```
CACCTACCGCGAGTACCTGGAAAACATGAACGACAAGAGGCCCCCCAGGATCATTAAGACAATCGCCT

CCAAGACCCAGAGCATTAAGAAGTACAGCACAGACATTCTGGGCAACCTGTATGAAGTGAAATCTAAG

AAGCACCCTCAGATCATCAAAAAGGGCAAAAGGCCGGCGGCCACGAAAAAGGCCGGCCAGGCAAAAAA

GAAAAAGggatcctacccatacgatgttccagattacgcttacccatacgatgttccagattacgctt accCatacgatgttccagattacgcttaaGaattctagcaataaaggatcgtttattttcattggaag cgtgtgttggttttttgatcaggcgcgGGTACCGAACGCTGACGTCATCAACCCGCTCCAAGGAATCG

CGGGCCCAGTGTCACTAGGCGGGAACACCCAGCGCGCGTGCGCCCTGGCAGGAAGATGGCTGTGAGGG

ACAGGGGAGTGGCGCCCTGCAATATTTGCATGTCGCTATGTGTTCTGGGAAATCACCATAAACGTGAA

ATGTCTTTGGATTTGGGAATCTTATAAGTTCTGTATGAGACCACATATAGTAATGAAATTATTGGCAC

GTTTTAGTACTCTGGAAACAGAATCTACTAAAACAAGGCAAAATGCCGTGTTTATCTCGTCAACTTGT

TGGCGAGATTTTTGGTACCaggaacccctagtgatggagttggccactccctctctgcgcgctcgctc gctcactgaggccgggcgaccaaaggtcgcccgacgcccgggctttgcccgggcggcctcagtgagcg agcgagcgcgcagctgcctgcaggggcgcctgatgcggtattttctccttacgcatctgtgcggtatt tcacaccgcatacgtcaaagcaaccatagtacgcgccctgtagcggcgcattaagcgcggcgggtgtg gtggttacgcgcagcgtgaccgctacacttgccagcgccctagcgcccgctcctttcgctttcttccc ttcctttctcgccacgttcgccggctttccccgtcaagctctaaatcggggggctccctttagggttcc gatttagtgctttacggcacctcgaccccaaaaaacttgatttgggtgatggttcacgtagtgggcca tcgccctgatagacggtttttcgccctttgacgttggagtccacgttctttaatagtggactcttgtt ccaaactggaacaacactcaaccctatctcgggctattctttgatttataagggattttgccgattt cggcctattggttaaaaaatgagctgatttaacaaaaatttaacgcgaattttaacaaaatattaacg tttacaattttatggtgcactctcagtacaatctgctctgatgccgcatagttaagccagccccgaca cccgccaacacccgctgacgcgccctgacgggcttgtctgctcccggcatccgcttacagacaagctg tgaccgtctccgggagctgcatgtgtcagaggttttcaccgtcatcaccgaaacgcgcgagacgaaag ggcctcgtgatacgcctatttttataggttaatgtcatgataataatggtttcttagacgtcaggtgg cacttttcggggaaatgtgcgcggaacccctatttgtttatttttctaaatacattcaaatatgtatc cgctcatgagacaataaccctgataaatgcttcaataatattgaaaaaggaagagtatgagtattcaa catttccgtgtcgcccttattcccttttttgcggcattttgccttcctgtttttgctcacccagaaac gctggtgaaagtaaaagatgctgaagatcagttgggtgcacgagtgggttacatcgaactggatctca acagcggtaagatccttgagagttttcgccccgaagaacgttttccaatgatgagcacttttaaagtt ctgctatgtggcgcggtattatcccgtattgacgccgggcaagagcaactcggtcgccgcatacacta ttctcagaatgacttggttgagtactcaccagtcacagaaaagcatcttacggatggcatgacagtaa gagaattatgcagtgctgccataaccatgagtgataacactgcggccaacttacttctgacaacgatc ggaggaccgaaggagctaaccgcttttttgcacaacatggggggatcatgtaactcgccttgatcgttg ggaaccggagctgaatgaagccataccaaacgacgagcgtgacaccacgatgcctgtagcaatggcaa caacgttgcgcaaactattaactggcgaactacttactctagcttcccggcaacaattaatagactgg atggaggcggataaagttgcaggaccacttctgcgctcggcccttccggctggctggtttattgctga taaatctggagccggtgagcgtggaagccgcggtatcattgcagcactggggccagatggtaagccct cccgtatcgtagttatctacacgacggggagtcaggcaactatggatgaacgaaatagacagatcgct gagataggtgcctcactgattaagcattggtaactgtcagaccaagtttactcatatatactttagat tgatttaaaacttcattttttaatttaaaaggatctaggtgaagatcctttttgataatctcatgacca
```

-continued aaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggt ttgtttgccggatcaagagctaccaactctttttccgaaggtaactggcttcagcagagcgcagatac caaatactgtccttctagtgtagccgtagttaggccaccacttcaagaactctgtagcaccgcctaca tacctcgctctgctaatcctgttaccagtggctgctgccagtggcgataagtcgtgtcttaccgggtt ggactcaagacgatagttaccggataaggcgcagcggtcgggctgaacggggggttcgtgcacacagc ccagcttggagcgaacgacctacaccgaactgagatacctacagcgtgagctatgagaaagcgccacg cttcccgaagggagaaaggcggacaggtatccggtaagcggcagggtcggaacaggagagcgcacgag ggagcttccagggggaaacgcctggtatctttatagtcctgtcgggtttcgccacctctgacttgagc gtcgatttttgtgatgctcgtcaggggggcggagcctatggaaaaacgccagcaacgcggcctttttta cggttcctggccttttgctggccttttgctcacatgt SEQ ID NO: 19, Version 4 of vector 2
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGAaaaaatctcgccaacaagttgacgagatacaacacggcattttgccttgtttttagtagattct gtttccagagtactaaaacacatttcctctctatacaaatgCGGTGTTTCGTCCTTTCCACAAGATAT

ATAAAGCCAAGAAATCGAAATACTTTCAAGTTACGGTAAGCATATGATAGTCCATTTTAAAACATAAT

TTTAAAACTGCAAACTACCCAAGAAATTATTACTTTCTACGTCACGTATTTTGTACTAATATCTTTGT

GTTTACAGTCAAATTAATTCCAATTATCTCTCTAACAGCCTTGTATCGTATATGCAAATATGAAGGAA

TCATGGGAAATAGGCCCTCctcgagGtttaaacaagcttgcatgtctaagctagaccccttcagattaa aaataactgaggtaagggcctgggtaggggaggtggtgtgagacgctcctgtctctcctctatctgcc catcggccctttggggaggaggaatgtgcccaaggactaaaaaaaggccatggagccagaggggcgag ggcaacagacctttcatgggcaaaccttggggccctgctgtctagcatgccccactacgggtctaggc tgcccatgtaaggaggcaaggcctggggacacccgagatgcctggttataattaacccagacatgtgg ctgcccccccccccaacacctgctgcctctaaaaataaccctgtccctggtggatcccctgcatgc gaagatcttcgaacaaggctgtggggggactgagggcaggctgtaacaggcttggggggccagggcttat acgtgcctgggactcccaaagtattactgttccatgttcccggcgaagggccagctgtcccccgccag ctagactcagcacttagtttaggaaccagtgagcaagtcagcccttggggcagcccatacaaggccat ggggctgggcaagctgcacgcctgggtccggggtgggcacggtgcccgggcaacgagctgaaagctca tctgctctcaggggcccctccctggggacagcccctcctggctagtcacaccctgtaggctcctctat ataacccaggggcacaggggctgccctcattctaccaccacctccacagcacagacagacactcagga gccagccagcggcgcgcccaccggtgccaccATGGCCCCAAAGAAGAAGCGGAAGGTCGGTATCCACG

GAGTCCCAGCAGCCAAGCGGAACTACATCCTGGGCCTGGACATCGGCATCACCAGCGTGGGCTACGGC

ATCATCGACTACGAGACACGGGACGTGATCGATGCCGGCGTGCGGCTGTTCAAAGAGGCCAACGTGGA

AAACAACGAGGGCAGGCGGAGCAAGAGAGGCGCCAGAAGGCTGAAGCGGCGGAGGCGGCATAGAATCC

AGAGAGTGAAGAAGCTGCTGTTCGACTACAACCTGCTGACCGACCACAGCGAGCTGAGCGGCATCAAC

CCCTACGAGGCCAGAGTGAAGGGCCTGAGCCAGAAGCTGAGCGAGGAAGAGTTCTCTGCCGCCCTGCT

GCACCTGGCCAAGAGAAGAGGCGTGCACAACGTGAACGAGGTGGAAGAGGACACCGGCAACGAGCTGT

CCACCAAAGAGCAGATCAGCCGGAACAGCAAGGCCCTGGAAGAGAAATACGTGGCCGAACTGCAGCTG

GAACGGCTGAAGAAAGACGGCGAAGTGCGGGGCAGCATCAACAGATTCAAGACCAGCGACTACGTGAA

AGAAGCCAAACAGCTGCTGAAGGTGCAGAAGGCCTACCACCAGCTGGACCAGAGCTTCATCGACACCT

-continued

```
ACATCGACCTGCTGGAAACCCGGCGGACCTACTATGAGGGACCTGGCGAGGGCAGCCCCTTCGGCTGG

AAGGACATCAAAGAATGGTACGAGATGCTGATGGGCCACTGCACCTACTTCCCCGAGGAACTGCGGAG

CGTGAAGTACGCCTACAACGCCGACCTGTACAACGCCCTGAACGACCTGAACAATCTCGTGATCACCA

GGGACGAGAACGAGAAGCTGGAATATTACGAGAAGTTCCAGATCATCGAGAACGTGTTCAAGCAGAAG

AAGAAGCCCACCCTGAAGCAGATCGCCAAAGAAATCCTCGTGAACGAAGAGGATATTAAGGGCTACAG

AGTGACCAGCACCGGCAAGCCCGAGTTCACCAACCTGAAGGTGTACCACGACATCAAGGACATTAGCG

CCCGGAAAGAGATTATTGAGAACGCCGAGCTGCTGGATCAGATTGCCAAGATCCTGACCATCTACCAG

AGCAGCGAGGACATCCAGGAAGAACTGACCAATCTGAACTCCGAGCTGACCCAGGAAGAGATCGAGCA

GATCTCTAATCTGAAGGGCTATACCGGCACCCACAACCTGAGCCTGAAGGCCATCAACCTGATCCTGG

ACGAGCTGTGGCACACCAACGACAACCAGATCGCTATCTTGAACCGGCTGAAGCTGGTGCCCAAGAAG

GTGGACCTGTCCCAGCAGAAAGAGATCCCCACCACCCTGGTGGACGACTTCATCCTGAGCCCCGTCGT

GAAGAGAAGCTTCATCCAGAGCATCAAAGTGATCAACGCCATCATCAAGAAGTACGGCCTGCCCAACG

ACATCATTATCGAGCTGGCCCGCGAGAAGAACTCCAAGGACGCCCAGAAAATGATCAACGAGATGCAG

AAGCGGAACCGGCAGACCAACGAGCGGATCGAGGAAATCATCCGGACCACCGGCAAAGAGAACGCCAA

GTACCTGATCGAGAAGATCAAGCTGCACGACATGCAGGAAGGCAAGTGCCTGTACAGCCTGGAAGCCA

TCCCTCTGGAAGATCTGCTGAACAACCCCTTCAACTATGAGGTGGACCACATCATCCCCAGAAGCGTG

TCCTTCGACAACAGCTTCAACAACAAGGTGCTCGTGAAGCAGGAAGAAACAGCAAGAAGGGCAACCG

GACCCCATTCCAGTACCTGAGCAGCAGCGAGAGCAAGATCAGCTACGAAACCTTCAAGAAGCACATCC

TGAATCTGGCGAAGGGCAAGGGCAGAATCAGCAAGACCAAGAAAGAGTATCTGCTGGAAGAACGGGAC

ATCAACAGGTTCTCCGTGCAGAAAGACTTCATCAACCGGAACCTGGTGGATACCAGATACGCCACCAG

AGGCCTGATGAACCTGCTGCGGAGCTACTTCAGAGTGAACAACCTGGACGTGAAAGTGAAGTCCATCA

ATGGCGGCTTCACCAGCTTTCTGCGGCGGAAGTGGAAGTTTAAGAAAGAGCGGAACAAGGGGTACAAG

CACCACGCCGAGGACGCCCTGATCATTGCCAACGCCGATTTCATCTTCAAAGAGTGGAAGAAACTGGA

CAAGGCCAAAAAAGTGATGGAAAACCAGATGTTCGAGGAAAAGCAGGCCGAGAGCATGCCCGAGATCG

AAACCGAGCAGGAGTACAAAGAGATCTTCATCACCCCCCACGAGATCAAGCACATTAAGGACTTCAAG

GACTACAAGTACAGCCACCGGGTGGACAAGAAGCCTAATAGAGAGCTGATTAACGACACCCTGTACTC

CACCCGGAAGGACGACAAGGGCAACACCCTGATCGTGAACAATCTGAACGGCCTGTACGACAAGGACA

ATGACAAGCTGAAAAAGCTGATCAACAAGAGCCCCGAAAAGCTGCTGATGTACCACCACGACCCCCAG

ACCTACCAGAAACTGAAGCTGATTATGGAACAGTACGGCGACGAGAAGAATCCCCTGTACAAGTACTA

CGAGGAAACCGGGAACTACCTGACCAAGTACTCCAAAAAGGACAACGGCCCCGTGATCAAGAAGATTA

AGTATTACGGCAACAAACTGAACGCCCATCTGGACATCACCGACGACTACCCCAACAGCAGAAACAAG

GTCGTGAAGCTGTCCCTGAAGCCCTACAGATTCGACGTGTACCTGGACAATGGCGTGTACAAGTTCGT

GACCGTGAAGAATCTGGATGTGATCAAAAAAGAAAACTACTACGAAGTGAATAGCAAGTGCTATGAGG

AAGCTAAGAAGCTGAAGAAGATCAGCAACCAGGCCGAGTTTATCGCCTCCTTCTACAACAACGATCTG

ATCAAGATCAACGGCGAGCTGTATAGAGTGATCGGCGTGAACAACGACCTGCTGAACCGGATCGAAGT

GAACATGATCGACATCACCTACCGCGAGTACCTGGAAAACATGAACGACAAGAGGCCCCCCAGGATCA

TTAAGACAATCGCCTCCAAGACCCAGAGCATTAAGAAGTACAGCACAGACATTCTGGGCAACCTGTAT

GAAGTGAAATCTAAGAAGCACCCTCAGATCATCAAAAAGGGCAAAAGGCCGGCGGCCACGAAAAAGGC

CGGCCAGGCAAAAAAGAAAAAGggatcctacccatacgatgttccagattacgcttacccatacgatg ttccagattacgcttaccCatacgatgttccagattacgcttaaGaattctagcaataaaggatcgtt tattttcattggaagcgtgtgttggtttttttgatcaggcgcgGGTACCGAACGCTGACGTCATCAACC
```

-continued

```
CGCTCCAAGGAATCGCGGGCCCAGTGTCACTAGGCGGGAACACCCAGCGCGCGTGCGCCCTGGCAGGA

AGATGGCTGTGAGGGACAGGGGAGTGGCGCCCTGCAATATTTGCATGTCGCTATGTGTTCTGGGAAAT

CACCATAAACGTGAAATGTCTTTGGATTTGGGAATCTTATAAGTTCTGTATGAGACCACATATAGTAA

TGAAATTATTGGCACGTTTTAGTACTCTGGAAACAGAATCTACTAAAACAAGGCAAAATGCCGTGTTT

ATCTCGTCAACTTGTTGGCGAGATTTTTGGTACCaggaacccctagtgatggagttggccactccctc tctgcgcgctcgctcgctcactgaggccgggcgaccaaaggtcgcccgacgcccgggctttgcccggg cggcctcagtgagcgagcgagcgcgcagctgcctgcaggggcgcctgatgcggtattttctccttacg catctgtgcggtatttcacaccgcatacgtcaaagcaaccatagtacgcgccctgtagcggcgcatta agcgcggcgggtgtggtggttacgcgcagcgtgaccgctacacttgccagcgccctagcgcccgctcc tttcgctttcttcccttcctttctcgccacgttcgccggctttccccgtcaagctctaaatcgggggc tccctttagggttccgatttagtgctttacggcacctcgaccccaaaaaacttgatttgggtgatggt tcacgtagtgggccatcgccctgatagacggtttttcgccctttgacgttggagtccacgttctttaa tagtggactcttgttccaaactggaacaacactcaaccctatctcgggctattcttttgatttataag ggattttgccgatttcggcctattggttaaaaaatgagctgatttaacaaaaatttaacgcgaatttt aacaaaatattaacgtttacaattttatggtgcactctcagtacaatctgctctgatgccgcatagtt aagccagccccgacacccgccaacacccgctgacgcgccctgacgggcttgtctgctcccggcatccg

AAGGACATCAAAGAATGGTACGAGATGCTGATGGGCCACTGCACCTACTTCCCCGAGGAACTGCGGAG

CGTGAAGTACGCCTACAACGCCGACCTGTACAACGCCCTGAACGACCTGAACAATCTCGTGATCACCA

GGGACGAGAACGAGAAGCTGGAATATTACGAGAAGTTCCAGATCATCGAGAACGTGTTCAAGCAGAAG

AAGAAGCCCACCCTGAAGCAGATCGCCAAAGAAATCCTCGTGAACGAAGAGGATATTAAGGGCTACAG

AGTGACCAGCACCGGCAAGCCCGAGTTCACCAACCTGAAGGTGTACCACGACATCAAGGACATTACCG

CCCGGAAAGAGATTATTGAGAACGCCGAGCTGCTGGATCAGATTGCCAAGATCCTGACCATCTACCAG

AGCAGCGAGGACATCCAGGAAGAACTGACCAATCTGAACTCCGAGCTGACCCAGGAAGAGATCGAGCA

GATCTCTAATCTGAAGGGCTATACCGGCACCCACAACCTGAGCCTGAAGGCCATCAACCTGATCCTGG

ACGAGCTGTGGCACACCAACGACAACCAGATCGCTATCTTCAACCGGCTGAAGCTGGTGCCCAAGAAG

GTGGACCTGTCCCAGCAGAAAGAGATCCCCACCACCCTGGTGGACGACTTCATCCTGAGCCCCGTCGT

GAAGAGAAGCTTCATCCAGAGCATCAAAGTGATCAACGCCATCATCAAGAAGTACGGCCTGCCCAACG

ACATCATTATCGAGCTGGCCCGCGAGAAGAACTCCAAGGACGCCCAGAAATGATCAACGAGATGCAG

AAGCGGAACCGGCAGACCAACGAGCGGATCGAGGAAATCATCCGGACCACCGGCAAAGAGAACGCCAA

GTACCTGATCGAGAAGATCAAGCTGCACGACATGCAGGAAGGCAAGTGCCTGTACAGCCTGGAAGCCA

TCCCTCTGGAAGATCTGCTGAACAACCCCTTCAACTATGAGGTGGACCACATCATCCCCAGAAGCGTG

TCCTTCGACAACAGCTTCAACAACAAGGTGCTCGTGAAGCAGGAAGAAACAGCAAGAAGGGCAACCG

GACCCCATTCCAGTACCTGAGCAGCAGCGAGAGCAAGATCAGCTACGAAACCTTCAAGAAGCACATCC

TGAATCTGGCCAAGGGCAAGGGCAGAATCAGCAAGACCAAGAAAGAGTATCTGCTGGAAGAACGGGAC

ATCAACAGGTTCTCCGTGCAGAAAGACTTCATCAACCGGAACCTGGTGGATACCAGATACGCCACCAG

AGGCCTGATGAACCTGCTGCGGAGCTACTTCAGAGTGAACAACCTGGACGTGAAAGTGAAGTCCATCA

ATGGCGGCTTCACCAGCTTTCTGCGGCGGAAGTGGAAGTTTAAGAAAGAGCGGAACAAGGGGTACAAG

CACCACGCCGAGGACGCCCTGATCATTGCCAACGCCGATTTCATCTTCAAAGAGTGGAAGAAACTGGA

CAAGGCCAAAAAAGTGATGGAAAACCAGATGTTCGAGGAAAAGCAGGCCGAGAGCATGCCCGAGATCG

AAACCGAGCAGGAGTACAAAGAGATCTTCATCACCCCCCACGAGATCAAGCACATTAAGGACTTCAAG
```

-continued

```
GACTACAAGTACAGCCACCGGGTGGACAAGAAGCCTAATAGAGAGCTGATTAACGACACCCTGTACTC

CACCCGGAAGGACGACAAGGGCAACACCCTGATCGTGAACAATCTGAACGGCCTGTACGACAAGGACA

ATGACAAGCTGAAAAAGCTGATCAACAAGAGCCCCGAAAAGCTGCTGATGTACCACCACGACCCCCAG

ACCTACCAGAAACTGAAGCTGATTATGGAACAGTACGGCGACGAGAAGAATCCCCTGTACAAGTACTA

CGAGGAAACCGGGAACTACCTGACCAAGTACTCCAAAAAGGACAACGGCCCCGTGATCAAGAAGATTA

ACTATTACGGCAACAAACTGAACGCCCATCTGGACATCACCGACGACTACCCCAACAGCAGAAACAAG

GTCGTGAAGCTGTCCCTGAAGCCCTACAGATTCGACGTGTACCTGGACAATGGCGTGTACAAGTTCGT

GACCGTGAAGAATCTGGATGTGATCAAAAAAGAAAACTACTACGAAGTGAATAGCAAGTGCTATGAGG

AAGCTAAGAAGCTGAAGAAGATCAGCAACCAGGCCGAGTTTATCGCCTCCTTCTACAACAACGATCTG

ATCAAGATCAACGGCGAGCTGTATAGAGTGATCGGCGTGAACAACGACCTGCTGAACCGGATCGAAGT

GAACATGATCGACATCACCTACCGCGAGTACCTGGAAAACATGAACGACAAGAGGCCCCCCAGGATCA

TTAAGACAATCGCCTCCAAGACCCAGAGCATTAAGAAGTACAGCACAGACATTCTGGGCAACCTGTAT

GAAGTGAAATCTAAGAAGCACCCTCAGATCATCAAAAAGGGCAAAAGGCCGGCGGCCACGAAAAAGGC

CGGCCAGGCAAAAAAGAAAAAGggatcctacccatacgatgttccagattaegcttacccatacgata ttccagattacgcttaccCatacgatgttccagattacgcttaaGaattctagcaataaaggatcgtt tattttcattggaagcgtgtgttggtttttttgatcaggcgcgGGTACCGAACGCTGACGTCATCAACC

CGCTCCAAGGAATCGCGGGCCCAGTGTCACTAGGCGGGAACACCCAGCGCGCGTGCGCCCTGGCAGGA

AGATGGCTGTGAGGGACAGGGGAGTGGCGCCCTGCAATATTTGCATGTCGCTATGTGTTCTGGGAAAT

CACCATAAACGTGAAATGTCTTTGGATTTGGGAATCTTATAAGTTCTGTATGAGACCACATATAGTAA

TGAAATTATTGGCACGTTTTAGTACTCTGGAAACAGAATCTACTAAAACAAGGCAAAATGCCGTGTTT

ATCTCGTCAACTTGTTGGCGAGATTTTTGGTACCaggaacccctagtgatggagttggccactccctc tctgcgcgctcgctcgctcactgaggccgggcgaccaaaggtcgcccgacgcccgggctttgcccggg cggcctcagtgagcgagcgagcgcgcagctgcctgcaggggcgcctgatgcggtattttctccttacg catctgtgcggtatttcacaccgcatacgtcaaagcaaccatagtacgcgccctgtagcggcgcatta agcgcggcgggtgtggtggttacgcgcagcgtgaccgctacacttgccagcgccctagcgcccgctcc tttcgctttcttcccttcctttctcgccacgttcgccggctttccccgtcaagctctaaatcgggggc tccctttagggttccgatttagtgctttacggcacctcgaccccaaaaaacttgatttgggtgatggt tcacgtagtgggccatcgccctgatagacggtttttcgccctttgacgttggagtccacgttctttaa tagtggactcttgttccaaactggaacaacactcaaccctatctcgggetattcttttgatttataag ggattttgccgatttcggcctattggttaaaaaatgagctgatttaacaaaaatttaacgcgaatttt aacaaaatattaacgtttacaattttatggtgcactctcagtacaatctgctctgatgccgcatagtt aagccagccccgacacccgccaacacccgctgacgcgccctgacgggcttgtctgctcccggcatccg cttacagacaagctgtgaccgtctccgggagctgcatgtgtcagaggttttcaccgtcatcaccgaaa cgcgcgagacgaaagggcctcgtgatacgcctatttttataggttaatgtcatgataataatggtttc ttagacgtcaggtggcacttttcggggaaatgtgcgcggaacccctatttgtttattttttctaaatac attcaaatatgtatccgctcatgagacaataaccctgataaatgcttcaataatattgaaaaaggaag agtatgagtattcaacatttccgtgtcgcccttattcccttttttgcggcattttgccttcctgtttt tgctcacccagaaacgctggtgaaagtaaaagatgctgaagatcagttgggtgcacgagtgggttaca tcgaactggatctcaacagcggtaagatccttgagagttttcgccccgaagaacgttttccaatgatg agcacttttaaagttctgctatgtggcgcggtattatcccgtattgacgccgggcaagagcaactcgg tcgccgcatacactattctcagaatgacttggttgagtactcaccagtcacagaaaagcatcttacgg
```

-continued atggcatgacagtaagagaattatgcagtgctgccataaccatgagtgataacactgcggccaactta cttctgacaacgatcggaggaccgaaggagctaaccgcttttttgcacaacatgggggatcatgtaac tcgccttgatcgttgggaaccggagctgaatgaagccataccaaacgacgagcgtgacaccacgatgc ctgtagcaatggcaacaacgttgcgcaaactattaactggcgaactacttactctagcttcccggcaa caattaatagactggatggaggcggataaagttgcaggaccacttctgcgctcggcccttccggctgg ctggtttattgctgataaatctggagccggtgagcgtggaagccgcggtatcattgcagcactgggc cagatggtaagccctcccgtatcgtagttatctacacgacggggagtcaggcaactatggatgaacga aatagacagatcgctgagataggtgcctcactgattaagcattggtaactgtcagaccaagtttactc atatatactttagattgatttaaaacttcattttttaatttaaaaggatctaggtgaagatccttttttg ataatctcatgaccaaaatcccttaacgtgagttttcgttccactgagcgtcagacccccgtagaaaag atcaaaggatcttcttgagatcctttttttctgcgcgtaatctgctgcttgcaaacaaaaaaaccacc gctaccagcggtggtttgtttgccggatcaagagctaccaactctttttccgaaggtaactggcttca gcagagcgcagataccaaatactgtccttctagtgtagccgtagttaggccaccacttcaagaactct gtagcaccgcctacatacctcgctctgctaatcctgttaccagtggctgctgccagtggcgataagtc gtgtcttaccgggttggactcaagacgatagttaccggataaggcgcagcggtcgggctgaacggggg gttcgtgcacacagcccagcttggagcgaacgacctacaccgaactgagatacctacagcgtgagcta tgagaaagcgccacgcttcccgaagggagaaaggcggacaggtatccggtaagcggcagggtcggaac aggagagcgcacgagggagcttccaggggggaaacgcctggtatctttatagtcctgtcgggtttcgcc acctctgacttgagcgtcgatttttgtgatgctcgtcaggggggcggagcctatggaaaaacgccagc aacgcggcctttttacggttcctggccttttgctggccttttgctcacatgt SEQ ID NO: 20, Version 1 of vector 3
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGAaaaaatctcgccaacaagttgacgagatataaacacggcattttgccttgtttttagtagattct gtttccagagtactaaaacacatttcctctctatacaaatgCGGTGTTTCGTCCTTTCCACAAGATAT

ATAAAGCCAAGAAATCGAAATACTTTCAAGTTAGGGTAAGCATATGATAGTCCATTTTAAAACATAAT

TTTAAAACTGCAAACTACCCAAGAAATTATTACTTTCTACGTCACGTATTTTGTACTAATATCTTTGT

GTTTACAGTCAAATTAATTCCAATTATCTCTCTAACAGCCTTGTATCGTATATGCAAATATGAAGGAA

TCATGGGAAATAGGCCCTCCTCGAGTCGAGTGGCTCCGGTGCCCGTCAGTGGGCAGAGCGCACATCGC

CCACAGTCCCCGAGAAGTTGGGGGGAGGGGTCGGCAATTGAACCGGTGCCTAGAGAAGGTGGCGCGGG

GTAAACTGGGAAAGTGATGTCGTGTACTGGCTCCGCCTTTTTCCCGAGGGTGGGGGAGAACCGTATAT

AAGTGCAGTAGTCGCCGTGAACGTTCTTTTTCGCAACGGGTTTGCCGCCAGAACACAGGTGTCGTGAC

CGCGGCCATGGCCCCAAAGAAGAAGCGGAAGGTCGGTATCCACGGAGTCCCAGCAGCCAAGCGGAACT

ACATCCTGGGCCTGGACATCGGCATCACCAGCGTGGGCTACGGCATCATCGACTACGAGACACGGGAC

GTGATCGATGCCGGCGTGCGGCTGTTCAAAGAGGCCAACGTGGAAAACAACGAGGGCAGGCGGAGCAA

GAGAGGCGCCAGAAGGCTGAAGCGGCGGAGGCGGCATAGAATCCAGAGAGTGAAGAAGCTGCTGTTCG

ACTACAACCTGCTGACCGACCACAGCGAGCTGAGCGGCATCAACCCCTACGAGGCCAGAGTGAAGGGC

CTGAGCCAGAAGCTGAGCGAGGAAGAGTTCTCTGCCGCCCTGCTGCACCTGGCCAAGAGAAGAGGCGT

GCACAACGTGAACGAGGTGGAAGAGGACACCGGCAACGAGCTGTCCACCAAAGAGCAGATCAGCCGGA

ACAGCAAGGCCCTGGAAGAGAAATACGTGGCCGAACTGCAGCTGGAACGGCTGAAGAAGACGGCGAA

GTGCGGGGCAGCATCAACAGATTCAAGACCAGCGACTACGTGAAAGAAGCCAAACAGCTGCTGAAGGT

-continued

```
GCAGAAGGCCTACCACCAGCTGGACCAGAGCTTCATCGACACCTACATCGACCTGCTGGAAACCCGGC

GGACCTACTATGAGGGACCTGGCGAGGGCAGCCCCTTCGGCTGGAAGGACATCAAAGAATGGTACGAG

ATGCTGATGGGCCACTGCACCTACTTCCCCGAGGAACTGCGGAGCGTGAAGTACGCCTACAACGCCGA

CCTGTACAACGCCCTGAACGACCTGAACAATCTCGTGATCACCAGGGACGAGAACGAGAAGCTGGAAT

ATTACGAGAAGTTCCAGATCATCGAGAACGTGTTCAAGCAGAAGAAGAAGCCCACCCTGAAGCAGATC

GCCAAAGAAATCCTCGTGAACGAAGAGGATATTAAGGGCTACAGAGTGACCAGCACCGGCAAGCCCGA

GTTCACCAACCTGAAGGTGTACCACGACATCAAGGACATTACCGCCCGGAAAGAGATTATTGAGAACG

CCGAGCTGCTGGATCAGATTGCCAAGATCCTGACCATCTACCAGAGCAGCGAGGACATCCAGGAAGAA

CTGACCAATCTGAACTCCGAGCTGAGCCAGGAAGAGATCGAGCAGATCTCTAATCTGAAGGGCTATAC

CGGCACCCACAACCTGAGCCTGAAGGCCATCAACCTGATCCTGGACGAGCTGTGGCACACCAACGACA

ACCAGATCGCTATCTTCAACCGGCTGAAGCTGGTGCCCAAGAAGGTGGACCTGTCCCAGCAGAAAGAG

ATCCCCACCACCCTGGTGGACGACTTCATCCTGAGCCCCGTCGTGAAGAGAAGCTTCATCCAGAGCAT

CAAAGTGATCAACGCCATCATCAAGAAGTACGGCCTGCCCAACGACATCATTATCGAGCTGGCCCGCG

AGAAGAACTCCAAGGACGCCCAGAAAATGATCAACGAGATGCAGAAGCGGAACCGGCAGACCAACGAG

CGGATCGAGGAAATCATCCGGACCACCGGCAAAGAGAACGCCAAGTACCTGATCGAGAAGATCAAGCT

GCACGACATGCAGGAAGGCAAGTGCCTGTACAGCCTGGAAGCCATCCCTCTGGAAGATCTGCTGAACA

ACCCCTTCAACTATGAGGTGGACCACATCATCCCCAGAAGCGTGTCCTTCGACAACAGCTTCAACAAC

AAGGTGCTCGTGAAGCAGGAAGAAAACAGCAAGAAGGGCAACCGGACCCCATTCCAGTACCTGAGCAG

CAGCGACAGCAAGATCAGCTACGAAACCTTCAAGAAGCACATCCTGAATCTGGCCAAGGGCAAGGGCA

GAATCAGCAAGACCAAGAAAGAGTATCTGCTGGAAGAACGGGACATCAACAGGTTCTCCGTGCAGAAA

GACTTCATCAACCGGAACCTGGTGGATACCAGATACGCCACCAGAGGCCTGATGAACCTGCTGCGGAG

CTACTTCAGAGTGAACAACCTGGACGTGAAAGTGAAGTCCATCAATGGCGGCTTCACCAGCTTTCTGC

GGCGGAAGTGGAAGTTTAAGAAAGAGCGGAACAAGGGGTACAAGCACCACGCCGAGGACGCCCTGATC

ATTGCCAACGCCGATTTCATCTTCAAAGAGTGGAAGAAACTGGACAAGGCCAAAAAAGTGATGGAAAA

CCAGATGTTCGAGGAAAAGCAGGCCGAGAGCATGCCCGAGATCGAAACCGAGCAGGAGTACAAAGAGA

TCTTCATCACCCCCCACCAGATCAAGCACATTAAGGACTTCAAGGACTACAAGTACAGCCACCGGGTG

GACAAGAAGCCTAATAGAGAGCTGATTAACGAGACCCTGTACTCCACCCGGAAGGACGACAAGGGCAA

CACCCTGATCGTGAACAATCTGAACGGCCTGTACGACAAGGACAATGACAAGCTGAAAAAGCTGATCA

ACAAGAGCCCCGAAAAGCTGCTGATGTACCACCACGACCCCCAGACCTACCAGAAACTGAAGCTGATT

ATGGAACAGTACGGCGACGAGAAGAATCCCCTGTACAAGTACTACGAGGAAACCGGGAACTACCTGAC

CAAGTACTCGAAAAAGGACAACGGCCCCGTGATCAAGAAGATTAAGTATTACGGCAACAAACTGAACG

CCCATCTGGACATCACCGACGACTACCCCAACAGCAGAAACAAGGTCGTGAAGCTGTCCCTGAAGCCC

TACAGATTCGACGTGTACCTGGACAATGGCGTGTACAAGTTCGTGACCGTGAAGAATCTGGATGTGAT

CAAAAAAGAAAACTACTACGAAGTGAATAGCAAGTGCTATGAGGAAGCTAAGAAGCTGAAGAAGATCA

GCAACCAGGCCGAGTTTATCGCCTCCTTCTACAACAACGATCTGATCAAGATCAACGGCGAGCTGTAT

AGAGTGATCGGCGTGAACAACGACCTGCTGAACCGGATCGAAGTGAACATGATCGACATCACCTACCG

CGAGTACCTGGAAAACATGAACGACAAGAGGCCCCCCAGGATCATTAAGACAATCGCCTCCAAGACCC

AGAGCATTAAGAAGTACAGCACAGACATTCTGGGCAACCTGTATGAAGTGAAATCTAAGAAGCACCCT

CAGATCATCAAAAAGGGCAAAAGGCCGGCGGCCACGAAAAAGGCCGGCCAGGCAAAAAAGAAAAAGgg atcctacccatacgatgttccagattacgcttacccatacgatgttccagattacgcttaccCatacg
```

-continued

```
atgttccagattacgcttaaGAATTCctagagctcgctgatcagcctcgactgtgccttctagttgcc agccatctgttgtttgccctcccccgtgccttccttgaccctggaaggtgccactcccactgtcctt tcctaataaaatgaggaaattgcatcgcattgtctgagtaggtgtcattctattctggggggtggggt ggggcaggacagcaagggggaggattgggaagagaatagcaggcatgctggggaGGTACCGAACGCTG

ACGTCATCAACCCGCTCCAAGGAATCGCGGGCCCAGTGTCACTAGGCGGGAACACCCAGCGCGCGTGC

GCCCTGGCAGGAAGATGGCTGTGAGGGACAGGGGAGTGGCGCCCTGCAATATTTGCATGTCGCTATGT

GTTCTGGGAAATCACCATAAACGTGAAATGTCTTTGGATTTGGGAATCTTATAAGTTCTGTATGAGAC

CACATATAGTAATGAAATTATTGGCACGTTTTAGTACTCTGGAAACAGAATCTACTAAAACAAGGCAA

AATGCCGTGTTTATCTCGTCAACTTGTTGGCGAGATTTTTGGTACCaggaaccccctagtgatggagtt ggccactccctctctgcgcgctcgctcgctcactgaggccgggcgaccaaaggtcgcccgacgcccgg gctttgcccgggcggcctcagtgagcgagcgagcgcgcagctgcctgcaggggcgcctgatgcggtat tttctccttacgcatctgtgcggtatttcacaccgcatacgtcaaagcaaccatagtacgcgccctgt agcggcgcattaagcgcggcgggtgtggtggttacgcgcagcgtgaccgctacacttgccagcgccct agcgcccgctcctttcgctttcttcccttcctttctcgccacgttcgccggctttccccgtcaagctc taaatcggggggctccctttagggttccgatttagtgctttacggcacctcgaccccaaaaaacttgat ttgggtgatggttcacgtagtgggccatcgccctgatagacggtttttcgccctttgacgttggagtc cacgttctttaatagtggactcttgttccaaactggaacaacactcaaccctatctcgggctattctt ttgatttataagggattttgccgatttcggcctattggttaaaaaatgagctgatttaacaaaaattt aacgcgaattttaacaaaatattaacgtttacaatttttatggtgcactctcagtacaatctgctctga tgccgcatagttaagccagccccgacacccgccaacacccgctgacgcgccctgacgggcttgtctgc tcccggcatccgcttacagacaagctgtgaccgtctccgggagctgcatgtgtcagaggttttcaccg tcatcaccgaaacgcgcgagacgaaagggcctcgtgatacgcctatttttataggttaatgtcatgat aataatggtttcttagacgtcaggtggcacttttcggggaaatgtgcgcggaaccccctatttgtttat ttttctaaatacattcaaatatgtatccgctcatgagacaataaccctgataaatgcttcaataatat tgaaaaaggaagagtatgagtattcaacatttccgtgtcgcccttattcccttttttgcggcattttg ccttcctgttttttgctcacccagaaacgctggtgaaagtaaaagatgctgaagatcagttgggtgcac gagtgggttacatcgaactggatctcaacagcggtaagatccttgagagttttcgccccgaagaacgt tttccaatgatgagcacttttaaagttctgctatgtggcgcggtattatcccgtattgacgccgggca agagcaactcggtcgccgcatacactattctcagaatgacttggttgagtactcaccagtcacagaaa agcatcttacggatggcatgacagtaagagaattatgcagtgctgccataaccatgagtgataacact gcggccaacttacttctgacaacgatcggaggaccgaaggagctaaccgcttttttgcacaacatggg ggatcatgtaactcgccttgatcgttgggaaccggagctgaatgaagccataccaaacgacgagcgtg acaccacgatgcctgtagcaatggcaacaacgttgcgcaaactattaactggcgaactacttactcta gcttcccggcaacaattaatagactggatggaggcggataaagttgcaggaccacttctgcgctcggc ccttccggctggctggtttattgctgataaatctggagccggtgagcgtggaagccgcggtatcattg cagcactggggccagatggtaagccctcccgtatcgtagttatctacacgacggggagtcaggcaact atggatgaacgaaatagacagatcgctgagataggtgcctcactgattaagcattggtaactgtcaga ccaagtttactcatatatactttagattgatttaaaacttcatttttaatttaaaaggatctaggtga agatcctttttgataatctcatgaccaaaatcccttaacgtgagttttcgttccactgagcgtcagac cccgtagaaaagatcaaaggatcttcttgagatcctttttttctgcgcgtaatctgctgcttgcaaac aaaaaaaccaccgctaccagcggtggtttgtttgccggatcaagagctaccaactctttttccgaagg
```

-continued taactggcttcagcagagcgcagataccaaatactgtccttctagtgtagccgtagttaggccaccac ttcaagaactctgtagcaccgcctacatacctcgctctgctaatcctgttaccagtggctgctgccag tggcgataagtcgtgtcttaccgggttggactcaagacgatagttaccggataaggcgcagcggtcgg gctgaacggggggttcgtgcacacagcccagcttggagcgaacgacctacaccgaactgagataccta cagcgtgagctatgagaaagcgccacgcttcccgaagggagaaaggcggacaggtatccggtaagcgg cagggtcggaacaggagagcgcacgagggagcttccaggggggaaacgcctggtatctttatagtcctg tcgggtttcgccacctctgacttgagcgtcgattttttgtgatgctcgtcaggggggcggagcctatgg aaaaacgccagcaacgcggcctttttacggttcctggccttttgctggcctttttgctcacatgt SEQ ID NO: 21, Version 2 of vector 3
cctgcaggcagctgcgcgctcgctcgctcactgaggccgcccgggcgtcgggcgacctttggtcgccc ggcctcagtgagcgagcgagcgcgcagagagggagtggccaactccatcactagggggttcctgcggcc TCTAGAaaaaatctcgccaacaagttgacgagataaacacggcattttgccttgttttagtagattct gtttccagagtactaaaacacatttcctctctatacaaatgCGGTGTTTCGTCCTTTCCACAAGATAT

ATAAAGCCAAGAAATCGAAATACTTTCAAGTTAGGGTAAGCATATGATAGTCCATTTTAAAACATAAT

TTTAAAACTGCAAACTACCCAAGAAATTATTACTTTCTACGTCACGTATTTTGTACTAATATCTTTGT

GTTTACAGTCAAATTAATTCCAATTATCTCTCTAACAGCCTTGTATCGTATATGCAAATATGAAGGAA

TCATGGGAAATAGGCCCTCCTCGAGCTAGACTAGCATGCTGCCCATGTAAGGAGGCAAGGCCTGGGGA

CACCCGAGATGCCTGGTTATAATTAACCCAGACATGTGGCTGCCCCCCCCCCCCCAACACCTGCTGCC

TCTAAAAATAACCCTGCATGCCATGTTCCCGGCGAAGGGCCAGCTGTCCCCCGCCAGCTAGACTCAGC

ACTTAGTTTAGGAACCAGTGAGCAAGTCAGCCCTTGGGGCAGCCCATACAAGGCCATGGGGCTGGGCA

AGCTGCACGCCTGGGTCCGGGGTGGGCACGGTGCCCGGGCAACGAGCTGAAAGCTCATCTGCTCTCAG

GGGCCCCTCCCTGGGGACAGCCCCTCCTGGCTAGTCACACCCTGTAGGCTCCTCTATATAACCCAGGG

GCACAGGGGCTGCCCTCATTCTACCACCACCTCCACAGCACAGACAGACACTCAGGAGCCAGCCAGCa ccggtgccacCATGGCCCCAAAGAAGAAGCGGAAGGTCGGTATCCACGGAGTCCCAGCAGCCAAGCGG

AACTACATCCTGGGCCTGGACATCGGCATCACCAGCGTGGGCTACGGCATCATCGACTACGAGACACG

GGACGTGATCGATGCCGGCGTGCGGCTGTTCAAAGAGGCCAACGTGGAAAACAACGAGGGCAGGCGGA

GCAAGAGAGGCGCCAGAAGGCTGAAGCGGCGGAGGCGGCATAGAATCCAGAGAGTGAAGAAGCTGCTG

TTCGACTACAACCTGCTGACCGACCACAGCGAGCTGAGCGGCATCAACCCCTACGAGGCCAGAGTGAA

GGGCCTGAGCCAGAAGCTGAGCGAGGAAGAGTTCTCTGCCGCCCTGCTGCACCTGGCCAAGAGAAGAG

GCGTGCACAACGTGAACGAGGTGGAAGAGGACACCGGCAACGAGCTGTCCACCAAAGAGCAGATCAGC

CGGAACAGCAAGGCCCTGGAAGAGAAATACGTGGCCGAACTGCAGCTGGAACGGCTGAAGAAAGACGG

CGAAGTGCGGGGCAGCATCAAGAGATTCAAGACCAGCGACTACGTGAAAGAAGCCAAACAGCTGCTGA

AGGTGCAGAAGGCCTACCACCAGCTGGACCAGAGCTTCATCGACACCTACATCGACCTGCTGGAAACC

CGGCGGACCTACTATGAGGGACCTGGCGAGGGCAGCCCCTTCGGCTGGAAGGACATCAAAGAATGGTA

CGAGATGCTGATGGGCCACTGCACCTACTTCCCCGAGGAACTGCGGAGCGTGAAGTACGCCTACAACG

CCGACCTGTACAACGCCCTGAACGACCTGAACAATCTCGTGATCACCAGGGACGAGAACGAGAAGCTG

GAATATTACGAGAAGTTCCAGATCATCGAGAACGTGTTCAAGCAGAAGAAGAAGCCCACCCTGAAGCA

GATCGCCAAAGAAATCCTCGTGAACGAAGAGGATATTAAGGGCTACAGAGTGACCAGCACCGGCAAGC

CCGAGTTCACCAACCTGAAGGTGTACCACGACATCAAGGACATTACCGCCCGGAAAGAGATTATTGAG

AACGCCGAGCTGCTGGATCAGATTGCCAAGATCCTGACCATCTACCAGAGCAGCGAGGACATCCAGGA

AGAACTGACCAATCTGAACTCCGAGCTGACCCAGGAAGAGATCGAGCAGATCTCTAATCTGAAGGGCT

-continued

```
ATACCGGCACCCACAACCTGAGCCTGAAGGCCATCAACCTGATCCTGGACGAGCTGTGGCACACCAAC

GACAACCAGATCGCTATCTTCAACCGGCTGAAGCTGGTGCCCAAGAAGGTGGACCTGTCCCAGCAGAA

AGAGATCCCCACCACCCTGGTGGACGACTTCATCCTGAGCCCCGTCGTGAAGAGAAGCTTCATCCAGA

GCATCAAAGTGATCAACGCCATCATCAAGAAGTACGGCCTGCCCAACGACATCATTATCGAGCTGGCC

CGCGAGAAGAACTCCAAGGACGCCCAGAAAATGATCAACGAGATGCAGAAGCGGAACCGGCAGACCAA

CGAGCGGATCGAGGAAATCATCCGGACCACCGGCAAAGAGAACGCCAAGTACCTGATCGAGAAGATCA

AGCTGCACGACATGCAGGAAGGCAAGTGCCTGTACAGCCTGGAAGCCATCCCTCTGGAAGATCTGCTG

AACAACCCCTTCAACTATGAGGTGGACCACATCATCCCCAGAAGCGTGTCCTTCGACAACAGCTTCAA

CAACAAGGTGCTCGTGAAGCAGGAAGAAACAGCAAGAAGGGCAACCGGACCCCATTCCAGTACCTGA

GCAGCAGCGACAGCAAGATCAGCTACGAAACCTTCAAGAAGCACATCCTGAATCTGGCCAAGGGCAAG

GGCAGAATCAGCAAGACCAAGAAAGAGTATCTGCTGGAAGAACGGGACATCAACAGGTTCTCCGTGCA

GAAAGACTTCATCAACCGGAACCTGGTGGATACCAGATACGCCACCAGAGGCCTGATGAACCTGCTGC

GGAGCTACTTCAGAGTGAACAACCTGGACGTGAAAGTGAAGTCCATCAATGGCGGCTTCACCAGCTTT

CTGCGGCGGAAGTGGAAGTTTAAGAAAGAGCGGAACAAGGGGTACAAGCACCACGCCGAGGACGCCCT

GATCATTGCCAACGCCGATTTCATCTTCAAAGAGTGGAAGAAACTGGACAAGGCCAAAAAAGTGATGG

AAAACCAGATGTTCGAGGAAAAGCAGGCCGAGAGCATGCCCGAGATCGAAACCGAGCAGGAGTACAAA

GAGATCTTCATCACCCCCCACCAGATCAAGCACATTAAGGACTTCAAGGACTACAAGTACAGCCACCG

GGTGGACAAGAAGCCTAATAGAGAGCTGATTAACGACACCCTGTACTCCACCCGGAAGGACGACAAGG

GCAACACCCTGATCGTGAACAATCTGAACGGCCTGTACGACAAGGACAATGACAAGCTGAAAAAGCTG

ATCAACAAGAGCCCCGAAAAGCTGCTGATGTACCACCACGACCCCCAGACCTACCAGAAACTGAAGCT

GATTATGGAACAGTACGGCGACGAGAAGAATCCCCTGTACAAGTACTACGAGGAAACCGGGAACTACC

TGACCAAGTACTCCAAAAAGGACAACGGCCCCGTGATCAAGAAGATTAAGTATTACGGCAACAAACTG

AACGCCCATCTGGACATCACCGACGACTACCCCAACAGCAGAAACAAGGTCGTGAAGCTGTCCCTGAA

GCCCTACAGATTCGACGTGTACCTGGACAATGGCGTGTACAAGTTCGTGACCGTGAAGAATCTGGATG

TGATCAAAAAAGAAAACTACTACGAAGTGAATAGCAAGTGCTATGAGGAAGCTAAGAAGCTGAAGAAG

ATCAGCAACCAGGCCGAGTTTATCGCCTCCTTCTACAACAACGATCTGATCAAGATCAACGGCGAGCT

GTATAGAGTGATCGGCGTGAACAACGACCTGCTGAACCGGATCGAAGTGAAGATGATCGACATCACCT

ACCGCGAGTACCTGGAAAACATGAACGACAAGAGGCCCCCCAGGATCATTAAGACAATCGCCTCCAAG

ACCCAGAGCATTAAGAAGTACAGCACAGACATTCTGGGCAACCTGTATGAAGTGAAATCTAAGAAGCA

CCCTCAGATCATCAAAAAGGGGCAAAAGGCCGGCGGCCACGAAAAAGGCCGGCCAGGCAAAAAAGAAAA

AGggatcctacccatacgatgttccagattacgcttacccatacgatgttccagattacgcttaccCa tacgatgttccagattacgcttaaGAATTCctagagctcgctgatcagcctcgactgtgccttctagt tgccagccatctgttgtttgcccctcccccgtgccttccttgacctggaaggtgccactcccactgt cctttcctaataaaatgaggaaattgcatcgcattgtctgagtaggtgtcattctattctgggggtg gggtggggcaggacagcaaggggggaggattgggaagagaatagcaggcatgctgggaGGTACCGAAC

GCTGACGTCATCAACCCGCTCCAAGGAATCGCGGGCCCAGTGTCACTAGGCGGGAACACCCAGCGCGC

GTGCGCCCTGGCAGGAAGATGGCTGTGAGGGACAGGGGAGTGGCGCCCTGCAATATTTGCATGTCGCT

ATGTGTTCTGGGAAATCACCATAAACGTGAAATGTCTTTGGATTTGGGAATCTTATAAGTTCTGTATG

AGACCACATATAGTAATGAAATTATTGGCACGTTTTAGTACTCTGGAAACAGAATCTACTAAAACAAG

GCAAAATGCCGTGTTTATCTCGTCAACTTGTTGGCGAGATTTTTGGTACCaggaacccctagtgatgg
```

-continued

```
agttggccactccctctctgcgcgctcgctcgctcactgaggccgggcgaccaaaggtcgcccgacgc ccgggctttgcccgggcggcctcagtgagcgagcgagcgcgcagctgcctgcaggggcgcctgatgcg gtattttctccttacgcatctgtgcggtatttcacaccgcatacgtcaaagcaaccatagtacgcgcc ctgtagcggcgcattaagcgcggcgggtgtggtggttacgcgcagcgtgaccgctacacttgccagcg ccctagcgcccgctcctttcgctttcttcccttcctttctcgccacgttcgccggctttccccgtcaa gctctaaatcggggggctccctttagggttccgatttagtgctttacggcacctcgaccccaaaaaact tgatttgggtgatggttcacgtagtgggccatcgccctgatagacggtttttcgccctttgacgttgg agtccacgttctttaatagtggactcttgttccaaactggaacaacactcaaccctatctcgggctat tcttttgatttataagggattttgccgatttcggcctattggttaaaaaatgagctgatttaacaaaa atttaacgcgaattttaacaaaatattaacgtttacaattttatggtgcactctcagtacaatctgct ctgatgccgcatagttaagccagccccgacacccgccaacacccgctgacgcgccctgacgggcttgt ctgctcccggcatccgcttacagacaagctgtgaccgtctccgggagctgcatgtgtcagaggttttc accgtcatcaccgaaacgcgcgagacgaaagggcctcgtgatacgcctatttttataggttaatgtca tgataataatggtttcttagacgtcaggtggcacttttcggggaaatgtgcgcggaacccctatttgt ttattttttctaaatacattcaaatatgcatccgctcatgagacaataaccctgataaatgcttcaata atattgaaaaaggaagagtatgagtattcaacatttccgtgtcgcccttattccctttttttgcggcat tttgccttcctgtttttgctcacccagaaacgctggtgaaagtaaaagatgctgaagatcagttgggt gcacgagtgggttacatcgaactggatctcaacagcggtaagatccttgagagttttcgccccgaaga acgttttccaatgatgagcacttttaaagttctgctatgtggcgcggtattatcccgtattgacgccg ggcaagagcaactcggtcgccgcatacactattctcagaatgacttggttgagtactcaccagtcaca gaaaagcatcttacggatggcatgacagtaagagaattatgcagtgctgccataaccatgagtgataa cactgcggccaacttacttctgacaacgatcggaggaccgaaggagctaaccgcttttttgcacaaca tgggggatcatgtaactcgccttgatcgttgggaaccggagctgaatgaagccataccaaacgacgag cgtgacaccacgatgcctgtagcaatggcaacaacgttgcgcaaactattaactggcgaactacttac tctagcttcccggcaacaattaatagactggatggaggcggataaagttgcaggaccacttctgcgct cggcccttccggctggctggtttattgctgataaatctggagccggtgagcgtggaagccgcggtatc attgcagcactggggccagatggtaagccctcccgtatcgtagttatctacacgacggggagtcaggc aactatggatgaacgaaatagacagatcgctgagataggtgcctcactgattaagcattggtaactgt cagaccaagtttactcatatatactttagattgatttaaaacttcattttttaatttaaaaggatctag gtgaagatcctttttgataatctcatgaccaaaatcccttaacgtgagttttcgttccactgagcgtc agaccccgtagaaaagatcaaaggatcttcttgagatcctttttttctgcgcgtaatctgctgcttgc aaacaaaaaaaccaccgctaccagcggtggtttgtttgccggatcaagagctaccaactctttttccg aaggtaactggcttcagcagagcgcagataccaaatactgtccttctagtgtagccgtagttaggcca ccacttcaagaactctgtagcaccgcctacatacctcgctctgctaatcctgttaccagtggctgctg ccagtggcgataagtcgtgtcttaccgggttggactcaagacgatagttaccggataaggcgcagcgg tcgggctgaacggggggttcgtgcacacagcccagcttggagcgaacgacctacaccgaactgagata cctacagcgtgagctatgagaaagcgccacgcttcccgaagggagaaaggcggacaggtatccggtaa gcggcagggtcggaacaggagagcgcacgagggagcttccagggggaaacgcctggtatctttatagt cctgtcgggtttcgccacctctgacttgagcgtcgatttttgtgatgctcgtcaggggggcggagcct atggaaaaacgccagcaacgcggcctttttacggttcctggccttttgctggccttttgctcacatgt
```

-continued

SEQ ID NO: 22, Version 3 of vector 3
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGAaaaaatctcgccaacaagttgacgagataaacacggcattttgccttgtttttagtagattct gtttccagagtactaaaacacatttcctctctatacaaatgCGGTGTTTCGTCCTTTCCACAAGATAT

ATAAAGCCAAGAAATCGAAATACTTTCAAGTTACGGTAAGCATATGATAGTCCATTTTAAAACATAAT

TTTAAAACTGCAAACTACCCAAGAAATTATTACTTTCTACGTCACGTATTTTGTACTAATATCTTTGT

GTTTACAGTCAAATTAATTCCAATTATCTCTCTAACAGCCTTGTATCGTATATGCAAATATGAAGGAA

TCATGGGAAATAGGCCCTCCTCGAGGAGCTCCACCGCGGTGGCGGCCGTCCGCCtTCGGCACCATCCT

CACGACACCCAAATATGGCGACGGGTGAGGAATGGTGGGGAGTTATTTTTAGAGCGGTGAGGAAGGTG

GGCAGGCAGCAGGTGTTGGCGCTCTAAAAATAACTCCCGGGAGTTATTTTTAGAGCGGAGGAATGGTG

GACACCCAAATATGGCGACGGTTCCTCACCCGTCGCCATATTTGGGTGTCCGCCCTCGGCCGGGGCCG

CATTCCTGGGGGCCGGGCGGTGCTCCCGCCCGCCTCGATAAAAGGCTCCGGGGCCGGCGGCGGCCCAC

GAGCTACCCGGAGGAGCGGGAGGCGCCAAGCTCTAGAACTAGTGGATCCCCCGGGCTGCAGGAATTCG

ATATaccggtgccaccATGGCCCCAAAGAAGAAGCGGAAGGTCGGTATCCACGGAGTCCCAGCAGCCA

AGCGGAACTACATCCTGGGCCTGGACATCGGCATCACCAGCGTGGGCTACGGCATCATCGACTACGAG

ACACGGGACGTGATCGATGCCGGCGTGCGGCTGTTCAAAGAGGCCAACGTGGAAAACAACGAGGGCAG

GCGGAGCAAGAGAGGCGCCAGAAGGCTGAAGCGGCGGAGGCGGCATAGAATCCAGAGAGTGAAGAAGC

TGCTGTTCGACTACAACCTGCTGACCGACCACAGCGAGCTGAGCGGCATCAACCCCTACGAGGCCAGA

GTGAAGGGCCTGAGCCAGAAGCTGAGCGAGGAAGAGTTCTCTGCCGCCCTGCTGCACCTGGCCAAGAG

AAGAGGCGTGCACAACGTGAACGAGGTGGAAGAGGACACCGGCAACGAGCTGTCCACCAAAGAGCAGA

TCAGCCGGAACAGCAAGGCCCTGGAAGAGAAATACGTGGCCGAACTGCAGCTGGAACGGCTGAAGAAA

GACGGCGAAGTGCGGGGCAGCATCAACAGATTCAAGACCAGCGACTACGTGAAAGAAGCCAAACAGCT

GCTGAAGGTGCAGAAGGCCTACCACCAGCTGGACCAGAGCTTCATCGACACCTACATCGACCTGCTGG

AAACCCGGCGGACCTACTATGAGGGACCTGGCGAGGGCAGCCCCTTCGGCTGGAAGGACATCAAAGAA

TGGTACGAGATGCTGATGGGCCACTGCACCTACTTCCCCGAGGAACTGCGGAGCGTGAAGTACGCCTA

CAACGCCGACCTGTACAACGCCCTGAACGACCTGAACAATCTCGTGATCACCAGGGACGAGAACGAGA

AGCTGGAATATTACGAGAAGTTCCAGATCATCGAGAACGTGTTCAAGCAGAAGAAGAAGCCCACCCTG

AAGCAGATCGCCAAAGAAATCCTCGTGAACGAAGAGGATATTAAGGGCTACAGAGTGACCAGCACCGG

CAAGCCCGAGTTCACCAACCTGAAGGTGTACCACGACATCAAGGACATTACCGCCCGGAAAGAGATTA

TTGAGAACGCCGAGCTGCTGGATCAGATTGCCAAGATCCTGACCATCTACCAGAGCAGCGAGGACATC

CAGGAAGAACTGACCAATCTGAACTCCGAGCTGACCCAGGAAGAGATCGAGCAGATCTCTAATCTGAA

GGGCTATACCGGCACCCACAACCTGAGCCTGAAGGCCATCAACCTGATCCTGGACGAGCTGTGGCACA

CCAACGACAACCAGATCGCTATCTTCAACCGGCTGAAGCTGGTGCCCAAGAAGGTGGACCTGTCCCAG

CAGAAAGAGATCCCCACCACCCTGGTGGACGACTTCATCCTGAGCCCCGTCGTGAAGAGAAGCTTCAT

CCAGAGCATCAAAGTGATCAACGCCATCATCAAGAAGTACGGCCTGCCCAACGACATCATTATCGAGC

TGGCCCGCGAGAAGAACTCCAAGGACGCCCAGAAAATGATCAACGAGATGCAGAAGCGGAACCGGCAG

ACCAACGAGCGGATCGAGGAAATCATCCGGACCACCGGCAAAGAGAACGCCAAGTACCTGATCGAGAA

GATCAAGCTGCACGACATGCAGGAAGGCAAGTGCCTGTACAGCCTGGAAGCCATCCCTCTGGAAGATC

TGCTGAACAACCCCTTCAACTATGAGGTGGACCACATCATCCCCAGAAGCGTGTCCTTCGACAACAGC

TTCAACAACAAGGTGCTCGTGAAGCAGGAAGAAAACAGCAAGAAGGGCAACCGGACCCCATTCCAGTA

-continued

```
CCTGAGCAGGAGCGACAGCAAGATCAGCTAGGAAACCTTCAAGAAGCACATCCTGAATCTGGCCAAGG

GCAAGGGCAGAATCAGCAAGACCAAGAAAGAGTATCTGCTGGAAGAACGGGACATCAACAGGTTCTCC

GTGCAGAAAGACTTCATCAACCGGAACCTGGTGGATACCAGATACGCCACCAGAGGCCTGATGAACCT

GCTGCGGAGCTACTTCAGAGTGAACAACCTGGACGTGAAAGTGAAGTCCATCAATGGCGGCTTCACCA

GCTTTCTGCGGCGGAAGTGGAAGTTTAAGAAAGAGCGGAACAAGGGGTACAAGCACCACGCCGAGGAC

GCCCTGATCATTGCCAACGCCGATTTCATCTTCAAAGAGTGGAAGAAACTGGACAAGGCCAAAAAAGT

GATGGAAAACCAGATGTTCGAGGAAAAGCAGGCCGAGAGCATGCCCGAGATCGAAACCGAGCAGGAGT

ACAAAGAGATCTTCATCACCCCCCCCACCAGATCAAGCACATTAAGGACTTCAAGGACTACAAGTACAGC

CACCGGGTGGACAAGAAGCCTAATAGAGAGCTGATTAACGACACCCTGTACTCCACCCGGAAGGACGA

CAAGGGCAACACCCTGATCGTGAACAATCTGAACGGCCTGTACGACAAGGACAATGACAAGCTGAAAA

AGCTGATCAACAAGAGCCCCGAAAAGCTGCTGATGTACCACCACGACCCCCAGACCTACCAGAAACTG

AAGCTGATTATGGAACAGTACGGCGACGAGAAGAATCCCCTGTACAAGTACTACGAGGAAACCGGGAA

CTACCTGACCAAGTACTCCAAAAAGGACAACGGCCCCGTGATCAAGAAGATTAAGTATTACGGCAACA

AACTGAACGCCCATCTGGACATCACCGACGACTACCCCAACAGCAGAAACAAGGTCGTGAAGCTGTCC

CTGAAGCCCTACAGATTCGACGTGTACCTGGACAATGGCGTGTACAAGTTCGTGACCGTGAAGAATCT

GGATGTGATCAAAAAAGAAAACTACTACGAAGTGAATAGCAAGTGCTATGAGGAAGCTAAGAAGCTGA

AGAAGATCAGCAACCAGGCCGAGTTTATCGCCTCCTTCTACAACAACGATCTGATCAAGATCAACGGC

GAGCTGTATAGAGTGATCGGCGTGAACAACGACCTGCTGAACCGGATCGAAGTGAACATGATCGACAT

CACCTAGCGCGAGTACCTGGAAAACATGAACGACAAGAGGCCCCCCAGGATCATTAAGACAATCGCCT

CCAAGACCCAGAGCATTAAGAAGTACAGCACAGACATTCTGGGCAACCTGTATGAAGTGAAATCTAAG

AAGCACCCTCAGATCATCAAAAAGGGCAAAAGGCCGGCGGCCACGAAAAAGGCCGGCCAGGCAAAAAA

GAAAAAGggatcctacccatacgatgttccagattacgcttacccatacgatgttccagattacgctt accCatacgatgttccagattacgcttaaGAATTCctagagctcgctgatcagcctcgactgtgcctt ctagttgccagccatctgttgtttgcccctcccccgtgccttccttgaccctggaaggtgccactccc actgtcctttcctaataaaatgaggaaattgcatcgcattgtctgagtaggtgtcattctattctggg gggtggggtggggcaggacagcaagggggaggattgggaagagaatagcaggcatgctggggaGGTAC

CGAACGCTGACGTCATCAACCCGCTCCAAGGAATCGCGGGCCCAGTGTCACTAGGCGGGAACACCCAG

CGCGCGTGCGCCCTGGCAGGAAGATGGCTGTGAGGGACAGGGGAGTGGCGCCCTGCAATATTTGCATG

TCGCTATGTGTTCTGGGAAATCACCATAAACGTGAAATGTCTTTGGATTTGGGAATCTTATAAGTTCT

GTATGAGACCACATATAGTAATGAAATTATTGGCACGTTTTAGTACTCTGGAAACAGAATCTACTAAA

ACAAGGCAAAATGCCGTGTTTATCTCGTCAACTTGTTGGCGAGATTTTTGGTACCaggaaccccctagt gatggagttggccactccctctctgcgcgctcgctcgctcactgaggccgggcgaccaaaggtcgccc gacgcccgggctttgcccgggcggcctcagtgagcgagcgagcgcgcagctgcctgcaggggcgcctg atgcggtattttctccttacgcatctgtgcggtatttcacaccgcatacgtcaaagcaaccatagtac gcgccctgtagcggcgcattaagcgcggcgggtgtggtggttacgcgcagcgtgaccgctacacttgc cagcgccctagcgcccgctcctttcgctttcttcccttccttctctcgccacgttcgccggctttcccc gtcaagctctaaatcggggggctccctttagggttccgatttagtgctttacggcacctcgaccccaaa aaacttgatttgggtgatggttcacgtagtgggccatcgccctgatagacggttttttcgccctttgac gttggagtccacgttctttaatagtggactcttgttccaaactggaacaacactcaaccctatctcgg gctattcttttgatttataagggattttgccgatttcggcctattggttaaaaaatgagctgatttaa caaaaatttaacgcgaattttaacaaaatattaacgtttacaattttatggtgcactctcagtacaat
```

-continued

```
ctgctctgatgccgcatagttaagccagccccgacacccgccaacacccgctgacgcgccctgacggg cttgtctgctcccggcatccgcttacagacaagctgtgaccgtctccgggagctgcatgtgtcagagg ttttcaccgtcatcaccgaaacgcgcgagacaaaagggcctcgtgatacgcctattttttataggttaa tgtcatgataataatggtttcttagacgtcaggtggcactttttcggggaaatgtgcgcggaacccta tttgtttattttttctaaatacattcaaatatgtatccgctcatgagacaataaccctgataaatgctt caataatattgaaaaaggaagagtatgagtattcaacatttccgtgtcgcccttattccttttttttgc ggcattttgccttcctgttttttgctcacccagaaacgctggtgaaagtaaaagatgctgaagatcagt tgggtgcacgagtgggttacatcgaactggatctcaacagcggtaagatccttgagagttttcgcccc gaagaacgttttccaatgatgagcacttttaaagttctgctatgtggcgcggtattatcccgtattga cgccgggcaagagcaactcggtcgccgcatacactattctcagaatgacttggttgagtactcaccag tcacagaaaagcatcttacggatggcatgacagtaagagaattatgcagtgctgccataaccatgagt gataacactgcggccaacttacttctgacaacgatcggaggaccgaaggagctaaccgcttttttgca caacatgggggatcatgtaactcgccttgatcgttgggaaccggagctgaatgaagccataccaaacg acgagcgtgacaccacgatgcctgtagcaatggcaacaacgttgcgcaaactattaactggcgaacta cttactctagcttcccggcaacaattaatagactggatggaggcggataaagttgcaggaccacttct gcgctcggcccttccggctggctggtttattgctgataaatctggagccggtgagcgtggaagccgcg gtatcattgcagcactggggccagatggtaagccctcccgtatcgtagttatctacacgacggggagt caggcaactatggatgaacgaaatagacagatcgctgagataggtgcctcactgattaagcattggta actgtcagaccaagtttactcatatatactttagattgatttaaaacttcatttttaatttaaaagga tctaggtgaagatcctttttgataatctcatgaccaaaatcccttaacgtgagttttcgttccactga gcgtcagacccgtagaaaagatcaaaggatcttcttgagatcctttttttctgcgcgtaatctgctg cttgcaaacaaaaaaccaccgctaccagcggtggtttgtttgccggatcaagagctaccaactctttt tccgaaggtaactggcttcagcagagcgcagataccaaatactgtccttctagtgtagccgtagtta ggccaccacttcaagaactctgtagcaccgcctacatacctcgctctgctaatcctgttaccagtggc tgctgccagtggcgataagtcgtgtcttaccgggttggactcaagacgatagttaccggataaggcgc agcggtcgggctgaacggggggttcgtgcacacagcccagcttggagcgaacgacctacaccgaactg agatacctacagcgtgagctatgagaaagcgccacgcttcccgaaggagaaaaggcggacaggtatcc ggtaagcggcagggtcggaacaggagagcgcacgagggagcttccaggggggaaacgcctggtatcttt atagtcctgtcgggtttcgccacctctgacttgagcgtcgatttttgtgatgctcgtcaggggggcgg agcctatggaaaaacgccagcaacgcggcctttttacggttcctggccttttgctggccttttgctca catgt
```

SEQ ID NO: 23, Version 4 of vector 3

```
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGAaaaaatctcgccaacaagttgacgagataaacacggcattttgccttgttttagtagattct gtttccagagtactaaaacacatttcctctctatacaaatgCGGTGTTTCGTCCTTTCCACAAGATAT

ATAAAGCCAAGAAATCGAAATACTTTCAAGTTAGGGTAAGCATATGATAGTCCATTTTAAAACATAAT

TTTAAAACTGCAAACTACCCAAGAAATTATTACTTTCTACGTCACGTATTTTGTACTAATATCTTTGT

GTTTACAGTCAAA7TAATTCCAATTATCTCTCTAACAGCCTTGTATCGTATATGCAAATATGAAGGAA

TCATGGGAAATAGGCCCTCCTCGAGGtttaaacaagcttgcatgtctaagctagacccttcagattaa aaataactgaggtaagggcctgggtaggggaggtggtgtgagacgctcctgtctctcctctatctgcc
```

-continued catcggccctttggggaggaggaatgtgcccaaggactaaaaaaaggccatggagccagaggggcgag ggcaacagacctttcatgggcaaaccttggggccctgctgtctagcatgccccactacgggtctaggc tgcccatgtaaggaggcaaggcctggggacacccgagatgcctggttataattaacccagacatgtgg ctgcccccccccccaacacctgctgcctctaaaaataaccctgtccctggtggatccctgcatgc gaagatcttcgaacaaggctgtgggggactgagggcaggctgtaacaggcttgggggccagggcttat acgtgcctgggactcccaaagtattactgttccatgttcccggcgaagggccagctgtcccccgccag ctagactcagcacttagtttaggaaccagtgagcaagtcagcccttggggcagcccatacaaggccat ggggctgggcaagctgcacgcctgggtccggggtgggcacggtgcccgggcaacgagctgaaagctca tctgctctcaggggcccctccctggggacagcccctcctggctagtcacaccctgtaggctcctctat ataacccaggggcacaggggctgccctcattctaccaccacctccacagcacagacagacactcagga gccagccagcggcgcgcccaccggtgccaccATGGCCCCAAAGAAGAAGCGGAAGGTCGGTATCCACG

GAGTCCCAGCAGCCAAGCGGAACTACATCCTGGGCCTGGACATCGGCATCACCAGCGTGGGCTACGGC

ATCATCGACTACGAGACACGGGACGTGATCGATGCCGGCGTGCGGCTGTTCAAAGAGGCCAACGTGGA

AAACAACGAGGGCAGGCGGAGCAAGAGAGGCGCCAGAAGGCTGAAGCGGCGGAGGCGGCATAGAATCC

AGAGAGTGAAGAAGCTGCTGTTCGACTACAACCTGCTGACCGACCACAGCGAGCTGAGCGGCATCAAC

CCCTACGAGGCCAGAGTGAAGGGCCTGAGCCAGAAGCTGAGCGAGGAAGAGTTCTCTGCCGCCCTGCT

GCACCTGGCCAAGAGAAGAGGCGTGCACAACGTGAACGAGGTGGAAGAGGACACCGGCAACGAGCTGT

CCACCAAAGAGCAGATCAGCCGGAACAGCAAGGCCCTGGAAGAGAAATACGTGGCCGAACTGCAGCTG

GAACGGCTGAAGAAAGACGGCGAAGTGCGGGGCAGCATCAACAGATTCAAGACCAGCGACTACGTGAA

AGAAGCGAAACAGCTGCTGAAGGTGGAGAAGGCCTACCACCAGCTGGACCAGAGCTTCATCGACACCT

ACATCGACCTGCTGGAAACCCGGCGGACCTACTATGAGGGACCTGGCGAGGGCAGCCCCTTCGGCTGG

AAGGACATCAAAGAATGGTACGAGATGCTGATGGGCCACTGCACCTACTTCCCCGAGGAACTGCGGAG

CGTGAAGTACGCCTACAACGCCGACCTGTACAACGCCCTGAACGACCTGAACAATCTCGTGATCACCA

GGGACGAGAACGAGAAGCTGGAATATTACGAGAAGTTCCAGATCATCGAGAACGTGTTCAAGCAGAAG

AAGAAGCCCACCCTGAAGCAGATCGCCAAAGAAATCCTCGTGAACGAAGAGGATATTAAGGGCTACAG

AGTGACCAGCACCGGCAAGCCCGAGTTCACCAACCTGAAGGTGTACCACGACATCAAGGACATTACCG

CCCGGAAAGAGATTATTGAGAACGCCGAGCTGCTGGATCAGATTGCCAAGATCCTGACCATCTACCAG

AGCAGCGAGGACATCCAGGAAGAACTGACCAATCTGAACTCCGAGCTGACCCAGGAAGAGATCGAGCA

GATCTCTAATCTGAAGGGCTATACCGGCACCCACAACCTGAGCCTGAAGGCCATCAACCTGATCCTGG

ACGAGCTGTGGCACACCAACGACAACCAGATCGCTATCTTCAACCGGCTGAAGCTGGTGCCCAAGAAG

GTGGACCTGTCCCAGCAGAAAGAGATCCCCACCACCCTGGTGGACGACTTCATCCTGAGCCCCGTCGT

GAAGAGAAGCTTCATCCAGAGCATCAAAGTGATCAACGCCATCATCAAGAAGTACGGCCTGCCCAACG

ACATCATTATCGAGCTGGCCCGCGAGAAGAACTCCAAGGACGCCCAGAAAATGATCAACGAGATGCAG

AAGCGGAACCGGCAGACCAACGAGCGGATCGAGGAAATCATCCGGACCACCGGCAAAGAGAACGCCAA

GTACCTGATCGAGAAGATCAAGCTGCACGACATGCAGGAAGGCAAGTGCCTGTACAGCCTGGAAGCCA

TCCCTCTGGAAGATCTGCTGAACAACCCCTTCAACTATGAGGTGGACCACATCATCCCCAGAAGCGTG

TCCTTCGACAACAGCTTCAACAACAAGGTGCTCGTGAAGCAGGAAGAAAACAGCAAGAAGGGCAACCG

GACCCCATTCCAGTACCTGAGCAGCAGCGACAGCAAGATCAGCTACGAAACCTTCAAGAAGCACATCC

TGAATCTGGCCAAGGGCAAGGGCAGAATCAGCAAGACCAAGAAAGAGTATCTGCTGGAAGAACGGGAC

ATCAACAGGTTCTCCGTGCAGAAAGACTTCATCAACCGGAACCTGGTGGATACCAGATACGCCACCAG

-continued

AGGCCTGATGAACCTGCTGCGGAGCTACTTCAGAGTGAACAACCTGGACGTGAAAGTGAAGTCCATCA

ATGGCGGCTTCACCAGCTTTCTGCGGCGGAAGTGGAAGTTTAAGAAAGAGCGGAACAAGGGGTACAAG

CACCACGCCGAGGACGCCCTGATCATTGCCAACGCCGATTTCATCTTCAAAGAGTGGAAGAAACTGGA

CAAGGCCAAAAAAGTGATGGAAAACCAGATGTTCGAGGAAAAGCAGGCCGAGAGCATGCCCGAGATCG

AAACCGAGGAGGAGTAGAAAGAGATCTTCATCACCCCCCACCAGATCAAGCACATTAAGGACTTCAAG

GACTACAAGTACAGCCACCGGGTGGACAAGAAGCCTAATAGAGAGCTGATTAACGACACCCTGTACTC

CACCCGGAAGGACGACAAGGGCAACACCCTGATCGTGAACAATCTGAACGGCCTGTACGACAAGGACA

ATGACAAGCTGAAAAAGCTGATCAACAAGAGCCCCGAAAAGCTGCTGATGTACCACCACGACCCCCAG

ACCTACCAGAAACTGAAGCTGATTATGGAACAGTACGGCGACGAGAAGAATCCCCTGTACAAGTACTA

CGAGGAAACCGGGAACTACCTGACCAAGTACTCCAAAAAGGACAACGGCCCCGTGATCAAGAAGATTA

AGTATTACGGCAACAAACTGAACGCCCATCTGGACATCACCGACGACTACCCCAACAGCAGAAACAAG

GTCGTGAAGCTGTCCCTGAAGCCCTACAGATTCGACGTGTACCTGGACAATGGCGTGTACAAGTTCGT

GACCGTGAAGAATCTGGATGTGATCAAAAAAGAAAACTACTACGAAGTGAATAGCAAGTGCTATGAGG

AAGCTAAGAAGCTGAAGAAGATCAGCAACCAGGCCGAGTTTATCGCCTCCTTCTACAACAACGATCTG

ATCAAGATCAACGGCGAGCTGTATAGAGTGATCGGCGTGAACAACGACCTGCTGAACCGGATCGAAGT

GAACATGATCGACATCACCTACCGCGAGTACCTGGAAAACATGAACGACAAGAGGCCCCCCAGGATCA

TTAAGACAATCGCCTCCAAGACCCAGAGCATTAAGAAGTACAGCACAGACATTCTGGGCAACCTGTAT

GAAGTGAAATCTAAGAAGCACCCTCAGATCATCAAAAAGGGCAAAAGGCCGGCGGCCACGAAAAAGGC

CGGCCAGGCAAAAAAGAAAAAGggatcctacccatacgatgttccagattacgcttacccatacgatg ttccagattacgcttaccCatacgatgttccagattacgcttaaGAATTCctagagctcgctgatcag cctcgactgtgccttctagttgccagccatctgttgtttgcccctccccgtgccttccttgaccctg gaaggtgccactcccactgtcctttcctaataaaatgaggaaattgcatcgcattgtctgagtaggtg tcattctattctggggggtggggtggggcaggacagcaaggggggaggattgggaagagaatagcaggc atgctggggaGGTACCGAACGCTGACGTCATCAACCCGCTCCAAGGAATCGCGGGCCCAGTGTCACTA

GGCGGGAACACCCAGCGCGCGTGCGCCCTGGCAGGAAGATGGCTGTGAGGGACAGGGGAGTGGCGCCC

TGCAATATTTGCATGTCGCTATGTGTTCTGGGAAATCACCATAAACGTGAAATGTCTTTGGATTTGGG

AATCTTATAAGTTCTGTATGAGACCACATATAGTAATGAAATTATTGGCACGTTTTAGTACTCTGGAA

ACAGAATCTACTAAAACAAGGCAAAATGCCGTGTTTATCTCGTCAACTTGTTGGCGAGATTTTTGGTA

CCaggaacccctagtgatggagttggccactccctctctgcgcgctcgctcgctcactgaggccgggc gaccaaaggtcgcccgacgcccgggctttgcccgggcggcctcagtgagcgagcgagcgcgcagctgc ctgcaggggcgcctgatgcggtattttctccttacgcatctgtgcggtatttcacaccgcatacgtca aagcaaccatagtacgcgccctgtagcggcgcattaagcgcggcgggtgtggtggttacgcgcagcgt gaccgctacacttgccagcgccctagcgcccgctcctttcgctttcttcccttcctttctcgccacgt tcgccggctttccccgtcaagctctaaatcggggggctcccctttagggttccgatttagtgctttacgg cacctcgaccccaaaaaacttgatttgggtgatggttcacgtagtgggccatcgccctgatagacggt ttttcgccctttgacgttggagtccacgttctttaatagtggactcttgttccaaactggaacaacac tcaaccctatctcgggctattcttttgatttataagggattttgccgatttcggcctattggttaaaa aatgagctgatttaacaaaaatttaacgcgaattttaacaaaatattaacgtttacaattttatggtg cactctcagtacaatctgctctgatgccgcatagttaagccagccccgacacccgccaacacccgctg acgcgccctgacgggcttgtctgctcccggcatccgcttacagacaagctgtgaccgtctccgggagc tgcatgtgtcagaggttttcaccgtcatcaccgaaacgcgcgagacgaaagggcctcgtgatacgcct -continued atttttataggttaatgtcatgataataatggtttcttagacgtcaggtggcacttttcggggaaatg tgcgcggaacccctatttgtttattttttctaaatacattcaaatatgtatccgctcatgagacaataa ccctgataaatgcttcaataatattgaaaaaggaagagtatgagtattcaacatttccgtgtcgccct tattcccttttttgcggcattttgccttcctgttttttgctcacccagaaacgctggtgaaagtaaaag atgctgaagatcagttgggtgcacgagtgggttacatcgaactggatctcaacagcggtaagatcctt gagagttttcgccccgaagaacgttttccaatgatgagcacttttaaagttctgctatgtggcgcggt attatcccgtattgacgccgggcaagagcaactcggtcgccgcatacactattcCcagaatgacttgg ttgagtactcaccagtcacagaaaagcatcttacggatggcatgacagtaagagaattatgcagtgct gccataaccatgagtgataacactgcggccaacttacttctgacaacgatcggaggaccgaaggagct aaccgcttttttgcacaacatgggggatcatgtaactcgccttgatcgttgggaaccggagctgaatg aagccataccaaacgacgagcgtgacaccacgatgcctgtagcaatggcaacaacgttgcgcaaacta ttaactggcgaactacttactctagcttcccggcaacaattaatagactggatggaggcggataaagt tgcaggaccacttctgcgctcggcccttccggctggctggtttattgctgataaatctggaaccggtg agcgtggaagccgcggtatcattgcagcactggggccagatggtaagccctcccgtatcgtagttatc tacacgacggggagtcaggcaactatggatgaacgaaatagacagatcgctgagataggtgcctcact gattaagcattggtaactgtcagaccaagtttactcatatatactttagattgatttaaaacttcatt tttaatttaaaaggatctaggtgaagatcctttttgataatctcatgaccaaaatcccttaacgtgag ttttcgttccactgagcgtcagaccccgtagaaaagatcaaaggatcttcttgagatcctttttttct gcgcgtaatctgctgcttgcaaacaaaaaaaccaccgctaccagcggtggtttgtttgccggatcaag agctaccaactcttttttccgaaggtaactggcttcagcagagcgcagataccaaatactgtccttcta gtgtagccgtagttaggccaccacttcaagaactctgtagcaccgcctacatacctcgctctgctaat cctgttaccagtggctgctgccagtggcgataagtcgtgtcttaccgggttggactcaagacgatagt taccggataaggcgcagcggccgggctgaacggggggttcgtgcacacagcccagcttggagcgaacg acctacaccgaactgagatacctacagcgtgagctatgagaaagcgccacgcttcccgaagggagaaa ggcggacaggtatccggtaagcggcagggtcggaacaggagagcgcacgagggagcttccaggggggaa acgcctggtatctttatagtcctgtcgggtttcgccacctctgacttgagcgtcgatttttgtgatgc tcgtcaggggggcggagcctatggaaaaacgccagcaacgcggcctttttacggttcctggccttttg ctggcctttttgctcacatgt SEQ ID NO: 24, polynucleotide encoding SV40 intron
tctagaggatccggtactcgaggaactgaaaaaccagaaagttaactggtaagtttagtctt tttgtcttttatttcaggtcccggatccggtggtggtgcaaatcaaagaactgctcctcagt ggatgttgcctttacttctaggcctgtacggaagtgttac SEQ ID NO: 25
NNGRR (R = A or G; N can be any nucleotide residue, e.g., any of A, G, C, or T)

SEQ ID NO: 26
NNGRRN (R = A or G, N can be any nucleotide residue, e.g., any of A, G, C, or T)

SEQ ID NO: 27
NNGRRT (R = A or G, N can be any nucleotide residue, e.g., any of A, G, C, or T)

-continued

SEQ ID NO: 28
NNGRRV (R = A or G, N can be any nucleotide residue, e.g., any of A, G, C, or T)

SEQ ID NO: 29, Version 3 of vector 5
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGACTCGAGGAGCTCCACCGCGGTGGCGGCCGTCCGCCtTCGGCACCATCCTCACGACACCCAAA

TATGGCGACGGGTGAGGAATGGTGGGGAGTTATTTTTAGAGCGGTGAGGAAGGTGGGCAGGCAGCAGG

TGTTGGCGCTCTAAAAATAACTCCCGGGAGTTATTTTTAGAGCGGAGGAATGGTGGACACCCAAATAT

GGCGACGGTTCCTCACCCGTCGCCATATTTGGGTGTCCGCCCTCGGCCGGGGCCGCATTCCTGGGGGC

CGGGCGGTGCTCCCGCCCGCCTCGATAAAAGGCTCCGGGGCCGGCGGCGGCCCACGAGCTACCCGGAG

GAGCGGGAGGCGCCAAGCTCTAGAACTAGTGGATCCCCCGGGCTGCAGGAATTCGATATCCATGGtct agaggatccggtactcgaggaactgaaaaaccagaaagttaactggtaagtttagtcttttttgtcttt tatttcaggtcccggatccggtggtggtgcaaatcaaagaactgctcctcagtggatgttgcctttac ttctaggcctgtacggaagtgttacgccaCCATGGCCCCAAAGAAGAAGCGGAAGGTCGGTATCCACG

GAGTCCCAGCAGCCAAGCGGAACTACATCCTGGGCCTGGACATCGGCATCACCAGCGTGGGCTACGGC

ATCATCGACTACGAGACACGGGACGTGATCGATGCCGGCGTGCGGCTGTTCAAAGAGGCCAACGTGGA

AAACAACGAGGGCAGGCGGAGCAAGAGAGGCGCCAGAAGGCTGAAGCGGCGGAGGCGGCATAGAATCC

AGAGAGTGAAGAAGCTGCTGTTCGACTACAACCTGCTGACCGACCACAGCGAGCTGAGCGGCATCAAC

CCCTACGAGGCCAGAGTGAAGGGCCTGAGCCAGAAGCTGAGCGAGGAAGAGTTCTCTGCCGCCCTGCT

GCACCTGGCCAAGAGAAGAGGCGTGCACAACGTGAACGAGGTGGAAGAGGACACCGGCAACGAGCTGT

CCACCAAAGAGCAGATCAGCCGGAACAGCAAGGCCCTGGAAGAGAAATACGTGGCCGAACTGCAGCTG

GAACGGCTGAAGAAAGACGGCGAAGTGCGGGGCAGCATCAACAGATTCAAGACCAGCGACTACGTGAA

AGAAGCCAAACAGCTGCTGAAGGTGCAGAAGGCCTACCACCAGCTGGACCAGAGCTTCATCGACACCT

ACATCGACCTGCTGGAAACCCGGCGGACCTACTATGAGGGACCTGGCGAGGGCAGCCCCTTCGGCTGG

AAGGACATCAAAGAATGGTACGAGATGCTGATGGGCCACTGCACCTACTTCCCCGAGGAACTGCGGAG

CGTGAAGTACGCCTACAACGCCGACCTGTACAACGCCCTGAACGACCTGAACAATCTCGTGATCACCA

GGGACGAGAACGAGAAGCTGGAATATTACGAGAAGTTCCAGATCATCGAGAACGTGTTCAAGCAGAAG

AAGAAGCCCACCCTGAAGCAGATCGCCAAAGAAATCCTCGTGAACGAAGAGGATATTAAGGGCTACAG

AGTGACCAGCACCGGCAAGCCCGAGTTCACCAACCTGAAGGTGTACCACGACATCAAGGACATTACCG

CCCGGAAAGAGATTATTGAGAACGCCGAGCTGCTGGATCAGATTGCCAAGATCCTGACCATCTACCAG

AGCAGCGAGGACATCCAGGAAGAACTGACCAATCTGAACTCCGAGCTGACCCAGGAAGAGATCGAGCA

GATCTCTAATCTGAAGGGCTATACCGGCACCCACAACCTGAGCCTGAAGGCCATCAACCTGATCCTGG

ACGAGCTGTGGCACACCAACGACAACCAGATCGCTATCTTCAACCGGCTGAAGCTGGTGCCCAAGAAG

GTGGACCTGTCCCAGCAGAAAGAGATCCCCACCACCCTGGTGGACGACTTCATCCTGAGCCCCGTCGT

GAAGAGAAGCTTCATCCAGAGCATCAAAGTGATCAACGCCATCATCAAGAAGTACGGCCTGCCCAACG

ACATCATTATCGAGCTGGCCCGCGAGAAGAACTCCAAGGACGCCCAGAAAATGATCAACGAGATGCAG

AAGCGGAACCGGCAGACCAACGAGCGGATCGAGGAAATCATCCGGACCACCGGCAAAGAGAACGCCAA

GTACCTGATCGAGAAGATCAAGCTGCACGACATGCAGGAAGGCAAGTGCCTGTACAGCCTGGAAGCCA

TCCCTCTGGAAGATCTGCTGAACAACCCCTTCAACTATGAGGTGGACCACATCATCCCCAGAAGCGTG

TCCTTCGACAACAGCTTCAACAACAAGGTGCTCGTGAAGCAGGAAGAAAACAGCAAGAAGGGCAACCG

GACCCCATTCCAGTACCTGAGCAGCAGCGACAGCAAGATCAGCTACGAAACCTTCAAGAAGCACATCC

-continued

```
TGAATCTGGCCAAGGGCAAGGGCAGAATCAGCAAGACCAAGAAAGAGTATCTGCTGGAAGAACGGGAC

ATCAACAGGTTCTCCGTGCAGAAAGACTTCATCAACCGGAACCTGGTGGATACCAGATACGCCACCAG

AGGCCTGATGAACCTGCTGCGGAGCTACTTCAGAGTGAACAACCTGGACGTGAAAGTGAAGTCCATCA

ATGGCGGCTTCACCAGCTTTCTGCGGCGGAAGTGGAAGTTTAAGAAAGAGCGGAACAAGGGGTACAAG

CACCACGCCGAGGACGCCCTGATCATTGCCAACGCCGATTTCATCTTCAAAGAGTGGAAGAAACTGGA

CAAGGCCAAAAAAGTGATGGAAAACCAGATGTTCGAGGAAAAGCAGGCCGAGAGCATGCCCGAGATCG

AAACCGAGCAGGAGTACAAAGAGATCTTCATCACCCCCCCACCAGATCAAGCACATTAAGGACTTCAAG

GACTACAAGTACAGCCACCGGGTGGACAAGAAGCCTAATAGAGAGCTGATTAACGACACCCTGTACTC

CACCCGGAAGGACGACAAGGGCAACACCCTGATCGTGAACAATCTGAACGGCCTGTACGACAAGGACA

ATGACAAGCTGAAAAAGCTGATCAACAAGAGCCCCGAAAAGCTGCTGATGTACCACCACGACCCCCAG

ACCTACCAGAAACTGAAGCTGATTATGGAACAGTACGGCGACGAGAAGAATCCCCTGTACAAGTACTA

CGAGGAAACCGGGAACTACCTGACCAAGTACTCCAAAAAGGACAACGGCCCCGTGATCAAGAAGATTA

AGTATTACGGCAACAAACTGAACGCCCATCTGGACATCACCGACGACTACCCCAACAGCAGAAACAAG

GTCGTGAAGCTGTCCCTGAAGCCCTACAGATTCGACGTGTACCTGGACAATGGCGTGTACAAGTTCGT

GACCGTGAAGAATCTGGATGTGATCAAAAAAGAAAACTACTACGAAGTGAATAGCAAGTGCTATGAGG

AAGCTAAGAAGCTGAAGAAGATCAGCAACCAGGCCGAGTTTATCGCCTCCTTCTACAACAACGATCTG

ATCAAGATCAACGGCGAGCTGTATAGAGTGATCGGCGTGAACAACGACCTGCTGAACCGGATCGAAGT

GAACATGATCGACATCACCTACCGCGAGTACCTGGAAAACATGAACGACAAGAGGCCCCCCAGGATCA

TTAAGACAATCGCCTCCAAGACCCAGAGCATTAAGAAGTACAGCACAGACATTCTGGGCAACCTGTAT

GAAGTGAAATCTAAGAAGCACCCTCAGATCATCAAAAAGGGCAAAAGGCCGGCGGCCACGAAAAAGGC

CGGCCAGGCAAAAAAGAAAAAGggatccGAATTCtagcaataaaggatcgtttattttcattggaagc gtgtgttggttttttgatcaggcgcgGGTACCAAAAATCTCGCCAACAAGTTGACGAGATAAACACGG CATTTTGCCTTGTTTTAGTAGATTCTGTTTCCAGAGTACTAAAACacatttcctctctatacaaatgC

GGTGTTTCGTCCTTTCCACAAGATATATAAAGCCAAGAAATCGAAATACTTTCAAGTTACGGTAAGCA

TATGATAGTCCATTTTAAAACATAATTTTAAAACTGCAAACTACCCAAGAAATTATTACTTTCTACGT

CACGTATTTTGTACTAATATCTTTGTGTTTACAGTCAAATTAATTCCAATTATCTCTCTAACAGCCTT

GTATCGTATATGCAAATATGAAGGAATCATGGGAAATAGGCCCTCCTCGACTAGTAGAAAAATCTCGC

CAACAAGTTGACGAGATAAACACGGCATTTTGCCTTGTTTTAGTAGATTCTGTTTCCAGAGTACTAAA

ACGTGCCAATAATTTCATTACTATATCGGTGTTTCGTCCTTTCCACAAGATATATAAAGCCAAGAAAT

CGAAATACTTTCAAGTTACGGTAAGCATATGATAGTCCATTTTAAAACATAATTTTAAAACTGCAAAC

TACCCAAGAAATTATTACTTTCTACGTCACGTATTTTGTACTAATATCTTTGTGTTTACAGTCAAATT

AATTCCAATTATCTCTCTAACAGCCTTGTATCGTATATGCAAATATGAAGGAATCATGGGAAATAGGC

CCTCGGTACCaggaacccctagtgatggagttggccactccctctctgcgcgctcgctcgctcactga ggccgggcgaccaaaggtcgcccgacgcccgggctttgcccgggcggcctcagtgagcgagcgagcgc gcagctgcctgcaggggcgcctgatgcggtattttctccttacgcatctgtgcggtatttcacaccgc atacgtcaaagcaaccatagtacgcgccctgtagcggcgcattaagcgcggcgggtgtggtggttacg cgcagcgtgaccgctacacttgccagcgccctagcgcccgctcctttcgctttcttcccttcctttct cgccacgttcgccggctttccccgtcaagctctaaatcggggggctccctttagggttccgatttagtg ctttacggcacctcgaccccaaaaaacttgatttgggtgatggttcacgtagtgggccatcgccctga tagacggtttttcgccctttgacgttggagtccacgttctttaatagtggactcttgttccaaactgg
```

-continued aacaacactcaaccctatctcgggctattcttttgatttataagggattttgccgatttcggcctatt ggttaaaaaatgagctgatttaacaaaaatttaacgcgaattttaacaaaatattaacgtttacaatt ttatggtgcactctcagtacaatctgctctgatgccgcatagttaagccagccccgacacccgccaac acccgctgacgcgccctgacgggcttgtctgctcccggcatccgcttacagacaagctgtgaccgtct ccgggagctgcatgtgtcagaggttttcaccgtcatcaccgaaacgcgcgagacgaaagggcctcgtg atacgcctattttttataggttaatgtcatgataataatggtttcttagacgtcaggtggcacttttcg gggaaatgtgcgcggaacccctatttgtttatttttctaaatacattcaaatatgtatccgctcatga gacaataaccctgataaatgcttcaataatattgaaaaaggaagagtatgagtattcaacatttccgt gtcgcccttattcccttttttgcggcattttgccttcctgttttttgctcacccagaaacgctggtgaa agtaaaagatgctgaagatcagttgggtgcacgagtgggttacatcgaactggatctcaacagcggta agatccttgagagttttcgccccgaagaacgttttccaatgatgagcacttttaaagttctgctatgt ggcgcggtattatcccgtattgacgccgggcaagagcaactcggtcgccgcatacactattctcagaa tgacttggttgagtactcaccagtcacagaaaagcatcttacggatggcatgacagtaagagaattat gcagtgctgccataaccatgagtgataacactgcggccaacttacttctgacaacgatcggaggaccg aaggagctaaccgctttttttgcacaacatgggggatcatgtaactcgccttgatcgttgggaaccgga gctgaatgaagccataccaaacgacgagcgtgacaccacgatgcctgtagcaatggcaacaacgttgc gcaaactattaactggcgaactacttactctagcttcccggcaacaattaatagactggatggaggcg gataaagttgcaggaccacttctgcgctcggcccttccggctggctggtttattgctgataaatctgg agccggtgagcgtggaagccgcggtatcattgcagcactggggccagatggtaagccctcccgtatcg tagttatctacacgacggggagtcaggcaactatggatgaacgaaatagacagatcgctgagataggt gcctcactgattaagcattggtaactgtcagaccaagtttactcatatatactttagattgatttaaa acttcattttttaatttaaaaggatctaggtgaagatcctttttgataatctcatgaccaaaatccctt aacgtgagttttcgttccactgagcgtcagaccccgtagaaaagatcaaaggatcttcttgagatcct ttttttctgcgcgtaatctgctgcttgcaaacaaaaaaaccaccgctaccagcggtggtttgtttgcc ggatcaagagctaccaactctttttccgaaggtaactggcttcagcagagcgcagataccaaatactg tccttctagtgtagccgtagttaggccaccacttcaagaactctgtagcaccgcctacatacctcgct ctgctaatcctgttaccagtggctgctgccagtggcgataagtcgtgtcttaccgggttggactcaag acgatagttaccggataaggcgcagcggtcgggctgaacggggggttcgtgcacacagcccagcttgg agcgaacgacctacaccgaactgagatacctacagcgtgagctatgagaaagcgccacgcttcccgaa gggagaaaggcggacaggtatccggtaagcggcagggtcggaacaggagagcgcacgagggagcttcc agggggaaacgcctggtatctttatagtcctgtcgggtttcgccacctctgacttgagcgtcgatttt tgtgatgctcgtcaggggggcggagcctatggaaaaacgccagcaacgcggcctttttacggttcctg gccttttgctggccttttgctcacatgt SEQ ID NO: 30, Version 4 of vector 5
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc TCTAGACTCGAGagcttgcatgtctaagctagacccttcagattaaaaataactgaggtaagggcctg ggtaggggaggtggtgtgagacgctcctgtctctcctctatctgcccatcggccctttggggaggagg aacgtgcccaaggactaaaaaaaggccatggagccagaggggcgaggcaacagacctttcatgggca aaccttggggccctgctgtctagcatgccccactacgggtctaggctgcccatgtaaggaggcaaggc ctggggacacccgagatgcctggttataattaacccagacatgtggctgccccccccccccccaacacc -continued

```
tgctgcctctaaaaataaccctgtccctggtggatcccctgcatgcgaagatcttcgaacaaggctgt gggggactgagggcaggctgtaacaggcttgggggccagggcttatacgtgcctgggactcccaaagt attactgttccatgttcccggcgaagggccagctgtcccccgccagctagactcagcacttagtttag gaaccagtgagcaagtcagcccttggggcagcccatacaaggccatggggctgggcaagctgcacgcc tgggtccggggtgggcacggtgcccgggcaacgagctgaaagctcatctgctctcaggggcccctccc tggggacagcccctcctggctagtcacaccctgtaggctcctctatataacccaggggcacaggggct gccctcattctaccaccacctccacagcacagacagacactcaggagccagccagcCCATGGtctaga ggatccggtactcgaggaactgaaaaaccagaaagttaactggtaagtttagtcttttgtcttttat ttcaggtcccggatccggtggtggtgcaaatcaaagaactgctcctcagtggatgttgcctttacttc taggcctgtacggaagtgttacgccaCCATGGCCCCAAAGAAGAAGCGGAAGGTCGGTATCCACGGAG

TCCCAGCAGCCAAGCGGAACTACATCCTGGGCCTGGACATCGGCATCACCAGCGTGGGCTACGGCATC

ATCGACTACGAGACACGGGACGTGATCGATGCCGGCGTGCGGCTGTTCAAAGAGGCCAACGTGGAAAA

CAACGAGGGCAGGCGGAGCAAGAGAGGCGCCAGAAGGCTGAAGCGGCGGAGGCGGCATAGAATCCAGA

GAGTGAAGAAGCTGCTGTTCGACTACAACCTGCTGACCGACCACAGCGAGCTGAGCGGCATCAACCCC

TACGAGGCCAGAGTGAAGGGCCTGAGCCAGAAGCTGAGCGAGGAAGAGTTCTCTGCCGCCCTGCTGCA

CCTGGCCAAGAGAAGAGGCGTGCACAACGTGAACGAGGTGGAAGAGGACACCGGCAACGAGCTGTCCA

CCAAAGAGCAGATCAGCCGGAACAGCAAGGCCCTGGAAGAGAAATACGTGGCCGAACTGCAGCTGGAA

CGGCTGAAGAAAGACGGCGAAGTGCGGGGCAGCATCAACAGATTCAAGACCAGCGACTACGTGAAAGA

AGCCAAACAGCTGCTGAAGGTGCAGAAGGCCTACCACCAGCTGGACCAGAGCTTCATCGACACCTACA

TCGACCTGCTGGAAACCCGGCGGACCTACTATGAGGGACCTGGCGAGGGCAGCCCCTTCGGCTGGAAG

GACATCAAAGAATGGTACGAGATGCTGATGGGCCACTGCACCTACTTCCCCGAGGAACTGCGGAGCGT

GAAGTACGCCTACAACGCCGACCTGTACAACGCCCTGAACGACCTGAACAATCTCGTGATCACCAGGG

ACGAGAACGAGAAGCTGGAATATTACGAGAAGTTCCAGATCATCGAGAACGTGTTCAAGCAGAAGAAG

AAGCCCACCCTGAAGCAGATCGCCAAAGAAATCCTCGTGAACGAAGAGGATATTAAGGGCTACAGAGT

GACCAGCACCGGCAAGCCCGAGTTCACCAACCTGAAGGTGTACCACGACATCAAGGACATTACCGCCC

GGAAAGAGATTATTGAGAACGCCGAGCTGCTGGATCAGATTGCCAAGATCCTGACCATCTACCAGAGC

AGCGAGGACATCCAGGAAGAACTGACCAATCTGAACTCCGAGCTGACCCAGGAAGAGATCGAGCAGAT

CTCTAATCTGAAGGGCTATACCGGCACCCACAACCTGAGCCTGAAGGCCATCAACCTGATCCTGGACG

AGCTGTGGCACACCAACGACAACCAGATCGCTATCTTCAACCGGCTGAAGCTGGTGCCCAAGAAGGTG

GACCTGTCCCAGCAGAAAGAGATCCCCACCACCCTGGTGGACGACTTCATCCTGAGCCCCGTCGTGAA

GAGAAGCTTCATCCAGAGCATCAAAGTGATCAACGCCATCATCAAGAAGTACGGCCTGCCCAACGACA

TCATTATCGAGCTGGCCCGCGAGAAGAACTCCAAGGACGCCCAGAAAATGATCAACGAGATGCAGAAG

CGGAACCGGCAGACCAACGAGCGGATCGAGGAAATCATCCGGACCACCGGCAAAGAGAACGCCAAGTA

CCTGATCGAGAAGATCAAGCTGCACGACATGCAGGAAGGCAAGTGCCTGTACAGCCTGGAAGCCATCC

CTCTGGAAGATCTGCTGAACAACCCCTTCAACTATGAGGTGGACCACATCATCCCCAGAAGCGTGTCC

TTCGACAACAGCTTCAACAACAAGGTGCTCGTGAAGCAGGAAGAAACAGCAAGAAGGGCAACCGGAC

CCCATTCCAGTACCTGAGCAGCAGCGACAGCAAGATCAGCTACGAAACCTTCAAGAAGCACATCCTGA

ATCTGGCCAAGGGCAAGGGCAGAATCAGCAAGACCAAGAAAGAGTATCTGCTGGAAGAACGGGACATC

AACAGGTTCTCCGTGCAGAAAGACTTCATCAACCGGAACCTGGTGGATACCAGATACGCCACCAGAGG

CCTGATGAACCTGCTGCGGAGCTACTTCAGAGTGAACAACCTGGACGTGAAAGTGAAGTCCATCAATG

GCGGCTTGACCAGCTTTCTGCGGCGGAAGTGGAAGTTTAAGAAAGAGCGGAACAAGGGGTACAAGCAC
```

-continued

```
CACGCCGAGGACGCCCTGATCATTGCCAACGCCGATTTCATCTTCAAAGAGTGGAAGAAACTGGACAA

GGCCAAAAAAGTGATGGAAAACCAGATGTTCGAGGAAAAGCAGGCCGAGAGCATGCCCGAGATCGAAA

CCGAGCAGGAGTACAAAGAGATCTTCATCACCCCCCCACCAGATCAAGCACATTAAGGACTTCAAGGAC

TACAAGTACAGCCACCGGGTGGACAAGAAGCCTAATAGAGAGCTGATTAACGACACCCTGTACTCCAC

CCGGAAGGACGACAAGGGCAACACCCTGATCGTGAACAATCTGAACGGCCTGTACGACAAGGACAATG

ACAAGCTGAAAAAGCTGATCAACAAGAGCCCCGAAAAGCTGCTGATGTACCACCACGACCCCCAGACC

TACCAGAAACTGAAGCTGATTATGGAACAGTACGGCGACGAGAAGAATCCCCTGTACAAGTACTACGA

GGAAACCGGGAACTACCTGACCAAGTACTCCAAAAAGGACAACGGCCCCGTGATCAAGAAGATTAAGT

ATTACGGCAACAAACTGAACGCCCATCTGGACATCACCGACGACTACCCCAACAGCAGAAACAAGGTC

GTGAAGCTGTCCCTGAAGCCCTACAGATTCGACGTGTACCTGGACAATGGCGTGTACAAGTTCGTGAC

CGTGAAGAATCTGGATGTGATCAAAAAAGAAAACTACTACGAAGTGAATAGCAAGTGCTATGAGGAAG

CTAAGAAGCTGAAGAAGATCAGCAACCAGGCCGAGTTTATCGCCTCCTTCTACAACAACGATCTGATC

AAGATCAACGGCGAGCTGTATAGAGTGATCGGCGTGAACAACGACCTGCTGAACCGGATCGAAGTGAA

CATGATCGACATCACCTACCGCGAGTACCTGGAAAACATGAACGACAAGAGGCCCCCCAGGATCATTA

AGACAATCGCCTCCAAGACCCAGAGCATTAAGAAGTACAGCACAGACATTCTGGGCAACCTGTATGAA

GTGAAATCTAAGAAGCACCCTCAGATCATCAAAAAGGGCAAAAGGCCGGCGGCCACGAAAAAGGCCGG

CCAGGCAAAAAAGAAAAAGggatccGAATTCtagcaataaaggatcgtttattttcattggaagcgtg tgttggtttttttgatcaggcgcgGGTACCAAAAATCTCGCCAACAAGTTGACGAGATAAACACGGCAT TTTGCCTTGTTTTAGTAGATTCTGTTTCCAGAGTACTAAAAcatttcctctctatacaaatgCGGT

GTTTCGTCCTTTCCACAAGATATATAAAGCCAAGAAATCGAAATACTTTCAAGTTACGGTAAGCATAT

GATAGTCCATTTTAAAACATAATTTTAAAACTGCAAACTACCCAAGAAATTATTACTTTCTACGTCAC

GTATTTTGTACTAATATCTTTGTGTTTACAGTCAAATTAATTCCAATTATCTCTCTAACAGCCTTGTA

TCGTATATGCAAATATGAAGGAATCATGGGAAATAGGCCCTCCTCGACTAGTAGAAAAATCTCGCCAA

CAAGTTGACGAGATAAACACGGCATTTTGCCTTGTTTTAGTAGATTCTGTTTCCAGAGTACTAAAACG

TGCCAATAATTTCATTACTATATCGGTGTTTCGTCCTTTCCACAAGATATATAAAGCCAAGAAATCGA

AATACTTTCAAGTTACGGTAAGCATATGATAGTCCATTTTAAAACATAATTTTAAAACTGCAAACTAC

CCAAGAAATTATTACTTTCTACGTCACGTATTTTGTACTAATATCTTTGTGTTTACAGTCAAATTAAT

TCCAATTATCTCTCTAACAGCCTTGTATCGTATATGCAAATATGAAGGAATCATGGGAAATAGGCCCT

CGGTACCaggaacccctagtgatggagttggccactccctctctgcgcgctcgctcgctcactgaggc cgggcgaccaaaggtcgcccgacgcccgggctttgcccgggcggcctcagtgagcgagcgagcgcgca gctgcctgcaggggcgcctgatgcggtattttctccttacgcatctgtgcggtatttcacaccgcata cgtcaaagcaaccatagtacgcgccctgtagcggcgcattaagcgcggcgggtgtggtggttacgcgc agcgtgaccgctacacttgccagcgccctagcgcccgctcctttcgctttcttcccttcctttctcgc cacgttcgccggctttccccgtcaagctctaaatcggggggctccctttagggttccgatttagtgctt tacggcacctcgaccccaaaaaacttgatttgggtgatggttcacgtagtgggccatcgccctgatag acggtttttcgccctttgacgttggagtccacgttctttaatagtggactcttgttccaaactggaac aacactcaaccctatctcgggctattctttttgatttataagggattttgccgatttcggcctattggt taaaaaatgagctgatttaacaaaaatttaacgcgaatttttaacaaaatattaacgtttacaatttta tggtgcactctcagtacaatctgctctgatgccgcatagttaagccagccccgacacccgccaacacc cgctgacgcgccctgacgggcttgtctgctcccggcatccgcttacagacaagctgtgaccgtctccg
```

-continued ggagctgcatgtgtcagaggttttcaccgtcatcaccgaaacgcgcgagacgaaagggcctcgtgata cgcctattttataggttaatgtcatgataataatggtttcttagacgtcaggtggcacttttcggggg aaatgtgcgcggaacccctatttgtttattttttctaaatacattcaaatatgtatccgctcatgagac aataaccctgataaatgcttcaataatattgaaaaaggaagagtatgagtattcaacatttccgtgtc gcccttattcccttttttgcggcattttgccttcctgttttttgctcacccagaaacgctggtgaaagt aaaagatgctgaagatcagttgggtgcacgagtgggttacatcgaactggatctcaacagcggtaaga tccttgagagttttcgccccgaagaacgttttccaatgatgagcacttttaaagttctgctatgtggc gcggtattatcccgtattgacgccgggcaagagcaactcggtcgccgcatacactattctcagaatga cttggttgagtactcaccagtcacagaaaagcatcttacggatggcatgacagtaagagaattatgca gtgctgccataaccatgagtgataacactgcggccaacttacttctgacaacgatcggaggaccgaag gagctaaccgctttttttgcacaacatgggggatcatgtaactcgccttgatcgttgggaaccggagct gaatgaagccataccaaacgacgagcgtgacaccacgatgcctgtagcaatggcaacaacgttgcgca aactattaactggcgaactacttactctagcttcccggcaacaattaatagactggatggaggcggat aaagttgcaggaccacttctgcgctcggcccttccggctggctggtttattgctgataaatctggagc cggtgagcgtggaagccgcggtatcattgcagcactggggccagatggtaagccctcccgtatcgtag ttatctacacgacggggagtcaggcaactatggatgaacgaaatagacagatcgctgagataggtgcc tcactgattaagcattggtaactgtcagaccaagtttactcatatatactttagattgatttaaaact tcattttttaattttaaaaggatctaggtgaagatcctttttgataatctcatgaccaaaatcccttaac gtgagttttcgttccactgagcgtcagacccgtagaaaagatcaaaggatcttcttgagatcctttt tttctgcgcgtaatctgctgcttgcaaacaaaaaaaccaccgctaccagcggtggtttgtttgccgga tcaagagctaccaactctttttccgaaggtaactggcttcagcagagcgcagataccaaatactgtcc ttctagtgtagccgtagttaggccaccacttcaagaactctgtagcaccgcctacatacctcgctctg ctaatcctgttaccagtggctgctgccagtggcgataagtcgtgccttaccgggttggactcaagacg atagttaccggataaggcgcagcggtcgggctgaacggggggttcgtgcacacagcccagcttggagc gaacgacctacaccgaactgagatacctacagcgtgagctatgagaaagcgccacgcttcccgaaggg agaaaggcggacaggtatccggtaagcggcagggtcggaacaggagagcgcacgagggagcttccagg gggaaacgcctggtatctttatagtcctgtcgggtttcgccacctctgacttgagcgtcgatttttgt gatgctcgtcaggggggcggagcctatggaaaaacgccagcaacgcggcctttttacggttcctggcc ttttgctggcctttgctcacatgt SEQ ID NO: 31, codon optimized polynucleotide encoding *S. aureas* Cas9

[SEQ ID NO: 31]

atgaaaagga actacattct ggggctggac atcgggatta caagcgtggg gtatgggatt attgactatg aaacaaggga cgtgatcgac gcaggcgtca gactgttcaa ggaggccaac gtggaaaaca tgagggacg gagaagcaag aggggagcca ggcgcctgaa acgacggaga aggcacagaa tccagagggt gaagaaactg ctgttcgatt acaacctgct gaccgaccat tctgagctga gtggaattaa tccttatgaa gccagggtga aaggcctgag tcagaagctg tcagaggaag agtttccgc agctctgctg cacctggcta agcgccgagg agtgcataac gtcaatgagg tggaagagga caccggcaac gagctgtcta caaaggaaca gatctcacgc aatagcaaag ctctggaaga agtatatgtc gcagagctgc agctggaacg gctgaagaaa gatggcgagg tgagagggtc aattaatagg ttcaagacaa gcgactacgt caaagaagcc aagcagctgc tgaaagtgca gaaggcttac caccagctgg atcagagctt catcgatact tatatcgacc tgctggagac tcggagaacc tactatgagg accaggagag agggagcccc

```
ttcggatgga aagacatcaa ggaatggtac gagatgctga tgggacattg cacctatttt ccagaagagc tgagaagcgt caagtacgct tataacgcag atctgtacaa cgccctgaat gacctgaaca acctggtcat caccagggat gaaaacgaga aactggaata ctatgagaag ttccagatca tcgaaaacgt gtttaagcag aagaaaaagc ctacactgaa acagattgct aaggagatcc tggtcaacga agaggacatc aagggctacc gggtgacaag cactggaaaa ccagagttca ccaatctgaa agtgtatcac gatattaagg acatcacagc acggaaagaa atcattgaga acgccgaact gctggatcag attgctaaga tcctgactat ctaccagagc tccgaggaca tccaggaaga gctgactaac ctgaacagcg agctgaccca ggaagagatc gaacagatta gtaatctgaa ggggtacacc ggaacacaca acctgtccct gaaagctatc aatctgattc tggatgagct gtggcataca aacgacaatc agattgcaat ctttaaccgg ctgaagctgg tcccaaaaaa ggtggacctg agtcagcaga aagagatccc aaccacactg gtggacgatt tcattctgtc acccgtggtc aagcggagct tcatccagag catcaaagtg atcaacgcca tcatcaagaa gtacggcctg cccaatgata tcattatcga gctggctagg gagaagaaca gcaaggacgc acagaagatg atcaatgaga tgcagaaacg aaaccggcag accaatgaac gcattgaaga gattatccga actaccggga aagagaacgc aaagtacctg attgaaaaaa tcaagctgca cgatatgcag gagggaaagt gtctgtattc tctggaggcc tccccctgg  aggacctgct gaacaatcca ttcaactacg aggtcgatca tattatcccc agaagcgtgt ccttcgacaa ttcctttaac aacaaggtgc tggtcaagca ggaagagaac tctaaaaagg gcaataggac tcctttccag tacctgtcta gttcagattc caagatctct tacgaaacct ttaaaaagca cattctgaat ctggccaaag gaaagggccg catcagcaag accaaaaagg agtacctgct ggaagagcgg gacatcaaca gattctccgt ccagaaggat tttattaacc ggaatctggt ggacacaaga tacgctactc gcggcctgat gaatctgctg cgatcctatt tccgggtgaa caatctggat gtgaaagtca agtccatcaa cggcgggttc acatcttttc tgaggcgcaa atggaagttt aaaaaggagc gcaacaaagg gtacaagcac catgccgaag atgctctgat tatcgcaaat gccgacttca tctttaagga gtggaaaaag ctggacaaag ccaagaaagt gatggagaac cagatgttcg aagagaagca ggccgaatct atgcccgaaa tcgagacaga acaggagtac aaggagattt tcatcactcc tcaccagatc aagcatatca aggatttcaa ggactacaag tactctcacc gggtggataa aaagcccaac agagagctga tcaatgacac cctgtatagt acaagaaaag acgataaggg gaatac_cctg attgtgaaca atctgaacgg actgtacgac aaagataatg acaagctgaa aaagctgatc aacaaaagtc ccgagaagct gctgatgtac caccatgatc ctcagacata tcagaaactg aagctgatta tggagcagta cggcgacgag aagaacccac tgtataagta ctatgaagag actgggaact acctgaccaa gtatagcaaa aaggataatg gccccgtgat caagaagatc aagtactatg ggaacaagct gaatgcccat ctggacatca gacgattacc ctaacagt cgcaacaagg tggtcaagct gtcactgaag ccatacagat cgatgtctct atctggacaac ggcgtgtata aatttgtgac tgtcaagaat ctggatgtca tcaaaaagga gaactactat gaagtgaata gcaagtgcta cgaagaggct aaaaagctga aaaagattag caaccaggca gagttcatcg cctcctttta caacaacgac ctgattaaga tcaatggcga actgtatagg gtcatcgggg tgaacaatga tctgctgaac cgcattgaag tgaatatgat tgacatcact taccgagagt atctggaaaa catgaatgat aagcgcccccc ctcgaattat caaaacaatt
```

-continued gcctctaaga ctcagagtat caaaaagtac tcaaccgaca ttctgggaaa cctgtatgag gtgaagagca aaaagcaccc tcagattatc aaaaagggc SEQ ID NO: 32, codon optimized polynucleotide encoding *S. aureas* Cas9
[SEQ ID NO: 32]

atgaagcgga actacatcct gggcctggac atcggcatca ccagcgtggg ctacggcatc atcgactacg agacacggga cgtgatcgat gccggcgtgc ggctgttcaa agaggccaac gtggaaaaca cgagggcag gcggagcaag agaggcgcca gaaggctgaa gcggcggagg cggcatagaa tccagagagt gaagaagctg ctgttcgact acaacctgct gaccgaccac agcgagctga gcggcatcaa cccctacgag gccagagtga agggcctgag ccagaagctg agcgaggaag agttctctgc cgccctgctg cacctggcca agagaagagg cgtgcacaac gtgaacgagg tggaagagga caccggcaac gagctgtcca ccaaagagca gatcacccgg aacagcaagg ccctggaaga gaaatacgtg gccgaactgc agctggaacg gctgaagaaa gacggcgaag tgcggggcag catcaacaga ttcaagacca gcgactacgt gaaagaagcc aaacagctgc tgaaggtgca gaaggcctac caccagctgg accagagctt catcgacacc tacatcgacc tgctggaaac ccggcggacc tactatgagg gacctggcga gggcagcccc ttcggctgga aggacatcaa agaatggtac gagatgctga tgggccactg cacctacttc cccgaggaac tgcggagcgt gaagtacgcc tacaacgccg acctgtacaa cgccctgaac gacctgaaca atctcgtgat caccagggac gagaacgaga gctggaata ttacgagaag ttccagatca tcgagaacgt gttcaagcag aagaagaagc ccaccctgaa gcagatcgcc aaagaaatcc tcgtgaacga agaggatatt aagggctaca gagtgaccag caccggcaag cccgagttca ccaacctgaa ggtgtaccac gacatcaagg acattaccgc ccggaaagag attattgaga cgccgagct gctggatgag attgccaaga tcctgaccat ctaccagagc agcgaggaca tccaggaaga actgaccaat ctgaactccg agctgaccca ggaagagatc gagcagatct ctaatctgaa gggctatacc ggcacccaca acctgagcct gaaggccatc aacctgatcc tggacgagct gtggcacacc aacgacaacc agatcgctat cttcaaccgg ctgaagctgg tgcccaagaa ggtggacctg tcccagcaga agagatcccc caccaccctg gtggacgact tcatcctgag ccccgtcgtg aagagaagct tcatccagag catcaaagtg atcaacgcca tcatcaagaa gtacggcctg cccaacgaca tcattatcga gctggcccgc gagaagaact ccaaggacgc ccagaaaatg atcaacgaga tgcagaagcg gaaccggcag accaacgagc ggatcgagga aatcatccgg accaccggca agagaaacgc caagtacctg atcgagaaga tcaagctgca cgacatgcag gaaggcaagt gcctgtacag cctggaagcc atccctctgg aagatctgct gaacaacccc ttcaactatg aggtggacca tatcatcccc agaagcgtgt ccttcgacaa cagcttcaac aacaaggtgc tcgtgaagca ggaagaaaac agcaagaagg caaccggac cccattccag tacctgagca gcagcgacag caagatcagc tacgaaacct tcaagaagca catcctgaat ctggccaagg caagggcag aatcagcaag accaagaaag agtatctgct ggaagaacgg gacatcaaca ggttctccgt gcagaaagac ttcatcaacc ggaacctggt ggataccaga tacgccacca gaggcctgat gaacctgctg cggagctact tccaggtgaa caacctggac gtgaaagtga gtccatcaa tggcggcttc accagctttc tgcggcggaa gtggaagttt aagaaagagc ggaacaaggg gtacaagcac cacgccgagg acgccctgat cattgccaac gccgatttca tcttcaaaga gtggaagaaa ctggacaagc caaaaaagt gatggaaaac cagatgttcg aggaaaagca ggccgagagc atgcccgaga tcgaaaccga gcaggagtac aaagagatct tcatcacccc ccaccagatc -continued

```
aagcacatta aggacttcaa ggactacaag tacagccacc gggtggacaa gaagcctaat agagagctga ttaacgacac cctgtactcc acccggaagg acgacaaggg caacaccctg atcgtgaaca atctgaacgg cctgtacgac aaggacaatg acaagctgaa aaagctgatc aacaagagcc ccgaaaagct gctgatgtac caccacgacc cccagaccta ccagaaactg aagctgatta tggaacagta cggcgacgag aagaatcccc tgtacaagta ctacgaggaa accgggaact acctgaccaa gtactccaaa aaggacaacg cccccgtgat caagaagatt aagtattacg gcaacaaact gaacgcccat ctggacatca ccgacgacta ccccaacagc agaaacaagg tcgtgaagct gtccctgaag ccctacagat tcgacgtgta cctggacaat ggcgtgtaca agttcgtgac cgtgaagaat ctggatgtga tcaaaaaaga aaactactac gaagtgaata gcaagtgcta tgaggaagct aagaagctga agaagatcag caaccaggcc gagtttatcg cctccttcta caacaacgat ctgatcaaga tcaacggcga gctgtataga gtgatcggcg tgaacaacga cctgctgaac cggatcgaag tgaacatgat cgacatcacc taccgcgagt acctggaaaa catgaacgac aagaggcccc ccaggatcat taagacaatc gcctccaaga cccagagcat taagaagtac agcacagaca ttctgggcaa cctgtatgaa gtgaaatcta agaagcaccc tcagatcatc aaaaagggc
```

SEQ ID NO: 33, codon optimized polynucleotide encoding *S. aureas* Cas9

[SEQ ID NO: 33]
```
atgaagcgca actacatcct cggactggac atcggcatta cctccgtggg atacggcatc atcgattacg aaactaggga tgtgatcgac gctggagtca ggctgttcaa agaggcgaac gtggagaaca acgaggggcg cgcgctcaaag aggggggccc gccggctgaa gcgccgccgc agacatagaa tccagcgcgt gaagaagctg ctgttcgact acaaccttct gaccgaccac tccgaacttt ccggcatcaa cccatatgag gctagagtga agggattgtc ccaaaagctg tccgaggaag agttctccgc cgcgttgctc cacctcgcca agcgcagggg agtgcacaat gtgaacgaag tggaagaaga taccggaaac gagctgtcca ccaaggagca gatcagccgg aactccaagg ccctggaaga aaatacgtg gcggaactgc aactggagcg gctgaagaaa gacggagaag tgcgcggctc gatcaaccgc ttcaagacct cggactacgt gaaggaggcc aagcagctcc tgaaagtgca aaaggcctat caccaacttg accagtcctt tatcgatacc tacatcgatc tgctcgagac tcggcggact tactacgagg tccaggggga gggctccccca tttggttgga aggatattaa ggagtggtac gaaatgctga tgggacactg cacatacttc cctgaggagc tgcggagcgt gaaatacgca tacaacgcag acctgtacaa cgcgctgaac gacctgaaca atctcgtgat cacccgggac gagaacgaaa agctcgagta ttacgaaaag ttccagatta ttgagaacgt gttcaaacag aagaagaagc cgacactgaa gcagattgcc aaggaaatcc tcgtgaacga agaggacatc aagggctatc gagtgacctc aacgggaaag ccggagttca ccaatctgaa ggtctaccac gacatcaaag acattaccgc ccggaaggag atcattgaga cgcggagct gttggaccag attgcgaaga ttctgaccat ctaccaatcc tccgaggata ttcaggaaga actcaccaac ctcaacagcg aactgaccca ggaggagata gagcaaatct ccaacctgaa gggctacacc ggaactcata acctgagcct gaaggccatc aacttgatcc tggacgagct gtggcacacc aacgataacc agatcgctat tttcaatcgg ctgaagctgg tccccaagaa agtggacctc tcacaacaaa aggagatccc tactaccctt gtggacgatt tcattctgtc ccccgtggtc aagagaagct catacagtc aatcaaagtg atcaatgcca ttatcaagaa atacggtctg cccaacgaca ttatcattga gctcgcccgc
```

-continued gagaagaact cgaaggacgc ccagaagatg attaacgaaa tgcagaagag gaaccgacag actaacgaac ggatcgaaga aatcatccgg accaccggga aggaaaacgc gaagtacctg atcgaaaaga tcaagctcca tgacatgcag gaaggaaagt gtctgtactc gctggaggcc attccgctgg aggacttgct gaacaaccct tttaactacg aagtggatca tatcattccg aggagcgtgt cattcgacaa ttccttcaac aacaaggtcc tcgtgaagca ggaggaaaac tcgaagaagg gaaaccgcac gccgttccag tacctgagca gcagcgactc caagatttcc tacgaaacct tcaagaagca catcctcaac ctggcaaagg ggaagggtcg catctccaag accaagaagg aatatctgct ggaagaaaga gacatcaaca gattctccgt gcaaaaggac ttcatcaacc gcaacctcgt ggatactaga tacgctactc ggggtctgat gaacctcctg agaagctact ttagagtgaa caatctggac gtgaaggtca agtcgattaa cggaggtttc acctccttcc tgcggcgcaa gtggaagttc aagaaggaac ggaacaaggg ctacaagcac cacgccgagg acgccctgat cattgccaac gccgacttca tcttcaaaga atggaagaaa cttgacaagg ctaagaaggt catggaaaac cagatgttcg aagaaaagca ggccgagtct atgcctgaaa tcgagactga acaggagtac aaggaaatct ttattacgcc acaccagatc aaacacatca aggatttcaa ggattacaag tactcacatc gcgtggacaa aaagccgaac agggaactga tcaacgacac cctctactcc acccggaagg atgacaaagg gaataccctc atcgtcaaca accttaacgg cctgtacgac aaggacaacg ataagctgaa gaagctcatt aacaagtcgc ccgaaaagtt gctgatgtac caccacgacc ctcagactta ccagaagctc aagctgatca tggagcagta tggggacgag aaaaacccgt tgtacaagta ctacgaagaa actgggaatt atctgactaa gtactccaag aaagataacg gccccgtgat taagaagatt aagtactacg gcaacaagct gaacgcccat ctggacatca ccgatgacta ccctaattcc cgcaacaagg tcgtcaagct gagcctcaag ccctaccggt ttgatgtgta ccttgacaat ggagtgtaca agttcgtgac tgtgaagaac cttgacgtga tcaagaagga gaactactac gaagtcaact ccaagtgcta cgaggaagca aagaagttga agaagatctc gaaccaggcc gagttcattg cctccttcta taacaacgac ctgattaaga tcaacggcga actgtaccgc gtcattggcg tgaacaacga tctcctgaac cgcatcgaag tgaacatgat cgacatcact taccgggaat acctggagaa tatgaacgac aagcgcccgc cccggatcat taagactatc gcctcaaaga cccagtcgat caagaagtac agcaccgaca tcctgggcaa cctgtacgag gtcaaatcga gaagcacccc ccagatcatc aagaaggga SEQ ID NO: 34, codon optimized polynucleotide encoding *S. aureas* Cas9

[SEQ ID NO: 34]

atggcccaaagaagaagcggaaggtcggtatccacggagtcccagcagccaagcggaactacatcct gggcctggacatcggcatcaccagcgtgggctacggcatcatcgactacgagacacgggacgtgatcg atgccggcgtgcggctgttcaaagaggccaacgtggaaaacaacgagggcaggcggagcaagagaggc gccagaaggctgaagcggcggaggcggcatagaatccagagagtgaagaagctgctgttcgactacaa cctgctgaccgaccacagcgagctgagcggcatcaacccctacgaggccagagtgaagggcctgagcc agaagctgagcgaggaagagttctctgccgccctgctgcacctggccaagagaagaggcgtgcacaac gtgaacaaggtggaagaggacaccggcaacgagctgtccaccagagagcagatcagccggaacagcaa ggccctggaagagaaatacgtggccgaactgcagctggaacggctgaagaaagacggcgaagtgcggg gcagcatcaacagattcaagaccagcgactacgtgaaagaagccaaacagctgctgaaggtgcagaag gcctaccaccagctggaccagagcttcatcgacacctacatcgacctgctggaaacccggcggacta ctatgagggacctggcgagggcagccccttcggctggaaggacatcaaagaatggtacgagatgctga -continued tgggccactgcacctacttccccgaggaactgcggagcgtgaagtacgcctacaacgccgacctgtac aacgccctgaacgacctgaacaatctcgtgatcaccagggacgagaacgagaagctggaatattacga gaagttccagatcatcgagaacgtgttcaagcagaagaagaagcccaccctgaagcagatcgccaaag aaatcctcgtgaacgaagaggatattaagggctacagagtgaccagcaccggcaagcccgagttcacc aacctgaaggtgtaccacgacatcaaggacattaccgcccggaaagagattattgagaacgccgagct gctggatcagattgccaagatcctgaccatctaccagagcagcgaggacatccaggaagaactgacca atctgaactccgagctgacccaggaagagatcgagcagatctctaatctgaagggctataccggcacc cacaacctgagcctgaaggccatcaacctgatcctggacgagctgtggcacaccaacgcacaaccagat cgctatcttcaaccggctgaagctggtgcccaagaaggtggacctgtcccagcagaaagagatcccca ccaccctggtggacgacttcatcctgagccccgtcgtgaagagaagcttcatccagagcatcaaagtg atcaacgccatcatcaagaagtacggcctgcccaacgacatcattatcgagctggcccgcgagaagaa ctccaaggacgcccagaaaatgatcaacgagatgcagaagcggaaccggcagaccaacgagcggatcg aggaaatcatccggaccaccggcaaagagaacgccaagcacctgatcgagaagatcaagctgcacgac atgcaggaaggcaagtgcctgtacagcctggaagccatccctctggaagatctgctgaacaacccctt caactatgaggtggaccacatcatccccagaagcgtgtccttcgacaacagcttcaacaacaaggtgc tcgtgaagcaggaagaaaacagcaagaagggcaaccggacccccattccagtacctgagcagcagcgac agcaagatcagctacgaaaccttcaagaagcacatcctgaatctggccaagggcaagggcagaatcag caagaccaagaaagagtatctgctggaagaacgggacatcaacaggttctccgtgcagaaagacttca tcaaccggaacctggtggataccagatacgccaccagaggcctgatgaacctgctgcggagctacttc agagtgaacaacctggacgtgaaagtgaagtccatcaatggcggcttcaccagctttctgcggcggaa gtggaagtttaagaaagagcggaacaaggggtacaagcaccacgccgaggacgccctgatcattgcca acgccgatttcatcttcaaagagtggaagaaactggacaaggccaaaaaagtgatggaaaaccagatg ttcgaggaaaggcaggccgagagcatgcccgagatcgaaaccgagcaggagtacaaagagatcttcat cacccccaccagatcaagcacattaaggacttcaaggactacaagtacagccaccgggtggacaaga agcctaatagagagctgattaacgacaccctgtactccacccggaaggacgacaagggcaacaccccta atcgtgaacaatctgaacggcctgtacgacaaggacaatgacaagctgaaaaagctgatcaacaagag cccc gaaaagctgctgatgtaccaccacgacccccagacctaccagaaactgaagctgattatggaac agtacggcgacgagaagaatcccctgtacaagtactacgaggaaaccgggaactacctgaccaagtac tccaaaaaggacaacggcccccgtgatcaagaagattaagtattacggcaacaaactgaacgcccatct ggacatcaccgacgactaccccaacagcagaaacaaggtcgtgaagctgtccctgaagcccctacagat tcgacgtgtacctggacaatggcgtgtacaagttcgtgaccgtgaagaatctggatgtgatcaaaaaa gaaaactactacgaagtgaatagcaagtgctatgaggaagctaagaagctgaagaagatcagcaacca ggccgagtttatcgcctccttctacaacaacgatctgatcaagatcaacggcgagctgtatagagtga tcggcgtgaacaacgacctgctgaaccggatcgaagtgaacatgatcgacatcacctaccgcgagtac ctggaaaacatgaacgacaagaggccccccaggatcactaagacaatcgcctccaagacccagagcat taagaagtacagcacagacattctgggcaacctgtatgaagtgaaatctaagaagcaccctcagatca tcaaaaagggcaaaaggccggcggccacgaaaaaggccggccaggcaaaaaagaaaaag SEQ ID NO: 35, codon optimized polynucleotide encoding *S. aureas* Cas9
[SEQ ID NO: 35]
accggtgcca ccatgtaccc atacgatgtt gcagattacg cttcgccgaa gaaaaagcgc aaggtcgaag cgtccatgaa aaggaactac attctggggc tggacatcgg gattacaagc -continued

```
gtggggtatg ggattattga ctatgaaaca agggacgtga tcgacgcagg cgtcagactg ttcaaggagg ccaacgtgga aaacaatgag ggacggagaa gcaagagggg agccaggcgc ctgaaacgac ggagaaggca cagaatccag agggtgaaga aactgctgtt cgattacaac ctgctgaccg accattctga gctgagtgga attaatcctt atgaagccag ggtgaaaggc ctgagtcaga agctgtcaga ggaagagttt tccgcagctc tgctgcacct ggctaagcgc cgaggagtgc ataacgtcaa tgaggtggaa gaggacaccg gcaacgagct gtctacaaag gaacagatct cacgcaatag caaagctctg gaagagaagt atgtcgcaga gctgcagctg gaacggctga agaaagatgg cgaggtgaga gggtcaatta ataggttcaa gacaagcgac tacgtcaaag aagccaagca gctgctgaaa gtgcagaagg cttaccacca gctggatcag agcttcatcg atacttatat cgacctgctg gagactcgga gaacctacta tgagggacca ggagaaggga gccccttcgg atggaaagac atcaaggaat ggtacgagat gctgatggga cattgcacct attttccaga gagctgaga agcgtcaagt acgcttataa cgcagatct tacaacgccc tgaatgacct gaacaacctg gtcatcacca gggatgaaaa cgagaaactg gaatactatg agaagttcca gatcatcgaa aacgtgttta agcagaagaa aaagcctaca ctgaaacaga ttgctaagga gatcctggtc aacgaagagg acatcaaggg ctaccgggtg acaagcactg gaaaaccaga gttcaccaat ctgaaagtgt atcacgatat taaggacatc acagcacgga aagaaatcat tgagaacgcc gaactgctgg atcagattgc taagatcctg actatctacc agagctccga ggacatccag gaagagctga ctaacctgaa cagcgagctg acccaggaag agatcgaaca gattagtaat ctgaaggggt acaccggaac acacaacctg tccctgaaag ctatcaatct gattctggat gagctgtggc atacaaacga caatcagatt gcaatcttta accggctgaa gctggtccca aaaaaggtgg acctgagtca gcagaaagag atcccaacca cactggtgga cgatttcatt ctgtcacccg tggtcaagcg gagcttcatc cagagcatca aagtgatcaa cgccatcatc aagaagtacg gcctgcccaa tgatatcatt atcgagctgg ctagggagaa gaacagcaag gacgcacaga agatgatcaa tgagatgcag aaacgaaacc ggcagaccaa tgaacgcatt gaagagatta tccgaactac cgggaaagag aacgcaaagt acctgattga aaaaatcaag ctgcacgata tgcaggaggg aaagtgtctg tattctctgg aggccatccc cctggaggac ctgctgaaca atccattcaa ctacgaggtc gatcatatta tccccagaag cgtgtccttc gacaattcct ttaacaacaa ggtgctggtc aagcaggaag agaactctaa aaagggcaat aggactcctt tccagtacct gtctagttca gattccaaga tctcttacga aacctttaaa aagcacattc tgaatctggc caaaggaaag ggccgcatca gcaagaccaa aaaggagtac ctgctggaag agcgggacat caacagattc tccgtccaga aggattttat taaccggaat ctggtggaca caagatacgc tactcgcggc ctgatgaatc tgctgcgatc ctatttccgg gtgaacaatc tggatgtgaa agtcaagtcc atcaacggcg ggttcacatc ttttctgagg cgcaaatgga gtttaaaaa ggagcgcaac aaagggtaca gcaccatgc cgaagatgct ctgattatcg caaatgccga cttcatcttt aaggagtgga aaaagctgga caaagccaag aaagtgatgg agaaccagat gttcgaagag aagcaggccg aatctatgcc cgaaatcgag acagaacagg agtacaagga gattttcatc actcctcacc agatcaagca tatcaaggat ttcaaggact acaagtactc tcaccgggtg gataaaaagc ccaacagaga gctgatcaat gacaccctgt atagtacaag aaaagacgat aaggggaata ccctgattgt gaacaatctg aacggactgt acgacaaaga taatgacaag ctgaaaaagc tgatcaacaa aagtcccgag aagctgctga tgtaccacca tgatcctcag
```

-continued

```
acatatcaga aactgaagct gattatggag cagtacggcg acgagaagaa cccactgtat aagtactatg aagagactgg gaactacctg accaagtata gcaaaaagga taatggcccc gtgatcaaga agatcaagta ctatgggaac aagctgaatg cccatctgga catcacagac gattacccta acagtcgcaa caaggtggtc aagctgtcac tgaagccata cagattcgat gtctatctgg acaacggcgt gtataaattt gtgactgtca agaatctgga tgtcatcaaa aaggagaact actatgaagt gaatagcaag tgctacgaag aggctaaaaa gctgaaaaag attagcaacc aggcagagtt catcgcctcc ttttacaaca acgacctgat taagatcaat ggcgaactgt atagggtcat cggggtgaac aatgatctgc tgaaccgcat tgaagtgaat atgattgaca tcacttaccg agagtatctg gaaaacatga atgataagcg cccccctcga attatcaaaa caattgcctc taagactcag agtatcaaaa agtactcaac cgacattctg ggaaacctgt atgaggtgaa gagcaaaaag caccctcaga ttatcaaaaa gggctaagaa ttc
```

SEQ ID NO: 36, codon optimized polynucleotide encoding *S. aureas* Cas9
[seq id no: 36]

```
atggccccaaagaagaagcggaaggtcggtatccacggagtcccagcagccaagcggaactacatcct gggcctggacatcggcatcaccagcgtgggctacggcatcatcgactacgagacacgggacgtgatcg atgccggcgtgcggctgttcaaagaggccaacgtggaaaacaacgagggcaggcggagcaagagaggc gccagaaggctgaagcgacggaggcggcatagaatccagagagtgaagaagctgctgttcgactacaa cctgctgaccgaccacagcgagctgagcggcatcaacccctacgaggccagagtgaagggcctgagcc agaagctgagcgaggaagagttctctgccgccctgctgcacctggccaagagaagaggcgtgcacaac gtgaacgaggtggaagaggacaccggcaacgagctgtccaccaaagagcagatcagccggaacagcaa ggccctggaagagaaatacgtggccgaactgcagctggaacggctgaagaaagacggcgaagtgcggg gcagcatcaacagattcaagaccagcgactacgtaaaagaagccaaacagctgctgaaggtgcagaag gcctaccaccagctggaccagagcttcatcgacacctacatcgacctgctggaaacccggcggaccta ctatgagggacctggcgagggcagcccccttcggctggaaggacatcaaagaatggtacgagatgctga tgggccactgcacctacctccccgaggaaccgcggagcgtgaagcacgcctacaacgccgacctgtac aacgccctgaacgacctgaacaatctcgtgatcaccagggacgagaacgagaagctggaatattacga gaagttccagatcatcgagaacgtgttcaagcagaagaagaagcccaccctgaagcagatcgccaaag aaatcctcgtgaacgaagaggatattaagggctacagagtgaccagcaccggcaagcccgagttcacc aacctgaaggtgtaccacgacatcaaggacattaccgcccggaaagagattattgagaacgccgagct gctggatcagattgccaagatcctgaccatctaccagagcagcgaggacatccaggaagaactgacca atctgaactccgagctgacccaggaagagatcgagcagatctctaatctgaagggctataccggcacc cacaacctgagcctgaaggccatcaacctgatcctggacgagctgtggcacaccaacgacaaccagat cgctatcttcaaccggctgaagctggtgcccaagaaggtggacctgtcccagcagaaagagaCcccca ccacccctggtggacgacttcatcctgagccccgtcgtgaagagaagcttcatccagagcatcaaagtg atcaacgccatcatcaagaagtacggcctgcccaacgacatcattatcgagctggcccgcgagaagaa ctccaaggacgcccagaaaatgatcaacgagatgcagaagcggaacaggcagaccaacgagcggatcg aggaaatcatccggaccaccggcaaagagaacgccaagtacctgatcgagaagatcaagctgcacgac atgcaggaaggcaagtgcctgtacagcctggaagccatccctctggaagatctgctgaacaacccctt caactatgaggtggaccacatcatccccagaagcgtgtccttcgacaacagcttcaacaacaaggtgc tcgtgaagcaggaagaaacagcaagaagggcaaccggaccccattccagtacctgagcagcagcgac
```

-continued

```
agcaagatcagctacgaaaccttcaagaagcacatcctgaatctggccaagggcaagggcagaatcag caagaccaagaaagagtatctgctggaagaacgggacatcaacaggttctccgtgcagaaagacttca tcaaccggaacctggtggataccagatacgccaccagaggcctgatgaacctgctgcggagctacttc agagtgaacaacctggacgtgaaagtgaagtccatcaatggcggcttcaccagctttctgcggcggaa gtggaagtttaagaaagagcggaacaaggggtacaagcaccacgccgaggacgccctgatcattgcca acgccgatttcatcttcaaagagtggaagaaactggacaaggccaaaaaagtgatggaaaaccagatg ttcgaggaaaagcaggccgagagcatgcccgagatcgaaaccgagcaggagtacaaagagatcttcat cacccccaccagatcaagcacattaaggacttcaaggactacaagtacagccaccgggtggacaaga agcctaatagagagctgattaacgacaccctgtactccacccggaaggacgacaagggcaacaccctg atcgtgaacaatctgaacggcctgtacgacaaggacaatgacaagctgaaaaagctgatcaacaagag ccccgaaaagctgctgatgtaccaccacgacccccagacctaccagaaactgaagctgattatggaac agtacggcgacgagaagaatcccctgtacaagtactacgaggaaaccgggaactacctgaccaagtac tccaaaaaggacaacggcccccgtgatcaagaagattaagtactacggcaacaaactgaacgcccatct ggacatcaccgacgactaccccaacagcagaaacaaggtcgtgaagctgtccctgaagccctacagat tcgacgtgtacctggacaatggcgtgtacaagttcgtgaccgtgaagaatctggatgtgatcaaaaaa gaaaactactacgaagtgaatagcaagtgctatgaggaagctaagaagctgaagaagatcagcaacca ggccgagtttatcgcctccttctacaacaacgatctgatcaagatcaacggcgagctgtatagagtga tcggcgtgaacaacgacctgctgaaccggatcgaagtgaacatgatcgacatcacctaccgcgagtac ctggaaaacatgaacgacaagaggccccccaggatcattaagacaatcgcctccaagacccagagcat taagaagtacagcacagacattctgggcaacctgtatgaagtgaaatctaagaagcaccctcagatca tcaaaaagggcaaaaggccggcggccacgaaaaaggccggccaggcaaaaagaaaaag
```

SEQ ID NO: 37, polynucleotide sequence of *S. aureus* Cas9

[SEQ ID NO: 37]
```
aagcggaactacatcctgggcctggacatcggcatcaccagcgtgggctacggcatcaccgactacga gacacgggacgtgatcgatgccggcgtgcggctgttcaaagaggccaacgtggaaaacaacgagggca ggcggagcaagagaggcgccagaaggctgaagcggcggaggcggcatagaatccagagagtgaagaag ctgctgttcgactacaacctgctgaccgaccacagcgagctgagcggcatcaaccctacgaggccag agtgaagggcctgagccagaagctgagcgaggaagagttctctgccgccctgctgcacctggccaaga gaagaggcgtgcacaacgtgaacgaggtggaagaggacaccggcaacgagctgtccaccaaagagcag atcagccggaacagcaaggcctggaagagaaatacgtgaccgaactgcagctggaacggctgaagaa agacggcgaagtgcggggcagcatcaacagattcaagaccagcgactacgtgaaagaagccaaacaac tgctgaaggtgcagaaggcctaccaccagctggaccagagcttcatcgacacctacatcgacctgctg gaaacccggcggacctactatgagggacctggcgagggcagcccttcggctggaaggacatcaaaga atggtacgagatgctgatgggccactgcacctacttccccgaggaactgcggagcgtgaagtacgcct acaacgccgacctgtacaacgccctgaacgacctgaacaatctcgtgatcaccagggacgagaacgag aagctggaatattacgagaagttccagatcatcgagaacgtgttcaagcagaagaagaagcccaccct gaagcagatcgccaagaaatcctcgtgaacgaagaggatattaagggctacagagtgaccagcaccg gcaagcccgagttcaccaacctgaaggtgtaccacgacatcaaggacattaccgcccggaaagagatt attgagaacgccgagctgctggatcagattgccaagatcctgaccatctaccagagcagcgaggacat ccaggaagaactgaccaatctgaactccgagctgaccoaggaagagatcgagcagatctctaatctga agggctataccggcacccacaacctgagcctgaaggccatcaacctgatcctggacgagctgtggcac accaacgacaaccagatcgctatcttcaaccggctgaagctggtgcccaagaaggtggacctgtccca
```

-continued gcagaaagagatccccaccaccctggtggaogacttcatcctgagcoccgtcgtgaagagaagcttca tccagagcatcaaagtgatcaacgccatcatcaagaagtacggcctgcccaacgacatcattatcgag ctggcccgcgagaagaactccaaggacgcccagaaaatgatcaacgagatgcagaagcggaaccggca gaccaacgagcggatcgaggaaatcatccggaccaccggcaaagagaacgccaagtacctgatcgaga agatcaagctgcacgacatgcaggaaggcaagtgcctgtacagcctggaagccatccctctggaagat ctgctgaacaaccccttcaactatgaggtggaccacatcatccccagaagcgtgcccttcaacaacag cttcaacaacaaggtgctcgtgaagcaggaagaaacagcaagaagggcaaccggaccccattccagt acctgagcagcagcgacagcaagatcagctacgaaaccttcaagaagcacatcctgaatctggccaag ggcaagggcagaatcagcaagaccaagaaagagtatctgctggaagaacgggacatcaacaggttctc cgtgcagaaagacttcatcaaccggaacctggtggataccagatacgccaccagaggcctgatgaacc tgctgcggagctacttcagagtgaacaacctggacgtgaaagtgaagtccatcaatggcggcttcacc agctttctgcggcggaagtgaaagtttaagaaagagcggaacaaggggtacaagcaccacgccgagga cgccctgatcattgccaacgccgatttcatcttcaaagagtggaagaaactggacaaggccaaaaaag tgatggaaaaccagatgttcgaggaaaagcaggccgagagcatgcccgagatcgaaaccgagcaggag tacaaagagatcttcatcacccccaccagatcaagcacattaaggacttcaaggactacaagtacag ccaccgggtggacaagaagcctaatagagagctgattaacgacaccctgtactccacccggaaggacg acaagggcaacaccctgatcgtgaacaatctgaacggcctgtacgacaaggacaatgacaagctgaaa aagctgatcaacaagagccccgaaaagctgctgatgtaccaccacgacccccagacctaccagaaact gaagctgattatggaacagtacggcgacgagaagaatcccctgtacaagtactacgaggaaaccggga actacctgaccaagtactccaaaaaggacaacggccccgtgatcaagaagattaagtattacggcaac aaactgaacgcccatctggacatcaccgacgactaccccaacagcagaaacaaggtcgcgaagctgtc cctgaagccctacagattcgacgtgtacctggacaatggcgtgtacaagttcgtgaccgtgaagaatc tggatgtgatcaaaaaagaaaactactacgaagtgaatagcaagtgctatgaggaagctaagaagctg aagaagatcagcaaccaggccgagtttatcgcctccttctacaacaacgatctgatcaagatcaacgg cgagctgtatagagtgatcggcgtgaacaacgacctgctgaaccggatcgaagtgaacatgatcgaca tcacctaccgcaagtacctggaaaacatgaacgacaagaggccccccaggatcattaagacaatcgcc tccaagacccagagcattaagaagtacagcacagacattctgggcaacctgtatgaagtgaaatctaa gaagcaccctcagatcatcaaaaagggc SEQ ID NO: 38, pDO242 (SaCas9 used in all JCR89/91 projects and
JCR157/160 projects for in vitro work; SaCas9 in uppercase)
[SEQ ID NO: 38]
ctaaattgtaagcgttaatattttgttaaaattcgcgttaaattttttgttaaatcagctcattttta accaataggccgaaatcggcaaaatcccttataaatcaaaagaatagaccgagatagggttgagtgtt gttccagtttggaacaagagtccactattaaagaacgtggactccaacgtcaaagggcgaaaaaccgt ctatcagggcgatggcccactacgtgaaccatcaccctaatcaagttttttggggtcgaggtgccgta aagcactaaatcggaaccctaaagggagcccccgatttagagcttgacggggaaagccggcgaacgtg gcgagaaaggaagggaagaaagcgaaaggagcgggcgccaggcgctggcaagtgtagcggtcacgct gcgcgtaaccaccacacccgcgcgcttaatgcgccgctacagggcgcgtcccattcgccattcaggc tgcgcaactgttgggaagggcgatcggtgcgggcctcttcgctattacgccagctggcgaaaggggga tgtgctgcaaggcgattaagttgggtaacgccagggttttcccagtcacgacgttgtaaaacgacggc cagtgagcgcgcgtaatacgactcactatagggcgaattgggtacCtttaattctagtactatgcaTg cgttgacattgattattgactagttattaatagtaatcaattacggggtcattagttcatagcccata -continued tatggagttccgcgttacataacttacggtaaatggcccgcctggctgaccgcccaacgaccccgcc cattgacgtcaataatgacgtatgttcccatagtaacgccaatagggactttccattgacgtcaatgg gtggagtatttacggtaaactgcccacttggcagtacatcaagtgtatcatatgccaagtacgccccc tattgacgtcaatgacggtaaatggcccgcctggcattatgcccagtacatgaccttatgggactttc ctacttggcagtacatctacgtattagtcatcgctattaccatggtgatgcggttttggcagtacatc aatgggcgtggatagcggtttgactcacggggatttccaagtctccacccccattgacgtcaatgggag tttgttttggcaccaaaatcaacgggactttccaaaatgtcgtaacaactccgccccattgacgcaaa tgggcggtaggcgtgtacggtgggaggtctatataagcagagctctctggctaactaccggtgccacc

ATGAAAAGGAACTACATTCTGGGGCTGGACATCGGGATTACAAGCGTGGGGTATGGGATTATTGACTA

TGAAACAAGGGACGTGATCGACGCAGGCGTCAGACTGTTCAAGGAGGCCAACGTGGAAAACAATGAGG

GACGGAGAAGCAAGAGGGGAGCCAGGCGCCTGAAACGACGGAGAAGGCACAGAATCCAGAGGGTGAAG

AAACTGCTGTTCGATTACAACCTGCTGACCGACCATTCTGAGCTGAGTGGAATTAATCCTTATGAAGC

CAGGGTGAAAGGCCTGAGTCAGAAGCTGTCAGAGGAAGAGTTTTCCGCAGCTCTGCTGCACCTGGCTA

AGCGCCGAGGAGTGCATAACGTCAATGAGGTGGAAGAGGACACCGGCAACGAGCTGTCTACAAAGGAA

CAGATCTCACGCAATAGCAAAGCTCTGGAAGAGAAGTATGTCGCAGAGCTGCAGCTGGAACGGCTGAA

GAAAGATGGCGAGGTGAGAGGGTCAATTAATAGGTTCAAGACAAGCGACTACGTCAAAGAAGCCAAGC

AGCTGCTGAAAGTGCAGAAGGCTTACCACCAGCTGGATCAGAGCTTCATCGATACTTATATCGACCTG

CTGGAGACTCGGAGAACCTACTATGAGGGACCAGGAGAAGGGAGCCCCTTCGGATGGAAAGACATCAA

GGAATGGTACGAGATGCTGATGGGACATTGCACCTATTTTCCAGAAGAGCTGAGAAGCGTCAAGTACG

CTTATAACGCAGATCTGTACAACGCCCTGAATGACCTGAACAACCTGGTCATCACCAGGGATGAAAAC

GAGAAACTGGAATACTATGAGAAGTTCCAGATCATCGAAAACGTGTTTAAGCAGAAGAAAAAGCCTAC

ACTGAAACAGATTGCTAAGGAGATCCTGGTCAACGAAGAGGACATCAAGGGCTACCGGGTGACAAGCA

CTGGAAAACCAGAGTTCACCAATCTGAAAGTGTATCACGATATTAAGGACATCACAGCACGGAAAGAA

ATCATTGAGAACGCCGAACTGCTGGATCAGATTGCTAAGATCCTGACTATCTACCAGAGCTCCGAGGA

CATCCAGGAAGAGCTGACTAACCTGAACAGCGAGCTGACCCAGGAAGAGATCGAACAGATTAGTAATC

TGAAGGGGTACACCGGAACACACAACCTGTCCCTGAAAGCTATCAATCTGATTCTGGATGAGCTGTGG

CATACAAACGACAATCAGATTGCAATCTTTAACCGGCTGAAGCTGGTCCCAAAAAAGGTGGACCTGAG

TCAGCAGAAAGAGATCCCAACCACACTGGTGGACGATTTCATTCTGTCACCCGTGGTCAAGCGGAGCT

TCATCCAGAGCATCAAAGTGATCAACGCCATCATCAAGAAGTACGGCCTGCCCAATGATATCATTATC

GAGCTGGCTAGGGAGAAGAACAGCAAGGACGCACAGAAGATGATCAATGAGATGCAGAAACGAAACCG

GCAGACCAATGAACGCATTGAAGAGATTATCCGAACTACCGGGAAAGAGAACGCAAAGTACCTGATTG

AAAAAATCAAGCTGCACGATATGCAGGAGGGAAAGTGTCTGTATTCTCTGGAGGCCATCCCCCTGGAG

GACCTGCTGAACAATCCATTCAACTACGAGGTCGATCATATTATCCCCAGAAGCGTGTCCTTCGACAA

TTCCTTTAACAACAAGGTGCTGGTCAAGCAGGAAGAGAACTCTAAAAAGGGCAATAGGACTCCTTTCC

AGTACCTGTCTAGTTCAGATTCCAAGATCTCTTACGAAACCTTTAAAAAGCACATTCTGAATCTGGCC

AAAGGAAAGGGCCGCATCAGCAAGACCAAAAAGGAGTACCTGCTGGAAGAGCGGGACATCAACAGATT

CTCCGTCCAGAAGGATTTTATTAACCGGAATCTGGTGGACACAAGATACGCTACTCGCGGCCTGATGA

ATCTGCTGCGATCCTATTTCCGGGTGAACAATCTGGATGTGAAAGTCAAGTCCATCAACGGCGGGTTC

ACATCTTTTCTGAGGCGCAAATGGAAGTTTAAAAAGGAGCGCAACAAAGGGTACAAGCACCATGCCGA

AGATGCTCTGATTATCGCAAATGCCGACTTCATCTTTAAGGAGTGGAAAAAGCTGGACAAAGCCAAGA

-continued

```
AAGTGATGGAGAACCAGATGTTCGAAGAGAAGCAGGCCGAATCTATGCCCGAAATCGAGACAGAACAG

GAGTACAAGGAGATTTTCATCACTCCTCACCAGATCAAGCATATCAAGGATTTCAAGGACTACAAGTA

CTCTCACCGGGTGGATAAAAAGCCCAACAGAGAGCTGATCAATGACACCCTGTATAGTACAAGAAAAG

ACGATAAGGGGAATACCCTGATTGTGAACAATCTGAACGGACTGTACGACAAAGATAATGACAAGCTG

AAAAAGCTGATCAACAAAAGTCCCGAGAAGCTGCTGATGTACCACCATGATCCTCAGACATATCAGAA

ACTGAAGCTGATTATGGAGCAGTACGGCGACGAGAAGAACCCACTGTATAAGTACTATGAAGAGACTG

GGAACTACCTGACCAAGTATAGCAAAAAGGATAATGGCCCCGTGATCAAGAAGATCAAGTACTATGGG

AACAAGCTGAATGCCCATCTGGACATCACAGACGATTACCCTAACAGTCGCAACAAGGTGGTCAAGCT

GTCACTGAAGCCATACAGATTCGATGTCTATCTGGACAACGGCGTGTATAAATTTGTGACTGTCAAGA

ATCTGGATGTCATCAAAAAGGAGAACTACTATGAAGTGAATAGCAAGTGCTACGAAGAGGCTAAAAAG

CTGAAAAAGATTAGCAACCAGGCAGAGTTCATCGCCTCCTTTTACAACAACGACCTGATTAAGATCAA

TGGCGAACTGTATAGGGTCATCGGGGTGAACAATGATCTGCTGAACCGCATTGAAGTGAATATGATTG

ACATCACTTACCGAGAGTATCTGGAAAACATGAATGATAAGCGCCCCCCTCGAATTATCAAAACAATT

GCCTCTAAGACTCAGAGTATCAAAAAGTACTCAACCGACATTCTGGGAAACCTGTATGAGGTGAAGAG

CAAAAAGCACCCTCAGATTATCAAAAAGGGCagcggaggcaagcgtcctgctgctactaagaaagctg gtcaagctaagaaaaagaaaggatcctacccatacgatgttccagattacgcttaagaattcctagag ctcgctgatcagcctcgactgtgccttctagttgccagccatctgttgtttgccctcccccgtgcct tccttgaccctggaaggtgccactcccactgtcctttcctaataaaatgaggaaattgcatcgcattg tctgagtaggtgtcattctattctggggggtggggtggggcaggacagcaagggggaggattgggaag agaatagcaggcatgctggggaggtagcggccgcCCgcggtggagctccagcttttgttccctttagt gagggttaattgcgcgcttggcgtaatcatggtcatagctgtttcctgtgtgaaattgttatccgctc acaattccacacaacatacgagccggaagcataaagtgtaaagcctggggtgcctaatgagtgagcta actcacattaattgcgttgcgctcactgcccgctttccagtcgggaaacctgtcgtgccagctgcatt aatgaatcggccaacgcgcggggagaggcggtttgcgcattgggcgctcttccgcttcctcgctcact gactcgctgcgctcggtcgttcggctgcggcgagcggtatcagctcactcaaaggcggtaatacggtt atccacagaatcaggggataacgcaggaaagaacatgtgagcaaaaggccagcaaaaggccaggaacc gtaaaaaggccgcgttgctggcgtttttccataggctccgcccccctgacgagcatcacaaaaatcga cgctcaagtcagaggtggcgaaacccgacaggactataaagataccaggcgtttccccctggaagctc cctcgtgcgctctcctgttccgaccctgccgcttaccggatacctgtccgcctttctcccttcgggaa gcgtggcgctttctcatagctcacgctgtaggtatctcagttcggtgtaggtcgttcgctccaagctg ggctgtgtgcacgaacccccccgttcagcccgaccgctgcgccttatccggtaactatcgtcttgagtc caacccggtaagacacgacttatcgccactggcagcagccactggtaacaggattagcagagcgaggt atgtaggcggtgctacagagttcttgaagtggtggcctaactacggctacactagaaggacagtattt ggtatctgcgctctgctgaagccagttaccttcggaaaaagagttggtagctcttgatccggcaaaca aaccaccgctggtagcggtggtttttttgtttgcaagcagcagattacgcgcagaaaaaaaggatctc aagaagatcctttgatcttttctacggggtctgacgctcagtagaacgaaaactcacgttaagggatt ttggtcatgagattatcaaaaaggatcttcacctagatccttttaaattaaaaatgaagttttaaatc aatctaaagtatatatgagtaaacttggtctgacagttaccaatgcttaatcagtgaggcacctatct cagcgatctgtctatttcgttcatccatagttgcctgactccccgtcgtgtagataactacgatacgg gagggcttaccatctggccccagtgctgcaatgataccgcgagacccacgctcaccggctccagattt atcagcaataaaccagccagccggaagggccgagcgcagaagtggtcctgcaactttatccgcctcca
```

-continued tccagtctattaattgttgccgggaagctagagtaagtagttcgccagttaatagtttgcgcaacgtt gttgccattgctacaggcatcgtggtgtcacgctcgtcgtttggtatggcttcattcagctccggttc ccaacgatcaaggcgagttacatgatcccccatgttgtgcaaaaaagcggttagctccttcggtcctc cgatcgttgtcagaagtaagttggccgcagtgttatcactcatggttatggcagcactgcataattct cttactgtcatgccatccgtaagatgctttttctgtgactggtgagtactcaaccaagtcattctgaga atagtgtatgcggcgaccgagttgctcttgcccggcgtcaatacgggataataccgcgccacatagca gaactttaaaagtgctcatcattggaaaacgttcttcggggcgaaaactctcaaggatcttaccgctg ttgagatccagttcgatgtaacccactcgtgcacccaactgatcttcagcatctttttactttcaccag cgtttctgggtgagcaaaaacaggaaggcaaaatgccgcaaaaaagggaataagggcgacacggaaat gttgaatactcatactcttcctttttcaatattattgaagcatttatcaggttattgtctcatgagc ggatacatatttgaatgtatttagaaaaataaacaaataggggttccgcgcacatttccccgaaaagt gccac SEQ ID NO: 39, amino acid sequence of an *S. aureus* Cas9 molecule

[SEQ ID NO: 39]

MKRNYILGLDIGITSVGYGIIDYETRDVIDAGVRLFKEANVENNEGRRSKRGARRLKRRRRH

RIQRVKKLLFDYNLLTDHSELSGINPYEARVKGLSQKLSEEEFSAALLHLAKRRGVHNVNEV

EEDTGNELSTKEQISRNSKALEEKYVAELQLERLKKDGEVRGSINRFKTSDYVKEAKQLLKV

QKAYHQLDQSFIDTYIDLLETRRTYYEGPGEGSPFGWKDIKEWYEMLMGHCTYFPEELRSVK

YAYNADLYNALNDLNNLVITRDENEKLEYYEKFQIIENVFKQKKKPTLKQIAKEILVNEEDI

KGYRVTSTGKPEFTNLKVYHDIKDITARKEIIENAELLDQIAKILTIYQSSEDIQEELTNLN

SELTQEEIEQISNLKGYTGTHNLSLKAINLILDELWHTNDNQIAIFNRLKLVPKKVDLSQQK

EIPTTLVDDFILSPVVKRSFIQSIKVINAIIKKYGLPNDIIIELAREKNSKDAQKMINEMQK

RNRQTNERIEEIIRTTGKENAKYLIEKIKLHDMQEGKCLYSLEAIPLEDLLNNPFNYEVDHI

IPRSVSFDNSFNNKVLVKQEENSKKGNRTPFQYLSSSDSKISYETFKKHILNLAKGKGRISK

TKKEYLLEERDINRFSVQKDFINRNLVDTRYATRGLMNLLRSYFRVNNLDVKVKSINGGFTS

FLRRKWKFKKERNKGYKHKAEDALIIANADFIFKEWKKLDKAKKVMENQMFEEKQAESMPEI

ETEQEYKEIFITPHQIKHIKDFKDYKYSHRVDKKPNRELINDTLYSTRKDDKGNTLIVNNLN

GLYDKDNDKLKKLINKSPEKLLMYHHDPQTYQKLKLIMEQYGDEKNPLYKYYEETGNYLTKY

SKKDNGPVIKKIKYYGNKLNAHLDITDDYPNSRNKVVKLSLKPYRFDVYLDNGVYKFVTVKN

LDVIKKENYYEVNSKCYEEAKKLKKISNQAEFIASFYNNDLIKINGELYRVIGVNNDLLNRI

EVNMIDITYREYLENMNDKRPPRIIKTIASKTQSIKKYSTDILGNLYEVKSKKHPQIIKKG

SEQ ID NO: 40, amino acid sequence of an *S. aureus* Cas9

[SEQ ID NO: 40]

KRNYILGLDIGITSVGYGIIDYETRDVIDAGVRLFKEANVENNEGRRSKRGARRLKRRRRHR

IQRVKKLLFDYNLLTDHSELSGINPYEARVKGLSQKLSEEEFSAALLHLAKRRGVHNVNEVE

EDTGNELSTKEQISRNSKALEEKYVAELQLERLKKDGEVRGSINRFKTSDYVKEAKQLLKVQ

KAYHQLDQSFIDTYIDLLETRRTYYEGPGEGSPFGWKDIKEWYEMLMGHCTYFPEELRSVKY

AYNADLYNALNDLNNLVITRDENEKLEYYEKFQIIENVFKQKKKPTLKQIAKEILVNEEDIK

GYRVTSTGKPEFTNLKVYHDIKDITARKEIIENAELLDQIAKILTIYQSSEDIQEELTNLNS

ELTQEEIEQISNLKGYTGTHNLSLKAINLILDELWHTNDNQIAIFNRLKLVPKKVDLSQQKE

IPTTLVDDFILSPVVKRSFIQSIKVINAIIKKYGLPNDIIIELAREKNSKDAQKMINEMQKR

NRQTNERIEEIIRTTGKENAKYLIEKIKLHDMQEGKCLYSLEAIPLEDLLNNPFNYEVDHII

-continued

PRSVSFDNSFNNKVLVKQEENSKKGNRTPFQYLSSSDSKISYETFKKHILNLAKGKGRISKT

KKEYLLEERDINRFSVQKDFINRNLVDTRYATRGLMNLLRSYFRVNNLDVKVKSINGGFTSF

LRRKWKFKKERNKGYKHHAEDALIIANADFIFKEWKKLDKAKKVMENQMFEEKQAESMPEIE

TEQEYKEIFITPHQIKHIKDFKDYKYSHRVDKKPNRELINDTLYSTRKDDKGNTLIVNNLNG

LYDKDNDKLKKLINKSPEKLLMYHHDPQTYQKLKLIMEQYGDEKNPLYKYYEETGNYLTKYS

KKDNGPVIKKIKYYGNKLNAHLDITDDYPNSRNKVVKLSLKPYRFDVYLDNGVYKFVTVKNL

DVIKKENYYEVNSKCYEEAKKLKKISNQAEFIASFYNNDLIKINGELYRVIGVNNDLLNRIE

VNMIDITYREYLENMNDKRPPRIIKTIASKTQSIKKYSTDILGNLYEVKSKKHPQIIKKG

SEQ ID NO: 41, Version 1 of vector 5
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc

TCTAGACTCGAGTCGAGTGGCTCCGGTGCCCGTCAGTGGGCAGAGCGCACATCGCCCACAGTCCCCGA

GAAGTTGGGGGGAGGGGTCGGCAATTGAACCGGTGCCTAGAGAAGGTGGCGCGGGGTAAACTGGGAAA

GTGATGTCGTGTACTGGCTCCGCCTTTTTCCCGAGGGTGGGGGAGAACCGTATATAAGTGCAGTAGTC

GCCGTGAACGTTCTTTTTCGCAACGGGTTTGCCGCCAGAACACAGGTGTCGTGACCGCGGCCATGGtC tagaggatccggtactcgaggaactgaaaaaccagaaagttaactggtaagcttagtcttttttgtctt ttatttcaggtcccggatccggtggtggtgcaaatcaaagaactgctcctcagtggatgttgccttta cttctaggcctgtacggaagtgttacgccaCCATGGCCCCAAAGAAGAAGCGGAAGGTCGGTATCCAC

GGAGTCCCAGCAGCCAAGCGGAACTACATCCTGGGCCTGGACATCGGCATCACCAGCGTGGGCTACGG

CATCATCGACTACGAGACACGGGACGTGATCGATGCCGGCGTGCGGCTGTTCAAAGAGGCCAACGTGG

AAAACAACGAGGGCAGGCGGAGCAAGAGAGGCGCCAGAAGGCTGAAGCGGCGGAGGCGGCATAGAATC

CAGAGAGTGAAGAAGCTGCTGTTCGACTACAACCTGCTGACCGACCACAGCGAGCTGAGCGGCATCAA

CCCCTACGAGGCCAGAGTGAAGGGCCTGAGCCAGAAGCTGAGCGAGGAAGAGTTCTCTGCCGCCCTGC

TGCACCTGGCCAAGAGAAGAGGCGTGCACAACGTGAACGAGGTGGAAGAGGACACCGGCAACGAGCTG

TCCACCAAAGAGCAGATCAGCCGGAACAGCAAGGCCCTGGAAGAGAAATACGTGGCCGAACTGCAGCT

GGAACGGCTGAAGAAAGACGGCGAAGTGCGGGGCAGCATCAACAGATTCAAGACCAGCGACTACGTGA

AAGAAGCCAAACAGCTGCTGAAGGTGCAGAAGGCCTACCACGAGCTGGACCAGAGCTTCATCGACACC

TACATCGACCTGCTGGAAACCCGGCGGACCTACTATGAGGGACCTGGCGAGGGCAGCCCCTTCGGCTG

GAAGGACATCAAAGAATGGTACGAGATGCTGATGGGCCACTGCACCTACTTCCCCGAGGAACTGCGGA

GCGTGAAGTACGCCTACAACGCCGACCTGTACAACGCCCTGAACGACCTGAACAATCTCGTGATCACC

AGGGACGAGAACGAGAAGCTGGAATATTACGAGAAGTTCCAGATCATCGAGAACGTGTTCAAGCAGAA

GAAGAAGCCCACCCTGAAGCAGATCGCCAAAGAAATCCTCGTGAACGAAGAGGATATTAAGGGCTACA

GAGTGACCAGCACCGGCAAGCCCGAGTTCACCAACCTGAAGGTGTACCACGACATCAAGGACATTACC

GCCCGGAAAGAGATTATTGAGAACGCCGAGCTGCTGGATCAGATTGCCAAGATCCTGACCATCTACCA

GAGCAGCGAGGACATCCAGGAAGAACTGACCAATCTGAACTCCGAGCTGACCCAGGAAGAGATCGAGC

AGATCTCTAATCTGAAGGGCTATACCGGCACCCACAACCTGAGCCTGAAGGCCATCAACCTGATCCTG

GACGAGCTGTGGCACACCAACGACAACCAGATCGCTATCTTCAACCGGCTGAAGCTGGTGCCCAAGAA

GGTGGACCTGTCCCAGCAGAAAGAGATCCCCACCACCCTGGTGGACGACTTCATCCTGAGCCCCGTCG

TGAAGAGAAGCTTCATCCAGAGCATCAAAGTGATCAACGCCATCATCAAGAAGTACGGCCTGCCCAAC

GACATCATTATCGAGCTGGCCCGCGAGAAGAACTCCAAGGACGCCCAGAAAATGATCAACGAGATGCA

GAAGCGGAACCGGCAGACCAACGAGCGGATCGAGGAAATCATCCGGACCACCGGCAAAGAGAACGCCA

```
AGTACCTGATCGAGAAGATCAAGCTGCACGACATGCAGGAAGGCAAGTGCCTGTACAGCCTGGAAGCC

ATCCCTCTGGAAGATCTGCTGAACAACCCCTTCAACTATGAGGTGGACCACATCATCCCCAGAAGCGT

GTCCTTCGACAACAGCTTCAACAACAAGGTGCTCGTGAAGCAGGAAGAAACAGCAAGAAGGGCAACC

GGACCCCATTCCAGTACCTGAGCAGCAGCGACAGCAAGATCAGCTACGAAACCTTCAAGAAGCACATC

CTGAATCTGGCCAAGGGCAAGGGCAGAATCAGCAAGACCAAGAAAGAGTATCTGCTGGAAGAACGGGA

CATCAACAGGTTCTCCGTGCAGAAAGACTTCATCAACCGGAACCTGGTGGATACCAGATACGCCACCA

GAGGCCTGATGAACCTGCTGCGGAGCTACTTCAGAGTGAACAACCTGGACGTGAAAGTGAAGTCCATC

AATGGCGGCTTCACCAGCTTTCTGCGGCGGAAGTGGAAGTTTAAGAAAGAGCGGAACAAGGGGTACAA

GCACCACGCCGAGGACGCCCTGATCATTGCCAACGCCGATTTCATCTTCAAAGAGTGGAAGAAACTGG

ACAAGGCCAAAAAAGTGATGGAAAACCAGATGTTCGAGGAAAAGCAGGCCGAGAGCATGCCCGAGATC

GAAACCGAGCAGGAGTACAAAGAGATCTTCATCACCCCCCACCAGATCAAGCACATTAAGGACTTCAA

GGACTACAAGTACAGCCACCGGGTGGACAAGAAGCCTAATAGAGAGCTGATTAACGACACCCTGTACT

CCACCCGGAAGGACGACAAGGGCAACACCCTGATCGTGAACAATCTGAACGGCCTGTACGACAAGGAC

AATGACAAGCTGAAAAAGCTGATCAACAAGAGCCCCGAAAAGCTGCTGATGTACCACCACGACCCCCA

GACCTACCAGAAACTGAAGCTGATTATGGAACAGTACGGCGACGAGAAGAATCCCCTGTACAAGTACT

ACGAGGAAACCGGGAACTACCTGACCAAGTACTCCAAAAAGGACAACGGCCCCGTGATCAAGAAGATT

AAGTATTACGGCAACAAACTGAACGCCCATCTGGACATCACCGACGACTACCCCAACAGCAGAAACAA

GGTCGTGAAGCTGTCCCTGAAGCCCTACAGATTCGACGTGTACCTGGACAATGGCGTGTACAAGTTCG

TGACCGTGAAGAATCTGGATGTGATCAAAAAAGAAAACTACTACGAAGTGAATAGCAAGTGCTATGAG

GAAGCTAAGAAGCTGAAGAAGATCAGCAACCAGGCCGAGTTTATCGCCTCCTTCTACAACAACGATCT

GATCAAGATCAACGGCGAGCTGTATAGAGTGATCGGCGTGAACAACGACCTGCTGAACCGGATCGAAG

TGAACATGATCGACATCACCTACCGCGAGTACCTGGAAAACATGAACGACAAGAGGCCCCCCAGGATC

ATTAAGACAATCGCCTCCAAGACCCAGAGCATTAAGAAGTACAGCACAGACATTCTGGGCAACCTGTA

TGAAGTGAAATCTAAGAAGCACCCTCAGATCATCAAAAAGGGCAAAAGGCCGGCGGCCACGAAAAAGG

CCGGCCAGGCAAAAAAGAAAAAGggatccGAATTCtagcaataaaggatcgtttattttcattggaag cgtgtgttggttttttgatcaggcgcgGGTACCAAAAATCTCGCCAACAAGTTGACGAGATAAACACG GCATTTTGCCTTGTTTTAGTAGATTCTGTTTCCAGAGTACTAAAACacatttcctctctatacaaatg

CGGTGTTTCGTCCTTTCCACAAGATATATAAAGCCAAGAAATCGAAATACTTTCAAGTTAGGGTAAGC

ATATGATAGTCCATTTTAAAACATAATTTTAAAACTGCAAACTAGCCAAGAAATTATTACTTTCTACG

TCACGTATTTTGTACTAATATCTTTGTGTTTACAGTCAAATTAATTCCAATTATCTCTCTAACAGCCT

TGTATCGTATATGCAAATATGAAGGAATCATGGGAAATAGGCCCTCCTCGACTAGTAGAAAAATCTCG

CCAACAAGTTGACGAGATAAACACGGCATTTTGCCTTGTTTTAGTAGATTCTGTTTCCAGAGTACTAA

AACGTGCCAATAATTTCATTACTATATCGGTGTTTCGTCCTTTCCACAAGATATATAAAGCCAAGAAA

TCGAAATACTTTCAAGTTACGGTAAGCATATGATAGTCCATTTTAAAACATAATTTTAAAACTGCAAA

CTACCCAAGAAATTATTACTTTCTACGTCACGTATTTTGTACTAATATCTTTGTGTTTACAGTCAAAT

TAATTCCAATTATCTCTCTAACAGCCTTGTATCGTATATGCAAATATGAAGGAATCATGGGAAATAGG

CCCTCGGTACCaggaacccctagtgatggagttggccactccctctctgcgcgctcgctcgctcactg aggccgggcgaccaaaggtcgcccgacgcccgggctttgcccgggcggcctcagtgagcgagcgagcg cgcagctgcctgcaggggcgcctgatgcggtattttctccttacgcatctgtgcggtatttcacaccg catacgtcaaagcaaccatagtacgcgccctgtagcggcgcattaagcgcggcgggtgtggtggttac gcgcagcgtgaccgctacacttgccagcgccctagcgcccgctcctttcgctttcttcccttcctttc
```

-continued

```
tcgccacgttcgccggctttccccgtcaagctctaaatcgggggctccctttagggttccgatttagt gctttacggcacctcgaccccaaaaaacttgatttgggtgatggttcacgtagtgggccatcaccctg atagacggtttttcgccctttgacgttggagtccacgttctttaatagtggactcttgttccaaactg gaacaacactcaaccctatctcgggctattcttttgatttataagggattttgccgatttcggcctat tggttaaaaaatgagctgatttaacaaaaatttaacgcgaatttttaacaaaatattaacgtttacaat tttatggtgcactctcagtacaatctgctctgatgccgcatagttaagccagcccgacacccgccaa cacccgctgacgcgccctgacgggcttgtctgctcccggcatccgcttacagacaagctgtgaccgtc tccgggagctgcatgtgtcagaggttttcaccgtcatcaccgaaacgcgcgagacgaaagggcctcgt gatacgcctattttttataagttaatgtcatgataataatggtttcttagacgtcaggtggcacttttc ggggaaatgtgcgcggaacccctatttgtttattttttctaaatacattcaaatatgtatccgctcatg agacaataaccctgataaatgcttcaataatattgaaaaaggaagagtatgagtattcaacatttccg tgtcgcccttattccctttttttgcggcattttgccttcctgtttttgctcacccagaaacgctggtga aagtaaaagatgctgaagatcagttgggtgcacgagtgggttacatcgaactggatctcaacagcggt aagatccttgagagttttcgccccgaagaacgttttccaatgatgagcacttttaaagttctgctatg tggcgcggtattatcccgtattgacgccgggcaagagcaactcggtcgccgcatacactattctcaga atgacttggttgagtactcaccagtcacagaaaagcatcttacggatggcatgacagtaagagaatta tgcagtgctgccataaccatgagtgataacactgcggccaacttacttctgacaacgatcggaggacc gaaggagctaaccgcttttttgcacaacatgggggatcatgtaactcgccttgatcgttgggaaccgg agctgaatgaagccataccaaacgacgagcgtgacaccacgatgcctgtagcaatggcaacaacgttg cgcaaactattaactggcgaactacttactctagcttcccggcaacaattaatagactggatggaggc ggataaagttgcaggaccacttctgcgctcggcccttccggctggctggtttattgctgataaatctg gagccggtgagcgtggaagccgcggtatcattgcagcactggggccagatggtaagccctcccgtatc gtagttatctacacgacggggagtcaggcaactatggatgaacgaaatagacagatcgctgagatagg tgcctcactgattaagcattggtaactgtcagaccaagtttactcatatatactttagattgatttaa aacttcattttttaatttaaaaggatctaggtgaagatcctttttgataatctcatgaccaaaatccct taacgtgagttttcgttccactgagcgtcagacccgtagaaaagatcaaaggatcttcttgagatcc ttttttttctgcgcgtaatctgctgcttgcaaacaaaaaaaccaccgctaccagcggtggtttgtttgc cggatcaagagctaccaactctttttccgaaggtaactggcttcagcagagcgcagataccaaatact gtccttctagtgtagccgtagttaggccaccacttcaagaactctgtagcaccgcctacatacctcgc tctgctaatcctgttaccagtggctgctgccagtggcgataagtcgtgtcttaccgggttggactcaa gacgatagttaccggataaggcgcagcggtcgggctgaacggggggttcgtgcacacagcccagcttg gagcgaacgacctacaccgaactgagatacctacagcgtgagctatgagaaagcgccacgcttcccga agggagaaaggcggacaggtatccggtaagcggcagggtcggaacaggagagcgcacgagggagcttc caggggaaacgcctggtatctttatagtcctgtcgggtttcgccacctctgacttgagcgtcgattt ttgtgatgctcgtcaggggggcggagcctatggaaaaacgccagcaacgcggcctttttacggttcct ggccttttgctggccttttgctcacatgt
```

SEQ ID NO: 42, Version 2 of vector 5
```
cctgcaggcagctgcgcgctcgctcgctcactgaggccgcccgggcgtcgggcgacctttggtcgccc ggcctcagtgagcgagcgagcgcgcagagagggagtggccaactccatcactaggggttcctgcggcc

TCTAGACTCGAGCTAGACTAGCATGCTGCCCATGTAAGGAGGCAAGGCCTGGGGACACCCGAGATGCC

TGGTTATAATTAACCCAGACATGTGGCTGCCCCCCCCCCCCCCAACACCTGCTGCCTCTAAAAATAACC
```

```
CTGCATGCCATGTTCCCGGCGAAGGGCCAGCTGTCCCCCGCCAGCTAGACTCAGCACTTAGTTTAGGA

ACCAGTGAGCAAGTCAGCCCTTGGGGCAGCCCATACAAGGCCATGGGGCTGGGCAAGCTGCACGCCTG

GGTCCGGGGTGGGCACGGTGCCCGGGCAACGAGCTGAAAGCTCATCTGCTCTCAGGGGCCCCTCCCTG

GGGACAGCCCCTCCTGGCTAGTCACACCCTGTAGGCTCCTCTATATAACCCAGGGGCACAGGGGCTGC

CCTCATTCTAGCACCACCTCCACAGCACAGACAGACACTCAGGAGCCAGCCAGCCATGGtctagagga tccggtactcgaggaactgaaaaaccagaaagttaactggtaagtttagtctttttgtctttttatttc aggtcccggatccggtggtggtgcaaatcaaagaactgctcctcagtggatgttgcctttacttctag gcctgtacggaagtgttacgccaCCATGGCCCCAAAGAAGAAGCGGAAGGTCGGTATCCACGGAGTCC

CAGCAGCCAAGCGGAACTACATCCTGGGCCTGGACATCGGCATCACCAGCGTGGGCTACGGCATCATC

GACTACGAGACACGGGACGTGATCGATGCCGGCGTGCGGCTGTTCAAAGAGGCCAACGTGGAAAACAA

CGAGGGCAGGCGGAGCAAGAGAGGCGCCAGAAGGCTGAAGCGGCGGAGGCGGCATAGAATCCAGAGAG

TGAAGAAGCTGCTGTTCGACTACAACCTGCTGACCGACCACAGCGAGCTGAGCGGCATCAACCCCTAC

GAGGCCAGAGTGAAGGGCCTGAGCCAGAAGCTGAGCGAGGAAGAGTTCTCTGCCGCCCTGCTGCACCT

GGCCAAGAGAAGAGGCGTGCACAACGTGAACGAGGTGGAAGAGGACACCGGCAACGAGCTGTCCACCA

AAGAGCAGATCAGCCGGAACAGCAAGGCCCTGGAAGAGAAATACGTGGCCGAACTGCAGCTGGAACGG

CTGAAGAAAGACGGCGAAGTGCGGGGCAGCATCAACAGATTCAAGACCAGCGACTACGTGAAAGAAGC

CAAACAGCTGCTGAAGGTGCAGAAGGCCTACCACCAGCTGGACCAGAGCTTCATCGACACCTACATCG

ACCTGCTGGAAACCCGGCGGACCTACTATGAGGGACCTGGCGAGGGCAGCCCCTTCGGCTGGAAGGAC

ATCAAAGAATGGTACGAGATGCTGATGGGCCACTGCACCTACTTCCCCGAGGAACTGCGGAGCGTGAA

GTACGCCTACAACGCCGACCTGTACAACGCCCTGAACGACCTGAACAATCTCGTGATCACCAGGGACG

AGAACGAGAAGCTGGAATATTACGAGAAGTTCCAGATCATCGAGAACGTGTTCAAGCAGAAGAAGAAG

CCCACCCTGAAGCAGATCGCCAAAGAAATCCTCGTGAACGAAGAGGATATTAAGGGCTACAGAGTGAC

CAGCACCGGCAAGCCCGAGTTCACCAACCTGAAGGTGTACCACGACATCAAGGACATTACCGCCCGGA

AAGAGATTATTGAGAACGCCGAGCTGCTGGATCAGATTGCCAAGATCCTGACCATCTACCAGAGCAGC

GAGGACATCCAGGAAGAACTGACCAATCTGAACTCCGAGCTGACCCAGGAAGAGATCGAGCAGATCTC

TAATCTGAAGGGCTATACCGGCACCCACAACCTGAGCCTGAAGGCCATCAACCTGATCCTGGACGAGC

TGTGGCACACCAACGACAACCAGATCGCTATCTTCAACCGGCTGAAGCTGGTGCCCAAGAAGGTGGAC

CTGTCCCAGCAGAAAGAGATCCCCACCACCCTGGTGGACGACTTCATCCTGAGCCCCGTCGTGAAGAG

AAGCTTCATCCAGAGCATCAAAGTGATCAACGCCATCATCAAGAAGTACGGCCTGCCCAACGACATCA

TTATCGAGCTGGCCCGCGAGAAGAACTCCAAGGACGCCCAGAAAATGATCAACGAGATGCAGAAGCGG

AACCGGCAGACCAACGAGCGGATCGAGGAAATCATCCGGACCACCGGCAAAGAGAACGCCAAGTACCT

GATCGAGAAGATCAAGCTGCACGACATGCAGGAAGGCAAGTGCCTGTACAGCCTGGAAGCCATCCCTC

TGGAAGATCTGCTGAACAACCCCTTCAACTATGAGGTGGACCACATCATCCCCAGAAGCGTGTCCTTC

GACAACAGCTTCAACAACAAGGTGCTCGTGAAGCAGGAAGAAAACAGCAAGAAGGGCAACCGGACCCC

ATTCCAGTACCTGAGCAGCAGCGACAGCAAGATCAGCTACGAAACCTTCAAGAAGCACATCCTGAATC

TGGCCAAGGGCAAGGGCAGAATCAGCAAGACCAAGAAAGAGTATCTGCTGGAAGAACGGGACATCAAC

AGGTTCTCCGTGCAGAAAGACTTCATCAACCGGAACCTGGTGGATACCAGATACGCCACCAGAGGCCT

GATGAACCTGCTGCGGAGCTACTTCAGAGTGAACAACCTGGACGTGAAAGTGAAGTCCATCAATGGCG

GCTTCACCAGCTTTCTGCGGCGGAAGTGGAAGTTTAAGAAAGAGCGGAACAAGGGGTACAAGCACCAC

GCCGAGGACGCCCTGATCATTGCCAACGCCGATTTCATCTTCAAAGAGTGGAAGAAACTGGACAAGGC
```

-continued

```
CAAAAAAGTGATGGAAAACCAGATGTTCGAGGAAAAGCAGGCCGAGAGCATGCCCGAGATCGAAACCG

AGCAGGAGTACAAAGAGATCTTCATCACCCCCCACCAGATCAAGCACATTAAGGACTTCAAGGACTAC

AAGTACAGCCACCGGGTGGACAAGAAGCCTAATAGAGAGCTGATTAACGACACCCTGTACTCCACCCG

GAAGGACGACAAGGGCAACACCCTGATCGTGAACAATCTGAACGGCCTGTACGACAAGGACAATGACA

AGCTGAAAAAGCTGATCAACAAGAGCCCCGAAAAGCTGCTGATGTACCACCACGACCCCCAGACCTAG

CAGAAACTGAAGCTGATTATGGAACAGTACGGCGACGAGAAGAATCCCCTGTACAAGTACTAGGAGGA

AACCGGGAACTACCTGACCAAGTACTCCAAAAAGGACAACGGCCCCGTGATCAAGAAGATTAAGTATT

ACGGCAACAAACTGAACGCCCATCTGGACATCAGCGACGACTACCCCAACAGCAGAAACAAGGTCGTG

AAGCTGTCCCTGAAGCCCTACAGATTCGACGTGTACCTGGACAATGGCGTGTACAAGTTCGTGACCGT

GAAGAATCTGGATGTGATCAAAAAAGAAAACTACTACGAAGTGAATAGCAAGTGCTATGAGGAAGCTA

AGAAGCTGAAGAAGATCAGCAACCAGGCCGAGTTTATCGCCTCCTTCTACAACAACGATCTGATCAAG

ATCAACGGCGAGCTGTATAGAGTGATCGGCGTGAACAACGACCTGCTGAACCGGATCGAAGTGAACAT

GATCGACATCACCTACCGCGAGTACCTGGAAAACATGAACGACAAGAGGCCCCCCAGGATCATTAAGA

CAATCGCCTCCAAGACCCAGAGCATTAAGAAGTACAGCACAGACATTCTGGGCAACCTGTATGAAGTG

AAATCTAAGAAGCACCCTCAGATCATCAAAAAGGGCAAAAGGCCGGCGGCCACGAAAAAGGCCGGCCA

GGCAAAAAAGAAAAAGggatccGAATTCtagcaataaaggatcgtttattttcattggaagcgtgtgt tggtttttgatcaggcgcgGGTACCAAAAATCTCGCCAACAAGTTGACGAGATAAACACGGCATTTT GCCTTGTTTTAGTAGATTCTGTTTCCAGAGTACTAAAACacatttcctctctatacaaatgCGGTGTT

TCGTCCTTTCCACAAGATATATAAAGCCAAGAAATCGAAATACTTTCAAGTTACGGTAAGCATATGAT

AGTCCATTTTAAAACATAATTTTAAAACTGCAAACTACCCAAGAAATTATTACTTTCTACGTCACGTA

TTTTGTACTAATATCTTTGTGTTTACAGTCAAATTAATTCCAATTATCTCTCTAACAGCCTTGTATCG

TATATGCAAATATGAAGGAATCATGGGAAATAGGCCCTCCTCGACTAGTAGAAAAATCTCGCCAACAA

GTTGACGAGATAAACACGGCATTTTGCCTTGTTTTAGTAGATTCTGTTTCCAGAGTACTAAAACGTGC

CAATAATTTCATTACTATATCGGTGTTTCGTCCTTTCCACAAGATATATAAAGCCAAGAAATCGAAAT

ACTTTCAAGTTACGGTAAGCATATGATAGTCCATTTTAAAACATAATTTTAAAACTGCAAACTACCCA

AGAAATTATTACTTTCTACGTCACGTATTTTGTACTAATATCTTTGTGTTTACAGTCAAATTAATTCC

AATTATCTCTCTAACAGCCTTGTATCGTATATGCAAATATGAAGGAATCATGGGAAATAGGCCCTCGG

TACCaggaacccctagtgatggagttggccactccctctctgcgcgctcgctcgctcactgaggccgg gcgaccaaaggtcgcccgacgcccgggctttgcccgggcggcctcagtgagcgagcgagcgcgcagct gcctgcaggggcgcctgatgcggtattttctccttacgcatctgtgcggtatttcacaccgcatacgt caaagcaaccatagtacgcgccctgtagcggcgcattaagcgcggcgggtgtggtggttacgcgcagc gtgaccgctacacttgccagcgccctagcgcccgctcctttcgctttcttcccttcctctctcgccac gttcgccggctttccccgtcaagctctaaatcggggggctccctttagggttccgatttagtgctttac ggcacctcgacccccaaaaaacttgatttgggtgatggttcacgtagtgggccatcgccctgatagacg gtttttcgccctttgacgttggagtccacgttctttaatagtggactcttgttccaaactggaacaac actcaaccctatctcgggctattcttttgatttataagggattttgccgatttcggcctattggttaa aaaatgagctgatttaacaaaaatttaacgcgaattttaacaaaatattaacgtttacaattttatgg tgcactctcagtacaatctgctctgatgccgcatagttaagccagccccgacacccgccaacacccgc tgacgcgccctgacgggcttgtctgctcccggcatccgcttacagacaagctgtgaccgtctccggga gctgcatgtgtcagaggttttcaccgtcatcaccgaaacgcgcgagacgaaagggcctcgtgatacgc ctattttttataggttaatgtcatgataataatggtttcttagacgtcaggtggcacttttcggggaaa
```

-continued tgtgcgcggaaccctatttgtttattttttctaaatacattcaaatatgtatccgctcatgagacaat aaccctgataaatgcttcaataatattgaaaaagaaagagtatgagtattcaacatttccgtgtcgcc cttattcccttttttgcggcattttgccttcctgtttttgctcaaccagaaacgctggtgaaagtaaa agatgctgaagatcagttgggtgcacgagtgggttacatcgaactggatctcaacagcggtaagatcc ttgagagttttcgccccgaagaacgttttccaatgatgagcacttttaaagttctgctatgtggcgcg gtattatcccgtattgacgccgggcaagagcaactcggtcgccgcatacactattctcagaatgactt ggttgagtactcaccagccacagaaaagcatcttacggatgacatgacagtaagagaactatgcagcg ctgccataaccatgagtgataacactgcggccaacttacttctgacaacgatcggaggaccgaaggag ctaaccgcttttttgcacaacatgggggatcatgtaactcgcctCgatcgttgggaaccggagctgaa tgaagccataccaaacgacgagcgtgacaccacgatgcctgtagcaatggcaacaacgttgcgcaaac tattaactggcgaactacttactctagcttcccggcaacaattaatagactggatggaggcggataaa gttgcaggaccacttctgcgctcggcccttccggctggctggtttattgctgatasatctggagccgg tgagcgtggaagccgcggtatcattgcagcactggggccagatggtaagccctcccgtatcgtagtta tctacacgacggggagtcaggcaactacggatgaacgaaatagacagatcgctgagataggtgcctca ctgattaagcattggtaactgtcagaccaagtttactcatatatactttagattgatttaaaacttca tttttaatttaaaaggatctaggtgaagatcctttttgataatctcatgaccaaaatcccttaacgtg agttttcgttccactgagcgtcagaccccgtagaaaagatcaaaggatcttcttgagatcctttttttt ctgcgcgtaatctgctgcttgcaaacaaaaaaaccaccgctaccagcggtggtttgtttgccggatca agagctaccaactctttttccgaaggtaactggcttcagcagagcgcagataccaaatactgtccttc tagtgtagccgtagttaggccaccacttcaagaactctgtagcaccgcctacatacctcgctctgcta atcctgttaccagtggctgctgccagtggcgataagtcgtgtcttaccgggttggactcaagacgata gttaccggataaggcgcagcggtcgggctgaacggggggttcgtgcacacagcccagcttggagcgaa cgacctacaccgaactgagatacctacagcgtgagctatgagaaagcgccacgcttcccgaagggaga aaggcggacaggtatccggtaagcggcagggtcggaacaggagagcgcacgagggagcttccaggggg aaacgcctggtatctttatagtcctgtcgggtttcgccacctctgacttgagcgtcgattttgtgat gctcgtcaggggggcggagcctatggaaaaacgccagcaacgcggcctttttacggttcctggcctt tgctggcctttttgctcacatgt

What is claimed is:

1. A DNA targeting system comprising a single vector encoding:

(a) a first guide RNA (gRNA) molecule targeting intron 44 of dystrophin;

(b) a second gRNA molecule targeting intron 55 of dystrophin; and (c) a Clustered Regularly Interspaced Short Palindromic Repeats Associated 9 (Cas9) protein; and (d) one or more Cas9 gRNA scaffolds, wherein the single vector comprises:

a first promoter comprising a U6 promoter and driving expression of the first gRNA molecule;

a second promoter driving expression of the Cas9 protein; and a third promoter comprising a H1 promoter driving expression of the second gRNA molecule, wherein the first promoter is upstream of the second promoter and drives expression in a direction opposite to the second and third promoters.

2. The system of claim 1, wherein expression of the Cas9 protein is driven by a constitutive promoter or a muscle-specific promoter.

3. The system of claim 2, where the muscle-specific promoter comprises a MHCK7 promoter, a CK8 promoter, or a Spc512 promoter.

4. The system of claim 1, wherein the first gRNA targets the polynucleotide of SEQ ID NO: 2.

5. The system of claim 1, wherein the second gRNA targets the polynucleotide of SEQ ID NO: 3.

6. The system of claim 1, wherein the Cas9 protein is *Streptococcus pyogenes* Cas9 (SpCas9), *Staphylococcus aureus* Cas9 (SaCas9), or *Streptococcus thermophilus* Cas9 (St1Cas9) protein.

7. The system of claim 6, wherein the Cas9 gRNA scaffold comprises or is encoded by the polynucleotide of SEQ ID NO: 4.

8. The system of claim 1, wherein the Cas9 protein is a SaCas9 protein encoded by the polynucleotide of SEQ ID NO: 11.

9. The system of claim 1, wherein the vector comprises at least one polynucleotide selected from SEQ ID NOs: 1-13 and 24.

10. The system of claim 1, wherein the vector comprises a polynucleotide sequence that is selected from SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 41, SEQ ID NO: 42, SEQ ID NO: 29, and SEQ ID NO: 30.

11. The system of claim 1, wherein the vector is a viral vector.

12. The system of claim 1, wherein the vector comprises a ubiquitous promoter or a tissue-specific promoter operably linked to the polynucleotide sequence encoding the first gRNA molecule, the second gRNA molecule, and/or the Cas9 protein.

13. A cell comprising the system of claim 1.

14. A kit comprising the system of claim 1.

15. A method of correcting a mutant dystrophin gene in a cell, the method comprising administering to the cell the system of claim 1.

16. The system of claim 1, wherein the first promoter is encoded by the polynucleotide of SEQ ID NO: 5.

17. The system of claim 1, wherein the third promoter is encoded by the polynucleotide of SEQ ID NO: 6.

\* \* \* \* \*